United States Patent
Matsuoka et al.

(10) Patent No.: US 7,553,969 B1
(45) Date of Patent: *Jun. 30, 2009

(54) SUBSTITUTED PHENETHYLAMINE DERIVATIVES

(75) Inventors: Hiroharu Matsuoka, Shizuoka (JP);
Tsutomu Sato, Shizuoka (JP);
Tadakatsu Takahashi, Shizuoka (JP);
Dong Ick Kim, Kyunggi-do (KR);
Kyung Yun Jung, Kyunggi-do (KR);
Chan Hee Park, Kyunggi-do (KR)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/890,219

(22) PCT Filed: Jan. 28, 2000

(86) PCT No.: PCT/JP00/00444

§ 371 (c)(1),
(2), (4) Date: Dec. 12, 2001

(87) PCT Pub. No.: WO00/44770

PCT Pub. Date: Aug. 3, 2000

(30) Foreign Application Priority Data

Jan. 28, 1999 (JP) .................................. 11-020523
Oct. 4, 1999 (JP) .................................. 11-283163

(51) Int. Cl.
*C07D 211/72* (2006.01)
*C07C 233/00* (2006.01)

(52) U.S. Cl. ...................... 546/312; 564/164

(58) Field of Classification Search ................ 564/282,
564/306, 157, 164; 514/613, 646, 621, 269,
514/365; 544/301; 548/131; 614/646; 546/312
See application file for complete search history.

(56) References Cited

U.S. PATENT DOCUMENTS

| | | | |
|---|---|---|---|
| 4,595,677 A | | 6/1986 | Riniker et al. |
| 5,643,878 A | * | 7/1997 | Bold et al. ..................... 514/19 |
| 6,225,285 B1 | * | 5/2001 | Luo et al. ...................... 514/12 |
| 6,255,285 B1 | * | 7/2001 | Kotake et al. ................. 514/18 |
| 6,586,630 B1 | * | 7/2003 | Matsuoka et al. ........... 564/153 |

FOREIGN PATENT DOCUMENTS

| | | |
|---|---|---|
| EP | 0 111 266 A2 | 6/1984 |
| EP | 0 410 411 | 1/1991 |
| EP | 0 647 656 A1 | 4/1995 |
| JP | 06-220088 A | 8/1994 |
| JP | 07138284 | 5/1995 |
| JP | 07-188282 A | 7/1995 |
| WO | WO 94/03483 A1 | 2/1994 |
| WO | WO 96/40208 A1 | 6/1996 |
| WO | WO 97/19908 A1 | 6/1997 |
| WO | WO 97/48713 A1 | 12/1997 |
| WO | 9909053 * | 2/1999 |
| WO | WO 99/21846 A1 | 5/1999 |

OTHER PUBLICATIONS

Ca 130:196468, "Parallel solid phase synthesis of tretrasubstituted dietyhlenetriamines via selective amide alkylation and exhaustive reduction of N-acylated dipeptides", Nefzi et. al.*
Ca 136:215417, "B lymphocyte stimulator protein (BLys) binding polypeptides for diagnosis and treatment of immunological disorders", Beltzer et. al.*
Ca 117:27161, "Preparation of pyrrolidinylphosphonate-containing peptides as antiviral agents", Haebich et. al.*
Ca 140:703, "Antitubercular drug: compositions and methods", Protopopova et. al.*
Hcaplus 101:66177.*
Hisanori Takanashi et al. "GM-109: A Novel, Selective Motilin Receptor Antagonist in the Smooth Muscle of the Rabbit Small Intestine", The Journal of Pharmacology and Experimental Therapeutics, vol. 273, No. 2, pp. 624-628.
P. Poitras et al. "Motilin Synthetic Analogues and Motilin Receptor Antagonists", Biochemical and Biophysical Research Communications, vol. 205, No. 1, 1994, pp. 449-454.
Inge Depoortere et al. "Antagonistic Properties of [Phe$^3$, Leu$^{13}$] Porcine Motilin", European Journal of Pharmacology 286 (1995) pp. 241-247.
Budavari, S. et al., "The Merk Index", (1996) Merck & Co., Inc., pp. 1677, 1253, and 1690.

* cited by examiner

*Primary Examiner*—Janet L Andres
*Assistant Examiner*—Binta M Robinson
(74) *Attorney, Agent, or Firm*—Browdy and Neimark, P.L.L.C.

(57) ABSTRACT

Substituted phenethylamine compounds of Formula (1) that function as motilin receptor antagonists:
Formula (1).

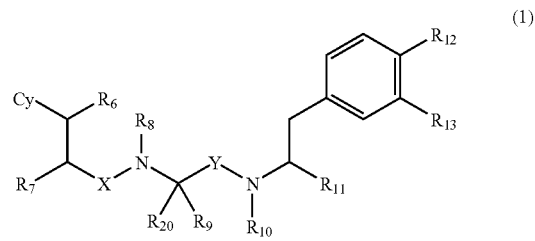

18 Claims, No Drawings

SUBSTITUTED PHENETHYLAMINE DERIVATIVES

REFERENCE TO RELATED APPLICATIONS

The present application is the national stage under 35 U.S.C. §371 of international application PCT/JP00/00444, filed Jan. 28, 2000 which designated the United States, and which application was not published in the English language.

TECHNICAL FIELD

This invention relates to substituted phenethylamine derivatives that function as a motilin receptor antagonist and that are useful as medicines.

BACKGROUND ART

Motilin, which is one of the gastrointestinal hormones, is a straight-chained peptide consisting of 22 amino acids and is well known to be responsible for regulating the motility of the gastrointestinal tract in animals including human. It has been reported that exogenously administered motilin causes contractions in humans and dogs that are similar to interdigestive migrating contractions, thus promoting gastric emptying (Itoh et al., Scand. J. Gastroenterol., 11, 93-110 (1976); Peeters et al., Gastroenterology 102, 97-101 (1992)). Hence, erythromycin derivatives which are an agonist of motilin are under development as an gastrointestinal tract motor activity enhancer (Satoh et al., J. Pharmacol. Exp. Therap., 271, 574-579 (1994); Lartey et al., J. Med. Chem., 38, 1793-1798 (1995); Drug of the Future, 19, 910-912 (1994)).

Peptide and polypeptide derivatives have been reported as antagonists of motilin receptors (Depoortere et al., Eur. J. Pharmacol., 286, 241-247 (1995); Poitras et al., Biochem. Biophys. Res. Commun., 205, 449-454 (1994); Takanashi et al., J. Pharmacol. Exp. Ther., 273, 624-628 (1995)). These derivatives are used as a pharmacological tool in the study of the action of motilin on the motility of the gastrointestinal tract and in the research and development of medicines in the field of the art contemplated by the invention.

Motilin receptors had been known to occur principally in the duodenum but recently it has been shown that they also occur in the large intestine, or the lower part of the gastrointestinal tract (William et al., Am. J. Physiol., 262, G50-G55 (1992)), and this indicates the possibility that motilin is involved not only in the motility of the upper part of the gastrointestinal tract but also in the motility of its lower part.

Reports have also been made of the cases of hypermotilinemia in patients with irritable bowel syndrome who were manifesting diarrhea and in patients with irritable bowel syndrome who were under stress (Preston et al., Gut, 26, 1059-1064 (1985); Fukudo et al., Tohoku J. Exp. Med., 151, 373-385 (1987)) and this suggests the possibility that increased blood motilin levels are involved in the disease. Other diseases that have been reported to involve hypermotilinemia include crohn's disease, ulcerative colitis, pancreatitis, diabetes mellitus, obesity, malabsorption syndrome, bacterial diarrhea, atrophic gastritis and postgastroenterectomy syndrome. The antagonists of motilin receptors have the potential to ameliorate irritable bowel syndrome and other diseased states accompanied by increased blood motilin levels.

DISCLOSURE OF INVENTION

An object of the present invention is to provide substituted phenethylamine derivatives that function as an antagonist of motilin receptors and which are useful as medicines.

The present inventors conducted repeated intensive studies in an attempt to develop compounds having an outstanding motilin receptor antagonistic action. As a result, they found that substituted phenethylamine derivatives represented by Formula (1) were an excellent antagonist of motilin receptors. The present invention has been accomplished on the basis of this finding.

Thus, the present invention provides compounds of Formula (1):

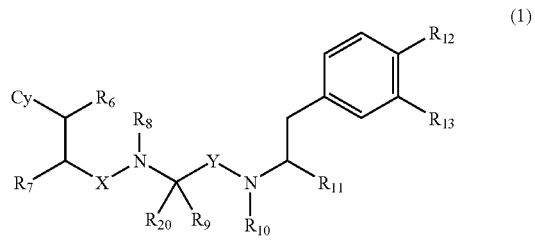

wherein:

Cy is a group of Formula (2):

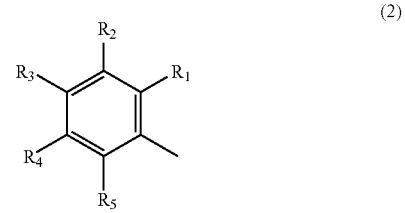

an optionally substituted heterocyclic ring, $C_{3-7}$cycloalkyl or phenyl;

$R_1$, $R_2$, $R_3$, $R_4$ and $R_5$, are hydrogen, halogen, hydroxy, amino, trifluoromethyl or nitrile and at least one of $R_1$, $R_2$, $R_3$, $R_4$ and $R_5$ is halogen, trifluoromethyl or nitrile;

$R_6$ is hydrogen, optionally substituted straight-chained or branched $C_{1-3}$alkyl, amino or hydroxy;

$R_7$ is hydrogen, optionally substituted straight-chained or branched $C_{1-3}$alkyl, optionally substituted amino or hydroxy;

$R_8$ is hydrogen, methyl or ethyl;

$R_9$ is optionally substituted straight-chained or branched $C_{1-6}$alkyl, optionally substituted straight-chained or branched $C_{2-6}$alkenyl, optionally substituted straight-chained or branched $C_{2-6}$alkynyl, $C_{3-7}$cycloalkyl or optionally substituted phenyl;

$R_{20}$ is hydrogen or straight-chained or branched $C_{1-3}$alkyl or $R_9$ and $R_{20}$ may together form $C_{3-7}$cycloalkyl;

$R_{10}$ is hydrogen or straight-chained or branched $C_{1-3}$alkyl;

$R_{11}$ is hydrogen, optionally substituted straight-chained or branched $C_{1-3}$alkyl, —CO—N($R_{14}$)$R_{15}$, carboxyl or an optionally substituted heterocyclic ring;

$R_{12}$ is hydroxy or —$OR_{16}$;

$R_{13}$ is hydrogen, straight-chained or branched $C_{1-6}$alkyl, straight-chained or branched $C_{2-6}$alkenyl, straight-chained or branched $C_{2-6}$alkynyl or a group of Formula (3):

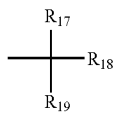

$R_{14}$ and $R_{15}$, which may be the same or different, are hydrogen, optionally substituted straight-chained or branched $C_{1-4}$alkyl, $C_{3-7}$cycloalkyl, straight-chained or branched $C_{1-4}$alkyloxy, straight-chained or branched $C_{1-4}$alkylsulfonyl or a heterocyclic ring, or $R_{14}$ and $R_{15}$, as —N($R_{14}$)$R_{15}$, form optionally substituted 3- to 7-membered cyclic amine;

$R_{16}$ is straight-chained $C_{1-4}$alkyl;
$R_{17}$ is hydrogen or methyl;
$R_{18}$ and $R_{19}$ together form cycloalkyl or $C_{3-7}$cycloalkenyl;
X is carbonyl or methylene;
Y is carbonyl or methylene;

provided that
when Cy is 3-indolyl,
(i) $R_{11}$ is an optionally substituted heterocyclic ring; or
(ii) $R_6$ is hydrogen, $R_7$ is amino, $R_8$ is methyl, $R_9$ is isopropyl, $R_{20}$ is hydrogen, $R_{10}$ is methyl, $R_{11}$ is carbamoyl, $R_{12}$ is hydroxy, $R_{13}$ is tert-butyl, X is carbonyl and Y is carbonyl, and
when Cy is cyclohexyl or phenyl, $R_{11}$ is an optionally substituted heterocyclic ring, or hydrates or pharmaceutically acceptable salts thereof.

The present invention also provides a medicine containing a compound of Formula (1) as an active ingredient. Further, the present invention provides a motilin receptor antagonist composition containing the compound. The present invention also provides a gastrointestinal motility suppressor agent containing the compound as an active ingredient. Further, the present invention provides a therapeutic of hypermotilinemia containing the compound as an active ingredient.

The present invention also provides compounds of Formula (4):

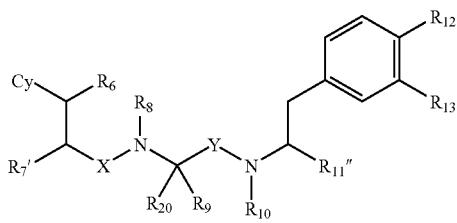

wherein
Cy, $R_6$, $R_8$, $R_9$, $R_{20}$, $R_{10}$, $R_{12}$, $R_{13}$, X and Y are as defined in claim 1;
$R_7'$ is hydrogen, straight-chained or branched $C_{1-3}$alkyl optionally having at least one protected substituent, amino optionally having at least one protected substituent or protected hydroxy;
$R_{11}''$ is hydrogen, optionally substituted straight-chained or branched $C_{1-3}$alkyl, —CO—N($R_{14}$)$R_{15}$, wherein $R_{14}$ and $R_{15}$ are as defined in claim 1, carboxyl, straight-chained or branched $C_{1-3}$alkyl having protected amino or an optionally substituted heterocyclic ring;

or hydrates or pharmaceutically acceptable salts thereof.

The present invention also provides compounds of Formula (5):

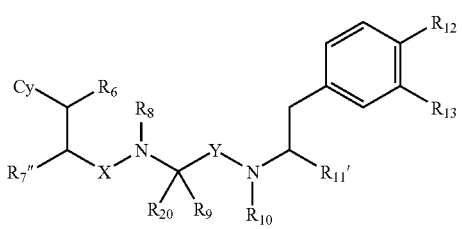

wherein:
Cy, $R_6$, $R_8$, $R_9$, $R_{20}$, $R_{10}$, $R_{12}$, $R_{13}$, X and Y are as defined in claim 1;
$R_7''$ is hydrogen, straight-chained or branched $C_{1-3}$alkyl optionally having at least one optionally protected substituent, amino optionally having at least one optionally protected substituent or optionally protected hydroxy;
$R_{11}'$ is hydrogen, straight-chained or branched $C_{1-3}$alkyl optionally having at least one protected substituent, —CO—N($R_{14}$)$R_{15}$ wherein $R_{14}$ and $R_{15}$ are as defined in claim 1, carboxyl or an optionally substituted heterocyclic ring; or hydrates or pharmaceutically acceptable salts thereof.

The present invention also provides compounds of Formula (6):

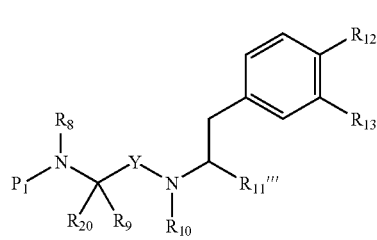

wherein:
$R_8$, $R_9$, $R_{20}$, $R_{10}$, $R_{12}$, $R_{13}$ and Y are as defined in claim 1;
$P_1$ is hydrogen or a protecting group of amine;
$R_{11}'''$ is hydrogen, optionally substituted straight-chained or branched $C_{1-3}$alkyl, —CO—N($R_{14}$)$R_{15}$ wherein $R_{14}$ and $R_{15}$ are as defined in claim 1, carboxyl, straight-chained or branched $C_{1-3}$alkyl having protected amino or an optionally substituted heterocyclic ring;

or hydrates or pharmaceutically acceptable salts thereof.

The present invention also provides compounds of Formula (7):

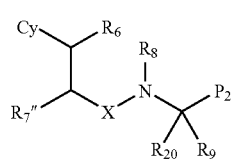

wherein:
Cy, $R_6$, $R_8$, $R_9$, $R_{20}$ and X are as defined in claim 1;

$R_7''$ is hydrogen, straight-chained or branched $C_{1-3}$alkyl optionally having at least one optionally protected substituent, amino optionally having at least one optionally protected substituent or optionally protected hydroxy;

$P_2$ is optionally protected carboxyl, formyl or methyl having a leaving group;

or hydrates or pharmaceutically acceptable salts thereof.

The present invention also provides compounds of Formula (8)

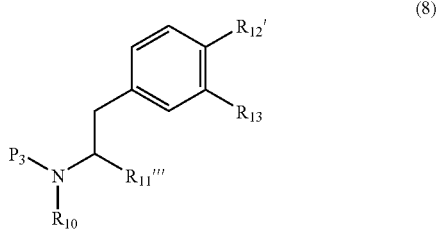

(8)

wherein:

$R_{10}$ and $R_{13}$ are as defined in claim 1;

$P_3$ is hydrogen or a protecting group of amine;

$R_{11}''''$ is hydrogen, optionally substituted straight-chained or branched $C_{1-3}$alkyl, —CO—N($R_{14}$)$R_{15}$ wherein $R_{14}$ and $R_{15}$ are as defined in claim 1, carboxyl, straight-chained or branched $C_{1-3}$alkyl having protected amino or an optionally substituted heterocyclic ring;

$R_{12}'$ is hydroxy or —O$R_{16}$, wherein $R_{16}$ is as defined in claim 1;

or hydrates or pharmaceutically acceptable salts thereof.

The present invention also provides compounds of Formula (9)

(9)

wherein:

Cy and $R_6$ are as defined in claim 1;

$R_7''$ is hydrogen, straight-chained or branched $C_{1-3}$alkyl optionally having at least one optionally protected substituent, amino optionally having at least one optionally protected substituent or optionally protected hydroxy;

$P_4$ is optionally protected carboxyl, formyl or methyl having a leaving group;

or hydrates or pharmaceutically acceptable salts thereof.

The present invention also provides compounds of Formula (10)

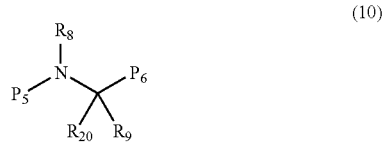

(10)

wherein:

$R_8$, $R_9$ and $R_{20}$ are as defined in claim 1;

$P_5$ is hydrogen or a protecting group of amine;

$P_6$ is optionally protected carboxyl, formyl or methyl having a leaving group;

or hydrates or pharmaceutically acceptable salts thereof.

In the definition of the compounds of Formula (1), halogen as $R_1$, $R_2$, $R_3$, $R_4$ and $R_5$ of Formula (2) as Cy is preferably fluorine or chlorine, with fluorine being more preferred. When at least 2 of $R_1$ to $R_5$ are halogen, they may be the same or different halogen, however it is preferable that they are the same. The number of halogen atoms is preferably 1 to 3 and more preferably 1 or 2.

Preferably, at least one of $R_1$, $R_2$, $R_3$, $R_4$ and $R_5$ of Formula (2) as Cy is halogen, trifluoromethyl or nitrile and the others are independently hydrogen or hydroxy. Preferably, $R_3$ is halogen, trifluoromethyl or nitrile or $R_2$ and $R_3$ are the same kind of halogen. Preferred compounds include those in which $R_3$ is halogen and $R_1$, $R_2$, $R_4$ and $R_5$ are hydrogen; those in which $R_2$ and $R_3$ are the same halogen and $R_1$, $R_4$ and $R_5$ are hydrogen; and those in which at least one of $R_1$, $R_2$, $R_3$, $R_4$ and $R_5$ is trifluoromethyl or nitrile and the others are hydrogen, halogen or hydroxy.

Preferred examples of the group of Formula (2) as Cy include 4-fluorophenyl, 3-fluorophenyl, 3,4-difluorophenyl, 4-chlorophenyl, 3-chlorophenyl, 3,4-dichlorophenyl, 2-fluoro-4-hydroxyphenyl, 3-fluoro-4-hydroxyphenyl, 4-trifluoromethylphenyl and 4-cyanophenyl, more preferably 4-fluorophenyl and 4-chlorophenyl, with 4-fluorophenyl being most preferred.

Preferred examples of the heterocyclic ring of the optionally substituted heterocyclic ring as Cy include aliphatic or aromatic 5- to 7-membered mono- or fused-rings containing at least one hetero atom selected from among N, S and O; specific examples include pyridyl, pyrazinyl, furyl, thienyl, pyrrolyl, imidazolyl, indolyl, quinolinyl, benzoimidazolyl, benzodiazepinyl, benzofuryl, pyrrolidinyl, piperazinyl, piperidinyl and tetrahydroisoquinolinyl, with indolyl being preferred.

Exemplary substituents of the optionally substituted heterocyclic ring as Cy include hydroxy, methoxy, amino, methyl, ethyl, trifluoromethyl, carboxy, methoxycarbonyl and oxo. The heterocyclic ring may have one or more of the above-mentioned substituents, which may be the same or different.

Preferably, the optionally substituted heterocyclic ring of Cy is 3-indolyl.

Preferably, the $C_{3-7}$cycloalkyl as Cy is cyclopentyl or cyclohexyl.

While Cy has the definitions set forth above, Cy is preferably Formula (2) or an optionally substituted heterocyclic ring, more preferably 4-fluorophenyl, 3-fluorophenyl, 3,4-difluorophenyl, 4-chlorophenyl, 3-chlorophenyl, 3,4-dichlorophenyl, 2-fluoro-4-hydroxyphenyl, 3-fluoro-4-hydroxyphenyl, 4-trifluoromethylphenyl, 4-cyanophenyl and 3-indolyl, with 4-fluorophenyl being particularly preferred.

The alkyl of the optionally substituted straight-chained or branched $C_{1-3}$alkyl as $R_6$ is preferably methyl or ethyl.

Exemplary substituents of the optionally substituted straight-chained or branched $C_{1-3}$alkyl as $R_6$ include halogen, with fluorine being preferred. The alkyl may have one or more of the above-mentioned substituents, which may be the same or different.

The optionally substituted straight-chained or branched $C_{1-3}$alkyl as $R_6$ is preferably methyl, ethyl, fluoromethyl or trifluoromethyl, with methyl being particularly preferred.

While $R_6$ has the definitions set forth above, $R_6$ is preferably hydrogen or methyl.

The alkyl of the optionally substituted straight-chained or branched $C_{1-3}$alkyl as $R_7$ is preferably methyl.

Exemplary substituents of the optionally substituted straight-chained or branched $C_{1-3}$alkyl as $R_7$ include halogen, hydroxy and amino, with hydroxy being preferred. The alkyl may have one or more of the above-mentioned substituents, which may be the same or different.

The optionally substituted straight-chained or branched $C_{1-3}$alkyl as $R_7$ is preferably methyl or trifluoromethyl, with methyl being particularly preferred.

Exemplary substituents of the optionally substituted amino as $R_7$ include straight-chained or branched $C_{1-3}$alkyl, with methyl and ethyl being preferred. The amino may have one or more of the above-mentioned substituents, which may be the same or different.

The optionally substituted amino as $R_7$ is preferably amino optionally substituted with one or more of the same or different kinds of straight-chained or branched $C_{1-3}$alkyl; specific examples include amino, methylamino, dimethylamino and ethylamino, with amino and methylamino being particularly preferred.

While $R_7$ has the definitions set forth above, $R_7$ is preferably hydrogen or optionally substituted amino, with hydrogen, amino and methylamino being particularly preferred.

$R_8$ is preferably hydrogen or methyl.

The alkyl of the optionally substituted straight-chained or branched $C_{1-6}$alkyl as $R_9$ is preferably straight-chained or branched $C_{1-5}$alkyl, e.g., methyl, ethyl, isopropyl, isobutyl, sec-butyl, tert-butyl, 3-pentyl and neopentyl.

Exemplary substituents of the optionally substituted straight-chained or branched $C_{1-6}$alkyl as $R_9$ include substituted or unsubstituted phenyl (e.g., phenyl, tolyl, para-hydroxyphenyl and para-fluorophenyl), $C_{3-7}$cycloalkyl, heterocyclic rings (e.g., pyrazyl, furyl, thienyl, pyrrolyl, imidazolyl and quinolinyl) and halogen, with phenyl, cyclohexyl and thienyl being preferred.

The optionally substituted straight-chained or branched $C_{1-6}$alkyl as $R_9$ is preferably methyl, isopropyl, isobutyl, sec-butyl, tert-butyl, 3-pentyl, neopentyl, para-fluorobenzyl, 2-thienylmethyl, 3-indolylmethyl, benzyl, para-hydroxybenzyl, phenethyl or cyclohexylmethyl.

The alkenyl of the optionally substituted straight-chained or branched $C_{2-6}$alkenyl as $R_9$ is preferably vinyl, 2-propenyl, 2-propen-1-yl, 2-buten-1-yl or 2-isobuten-1-yl, with 2-propen-1-yl being more preferred.

Exemplary substituents of the optionally substituted straight-chained or branched $C_{2-6}$alkenyl as $R_9$ include phenyl, tolyl, para-hydroxyphenyl and para-fluorophenyl.

The optionally substituted straight-chained or branched $C_{2-6}$alkenyl as $R_9$ is preferably 2-propen-1-yl.

The alkynyl of the optionally substituted straight-chained or branched $C_{2-6}$alkynyl as $R_9$ is preferably ethynyl, propargyl or 2-butyn-1-yl, with 2-butyn-1-yl being preferred.

Exemplary substituents of the optionally substituted straight-chained or branched $C_{2-6}$alkynyl as $R_9$ include halogen, phenyl, tolyl, para-hydroxyphenyl and para-fluorophenyl.

The optionally substituted straight-chained or branched $C_{2-6}$alkynyl as $R_9$ is preferably 2-butyn-1-yl.

The $C_{3-7}$cycloalkyl as $R_9$ is preferably cyclopentyl or cyclohexyl.

Exemplary substituents of the optionally substituted phenyl as $R_9$ include hydroxy, amino, methyl, ethyl and halogen. The phenyl may have one or more of the above-mentioned substituents, which may be the same or different.

The optionally substituted phenyl as $R_9$ is preferably phenyl.

The $C_{3-7}$cycloalkyl formed by $R_9$ and $R_{20}$ is preferably cyclopentyl or cyclohexyl.

While $R_9$ has the definitions set forth above, $R_9$ is preferably isopropyl, isobutyl, sec-butyl, tert-butyl, 3-pentyl, neopentyl, cyclohexyl, 2-thienylmethyl, 3-indolylmethyl, phenyl, benzyl, para-hydroxybenzyl, para-fluorobenzyl or cyclohexylmethyl, with isopropyl being particularly preferred.

The straight-chained or branched $C_{1-3}$alkyl as $R_{20}$ is preferably methyl.

$R_{20}$ is preferably hydrogen.

$R_{10}$ is preferably hydrogen or methyl.

The alkyl of the optionally substituted straight-chained or branched $C_{1-3}$alkyl as $R_{11}$ is preferably methyl.

Exemplary substituents of the optionally substituted straight-chained or branched $C_{1-3}$alkyl as $R_{11}$ include amino optionally substituted with one or more of the same or different kind of straight-chained or branched $C_{1-3}$alkyl (e.g., amino, methylamino, dimethylamino and ethylamino), optionally substituted 3- to 7-membered cyclic amino (exemplary substituents of the cyclic amino include hydroxy, amino, carboxyl, carbamoyl and methyl), hydroxy, methoxy, halogen, carbamoyl, methanesulfonyl, ureide, guanidyl, N'-cyano-N''-methylguanidyl, sulfamoylamino, carbamoylmethylamino and methanesulfonylamino, with amino, hydroxy, carbamoyl, methanesulfonyl, ureide, sulfamoylamino, methanesulfonylamino and carbamoylmethylamino being preferred. The alkyl may have one or more of the above-mentioned substituents, which may be the same or different.

The optionally substituted straight-chained or branched $C_{1-3}$alkyl as $R_{11}$ is preferably methyl, aminomethyl, hydroxymethyl, carbamoylmethyl, methanesulfonylmethyl, ureidemethyl, guanidylmethyl, sulfamoylaminomethyl or methanesulfonylaminomethyl, with methyl, hydroxymethyl and methanesulfonylmethyl being more preferred.

The alkyl of the optionally substituted straight-chained or branched $C_{1-4}$alkyl as $R_{14}$ and $R_{15}$ of —CO—N($R_{14}$)$R_{15}$ as $R_{11}$ is preferably methyl, ethyl, propyl, isopropyl, isobutyl, sec-butyl or tert-butyl, with methyl and ethyl being more preferred.

Exemplary substituents of the optionally substituted straight-chained or branched $C_{1-4}$alkyl as $R_{14}$ and $R_{15}$ in —CO—N($R_{14}$)$R_{15}$ as $R_{11}$ include optionally substituted straight-chained or branched $C_{1-3}$alkoxy (exemplary substituents of the optionally substituted straight-chained or branched $C_{1-3}$alkoxy include hydroxy, amino, carboxyl and carbamoyl), hydroxy, amino, methylamino, dimethylamino, carbamoyl and methanesulfonyl, with hydroxy, methoxy and methanesulfonyl being preferred.

Examples of the optionally substituted straight-chained or branched $C_{1-4}$alkyl as $R_{14}$ and $R_{15}$ in —CO—N($R_{14}$)$R_{15}$ as $R_{11}$ include methyl, ethyl, propyl, isopropyl, tert-butyl, hydroxymethyl, methoxymethyl, 2-hydroxyethyl, 2-aminoethyl, 2-hydroxy-2-methylpropyl, 2-hydroxy-2-methylpropyl, 2-amino-2-methylpropyl and methanesulfonylmethyl, with methyl, ethyl, propyl, isopropyl, tert-butyl, hydroxymethyl, methoxymethyl and methanesulfonylmethyl being preferred.

The $C_{3-7}$cycloalkyl as $R_{14}$ and $R_{15}$ in —CO—N($R_{14}$)$R_{15}$ as $R_{11}$ is preferably cyclopropyl.

The straight-chained or branched $C_{1-4}$alkyloxy as $R_{14}$ and $R_{15}$ in —CO—N($R_{14}$)$R_{15}$ as $R_{11}$ is preferably methoxy.

The straight-chained or branched $C_{1-4}$alkylsulfonyl as $R_{14}$ and $R_{15}$ in —CO—N($R_{14}$)$R_{15}$ as $R_{11}$ is preferably methanesulfonyl.

Examples of the heterocyclic ring as $R_{14}$ and $R_{15}$ in —CO—N($R_{14}$)$R_{15}$ as $R_{11}$ include aliphatic or aromatic 5- or 6-membered rings containing at least one hetero atom selected from among N, S and O; specific examples include 2-pyridyl, 3-pyridyl, 4-pyridyl, pyrazinyl, furyl, thienyl, pyrrolyl, oxazolyl, thiazolyl, oxadiazolyl, thiadiazolyl and triazolyl, with 2-pyridyl being preferred.

The 3- to 7-membered cyclic amine of the optionally substituted 3- to 7-membered cyclic amine as —N($R_{14}$)$R_{15}$ as $R_{11}$ include aziridine, azetidine, pyrrolidine, piperidine, piperazine and morpholine, with piperazine and morpholine being preferred. Exemplary substituents of the optionally substituted 3- to 7-membered cyclic amine include hydroxy, amino, carboxyl, alkoxycarbonyl, carbamoyl, methyl, carboxymethyl, alkoxycarbonylmethyl and methylsulfonyl.

The optionally substituted 3- to 7-membered cyclic amine as —N($R_{14}$)$R_{15}$ of —CO—N($R_{14}$)$R_{15}$ as $R_{11}$ is preferably 4-carboxymethylpiperazine, 4-ethoxycarbonylpiperazine, 4-methylsulfonylpiperazine or morpholine.

The —CO—N($R_{14}$)$R_{15}$ as $R_{11}$ is preferably carbamoyl, methylcarbamoyl, ethylcarbamoyl, propylcarbamoyl, isopropylcarbamoyl, cyclopropylcarbamoyl, tert-butylcarbamoyl, 2-pyridylcarbamoyl, methanesulfonylmethylcarbamoyl, 4-ethoxycarbonylmethyl-1-piperazinecarbonyl, methoxymethylcarbamoyl, methoxycarbamoyl, 1-morpholinylcarbonyl, 4-carboxymethyl-1-piperazinecarbonyl and 4-methylsulfonyl-1-piperazinecarbonyl, with carbamoyl and ethylcarbamoyl being more preferred.

Examples of the heterocyclic ring of the optionally substituted heterocyclic ring as $R_{11}$ include aliphatic or aromatic 5- or 6-membered rings containing at least one hetero atom selected from among N, S and O. Exemplary substituents of the heterocyclic ring include oxo, hydroxy, methyl, ethyl and trifluoromethyl; the heterocyclic ring may have one or more of the above-mentioned substituents, which may be the same or different. Specific examples of the optionally substituted heterocyclic ring include furyl, thienyl, pyrrolyl, oxazolyl, 2-thiazolyl, 1,3,4-oxadiazol-2-yl, 1,2,4-oxadiazol-5-yl, 1,3,4-thiadiazol-2-yl, 1,3,4-triazol-2-yl, tetrazolyl, pyridyl, pyrimidinyl, pyridazinyl, pyrazinyl, 4-pyrimidinon-2-yl, 6-methyl-4-pyrimidinon-2-yl and imidazolidine-2,4-dion-5-yl, with 2-thiazolyl, 1,3,4-oxadiazol-2-yl, 1,2,4-oxadiazol-5-yl, 1,3,4-triazol-2-yl and 6-methyl-4-pyrimidino-2-yl being preferred.

While $R_{11}$ has the definitions set forth above, $R_{11}$ is preferably methyl, hydroxymethyl, carbamoylmethyl, methanesulfonylmethyl, ureidemethyl, sulfamoylaminomethyl, methanesulfonylaminomethyl, carbamoyl, methylcarbamoyl, ethylcarbamoyl, propylcarbamoyl, isopropylcarbamoyl, cyclopropylcarbamoyl, tert-butylcarbamoyl, 2-pyridylcarbamoyl, methanesulfonylmethylcarbamoyl, 4-ethoxycarbonylmethyl-1-piperazinecarbonyl, methoxymethylcarbamoyl, methoxycarbamoyl, 1-morpholinylcarbonyl, 4-carboxymethyl-1-piperazinecarbonyl, 4-methylsulfonyl-1-piperazinecarbonyl, 2-thiazolyl, 1,3,4-oxadiazol-2-yl, 1,2,4-oxadiazol-5-yl, 1,3,4-triazol-2-yl and 6-methyl-4-pyrimidinon-2-yl, with carbamoyl and ethylcarbamoyl being more preferred.

The straight-chained $C_{1-4}$alkyl as $R_{16}$ of —$OR_{16}$ as $R_{12}$ is preferably methyl.

$R_{12}$ is preferably hydroxy.

The straight-chained or branched $C_{1-6}$alkyl as $R_{13}$ is preferably straight-chained or branched $C_{2-5}$alkyl, more preferably branched $C_{3-5}$alkyl, and most preferably tert-butyl.

The straight-chained or branched $C_{2-6}$alkenyl as $R_{13}$ is preferably straight-chained or branched $C_{3-5}$alkenyl and more preferably branched $C_{3-5}$alkenyl.

The straight-chained or branched $C_{2-6}$alkynyl as $R_{13}$ is preferably straight-chained or branched $C_{3-5}$alkynyl and more preferably branched $C_{3-5}$alkynyl.

$R_{17}$ in Formula (3) as $R_{13}$ is preferably methyl.

The $C_{3-7}$cycloalkyl formed by $R_{18}$ and $R_{19}$ in Formula (3) as $R_{13}$ is preferably $C_{3-5}$cycloalkyl.

The $C_{3-7}$ cycloalkenyl formed by $R_{18}$ and $R_{19}$ in Formula (3) as $R_{13}$ is preferably $C_{3-5}$cycloalkenyl.

While $R_{13}$ has the definitions set forth above, $R_{13}$ is preferably isopropyl, tert-butyl, 1,1-dimethylpropyl and 1,1-dimethyl-2-propenyl, with tert-butyl being more preferred.

X is preferably carbonyl or methylene.

Y is preferably carbonyl or methylene.

Examples of compounds of Formula (1)

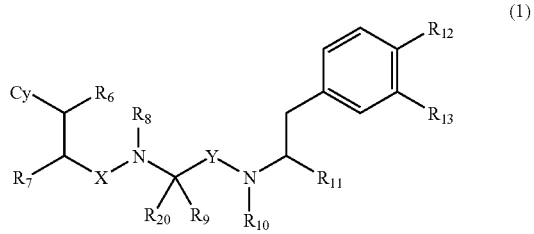

(1)

wherein:

Cy, $R_6$, $R_7$, $R_8$, $R_9$, $R_{20}$, $R_{10}$, $R_{11}$, $R_{12}$, $R_{13}$, X and Y are as defined as above include those compounds of which Cy is a group of Formula (2) in which at least one of $R_1$, $R_2$, $R_3$, $R_4$ and $R_5$ is halogen and the others are hydrogen or hydroxy; $R_6$ is hydrogen or methyl; $R_7$ is hydrogen or optionally substituted amino; $R_8$ is hydrogen or methyl; $R_9$ is methyl, isopropyl, isobutyl, sec-butyl, tert-butyl, 3-pentyl, neopentyl, cyclohexyl, phenyl, benzyl, para-hydroxybenzyl, para-fluorobenzyl or cyclohexylmethyl; $R_{20}$ is hydrogen; $R_{10}$ is hydrogen or methyl; $R_{11}$ is methyl, hydroxymethyl, carbamoylmethyl, methanesulfonylmethyl, ureidemethyl, sulfamoylaminomethyl, methanesulfonylaminomethyl, carbamoyl, methylcarbamoyl, ethylcarbamoyl, n-propylcarbamoyl, isopropylcarbamoyl, cyclopropylcarbamoyl, tert-butylcarbamoyl, 2-pyridylcarbamoyl, methanesulfonylmethylcarbamoyl, methoxymethylcarbamoyl, methoxycarbamoyl, 1-morpholinylcarbonyl, 4-carboxymethyl-1-piperazinecarbonyl, 4-ethoxycarbonylmethyl-1-piperazinecarbonyl, 4-methylsulfonyl-1-piperazinecarbonyl, 2-thiazolyl, 1,3,4-oxadiazol-2-yl, 1,2,4-oxadiazol-5-yl, 1,3,4-triazol-2-yl or 6-methyl-4-pyrimidinon-2-yl; $R_{12}$ is hydroxy; $R_{13}$ is isopropyl, tert-butyl (tBu), 1,1-dimethylpropyl or 1,1-dimethyl-2-propenyl. More preferred compounds are Phe(4-F)-N-Me-Val-N-Me-Tyr(3-tBu)-NH$_2$, Phe(4-Cl)-N-Me-Val-N-Me-Tyr(3-tBu)-NH$_2$, Phe(3,4-F$_2$)-N-Me-Val-N-Me-Tyr(3-tBu)-NH$_2$, Phe(3-F)-N-Me-Val-N-Me-Tyr(3-tBu)-NH$_2$, Phe(4-F)-N-Me-Val-N-Me-Tyr(3-tBu)-NHOMe, 2-((2-amino-3-(4-fluorophenyl)propionyl)-N-methylamino)-3-methylbutyric acid 2-(3-tert-butyl-4-hydroxyphenyl)-1-(2-pyridylcarbamoyl)ethylamide, N-(2-(2-((2-amino-3-(4-fluorophenyl)propionyl)-N-methylamino)-3-methyl-butyrylamino)-3-(3-tBu-4-hydroxyphenyl)propyl)urea, N-(2-(2-(2-amino-3-(4-fluorophenylpropanoyl-N-methylamino)-3-methyl)butyrylamino)-3-(3-tert-butyl-4-hydroxyphenyl)propyl)sulfamide, N-[2-(3-tert-butyl-4-hydroxyphenyl)-1-(methanesulfonylaminomethyl)ethyl]-2-[N-(4-fluorophenylalanynoyl)methylamino]-3-methylbutanamide, 2-((2-amino-3-(4-fluorophenyl)propionyl)-N-methylamino)-3-methylbutyric acid 2-(3-t-butyl-4-hydroxyphenyl)-1-carbamidemethylethylamide, 2-((2-amino-3-(4-fluorophenyl)propionyl)-N-methylamino)-3-methylbutyric acid 2-(3-t-butyl-4-hydroxyphenyl)-1-methanesulfonylmethylethylamide, 2-(2-((2-amino-3-(4-fluorophenyl)propionyl)-N-methylamino)-3-methyl-butyrylamino)-3-(3-tBu-4-hydroxyphenyl)propanol, 2-(1-(2-((2-amino-3-(4-fluorophenyl)propionyl)-N-methylamino)-3-methyl-butyrylamino)-2-(3-tert-butyl-4-hydroxyphenyl)ethyl)-6-methyl-4-pyrimidinone, 2-((2-amino-3-(4-fluorophenyl)propionyl)-N-methylamino)-3-methylbutyric acid 2-(3-t-butyl-4-hydroxyphenyl)-1-(1,3,4-oxadiazol-2-yl)ethylamide, 2-((2-amino-3-(4-fluorophehyl)propionyl)-N-methylamino)-3-methylbutyric acid 2-(3-t-butyl-4-hydroxyphenyl)-1-(1,2,4-oxadiazol-5-yl)ethylamide, 2-((2-amino-3-(4-fluorophenyl)propionyl)-N-methylamino)-3-methylbutyric acid 2-(3-tert-butyl-4-hydroxyphenyl)-1-(thiazol-2-yl)ethylamide, 2-((2-amino-3-(4-fluorophenyl)propionyl)-N-methylamino)-3-methylbutyric acid 2-(3-t-butyl-4-hydroxyphenyl)-1-(1,3,4-triazol-2-yl)ethylamide, Tyr(2-F)-N-Me-Val-N-Me-Tyr(3-tBu)-NH$_2$, Tyr(3-F)-N-Me-Val-N-Me-Tyr(3-tBu)-NH$_2$, Phe(4-F)-N-Me-Val-Tyr(3-tBu)-NH$_2$, N-Me-Phe(4-F)-N-Me-Val-Tyr(3-tBu)-NH$_2$, N-Et-Phe(4-F)-N-Me-Val-Tyr(3-tBu)-NH$_2$, Phe(4-F)-N-Me-Val-Tyr(3-tBu)-NHMe, N-Me-Phe(4-F)-N-Me-Val-Tyr(3-tBu)-NHMe, N-Et-Phe(4-F)-N-Me-Val-Tyr(3-tBu)-NHMe, N-Me-Phe(4-F)-N-Me-Val-N-Me-Tyr(3-tBu)-NH$_2$, N-Et-Phe(4-F)-N-Me-Val-N-Me-Tyr(3-tBu)-NH$_2$. Phe(4-F)-N-Me-Val-N-Me-Tyr(3-tBu)-NHMe, N-Me-Phe(4-F)-N-Me-Val-N-Me-Tyr(3-tBu)-NHMe, N-Et-Phe(4-F)-N-Me-Val-N-Me-Tyr(3-tBu)-NHMe, Phe(4-F)-N-Me-Val-N-Et-Tyr(3-tBu)-NH$_2$, N-Me-Phe(4-F)-N-Me-Val-N-Et-Tyr(3-tBu)-NH$_2$, N-Et-Phe(4-F)-N-Me-Val-N-Et-Tyr(3-tBu)-NH$_2$, Phe(4-F)-N-Me-Val-N-Et-Tyr(3-tBu)-NHMe, N-Me-Phe(4-F)-N-Me-Val-N-Et-Tyr(3-tBu)-NHMe, N-Et-Phe(4-F)-N-Me-Val-N-Et-Tyr(3-tBu)-NHMe, Phe(4-F)-N-Me-Val-Tyr(3-tBu)-NHtBu, Phe(4-F)-N-Me-Val-N-Me-Tyr(3-tBu)-NHCH$_2$SO$_2$CH$_3$, Phe(4-F)-N-Me-Val-Tyr(3-tBu)-NHEt, N-Me-Phe(4-F)-N-Me-Val-Tyr(3-tBu)-NHEt, N-Et-Phe(4-F)-N-Me-Val-Tyr(3-tBu)-NHEt, Phe(4-F)-N-Me-Val-Tyr(3-tBu)-NHCH$_2$OH, N-Me-Phe(4-F)-N-Me-Val-Tyr(3-tBu)-NHCH$_2$OH, N-Et-Phe(4-F)-N-Me-Val-Tyr(3-tBu)-NHCH$_2$OH, Phe(4-F)-N-Me-Val-N-Me-Tyr(3-tBu)-NHEt, N-Me-Phe(4-F)-N-Me-Val-N-Me-Tyr(3-tBu)-NHEt, N-Et-Phe(4-F)-N-Me-Val-N-Me-Tyr(3-tBu)-NHEt, Phe(4-F)-N-Me-Val-N-Me-Tyr(3-tBu)-NHCH$_2$OH, N-Me-Phe(4-F)-N-Me-Val-N-Me-Tyr(3-tBu)-NHCH$_2$OH, N-Et-Phe(4-F)-N-Me-Val-N-Me-Tyr(3-tBu)-NHCH$_2$OH, Phe(4-F)-N-Me-Val-N-Et-Tyr(3-tBu)-NHEt, N-Me-Phe(4-F)-N-Me-Val-N-Et-Tyr(3-tBu)-NHEt, N-Et-Phe(4-F)-N-Me-Val-N-Et-Tyr(3-tBu)-NHEt, Phe(4-F)-N-Me-Val-N-Et-Tyr(3-tBu)-NHCH$_2$OH, N-Me-Phe(4-F)-N-Me-Val-N-Et-Tyr(3-tBu)-NHCH$_2$OH, N-Et-Phe(4-F)-N-Me-Val-N-Et-Tyr(3-tBu)-NHCH$_2$OH, Phe(4-F)-N-Me-Val-N-Me-Tyr(3-tBu)-NHcPr and Phe(4-F)-N-Me-Val-Tyr(3-tBu)-NHnPr Phe(4-F)-N-Me-Val-Tyr(3-tBu)-NHiPr. Particularly preferred compounds are Phe(4-F)-N-Me-Val-N-Me-Tyr(3-tBu)-NH$_2$, Phe(4-Cl)-N-Me-Val-N-Me-Tyr(3-tBu)-NH$_2$, Phe(3,4-F$_2$)-N-Me-Val-N-Me-Tyr(3-tBu)-NH$_2$, N-Me-Phe(4-F)-N-Me-Val-Tyr(3-tBu)-NHEt, 2-((2-amino-3-(4-fluorophenyl)propionyl)-N-methylamino)-3-methylbutyric acid 2-(3-tert-butyl-4-hydroxyphenyl)-1-(2-pyridylcarbamoyl)ethylamide, 2-((2-amino-3-(4-fluorophenyl)propionyl)-N-methylamino)-3-methylbutyric acid 2-(3-t-butyl-4-hydroxyphenyl)-1-methanesulfonylmethylethylamide and 2-(2-((2-amino-3-(4-fluorophenyl)propionyl)-N-methylamino)-3-methyl-butyrylamino)-3-(3-tBu-4-hydroxyphenyl)propanol.

Compounds of Formulae (4) to (10) are useful intermediates for synthesizing the compounds of Formula (1). Various protected functional groups are defined in Formulae (4) to (10); specific examples of protecting groups are shown below:

Examples of the protecting groups of the protected substituent of the straight-chained or branched $C_{1-3}$alkyl as $R_7'$ include those which are known as useful protecting groups of amino or hydroxy; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl, benzyloxymethyl, t-butyl and tetrahydropyranyl. Examples of the protecting groups of the protected substituent of the amino as $R_7'$ include those which are known as useful protecting groups of amino; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl and benzyloxymethyl. Examples of the protecting groups of the protected hydroxy include those which are known as useful protecting groups of hydroxy; specific examples are benzyloxycarbonyl, t-butoxycarbonyl, 9-fluorenylmethyloxycarbonyl, allyloxycarbonyl, benzoyl, acetyl, trifluoroacetyl, trimethylsilyl, t-butyldimethylsilyl, benzyl, benzyloxymethyl, t-butyl and tetrahydropyranyl.

Examples of the protecting groups of the protected amino of the straight-chained or branched $C_{1-3}$alkyl as $R_{11}"$ include those which are known as useful protecting groups of amino; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl and benzyloxymethyl.

Examples of the protecting groups of the optionally protected substituent of the straight-chained or branched $C_{1-3}$alkyl as $R_7"$ include those which are known as useful protecting groups of amino or hydroxy; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl, benzyloxymethyl, t-butyl and tetrahydropyranyl. Examples of the protecting groups of the optionally protected substituent of the amino as $R_7"$ include those which are known as useful protecting groups of amino; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl and benzyloxymethyl. Examples of the protecting groups of the optionally protected hydroxy as $R_7"$ include those which are known as useful protecting groups of hydroxy; specific examples are benzyloxycarbonyl, t-butoxycarbonyl, 9-fluorenylmethyloxycarbonyl, allyloxycarbonyl, benzoyl, acetyl, trifluoroacetyl, trimethylsilyl, t-butyldimethylsilyl, benzyl, benzyloxymethyl, t-butyl and tetrahydropyranyl.

Examples of the protecting groups of the protected substituent of the straight-chained or, branched $C_{1-3}$alkyl as $R_{11}'$ include those which are known as useful protecting groups of amino or hydroxy; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl, benzyloxymethyl, t-butyl and tetrahydropyranyl.

Examples of the protecting groups of amine as $P_1$ include those which are known as useful protecting groups of amino; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl and benzyloxymethyl.

Examples of the protecting groups of the protected amino of the straight-chained or branched $C_{1-3}$alkyl as $R_{11}'''$ include those which are known as useful protecting groups of amino; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl and benzyloxymethyl.

Examples of the protecting groups of the optionally protected carboxyl as $P_2$ include those which are known as useful protecting groups of carboxyl; specific examples are methyl, ethyl, t-butyl, allyl, benzyl, 2,2,2-trichloroethyl, trimethylsilyl and t-butyldimethylsilyl.

Examples of the protecting groups of amine as $P_3$ include those which are known as useful protecting groups of amino; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl and benzyloxymethyl.

Examples of the protecting groups of the protected amino of the straight-chained or branched $C_{1-3}$alkyl as $R_{11}''''$ include those which are known as useful protecting groups of amino; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl and benzyloxymethyl.

Examples of the protecting groups of the optionally protected carboxyl as $P_4$ include those which are known as useful protecting groups of carboxyl; specific examples are methyl, ethyl, t-butyl, allyl, benzyl, 2,2,2-trichloroethyl, trimethylsilyl and t-butyldimethylsilyl.

Examples of the protecting groups of amine as $P_5$ include those which are known as useful protecting groups of amino; specific examples are benzyloxycarbonyl, t-butoxycarbonyl, 9-fluorenylmethyloxycarbonyl, allyloxycarbonyl, benzoyl, acetyl, trifluoroacetyl, benzenesulfonyl, p-toluenesulfonyl, trimethylsilyl, t-butyldimethylsilyl, benzyl and benzyloxymethyl.

Examples of the protecting groups of the optionally protected carboxyl as $P_6$ include those which are known as useful protecting groups of carboxyl; specific examples are methyl, ethyl, t-butyl, allyl, benzyl, 2,2,2-trichloroethyl, trimethylsilyl and t-butyldimethylsilyl.

Salt-forming acids include inorganic acids such as hydrochloric acid, hydrobromic acid, hydroiodic acid, sulfuric acid and phosphoric acid, as well as organic acids such as acetic acid, oxalic acid, maleic acid, fumaric acid, citric acid, succinic acid, tartaric acid, methanesulfonic acid and trifluoroacetic acid.

The compounds of the present invention can occur as optical isomers and the respective optical isomers and mixtures thereof are all included within the scope of the invention.

The compounds of the present invention can also be obtained as hydrates.

The subject application claims priority on the basis of Japanese Patent Application Nos. 11-20523 and 11-283163 all disclosures in their specification shall be incorporated herein by reference.

On the pages that follow, the present invention is described more specifically and the amino acids that constitute peptides, the amino acids protected by protecting groups, the protecting groups, reagents and solvents are represented by the following abbreviations: Val: valine, Phe: phenylalanine, Tyr: tyrosine, Z: benzyloxycarbonyl, Boc: tert-butoxycarbonyl, CMPI: 2-chloro-1-methylpyridinium iodide, PyCIU: chloro-N,N,N',N'-bis(tetramethylene)formamidinium hexafluorophosphate, DIC: N,N'-diisopropylcarbodiimide, HOBT: 1-hydroxylbenzotriazole monohydrate, NMM: N-methylmorpholine, TEA: triethylamine, DIEA: diisopropylethylamine, TFA: trifluoroacetic acid, THF: tetrahydrofuran, DMF: N,N-dimethylformamide, CH: chloroform, MC: methylene chloride, M: methanol, N: concentrated aqueous ammonia, EA: ethyl acetate, H and nHx: n-hexane and ACT: acetone.

BEST MODE FOR CARRYING OUT THE INVENTION

The compounds of Formula (1)

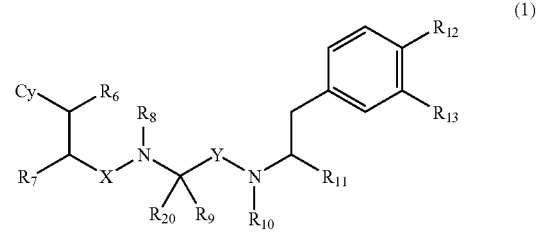

wherein Cy, $R_6$, $R_7$, $R_8$, $R_9$, $R_{20}$, $R_{10}$, $R_{11}$, $R_{12}$, $R_{13}$, X and Y are as defined above can basically be produced by binding Compound (1), Compound (II) and Compound (III), which are represented by the following formulae and in which functional groups other than those involved in bond formation are protected as required:

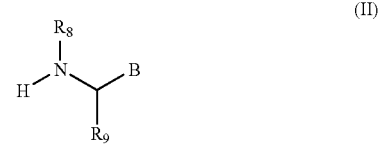

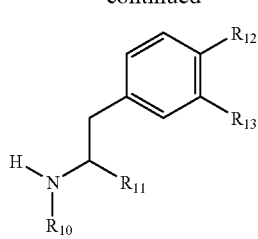 (III)

A and B in Formulae (I) to (III) are functional groups which can form a bond by the reaction with amino; specific examples are carboxyl, formyl, halomethylene of which halogen is chlorine, bromine or iodine, and sulfonyloxymethylene of which sulfonyl is methanesulfonyl, trifluoromethanesulfonyl, paratoluenesulfonyl and the like. $R_1$ to $R_{10}$, $R_{12}$ and $R_{13}$ are as defined above, provided that when they are reactive groups such as amino, hydroxy or carboxyl, they are protected by normally used appropriate protecting groups, if desired. $R_{11}$ is as defined above or is a functional group which is convertible to one of the above defined groups.

The compounds of Formula (1) may be produced by first binding Compound (II) and Compound (III), optionally followed by deprotection, and then binding the resultant compound with Compound (i), optionally followed by deprotection or conversion of the functional group(s). Alternatively, the compound of Formula (1) may be produced by first binding Compound (I) and Compound (II), optionally followed by deprotection, and then binding the resultant compound with Compound (III), optionally followed by deprotection or conversion of the functional group(s).

The compounds of the present invention may be produced by either the solid-phase process or the liquid-phase process. In the production by the solid-phase process, an automatic organic synthesizer can be used but it may be replaced by the manual procedure.

Almost all amino acids that are used for the production of the compounds of the present invention are commercially available and readily purchasable. Those which are not commercially available can be produced by well-known established methods such as the Strecker synthesis, the Bucherer method, the acetamido malonic ester method, the method of alkylating an amino group protected glycine ester and the Z-α-phosphonoglycine trimethylester method.

Compound (I), if it has a functional group such as amino and hydroxy, with the functional group being protected, is carboxylic acid (A is —$CO_2H$), aldehyde (A is —CHO), alkylhalide (A is —$CH_2$-Hal), sulfonate (A is —$CH_2$—$OSO_2R$) or the like. In this case, bond can be formed by reacting A of Compound (I) with the amino group of Compound (II).

Compound (II) can, in almost all cases, be derived from an α-amino acid and B is carboxyl (—$CO_2H$), formyl (—CHO), halomethyl (—$CH_2$-Hal), sulfonyloxymethyl ($RSO_2O$—$CH_2$—) or the like. The amino group of Compound (II) is reacted with A of Compound (I) to form bond and B of Compound (II) is reacted with the amino group of Compound (III) to form bond.

Compound (III) is an ethylamine derivative and can be generally derived from an amino acid. The amino group of Compound (III) is reacted with B of Compound (II) to form bond.

When A or B is carboxyl, various methods known in peptide synthesis may be used to activate the carboxyl for condensation with the amino group and such methods include the use of benzotriazol-1-yl-oxy-tris(dimethylamino)phosphonium hexafluorophosphate (BOP), the use of PyClU, the use of bromo tripyrrolidino phosphonium hexafluorophosphate (PyBrop), the use of chlorotripyrrolidino phosphonium hexafluorophosphate (PyClop), the use of O-(7-azabenzotriazol-1-yl)-1,1,3,3-tetramethyluronium hexafluorophosphate (HATU), the use of DIC, the use of N-ethyl-N'-3-dimethylaminopropyl carbodilmide (WSCI), the use of dicyclohexyl carbodiimide (DCC), the use of diphenylphosphorylazide (DPPA), the use of CMPI, the use of 2-bromo-1-methylpyridinium iodide (BMPI), the combination of one of these reagents with HOBT or N-hydroxysuccinimide (HONSu), the mixed acid anhydride method using isobutyl chloroformate or the like, the method of changing the carboxyl group to a pentafluorophenyl ester (OPfp), a p-nitrophenyl ester (ONP) or an N-hydroxysuccinimide ester (OSu), and the combination of one of these methods with HOBT. If necessary, a base such as TEA, DIEA, NMM or 4-dimethylaminopyridine (DMAP) may be added to accelerate the reaction.

When A or B is formyl, bond can be formed by conventional reductive bond forming reaction with amino group. When A or B is halomethylene or sulfonyloxymethylene, bond can be formed by substitution reaction with amino group.

The compounds of the present invention can also be produced by applying the specific methods of production to be described in the following Examples.

On the pages that follow, the production of the compounds of the invention is described more specifically by reference to Examples, to which the invention is by no means limited.

In order to demonstrate the utility of the compounds of the invention, typical examples of them were subjected to pharmacological tests on the motilin receptor antagonistic action and the results are described under Test Examples. The chemical structural formulae or chemical names of the compounds produced in Examples are set forth in Tables A-1 to A-10 and Tables B-1 to B-18.

TABLE A-1

| Example No. | Structural formula or chemical name |
|---|---|
| 1 | Phe(4-F)-N-Me-Val-N-Me-Tyr(3-tBu)-$NH_2$ |
| 2 | Phe(4-Cl)-N-Me-Val-N-Me-Tyr(3-tBu)-$NH_2$ |
| 3 | Phe(3,4-$F_2$)-N-Me-Val-N-Me-Tyr(3-tBu)-$NH_2$ |
| 4 | Phe(3-F)-N-Me-Val-N-Me-Tyr(3-tBu)-$NH_2$ |
| 5 | Phe(2-F)-N-Me-Val-N-Me-Tyr(3-tBu)-$NH_2$ |
| 6 | Phe(4-F)-N-Me-Val-N-Me-Tyr(3-tBu)-$NHSO_2Me$ TFAsalt |
| 7 | Phe(4-F)-N-Me-Val-N-Me-Tyr(3-tBu)-NHOMe |
| 8 | 2-((2-amino-3-(4-fluorophenyl)propionyl)-N-methylamino)-3-methylbutyric 2-(3-tertbutyl-4-hydroxyphenyl)-1-(2-pyridylcarbamoyl)ethylamide |
| 9 | N-(2-(2-((2-amino-3-(4-fluorophenyl)propionyl)-N-methylamino)-3-methyl-butyrylamino)-3-(3-tBu-4-hydroxyphenyl)propyl)urea |
| 10 | N-(2-(2-((2-amino-3-(4-fluorophenyl)propionyl)-N-methylamino)-3-methyl-butyrylamino)-3-(3-tBu-4-hydroxyphenyl)propyl)guanidine |
| 11 | N-(2-(2-((2-amino-3-(4-fluorophenyl)propionyl)-N-methylamino)-3- methyl-butyrylamino)-3-(3-tBu-4-hydroxyphenyl)propyl)-N'-cyano-N"-methylguanidine |
| 12 | 2-(2-(2-amino-3-(4-fluorophenylpropanoyl-N-methylamino)-3-methyl)butyrylamino)-3-(3-tertbutyl-4-hydroxyphenyl)propylsulfamide |

TABLE A-2

| Example No. | Structural formula or chemical name |
|---|---|
| 13 | 2-(2-(2-amino-3-(4-fluorophenylpropanoyl-N-methylamino)-3-methyl)butyrylamino)-3-(3-tertbutyl-4-hydroxyphenyl)propylaminoacetamide |
| 14 | N-[2-(3-tertbutyl-4-hydroxyphenyl)-1-(methanesulfonylaminomethyl)ethyl]-2-[N-(4-fluorophenylalaninoyl)methylamino]-3-methylbutanamide |
| 15 | 2-((2-amino-3-(4-fluorophenyl)propionyl)-N-methylamino)-3-methylbutyric acid 2-(3-t-butyl-4-hydroxyphenyl)-1-carbamidemethylethylamide |
| 16 | 2-((2-amino-3-(4-fluorophenyl)propionyl)-N-methylamino)-3-methylbutyric acid 2-(3-t-butyl-4-hydroxyphenyl)-1-methanesulfonylmethylethylamide |
| 17 | 2-(2-((2-amino-3-(4-fluorophenyl)propionyl)-N-methylamino)-3-methyl-butyrylamino)-3-(3-tBu-4-hydroxyphenyl)propanol |
| 18 | (2-(2-(2-amino-3-(4-fluorophenyl)propylamino)-3-methyl-butyrylamino)-3-(3-tBu-4-hydroxyphenyl)propyl)-methylsulfone |
| 19 | 2-(1-(2-((2-amino-3-(4-fluorophenyl)propionyl)-N-methylamino)-3-methyl-butyrylamino)-2-(3-tertbutyl-4-hydroxyphenyl)ethyl)-6-methyl-4-pyrimidinone |
| 20 | 5-(1-(2-((2-amino-3-(4-fluorophenyl)propanoyl)-N-methylamino)-3-methylbutyrylamino)-2-(3-tertbutyl-4-hydroxyphenyl)ethyl)imidazolidine-2,4-dione |
| 21 | 2-((2-amino-3-(4-fluorophenyl)propionyl)-N-methylamino)-3-methylbutyric acid 2-(3-t-butyl-4-hydroxyphenyl)-1-(1,3,4-oxadiazol-2-yl)ethylamide |

TABLE A-3

| Example No. | Structural formula or chemical name |
|---|---|
| 22 | 2-((2-amino-3-(4-fluorophenyl)propionyl)-N-methylamino)-3-methylbutyric acid 2-(3-t-butyl-4-hydroxyphenyl)-1-(1,2,4-oxadiazol-5-yl)ethylamide |
| 23 | 2-((2-amino-3-(4-fluorophenyl)propionyl)-N-methylamino)-3-methylbutyric acid 2-(3-tertbutyl-4-hydroxyphenyl)-1-(thiazol-2-yl)ethylamide |
| 24 | 2-((2-amino-3-(4-fluorophenyl)propionyl)-N-methylamino)-3-methylbutyric acid 2-(3-t-butyl-4-hydroxyphenyl)-1-(1,3,4-triazol-2-yl)ethylamide |
| 25 | 2-[2-amino-3-(4-fluorophenyl)propyl]amino-3-methylbutyric acid 2-(3-tertbutyl-4-hydroxyphenyl)-1-(thiazol-2-yl)ethylamide |

TABLE A-4

| Example No. | Structural formula or chemical name |
|---|---|
| 26 | Tyr(2-F)-N-Me-Val-N-Me-Tyr(3-tBu)-NH$_2$ |
| 27 | Tyr(3-F)-N-Me-Val-N-Me-Tyr(3-tBu)-NH$_2$ |
| 28 | Phe(4-F)-N-Me-Val-Tyr(3-tBu)-NH$_2$ |
| 29 | N-Me-Phe(4-F)-N-Me-Val-Tyr(3-tBu)-NH$_2$ |
| 30 | N-Et-Phe(4-F)-N-Me-Val-Tyr(3-tBu)-NH$_2$ |
| 31 | Phe(4-F)-N-Me-Val-Tyr(3-tBu)-NHMe |
| 32 | N-Me-Phe(4-F)-N-Me-Val-Tyr(3-tBu)-NHMe |
| 33 | N-Et-Phe(4-F)-N-Me-Val-Tyr(3-tBu)-NHMe |
| 34 | N-Me-Phe(4-F)-N-Me-Val-N-Me-Tyr(3-tBu)-NH$_2$ |
| 35 | N-Et-Phe(4-F)-N-Me-Val-N-Me-Tyr(3-tBu)-NH$_2$ |
| 36 | Phe(4-F)-N-Me-Val-N-Me-Tyr(3-tBu)-NHMe |
| 37 | N-Me-Phe(4-F)-N-Me-Val-N-Me-Tyr(3-tBu)-NHMe |
| 38 | N-Et-Phe(4-F)-N-Me-Val-N-Me-Tyr(3-tBu)-NHMe |
| 39 | Phe(4-F)-N-Me-Val-N-Et-Tyr(3-tBu)-NH$_2$ |
| 40 | N-Me-Phe(4-F)-N-Me-Val-N-Et-Tyr(3-tBu)-NH$_2$ |
| 41 | N-Et-Phe(4-F)-N-Me-Val-N-Et-Tyr(3-tBu)-NH$_2$ |
| 42 | Phe(4-F)-N-Me-Val-N-Et-Tyr(3-tBu)-NHMe |
| 43 | N-Me-Phe(4-F)-N-Me-Val-N-Et-Tyr(3-tBu)-NHMe |
| 44 | N-Et-Phe(4-F)-N-Me-Val-N-Et-Tyr(3-tBu)-NHMe |
| 45 | Phe(4-F)-N-Et-Val-Tyr(3-tBu)-NH$_2$ |
| 46 | N-Me-Phe(4-F)-N-Et-Val-Tyr(3-tBu)-NH$_2$ |

TABLE A-4-continued

| Example No. | Structural formula or chemical name |
|---|---|
| 47 | N-Et-Phe(4-F)-N-Et-Val-Tyr(3-tBu)-NH$_2$ |
| 48 | Phe(4-F)-N-Et-Val-Tyr(3-tBu)-NHMe |
| 49 | N-Me-Phe(4-F)-N-Et-Val-Tyr(3-tBu)-NHMe |
| 50 | N-Et-Phe(4-F)-N-Et-Val-Tyr(3-tBu)-NHMe |

TABLE A-5

| Example No. | Structural formula or chemical name |
|---|---|
| 51 | Phe(4-F)-N-Et-Val-N-Me-Tyr(3-tBu)-NH$_2$ |
| 52 | N-Me-Phe(4-F)-N-Et-Val-N-Me-Tyr(3-tBu)-NH$_2$ |
| 53 | N-Et-Phe(4-F)-N-Et-Val-N-Me-Tyr(3-tBu)-NH$_2$ |
| 54 | Phe(4-F)-N-Et-Val-N-Me-Tyr(3-tBu)-NHMe |
| 55 | N-Me-Phe(4-F)-N-Et-Val-N-Me-Tyr(3-tBu)-NHMe |
| 56 | N-Et-Phe(4-F)-N-Et-Val-N-Me-Tyr(3-tBu)-NHMe |
| 57 | Phe(4-F)-N-Et-Val-N-Et-Tyr(3-tBu)-NH$_2$ |
| 58 | N-Me-Phe(4-F)-N-Et-Val-N-Et-Tyr(3-tBu)-NH$_2$ |
| 59 | N-Et-Phe(4-F)-N-Et-Val-N-Et-Tyr(3-tBu)-NH$_2$ |
| 60 | Phe(4-F)-N-Et-Val-N-Et-Tyr(3-tBu)-NHMe |
| 61 | N-Me-Phe(4-F)-N-Et-Val-N-Et-Tyr(3-tBu)-NHMe |
| 62 | N-Et-Phe(4-F)-N-Et-Val-N-Et-Tyr(3-tBu)-NHMe |
| 63 | Phe(4-F)-N-Me-Val-Tyr(3-tBu)-NHtBu |
| 64 | Phe(4-F)-N-Me-Val-N-Me-Tyr(3-tBu)-NHCH$_2$SO$_2$CH$_3$ |
| 65 | 2-(2-amino-3-(4-fluorophenyl)propylamino)-N-(2-(3-tert-butyl-4-hydroxyphenyl)-1-carbamoylethyl)-N-methyl-3-methylbutanamide |
| 66 | 2-(2-amino-3-(4-fluorophenyl)-N-methylpropylamino)-N-(2-(3-tert-butyl-4-hydroxyphenyl)-1-carbamoylethyl)-N-methyl-3-methylbutanamide |
| 67 | 2-(N-acetyl-2-amino-3-(4-fluorophenyl)propylamino)-N-(2-(3-tert-butyl-4-hydroxyphenyl)-1-carbamoylethyl)-N-methyl-3-methylbutanamide |
| 68 | 2-(2-amino-3-(4-fluorophenyl)propylamino)-N-(2-(3-tert-butyl-4-hydroxyphenyl)-1-carbamoylethyl)-N-ethyl-3-methylbutanamide |
| 69 | 2-(2-amino-3-(4-fluorophenyl)propylamino)-N-(2-(3-tert-butyl-4-hydroxyphenyl)-1-hydroxymethylethyl)-3-methylbutanamide |
| 70 | 2-(2-amino-3-(4-fluorophenyl)-N-methylpropylamino)-N-(2-(3-tert-butyl-4-hydroxyphenyl)-1-hydroxymethylethyl)-3-methylbutanamide |

TABLE A-6

| Example No. | Structural formula or chemical name |
|---|---|
| 71 | 2-(2-amino-3-(4-fluorophenyl)propylamino)-N-(2-(3-tert-butyl-4-hydroxyphenyl)-1-methylethyl)-N-methyl-3-methylbutanamide |
| 72 | 2-(2-amino-3-(4-fluorophenyl)-N-methylpropylamino)-N-(2-(3-tert-butyl-4-hydroxyphenyl)-1-methylethyl)-N-methyl-3-methylbutanamide |
| 73 | 2-(N-acetyl-2-amino-3-(4-fluorophenyl)propylamino)-N-(2-(3-tert-butyl-4-hydroxyphenyl)-1-methylethyl)-N-methyl-3-methylbutanamide |
| 74 | 2-(2-amino-3-(4-fluorophenyl)propylamino)-N-(2-(3-tert-butyl-4-hydroxyphenyl)-1-methylethyl)-3-methylbutanamide |
| 75 | 2-((2-amino-3-(4-fluorophenyl)propyl)-N-methylamino)-N-(2-(3-tert-butyl-4-hydroxyphenyl)-1-methylethyl)-3-methylbutanamide |
| 76 | 2-(N-acetyl-2-amino-3-(4-fluorophenyl)propylamino)-N-(2-(3-tert-butyl-4-hydroxyphenyl)-1-methylethyl)-3-methylbutanamide |
| 77 | 2-((2-amino-3-(4-fluorophenyl)propyl)-N-methylamino)-N-(2-(3-tert-butyl-4-hydroxyphenyl)-1-hydroxymethylethyl)-N,3-dimethylbutanamide |

TABLE A-6-continued

| Example No. | Structural formula or chemical name |
|---|---|
| 78 | 2-(2-amino-3-(4-fluorophenyl)-N-methylpropylamino)-N-(1-aminomethyl-2-(3-tert-butyl-4-hydroxyphenyl)ethyl)-3-methylbutanamide |

TABLE A-7

| Example No. | Structural formula or chemical name |
|---|---|
| 101 | Phe(4-F)-N-Me-Val-Tyr(3-tBu)-NHEt |
| 102 | N-Me-Phe(4-F)-N-Me-Val-Tyr(3-tBu)-NHEt |
| 103 | N-Et-Phe(4-F)-N-Me-Val-Tyr(3-tBu)-NHEt |
| 104 | Phe(4-F)-N-Me-Val-N-Me-Tyr(3-tBu)-NHEt |
| 105 | N-Me-Phe(4-F)-N-Me-Val-N-Me-Tyr(3-tBu)-NHEt |
| 106 | N-Et-Phe(4-F)-N-Me-Val-N-Me-Tyr(3-tBu)-NHEt |
| 107 | Phe(4-F)-N-Me-Val-N-Et-Tyr(3-tBu)-NHEt |
| 108 | N-Me-Phe(4-F)-N-Me-Val-N-Et-Tyr(3-tBu)-NHEt |
| 109 | N-Et-Phe(4-F)-N-Me-Val-N-Et-Tyr(3-tBu)-NHEt |
| 110 | Phe(4-F)-N-Et-Val-Tyr(3-tBu)-NHEt |
| 111 | N-Me-Phe(4-F)-N-Et-Val-Tyr(3-tBu)-NHEt |
| 112 | N-Et-Phe(4-F)-N-Et-Val-Tyr(3-tBu)-NHEt |
| 113 | Phe(4-F)-N-Et-Val-N-Me-Tyr(3-tBu)-NHEt |
| 114 | N-Me-Phe(4-F)-N-Et-Val-N-Me-Tyr(3-tBu)-NHEt |
| 115 | N-Et-Phe(4-F)-N-Et-Val-Me-Tyr(3-tBu)-NHEt |
| 116 | Phe(4-F)-N-Et-Val-N-Et-Tyr(3-tBu)-NHEt |
| 117 | N-Me-Phe(4-F)-N-Et-Val-N-Et-Tyr(3-tBu)-NHEt |
| 118 | N-Et-Phe(4-F)-N-Et-Val-N-Et-Tyr(3-tBu)-NHEt |
| 119 | Phe(4-F)-N-Me-Val-Tyr(3-tBu)-NH-n-Pr |
| 120 | Phe(4-F)-N-Me-Val-Tyr(3-tBu)-NH-i-Pr |
| 121 | Phe(4-F)-N-Me-Val-N-Me-Tyr(3-tBu)-NH-c-Pr |
| 122 | Phe(4-F)-N-Me-Val-Tyr(3-tBu)-NHCH$_2$OH |
| 123 | N-Me-Phe(4-F)-N-Me-Val-Tyr(3-tBu)-NHCH$_2$OH |
| 124 | N-Et-Phe(4-F)-N-Me-Val-Tyr(3-tBu)-NHCH$_2$OH |
| 125 | N-Me-Phe(4-F)-N-Me-Val-N-Me-Tyr(3-tBu)-NHCH$_2$OH |

TABLE A-8

| Example No. | Structural formula or chemical name |
|---|---|
| 126 | N-Et-Phe(4-F)-N-Me-Val-N-Me-Tyr(3-tBu)-NHCH$_2$OH |
| 127 | Phe(4-F)-N-Me-Val-N-Et-Tyr(3-tBu)-NHCH$_2$OH |
| 128 | N-Me-Phe(4-F)-N-Me-Val-N-Et-Tyr(3-tBu)-NHCH$_2$OH |
| 129 | N-Et-Phe(4-F)-N-Me-Val-N-Et-Tyr(3-tBu)-NHCH$_2$OH |
| 130 | Phe(4-F)-N-Et-Val-N-Et-Tyr(3-tBu)-NHCH$_2$OH |
| 131 | N-Me-Phe(4F)-N-Et-Val-N-Et-Tyr(3-tBu)-NHCH$_2$OH |
| 132 | Phe(4-F)-N-Me-Val-N-Me-Tyr(3-tBu)-NHCH$_2$OH |
| 133 | (2S)-2-[(2S)-2-amino-3-(4-fluorophenyl)-N-methylpropanolyamino]-N-((1S)-1-{[3-(tert-butyl)-4-hydroxyphenyl]methyl}-2-morpholin-4-yl-2-oxoethyl)-3-methyl-N-methylbutanamide |
| 134 | (2S)-2-[(2S)-2-amino-3-(4-fluorophenyl)-N-methylpropanolyamino]-N-((1S)-1-{[3-(tert-butyl)-4-hydroxyphenyl]methyl}-2-[4-(methylsulfonyl)piperazinyl]-2-oxoethyl)-3-methyl-N-methylbutanamide |
| 135 | ethyl 2-[4-((2S)-2-{(2S)-2-[(2S)-2-amino-3-(4-fluorophenyl)-N-methylpropanolyamino]-3,N-dimethylbutanoylamino}-3-[3-(tert-butyl)-4-hydroxyphenyl]propanoyl)piperazinyl]acetate |
| 136 | 2-[4-((2S)-2-{(2S)-2-[(2S)-2-amino-3-(4-fluorophenyl)-N-methylpropanolyamino]-3,N-dimethylbutanoylamino}-3-[3-(tert-butyl)-4-hydroxyphenyl]propanoyl)piperazinyl]acetic acid |
| 137 | Phe(4-F)-N-Me-Val-N-Pr-Tyr(3-tBu)-NH$_2$ |
| 138 | Phe(4-F)-N-Me-Abu-N-Me-Tyr(3-tBu)-NH$_2$ |
| 139 | Phe(4-F)-N-Me-D-Abu-N-Me-Tyr(3-tBu)-NH$_2$ |
| 140 | Phe(4-F)-N-Me-Nva-N-Me-Tyr(3-tBu)-NH$_2$ |

TABLE A-9

| Example No. | Structural formula or chemical name |
|---|---|
| 141 | Phe(4-F)-N-Me-D-Nva-N-Me-Tyr(3-tBu)-NH$_2$ |
| 142 | Phe(4-F)-N-Me-Ile-N-Me-Tyr(3-tBu)-NH$_2$ |
| 143 | Phe(4-F)-N-Me-D-Ile-N-Me-Tyr(3-tBu)-NH$_2$ |
| 144 | Phe(4-F)-N-Me-Leu-N-Me-Tyr(3-tBu)-NH$_2$ |
| 145 | Phe(4-F)-N-Me-D-Leu-N-Me-Tyr(3-tBu)-NH$_2$ |
| 146 | (2S)-2-[(2S)-2-amino-3-(4-fluorophenyl)-N-methylpropanoylamino]-N-{(1S)-2-[3-(tert-butyl)-4-hydroxyphenyl]-1-carbamoylethyl}-N-methylpent-4-enamide |
| 147 | (2R)-2-[(2S)-2-amino-3-(4-fluorophenyl)-N-methylpropanoylamino]-N-{(1S)-2-[3-(tert-butyl)-4-hydroxyphenyl]-1-carbamoylethyl}-N-methylpent-4-enamide |
| 148 | Phe(4-F)-N-Me-Leu(γ-Me)-N-Me-Tyr(3-tBu)-NH$_2$ |
| 149 | Phe(4-F)-N-Me-D-Leu(γ-Me)-N-Me-Tyr(3-tBu)-NH$_2$ |
| 150 | Phe(4-F)-N-Me-Ala(□-CF$_3$)-N-Me-Tyr(3-tBu)-NH$_2$ |
| 151 | Phe(4-F)-N-Me-Chg-N-Me-Tyr(3-tBu)-NH$_2$ |
| 152 | Phe(4-F)-N-Me-D-Chg-N-Me-Tyr(3-tBu)-NH$_2$ |
| 153 | Phe(4-F)-N-Me-Cha-N-Me-Tyr(3-tBu)-NH$_2$ |
| 154 | Phe(4-F)-N-Me-D-Cha-N-Me-Tyr(3-tBu)-NH$_2$ |
| 155 | Phe(4-F)-N-Me-Phe-N-Me-Tyr(3-tBu)-NH$_2$ |
| 156 | Phe(4-F)-N-Me-D-Phe-N-Me-Tyr(3-tBu)-NH$_2$ |
| 157 | Phe(4-F)-N-Me-Phe(4-F)-N-Me-Tyr(3-tBu)-NH$_2$ |
| 158 | Phe(4-F)-N-Me-D-Phe(4-F)-N-Me-Tyr(3-tBu)-NH$_2$ |
| 159 | Phe(4-F)-N-Me-Phe(4-Cl)-N-Me-Tyr(3-tBu)-NH$_2$ |
| 160 | Phe(4-F)-N-Me-D-Phe(4-Cl)-N-Me-Tyr(3-tBu)-NH$_2$ |
| 161 | Phe(4-F)-N-Me-Tyr-N-Me-Tyr(3-tBu)-NH$_2$ |
| 162 | Phe(4-F)-N-Me-D-Tyr-N-Me-Tyr(3-tBu)-NH$_2$ |
| 163 | Phe(4-F)-N-Me-Ala(β-2-thienyl)-N-Me-Tyr(3-tBu)-NH$_2$ |

TABLE A-10

| Example No. | Structural formula or chemical name |
|---|---|
| 164 | Phe(4-F)-N-Me-D-Ala(β-2-thienyl)-N-Me-Tyr(3-tBu)-NH$_2$ |
| 165 | Phe(4-F)-N-Me-Ala(β-c-Pr)-N-Me-Tyr(3-tBu)-NH$_2$ |
| 166 | Phe(4-F)-N-Me-Phg-N-Me-Tyr(3-tBu)-NH$_2$ |
| 167 | Phe(4-F)-N-Me-α-Me-Phe-Tyr(3-tBu)-NH$_2$ |
| 168 | Phe(4-F)-N-Me-α-Me-Phe-Tyr(3-tBu)-NH$_2$ |
| 169 | Phe(4-F)-N-Me-α-Me-Leu-Tyr(3-tBu)-NH$_2$ |
| 170 | Phe(4-F)-N-Me-α-Me-D-Abu-Tyr(3-tBu)-NH$_2$ |
| 171 | Phe(4-F)-N-Me-α-Me-D-Val-Tyr(3-tBu)-NH$_2$ |
| 172 | (2S)-N-[(N-{(1S)-2-[3-(tert-butyl)-4-hydroxyphenyl]-1-carbamoylethyl}carbamoyl)cyclopentyl]-2-amino-3-(4-fluorophenyl)-N-methylpropanamide |
| 173 | (2S)-N-[(N-{(1S)-2-[3-(tert-butyl)-4-hydroxyphenyl]-1-carbamoylethyl}carbamoyl)cyclohexyl]-2-amino-3-(4-fluorophenyl)-N-methylpropanamide |
| 174 | Phe(4-F)-N-Me-Tle-Tyr(3-tBu)-NH$_2$ |
| 175 | Phe(4-F)-N-Me-Tle-N-Me-Tyr(3-tBu)-NH$_2$ |
| 176 | Phe(4-F)-N-Me-D-Phg-N-Me-Tyr(3-tBu)-NH$_2$ |
| 177 | (2S)-N-{(1S)-2-[3-(tert-butyl)-4-hydroxyphenyl]-1-carbamoylethyl}-2-[2-amino-3-(2-fluoro-4-pyridyl)-N-methylpropanoylamino]-3-methyl-N-methylbutanamide |
| 178 | (2S)-N-{(1S)-2-[3-(tert-butyl)-4-hydroxyphenyl]-1-carbamoylethyl}-2-[2-amino-3-(2-fluoro-5-pyridyl)-N-methylpropanoylamino]-3-methyl-N-methylbutanamide |
| 179 | (2S)-N-{(1S)-2-[3-(tert-butyl)-4-hydroxyphenyl]-1-carbamoylethyl}-2-{2-amino-N-methyl-3-[4-(trifluoromethyl)phenyl]propanoylamino}-3-methyl-N-methylbutanamide |
| 180 | (2S)-N-{(1S)-2-[3-(tert-butyl)-4-hydroxyphenyl]-1-carbamoylethyl}-2-{2-[(4-fluorophenyl)methyl]-3-hydroxy-N-methylpropanoylamino}-3-methyl-N-methylbutanamide |
| 181 | Ala(β-4-pyridyl)-N-Me-Val-N-Me-Tyr(3-tBu)-NH$_2$ |
| 182 | Phe(4-CN)-N-Me-Val-N-Me-Tyr(3-tBu)-NH$_2$ |
| 183 | Trp-N-Me-Val-N-Me-Tyr(3-tBu)-NH$_2$ |

TABLE B-1
| Example No. | Structural formula |
|---|---|
| 1 | 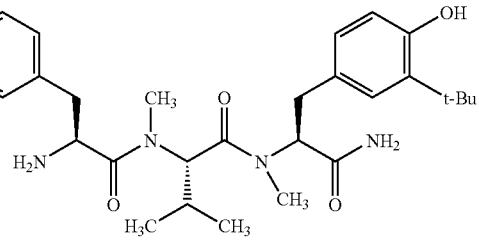 |
| 2 | 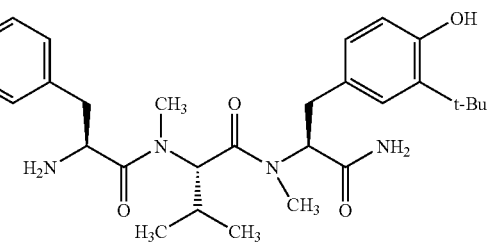 |
| 3 | 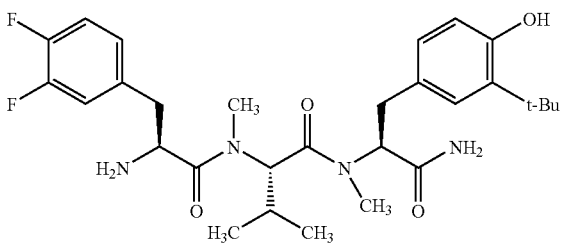 |
| 4 | 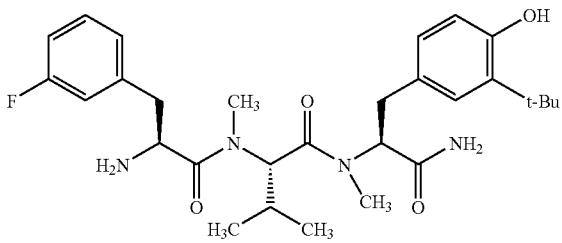 |
| 5 | 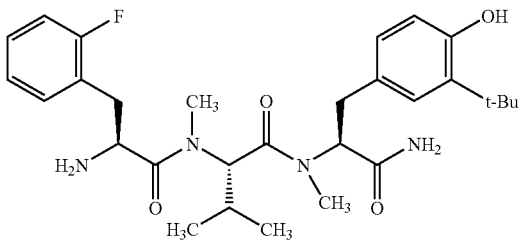 |

TABLE B-2
| Example No. | Structural formula |
|---|---|
| 6 | |
| 7 | |
| 8 | |
| 9 | |
| 10 | |
| 11 | |
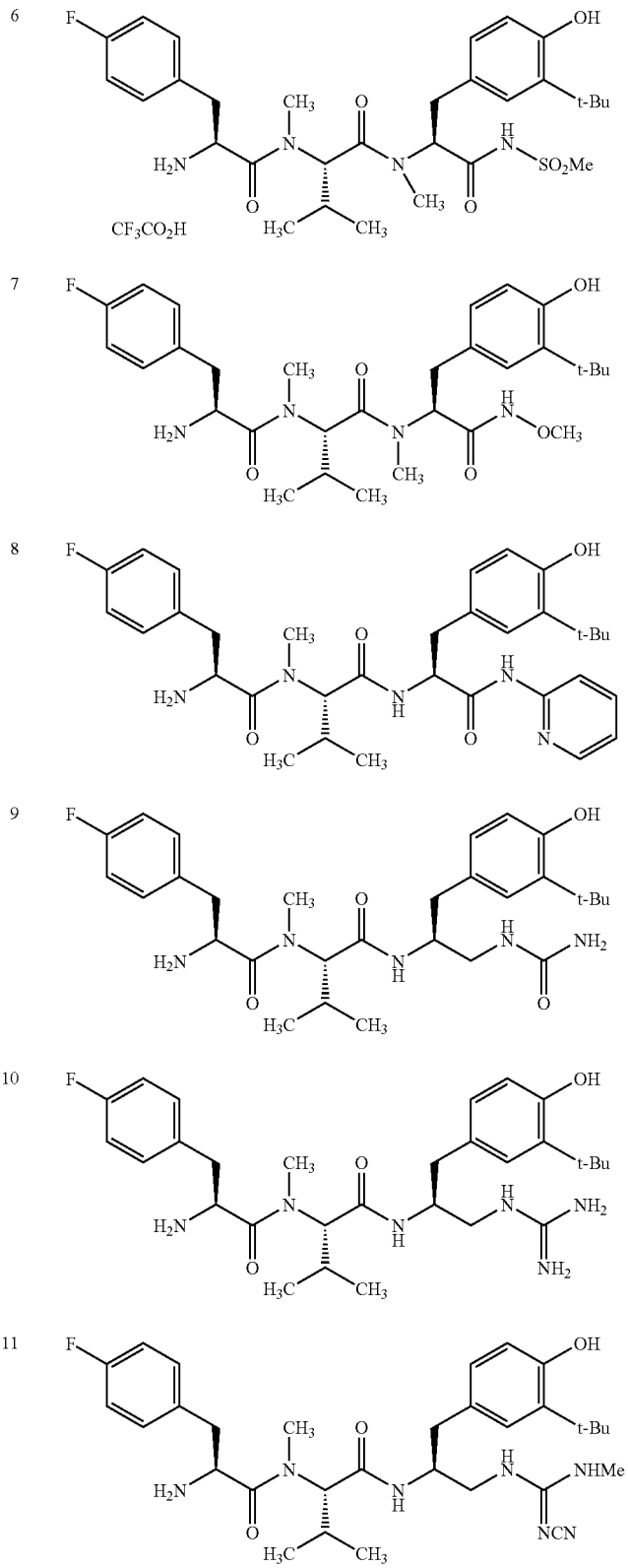

TABLE B-3
| Example No. | Structural formula |
|---|---|
| 12–17 | 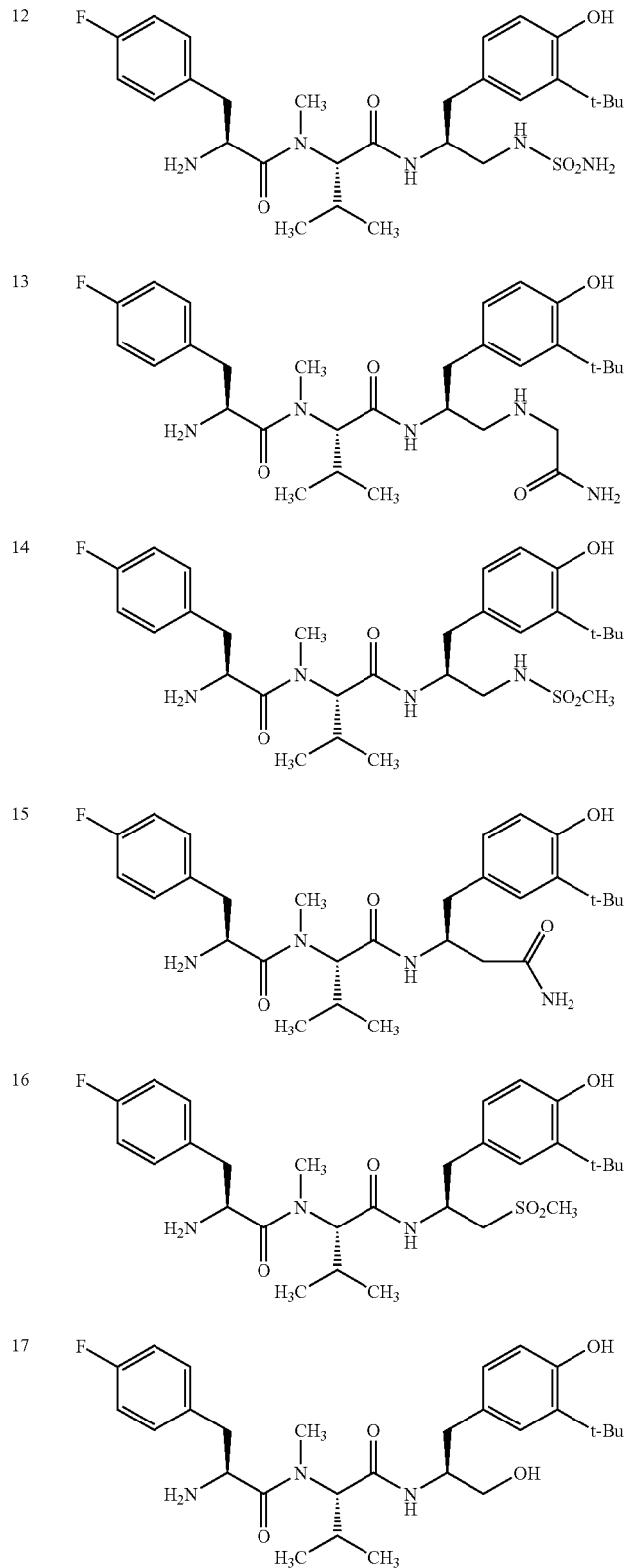 |

TABLE B-4
| Example No. | Structural formula |
|---|---|
| 18 | |
| 19 | |
| 20 | |
| 21 | |
| 22 | |
| 23 | |
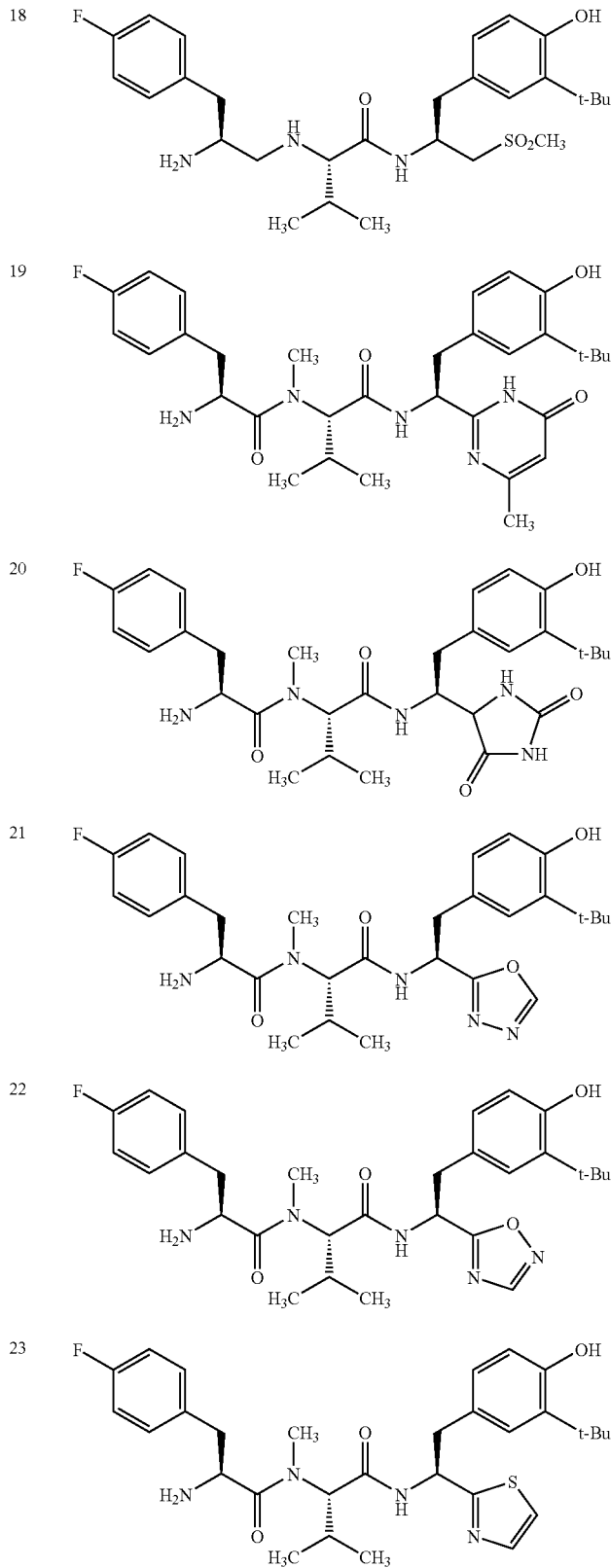

TABLE B-5
| Example No. | Structural formula |
|---|---|
| 24 | 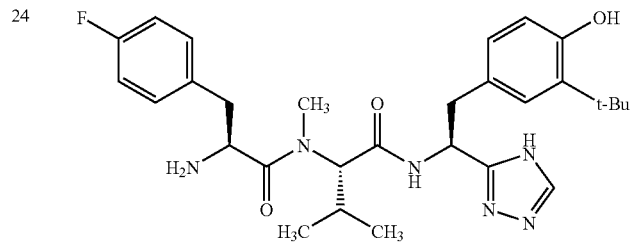 |
| 25 | 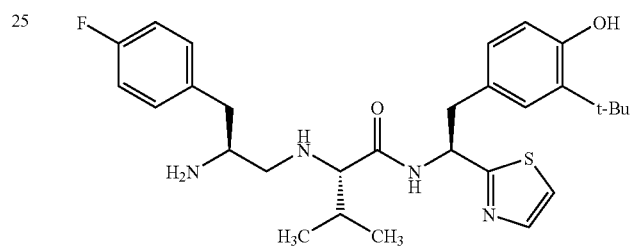 |
TABLE B-6
| Example No. | Structural formula |
|---|---|
| 26 | 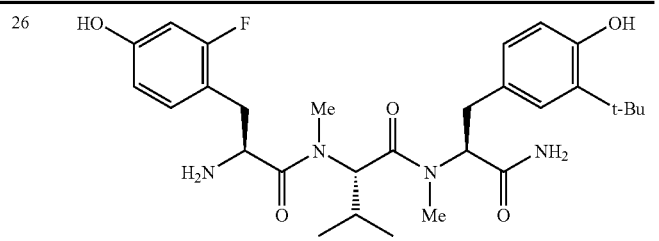 |
| 27 | 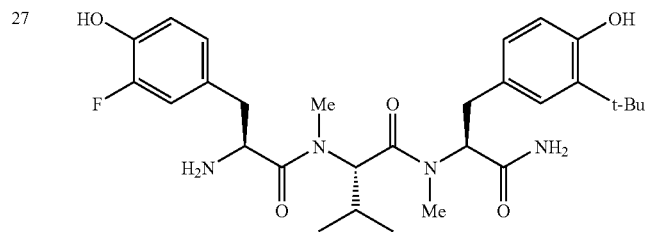 |
TABLE B-7
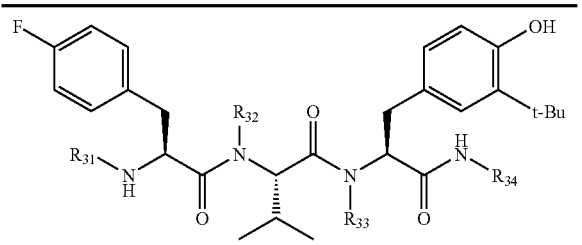
| Example No. | $R_{31}$ | $R_{32}$ | $R_{33}$ | $R_{34}$ |
|---|---|---|---|---|
| 28 | H | Me | H | H |
| 29 | Me | Me | H | H |
| 30 | Et | Me | H | H |
TABLE B-7-continued
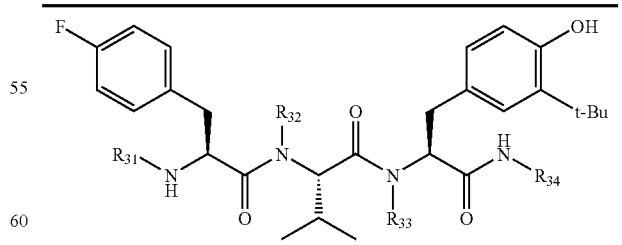
| Example No. | $R_{31}$ | $R_{32}$ | $R_{33}$ | $R_{34}$ |
|---|---|---|---|---|
| 31 | H | Me | H | Me |
| 32 | Me | Me | H | Me |
| 33 | Et | Me | H | Me |

TABLE B-7-continued

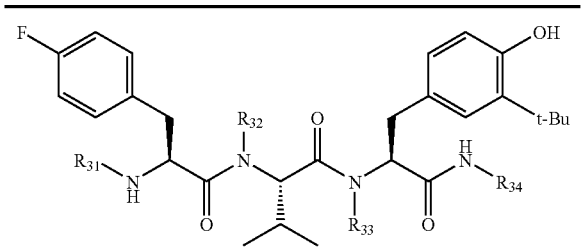

| Example No. | $R_{31}$ | $R_{32}$ | $R_{33}$ | $R_{34}$ |
|---|---|---|---|---|
| 34 | Me | Me | Me | H |
| 35 | Et | Me | Me | H |
| 36 | H | Me | Me | Me |
| 37 | Me | Me | Me | Me |
| 38 | Et | Me | Me | Me |
| 39 | H | Me | Et | H |
| 40 | Me | Me | Et | H |
| 41 | Et | Me | Et | H |
| 42 | H | Me | Et | Me |
| 43 | Me | Me | Et | Me |
| 44 | Et | Me | Et | Me |
| 45 | H | Et | H | H |
| 46 | Me | Et | H | H |
| 47 | Et | Et | H | H |
| 48 | H | Et | H | Me |
| 49 | Me | Et | H | Me |
| 50 | Et | Et | H | Me |
| 51 | H | Et | Me | H |
| 52 | Me | Et | Me | H |
| 53 | Et | Et | Me | H |
| 54 | H | Et | Me | Me |
| 55 | Me | Et | Me | Me |
| 56 | Et | Et | Me | Me |
| 57 | H | Et | Et | H |
| 58 | Me | Et | Et | H |
| 59 | Et | Et | Et | H |
| 60 | H | Et | Et | Me |
| 61 | Me | Et | Et | Me |
| 62 | Et | Et | Et | Me |
| 101 | H | Me | H | Et |
| 102 | Me | Me | H | Et |
| 103 | Et | Me | H | Et |
| 122 | H | Me | H | $CH_2OH$ |
| 123 | Me | Me | H | $CH_2OH$ |
| 124 | Et | Me | H | $CH_2OH$ |
| 104 | H | Me | Me | Et |
| 105 | Me | Me | Me | Et |
| 106 | Et | Me | Me | Et |
| 132 | H | Me | Me | $CH_2OH$ |
| 125 | Me | Me | Me | $CH_2OH$ |
| 126 | Et | Me | Me | $CH_2OH$ |
| 107 | H | Me | Et | Et |
| 108 | Me | Me | Et | Et |
| 109 | Et | Me | Et | Et |
| 127 | H | Me | Et | $CH_2OH$ |
| 128 | Me | Me | Et | $CH_2OH$ |
| 129 | Et | Me | Et | $CH_2OH$ |

TABLE B-8

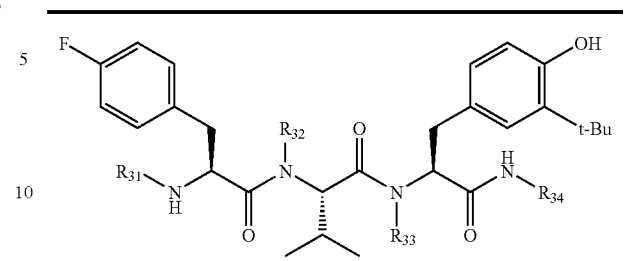

| Example No. | $R_{31}$ | $R_{32}$ | $R_{33}$ | $R_{34}$ |
|---|---|---|---|---|
| 110 | H | Et | H | Et |
| 111 | Me | Et | H | Et |
| 112 | Et | Et | H | Et |
| 113 | H | Et | Me | Et |
| 114 | Me | Et | Me | Et |
| 115 | Et | Et | Me | Et |
| 116 | H | Et | Et | Et |
| 117 | Me | Et | Et | Et |
| 118 | Et | Et | Et | Et |
| 130 | H | Et | Et | $CH_2OH$ |
| 131 | Me | Et | Et | $CH_2OH$ |
| 121 | H | Me | Me | cPr |
| 119 | H | Me | H | nPr |
| 120 | H | Me | H | iPr |
| 137 | H | Me | nPr | H |
| 63 | H | Me | H | tBu |
| 64 | H | Me | Me | $CH_2SO_2CH_3$ |

TABLE B-9

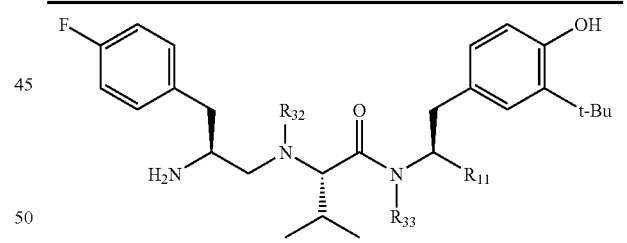

| Example No. | $R_{32}$ | $R_{33}$ | $R_{11}$ |
|---|---|---|---|
| 65 | H | Me | $CONH_2$ |
| 66 | Me | Me | $CONH_2$ |
| 67 | Ac | Me | $CONH_2$ |
| 68 | H | Et | $CONH_2$ |
| 69 | H | H | $CH_2OH$ |
| 70 | Me | H | $CH_2OH$ |
| 71 | H | Me | Me |
| 72 | Me | Me | Me |
| 73 | Ac | Me | Me |
| 74 | H | H | Me |
| 75 | Me | H | Me |
| 76 | Ac | H | Me |
| 77 | Me | Me | $CH_2OH$ |
| 78 | Me | H | $CH_2NH_2$ |

TABLE B-10
| Example No. | Structural formula |
|---|---|
| 133 | 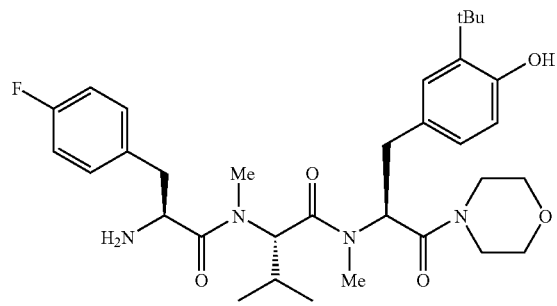 |
| 134 | 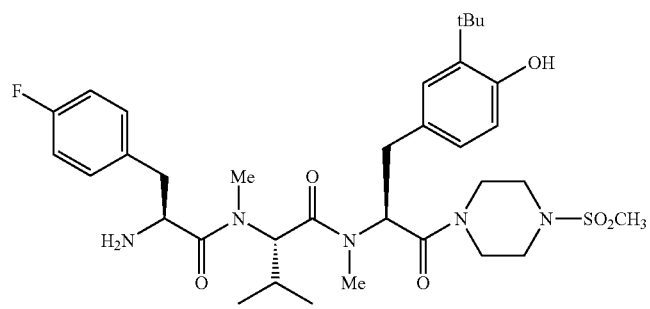 |
| 135 | 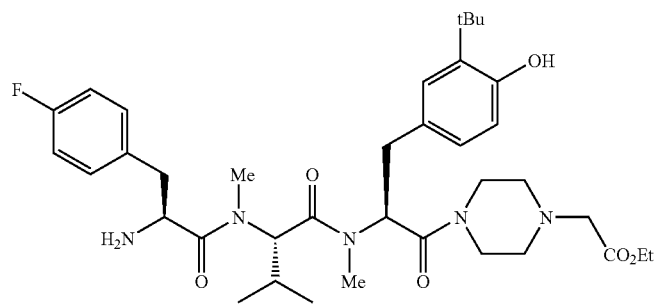 |
| 136 | 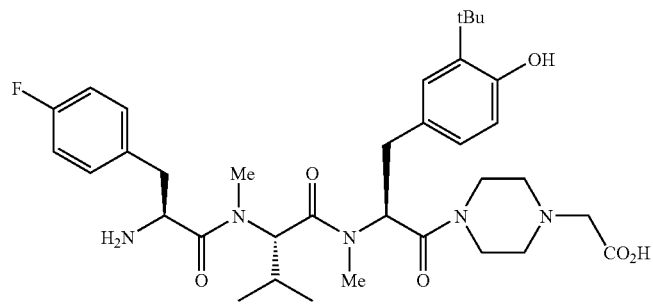 |
| 138 | 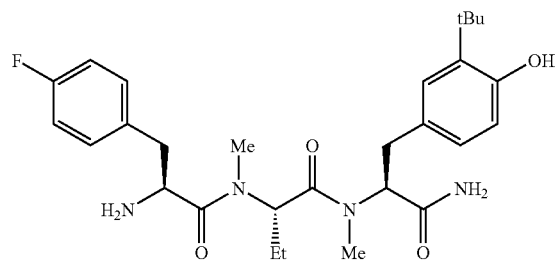 |

TABLE B-10-continued
| Example No. | Structural formula |
| --- | --- |
| 139 | 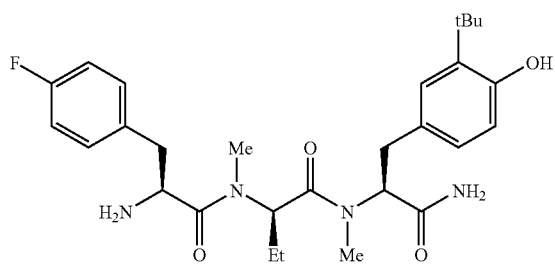 |
TABLE B-11
| Example No. | Structural formula |
| --- | --- |
| 140 | 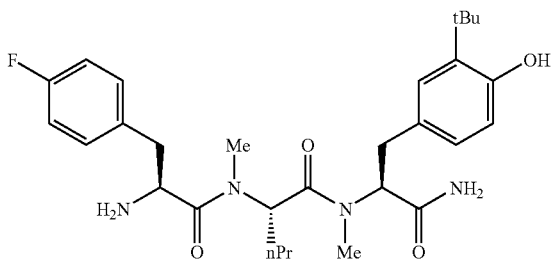 |
| 141 | 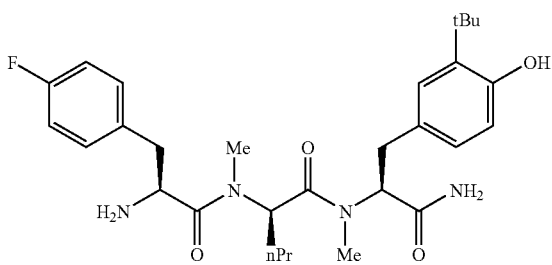 |
| 142 | 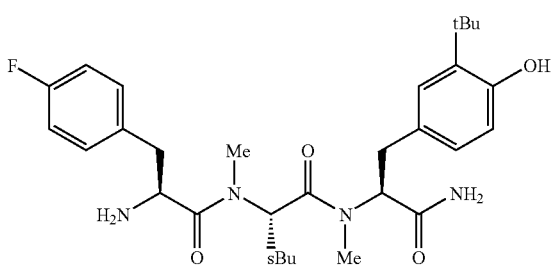 |
| 143 | 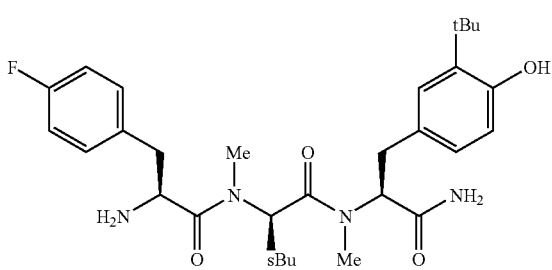 |

TABLE B-11-continued
| Example No. | Structural formula |
|---|---|
| 144 | 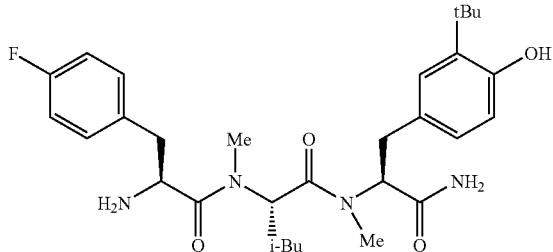 |
| 145 | 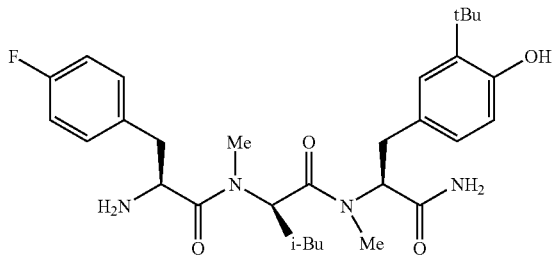 |
| 146 | 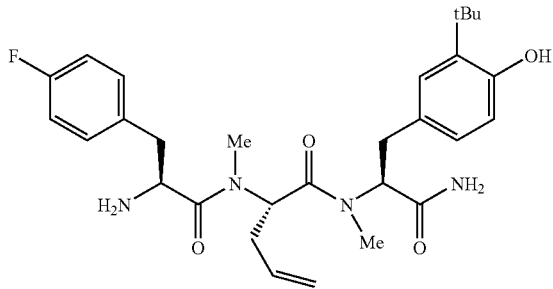 |
TABLE B-12
| Example No. | Structural formula |
|---|---|
| 147 | 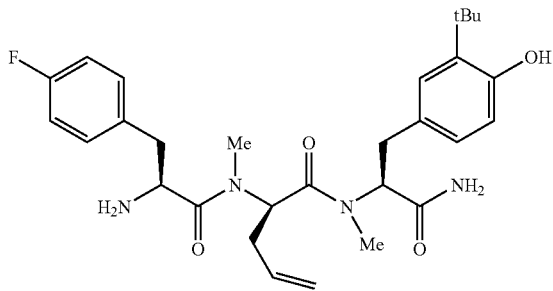 |

TABLE B-12-continued
| Example No. | Structural formula |
| --- | --- |
| 148 | 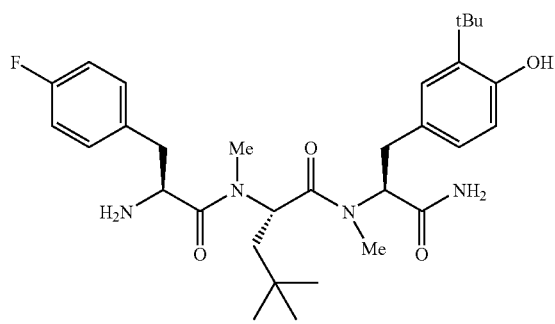 |
| 149 | 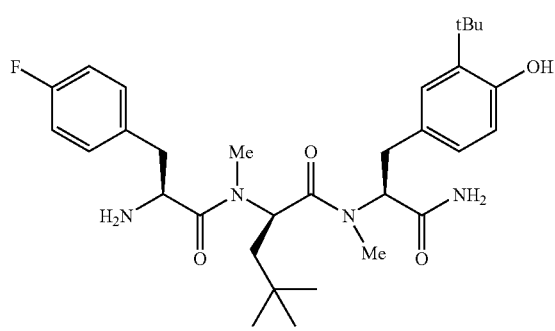 |
| 150A, 150B | 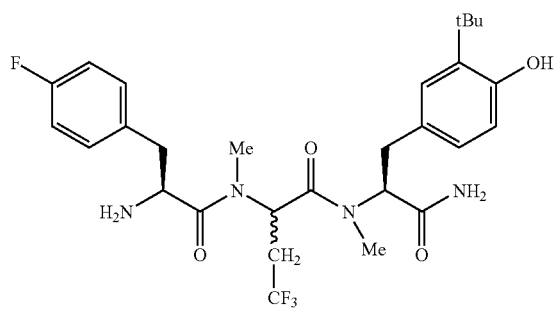 |
| 151 | 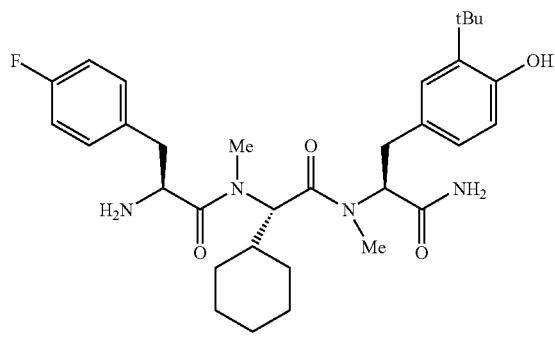 |

TABLE B-12-continued
| Example No. | Structural formula |
|---|---|
| 152 | 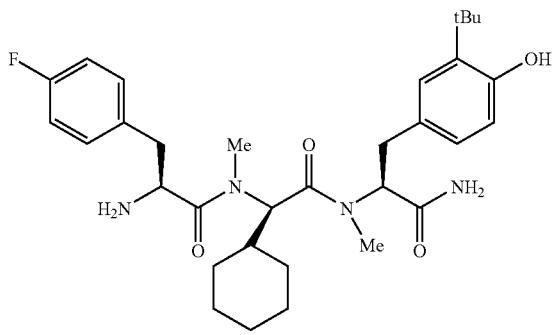 |
TABLE B-13
| Example No. | Structural formula |
|---|---|
| 153 | 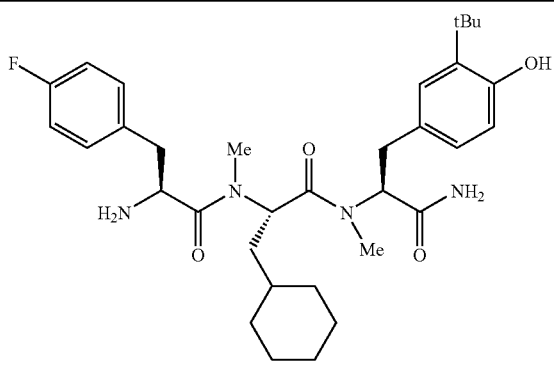 |
| 154 | 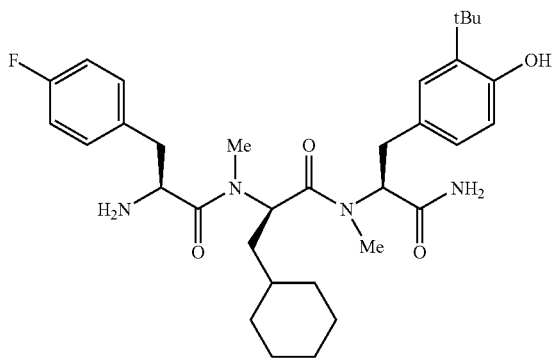 |
| 155 | 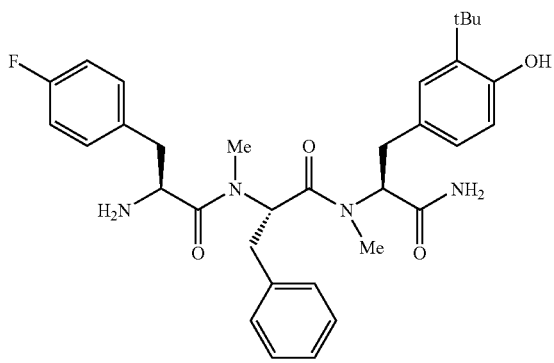 |

TABLE B-13-continued
| Example No. | Structural formula |
|---|---|
| 156 | 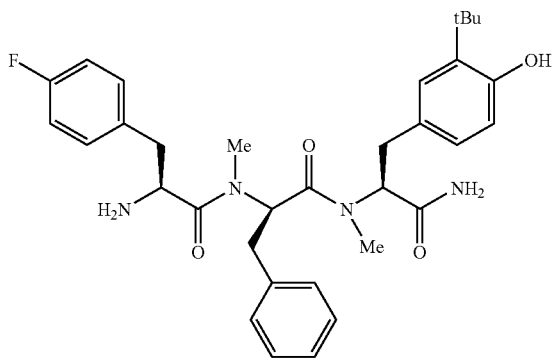 |
| 157 | 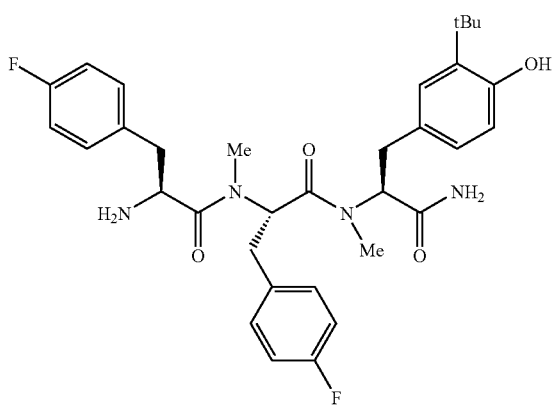 |
TABLE B-14
| Example No. | Structural formula |
|---|---|
| 158 | 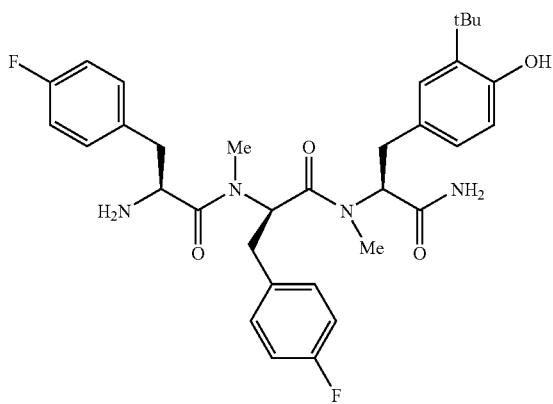 |

TABLE B-14-continued
| Example No. | Structural formula |
| --- | --- |
| 159 | 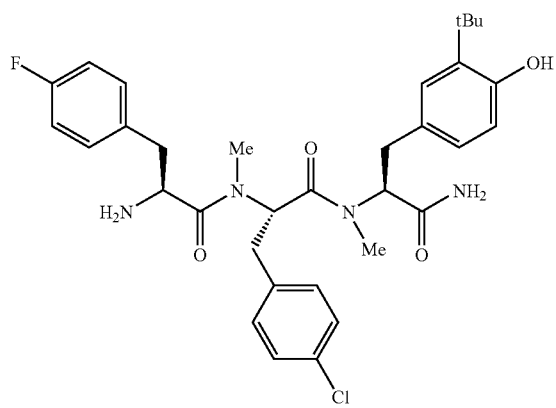 |
| 160 | 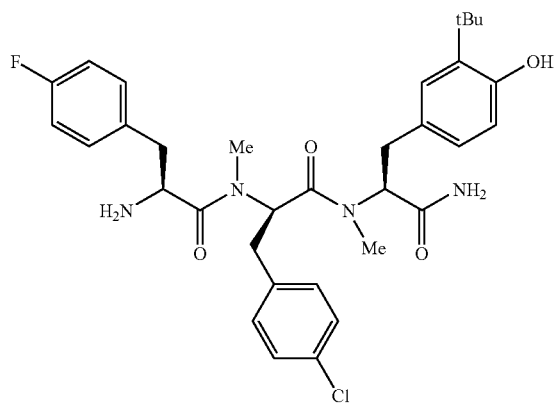 |
| 161 | 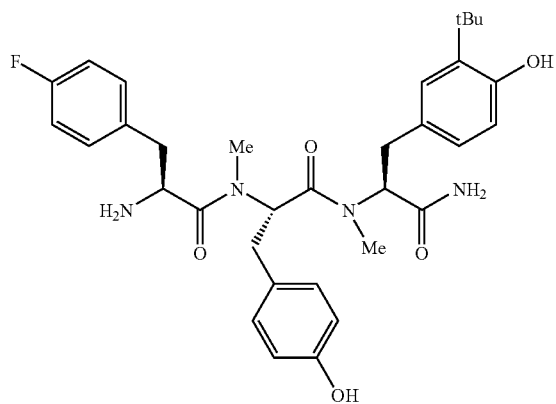 |

TABLE B-14-continued
| Example No. | Structural formula |
|---|---|
| 162 | 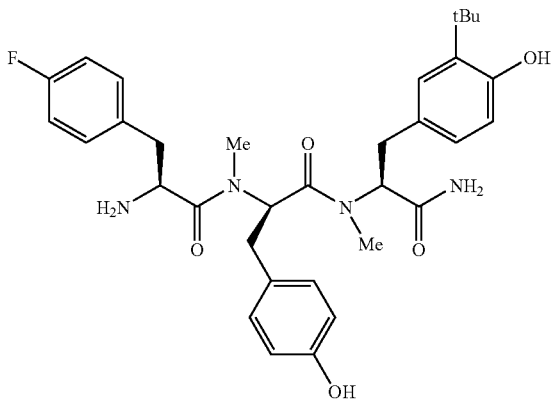 |
TABLE B-15
| Example No. | Structural formula |
|---|---|
| 163 | 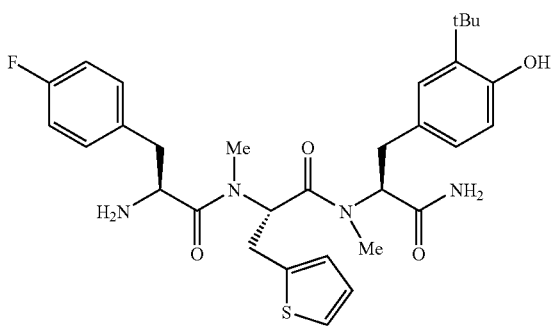 |
| 164 | 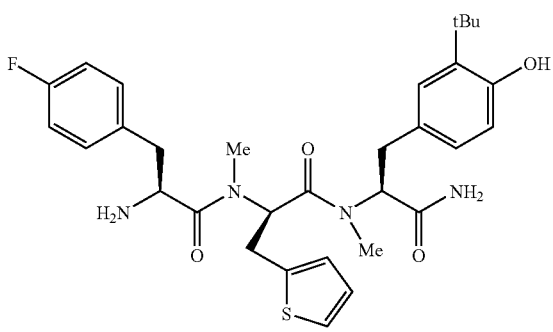 |
| 165 | 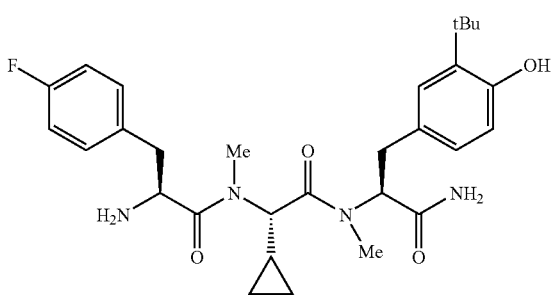 |

TABLE B-15-continued
| Example No. | Structural formula |
| --- | --- |
| 166 | 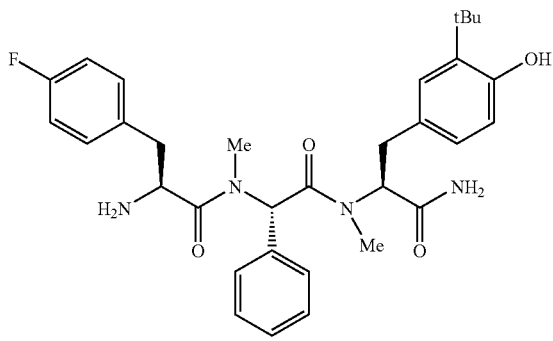 |
| 167 | 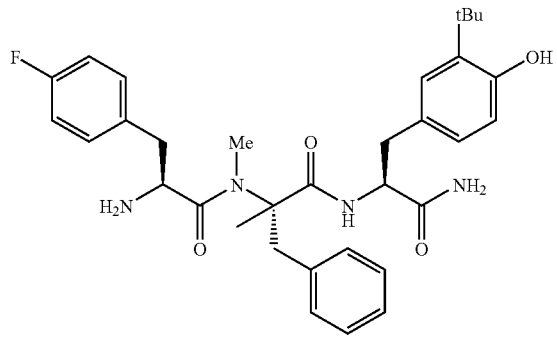 |
| 168 | 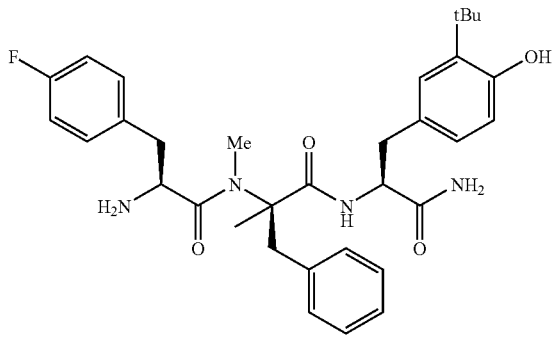 |
TABLE B-16
| Example No. | Structural formula |
| --- | --- |
| 169 | 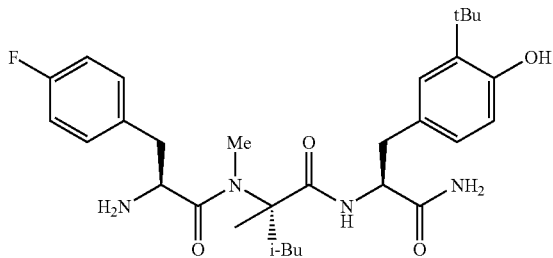 |

TABLE B-16-continued
| Example No. | Structural formula |
| --- | --- |
| 170 | 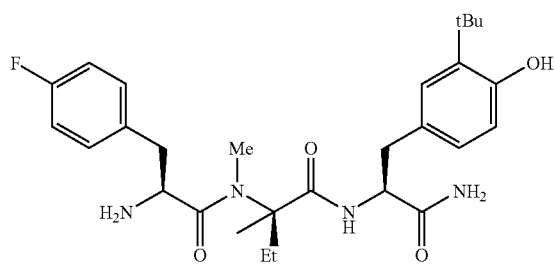 |
| 171 | 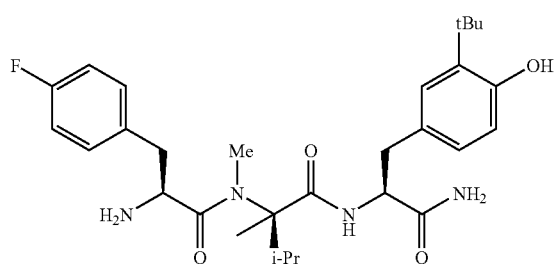 |
| 172 | 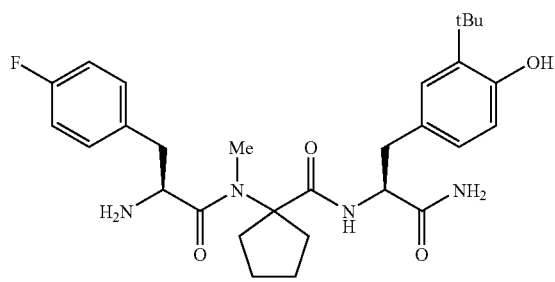 |
| 173 | 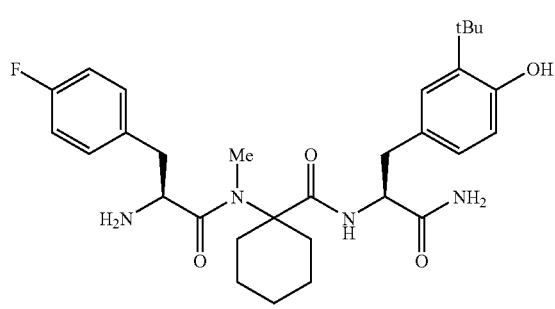 |
| 174 | 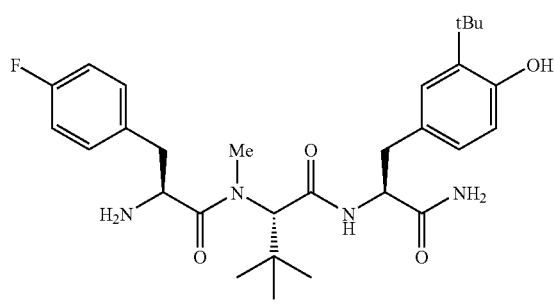 |

TABLE B-17
| Example No. | Structural formula |
|---|---|
| 175 | 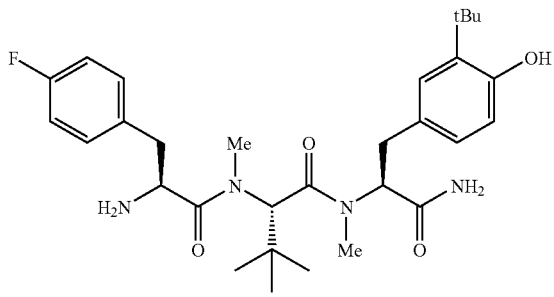 |
| 176 | 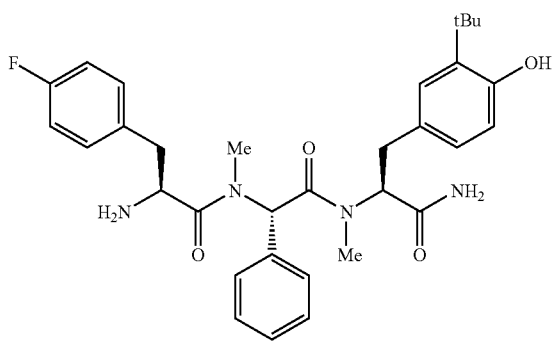 |
| 177A, 177B | 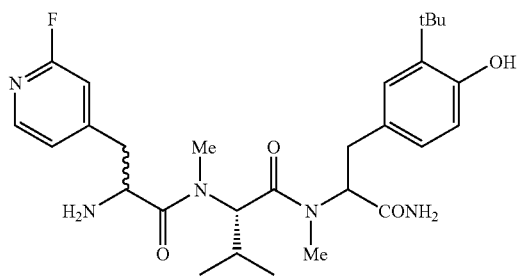 |
| 178A, 178B | 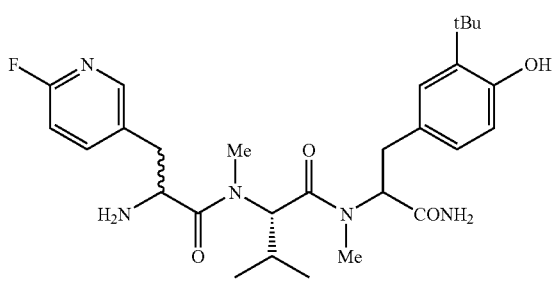 |
| 179A, 179B | 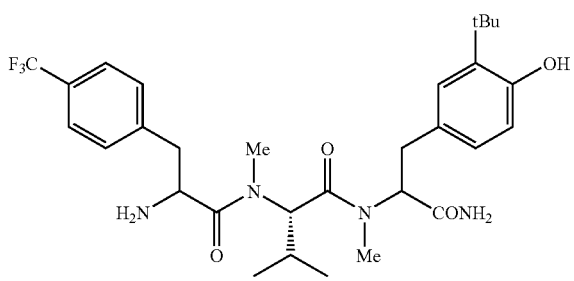 |

TABLE B-17-continued

| Example No. | Structural formula |
| --- | --- |
| 180A, 180B | 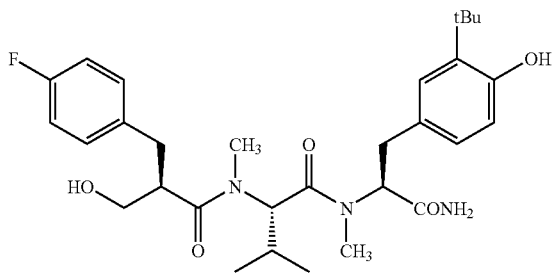 |

TABLE B-18

| Example No. | Structural formula |
| --- | --- |
| 181 | 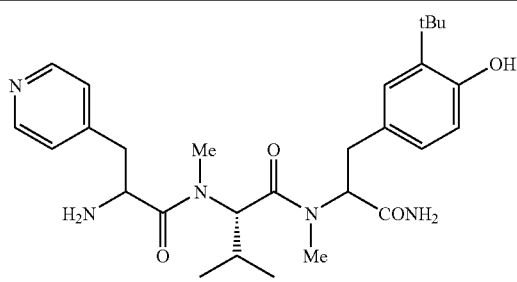 |
| 182 | 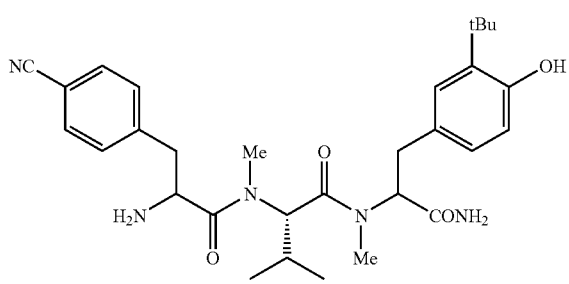 |
| 183 | 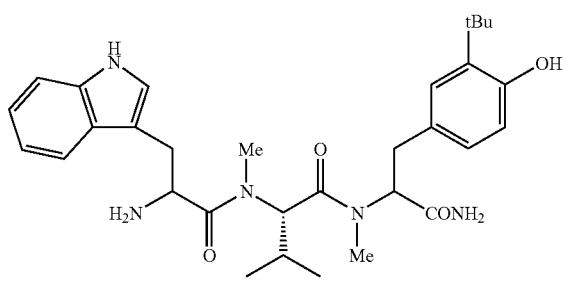 |

In the following Examples, Merck Silica gel 60 (0.063-0.200 mm) or Merck Silica gel 60 (0.040-0.063 mm) was used for silica gel column chromatography unless otherwise stated.

In the following examples, mass spectra (MA) and $^1$H-NMR were taken by the following equipment:

MA (EI-MS): SHIMADZU GCMS-QP5050A or SHIMADZU GCMS-QP1000.

MA (ESI-MS): Extrel ELQ400

MA (FAB-MS): JASCO 70-250SEQ $^1$H-NMR: JEOL JNM-EX-270 (270 MHz) or Bruker ARX300 (300 MHz)

Reaction conditions, data from the equipment, yielded amount and the like of Example 28 onward were shown in Tables in which "Reaction time" means stirring time and "Column sol." means the eluting solvent for silica gel column chromatography.

In the following Examples, the retention time (min.) on HPLC is measured under the following conditions:

Apparatus: HITACHI L-6300 or Young Lin M930

Column: µBONDASPHERE 5µ C18 100 A (3.9×150 mm)

Detecting conditions: linear gradient of B (10-80%) using A (0.1% TFA/distilled water) and B (0.1% TFA/acetonitrile), 35 min., flow of rate 1 ml/min, detected at 280 nm (UV).

EXAMPLE 1

Phe(4-F)-N-Me-Val-N-Me-Tyr(3-tBu)-NH$_2$ (1) Synthesis of Tyr(3-tBu)-OMe

To a solution of Tyr-OMe.HCl (500 g, 2.16 mol) in tert-butyl acetate (4500 ml), 70% HCl$_4$ (278 ml, 3.24 mol) was added and stirred for 4.5 days at room temperature. The reaction mixture was evaporated under reduced pressure; the thus obtained residue was dissolved in ethyl acetate, poured into a saturated aqueous NaHCO$_3$ solution and stirred. The organic layer was collected and washed with a saturated aqueous NaHCO$_3$ solution and saturated brine, dried over anhydrous magnesium sulfate and evaporated to remove the solvent under reduced pressure. The thus obtained residue was mixed with ether (950 ml) and at room temperature, stirred overnight. The thus precipitated crystals were collected by filtration to give Tyr(3-tBu)-OMe (242 g, 45%).

$^1$H-NMR (CDCl$_3$): δ 1.38 (9H, s), 2.83 (1H, dd, J=13.7, 7.4 Hz), 3.02 (1H, dd, J=13.7, 5.1 Hz), 3.70 (1H, dd, J=7.4, 5.1 Hz), 3.73 (3H, s), 6.55 (1H, d, J=7.9 Hz), 6.85 (1H, dd, J=7.9, 1.7 Hz), 7.04 (1H, d, J=1.7 Hz)

(2) Synthesis of Z-Tyr(3-t-Bu)-OMe

To a solution of Tyr(3-tBu)-OMe (41.4 g, 0.165 mol) in 1,4-dioxane (170 ml) and H$_2$O (170 ml), under cooling with ice, sodium carbonate (26.2 g, 0.247 mol) was added and then Z—Cl (24.7 ml 0.173 mol) was further added over 25 min., followed by stirring for 2.5 hours at room temperature. The reaction mixture was mixed with water, extracted with chloroform, dried over anhydrous magnesium sulfate and evaporated to remove the solvent under reduced pressure. The thus precipitated crystals were collected by filtration, washed with n-hexane and dried to give Z-Tyr(3-t-Bu)-OMe (54.7 g, 86%).

$^1$H-NMR (CDCl$_3$): δ 1.36 (9H, s), 3.04 (2H, brd, J=5.6 Hz), 3.72 (3H, s), 4.57-4.68 (1H, m), 4.97 (1H, brs), 5.10 (2H, s), 5.20 (1H, brd, J=7.9 Hz), 6.55 (1H, d, J=7.9 Hz), 6.78 (1H, dd, J=7.9, 2.0 Hz), 6.95 (1H, d, J=2.0 Hz), 7.26-7.41 (5H, m)

(3) Synthesis of Z-Phe(3-tBu-4-benzyloxy)-OMe

A solution of Z-Tyr(3-tBu)-OMe (1.0 g, 2.60 mmol), benzyl bromide (0.56 ml, 4.68 mmol) and potassium carbonate (1.08 g, 7.79 mmol) in DMSO (5 ml) was stirred overnight. The resulting mixture was mixed with a saturated aqueous ammonium chloride solution, extracted with ethyl acetate. The organic layer was washed with water and then saturated brine, dried over anhydrous magnesium sulfate and evaporated to remove the solvent under reduced pressure; the thus obtained residue was subjected to silica gel column chromatography (developing solvent: ethyl acetate:n-hexane=1:5) to give Z-Phe(3-tBu-4-benzyloxy)-OMe (1.44 g, 99%).

$^1$H-NMR (CDCl$_3$): δ 1.36 (9H, s), 3.05 (2H, d, J=5.6 Hz), 3.71 (3H, s), 4.60-4.68 (1H, m), 5.06 (2H, s), 5.09 (2H, s), 5.24 (1H, brd, J=8.3 Hz), 6.82 (1H, d, J=8.5 Hz), 6.88 (1H, dd, J=8.5, 1.8 Hz), 7.00 (1H, d, J=1.8 Hz), 7.27-7.50 (10H, m)

(4) Synthesis of Z-N-Me-Phe(3-tBu-4-benzyloxy)-NH$_2$

To a solution of Z-Phe(3-tBu-4-benzyloxy)-OMe (1.44 g, 2.60 mmol) in 1,4-dioxane (30 ml), a 2N aqueous sodium hydroxide solution (3 ml) was added and stirred for 2 hours. The resulting mixture was mixed with water and washed with ethyl acetate; the aqueous layer was rendered acidic by the addition of dilute hydrochloric acid and extracted with ethyl acetate. The organic layer was dried over anhydrous magnesium sulfate and evaporated to remove the solvent under reduced pressure, giving crude Z-Phe(3-tBu-4-benzyloxy)-OH (1.35 g).

To a solution of the thus obtained crude Z-Phe(3-tBu-4-benzyloxy)-OH (1.35 g) in THF (7 ml), under cooling with ice, methyl iodide (1.3 ml, 20.8 mmol) was added and then sodium hydride (60% in oil, 312 mg, 7.8 mmol) was added slowly, followed by stirring for 21 hours at room temperature. The resulting mixture was mixed with water, rendered acidic by the addition of dilute hydrochloric acid, and extracted with ethyl acetate. The organic layer was washed with saturated brine, dried over anhydrous magnesium sulfate and evaporated to remove the solvent under reduced pressure, giving crude Z-N-Me-Phe(3-tBu-4-benzyloxy)-OH (1.60 g).

To a solution of the thus obtained crude Z-N-Me-Phe(3-tBu-4-benzyloxy)-OH (1.60 g) in THF (25 ml), under cooling with ice, ethyl chloroformate (0.27 ml, 2.86 mmol) and NMM (0.31 ml, 2.86 mmol) were added in that order. The mixture was stirred for 15 min. and further stirred for another 15 min. while bubbling gaseous ammonia therein. The resultant mixture was left standing at room temperature, diluted with ethyl acetate and washed with water and then saturated brine. The organic layer was dried over anhydrous magnesium sulfate and evaporated to remove the solvent under reduced pressure; the thus obtained residue was subjected to silica gel column chromatography (developing solvent: ethyl acetate:n-hexane=2:1) to give Z-N-Me-Phe(3-tBu-4-benzyloxy)-NH$_2$ (1.08 g, 88%, in 3 steps).

$^1$H-NMR (CDCl$_3$): δ 1.37 (9H, s), 2.87 (3H, s), 2.86-2.99 (1H, m), 3.21-3.35 (1H, m), 4.73-4.95 (1H, m), 5.06 (2H, s), 5.09 (2H, s), 5.67, 5.83 and 6.13 (3/2H, brs), 6.78-7.47 (27/2H, m)

(5) Synthesis of N-Me-Tyr(3-tBu)-NH$_2$

To a solution of Z-N-Me-Phe(3-tBu-4-benzyloxy)-NH$_2$ (1.08 g, 2.28 mmol) in methanol (20 ml), 10% palladium/carbon (100 mg) was added and stirred in a hydrogen atmosphere at room temperature overnight. The mixture was filtered and the filtrate was concentrated under reduced pressure; the thus obtained residue was subjected to silica gel column chromatography (developing solvent: chloroform:methanol:aqueous ammonia=100:10:1) to give N-Me-Tyr(3-tBu)-NH$_2$ (0.55 g, 96%).

$^1$H-NMR (CDCl$_3$): δ 1.40 (9H, s), 2.31 (3H, s), 2.63 (1H, dd, J=14.7, 10.7 Hz), 3.10-3.19 (2H, m), 5.24 (1H, brs), 5.38 (1H, brs), 6.63 (1H, d, J=7.9 Hz), 6.91 (1H, dd, J=7.9, 1.8 Hz), 7.05 (1H, brs), 7.10 (1H, d, J=1.8 Hz)

(6) Synthesis of Z-N-Me-Val-N-Me-Tyr(3-tBu)-NH$_2$

To a solution of Z-N-Me-Val-OH (700 mg, 2.64 mmol), N-Me-Tyr(3-tBu)-NH$_2$ (0.55 g, 2.20 mmol) and CMPI (674 mg 2.64 mmol) in THF (22 ml), under cooling with ice, TEA (0.61 ml) was added and stirred at room temperature overnight. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: ethyl acetate:n-hexane=3:2) to give Z-N-Me-Val-N-Me-Tyr(3-tBu)-NH$_2$ (0.98 g, 90%).

$^1$H-NMR (CDCl$_3$):(four rotamers) δ 0.07, 0.32, 0.63, 0.74, 0.79, 0.81, 0.84 and 0.89 (6H, d, J=6.3-6.6 Hz), 1.30, 1.33, 1.37 and 1.39 (9H, s), 2.13-2.33 (1H, m), 2.34, 2.41, 2.78, 2.87 and 2.98 (6H, s), 2.79-3.22 (2H, m), 4.40 and 4.32 (1H, d, J=10.6 Hz), 4.60-5.43 (5H, m), 5.96 (1H, brs), 6.23-7.12 (3H, m), 7.26-7.47 (5H, m)

(7) Synthesis of N-Me-Val-N-Me-Tyr(3-tBu)-NH$_2$ (Intermediate I-b3 in the following Tables)

A mixture of Z-N-Me-Val-N-Me-Tyr(3-tBu)-NH$_2$ (0.98 g, 1.97 mmol) and 20% palladium hydroxide/carbon (0.10 g) in methanol (20 ml) was stirred at room temperature in a hydrogen atmosphere for 1.5 hours. The reaction mixture was filtered and the filtrate was concentrated under reduced pressure; the thus obtained residue was subjected to silica gel column chromatography (developing solvent: chloroform: methanol:aqueous ammonia=100:10:1) to give N-Me-Val-N-Me-Tyr(3-tBu)-NH$_2$ (0.71 g, 99%).

$^1$H-NMR (CDCl$_3$):(two rotamers) δ 0.35, 0.71, 0.92 and 0.96 (6H, d, J=6.9 Hz), 1.36 and 1.37 (9H, s), 1.73-1.81 and 2.03-2.17 (1H, m), 1.74 and 2.23 (3H, s), 2.64 (1H, d, J=9.2 Hz), 2.90-3.04 (1H, m), 2.93 and 3.00 (3H, s), 3.19 and 4.60 (1H, dd, J=14.7, 5.8 and 10.7, 3.8 Hz), 5.29, 5.32 and 6.06 (2H, brs), 5.59 (1H, dd, J=10.4, 5.8 Hz), 6.54 and 6.60 (1H, d, J=7.9 Hz), 6.79 and 6.93 (1H, dd, J=7.9, 2.0 and 1.7 Hz), 7.01 and 7.07 (1H, d, J=2.0 and 1.7 Hz), 8.10 (1H, brs)

(8) Synthesis of Z-Phe(4-F)-N-Me-Val-N-Me-Tyr(3-tBu)-NH$_2$

To a solution of Z-Phe(4-F)—OH (1.09 g, 3.44 mmol), N-Me-Val-N-Me-Tyr(3-tBu)-NH$_2$ (1.04 g, 2.87 mmol) and CMPI (878 mg, 3.44 mmol) in THF (30 ml), TEA (0.96 ml, 6.88 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: n-hexane:ethyl acetate=1:3) to give Z-Phe(4-F)-N-Me-Val-N-Me-Tyr(3-tBu)-NH$_2$ (1.73 g, 91%).

$^1$H-NMR (CDCl$_3$):(two rotamers) δ 0.57, 0.73, 0.75 and 0.90 (6H, d, J=6.3-6.6 Hz), 1.33 and 1.39 (9H, s), 2.18-3.43 (5H, m), 2.40 and 3.03 (3H, s), 2.74 and 3.01 (3H, s), 4.62-5.49 (7H, m), 5.95 (1H, brs), 6.44 (1H, d, J=7.9 Hz), 6.57-7.35 (12H, m)

(9) Synthesis of Phe(4-F)-N-Me-Val-N-Me-Tyr(3-tBu)-NH$_2$

A mixture of Z-Phe(4-F)-N-Me-Val-N-Me-Tyr(3-tBu)-NH$_2$ (1.73 g, 2.61 mmol) and 10% palladium/carbon (340 mg) in methanol (50 ml) was stirred at room temperature in a hydrogen atmosphere for 17 hours. The reaction mixture was filtered and the filtrate was concentrated under reduced pressure; the thus obtained residue was subjected to silica gel column chromatography (developing solvent: chloroform: methanol:aqueous ammonia=100:10:1) to give Phe(4-F)-N-Me-Val-N-Me-Tyr(3-tBu)-NH$_2$ (1.25 g, 91%). EI-MS:528 (M$^+$)

$^1$H-NMR (CDCl$_3$):(two rotamers) δ 0.50, 0.76, 0.79 and 0.93 (6H, d, J=6.3-6.9 Hz), 1.34 and 1.39 (9H, s), 2.19-2.95 (5H, m), 2.50 and 3.03 (3H, s), 2.81 and 3.02 (3H, s), 3.17 and 3.34 (1H, dd, J=15.2, 5.9 and 13.9, 6.9 Hz), 3.66 and 3.84 (1H, dd, J=8.9, 4.6 and 8.6, 4.6 Hz), 4.91 and 5.07 (1H, d, J=10.6 Hz), 5.07, 5.19, 5.30, 5.98 and 6.64 (2H, brs), 5.49 (1H, dd, J=10.6, 5.9 Hz), 6.35 and 6.62 (1H, d, J=7.9 Hz), 6.74 (2/3H, dd, J=7.9, 1.7 Hz), 6.95-7.11 (19/3H, m)

EXAMPLE 2

Phe(4-Cl)-N-Me-Val-N-Me-Tyr(3-tBu)-NH$_2$

(1) Synthesis of Boc-Phe(4-Cl)-N-Me-Val-N-Me-Tyr(3-tBu)-NH$_2$

To a solution of Boc-Phe(4-Cl)-OH (354 mg, 1.18 mmol), N-Me-Val-N-Me-Tyr(3-tBu)-NH$_2$ (0.33 g, 0.908 mmol) and CMPI (301 mg, 1.18 mmol) in THF (8 ml), TEA (0.38 ml, 2.72 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: chloroform:methanol:aqueous ammonia=40:1:0.05) to give Boc-Phe(4-Cl)-N-Me-Val-N-Me-Tyr(3-tBu)-NH$_2$ (0.45 g, 77%).

(2) Phe(4-Cl)-N-Me-Val-N-Me-Tyr(3-tBu)-NH$_2$

To a solution of Boc-Phe(4-Cl)-N-Me-Val-N-Me-Tyr(3-tBu)-NH$_2$ (0.45 g, 0.697 mmol) in methylene chloride (4 ml), TFA (3 ml) was added, stirred for 20 min. and evaporated to remove the solvent under reduced pressure. The thus obtained residue was mixed with a saturated aqueous NaHCO$_3$ solution, and extracted with methylene chloride. The organic layer was dried over anhydrous sodium sulfate and evaporated to remove the solvent under reduced pressure; the thus obtained residue was subjected to silica gel column chromatography (developing solvent: chloroform:methanol:aqueous ammonia=30:1:0.1) to give Phe(4-Cl)-N-Me-Val-N-Me-Tyr(3-tBu)-NH$_2$ (355 mg, 93%). EI-MS:544 and 546 (M$^+$)

$^1$H-NMR (CDCl$_3$):(two rotamers) δ 0.49, 0.75, 0.78 and 0.93 (6H, d, J=6.3-6.9 Hz), 1.34 and 1.38 (9H, s), 2.10-2.92 (5H, m), 2.50 and 3.04 (3H, s), 2.80 and 3.01 (3H, s), 3.13 and 3.33 (1H, dd, J=15.2, 5.9 and 13.9, 6.9 Hz), 3.67 and 3.85 (1H, dd, J=8.9, 5.0 and 8.6, 5.0 Hz), 4.90 and 5.06 (1H, d, J=10.6 Hz), 5.33, 5.41, 5.99 and 6.61 (2H, brs), 5.49 (1H, dd, J=10.6, 5.9 Hz), 6.37 and 6.63 (1H, d, J=7.9 Hz), 6.72 and 6.98 (1H, dd, J=7.9, 1.7 Hz), 7.07-7.10 (3H, m), 7.25-7.31 (2H, m)

EXAMPLE 3

Phe(3,4-F$_2$)—N-Me-Val-N-Me-Tyr(3-tBu)-NH$_2$ (1) Synthesis of Fmoc-Phe(3,4-F$_2$)—N-Me-Val-N-Me-Tyr(3-tBu)-NH$_2$ To a solution of Fmoc-Phe(3,4-F$_2$)—OH (500 mg, 1.18 mmol), N-Me-Val-N-Me-Tyr(3-tBu)-NH$_2$ (0.33 g, 0.908 mmol) and CMPI (301 mg, 1.18 mmol) in THF (8 ml), TEA (0.38 ml, 2.72 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: chloroform:methanol:aqueous ammonia=60:1:0.05), giving Fmoc-Phe(3,4-F$_2$)—N-Me-Val-N-Me-Tyr(3-tBu)-NH$_2$ (0.56 g, 80%).

(2) Synthesis of Phe(3,4-F$_2$)—N-Me-Val-N-Me-Tyr(3-tBu)-NH$_2$

To a solution of Fmoc-Phe(3,4-F$_2$)—N-Me-Val-N-Me-Tyr(3-tBu)-NH$_2$ (0.55 g, 0.715 mmol) in methylene chloride (5 ml), diethylamine (5 ml) was added, stirred for 4 hours and then evaporated to remove the solvent under reduced pressure. The thus obtained residue was subjected to silica gel column chromatography (developing solvent: chloroform:ethanol:aqueous ammonia=60:1:0.1) to give Phe(3,4-F$_2$)—N-Me-Val-N-Me-Tyr(3-tBu)-NH$_2$ (381 mg, 97%).

EI-MS: 546 (M$^+$)

$^1$H-NMR (CDCl$_3$):(two rotamers) δ 0.51, 0.74, 0.79 and 0.93 (6H, d, J=6.3-6.9 Hz), 1.33 and 1.38 (9H, s), 2.10-2.93 (5H, m), 2.51 and 3.03 (3H, s), 2.83 and 3.01 (3H, s), 3.17 and 3.33 (1H, dd, J=14.8, 5.9 and 13.9, 6.6 Hz), 3.66 and 3.84 (1H, dd, J=8.4, 5.0 and 8.6, 4.3 Hz), 4.88 and 5.07 (1H, d, J=10.6 Hz), 5.41, 5.9 (1H, brs), 5.41-5.51 (1H, m), 6.43 and 6.64 (1H, d, J=7.9 Hz), 6.75 (2/5H, dd, J=7.9, 1.7 Hz), 6.84-7.16 (28/5H, m)

EXAMPLE 4

Phe(3-F)-N-Me-Val-N-Me-Tyr(3-tBu)-NH$_2$ (1) Synthesis of Boc-Phe(3-F)-N-Me-Val-N-Me-Tyr(3-tBu)-NH$_2$ To a solution of Boc-Phe(3-F)—OH (0.20 g, 0.706 mmol), N-Me-Val-N-Me-Tyr(3-tBu)-NH$_2$ (0.21 g, 0.578 mmol) and CMPI (0.20 g, 0.783 mmol) in THF (6 ml), TEA (0.30 ml, 2.15 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: chloroform:methanol:aqueous ammonia=60:1:0.05) to give Boc-Phe(3-F)-N-Me-Val-N-Me-Tyr(3-tBu)-NH$_2$ (0.33 g, 91%).

(2) Synthesis of Phe(3-F)-N-Me-Val-N-Me-Tyr(3-tBu)-NH$_2$

To a solution of Boc-Phe(3-F)-N-Me-Val-N-Me-Tyr(3-tBu)-NH$_2$ (0.33 g, 0.525 mmol) in methylene chloride (3 ml), TFA (1.5 ml) was added, stirred for 15 min. and then evaporated to remove the solvent under reduced pressure. The residue was mixed with methylene chloride, washed with a saturated aqueous NaHCO$_3$ solution, dried over anhydrous magnesium sulfate and evaporated to remove the solvent under reduced pressure. The thus obtained residue was subjected to silica gel column chromatography (developing solvent: chloroform:methanol:aqueous ammonia=40:1:0.1) to give Phe(3-F)-N-Me-Val-N-Me-Tyr(3-tBu)-NH$_2$ (241 mg, 87%).

EI-MS:528(M$^+$)

$^1$H-NMR (CDCl$_3$):(two rotamers) δ 0.51, 0.73, 0.78 and 0.93 (6H, d, J=6.3-6.6 Hz), 1.33 and 1.38 (9H, s), 2.10-2.96 (5H, m), 2.46 and 3.03 (3H, s), 2.78 and 3.01 (3H, s), 3.16 and 3.35 (1H, dd, J=14.8, 5.9 and 13.9, 6.6 Hz), 3.70 and 3.90 (1H, dd, J=8.3, 5.6 and 8.6, 5.0 Hz), 4.89 and 5.06 (1H, d, J=10.6 Hz), 5.42, 5.99 (1H, brs), 5.43-5.52 (1H, m), 6.41 and 6.64 (1H, d, J=7.9 Hz), 6.72 (2/5H, dd, J=7.9, 1.7 Hz), 6.83-6.99 (18/5H, m), 7.10 (2/5H, d, J=1.7 Hz), 7.22-7.33 (1H, m)

EXAMPLE 5

Phe(2-F)-N-Me-Val-N-Me-Tyr(3-tBu)-NH$_2$ (1) Synthesis of Boc-Phe(2-F)-N-Me-Val-N-Me-Tyr(3-tBu)-NH$_2$ To a solution of Boc-Phe(2-F)-OH (0.20 g, 0.706 mmol), N-Me-Val-N-Me-Tyr(3-tBu)-NH$_2$ (0.21 g, 0.578 mmol) and CMPI (0.20 g, 0.783 mmol) in THF (6 ml), TEA (0.30 ml, 2.15 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: chloroform:methanol:aqueous ammonia=60:1:0.05) to give Boc-Phe(2-F)-N-Me-Val-N-Me-Tyr(3-tBu)-NH$_2$ (0.33 g, 91%).

(2) Synthesis of Phe(2-F)-N-Me-Val-N-Me-Tyr(3-tBu)-NH$_2$

To a solution of Boc-Phe(2-F)-N-Me-Val-N-Me-Tyr(3-tBu)-NH$_2$ (0.33 g, 0.525 mmol) in methylene chloride (3 ml), TFA (1.5 ml) was added, stirred for 15 min. and then evaporated to remove the solvent under reduced pressure. The residue was mixed with methylene chloride, washed with a saturated aqueous NaHCO$_3$ solution, dried over anhydrous magnesium sulfate and evaporated to remove the solvent under reduced pressure. The thus obtained residue was subjected to silica gel column chromatography (developing solvent: chloroform:methanol:aqueous ammonia=40:1:0.1) to give Phe(2-F)-N-Me-Val-N-Me-Tyr(3-tBu)-NH$_2$ (235 mg, 85%).

EI-MS:528 (M$^+$)

$^1$H-NMR (CDCl$_3$):(two rotamers) δ 0.45, 0.71, 0.79 and 0.93 (6H, d, J=5.9-6.6 Hz), 1.31 and 1.38 (9H, s), 2.10-2.89 (5H, m), 2.47 and 3.06 (3H, s), 2.76 and 3.01 (3H, s), 3.14 and 3.34 (1H, dd, J=14.3, 5.9 and 13.9, 6.6 Hz), 3.79 and 3.95 (1H, dd, J=8.4, 5.0 and 8.6, 4.3 Hz), 4.88 and 5.06 (1H, d, J=10.6

Hz), 5.37, 5.99 (1H, brs), 5.41-5.51 (1H, m), 6.43 (3/5H, d, J=7.9 Hz), 6.56 (2/5H, brs), 6.60-6.71 (1H, m), 6.92-7.29 (6H, m)

EXAMPLE 6

TFA salt of Phe(4-F)-N-Me-Val-N-Me-Tyr(3-tBu)-NHSO$_2$Me (1) Synthesis of Z-N-Me-Phe(3-tBu-4-benzyloxy)-NHSO$_2$Me To a solution of crude Z-N-Me-Phe(3-tBu-4-benzyloxy)-OH (0.95 g, 2.0 mmol), WSCI.HCl (0.77 g, 3.99 mmol) and methanesulfonamide (0.29 g, 3.0 mmol) in DMF (15 ml), DMAP (0.49 g, 0.99 mmol) was added under cooling with ice and stirred at room temperature overnight. The mixture was mixed with water and then with 2N hydrochloric acid, extracted with ethyl acetate. The organic layer was washed with saturated brine, dried over anhydrous magnesium sulfate and evaporated to remove the solvent under reduced pressure. The thus obtained residue was subjected to silica gel column chromatography (developing solvent: ethyl acetate:n-hexane 2:1) to give the titled compound (0.83 g, 75%).
$^1$H-NMR (CDCl$_3$): δ 1.36 (9H, s), 2.80 (s, 3H), 2.97-3.30 (m, 2H), 3.21 (s, 3H), 4.60-4.74 (m, 1H), 5.08 (s, 2H), 5.13 (s, 2H), 6.81 (d, 1H, J=8.2 Hz), 6.86-7.13 (m, 2H), 7.20-7.46 (m, 10H), 9.0 (brs, 1H)

(2) Synthesis of Z-N-Me-Val-N-Me-Tyr(3-t-Bu)-NHSO$_2$Me

A mixture of Z-N-Me-Tyr(3-tBu-4-benzyloxy)-NHSO$_2$Me (0.80 g, 1.45 mmol) and 20% palladium hydroxide/carbon (0.09 g) in methanol (15 ml) was stirred at room temperature overnight in a hydrogen atmosphere. The reaction mixture was filtered and the filtrate was evaporated to remove the solvent under reduced pressure, giving crude N-Me-Tyr(3-t-Bu)-NHSO$_2$Me (0.53 g).
To a solution of the crude N-Me-Tyr(3-t-Bu)-NHSO$_2$Me (0.51 g, 1.43 mmol), Z-N-Me-Val-OH 0.49 g, 1.86 mmol) and CMPI (0.51 g, 2.00 mmol) in THF (10 ml), TEA (0.60 ml, 4.29 mmol) was added under cooling with ice and stirred at room temperature overnight. The reaction mixture was mixed with water, rendered acidic by the addition of 2N hydrochloric acid and extracted with ethyl acetate. The organic layer was washed with saturated brine, dried over magnesium sulfate and evaporated to remove the solvent under reduced pressure; the thus obtained residue was subjected to silica gel column chromatography (developing solvent: ethyl acetate: n-hexane=2:3 containing 0.5% acetic acid) to give the titled compound (0.70 g, in 2 steps, 85%).

(3) Synthesis of Boc-Phe(4-F)-N-Me-Val-N-Me-Tyr (3-t-Bu)-NHSO$_2$Me

A mixture of Z-N-Me-Val-N-Me-Tyr(3-t-Bu)-NHSO$_2$Me (0.65 g, 1.13 mmol) and 20% palladium hydroxide/carbon (0.09 g) in methanol (10 ml) was stirred at room temperature for 2.5 hours in a hydrogen atmosphere. The reaction mixture was filtered and the filtrate was evaporated to remove the solvent under reduced pressure, giving crude N-Me-Val-N-Me-Tyr(3-t-Bu)-NHSO$_2$Me (0.50 g).
To a solution of the above crude compound (0.48 g, 1.09 mmol), Boc-Phe(4-F)-OH 0.40 g, 1.41 mmol) and CMPI (0.39 g, 1.53 mmol) in THF (8 ml), TEA (0.46 ml, 3.27 mmol) was added under cooling with ice and stirred at room temperature overnight for 22 hours. The reaction mixture was mixed with water, rendered acidic by the addition of 10% aqueous citric acid solution and extracted with ethyl acetate. The organic layer was washed with saturated brine, dried over magnesium sulfate and evaporated to remove the solvent under reduced pressure; the thus obtained residue was subjected to silica gel column chromatography (developing solvent: ethyl acetate:n-hexane=2:3 containing 5% acetic acid) to give the titled compound (0.50 g, in 2 steps, 65%).

(4) Synthesis of Phe(4-F)-N-Me-Val-N-Me-Tyr(3-t-Bu)-NHSO$_2$Me TFA salt

To a solution of Boc-Phe(4-F)-N-Me-Val-N-Me-Tyr(3-t-Bu)-NHSO$_2$Me (208 mg, 0.294 mmol) in methylene chloride (6 ml), TFA (3 ml) was added and stirred for 1.5 hours. The reaction mixture was evaporated under reduced pressure; the thus obtained residue was dissolved in a mixture of acetonitrile/water (1:10) (80 ml), which mixture containing 0.1% TFA, and lyophilized to give the titled compound (0.20 g, 94%).
EI-MS:606 (M$^+$)
$^1$H-NMR (DMSO-d$_6$):(three rotamers) δ 0.02 (d, 3/5H, J=5.9 Hz), 0.22 (d, 3/5H, J=5.9 Hz), 0.62 (d, 3/5H, J=7.6 Hz), 0.68 (d, 3/5H, J=6.6 Hz), 0.77 (d, 9/5H, J=6.6 Hz), 0.89 (d, 9/5H, J=6.3 Hz), 1.28 (s, 27/5H), 1.31 (s, 9/5H), 1.35 (s, 9/6H), 1.86-2.03 (m, 2/7H), 2.15-2.28 (m, 5/7H), 2.5-3.4 (m, 10H), 4.35-4.62 (m, 1H), 4.80-5.02 (1H), 5.11-5.42 (m, 1H), 6.55-7.18 (m, 7H), 8.0-8.2 (m, 3H), 8.98-9.06 (m, 1H), 11.2 (brs, 1H)

EXAMPLE 7

Phe(4-F)-N-Me-Val-N-Me-Tyr(3-tBu)-NHOMe (1) Synthesis of Z-N-Me-Phe(4-benzyloxy-3-tBu)-NHOMe To a solution of Z-N-Me-Phe(4-benzyloxy-3-tBu)-OH (3.8 g, 7.99 mmol) in THF (50 ml), ethyl chloroformate (0.85 ml, 8.78 mmol) was added under cooling with ice and then NMM (0.97 ml, 8.78 mmol) was slowly added dropwise. After stirring for 1 hour, MeONH$_2$ (1.0 g, 12.0 mmol) and TEA 2.23 ml (16.0 mmol) were added to the mixture, followed by stirring for 2 hours at room temperature. The mixture was mixed with water, and extracted with ethyl acetate. The organic layer was dried over magnesium sulfate and evaporated to remove the solvent under reduced pressure. The thus obtained residue was subjected to silica gel column chromatography (developing solvent: ethyl acetate:n-hexane=1:2) to give the titled compound (2.7 g, 67%).
$^1$H-NMR (CDCl$_3$): δ 1.39 (9H, s), 2.95 (3H, s), 2.99 (1H, m), 3.24 (1H, m), 3.64 (3H, s), 4.7 (1H, m), 5.1 (4H, d), 6.8-7.5 (13H, m), 9.06 (1H, s)

(2) Synthesis of N-Me-Tyr(3-tBu)-NHOMe

To a solution of Z-N-Me-Phe(4-benzyloxy-3-tBu)-NHOMe (2.7 g, 5.36 mmol) in MeOH (30 ml), palladium hydroxide/carbon (675 mg) was added and stirred in a hydrogen atmosphere for 2 hours. Insoluble matters were removed by filtration with Celite and the filtrate was concentrated under reduced pressure. The thus obtained residue was subjected to silica gel column chromatography (developing solvent: methylene chloride:methanol=20:1) to give the titled compound (1.24 g, 82%).

¹H-NMR (CDCl₃): δ 1.43 (9H, s), 2.45 (3H, s), 2.92 (2H, m), 3.12 (1H, m), 3.59 (3H, s), 6.77 (1H, d, J=9.4 Hz), 6.95 (1H, dd, J=2.8, 3.4 Hz), 7.13 (1H, d, J=3.15 Hz)

(3) Synthesis of Z-N-Me-Val-N-Me-Tyr(3-tBu)-NHOMe

To a solution of N-Me-Tyr(3-tBu)-NHOMe (1.24 g, 4.42 mmol), Z-N-Me-Val-OH (1.76 g, 6.63 mmol) and CMPI (1.7 g, 6.63 mmol) in THF (30 ml), TEA (1.23 ml, 8.84 mmol) was added and stirred overnight. The mixture was mixed with water, extracted with ethyl acetate. The organic layer was dried over anhydrous sodium sulfate and evaporated to remove the solvent under reduced pressure. The thus obtained residue was subjected to silica gel column chromatography (developing solvent: ethyl acetate:n-hexane=1:1) to give the titled compound (1.32 g, 57%).

¹H-NMR (CDCl₃): δ 0.43 (3H, m), 0.80 (3H, m), 1.36 (9H, s), 3.02 (9H, m), 3.65 (3H, s), 4.4 (1H, m), 5.1 (3H, m), 6.4-7.4 (8H, m)

(4) Synthesis of Boc-Phe(4-F)-N-Me-Val-N-Me-Tyr(3-tBu)-NHOMe

To a solution of Z-N-Me-Val-N-Me-Tyr(3-tBu)-NHOMe (1.23 g, 2.33 mmol) in MeOH (20 ml), palladium hydroxide/carbon (350 mg) was added and stirred in a hydrogen atmosphere for 1 hour. Insoluble matters were removed by filtration with Celite and the filtrate was concentrated under reduced pressure to give crude N-Me-Val-N-Me-Tyr(3-tBu)-NHOMe (0.91 g).

A solution of the thus obtained crude compound (0.98 g, 2.5 mmol), Boc-Phe(4-F)-OH (0.92 g, 3.25 mmol) and CMPI (0.83 g, 3.25 mmol) in THF 20 ml, TEA (0.52 ml, 3.75 mmol) was added and stirred overnight. The mixture was mixed with water, extracted with ethyl acetate. The organic layer was dried over anhydrous sodium sulfate and evaporated to remove the solvent under reduced pressure. The thus obtained residue was subjected to silica gel column chromatography (developing solvent: ethyl acetate:n-hexane=1:2), giving the titled compound (972 mg, 56%).

(6) Synthesis of Phe(4-F)-N-Me-Val-N-Me-Tyr(3-tBu)-NHOMe

To a solution of Boc-Phe(4-F)-N-Me-Val-N-Me-Tyr(3-tBu)-NHOMe (972 mg, 1.508 mmol) in methylene chloride (10 ml), TFA (7 ml) was added and stirred for 30 min. The mixture was concentrated under reduced pressure and the thus obtained residue was subjected to silica gel column chromatography (developing solvent: methylene chloride:methanol=20:1), giving the titled compound (288 mg, 34%).
EI-MS:558 (M⁺)

¹H-NMR (CDCl₃): δ 0.42 (3H, d, J=13.5 Hz), 0.79 (3H, d, J=13.2 Hz), 1.33 (9H, s), 2.10 (1H, m), 2.60 (1H, m), 2.90 (2H, m), 2.91 (3H, s), 3.07 (3H, s), 3.28 (1H, m), 3.68 (3H, s), 3.91 (1H, m), 4.82 (1H, d, J=10.7 Hz), 5.13 (1H, m), 6.60 (1H, d, J=10.4 Hz), 6.89 (1H, m), 7.0-7.3 (5H, m), 9.1 (1H, m)

EXAMPLE 8

2-((2-amino-3-(4-fluorophenyl)propionyl)-N-methylamino)-3-methylbutyric acid 2-(3-tert-butyl-4-hydroxyphenyl)-1-(2-pyridylcarbamoyl)ethylamide (1) Synthesis of N-benzyloxycarbonyl-3-tert-butyl-4-hydroxyphenylalanyl (2-pyridyl)amide To a solution of Z-Tyr(3-tBu)-OH (3.04 g, 8.19 mmol) in THF (8.2 ml), under cooling with ice N,N-carbonyldiimidazole (1.59 g, 9.83 mmol) was added and stirred for 1 hour. To the mixture, 2-aminopyridine (925 mg, 9.83 mmol) was then added and stirred for 2 hours under cooling with ice and then further 6.5 hours at room temperature. The mixture was mixed with water and extracted with ethyl acetate. The organic layer was washed with saturated brine, dried over anhydrous magnesium sulfate and evaporated to remove the solvent under reduced pressure. The thus obtained residue was subjected to silica gel column chromatography (developing solvent: ethyl acetate:n-hexane=1:2), giving the titled compound (2.16 g, 59%).

¹H-NMR (CDCl₃): δ 1.24 (9H, s), 2.95-3.20 (2H, m), 4.45-4.60 (1H, m), 5.11 (2H, dd, J=17.5, 12.2 Hz), 6.53 (1H, d, J=7.9 Hz), 6.85 (1H, d, J=7.9 Hz), 6.95-7.15 (2H, m), 7.32 (5H, brs), 7.67-7.73 (1H, m), 8.15-8.25 (2H, m)

(2) Synthesis of 3-tert-butyl-4-hydroxyphenylalanyl (2-pyridyl)amide

To a solution of N-benzyloxycarbonyl-3-tert-butyl-4-hydroxyphenylalanyl (2-pyridyl)amide (2.16 g, 4.83 mmol) in methanol (160 ml), 10% palladium/carbon (400 mg) was added and stirred in a hydrogen atmosphere at room temperature overnight. After filtering the reaction mixture, the filtrate was evaporated to remove the solvent under reduced pressure and the thus obtained residue was subjected to silica gel column chromatography (developing solvent: methanol:aqueous ammonia:methylene chloride=10:1:100), giving the titled compound (1.48 g, 98%).

¹H-NMR (CDCl₃): δ 1.36 (9H, s), 2.72-3.23 (2H, m), 3.67-3.72 (1H, m), 6.62 (1H, d, J=7.9 Hz), 6.85-6.88 (1H, m), 6.95-7.20 (2H, m), 7.70-7.77 (1H, m), 8.29-8.39 (2H, m)

(3) Synthesis of 2-(N-benzyloxycarbonyl-N-methylamino)-3-methylbutyric acid 2-(3-tert-butyl-4-hydroxyphenyl)-1-(2-pyridylcarbamoyl)ethylamide To a solution of 3-tert-butyl-4-hydroxyphenylalanyl (2-pyridyl)amide (1.48 g, 4.73 mmol), Z-N-Me-Val-OH (1.63 g, 6.15 mmol) and CMPI (1.57 g, 6.15 mmol) in THF 30 ml, TEA (1.5 ml, 10.88 mmol) was added under cooling with ice and stirred for 3 hours under cooling with ice. The mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate:n-hexane=1:2), giving the titled compound (1.74 g, 65%).

¹H-NMR (CDCl₃): δ 0.70-0.95 (6H, m), 1.26 (9H, s), 2.20-2.35 (1H, m), 2.70-3.10 (5H, m), 4.00-4.20 (1H, m), 4.65-4.80 (1H, m), 5.17 (2H, brs), 6.44 (1H, d, J=7.6 Hz), 6.60-6.85 (1H, m), 6.95-7.10 (2H, m), 7.36 (5H, brs), 7.60-7.75 (1H, m), 8.10-8.25 (2H, m)

(4) Synthesis of 3-methyl-2-methylaminobutyric acid 2-(3-tert-butyl-4-hydroxyphenyl)-1-(2-pyridylcarbamoyl)ethylamide To a solution of 2-(N-benzyloxycarbonyl-N-methylamino)-3-methylbutyric acid 2-(3-tert-butyl-4-hydroxyphenyl)-1-(2-pyridylcarbamoyl)ethylamide (1.74 g, 3.10 mmol) in methanol (50 ml), 10% palladium carbon (300 mg) was added and stirred in a hydrogen atmosphere at room temperature overnight. The reaction mixture was filtered and the filtrate was concentrated under reduced pressure. The thus obtained residue was subjected to silica gel column chromatography (developing solvent: methanol:aqueous ammonia:methylene chloride=5:0.1:100), giving the titled compound (1.30 g, 98%).

$^1$H-NMR (CDCl$_3$): δ 0.69 (3H, d, J=6.9 Hz), 0.85 (3H, d, J=6.9 Hz), 1.31 (9H, s), 1.95-2.11 (1H, m), 2.36 (3H, s), 2.81 (1H, d, J=4.6 Hz), 2.99-3.18 (2H, m), 4.73-4.81 (1H, m), 6.59 (1H, d, J=7.9 Hz), 6.94 (1H, dd, J=7.9, 2.0 Hz), 7.00-7.10 (2H, m), 7.65-7.72 (1H, m), 7.80 (1H, d, J=7.9 Hz), 8.18 (1H, d, J=8.6 Hz), 8.25 (1H, d, J=4.6 Hz),

(5) Synthesis of 2-((2-butoxycarbonylamino-3-(4-fluorophenyl)propionyl)-N-methylamino)-3-methylbutyric acid 2-(3-tert-butyl-4-hydroxyphenyl)-1-(2-pyridylcarbamoyl)ethylamide To a solution of 3-methyl-2-methylaminobutyric acid 2-(3-tert-butyl-4-hydroxyphenyl)-1-(2-pyridylcarbamoyl)ethylamide (1.25 g, 2.93 mmol), Boc-Phe(4-F)-OH (1.08 g, 3.81 mmol) and CMPI (973 mg, 3.81 mmol) in THF 19 ml, TEA (0.94 ml, 6.74 mmol) was added under cooling with ice and stirred for 4 hours under cooling with ice. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate:n-hexane=1:1), giving the titled compound (1.72 g, 85%).

$^1$H-NMR (CDCl$_3$): δ 0.65-1.02 (6H, m), 1.26 (9H, s), 1.34 (9H, s), 2.20-2.40 (1H, m), 2.75-3.15 (4H, m), 2.89 (3H, s), 4.20-4.35 (1H, m), 4.70-5.00 (2H, m), 6.61 (1H, d, J=7.9 Hz), 6.75-7.20 (7H, m), 7.60-7.80 (1H, m), 8.20-8.30 (2H, m)

(6) 2-((2-amino-3-(4-fluorophenyl)propionyl)-N-methylamino)-3-methylbutyric acid 2-(3-tert-butyl-4-hydroxyphenyl)-1-(2-pyridylcarbamoyl)ethylamide To a solution of 2-((2-butoxycarbonylamino-3-(4-fluorophenyl)propionyl)-N-methylamino)-3-methylbutyric acid 2-(3-tert-butyl-4-hydroxyphenyl)-1-(2-pyridylcarbamoyl)ethylamide (1.67 g, 2.41 mmol) in methylene chloride (30 ml), TFA (5 ml) was added and stirred at room temperature for 1.5 hours. The reaction mixture was evaporated under reduced pressure; the thus obtained residue was mixed with chloroform, washed with a saturated aqueous NaHCO$_3$ solution and saturated brine, dried over anhydrous magnesium sulfate and evaporated to remove the solvent under reduced pressure. The thus obtained residue was subjected to silica gel column chromatography (developing solvent: methanol:aqueous ammonia:methylene chloride=3:0.1:100), giving the titled compound (370 mg).

EI-MS:591 (M$^+$)

$^1$H-NMR (CDCl$_3$): δ 0.74 (2H, d, J=6.9 Hz), 0.77 (1H, d, J=6.9 Hz), 0.88 (1H, d, J=6.3 Hz), 0.95 (2H, d, J=6.3 Hz), 1.25 (9H, s), 2.24-2.44 (1H, m), 2.50-3.25 (4H, m), 2.78 (2.4H, s), 2.85 (0.6H, s), 3.55-3.65 (0.8H, m), 3.80-3.90 (0.2H, m), 4.00 (0.8H, d, J=10.9 Hz), 4.36 (0.2H, d, J=10.9 Hz), 4.65-4.80 (0.2H, m), 4.90-5.00 (0.8H, m), 6.55-7.20 (8H, m), 7.65-7.75 (1H, m), 8.15-8.25 (2H, m)

EXAMPLE 9

N-(2-(2-((2-amino-3-(4-fluorophenyl)propionyl)-N-methylamino)-3-methylbutyrylamino)-3-(3-tBu-4-hydroxyphenyl)propyl)urea

(1) Synthesis of Z-3-tBu-tyrosinol

To a solution of Z-Tyr(3-tBu)-OMe (7.4 g, 19 mmol) in THF (190 ml), lithium borohydride (1.25 g, 57.4 mmol) was added under cooling with ice and stirred for 1.5 hours at room temperature. The mixture was mixed with a saturated aqueous NH$_4$Cl solution and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: hexane:ethyl acetate=1:1), giving the titled compound (6.8 g, 99%).

$^1$H-NMR (CDCl$_3$): δ 1.38 (9H, s), 2.15 (1H, m), 2.78 (2H, brd, J=6.9 Hz), 3.5-3.8 (2H, m), 3.8-4.0 (1H, m), 4.86 (1H, s), 4.9-5.0 (1H, m), 5.09 (2H, s), 6.58 (1H, d, J=7.9 Hz), 6.88 (1H, brd, J=7.9 Hz), 7.05 (1H, brs), 7.34 (5H, s)

(2) Synthesis of 2-(benzyloxycarbonylamino)-3-(3-tBu-4-hydroxyphenyl)propylamine To a solution of Z-3-tBu-tyrosinol (2 g, 5.6 mmol), triphenylphosphine (1.76 g, 6.7 mmol), phthalimide (0.99 g, 6.7 mmol) in THF 50 ml, diethyl azodicarboxylate (DEAD) (1.05 ml, 6.7 mmol) was added under cooling with ice and stirred at the same temperature for 1 hour. The mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: hexane:ethyl acetate=2:1) to give (1-(1,3-dihydro-1,3-dioxoisoindol-2-yl)methyl-2-(3-tBu-4-hydroxyphenyl)ethyl)carbamic acid benzyl ester (3.2 g).

To the above compound (3.2 g), a 40% methylamine methanol solution (40 ml) was added at room temperature and stirred at the same temperature for 10 hours. The reaction mixture was concentrated under reduced pressure; the thus obtained residue was subjected to silica gel column chromatography (developing solvent: chloroform:methanol:aqueous ammonia=20:1:0.1), giving the titled compound (1.9 g).

$^1$H-NMR (CDCl$_3$): δ 1.37 (9H, s), 2.6-2.9 (4H, m), 3.7-3.9 (4/5H, m), 3.9-4.1 (1/5H, m) 4.8-4.9 (4/5H, m), 5.09 (2H, s), 5.4-5.5 (1/5H, m), 6.5-6.6 (1H, m), 6.84 (1H, d, J=7.3 Hz), 6.9-7.1 (1H, m), 7.33 (5H, s)

(3) Synthesis of N-(2-(benzyloxycarbonylamino)-3-(3-tBu-4-hydroxyphenyl)propyl)urea A mixture of 2-(benzyloxycarbonylamino)-3-(3-tBu-4-hydroxyphenyl)propylamine (1.0 g, 2.8 mmol), potassium cyanate (0.5 g, 5.5 mmol), acetic acid (0.5 ml), dioxane (10 ml) and water (10 ml) was stirred at 60° C. for 2 hours. The mixture was mixed with a saturated aqueous NaHCO$_3$ solution and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate:methanol=50:1), giving the titled compound (0.9 g, 80%).

$^1$H-NMR (CD$_3$OD): δ 1.35 (9H, s), 2.5-2.8 (2H, m), 3.0-3.2 (1H, m), 3.2-3.4 (1H, m), 3.7-3.9 (1H, m), 5.01 (2H, d, J=3.6 Hz), 6.63 (1H, d, 7.9 Hz), 6.84 (1H, brd, J=7.9 Hz), 7.04 (1H, brs), 7.2-7.4 (5H, m)

(4) Synthesis of N-(2-(2-(benzyloxycarbonyl-N-methylamino)-3-methylbutyrylamino)-3-(3-tBu-4-hydroxyphenyl)propyl)urea To a solution of N-(2-(benzyloxycarbonylamino)-3-(3-tBu-4-hydroxyphenyl)propyl)urea (0.9 g, 2.26 mmol) in methanol (20 ml), 10% palladium carbon (100 mg) was added and stirred in a hydrogen atmosphere at room temperature for 12 hours. After filtration, the filtrate was concentrated under reduced pressure to give N-(2-amino-3-(3-tBu-4-hydroxyphenyl)propyl)urea (0.54 g).

To a solution of the above compound (0.53 g, 2 mmol), Z-N-Me-Val-OH (0.69 g, 2.6 mmol) and CMPI (0.67 g, 2.6 mmol) in THF (20 ml), TEA (1 ml, 7.2 mmol) was added under cooling with ice and stirred at room temperature for 1.5 hours. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: chloroform:methanol:aqueous ammonia=20:1:0.1), giving the titled compound (0.98 g, 98%).

$^1$H-NMR (CDCl$_3$): δ 0.82 (3H, d, J=6.3 Hz), 0.88 (3H, d, J=6.3 Hz), 1.35 (9H, s), 2.1-2.3 (1H, m), 2.6-2.8 (2H, m), 2.76 (3H, s), 3.0-3.4 (2H, m), 3.9-4.1 (1H, m), 4.7-5.0 (2H, m), 5.0-5.1 (2H, m), 5.5-5.6 (1H, m), 6.4-7.0 (5H, m), 7.34 (5H, s)

(5) Synthesis of N-(2-(2-((2-(t-butoxycarbonylamino)-3-(4-fluorophenyl)propionyl)-N-methylamino)-3-methylbutyrylamino)-3-(3-tBu-4-hydroxyphenyl)propyl)urea To a solution of N-(2-(2-(benzyloxycarbonyl-N-methylamino)-3-methylbutyrylamino)-3-(3-tBu-4-hydroxyphenyl)propyl)urea (0.97 g, 1.95 mmol) in methanol (20 ml), 10% palladium carbon (100 mg) was added and stirred in a hydrogen atmosphere at room temperature for 3 hours. After filtering the reaction mixture, the filtrate was evaporated to remove the solvent under reduced pressure, giving N-(2-(2-amino-3-methylbutyrylamino)-3-(3-tBu-4-hydroxyphenyl)propyl)urea (0.72 g).

To a solution of the above crude compound (0.64 g, 1.85 mmol), Boc-Phe(4-F)-OH (0.63 g, 2.22 mmol) and CMPI (0.57 g, 2.23 mmol) in THF (18 ml), TEA (0.93 ml, 6.67 mmol) was added under cooling with ice and stirred at room temperature for 8 hours. The mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: chloroform:methanol: aqueous ammonia=20:1:0.1), giving the titled compound (0.79 g, 66%).

$^1$H-NMR (DMSO-d$_6$): δ 0.70, 0.75, 0.85, and 0.95 (total 6H, d, J=5.9-6.3 Hz), 1.2-1.4 (18H, m), 2.0-2.1 (1H, m), 2.4-2.9 (7H, m), 2.9-3.1 (2H, m), 3.8-4.0 (1H, m), 4.3-4.6 (2H, m), 5.39, 5.51 (2H, brs), 5.74 (1H, d, J=1.3 Hz), 5.9-6.0 (1H, m), 6.6-6.9 (2H, m), 6.9-7.1 (2H, m), 7.1-7.3 (3H, m), 7.60 and 7.73 (total 1H, brd), 9.02 (1H, s)

(6) Synthesis of N-(2-(2-((2-amino-3-(4-fluorophenyl)propionyl)-N-methylamino)-3-methylbutyrylamino)-3-(3-tBu-4-hydroxyphenyl)propyl)urea To a solution of N-(2-(2-((2-(t-butoxycarbonylamino)-3-(4-fluorophenyl)propionyl)-N-methylamino)-3-methylbutyrylamino)-3-(3-tBu-4-hydroxyphenyl)propyl)urea (0.75 g) in methylene chloride (6 ml), TFA (6 ml) was added under cooling with ice, stirred at room temperature for 1 hour and evaporated to remove the solvent under reduced pressure. The thus obtained residue was mixed with methylene chloride, washed with a saturated aqueous NaHCO$_3$ solution, dried over anhydrous magnesium sulfate and evaporated to remove the solvent under reduced pressure. The thus obtained residue was subjected to silica gel column chromatography (developing solvent: chloroform:methanol:aqueous ammonia=20: 1:0.1), giving the titled compound (480 mg, 76%).

FAB-MS:544 (M$^+$+1)

$^1$H-NMR (DMSO-d$_6$): δ 0.49, 0.73, and 0.85 (total 6H, d, J=6.0-6.6 Hz), 1.30 and 1.32 (total 9H, s), 2.0-2.2 (1H, m), 2.4-3.1 (9H, m), 3.7-4.1 (3H, m), 4.52 and 5.48 (total 2H, m), 5.8-6.0 (1H, m), 6.6-6.8 (2H, m), 6.9-7.3 (5H, m), 7.67 and 8.79 (total 1H, d, J=7.6-8.6 Hz), 9.01 and 9.06 (total 1H, s)

EXAMPLE 10

N-(2-(2-((2-amino-3-(4-fluorophenyl)propionyl)-N-methylamino)-3-methylbutyrylamino)-3-(3-tBu-4-hydroxyphenyl)propyl)guanidine (1) Synthesis of N-(2-(benzyloxycarbonylamino)-3-(3-tBu-4-hydroxyphenyl)propyl)carbamic acid t-Bu ester To a solution of (2-(benzyloxycarbonylamino)-3-(3-tBu-4-hydroxyphenyl)propyl)amine (1.46 g, 4.1 mmol) in dioxane (8 ml), an aqueous sodium carbonate solution (0.44 g, 4.1 mmol) (8 ml).and (Boc) 20 (0-9 g, 4.1 mmol) were added in that order under cooling with ice and stirred at the same temperature for 2.5 hours. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: hexane:ethyl acetate=2:1), giving the titled compound (1.7 g, 91%).

$^1$H-NMR (CDCl$_3$): δ 1.38 (9H, s), 1.42 (9H, s), 2.6-2.9 (2H, m), 3.1-3.3 (2H, m), 3.8-4.0 (1H, m), 4.7-4.8 (1H, m), 5.08 (2H, s), 6.58 (1H, d, J=8.9 Hz), 6.85 (1H, brd, J=8.9 Hz), 7.03 (1H, brs), 7.2-7.5 (5H, m)

(2) Synthesis of N-(2-(2-(benzyloxycarbonyl-N-methylamino)-3-methylbutyrylamino)-3-(3-tBu-4-hydroxyphenyl)propyl)carbamic acid t-Bu ester To a solution of N-(2-(benzyloxycarbonylamino)-3-(3-tBu-4-hydroxyphenyl)propyl)carbamic acid t-Bu ester (1.6 g, 3.5 mmol) in methanol (35 ml), 10% palladium carbon (160 mg) was added and stirred in a hydrogen atmosphere at room temperature for 1.5 hours. After filtration, the filtrate was concentrated under reduced pressure to give N-((2-amino-3-(3-tBu-4-hydroxyphenyl)propyl)carbamic acid t-Bu ester (1.1 g).

To a solution of the thus obtained crude compound (1.1 g, 3.42 mmol), Z-N-Me-Val-OH (1.08 g, 4.08 mmol) and CMPI (1.04 g, 4.07 mmol) in THF (35 ml), TEA (1.7 ml, 12.2 mmol) was added under cooling with ice and stirred at room temperature for 1 hour. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: hexane:ethyl acetate=2:1), giving the titled compound (1.8 g, 93%).

$^1$H-NMR (CDCl$_3$): δ 0.82 (3H, d, J=6.6 Hz), 0.90 (3H, d, J=6.2 Hz), 1.37 (9H, s), 1.42 (9H, s), 2.1-2.3 (1H, m), 2.5-2.8 (5H, m), 3.0-3.3 (2H, m), 3.9-4.3 (2H, m), 5.13 (2H, s), 6.44 (1H, d, J=7.9 Hz), 6.75 (1H, brd, J=7.9 Hz), 7.00 (1H, brs), 7.36 (5H, s)

(3) Synthesis of N-(2-(2-((2-(benzyloxycarbonylamino)-3-(4-fluorophenyl)propionyl)-N-methylamino)-3-methylbutyrylamino)-3-(3-tBu-4-hydroxyphenyl)propyl)carbamic acid t-Bu ester To a solution of N-(2-(2-(benzyloxycarbonyl-N-methylamino)-3-methylbutyrylamino)-3-(3-tBu-4-hydroxyphenyl)propyl)carbamic acid t-Bu ester. (1.8 g, 3.16 mmol) in methanol (35 ml), 10% palladium carbon (180 mg) was added and stirred for 1 hour in a hydrogen atmosphere at room temperature. After filtration, the filtrate was concentrated under reduced pressure to give N-(2-(2-(N-methylamino)-3-methylbutyrylamino)-3-(3-tBu-4-hydroxyphenyl)propyl) carbamic acid t-Bu ester (1.33 g).

To a solution of the thus obtained crude compound (1.33 g, 3.15 mmol), Z-Phe(4-F)-OH (1.2 g, 3.78 mmol) and CMPI (0.97 g, 3.78 mmol) in THF (35 ml), TEA (1.6 ml, 11.5 mmol) was added under cooling with ice and stirred at room temperature for 10 hours. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: hexane:ethyl acetate=1:1), giving the titled compound (1.48 g, 53%).

$^1$H-NMR (CDCl$_3$): δ 0.68, 0.75, 0.91, and 0.98 (total 6H, d, J=6.2-6.9 Hz), 1.35, 1.37, 1.40, and 1.42 (total 18H, m), 2.1-3.4 (10H, m), 4.0-4.5, 4.7-5.1, and 5.5-5.7 (total 7H, m), 6.3-7.5 (17H, m)

(4) Synthesis of 2-(2-((2-(benzyloxycarbonylamino)-3-(4-fluorophenyl)propionyl)-N-methylamino)-3-methylbutyrylamino)-3-(3-tBu-4-hydroxyphenyl)propylamine To a solution of N-(2-(2-((2-(benzyloxycarbonylamino)-3-(4-fluorophenyl)propionyl)-N-methylamino)-3-methylbutyrylamino)-3-(3-tBu-4-hydroxyphenyl)propyl)carbamic acid t-Bu ester (1.38 g) in methylene chloride (5 ml), TFA (5 ml) was added under cooling with ice, stirred at room temperature for 30 min. and evaporated under reduced pressure to remove the solvent. The thus obtained residue was mixed with methylene chloride, washed with a saturated aqueous NaHCO$_3$ solution, dried over anhydrous magnesium sulfate and evaporated to remove the solvent under reduced pressure; the thus obtained residue was subjected to silica gel column chromatography (developing solvent: chloroform:methanol:aqueous ammonia=20:1:0.1), giving the titled compound (1.1 g, 92%).

$^1$H-NMR (CDCl$_3$): δ 0.67, 0.76, 0.92, and 0.97 (total 6H, d, J=6.6-6.9 Hz), 1.35 and 1.37 (total 9H, s), 2.2-2.5 (1H, m), 2.4-3.1 (9H, m), 4.0-4.2 and 4.4-4.5 (total 2H, m), 4.7-5.1 (2H, m), 5.5-5.6 and 5.7-5.9 (total 1H, brd, J=7.6-8.1 Hz), 6.2-6.4, 6.5-6.7, and 6.8-7.4 (total 13H, m)

(5) Synthesis of N-(2-(2-((2-amino-3-(4-fluorophenyl)propionyl)-N-methylamino)-3-methylbutyrylamino)-3-(3-tBu-4-hydroxyphenyl)propyl)guanidine To a solution of 2-(2-((2-(benzyloxycarbonylamino)-3-(4-fluorophenyl)propionyl)-N-methylamino)-3-methylbutyrylamino)-3-(3-tBu-4-hydroxyphenyl)propylamine (580 mg, 0.91 mmol) in DMF (4.5 ml), 1H-pyrazole-1-carboxamidine hydrochloride (161 mg, 1.09 mmol) and DIEA (0.19 ml, 1.09 mmol) were added at room temperature and stirred at the same temperature for 18 hours. The reaction mixture was concentrated under reduced pressure and the thus obtained residue was subjected to silica gel column chromatography (aminopropylated silica gel (CHROMATOREX NH-DM1020, FUJI SILYSIA CHEMICAL LTD.), developing solvent: ethyl acetate:methanol=100:1 to 10:1) to give N-(2-(2-((2-(benzyloxycarbonylamino)-3-(4-fluorophenyl)propionyl)-N-methylamino)-3-methylbutyrylamino)-3-(3-tBu-4-hydroxyphenyl)propyl)guanidine (410 mg).

To a solution of the above compound (410 mg) in methanol (20 ml), 10% palladium carbon (40 mg) was added and stirred in a hydrogen atmosphere at room temperature for 5 hours. After filtration, the filtrate was concentrated under reduced pressure and the thus obtained residue was subjected to silica gel column chromatography (aminopropylated silica gel (CHROMATOREX NH-DM1020, FUJI SILYSIA CHEMICAL LTD.), developing solvent: ethyl acetate:methanol=5:1), giving the titled compound (250 mg, 76%).

FAB-MS:543 (M$^+$+1)

$^1$H-NMR (CD$_3$OD)): b 0.47, 0.53, 0.80, 0.90 (6H, d, J=6.3-6.9 Hz), 1.31, 1.37 (9H, s), 2.0-2.3 (1H, m), 2.41, 2.46, and 2.57 (total 3H, s), 2.5-3.4 (6H, m), 3.8-4.6 (3H, m), 6.6-7.3 (7H, m)

EXAMPLE 11

Synthesis of N-(2-(2-((2-amino-3-(4-fluorophenyl)propionyl)-N-methylamino)-3-methylbutyrylamino)-3-(3-tBu-4-hydroxyphenyl)propyl)-N'-cyano-N"-methylguanidine To a solution of 2-(2-((2-(benzyloxycarbonylamino)-3-(4-fluorophenyl)propionyl)-N-methylamino)-3-methylbutyrylamino)-3-(3-tBu-4-hydroxyphenyl)propylamine (500 mg, 0.79 mmol) in ethanol (4 ml), dimethyl N-cyanodithioiminocarbonate (127 mg, 0.87 mmol) was added at room temperature and stirred at the same temperature for 16 hours. The reaction mixture was concentrated under reduced pressure; the thus obtained residue was mixed with a 40% methylamine methanol solution (5 ml) at room temperature and stirred at the same temperature for 16 hours. The reaction mixture was concentrated under reduced pressure and the thus obtained residue was subjected to silica gel column chromatography (developing solvent: chloroform:methanol:aqueous ammonia=20:1:0.1) to give N-(2-(2-((2-(benzyloxycarbonylamino)-3-(4-fluorophenyl)propionyl)-N-methylamino)-3-methylbutyrylamino)-3-(3-tBu-4-hydroxyphenyl)propyl)-N'-cyano-N"-methylguanidine (450 mg).

To a solution of the above compound (440 mg) in methanol (6 ml), 10% palladium carbon (50 mg) was added and stirred in a hydrogen atmosphere at room temperature for 15 hours.

After filtration, the filtrate was concentrated under reduced pressure and the thus obtained residue was subjected to silica gel column chromatography (developing solvent: chloroform:methanol:aqueous ammonia=20:1:0.1), giving the titled compound (280 mg, 78%).

FAB-MS:582 (M$^+$+1)

$^1$H-NMR (CDCl$_3$): δ 0.62, 0.79, 0.87, and 0.91 (total 6H, d, J=6.3-6.6 Hz), 1.37 and 1.40 (total 9H, s), 2.1-2.4 (1H, m), 2.5-3.0 (10H, m), 3.1-3.4 (2H, m), 3.6-4.4 (3H, m), 5.8-6.1 (1H, m), 6.6-7.2 (7H, m), 8.68 (1H, d, J=6.6 Hz)

EXAMPLE 12

2-(2-(2-amino-3-(4-fluorophenylpropanoyl-N-methylamino)-3-methyl)butyrylamino)-3-(3-tert-butyl-4-hydroxyphenyl)propylsulfamide (1) Synthesis of 2-(2-(2-benzyloxycarbonylamino-3-(4-fluorophenylpropanoyl-N-methylamino)-3-methyl)butyrylamino)-3-(3-tert-butyl-4-hydroxyphenyl) propylsulfamide To a solution of 2-(2-(2-benzyloxycarbonylamino-3-(4-fluorophenylpropanoyl-N-methylamino)-3-methyl)butyrylamino)-3-(3-tert-butyl-4-hydroxyphenyl)propylamine (514 mg, 0.811 mmol) in 1,4-dioxane (8 ml), sulfamide (156 mg, 1.62 mmol) was added and stirred at 120° C. for 5 hours. The reaction mixture was evaporated under reduced pressure to remove the solvent; the thus obtained residue was mixed with water, and extracted with chloroform. The organic layer was washed with saturated brine, dried over anhydrous magnesium sulfate and evaporated to remove the solvent under reduced pressure; the thus obtained residue was subjected to silica gel column chromatography (developing solvent: methylene chloride:methanol=20:1), giving the titled compound (397 mg, 69%).

$^1$H-NMR (CDCl$_3$):(two rotamers) δ 0.69, 0.85 and 0.99 (6H, d, J=6.3-6.6 Hz), 1.36 and 1.37 (9H, s), 1.80-1.90 (1H, m), 2.22-2.40 (1H, m), 2.43 and 2.81 (3H, s), 2.60-3.10 (4H, m), 3.26-3.38 (1H, m), 3.70-3.80 (1H, m), 3.90-4.10 (1H, m),4.28-4.44 (1H, m), 4.72-5.30 (3H, m), 5.03 (2H, s), 6.52-6.66 (2H, m), 6.80-7.40 (10H, m)

(2) Synthesis of 2-(2-(2-amino-3-(4-fluorophenylpropanoyl-N-methylamino)-3-methyl)butyrylamino)-3-(3-tert-butyl-4-hydroxyphenyl)propylsulfamide A mixture of 2-(2-(2-benzyloxycarbonylamino-3-(4-fluorophenylpropanoyl-N-methylamino)-3-methyl)butyrylamino)-3-(3-tert-butyl-4-hydroxyphenyl)propylsulfamide (332 mg, 0.466 mmol) and 10% palladium carbon (40 mg) in methanol (5 ml) was stirred at room temperature in a hydrogen atmosphere overnight. After filtration, the filtrate was concentrated under reduced pressure and the thus obtained residue was subjected to silica gel column chromatography (developing solvent: chloroform:methanol:aqueous ammonia=200:10:1), giving the titled compound (180 mg, 67%).

FAB-MS:580 (M+H$^+$)

$^1$H-NMR (CDCl$_3$):(two rotamers) δ 0.63, 0.75, 0.81 and 0.93 (6H, d, J=6.3-6.6 Hz), 1.38 and 1.39 (9H, s), 2.20-3.42 (6H, m), 2.60 and 3.02 (3H, s), 3.49 (1H, s), 3.60-3.90 (2H, m), 4.30-4.44 (1H, m), 5.30-5.40 (1H, m), 6.56-7.16 (7H, m), 8.34-8.42 (1H, m)

EXAMPLE 13

2-(2-(2-amino-3-(4-fluorophenylpropanoyl-N-methylamino)-3-methyl)butyrylamino)-3-(3-tert-butyl-4-hydroxyphenyl)propylaminoacetamide (1) Synthesis of 2-(2-(2-benzyloxycarbonylamino-3-(4-fluorophenylpropanoyl-N-methylamino)-3-methyl)butyrylamino)-3-(3-tert-butyl-4-hydroxyphenyl) propylaminoacetic acid ethyl ester To a solution of 2-(2-(2-benzyloxycarbonylamino-3-(4-fluorophenylpropanoyl-N-methylamino)-3-methyl)butyrylamino)-3-(3-tert-butyl-4-hydroxyphenyl)propylamine (1.17 g, 1.84 mmol) in ethanol (18 ml), ethyl glyoxylate (0.7 ml, 2.76 mmol), acetic acid (1.8 ml) and sodium cyanoborohydride (173 mg, 2.76 mmol) were added and stirred for 1 hour. The reaction mixture was mixed with a saturated aqueous NaHCO$_3$ solution, extracted with ethyl acetate and washed with saturated brine. The resultant was dried over anhydrous magnesium sulfate and evaporated to remove the solvent under reduced pressure; the thus obtained residue was subjected to silica gel column chromatography (developing solvent: hexane:ethyl acetate:methylene chloride=2:3:1), giving the titled compound (900 mg, 68%).

$^1$H-NMR (CDCl$_3$):(two rotamers)δ0.65, 0.75, 0.91 and 0.97 (6H, d, J=6.2-6.9 Hz), 1.22 and 1.29 (3H, t, J=7.2 Hz), 1.35 and 1.36 (9H, s), 2.22-2.40 (1H, m), 2.42 and 2.90 (3H, s), 2.60-3.02 (5H, m), 3.22-3.46 (2H, m), 4.06-4.28 (2H, m), 4.47 (1H, d, J=12.2 Hz), 4.80-5.12 (3H, m), 5.29 (2H, s), 5.74 (1H, d, J=8.9 Hz), 6.58-7.42 (12H, m)

(2) Synthesis of 2-(2-(2-benzyloxycarbonylamino-3-(4-fluorophenylpropanoyl-N-methylamino)-3-methyl)butyrylamino)-3-(3-tert-butyl-4-hydroxyphenyl) propylaminoacetamide To a solution of 2-(2-(2-benzyloxycarbonylamino-3-(4-fluorophenylpropanoyl-N-methylamino)-3-methyl)butyrylamino)-3-(3-tert-butyl-4-hydroxyphenyl)propylaminoacetic acid ethyl ester (889 mg, 1.23 mmol) in methanol (24 ml), aqueous ammonia (16 ml) was added and stirred for 15 hours at room temperature. The reaction mixture was evaporated to remove the solvent under reduced pressure, extracted with ethyl acetate and washed with saturated brine. The resultant was dried over anhydrous magnesium sulfate and evaporated to remove the solvent under reduced pressure; the thus obtained residue was subjected to silica gel column chromatography (developing solvent: chloroform:methanol:aqueous ammonia=110:10:1), giving the titled compound (600 mg, 70%).

$^1$H-NMR (CDCl$_3$):(two rotamers)δ0.65, 0.75, 0.90 and 0.96 (6H, d, J=6.0-6.6 Hz), 1.36 and 1.37 (9H, s), 2.22-2.40 (1H, m), 2.47 and 2.82 (3H, s), 2.60-3.02 (4H, m), 3.24 and 3.26 (2H, s), 4.02-4.38 (2H, m), 4.76-5.08 (3H, m), 5.40-5.90 (3H, m), 6.56-7.38 (12H, m)

(3) Synthesis of 2-(2-(2-amino-3-(4-fluorophenyl-propanoyl-N-methylamino)-3-methyl)butyry-lamino)-3-(3-tert-butyl-4-hydroxyphenyl)propylami-noacetamide To a solution of 2-(2-(2-benzyloxycarbonylamino-3-(4-fluorophenylpropanoyl-N-methylamino)-3-methyl)butyry-lamino)-3-(3-tert-butyl-4-hydroxyphenyl)propylaminoac-etamide (595 mg, 0.860 mmol) in methanol (10 ml), 20% palladium hydroxide/carbon (150 mg) was added and stirred at room temperature in a hydrogen atmosphere overnight. After filtration, the filtrate was concentrated under reduced pressure and the thus obtained residue was subjected to silica gel column chromatography (developing solvent: methylene chloride:methanol:hexane=10:1:1), giving the titled compound (333 mg, 70%).

FAB-MS:558 (M+H$^+$)

$^1$H-NMR (CDCl$_3$):(two rotamers) δ0.66, 0.79 and 0.92 (6H, d, J=6.3-6.6 Hz), 1.36 and 1.39 (9H, s), 2.22-2.38 (1H, m), 2.63 and 2.91 (3H, s), 2.50-2.82 (4H, m), 3.12-3.28 (2H, m), 3.58-3.88 (2H, m), 4.18-4.40 (2H, m), 5.50-5.70 (1H, m), 6.58-7.14 (8H, m)

EXAMPLE 14

N-[2-(3-tert-butyl-4-hydroxyphenyl)-1-(methane-sulfonylaminomethyl)ethyl]-2-[N-(4-fluorophenyla-laminoyl)methylamino]-3-methylbutanamide

(1) Synthesis of N-Z-2-(4-benzyloxy-3-tert-butylphenyl)-1-hydroxymethylethylamine To a solution of Z-Phe(4-benzyloxy-3-tBu)-OMe (5.8 g, 12.2 mmol) in methanol/water (100 ml/20 ml), sodium borohydride (1.5 g, 36.6 mmol) was added and stirred at room temperature overnight. The reaction mixture was concentrated under reduced pressure, mixed with a saturated aqueous ammonium chloride solution and extracted with ethyl acetate. The organic layer was dried over magnesium sulfate and evaporated to remove the solvent under reduced pressure; the thus obtained residue was subjected to silica gel column chromatography (developing solvent: ethyl acetate:n-hexane=1:2), giving the titled compound (5.1 g, 94%).

(2) Synthesis of, 3-(4-benzyloxy-3-tert-butylphenyl)-2-benzyloxycarbonylaminopropylamine To a solution of N-Z-2-(4-benzyloxy-3-tert-butylphenyl)-1-hydroxymethylethylamine (5.09 g, 11.4 mmol), triphenylphosphine (4.41 g, 17.1 mmol) and phthalimide (2.51 g, 17.1 mmol) in THF (66 ml), diethyl azodicarboxylate (3.0 ml, 17.1 mmol) was added and stirred for 4 hours under cooling with ice. The reaction mixture was concentrated; a solution of the thus obtained residue in methanol (70 ml) was mixed with hydrazine (6 ml) and stirred at room temperature for 4 hours. The reaction mixture was mixed with water and extracted with ethyl acetate. The organic layer was dried over magnesium sulfate and evaporated to remove the solvent under reduced pressure. The thus obtained residue was subjected to silica gel column chromatography (developing solvent: methylene chloride:methanol=10:1), giving the titled compound (2.45 g, 49%).

(3) N-[3-(4-benzyloxy-3-tert-butylphenyl)-2-benzyloxycarbonylaminopropyl]methanesulfonamide To a solution of 3-(4-benzyloxy-3-tert-butylphenyl)-2-benzyloxycarbonylaminopropylamine (1.27 g, 2.84 mmol) in methylene chloride (29 ml), TEA (0.6 ml, 4.26 mmol) and then methanesulfonyl chloride.(0.3 ml, 3.69 mmol) were added slowly under cooling with ice. After stirring for 30 min., the mixture was mixed with water and extracted with chloroform. The organic layer was dried over magnesium sulfate and evaporated to remove the solvent under reduced pressure; the thus obtained residue was subjected to silica gel column chromatography (developing solvent: methylene chloride:ethyl acetate:n-hexane=1:1:2), giving the titled compound (1.23 g, 83%).

(4) Synthesis of 2-[N-(benzyloxycarbonyl)methy-lamino]-N-[2-(3-tert-butyl-4-hydroxyphenyl)-1-(methanesulfonylaminomethyl)ethyl]-3-methylbu-tanamide N-[3-(4-benzyloxy-3-tert-butylphenyl)-2-benzyloxycar-bonylaminopropyl]methanesulfonamide (1.2 g, 2.29 mmol) was dissolved in a mixture of methanol (23 ml) and methylene chloride (5 ml), mixed with palladium hydroxide/carbon (0.60 g) and stirred for 12 hours in a hydrogen atmosphere. After filtering off insoluble material using Celite, the filtrate was concentrated to give crude N-[2-amino-3-(4-benzyloxy-3-tert-butylphenyl)propyl]methanesulfonamide (0.68 g).

$^1$H-NMR (CDCl$_3$): δ 1.39 (s, 9H), 2.48 (dd, 1H, J=8.2, 13.9 Hz), 2.73 (dd, 1H, J=5.1, 13.3 Hz), 2.94 (dd, 1H, J=7.9, 11.9 Hz), 2.96 (s, 3H), 3.10-3.22 (m, 1H), 3.24 (dd, 1H, J=3.6, 12.2 Hz), 6.60 (d, 1H, J=7.9 Hz), 6.83 (dd, 1H, J=2.0, 7.9 Hz), 7.03 (d, 1H, J=2.0 Hz)

To a solution of the above crude compound (0.66 g), Z-N-Me-Val-OH (758 mg, 2.86 mmol) and CMPI (730 mg, 2.86 mmol) in THF (22 ml), TEA (0.91 ml, 6.59 mmol) was added under cooling with ice. The resultant was stirred overnight at room temperature, mixed with a saturated aqueous sodium bicarbonate solution and extracted with ethyl acetate. The organic layer was dried over magnesium sulfate and evaporated to remove the solvent under reduced pressure; the thus obtained residue was subjected to silica gel column chromatography (developing solvent: methylene chloride:ethyl acetate:n-hexane=1:3:2), giving the titled compound (1.08 g, 90%).

(5) Synthesis of 2-[N-(N-benzyloxycarbonyl-4-fluo-rophenylalaminoyl)methylamino]-N-[2-(3-tert-butyl-4-hydroxyphenyl)-1-(methanesulfonylaminomethyl)ethyl]-3-methylbutanamide To a solution of 2-[N-(benzyloxycarbonyl)methylamino]-N-[2-(3-tert-butyl-4-hydroxyphenyl)-1-(methanesulfony-laminomethyl)ethyl]-3-methylbutanamide (1.0 g, 1.83 mmol) in methanol (18 ml), palladium hydroxide/carbon (0.40 g) was added and stirred in a hydrogen atmosphere for 1.5 hours. After filtering off insoluble material using Celite, the filtrate was concentrated; to a solution of the thus obtained residue (0.75 g), Z-Phe(4-F)-OH (748 mg, 2.66 mmol) and CMPI (602 mg, 2.36 mmol) in THF 18 ml, TEA (0.82 ml, 5.44 mmol) was added under cooling with ice. The mixture was stirred at room temperature overnight, mixed with a saturated aqueous sodium bicarbonate solution and extracted with ethyl acetate. The organic layer was dried over magnesium sulfate and evaporated to remove the solvent under reduced pressure; the thus obtained residue was subjected to silica gel column chromatography (developing solvent: methylene chloride:ethyl acetate:n-hexane=1:3:2), giving the titled compound (827 mg, 64%).

(6) Synthesis of N-[2-(3-tert-butyl-4-hydroxyphenyl)-1-(methanesulfonylaminomethyl)ethyl]-2-[N-(4-fluorophenylalaminoyl)methylamino]-3-methylbutanamide To a solution of 2-[N-(N-benzyloxycarbonyl-4-fluorophenylalaminoyl)methylamino]-N-[2-(3-tert-butyl-4-hydroxyphenyl)-1-(methanesulfonylaminomethyl)ethyl]-3-methylbutanamide (680 mg, 0.95 mmol) in methanol (10 ml), palladium hydroxide/carbon (0.25 g) was added and stirred in a hydrogen atmosphere for 1 hour. After filtering off insoluble material using Celite, the filtrate was concentrated; the thus obtained residue was subjected to silica gel column chromatography (developing solvent: chloroform:methanol:concentrated aqueous ammonia 100:10:1), giving the titled compound (494 mg, 89%).

EI-MS:578 ($M^+$)

$^1$H-NMR (CDCl$_3$):(two rotamers) δ0.62 (d, 21/10H, J=6.9 Hz), 0.75 (d, 9/10H, J=6.6 Hz), 0.84 (d, 9/10H, J=6.6 Hz), 0.93 (d, 21/10H, J=6.3 Hz), 1.36 (s, 27/10H), 1.39 (s, 63/10H), 2.20-2.45 (m, 1H), 2.46-2.95 (m, 8H), 3.02-3.17 (m, 3H), 3.61-4.05 (m, 2H), 4.18-4.37 (m, 1H), 4.87-4.95 (m,7/10H), 5.23-5.35 (m, 3/10H), 5.55-5.70 (m, 3/10H), 6.20-6.50 (m, 7/10H), 6.60-7.20 (m, 7H), 8.01 (d, 1H, J=7.6 Hz)

EXAMPLE 15

2-((2-amino-3-(4-fluorophenyl)propionyl)-N-methylamino)-3-methylbutyric acid 2-(3-t-butyl-4-hydroxyphenyl)-1-carbamidomethylethylamide

(1) Synthesis of 2-(4-benzyloxy-3-t-butylphenyl)-1-hydroxymethylethyl carbamic acid benzyl ester To a solution of Z-Phe(3-tBu-4-benzyloxy)-OMe (2.46 g, 5.19 mmol) in THF (50 ml), lithium borohydride (339 mg, 15.57 mmol) was added under cooling with ice and stirred at room temperature for 3 hours. The reaction mixture was mixed with a saturated aqueous ammonium chloride solution and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: n-hexane:ethyl acetate=2:1), giving the titled compound (2.30 g, 99%).

$^1$H-NMR (CDCl$_3$): δ 1.38 (9H, s), 2.11 (1H, brs), 2.80 (2H, d, J=6.9 Hz), 3.54-3.77 (2H, m), 3.83-3.97 (1H, m), 4.88-4.97 (1H, m), 5.09 (4H, s), 6.85 (1H, d, J=8.3 Hz), 6.97 (1H, dd, J=8.3, 1.8 Hz), 7.11 (1H, d, J=1.8 Hz), 7.27-7.50 (10H, m)

(2) Synthesis of 2-(4-benzyloxy-3-t-butylphenyl)-1-methanesulfonyloxymethylethylcarbamic acid benzyl ester To a solution of 2-(4-benzyloxy-3-t-butylphenyl)-1-hydroxymethylethylcarbamic acid benzyl ester (1.87 g, 4.18 mmol) in pyridine (42 ml), methanesulfonyl chloride (0.36 ml, 4.60 mmol) was added under cooling with ice. After stirring for 1 hour, the mixture was mixed with water and extracted with ethyl acetate. The organic layer was washed with saturated brine, dried over anhydrous magnesium sulfate and evaporated to remove the solvent under reduced pressure, giving the titled compound (1.93 g, 88%).

$^1$H-NMR (CDCl$_3$): δ 1.38 (9H, s), 2.76-2.92 (2H, m), 2.96 (3H, s), 4.10-4.21 (2H, m), 4.21-4.32 (1H, m), 4.88-5.00 (1H, m), 5.09 (4H, s), 6.86 (1H, d, J=8.6 Hz), 6.98 (1H, brd, J=7.9 Hz), 7.11 (1H, brs), 7.30-7.48 (10H, m)

(3) Synthesis of 2-(4-benzyloxy-3-t-butylphenyl)-1-cyanomethylethylcarbamic acid benzyl ester To a solution of 2-(4-benzyloxy-3-t-butylphenyl)-1-methanesulfonyloxymethylethylcarbamic acid benzyl ester 1.93 g, 4.23 mmol) in DMSO (11 ml), potassium cyanide (827 mg, 12.7 mmol) was added and heated at 70° C. After stirring for 4 hours, the mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: n-hexane:ethyl acetate=2:1), giving the titled compound (1.42 g, 74%).

$^1$H-NMR (CDCl$_3$): δ 1.38 (9H, s), 2.46 (1H, dd, J=16.8, 4.0 Hz), 2.74 (1H, dd, J=16.8, 4.6 Hz), 2.82 (1H, dd, J=13.8, 8.4 Hz), 2.96 (1H, dd, J=13.8, 6.5 Hz), 4.07-4.18 (1H, m), 4.89-4.98 (1H, m), 5.09 (4H, s), 6.87 (1H, d, J=8.3 Hz), 6.99 (1H, dd, J=8.3, 1.5 Hz), 7.12 (1H, d, J=1.5 Hz), 7.36-7.47 (10H, m)

(4) Synthesis of 2-(3-t-butyl-4-hydroxyphenyl)-1-carbamidomethylethylamine

To a solution of 2-(4-benzyloxy-3-t-butylphenyl)-1-cyanomethylethylcarbamic acid benzyl ester (1.38 g, 3.03 mmol) in DMSO (24 ml), potassium carbonate (1.59 g) and 30% hydrogen peroxide (4.0 ml) were added under cooling with ice. After stirring at room temperature for 2 hours, the reaction mixture was mixed with water; the thus formed precipitates were collected by filtration to give 2-(4-benzyloxy-3-t-butylphenyl)-1-carbamidemethylethylcarbamic acid benzyl ester.

A mixture of the above crude compound, 20% palladium hydroxide/carbon (0.50 g) and methanol (30 ml) was stirred at room temperature in a hydrogen atmosphere for 8 hours. The reaction mixture was filtered and the filtrate was concentrated under reduced pressure; the thus obtained residue was subjected to silica gel column chromatography (developing solvent: chloroform:methanol:aqueous ammonia=100:10:1), giving the titled compound (639 mg, 84%).

$^1$H-NMR (DMSO): δ 1.33 (9H, s), 1.96 (1H, dd, J=14.5, 8.6 Hz), 2.12 (1H, dd, J=14.5, 4.0 Hz), 2.37 (1H, dd, J=13.4, 7.4 Hz), 2.46-2.55 (1H, m), 3.07-3.20 (1H, m), 6.68 (1H, d, J=8.2 Hz), 6.73 (1H, brs), 6.79 (1H, brd, J=8.2 Hz), 7.40 (1H, brs), 9.05 (1H, s)

(5) Synthesis of 2-(benzyloxycarbonyl)methylamino-3-methylbutyric acid 2-(3-t-butyl-4-hydroxyphenyl)-1-carbamidomethylethylamide To a solution of Z-N-Me-Val-OH (736 mg, 2.78 mmol), 2-(3-t-butyl-4-hydroxyphenyl)-1-carbamidomethylethylamine (579 mg, 2.32 mmol) and CMPI (710 mg, 2.78 mmol) in THF (23 ml), TEA (0.77 ml) was added under cooling with ice and stirred at room temperature for 4 hours. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate), giving the titled compound (1.09 g, 95%).

$^1$H-NMR (CDCl$_3$): δ 0.78-0.90 (6H, m), 1.37 (9H, s), 2.14-2.80 (5H, m), 2.72 (3H, s), 3.92-4.04 (1H, m), 4.32-4.48 (1H, m), 5.04, 5.15 (2H, brs), 5.27-5.37 (1H, m), 5.78, 6.03 (1H, brs), 6.38-6.82 (3H, m), 7.04 (1H, brs), 7.30-7.41 (5H, m).

(6) Synthesis of 3-methyl-2-methylaminobutyric acid 2-(3-t-butyl-4-hydroxyphenyl)-1-carbamidomethylethylamide To a solution of 2-(benzyloxycarbonyl)methylamino-3-methylbutyric acid 2-(3-t-butyl-4-hydroxyphenyl)-1-carbamidomethylethylamide (1.04 g, 2.09 mmol) in methanol (20 ml), 10% palladium carbon (100 mg) was added and stirred in a hydrogen atmosphere at room temperature for 1 hour. After filtration, the filtrate was concentrated under reduced pressure and the thus obtained residue was subjected to silica gel column chromatography (developing solvent: chloroform:methanol:aqueous ammonia=100:10:1), giving the titled compound (0.67 g, 88%).

$^1$H-NMR (CDCl$_3$): δ 0.68 (3H, d, J=6.9 Hz), 0.83 (3H, d, J=6.9 Hz), 1.38 (9H, s), 1.82-1.97 (1H, m), 2.27 (3H, s), 2.45 (1H, dd, J=15.8, 7.3 Hz), 2.68 (1H, d, J=4.6 Hz), 2.78-2.91 (2H, m), 4.41-4.56 (1H, m), 5.30 (1H, brs), 5.58 (11H, brs), 6.34 (1H, brs), 6.62 (1H, d, J=8.0 Hz), 6.92 (1H, dd, J=8.0, 2.0 Hz), 7.04 (1H, d, J=2.0 Hz), 7.63 (1H, brd, J=8.9 Hz)

(7) Synthesis of 2-((2-amino-3-(4-fluorophenyl)propionyl)-N-methylamino)-3-methylbutyric acid 2-(3-t-butyl-4-hydroxyphenyl)-1-carbamidomethylethylamide To a solution of Z-Phe(4-F)-OH (650 mg, 2.05 mmol), 3-methyl-2-methylaminobutyric acid 2-(3-t-butyl-4-hydroxyphenyl)-1-carbamidomethylethylamide (0.62 g, 1.71 mmol) and CMPI (524 mg, 2.05 mmol) in THF (17 ml), TEA (0.57 ml, 4.10 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate), giving 2-((2-benzyloxycarbonylamino-3-(4-fluorophenyl)propionyl)-N-methylamino)-3-methylbutyric acid 2-(3-t-butyl-4-hydroxyphenyl)-1-carbamidomethylethylamide (1.05 g, 93%).

A mixture of the above compound (1.16 g, 1.75 mmol) and 10% palladium carbon (120 mg) in methanol (18 ml) was stirred at room temperature in a hydrogen atmosphere for 3 hours. The reaction mixture was filtered and the filtrate was concentrated under reduced pressure; the thus obtained residue was subjected to silica gel column chromatography (developing solvent: chloroform:methanol:aqueous ammonia=100:10:1), giving the titled compound (761 mg, 82%).

EI-MS:528 (M$^+$)

$^1$H-NMR (CDCl$_3$): δ 0.67, 0.80, 0.90, 0.92 (6H, d, J=6.3-6.9 Hz), 1.37, 1.39 (9H, s), 2.21-3.22 (6H, m), 2.61, 2.89 (3H, s), 3.59-3.88, 4.34-4.48 (3H, m), 5.33, 5.42 (1H, brs), 5.90, 6.07 (1H, brs), 6.56-7.18 (7H, m), 8.71 (1H, brd, J=8.3 Hz)

EXAMPLE 16

2-((2-amino-3-(4-fluorophenyl)propionyl)-N-methylamino)-3-methylbutyric acid 2-(3-t-butyl-4-hydroxyphenyl)-1-methanesulfonylmethylethylamide

(1) Synthesis of 2-(4-benzyloxy-3-t-butylphenyl)-1-toluenesulfonyloxymethylethylcarbamic acid benzyl ester To a solution of 2-(4-benzyloxy-3-t-butylphenyl)-1-hydroxymethylethylcarbamic acid benzyl ester (2.07 g, 4.63 mmol) in pyridine (46 ml), toluenesulfonyl chloride (6.79 g, 35.6 mmol) was added under cooling with ice. After stirring for 6.5 hours, the mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: n-hexane:ethyl acetate=2:1), giving the titled compound (2.46 g, 88%).

$^1$H-NMR (CDCl$_3$): δ 1.36 (9H, s), 2.42 (3H, s), 2.72-2.86 (2H, m), 3.92-4.09 (3H, m), 4.84-4.95 (1H, m), 5.04 (2H, s), 5.07 (2H, s), 6.79 (1H, d, J=8.0 Hz), 6.87 (1H, brd, J=8.0 Hz), 7.06 (1H, brs), 7.26-7.48 (12H, m), 7.76 (2H, d, J=8.3 Hz)

(2) Synthesis of 2-(4-benzyloxy-3-t-butylphenyl)-1-methylthiomethylethylcarbamic acid benzyl ester To a solution of 2-(4-benzyloxy-3-t-butylphenyl)-1-toluenesulfonyloxymethylethylcarbamic acid benzyl ester 2.4 g, 3.99 mmol) in ethanol (40 ml), a solution of sodium methanethiolate (560 mg, 7.99 mmol) in methanol (4 ml) was added and stirred at 40° C. for 3 hours. The mixture was evaporated under reduced pressure to remove the solvent, mixed with a saturated aqueous ammonium chloride solution and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: n-hexane:ethyl acetate=5:1), giving the titled compound (1.63 g, 86%).

$^1$H-NMR (CDCl$_3$): δ 1.38 (9H, s), 2.12 (3H, s), 2.61 (2H, d, J=5.6 Hz), 2.85 (2H, d, J=6.3 Hz), 3.99-4.12 (1H, m), 4.80-4.91 (1H, m), 5.09 (4H, s), 6.85 (1H, d, J=8.3 Hz), 6.96 (1H, brd, J=7.6 Hz), 7.11 (1H, brs), 7.27-7.50 (10H, m)

(3) Synthesis of 2-(4-benzyloxy-3-t-butylphenyl)-1-methanesulfonylmethylethylcarbamic acid benzyl ester To a solution of benzyl ester of 2-(4-benzyloxy-3-t-butylphenyl)-1-methylthiomethylethylcarbamic acid (1.54 g, 3.23 mmol) in THF (75 ml) and water (25 ml), oxone (5.91 g, 6.46 mmol) was added at room temperature. After stirring for 1 hour, the mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: n-hexane:ethyl acetate=1:1), giving the titled compound (1.59 g, 97%).

$^1$H-NMR (CDCl$_3$): δ 1.38 (9H, s), 2.88 (3H, brs), 3.00 (2H, brd, J=6.9 Hz), 3.17 (1H, dd, J=14.8, 4.6 Hz), 4.19-4.30 (1H, m), 4.35-4.47 (1H, m), 5.07-5.18 (1H, m), 5.09 (2H, s), 5.10 (2H, s), 6.85 (1H, d, J=8.5 Hz), 6.97 (1H, dd, J=8.5, 1.7 Hz), 7.10 (1H, brs), 7.28-7.49 (10H, m)

(4) Synthesis of 2-(3-t-butyl-4-hydroxyphenyl)-1-methanesulfonylmethylethylamine A mixture of 2-(4-benzyloxy-3-t-butylphenyl)-1-methanesulfonylmethylethylcarbamic acid benzyl ester (1.0 g, 1.96 mmol) and 20% palladium hydroxide/carbon (0.08 g) in methanol (16 ml) was stirred at room temperature in a hydrogen atmosphere overnight. The reaction mixture was filtered and the filtrate was concentrated under reduced pressure; the thus obtained residue was subjected to silica gel column chromatography (developing solvent: chloroform:methanol:aqueous ammonia=100:10:1), giving the titled compound (0.56 g, 99%).

$^1$H-NMR (CDCl$_3$): 1.40 (9H, s), 2.64 (1H, dd, J=13.7, 7.9 Hz), 2.73 (1H, dd, J=13.7, 5.9 Hz), 2.93-3.03 (1H, m), 2.98 (3H, s), 3.13 (1H, dd, J=14.2, 2.0), 3.61-3.74 (1H, m), 6.62 (1H, d, J=7.9 Hz), 6.88 (1H, dd, J=7.9, 2.0), 7.05 (1H, d, J=2.0 Hz)

(5) Synthesis of 2-(benzyloxycarbonyl)methylamino-3-methylbutyric acid 2-(3-t-butyl-4-hydroxyphenyl)-1-methanesulfonylmethylethylamide To a solution of Z-N-Me-Val-OH (518 mg, 1.96 mmol), 2-(3-t-butyl-4-hydroxyphenyl)-1-methanesulfonylmethylethylamine (0.47 g, 1.63 mmol) and CMPI (500 mg, 1.96 mmol) in THF (16 ml), TEA (0.55 ml) was added under cooling with ice and stirred at room temperature for 2 hours. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: n-hexane:ethyl acetate=1:1), giving the titled compound (0.70 g, 81%).

$^1$H-NMR (CDCl$_3$): δ 0.83 (3H, d, J=6.6 Hz), 0.89 (3H, d, J=6.3 Hz), 1.38 (9H, s), 2.14-2.33 (1H, m), 2.64-2.97 (2H, m), 2.74 (3H, s), 2.91 (3H, s), 3.13 (1H, dd, J=14.6, 4.6 Hz), 3.29 (1H, dd, J=14.6, 6.9 Hz), 3.94 (1H, d, J=11.2 Hz), 4.43-4.57 (1H, m), 4.79 (1H, brs), 5.14 (2H, s), 6.40-6.84 (3H, m), 7.06 (1H, brs), 7.37 (5H, brs).

(6) Synthesis of 2-((2-amino-3-(4-fluorophenyl)propionyl)-N-methylamino)-3-methylbutyric acid 2-(3-t-butyl-4-hydroxyphenyl)-1-methanesulfonylmethylethylamide To a solution of 2-(benzyloxycarbonyl)methylamino-3-methylbutyric acid 2-(3-t-butyl-4-hydroxyphenyl)-1-methanesulfonylmethylethylamide (0.65 g, 1.22 mmol) in methanol (10 ml), 10% palladium carbon (130 mg) was added and stirred in a hydrogen atmosphere at room temperature for 30 min. After filtration, the filtrate was concentrated under reduced pressure. To a solution of the thus obtained residue, Z-Phe(4-F)-OH (465 mg, 1.47 mmol) and CMPI (375 mg, 1.47 mmol) in THF (15 ml), TEA (0.41 ml, 2.93 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent:n-hexane:ethyl acetate=1:1) to give 2-((2-benzyloxycarbonylamino-3-(4-fluorophenyl)propionyl)-N-methylamino)-3-methylbutyric acid 2-(3-t-butyl-4-hydroxyphenyl)-1-methanesulfonylmethylethylamide (484 mg, 57%). A mixture of the above compound (424 mg, 0.609 mmol) and 10% palladium carbon (43 mg) in methanol (16 ml) was stirred at room temperature in a hydrogen atmosphere for 2 hours. The reaction mixture was filtered and the filtrate was concentrated under reduced pressure; the thus obtained residue was subjected to silica gel column chromatography (developing solvent: methylene chloride:methanol=15:1), giving the titled compound (239 mg, 70%).

EI-MS:563 (M$^+$)

$^1$H-NMR (CDCl$_3$): δ 0.65, 0.78, 0.91, 0.93 (6H, d, J=6.6-7.3 Hz), 1.38, 1.39 (9H, s), 2.22-2.40 (1H, m), 2.46-3.40 (6H, m), 2.66 (3H, s), 2.93 (3H, s), 3.60-3.83 (1H, m), 3.87, 4.26 (1H, d, J=10.8 Hz), 4.38-4.67 (1H, m), 6.57-7.17, 8.88 (8H, m)

EXAMPLE 17

Synthesis of 2-(2-((2-amino-3-(4-fluorophenyl)propionyl)-N-methylamino)-3-methyl-butyrylamino)-3-(3-tBu-4-hydroxyphenyl)propanol

(1) Synthesis of 3-tBu-tyrosinol

To a solution of Z-3-tBu-tyrosinol (8.2 g, 23 mmol) in methanol (250 ml), 10% palladium carbon (800 mg) was added and stirred in a hydrogen atmosphere at room temperature for 10 hours. The reaction mixture was filtered and the filtrate was concentrated under reduced pressure to give the titled compound (5.1 g, 99%).

$^1$H-NMR (CDCl$_3$): δ 1.40 (9H, s), 2.45 (1H, dd, J=8.6, 13.5 Hz), 2.71 (1H, dd, 5.3, 13.5 Hz), 3.0-3.2 (1H, m), 3.38 (1H, dd, J=7.6, 10.5 Hz), 3.65 (1H, dd, J=3.6, 10.5 Hz), 6.61 (1H, d, J=7.9 Hz), 6.88 (1H, dd, J=2.0, 7.9 Hz), 7.06 (H, d, J=2.0 Hz)

(2) Synthesis of (2-(benzyloxycarbonyl-N-methylamino)-3-methyl-butyrylamino)-3-(3-tBu-4-hydroxyphenyl)propanol To a solution of 3-tBu-tyrosinol (1 g, 4.48 mmol), Z-N-Me-Val-OH (1.43 g, 5.4 mmol) and CMPI (1.38 g, 5.4 mmol) in THF (45 ml), TEA (2.2 ml, 15.8 mmol) was added under cooling with ice and stirred at room temperature for 13 hours. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: hexane:ethyl acetate=1:1), giving the titled compound (1.9 g, 90%).

$^1$H-NMR (CDCl$_3$): δ 0.84 (3H, d, J=6.6 Hz), 0.92 (3H, d, J=6.3 Hz), 2.1-2.3 (1H, m), 2.5-2.8 (5H, m), 3.5-3.7 (2H, m), 3.9-4.2 (2H, m), 5.13 (2H, s), 6.2-6.4 (1H, m), 6.45 (1H, d, J=7.6 Hz), 6.80 (1H, brd, J=7.6 Hz), 7.05 (1H, brs), 7.36 (5H, s)

(3) Synthesis of 2-(2-((2-(t-butoxycarbonylamino)-3-(4-fluorophenyl)propionyl)-N-methylamino)-3-methyl-butyrylamino)-3-(3-tBu-4-hydroxyphenyl)propanol To a solution of (2-(benzyloxycarbonyl-N-methylamino)-3-methylbutyrylamino)-3-(3-tBu-4-hydroxyphenyl)propanol (1.9 g, 4 mmol) in methanol (40 ml), 10% palladium carbon (190 mg) was added and stirred in a hydrogen atmosphere at room temperature for 3 hours. The reaction mixture was filtered and the filtrate was concentrated under reduced pressure to give (2-(N-methylamino)-3-methyl-butyrylamino)-3-(3-tBu-4-hydroxyphenyl)propanol (1.4 g).

To a solution of the above crude compound (1.4 g), Boc-Phe(4-F)-OH (1.4 g, 4.94 mmol) and CMPI (1.3 g, 5.09 mmol) in THF (40 ml), TEA (2 ml, 14.3 mmol) was added under cooling with ice and stirred at room temperature for 12 hours. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: hexane:ethyl acetate=1:1), giving the titled compound (1.9 g, 78%).

$^1$H-NMR (CDCl$_3$): δ 0.77, 0.92, and 1.02 (total 6H, d), 1.2-1.5 (18H, m), 2.2-3.1 (8H, m), 3.5-3.8 (2H, m), 4.0-4.3, 4.4-4.5, 4.7-4.9, and 5.2-5.4 (total 2H, m), 6.3-7.5 (8H, m)

(4) Synthesis of 2-(2-((2-amino-3-(4-fluorophenyl)propionyl)-N-methylamino)-3-methyl-butyrylamino)-3-(3-tBu-4-hydroxyphenyl)propanol To a solution of 2-(2-((2-(t-butoxycarbonylamino)-3-(4-fluorophenyl)propionyl)-N-methylamino)-3-methyl-butyrylamino)-3-(3-tBu-4-hydroxyphenyl)propanol (0.5 g) in methylene chloride (2 ml), TFA (2 ml) was added under cooling with ice, stirred for 1 hour at room temperature and evaporated to remove the solvent under reduced pressure. The thus obtained residue was mixed with methylene chloride, washed with a saturated aqueous NaHCO$_3$ solution, dried over anhydrous magnesium sulfate and evaporated to remove the solvent under reduced pressure. The thus obtained residue was subjected to silica gel column chromatography (developing solvent: chloroform:methanol:aqueous ammonia=20:1:0.1), giving the titled compound (250 mg, 60%).

EI-MS:501 (M$^+$)

$^1$H-NMR (CDCl$_3$): 0.68, 0.79, and 0.93 (total 6H, d, J=6.3-6.9 Hz), 1.36 and 1.39 (total 9H, s), 2.2-2.4 (1H, s), 2.5-3.2 (4H, m), 2.68 and 2.84 (total 3H, s), 3.5-3.9 (3H, m), 3.89 and 4.43 (total 1H, d, J=10.9 Hz), 4.0-4.4 (1H, m), 6.5-7.1 (7H, m), 6.58 and 8.41 (total 1H, d, J=6.9-7.6 Hz)

EXAMPLE 18

(2-(2-(2-amino-3-(4-fluorophenyl)propylamino)-3-methylbutyrylamino)-3-(3-tBu-4-hydroxyphenyl)propyl)methylsulfone (1) Synthesis of (2-(2-(benzyloxycarbonylamino)-3-methyl-butyrylamino)-3-(3-tBu-4-hydroxyphenyl)propyl)methylsulfone To a solution of (2-(benzyloxycarbonylamino)-3-(3-tBu-4-hydroxyphenyl)propyl)methylsulfone (797 mg, 1.56 mmol) in methanol (15 ml), 10% palladium hydroxide (80 mg) was added and stirred at room temperature for 12 hours in a hydrogen atmosphere. The reaction mixture was filtered and the filtrate was concentrated under reduced pressure to give (2-amino-3-(3-tBu-4-hydroxyphenyl)propyl)methylsulfone (400 mg, 90%).

To a solution of the above crude compound (400 mg, 1.4 mmol), Z-Val-OH (528 mg, 2.1 mmol) and CMPI (539 mg, 2.1 mmol) in THF (10 ml), TEA (0.58 ml, 4.2 mmol) was added under cooling with ice and stirred at room temperature for 2 hours. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: hexane:ethyl acetate=1:1), giving the titled compound (504 mg, 69%).

$^1$H-NMR (CDCl$_3$): δ 0.79 (3H, d, J=6.9 Hz), 0.91 (3H, d, J=6.6 Hz), 1.38 (9H, s), 2.0-2.2 (1H, m), 2.89 (3H, s), 2.97 (2H, d, J=6.9 Hz), 3.1-3.4 (2H, m), 3.94 (1H, dd, J=5.6, 7.9 Hz), 4.4-4.6 (1H, m), 5.10 (2H, s), 5.1-5.2 (1H, m), 5.35 (1H, brs), 6.59 (1H, d, J=8.3 Hz), 6.5-6.7 (1H, m), 6.88 (1H, brd, J=8.3 Hz), 7.05 (1H, brs), 7.34 (5H, s)

(2) Synthesis of (1-formyl-2-(4-fluorophenyl)ethyl)carbamic acid tBu ester

To a solution of Boc-Phe(4-F)-OH (1 g, 3.53 mmol) and O,N-dimethylhydroxylamine hydrochloride (0.38 g, 3.9 mmol) in methylene chloride (17 ml), TEA (1.1 ml, 7.9 mmol) and BOP (1.64 g, 3.7 mmol) were added under cooling with ice and stirred at room temperature for 1.5 hours. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: hexane:ethyl acetate=1:1), giving N-methoxy-N-methyl-2-(t-butoxycarbonylamino)-3-(4-fluorophenyl)propylamide (1.08 g, 94%).

To a solution of the above compound (1 g, 3.07 mmol) in ether (30 ml), lithium aluminum hydride (120 mg, 3.16 mmol) was added at −10° C. and stirred at the same temperature for 10 min. The reaction mixture was mixed with 15 ml of a solution of potassium hydrogen sulfate (630 mg, 4.63 mmol). The reaction mixture was extracted with ethyl acetate. The organic layer was washed with saturated brine, dried over sodium sulfate and evaporated to remove the solvent under reduced pressure; the thus obtained residue was subjected to silica gel column chromatography (developing solvent: hexane:ethyl acetate=2:1), giving the titled compound (0.8 g, 98%).

$^1$H-NMR (CDCl$_3$): δ 1.44 (9H, s), 3.0-3.2 (2H, m), 4.3-4.5 (1H, m), 5.02 (1H, brs), 7.00 (2H, t, J=8.6 Hz), 7.13 (2H, dd, J=5.4, 8.6 Hz), 9.63 (1H, s)

(3) Synthesis of (2-(2-(2-(t-butoxycarbonylamino)-3-(4-fluorophenyl)propylamino)-3-methyl-butyrylamino)-3-(3-tBu-4-hydroxyphenyl)propyl)methylsulfone To a solution of (2-(2-(benzyloxycarbonylamino)-3-methyl-butyrylamino)-3-(3-tBu-4-hydroxyphenyl)propyl)methylsulfone (500 mg, 0.96 mmol) in methanol (10 ml), 10% palladium carbon (50 mg) was added and stirred in a hydrogen atmosphere at room temperature for 12 hours. The reaction mixture was filtered and the filtrate was concentrated under reduced pressure to give (2-(2-amino-3-methyl-butyrylamino)-3-(3-tBu-4-hydroxyphenyl)propyl)methylsulfone (330 mg).

To a solution of the above crude compound (330 mg, 0.86 mmol) and (1-formyl-2-(4-fluorophenyl)ethyl)carbamic acid tBu ester (275 mg, 1.03 mmol) in methanol (8 ml), acetic acid (0.07 ml, 1.22 mmol) and sodium cyanoborohydride (85 mg, 1.29 mmol) were added in that order under cooling with ice and stirred at room temperature for 30 min. The reaction mixture was mixed with methylene chloride, washed with a saturated aqueous NaHCO$_3$ solution, dried over anhydrous magnesium sulfate and evaporated to remove the solvent under reduced pressure. The thus obtained residue was subjected to silica gel column chromatography (developing solvent: chloroform:methanol:aqueous ammonia 40:1:0.1), giving the titled compound. (520 mg, 95%).

$^1$H-NMR (CDCl$_3$): δ 0.68 (3H, d, J=5.6 Hz), 0.85 (3H, d, J=6.9 Hz), 1.38 (9H, s), 1.41 (9H, s), 1.9-2.1 (1H, m), 2.4-2.9 (5H, m), 2.9-3.1 (2H, m), 2.99 (3H, s), 3.1-3.3 (2H, m), 3.8-4.0 (1H, m), 4.47 (1H, d, J=8.9 Hz), 4.5-4.8 (1H, m), 5.56 (1H, brs), 6.64 (1H, d, J=7.9 Hz), 6.9-7.2 (6H, m), 7.7-7.9 (1H, m)

(4) Synthesis of (2-(2-(2-amino-3-(4-fluorophenyl)propylamino)-3-methyl-butyrylamino)-3-(3-tBu-4-hydroxyphenyl)propyl)methylsulfone To a solution of (2-(2-(2-(t-butoxycarbonylamino)-3-(4-fluorophenyl)propylamino)-3-methyl-butyrylamino)-3-(3-tBu-4-hydroxyphenyl.)propyl)methylsulfone (520 mg) in methylene chloride (2 ml), TFA (2 ml) was added under cooling with ice, stirred at room temperature for 30 min. and evaporated to remove the solvent under reduced pressure. The thus obtained residue was mixed with methylene chloride, washed with a saturated aqueous NaHCO$_3$ solution, dried over anhydrous magnesium sulfate and evaporated to remove the solvent under reduced pressure. The thus obtained residue was subjected to silica gel column chromatography (developing solvent: chloroform:methanol:aqueous ammonia=20:1:0.1), giving the titled compound (400 mg, 91%).

EI-MS:535 (M$^+$)

$^1$H-NMR (CDCl$_3$): δ 0.75 (3H, d, J=6.9 Hz), 0.89 (3H, d, J=6.9 Hz), 1.39 (9H, s), 2.0-2.1 (1H, m), 2.3-2.5 (2H, m), 2.53 (1H, dd, J=3.6, 11.6 Hz), 2.72 (1H, dd, J=4.6, 13.2 Hz), 2.80 (1H, d, J=4.6 Hz), 2.8-3.1 (5H, m), 3.19 (2H, d, J=5.9 Hz), 4.5-4.7 (1H, m),6.62 (1H, d, J=7.9 Hz), 6.93 (1H, dd, J=2.0, 7.9 Hz), 6.99 (2H, t, J=8.8 Hz), 7.0-7.2 (3H, m), 7.80 (1H, d, J=8.6 Hz)

EXAMPLE 19

2-(1-(2-((2-amino-3-(4-fluorophenyl)propionyl)-N-methylamino)-3-methyl-butyrylamino)-2-(3-tert-butyl-4-hydroxyphenyl)ethyl)-6-methyl-4-pyrimidinone (1) Synthesis of 3-(4-benzyloxy-3-tert-butylphenyl)-2-benzyloxycarbonylaminopropionitrile To a solution of Z-Phe(4-benzyloxy-3-tBu)-NH$_2$ (4.6 g, 10 mmol) in THF (20 ml), pyridine (1.6 ml, 20 mmol) and trifluoroacetic anhydride (1.55 ml, 11 mmol) were added under cooling with ice and stirred for 4.5 days at room temperature. The reaction mixture was evaporated under reduced pressure and the thus obtained residue was subjected to silica gel column chromatography (developing solvent: ethyl acetate:n-hexane=1:4), giving the titled compound (3.35 g, 99%).

$^1$H-NMR (CDCl$_3$): δ 1.37 (9H, s), 3.0 (2H, m), 4.85 (1H, brd), 5.03 (1H, brd), 5.10 (2H, s), 5.14 (2H, s), 6.69 (1H, d, J=8.58 Hz), 7.05 (1H, d, J=8.58 Hz) 7.2 (1H, s), 7.3-7.5 (10H, m)

(2) Synthesis of 2-[2-(4-benzyloxy-3-tert-butylphenyl)-1-benzyloxycarbonylaminoethyl]-6-methyl-4-pyrimidinone A solution of 3-(4-benzyloxy-3-tert-butylphenyl)-2-benzyloxycarbonylaminopropionitrile (3.48 g, 7.85 mmol) in saturated hydrochloric acid/ethanol (50 ml) was stirred at room temperature for 1.5 days. The reaction mixture was concentrated under reduced pressure and the thus obtained residue was dissolved in ethanol (70 ml); into the thus obtained solution, gaseous ammonia was blown under cooling with ice, followed by stirring at room temperature for 17 hours. The resultant was concentrated under reduced pressure; the thus obtained residue was dissolved in methanol (50 ml), mixed with methyl acetoacetate (0.640 ml) and potassium hydroxide (562 mg) and stirred at room temperature for 4.5 days. The mixture was mixed with a saturated aqueous ammonium chloride solution and extracted with methylene chloride. The organic layer was dried over anhydrous magnesium sulfate, evaporated to remove the solvent under reduced pressure; the thus obtained residue was subjected to silica gel column chromatography (developing solvent: n-hexane:ethyl acetate=2:1), giving the titled compound (1.76 g, 67%).

$^1$H-NMR (CDCl$_3$): δ 1.39 (9H, s), 2.25 (3H, s), 3.09 (2H, brd), 4.89 (1H, brd), 5.03 (2H, s), 5.07 (2H, s), 5.80 (1H, brd), 6.14 (1H, s), 6.79 (1H, d, J=8.24 Hz), 6.92 (1H, d, J=8.24 Hz), 6.96 (1H, s), 7.25-7.43 (10H, m)

(3) Synthesis of 2-[1-amino-2-(3-tert-butyl-4-hydroxyphenyl)ethyl]-6-methyl-4-pyrimidinone A suspension of 2-[2-(4-benzyloxy-3-tert-butylphenyl)-1-benzyloxycarbonylaminoethyl]-6-methyl-4-pyrimidinone (1.76 g, 3.35 mmol) and 20% palladium hydroxide/carbon (0.15 g) in methanol (30 ml) was stirred in a hydrogen atmosphere for 16 hours. The reaction mixture was filtered and the filtrate was concentrated under reduced pressure; the thus obtained residue was subjected to silica gel column chromatography (developing solvent: methylene chloride:methanol=10:1), giving the titled compound (824 mg, 82%).

$^1$H-NMR (CDCl$_3$): δ 1.37 (9H, s), 2.32 (3H, s), 2.74 (1H, dd, J=8.90, 9.24 Hz), 3.15 (1H, dd, J=4.28, 4.29 Hz), 4.09 (1H, m), 6.16 (1H, s), 6.59 (1H, d, J=7.92 Hz), 6.83 (1H, d, J=7.92 Hz), 6.99 (1H, s).

(4) Synthesis of 2-(1-(2-(benzyloxycarbonylmethylamino)-3-methylbutyrylamino)-2-(3-tert-butyl-4-hydroxyphenyl)ethyl)-6-methyl-4-pyrimidinone To a solution of Z-N-Me-Val-OH (678 mg, 2.55 mmol), 2-[1-amino-2-(3-tert-butyl-4-hydroxyphenyl)ethyl]-6-methyl-4-pyrimidinone (700 mg, 2.32 mmol) and CMPI (653 mg, 2.55 mmol) in THF (20 ml), TEA (0.97 ml) was added under cooling with ice and stirred at room temperature overnight. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: ethyl acetate:n-hexane=1:2), giving the titled compound (0.77 g, 61%).

$^1$H-NMR (CDCl$_3$): δ 0.79-0.90 (6H, m), 1.30 (9H, m), 2.2 (4H, m), 2.8-3.1 (5H, m), 4.3 (1H, d, J=7.3), 4.97 (1H, m), 5.1-5.25 (2H, m), 6.18 (1H, d, J=8.58), 6.41 (1H, d, J=8.58 Hz), 6.5-6.85 (2H, m), 7.3 (5H, m)

(5) Synthesis of 2-[2-(3-tert-butyl-4-hydroxyphenyl)-1-(3-methyl-2-methylaminobutyrylamino)ethyl]-6-methyl-4-pyrimidinone A mixture of 2-(1-(2-(benzyloxycarbonylmethylamino)-3-methyl-butyrylamino)-2-(3-tert-butyl-4-hydroxyphenyl)ethyl)-6-methyl-4-pyrimidinone (0.71 g, 1.294 mmol), 20% palladium hydroxide/carbon (0.15 g) and methanol (20 ml) was stirred in a hydrogen atmosphere for 4 hours. The reaction mixture was filtered and the filtrate was concentrated under reduced pressure; the thus obtained residue was subjected to silica gel column chromatography (developing solvent: methylene chloride:methanol=15:1), giving two diastereoisomers A and B of the titled compound, A (296 mg, 38%) being eluted first and then B (77 mg, 9.4%). (A)

$^1$H-NMR (CDCl$_3$): δ 0.72 (3H, d, J=6.93 Hz), 0.83 (3H, d, J=6.93 Hz), 1.34 (9H, s), 1.94 (1H, m), 2.28 (3H, s), 2.30 (3H, s), 2.77 (1H, d, J=4.62 Hz), 3.11 (2H, m), 5.04 (1H, d, J=7.59 Hz), 6.14 (1H, s), 6.61 (1H, d, J=7.92 Hz), 6.81 (1H, dd, J=7.92 Hz), 6.99 (1H, s), 7.84 (1H, d, J=6.92 Hz) (B)

$^1$H-NMR (CDCl$_3$): δ 0.84 (3H, d, J=6.93 Hz), 0.89 (3H, d, J=6.93 Hz), 1.33 (9H, s), 2.00 (1H, m), 2.14 (3H, s), 2.18 (3H, s), 2.78 (1H, d, J=4.95 Hz), 3.11 (2H, m), 5.10 (1H, d, J=6.60 Hz), 6.14 (1H, s), 6.63 (1H, d, J=7.92 Hz), 6.75 (1H, dd, J=7.92 Hz), 6.97 (1H, s), 7.81 (1H, d, J=7.26 Hz)

(6) Synthesis of 2-(1-(2-((2-butoxycarbonylamino-3-(4-fluorophenyl)propionyl)-N-methylamino)-3-methyl-butyrylamino)-2-(3-tert-butyl-4-hydroxyphenyl)ethyl)-6-methyl-4-pyrimidinone (A)

To a solution of Boc-Phe(4-F)-OH (200 mg, 0.707 mmol), 2-[2-(3-tert-butyl-4-hydroxyphenyl)-1-(3-methyl-2-methylaminobutyrylamino)ethyl]-6-methyl-4-pyrimidinone (A) (244 mg, 0.589 mmol) and CMPI (180 mg, 0.706 mmol) in THF (8 ml), TEA (0.25 ml, 4.7 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: acetone:n-hexane=1:2), giving the titled compound (0.33 g, 82%).

$^1$H-NMR (CDCl$_3$): (two rotamers) δ 0.75, 0.80 and 0.98 (6H, d, J=6.6, 6.9 Hz), 1.34 and 1.38 (9H, s), 1.4 (9H, s), 2.10 (1H, m), 2.3 and 2.4 (3H, s), 2.7 (3H, s), 2.85 (2H, m), 3.04 (2H, d, J=7.01 Hz), 4.12 and 4.58 (1H, d, J=9.6 Hz), 4.75 (1H, m), 5.05 (1H, m), 4.83 and 5.2 (1H, brd), 5.45 and 5.6 (1H, dd, J=7.4 Hz), 6.2 (1H, s), 6.6 (1H, m), 6.77 (1H, m), 7.0 (5H, m).

(7) Synthesis of 2-(1-(2-((2-butoxycarbonylamino-3-(4-fluorophenyl)propionyl)-N-methylamino)-3-methyl-butyrylamino)-2-(3-tert-butyl-4-hydroxyphenyl)ethyl)-6-methyl-4-pyrimidinone (B)

To a solution of Boc-Phe(4-F)-OH (63 mg, 0.222 mmol), 2-[2-(3-tert-butyl-4-hydroxyphenyl)-1-(3-methyl-2-methylaminobutyrylamino)ethyl]-6-methyl-4-pyrimidinone (B) (77 mg, 0.185 mmol) and CMPI (57 mg, 0.222 mmol) in THF (5 ml), TEA (0.08 ml, 0.573 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: acetone:n-hexane=1:2), giving the titled compound (0.098 g, 74%).

$^1$H-NMR (CDCl$_3$):(two rotamers) δ0.78 (6H, brd), 1.3-1.4 (18H, s), 1.8 (2H, brd), 2.25 (3H, brd), 2.8 and 3.20 (7H, brd), 4.1 (2H, m), 4.4 and 4.5 (1H, d, J=9.89 Hz), 4.7 and 5.17 (1H, brd), 5.3 and 5.58 (1H, d, J=9.89 Hz), 6.0 and 6.17 (1H, s), 6.6 (1H, brd), 6.7-7.2 (8H, m)

(8) Synthesis of 2-(1-(2-((2-amino-3-(4-fluorophenyl)propionyl)-N-methylamino)-3-methyl-butyrylamino)-2-(3-tert-butyl-4-hydroxyphenyl)ethyl)-6-methyl-4-pyrimidinone (A)

To a solution of 2-(1-(2-((2-butoxycarbonylamino-3-(4-fluorophenyl)propionyl)-N-methylamino)-3-methyl-butyrylamino)-2-(3-tert-butyl-4-hydroxyphenyl)ethyl)-6-methyl-4-pyrimidinone (A) (279 mg) in methylene chloride (8 ml), TFA (1.3 ml) was added under cooling with ice. The resultant mixture was stirred at room temperature for 1 hour and evaporated to remove the solvent under reduced pressure; the thus obtained residue was subjected to silica gel column chromatography (developing solvent: methylene chloride:methanol=15:1), giving the titled compound (225 mg, 95%).

$^1$H-NMR (CDCl$_3$):(two rotamers) δ 0.7 and 0.8 (6H, dd, J=6.6 and 6.59 Hz), 1.29 (9H, s), 2.14 and 2.275 (3H, s), 2.1-2.2 (1H, m), 2.67 and 2.78 (3H, s), 2.6-2.8 (2H, m), 3.07 (2H, m), 3.7-3.83 (1H, m), 4.15 and 4.62 (1H, d, J=9.87 Hz), 4.98 and 5.18 (1H, dd, J=6.5 and 7.6 Hz), 6.02 and 6.11 (1H, s), 6.55 and 6.8 (2H, m), 6.92 (1H, d, J=6.92 Hz), 6.93-7.15 (4H, m)

(9) Synthesis of 2-(1-(2-((2-amino-3-(4-fluorophenyl)propionyl)-N-methylamino)-3-methyl-butyrylamino)-2-(3-tert-butyl-4-hydroxyphenyl)ethyl)-6-methyl-4-pyrimidinone (B)

To a solution of 2-(1-(2-((2-butoxycarbonylamino-3-(4-fluorophenyl)propionyl)-N-methylamino)-3-methyl-butyrylamino)-2-(3-tert-butyl-4-hydroxyphenyl)ethyl)-6-methyl-4-pyrimidinone (B) (93 mg) in methylene chloride (5 ml), TFA (1 ml) was added under cooling with ice. The resultant mixture was stirred at room temperature for 1.5 hours and evaporated under reduced pressure to remove the solvent; the thus obtained residue was subjected to silica gel column chromatography (developing solvent: methylene chloride:methanol=15:1), giving the titled compound (70 mg, 91.8%).

$^1$H-NMR (CDCl$_3$):(two rotamers) δ 0.68, 0.78 and 0.86 (6H, dd, J=6.6 and 6.27 Hz), 1.3 and 1.32 (9H, s), 2.21 and 2.23 (3H, s), 2.2-2.4 (1H, brd), 2.6 and 2.8 (1H, m), 2.71-2.91 (3H, s), 3.00 (3H, m), 3.77 and 3.9 (1H, m), 3.97 and 4.52 (1H, d, J=9.37 Hz), 4.97 and 5.18 (1H, m), 6.12 (1H, d, J=3.3 Hz), 6.5-7.2 (8H, m)

EXAMPLE 20

5-(1-(2-(2-amino-3-(4-fluorophenyl)propanoyl)-N-methylamino)-3-methylbutyrylamino)-2-(3-tert-butyl-4-hydroxylphenyl)ethyl)imidazolidine-2,4-dione (1) Synthesis of Z-Tyr(3-tBu)-H To a solution of Z-Tyr(3-tBu)-OMe (3.30 g, 8.57 mmol) in THF (200 ml), diisobutyl aluminum hydride (1.0 M toluene solution) (42.9 ml, 42.9 mmol) was added dropwise at −78° C. over 15 min. After stirring for 1 hour, the mixture was mixed with methanol and a saturated aqueous NaHCO$_3$ solution and extracted with ethyl acetate. The organic layer was washed with water and then with saturated brine, dried over anhydrous magnesium sulfate and evaporated to remove the solvent under reduced pressure; the thus obtained residue was subjected to silica gel column chromatography (developing solvent: ethyl acetate:n-hexane=1:2), giving the titled compound (2.18 g, 72%).

NMR (CDCl$_3$): δ 1.37 (9H, s), 3.00-3.14 (2H, m), 4.40-4.52 (1H, m), 4.89 (1H, brs), 5.12 (2H, s), 5.22-5.32 (1H, m), 6.57 (1H, d, J=8.2 Hz), 6.82 (1H, d, J=8.2 Hz), 7.00 (1H, s), 7.30-7.42 (5H, m), 9.64 (1H, s)

(2) Synthesis of 5-(1-(benzyloxycarbonylamino)-2-(3-tert-butyl-4-hydroxylphenyl)ethyl)imidazolidine-2,4-dione To a solution of Z-Tyr(3-tBu)-H (2.18 g, 6.14 mmol) in ethanol (25 ml), potassium cyanide (480 mg, 7.37 mmol), 30% ammonium carbonate (1.77 g, 18.4 mmol) and water (25 ml) were added and stirred at 60° C. for 8 hours. The mixture was left for cooling and mixed with a saturated aqueous NaHCO$_3$ solution. The organic layer was extracted with ethyl acetate and washed with water and then with saturated brine, dried over anhydrous magnesium sulfate and evaporated to remove the solvent under reduced pressure; the thus obtained residue was subjected to silica gel column chromatography (developing solvent: ethyl acetate:n-hexane=1:1), giving the titled compound (1.38 g, 53%).

$^1$H-NMR (CDCl$_3$): δ 1.37 (9H, s), 2.90-3.00 (2H, m), 3.10-3.22 (1H, m), 4.27 (1H, brs), 5.06 (2H, s), 5.02-5.12 (1H, m), 6.07 (1H, brs), 6.57 (1H, d, J=8.2 Hz), 6.88 (1H, dd, J=2.0, 8.2 Hz), 7.10 (1H, d, J=2.0 Hz), 7.22-7.40 (5H, m)

(3) Synthesis of 5-(1-(2-(benzyloxycarbonyl-N-methylamino)-3-methylbutyrylamino)-2-(3-tert-butyl-4-hydroxylphenyl)ethyl)imidazolidine-2,4-dione To a solution of 5-(1-(benzyloxycarbonylamino)-2-(3-tert-butyl-4-hydroxylphenyl)ethyl)imidazolidine-2,4-dione (543 mg, 1.28 mmol) in methanol (10 ml), 10% palladium carbon (55 mg) was added and stirred at room temperature in a hydrogen atmosphere for 3 hours. The reaction mixture was filtered and the filtrate was concentrated under reduced pressure; to a solution of the thus obtained residue in THF (13 ml), Z-N-Me-Val-OH (509 mg, 1.92 mmol), CMPI (491 mg, 1.92 mmol) and TEA (0.535 ml, 3.84 mmol) were added under cooling with ice and stirred at room temperature for 3 hours. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate:n-hexane=2:1), giving the titled compound (365 mg, 53%).

GH-NMR (CDCl$_3$): δ 0.79 and 0.85 (6H, d, J=6.6 Hz), 2.14-2.26 (1H, m), 2.60 (3H, s), 2.70-2.92 (2H, m), 3.89 (1H, d, J=10.8 Hz), 4.27 (1H, brs), 4.62-4.74 (2H, m), 5.14 (2H, s), 6.28 (1H, d, J=7.9 Hz), 6.56-7.10 (3H, m), 7.30-7.42 (5H, m)

(4) Synthesis of 5-(1-(3-methyl-2-methylaminobutyrylamino)-2-(3-tert-butyl-4-hydroxylphenyl)ethyl) imidazolidine-2,4-dione To a solution of 5-(1-(2-(benzyloxycarbonyl-N-methylamino)-3-methylbutyrylamino)-2-(3-tert-butyl-4-hydroxylphenyl)ethyl)imidazolidine-2,4-dione (363 mg, 0.675 mmol) in methanol (10 ml), 10% palladium carbon (50 mg) was added and stirred at room temperature in a hydrogen atmosphere overnight. The reaction mixture was filtered and the filtrate was concentrated under reduced pressure to give the titled compound (261 mg, 96%).

EI-MS:404 (M$^+$)

$^1$H-NMR (DMSO-d$_6$): δ 0.79 and 0.82 (6H, d, J=6.3-6.6 Hz), 1.31 (9H, s), 1.90 (3H, s), 2.74-2.84 (2H, m), 4.02-4.14 (1H, m), 4.17 (1H, brs), 4.38-4.48 (1H, m), 6.64 (1H, d, J=8.2 Hz), 6.82 (1H, d, J=8.2 Hz), 6.99 (1H, s), 7.85 (1H, brs)

(5) Synthesis of 5-(1-(2-(2-(benzyloxycarbonylamino)-3-(4-fluorophenyl)propanoyl)-N-methylamino)-3-methylbutyrylamino)-2-(3-tert-butyl-4-hydroxylphenyl)ethyl)imidazolidine-2,4-dione To a solution of 5-(1-(3-methyl-2-methylaminobutyrylamino)-2-(3-tert-butyl-4-hydroxylphenyl)ethyl)imidazolidine-2,4-dione (254 mg, 0.629 mmol) in THF (6 ml), Z-Phe (4-F)-OH (239 mg, 0.755 mmol), CMPI (193 mg, 0.755 mmol) and TEA (0.219 ml, 1.57 mmol) were added under cooling with ice and stirred at room temperature for 4 hours. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate:n-hexane=1:1), giving the titled compound (168 mg, 38%).

$^1$H-NMR (CDCl$_3$):(two rotamers) δ0.62, 0.71, 0.94 and 0.98 (6H, d, J=6.0-6.6 Hz), 1.34 and 1.37 (9H, s), 2.26 and 2.92 (3H, s), 2.24-2.42 (1H, m), 2.64-3.12 (4H, m), 3.84-4.32 (2H, m), 4.50-4.82 (2H, m), 5.02-5.12 (2H, m), 5.20-5.64 (1H, m), 6.21 (1H, brs), 6.31 (1H, brs), 6.50-6.60 (2H, m), 6.86-7.14 (5H, m), 7.24-7.40 (5H, m), 7.50-8.00 (1H, m)

(6) Synthesis of 5-(1-(2-(2-amino-3-(4-fluorophenyl)propanoyl)-N-methylamino)-3-methylbutyrylamino)-2-(3-tert-butyl-4-hydroxylphenyl)ethyl)imidazolidine-2,4-dione To a solution of 5-(1-(2-(2-(benzyloxycarbonylamino)-3-(4-fluorophenyl)propanoyl)-N-methylamino)-3-methylbutyrylamino)-2-(3-tert-butyl-4-hydroxylphenyl)ethyl)imidazolidine-2,4-dione (157 mg, 0.223 mmol) in methanol (5 ml), 10% palladium carbon (50 mg) was added and stirred at room temperature in a hydrogen atmosphere overnight. The reaction mixture was filtered and the filtrate was concentrated under reduced pressure; the thus obtained residue was subjected to preparative TLC (developing solvent: chloroform: methanol:aqueous ammonia=100:10:1), giving the titled compound (83.0 mg, 65%).

FAB-MS:570 (M+H$^+$)

$^1$H-NMR (DMSO-d$_6$):(two rotamers) δ 0.48-0.84 (6H, m), 1.28, 1.32 and 1.33 (9H, s), 2.00-2.12 (1H, m), 2.28, 2.42 and 2.62 (3H, s), 2.40-3.10 (4H, m), 3.82-4.08 (2H, m), 4.24-4.50 (2H, m), 6.58-7.30 (7H, m), 7.66-8.30 (2H, m), 8.92-9.24 (2H, m)

EXAMPLE 21

2-((2-amino-3-(4-fluorophenyl)propionyl)-N-methylamino)-3-methylbutyric acid 2-(3-t-butyl-4-hydroxyphenyl)-1-(1,3,4-oxadiazol-2-yl)ethylamide

(1) Synthesis of 2-(3-t-butyl-4-hydroxyphenyl)-1-(1,3,4-oxadiazol-2-yl)ethylcarbamic acid benzyl ester To a solution of Z-Tyr(3-tBu)-OMe (4.0 g, 10.39 mmol) in ethanol (100 ml), hydrazine monohydrate (6.4 ml, 103.9 mmol) was added at room temperature. The mixture was stirred overnight and evaporated under reduced pressure to remove the solvent. The thus obtained residue was mixed with ethyl orthoformate (100 ml) and p-toluenesulfonic acid monohydrate (198 mg, 1.04 mmol) at room temperature. The mixture was stirred for 1.5 hours and mixed with 1N HCl (100 ml). The mixture was stirred for 20 min., and extracted with ethyl acetate. The organic layer was washed with a saturated aqueous sodium bicarbonate solution and then with saturated brine, dried over anhydrous magnesium sulfate and evaporated to remove the solvent under reduced pressure; the thus obtained residue was subjected to silica gel column chromatography (developing solvent: ethyl acetate:n-hexane=1:1), giving the titled compound (1.34 g, 33%).

$^{1}$H-NMR (CDCl$_{3}$): δ 1.32 (9H, s), 3.19 (2H, brs), 5.02 (1H, brs), 5.05-5.16 (2H, m), 5.35 (2H, brs), 6.53 (1H, d, J=7.9 Hz), 6.75 (1H, dd, J=7.9, 2.0 Hz), 6.85 (1H, d, J=2.0 Hz), 8.34 (1H, s)

(2) Synthesis of 2-(3-t-butyl-4-hydroxyphenyl)-1-(1,3,4-oxadiazol-2-yl)ethylamine To a solution of 2-(3-t-butyl-4-hydroxyphenyl)-1-(1,3,4-oxadiazol-2-yl)ethylcarbamic acid benzyl ester (1.25 g, 3.16 mmol) in methanol (30 ml), 10% palladium carbon (130 mg) was added and stirred in a hydrogen atmosphere at room temperature for 1 day. The reaction mixture was filtered and the filtrate was concentrated under reduced pressure; the thus obtained residue was subjected to silica gel column chromatography (developing solvent: chloroform:methanol:aqueous ammonia=100:10:1), giving the titled compound (0.80 g, 97%).

$^{1}$H-NMR (CDCl$_{3}$): δ 1.36 (9H, s), 3.02 (1H, dd, J=13.8, 7.9 Hz), 3.18 (1H, dd, J=13.8, 5.6 Hz), 4.47 (1H, dd, J=7.9, 5.6 Hz), 6.57 (1H, d, J=7.9 Hz), 6.84 (1H, dd, J=7.9, 2.0 Hz), 6.97 (1H, d, J=2.0 Hz), 8.40 (1H, s)

(3) Synthesis of 3-methyl-2-methylaminobutyric acid 2-(3-t-butyl-4-hydroxyphenyl)-1-(1,3,4-oxadiazol-2-yl)ethylamide To a solution of Z-N-Me-Val-OH (914 mg, 3.45 mmol), 2-(3-t-butyl-4-hydroxyphenyl)-1-(1,3,4-oxadiazol-2-yl) ethylamine (0.75 g, 2.87 mmol) and CMPI (881 mg, 3.45 mmol) in THF (30 ml), TEA (0.96 ml) was added under cooling with ice and stirred at room temperature for 2 hours. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate:n-hexane=1:1), giving 2-benzyloxycarbonylamino-3-methylbutyric acid 2-(3-t-butyl-4-hydroxyphenyl)-1-(1,3,4-oxadiazol-2-yl)ethylamide (1.28 g, 88%).

To a solution of the above compound (1.23 g) in methanol (24 ml), 10% palladium carbon (120 mg) was added and stirred in a hydrogen atmosphere at room temperature for 1 hour. The reaction mixture was filtered and the filtrate was concentrated under reduced pressure; the thus obtained residue was subjected to silica gel column chromatography (developing solvent: chloroform:methanol:aqueous ammonia=100:10:1), giving the titled compound (0.87 g, 96%).

$^{1}$H-NMR (CDCl$_{3}$): δ 0.70 (3H, d, J=6.9 Hz), 0.85 (3H, d, J=6.9 Hz), 1.35 (9H, s), 1.88-2.03 (1H, m), 2.34 (3H, s), 2.77 (1H, d, J=4.6 Hz), 3.12 (1H, dd, J=14.0, 8.4 Hz), 3.28 (1H, dd, J=14.0, 5.9 Hz), 5.45 (1H, brs), 5.61-5.71 (1H, m), 6.58 (1H, d, J=8.0 Hz), 6.68 (1H, dd, J=8.0, 2.0 Hz), 6.96 (1H, d, J=2.0 Hz), 7.84 (1H, brd, J=8.9 Hz), 8.35 (1H, s)

(4) Synthesis of 2-((2-amino-3-(4-fluorophenyl)propionyl)-N-methylamino)-3-methylbutyric acid 2-(3-t-butyl-4-hydroxyphenyl)-1-(1,3,4-oxadiazol-2-yl)ethylamide To a solution of Z-Phe(4-F)-OH (835 mg, 2.63 mmol), 3-methyl-2-methylaminobutyric acid 2-(3-t-butyl-4-hydrox yphenyl)-1-(1,3,4-oxadiazol-2-yl)ethylamide (0.82 g, 2.19 mmol) and CMPI (672 mg, 2.63 mmol) in THF (22 ml), TEA (0.74 ml, 5.26 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: n-hexane:ethyl acetate=1:1), giving 2-(2-benzyloxycarbonylamino-3-(4-fluorophenyl)propionyl)amino-N,3-dimethylbutyric acid 1-(1,3,4-oxadiazol-2-yl)-2-(3-t-butyl-4-hydroxyphenyl)ethylamide (1.31 g, 89%).

A mixture of the above compound (1.31 g, 1.95 mmol) and 10% palladium carbon (130 mg) in methanol (20 ml) was stirred at room temperature in a hydrogen atmosphere for 4 hours. The reaction mixture was filtered and the filtrate was concentrated under reduced pressure; the thus obtained residue was subjected to silica gel column chromatography (developing solvent: chloroform:methanol:aqueous ammonia=100:10:1), giving the titled compound (752 mg, 72%).

EI-MS:539 (M$^{+}$)

$^{1}$H-NMR (CDCl$_{3}$):(two rotamer) δ 0.75, 0.78, 0.89, 0.92 (6H, d, J=6.3-6.6 Hz), 1.29, 1.34 (9H, s), 2.24-2.45 (1H, m), 2.50-2.85 (2H, m), 2.82 (3H, s), 3.04-3.20 (3H, m), 3.52-3.60, 3.72-3.85 (1H, m), 3.99, 4.43 (1H, d, J=10.9 Hz), 5.42-5.53, 5.64-5.73 (1H, m), 6.42-7.18 (7H, m), 8.33, 8.42 (1H, s), 9.62 (1H, brd, J=9.2 Hz)

EXAMPLE 22

2-((2-amino-3-(4-fluorophenyl)propionyl)-N-methylamino)-3-methylbutyric acid 2-(3-t-butyl-4-hydroxyphenyl)-1-(1,2,4-oxadiazol-5-yl)ethylamide (1) Synthesis of N-Me-Val-Tyr(3-tBu)-NH$_{2}$ To a solution of Tyr(3-tBu)-OCH$_{3}$ (1.5 g, 5.97 mmol) in MeOH (10 ml), aqueous ammonia (10 ml) was added and stirred at room temperature overnight. The mixture was evaporated to remove the solvent under reduced pressure and the thus obtained residue was subjected to silica gel column chromatography (developing solvent: methylene chloride:methanol=10:1), giving Tyr(3-tBu)-NH$_{2}$ (1.4 g, 99%).

To a solution of the thus obtained Tyr(3-tBu)-NH$_{2}$ (1 g, 4.23 mmol), Z-N-Me-Val-OH (1.23 g, 4.63 mmol) and CMPI (1.2 g, 4.69 mmol) in THF (20 ml), TEA (1.8 ml) was added under cooling with ice and stirred at room temperature for 4 hours. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: ethyl acetate:n-hexane=2:1), giving Z-N-Me-Val-Tyr(3-tBu)-NH$_{2}$ (1.7 g, 83%).

A mixture of the thus obtained Z-N-Me-Val-Tyr(3-tBu)-NH$_{2}$ (1.7 g), 20% palladium hydroxide/carbon (0.15 g) and methanol (30 ml) was stirred at room temperature in a hydrogen atmosphere for 1 hour. The reaction mixture was filtered and the filtrate was concentrated under reduced pressure; the thus obtained residue was subjected to silica gel column chromatography (developing solvent: methylene chloride:methanol=10:1), giving the titled compound (1.07 g, 88%).

$^{1}$H-NMR (CDCl$_{3}$): δ 0.67 (3H, d, J=6.27 Hz), 0.80 (3H, d, J=6.6 Hz), 1.35 (9H, s), 1.91 (1H, m), 2.25 (3H, s), 2.76 (1H, d, J=4.62 Hz), 3.00 (2H, m), 4.75 (1H, q, J=6.6 Hz), 6.13 (1H, s), 6.55 (1H, s), 6.66 (1H, d, J=7.92 Hz), 6.89 (1H, d, J=7.59 Hz), 7.02 (1H, s), 7.84 (1H, d, J=7.91 Hz)

(2) Synthesis of Boc-Phe(4-F)-N-Me-Val-Tyr(3-tBu)-NH$_2$

To a solution of Boc-Phe(4-F)-OH (890 mg, 3.14 mmol), N-Me-Val-Tyr(3-tBu)-NH$_2$ (1 g, 2.86 mmol) and CMPI (804 mg, 3.15 mmol) in THF (20 ml), TEA (1.2 ml, 7.16 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: acetone:n-hexane=1:2), giving Boc-Phe(4-F)-N-Me-Val-Tyr (3-tBu)-NH$_2$ (1.5 g, 85%).

(3) Synthesis of 2-((2-tertbutoxycarbonylamino-3-(4-fluorophenyl)propionyl)-N-methylamino)-3-methylbutyric acid 2-(3-t-butyl-4-hydroxyphenyl)-1-(1,2,4-oxadiazol-5-yl)ethylamide A solution of Boc-Phe(4-F)-N-Me-Val-Tyr(3-tBu)-NH$_2$ (600 mg, 0.976 mmol) and N,N-dimethylacetamide (0.2 ml, 1.5 mmol) in dioxane (3 ml) was stirred at room temperature for 1 hour and mixed with a solution of sodium hydroxide (108 mg) and hydroxyamine hydrochloride (190 mg) in acetic acid/water (7 ml/3 ml). The mixture was stirred at room temperature for 10 min., mixed with water and filtered; a solution of the thus obtained precipitate in acetic acid/dioxane (10 ml/10 ml) was stirred at 60° C. overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate:n-hexane=1:1), giving the titled compound (474 mg, 76%).

$^1$H-NMR (CDCl$_3$):(two rotamers) δ 0.76, 0.8, 0.86 and 0.98 (6H, d, J=6.59, 6.93, 6.27, and 6.26 Hz), 1.28 and 1.32 (9H, s), 1.25 and 1.37 (9H, s), 2.15 (1H, m), 2.35 and 2.92 (3H, s), 2.9 (3H, m), 3.15 (1H, d, J=6.93 Hz), 4.12 and 4.49 (1H, d, J=6.92 Hz), 4.8 (1H, m), 5.38 and 5.5 (2H, m), 6.65 (1H, brd), 6.9-7.2 (7H, m), 8.37 (1H, brd)

(4) Synthesis of 2-((2-amino-3-(4-fluorophenyl)propionyl)-N-methylamino)-3-methylbutyric acid 2-(3-t-butyl-4-hydroxyphenyl)-1-(1,2,4-oxadiazol-5-yl)ethylamide To a solution of 2-((2-tertbutoxycarbonylamino-3-(4-fluorophenyl)propionyl)-N-methylamino)-3-methylbutyric acid 2-(3-t-butyl-4-hydroxyphenyl)-1-(1,2,4-oxadiazol-5-yl) ethylamide (440 mg) in methylene chloride (5 ml), TFA (1 ml) was added under cooling with ice. The mixture was stirred at room temperature for 1 hour and evaporated to remove the solvent under reduced pressure; the thus obtained residue was subjected to silica gel column chromatography (developing solvent: methylene chloride:methanol=15:1), giving the titled compound (370 mg, 99%).

$^1$H-NMR (CDCl$_3$):(two rotamers) δ 0.75 and 0.87 (total 6H,d and dd, J=6.59 and 6.92 Hz), 1.27 (9H, s), 2.17 (1H, m), 2.77 (2H, m), 2.83 (3H, s), 3.1 (1H, m), 3.55 (1H, m), 3.96 (1H, d, J=10.89 Hz), 5.7 (1H, m), 6.45 (1H, s), 6.59 (1H, d, J=5.94 Hz), 6.9 (1H, brd), 8.35 (1H, s), 9.5 (1H, d, J=8.91 Hz), 6.95 (2H, t, J=8.25 Hz), 7.06 (2H, t, J=8.25 Hz)

EXAMPLE 23

2-((2-amino-3-(4-fluorophenyl)propionyl)-N-methylamino)-3-methylbutyric acid 2-(3-tert-butyl-4-hydroxyphenyl)-1-(thiazol-2-yl)ethylamide

(1) Synthesis of N-benzyloxycarbonyl-3-tBu tyrosinylthioamide

To a solution of Z-Tyr(3-tBu)-NH$_2$ (2.08 g, 5.62 mmol) in dioxane (70 ml), Lawesson's reagent (1.36 g, 3.37 mmol) was added and stirred at 80° C. for 1 hour. The reaction mixture was evaporated to remove the solvent under reduced pressure and the thus obtained residue was subjected to silica gel column chromatography (developing solvent: ethyl acetate: n-hexane=1:3), giving the titled compound (1.66 g, 77%).

$^1$H-NMR (CDCl$_3$): δ 1.37 (9H, s), 3.01-3.14 (2H, m), 4.56-4.65 (1H, m), 5.08 (2H, s), 6.58 (1H, d, J=7.9 Hz), 6.90 (1H, dd, J=7.9, 1.7 Hz), 7.09 (1H, d, J=1.7 Hz), 7.20-7.40 (5H, m)

(2) Synthesis of N-benzyloxycarbonyl-2-(3-tert-butyl-4-hydroxylphenyl)-1-(thiazol-2-yl)ethylamine To a solution of N-benzyloxycarbonyl-3-tBu tyrosinylthioamide (21.49 g, 55.67 mmol) in ethanol (300 ml), bromoacetaldehyde diethylacetal (43 ml, 278 mmol) was added, stirred at 80° C. for 2 hours, further mixed with bromoacetaldehyde diethylacetal (43 ml, 278 mmol), stirred at 80° C. for 4 hours, further mixed with bromoacetaldehyde diethylacetal (43 ml, 278 mmol) and stirred at 80° C. for 3 hours. The mixture was evaporated to remove the solvent under reduced pressure and the thus obtained residue was subjected to silica gel column chromatography (developing solvent: ethyl acetate:n-hexane=1:3), giving the titled compound (15.32 g, 67%).

$^1$H-NMR (CDCl$_3$): δ 1.29 (9H, s), 3.10-3.30 (2H, m), 5.10 (2H, s), 5.20-5.40 (1H, m), 6.51 (1H, d, J=8.3 Hz), 6.74-6.78 (2H, m), 7.22 (1H, d, J=3.3 Hz), 7.20-7.40 (5H, brs), 7.76 (1H, d, J=3.3 Hz)

(3) Synthesis of 2-(3-tert-butyl-4-hydroxylphenyl)-1-(thiazol-2-yl)ethylamine To a solution of N-benzyloxycarbonyl-2-(3-tert-butyl-4-hydroxylphenyl)-1-(thiazol-2-yl)ethylamine (15.28 g, 37.27 mmol) in methylene chloride (1.1 l), thioanisole (8.75 ml, 74.54 mmol) was added. To the mixture, a solution of 1.0M boron tribromide in methylene chloride (186 ml, 186.34 mmol) was added dropwise under cooling with ice and stirred for 1 hour. The reaction mixture was mixed with water and alkalinized by 2N sodium hydroxide and extracted with methylene chloride. The organic layer was washed with saturated brine, dried over anhydrous magnesium sulfate and evaporated to remove the solvent under reduced pressure, giving the titled compound (9.46 g, 90%).

$^1$H-NMR (CDCl$_3$): δ 1.36 (9H, s), 2.82-3.27 (2H, m), 4.51-4.56 (1H, m), 6.57 (1H, d, J=7.9 Hz), 6.89 (1H, dd, J=7.9, 2.0 Hz), 6.99 (1H, d, J=2.0 Hz), 7.27 (1H, d, J=3.3 Hz), 7.76 (1H, d, J=3.3 Hz)

(4) Synthesis of 2-(N-tert-butoxycarbonyl-N-methylamino)-3-methylbutyric acid 2-(3-tert-butyl-4-hydroxyphenyl)-1-(thiazol-2-yl)ethylamide To a solution of 2-(3-tert-butyl-4-hydroxylphenyl)-1-(thiazol-2-yl)ethylamine (4.67 g, 16.64 mmol), Boc-N-Me-Val-OH (5.0 g, 21.63 mmol) and CMPI (5.53 g, 21.63 mmol) in THF (110 ml), TEA (5.33 ml, 38.27 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: methanol:aqueous ammonia:methylene chloride=3:0.1:100), giving the titled compound (8.10 g, 100%).

$^1$H-NMR (CDCl$_3$): δ 0.75-0.97 (6H, m), 1.29 (6H, s), 1.31 (3H, s), 1.41 (3H, s), 1.48 (6H, s), 2.10-2.35 (1H, m), 2.71 (1.5H, s), 2.73 (1.5H, s), 3.10-3.30 (2H, m), 3.90-4.10 (1H, m), 5.50-5.70 (1H, m), 6.58 (1H, d, J=7.9 Hz), 6.70-6.90 (2H, m), 7.20 (1H, d, J=3.0 Hz), 7.74-7.76 (1H, m)

(5) Synthesis of 3-methyl-2-methylaminobutyric acid 2-(3-tert-butyl-4-hydroxyphenyl)-1-(thiazol-2-yl)ethylamide To a solution of 2-(N-tert-butoxycarbonyl-N-methylamino)-3-methylbutyric acid 2-(3-tert-butyl-4-hydroxyphenyl)-1-(thiazol-2-yl)ethylamide (8.03 g, 16.42 mmol) in methylene chloride (80 ml), TFA (40 ml) was added and stirred at room temperature for 30 min. The reaction mixture was evaporated to remove the solvent under reduced pressure; the thus obtained residue was mixed with methylene chloride, washed with a 2N aqueous sodium hydroxide solution and saturated brine, dried over anhydrous magnesium sulfate and evaporated to remove the solvent under reduced pressure. The thus obtained residue was subjected to silica gel column chromatography (developing solvent: acetone:hexane=1:2), giving two diastereoisomers A and B of the titled compound, A (2.37 g, 37%) being eluted first and then B (2.17 g, 34%). (A)

$^1$H-NMR (CDCl$_3$): δ 0.65 (3H, d, J=6.9 Hz), 0.82 (3H, d, J=6.9 Hz), 1.33 (9H, s), 1.85-2.00 (1H, m), 2.32 (3H, s), 2.75 (1H, d, J=4.6 Hz), 3.09-3.37 (2H, m), 5.63-5.71 (1H, m), 6.61 (1H, d, J=7.9 Hz), 6.87-6.92 (2H, m), 7.22 (1H, d, J=3.0 Hz), 7.77 (1H, d, J=3.3 Hz) (B)

$^1$H-NMR (CDCl$_3$): δ 0.84 (3H, d, J=6.9 Hz), 0.92 (3H, d, J=6.9 Hz), 1.33 (9H, s), 1.95-2.15 (1H, m), 2.11 (3H, s), 2.68 (1H, d, J=5.0 Hz), 3.12-3.39 (2H, m), 5.60-5.69 (1H, m), 6.59 (1H, d, J=8.2 Hz), 6.87 (1H, dd, J=7.9, 2.0 Hz), 6.93 (1H, d, J=2.0 Hz), 7.22 (1H, d, J=3.3 Hz), 7.77 (1H, d, J=3.3 Hz)

(6) Synthesis of 2-((2-butoxycarbonylamino-3-(4-fluorophenyl)propionyl)-N-methylamino)-3-methylbutyric acid 2-(3-tert-butyl-4-hydroxyphenyl)-1-(thiazol-2-yl)ethylamide (A)

To a solution of 3-methyl-2-methylaminobutyric acid 2-(3-tert-butyl-4-hydroxyphenyl)-1-(thiazol-2-yl)ethylamide (A) (1.00 g, 2.57 mmol), Boc-Phe(4-F)-OH (947 mg, 3.34 mmol) and CMPI (853 mg, 3.34 mmol) in THF (17 ml), TEA (0.82 ml, 5.91 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate:n-hexane=1:2), giving the titled compound (1.55 g, 92%).

$^1$H-NMR (CDCl$_3$): δ 0.76 (3H, d, J=6.6 Hz), 0.86 (2H, d, J=6.6 Hz), 0.97 (1H, d, J=6.6 Hz), 1.26 (3H, s), 1.29 (6H, s), 1.37 (6H, s), 1.40 (3H, s), 2.15-2.40 (1H, m), 2.70-3.50 (4H, m), 2.78 (3H, s), 4.17 (0.3H, d, J=10.2 Hz), 4.49 (0.7H, d, J=11.2 Hz), 4.70-4.85 (1H, m), 5.25-5.80 (1H, m), 6.58 (1H, d, J=7.9 Hz), 6.75-7.30 (6H, m), 7.21 (0.7H, d, J=3.3 Hz), 7.23 (0.3H, d, J=3.3 Hz), 7.74 (0.3H, d, J=3.3 Hz), 7.77 (0.7H, d, J=3.3 Hz)

(7) Synthesis of 2-((2-butoxycarbonylamino-3-(4-fluorophenyl)propionyl)-N-methylamino)-3-methylbutyric acid 2-(3-tert-butyl-4-hydroxyphenyl)-1-(thiazol-2-yl)ethylamide (B)

To a solution of 3-methyl-2-methylaminobutyric acid 2-(3-tert-butyl-4-hydroxyphenyl)-1-(thiazol-2-yl)ethylamide (B) (1.00 g, 2.57 mmol), Boc-Phe(4-F)-OH (947 mg, 3.34 mmol) and CMPI (853 mg, 3.34 mmol) in THF (17 ml), TEA (0.82 ml, 5.91 mmol) was added under cooling with ice and stirred at room temperature overnight. The reaction mixture was mixed with water and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: ethyl acetate:n-hexane 1:2), giving the titled compound (1.54 g, 92%).

$^1$H-NMR (CDCl$_3$): δ 0.57 (1H, d, J=6.6 Hz), 0.62 (1H, d, J=6.9 Hz), 0.78 (4H, d, J=6.3 Hz), 1.33 (9H, s), 1.36 (9H, s), 2.10-2.30 (1H, m), 2.60-3.70 (4H, m), 2.82 (1.8H, s), 2.85 (1.2H, s), 3.99 (0.3H, d, J=10.6 Hz), 4.51 (0.7H, d, J=10.9 Hz), 4.70-4.90 (1H, m), 5.20-5.60 (1H, m), 6.59-7.21 (7H, m), 7.20 (1H, d, J=3.3 Hz), 7.71 (1H, d, J=3.3 Hz)

(8) Synthesis of 2-((2-amino-3-(4-fluorophenyl)propionyl)-N-methylamino)-3-methylbutyric acid 2-(3-tert-butyl-4-hydroxyphenyl)-1-(thiazol-2-yl)ethylamide (A)

To a solution of 2-((2-butoxycarbonylamino-3-(4-fluorophenyl)propionyl)-N-methylamino)-3-methylbutyric acid 2-(3-tert-butyl-4-hydroxyphenyl)-1-(thiazol-2-yl)ethylamide (A) (1.49 g, 2.28 mmol) in methylene chloride (20 ml), TFA (10 ml) was added and stirred at room temperature for 1.5 hours. The reaction mixture was evaporated to remove the solvent under reduced pressure; the thus obtained residue was mixed with methylene chloride, washed with a 2N aqueous sodium hydroxide solution and saturated brine, dried over anhydrous magnesium sulfate and evaporated to remove the solvent under reduced pressure. The thus obtained residue was subjected to silica gel column chromatography (developing solvent: methanol:aqueous ammonia:methylene chloride=3:0.1:100), giving the titled compound (430 mg).

EI-MS:554 (M$^+$)

$^1$H-NMR (CDCl$_3$): δ 0.75 (2.3H, d, J=6.9 Hz), 0.80 (0.7H, d, J=6.6 Hz), 0.90-0.92 (0.7H, m), 0.93 (2.3H, d, J=6.6 Hz), 1.24 (7H, s), 1.30 (2H, s), 2.25-2.65 (1H, m), 2.70-3.40 (4H, m), 2.79 (2.4H, s), 2.85 (0.6H, s), 3.50-3.60 (0.8H, m), 3.75-3.90 (0.2H, m), 3.97 (0.8H, d, J=10.9 Hz), 4.51 (0.2H, d, J=10.6 Hz), 5.45-5.60 (0.2H, m), 5.65-5.80 (0.8H, m), 6.55-7.20 (7H, m), 7.23 (1H, d, J=3.3 Hz), 7.76 (1H, d, J=3.3 Hz)

(9) Synthesis of 2-((2-amino-3-(4-fluorophenyl)propionyl)-N-methylamino)-3-methylbutyric acid 2-(3-tert-butyl-4-hydroxyphenyl)-1-(thiazol-2-yl)ethylamide (B)

To a solution of 2-((2-butoxycarbonylamino-3-(4-fluorophenyl)propionyl)-N-methylamino)-3-methylbutyric acid 2-(3-tert-butyl-4-hydroxyphenyl)-1-(thiazol-2-yl)ethylamide (B) (1.48 g, 2.26 mmol) in methylene chloride (20 ml), TFA (10 ml) was added and stirred at room temperature for 1.5 hours. The reaction mixture was evaporated to remove the solvent under reduced pressure; the thus obtained residue was mixed with methylene chloride, washed with a 2N aqueous sodium hydroxide solution and saturated brine, dried over anhydrous magnesium sulfate and evaporated to remove the solvent under reduced pressure. The thus obtained residue was subjected to silica gel column chromatography (developing solvent: methanol:aqueous ammonia:methylene chloride=3:0.1:100), giving the titled compound (587 mg).

EI-MS:554 (M⁺)

$^1$H-NMR (CDCl$_3$): δ 0.72 (1.5H, d, J=6.9 Hz), 0.786 (1.5H, d, J=6.3 Hz), 0.793 (1.5H, d, J=6.6 Hz), 0.88 (1.5H, d, J=6.3 Hz), 1.24 (5.4H, s), 1.33 (3.6H, s), 2.15-2.40 (1H, m), 2.40-3.35 (4H, m), 2.75 (1.8H, s), 2.87 (1.2H, s), 3.55-3.85 (1H, m), 3.86 (0.6H, d, J=10.9 Hz), 4.56 (0.4H, d, J=10.9 Hz), 5.50-5.65 (1H, m), 6.45-7.15 (7H, m), 7.17-7.20 (1H, m), 7.23 (1H, d, J=3.3 Hz), 7.76 (1H, d, J=3.0 Hz)

EXAMPLE 24

Synthesis of 2-((2-amino-3-(4-fluorophenyl)propionyl)-N-methylamino)-3-methylbutyric acid 2-(3-t-butyl-4-hydroxyphenyl)-1-(1,3,4-triazol-2-yl)ethylamide To a solution of Boc-Phe(4-F)-N-Me-Val-Tyr(3-tBu)-NH$_2$ (400 mg, 0.651 mmol) in methylene chloride (6.5 ml), dimethylformamide dimethylacetal (0.26 ml, 1.954 mmol) was added at room temperature. The mixture was stirred for 30 min. and evaporated to remove the solvent under reduced pressure. To a solution of the thus obtained residue in dioxane (6.5 ml), acetic acid (2 ml) and hydrazine monohydrate (48 µl, 0.977 mmol) were added at room temperature. The mixture was stirred for 40 min., mixed with water and filtered to collect the precipitated solid. The thus obtained solid was subjected to silica gel column chromatography (developing solvent: ethyl acetate), giving 2-((2-t-butoxycarbonylamino-3-(4-fluorophenyl)propionyl)-N-methylamino)-3-methylbutyric acid 2-(3-t-butyl-4-hydroxyphenyl)-1-(1,3,4-triazol-2-yl)ethylamide (384 mg, 93%).

To a solution of the above compound (421 mg) in methylene chloride (3 ml), TFA (1 ml) was added under cooling with ice. The mixture was stirred at room temperature for 30 min., mixed with a saturated aqueous sodium bicarbonate solution and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: chloroform:methanol:aqueous ammonia=100:10:1), giving the titled compound (175 mg, 49%).

EI-MS:538 (M⁺)

$^1$H-NMR (CDCl$_3$): δ 0.72, 0.87, 0.73-0.80 (6H, d, J=6.3-6.6 Hz), 1.22, 1.25 (9H, s), 2.24-2.41 (1H, m), 2.50-3.30 (4H, m), 2.78, 2.87 (3H, s), 3.47-3.58, 3.79-3.88 (1H, m), 4.00, 4.39 (1H, brd, J=10.6 Hz), 5.29-5.38, 5.40-5.50 (1H, m), 6.41-7.11 (7H, m), 7.52, 9.33 (1H, brd, J=8.3 Hz), 8.02, 8.10 (1H, s)

EXAMPLE 25

2-[2-amino-3-(4-fluorophenyl)propyl]amino-3-methylbutyric acid 2-(3-tert-butyl-4-hydroxyphenyl)-1-(thiazol-2-yl)ethylamide (1) Synthesis of 2-tert-butoxycarbonylamino-3-methylbutyric acid 2-(3-tert-butyl-4-hydroxyphenyl)-1-(thiazol-2-yl)ethylamide To a solution of Boc-Val-OH (890 mg, 4.09 mmol), 2-(3-tert-butyl-4-hydroxyphenyl)-1-(thiazol-2-yl)ethylamine (1.03 g, 3.73 mmol) and CMPI (653 mg, 1.05 mmol) in THF (10 ml), TEA (1 ml) was added under cooling with ice and stirred at room temperature overnight. The reaction mixture was mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: ethyl acetate:n-hexane=1:1), giving the titled compound (1.88 g, 99%).

$^1$H-NMR (CDCl$_3$): δ 0.79 and 0.89 (6H, d, J=6.93 Hz), 1.29 and 1.31 (9H, s), 1.42 and 1.44 (9H, s), 2.15 (1H, brd), 3.23 (2H, m), 3.89 (1H, m), 5.0 (1H, brd), 5.4 (0.7H, brd), 5.57 (1H, q, J=6.93 and 5.92 Hz), 6.56 (1H, q, J=4.62 and 4.29 Hz), 6.8 (3H, brd), 7.21 (1H, m), 7.75 (1H, t, J=2.07 and 3.3 Hz)

(2) Synthesis of 2-amino-3-methylbutyric acid 2-(3-tert-butyl-4-hydroxyphenyl)-1-(thiazol-2-yl)ethylamide To a solution of 2-(3-tert-butyl-4-hydroxyphenyl)-1-(thiazol-2-yl)ethylamine (1.7 g) in methylene chloride (14 ml), TFA (0.6 ml) was added under cooling with ice and stirred at room temperature for 2 hours. The mixture was evaporated to remove the solvent under reduced pressure; the thus obtained residue was subjected to silica gel column chromatography (developing solvent: methylene chloride:methanol:ethyl acetate=20:1:2), giving two diastereoisomers A and B of the titled compound, A (700 mg) being eluted first and then B (650 mg, 99%).

(A)

$^1$H-NMR (CDCl$_3$-CD$_3$OD): δ 0.89 (6H, brd), 1.28 (9H, s), 2.15 (1H, m), 3.18-3.7 (3H, m), 5.48 (1H, brd), 6.6 (1H, brd), 6.8 (2H, brd), 7.27 (1H, s), 7.7 (1H, s)

(B)

$^1$H-NMR (CDCl$_3$-CD$_3$OD): δ 0.72 (6H, d, J=6.27 Hz), 1.31 (9H, s), 1.92 (1H, brd), 3.04 (2H, brd), 3.28 (1H, dd, J=5.28 and 5.6 Hz), 5.55 (1H, m), 6.62 (1H, d, J=7.92 Hz), 6.86 (1H, brd), 6.97 (1H, s), 7.28 (1H, s), 7.68 (1H, d, J=2.64 Hz)

(3) Synthesis of 2-[2-tert-butoxycarbonylamino-3-(4-fluorophenyl)propyl]amino-3-methylbutyric acid 2-(3-tert-butyl-4-hydroxyphenyl)-1-(thiazol-2-yl)ethylamide (A)

To a solution of 2-amino-3-methylbutyric acid 2-(3-tert-butyl-4-hydroxyphenyl)-1-(thiazol-2-yl)ethylamide (A) (600 mg, 1.59 mmol) and (1-formyl-2-(4-fluorophenyl)ethyl) carbamic acid tBu ester (640 mg, 2.39 mmol) in MeOH (10 ml), NaBH$_3$CN (200 mg, 3.1 mmol) was added under cooling with ice and stirred at room temperature for one hour. The mixture was evaporated under reduced pressure, mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: ethyl acetate:n-hexane=1:1), giving the titled compound (935 mg, 93%).

$^1$H-NMR (CDCl$_3$): δ 0.75 and 0.83 (6H, d, J=6.93 and 6.59 Hz), 1.36 (9H, s), 1.42 (9H, s), 2.46 (2H, brd), 2.66 (2H, brd), 2.73 (1H, d, J=4.61 Hz), 2.81 (1H, d, J=7.26 Hz), 3.20 (2H, d, J=6.26 Hz), 3.6 (2H, m), 3.8 (1H, brd), 4.7 (1H, brd), 5.6 (1H, q, J=6.93 and 5.94 Hz), 6.61 (1H, d, J=7.92 Hz), 6.77 (1H, s), 6.85 (1H, d, J=7.92 Hz), 6.9-7.21 (8H, m), 7.66 (1H, d, J=2.97 Hz)

(4) Synthesis of 2-[2-tert-butoxycarbonylamino-3-(4-fluorophenyl)propyl]amino-3-methylbutyric acid 2-(3-tert-butyl-4-hydroxyphenyl)-1-(thiazol-2-yl)ethylamide (B)

To a solution of 2-amino-3-methylbutyric acid 2-(3-tert-butyl-4-hydroxyphenyl)-1-(thiazol-2-yl)ethylamide (B) (600 mg, 1.59 mmol) and 1-formyl-2-(4-fluorophenyl)ethyl)carbamic acid tBu ester (640 mg, 2.39 mmol) in MeOH (10 ml), NaBH$_3$CN (200 mg, 3.1 mmol) was added under cooling with ice and stirred at room temperature for one hour. The mixture was evaporated under reduced pressure, mixed with water and extracted with ethyl acetate. The organic layer was washed with saturated brine, dried over sodium sulfate and evaporated to remove the solvent under reduced pressure; the thus obtained residue was subjected to silica gel column chromatography (developing solvent: ethyl acetate:n-hexane=1:1), giving the titled compound (950 mg, 95%).

$^1$H-NMR (CDCl$_3$): δ 0.83 and 0.87 (6H, d, J=6.93 and 6.92 Hz), 1.34 (9H, s), 1.41 (9H, s), 2.00 (1H, brd), 2.31 (2H, brd), 2.6-2.81 (3H, brd), 2.81 (1H, d, J=7.26 Hz), 3.20 (2H, m), 3.6 (2H, m), 13.8 (1H, brd), 4.58 (1H, brd), 4.83 (1H, brd), 5.59 (2H, q, J=6.93 Hz), 6.60 (1H, d, J=7.92 Hz), 6.81 (1H, d, J=7.91 Hz), 6.88 (1H, s), 6.9-7.21 (8H, m), 7.74 (1H, d, J=2.29 Hz)

(5) Synthesis of 2-[2-amino-3-(4-fluorophenyl)propyl]amino-3-methylbutyric acid 2-(3-tert-butyl-4-hydroxyphenyl)-1-(thiazol-2-yl)ethylamide (A)

To a solution of 2-[2-tert-butoxycarbonylamino-3-(4-fluorophenyl)propyl]amino-3-methylbutyric acid 2-(3-tert-butyl-4-hydroxyphenyl)-1-(thiazol-2-yl)ethylamide (A) (300 mg) in methylene chloride (5 ml), TFA (1 ml) was added under cooling with ice. The mixture was stirred at room temperature for 1 hour and evaporated under reduced pressure; the thus obtained residue was subjected to silica gel column chromatography (developing solvent: methylene chloride:methanol=15:1), giving the titled compound (180 mg, 71%).

$^1$H-NMR (DMSO-d$_6$): δ 0.78 and 0.88 (6H, d, J=3.3 and 5.6 Hz), 1.28 (9H, s), 1.90 (1H, brd), 2.6 (1H, m), 2.7-3.0 (3H, brd), 3.1 (1H, brd), 3.4 (2H, m), 5.29 (1H, q, J=5.93 and 8.58 Hz), 6.69 (1H, d, J=7.92 Hz), 6.86 (1H, d, J=7.59 Hz), 6.95 (1H, s), 7.2 (4H, m), 7.62 (1H, d, J=2.97 Hz), 7.77 (1H, d, J=3.3 Hz)

(6) Synthesis of 2-[2-amino-3-(4-fluorophenyl)propyl]amino-3-methylbutyric acid 2-(3-tert-butyl-4-hydroxyphenyl)-1-(thiazol-2-yl)ethylamide (B)

To a solution of 2-[2-tert-butoxycarbonylamino-3-(4-fluorophenyl)propyl]amino-3-methylbutyric acid 2-(3-tert-butyl-4-hydroxyphenyl)-1-(thiazol-2-yl)ethylamide (B) (300 mg) in methylene chloride (5 ml), TFA (1 ml) was added under cooling with ice. The mixture was stirred at room temperature for 1 hour and evaporated under reduced pressure; the thus obtained residue was subjected to silica gel column chromatography (developing solvent: methylene chloride:methanol=15:1), giving the titled compound (193 mg, 76%).

$^1$H-NMR (DMSO-d$_6$): δ 0.61 (6H, q, J=6.6 and 12.54 Hz), 1.3 (9H, s), 1.72 (1H, s), 2.7-3.0 (4H, brd), 3.16 (1H, s), 3.28 (1H, m), 3.5 (1H, brd), 5.37 (1H, m), 6.65 (1H, d, J=8.25 Hz), 6.85 (1H, d, J=10.89 Hz), 7.0 (1H, s), 7.2 (4H, m), 7.68 (1H, d, J=2.97 Hz), 7.81 (1H, d, J=3.3 Hz)

EXAMPLE 26

Tyr(2-F)-N-Me-Val-N-Me-Tyr(3-tBu)-NH$_2$ (1) Synthesis of Boc-Tyr(2-F)-N-Me-Val-N-Me-Tyr(3-tBu)-NH$_2$ To a solution of Tyr(2-F)-OH (0.60 g, 3.01 mmol) and di-tert-butyl dicarbonate (0.69 g, 3.16 mmol) in dioxane/water (5 ml/5 ml), TEA (0.84 ml, 6.02 mmol) was added under cooling with ice and stirred for 2 hours. The reaction mixture was concentrated to approximately a half volume, mixed with a saturated aqueous NaHCO$_3$ solution and washed with ether. The aqueous layer was rendered acidic by the addition of 2N hydrochloric acid under cooling with ice, and extracted with chloroform. The organic layer was dried over anhydrous magnesium sulfate and evaporated to remove the solvent under reduced pressure, giving crude Boc-Tyr(2-F)-OH (0.85 g).

To a solution of the above crude Boc-Tyr(2-F)-OH (0.82 g), N-Me-Val-N-Me-Tyr(3-tBu)-NH$_2$ (0.77 g, 2.11 mmol) and CMPI (0.81 g, 3.17 mmol) in THF (5 ml), TEA (1.18 ml, 8.44 mmol) was added under cooling with ice and stirred at room temperature for 23 hours. The reaction mixture was mixed with water, and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: chloroform:methanol:concentrated aqueous ammonia=30:1:0.05), giving the titled compound (0.21 g, 15%).

(2) Synthesis of Tyr(2-F)-N-Me-Val-N-Me-Tyr(3-tBu)-NH$_2$

To a solution of Boc-Tyr(2-F)-N-Me-Val-N-Me-Tyr(3-tBu)-NH$_2$ (0.21 g, 0.326 mmol) in methylene chloride (3 ml), TFA (1.5 ml) was added and stirred for 15 min. The reaction mixture was concentrated under reduced pressure, mixed with a saturated aqueous NaHCO$_3$ solution, and extracted with chloroform. The organic layer was dried over anhydrous magnesium sulfate. The resultant was evaporated to remove the solvent under reduced pressure, giving the titled compound (173 mg, 82%).

EI-MS (M$^+$):544

$^1$H-NMR (DMSO-d$_6$-CDCl$_3$): δ 0.21 (6/5H, d, J=6.3 Hz), 0.59 (6/5H, d, J=6.6 Hz), 0.71 (9/5H, d, J=6.6 Hz), 0.84-0.98

(9/5H, m), 1.30 (27/5H, s), 1.37 (18/5H, s), 2.00-2.22 (1H, m), 2.10 (6/5H, s), 2.3-2.8 (2H, m), 2.44 (9/5H, s), 2.85 (9/5H, d, J=5.9 Hz), 3.1-3.8 (2H, m), 3.24 (6/5H, d, J=5.0 Hz), 3.94-4.20 (1H, m), 4.51 (2/5H, d, J=10.2 Hz), 4.78 (2/5H, dd, J=3.9, 11.2 Hz), 4.88 (3/5H, d, J=10.2 Hz), 5.41 (3/5H, dd, J=3.9, 10.2 Hz), 6.48-7.21 (7.7H, m), 7.60-7.75 (0.3H, m), 8.88 (1H, d, J=7.3 Hz), 9.47 (1H, brs)

EXAMPLE 27

Tyr(3-F)-N-Me-Val-N-Me-Tyr(3-tBu)-NH$_2$ (1) Synthesis of Boc-Tyr(3-F)-N-Me-Val-N-Me-Tyr (3-tBu)-NH$_2$ To a solution of Tyr(3-F)-OH (0.80 g, 4.02 mmol) and di-tert-butyl dicarbonate (0.92 g, 4.22 mmol) in dioxane/water (7 ml/7 ml), TEA (1.12 ml, 8.04 mmol) was added under cooling with ice and stirred for 2.5 hours. The reaction mixture was concentrated to approximately a half volume, mixed with a saturated aqueous NaHCO$_3$ solution and washed with ether. The aqueous layer was rendered acidic by the addition of 2N hydrochloric acid under cooling with ice, and extracted with chloroform. The organic layer was dried over anhydrous magnesium sulfate and evaporated to remove the solvent under reduced pressure, giving crude Boc-Tyr(3-F)-OH (1.18 g).

To a solution of the above crude Boc-Tyr(3-F)-OH (1.18 g), N-Me-Val-N-Me-Tyr(3-tBu)-NH$_2$ (1.10 g, 3.03 mmol) and CMPI (1.16 g, 4.55 mmol) in THF (6 ml), TEA (1.27 ml, 12.1 mmol) was added under cooling with ice and stirred at room temperature for 27 hours. The reaction mixture was mixed with water, and extracted with ethyl acetate. The organic layer was washed with saturated brine, dried over anhydrous magnesium sulfate and evaporated to remove the solvent under reduced pressure; the thus obtained residue was subjected to silica gel column chromatography (developing solvent: chloroform:methanol:concentrated aqueous ammonia=30:1: 0.05), giving the titled compound (0.19 g, 10%).

(2) Synthesis of Tyr(3-F)-N-Me-Val-N-Me-Tyr(3-tBu)-NH$_2$

To a solution of Boc-Tyr(3-F)-N-Me-Val-N-Me-Tyr(3-tBu)-NH$_2$ (0.19 g, 0.294 mmol) in methylene chloride (3 ml), TFA (1.5 ml) was added and stirred for 15 min. The reaction mixture was concentrated under reduced pressure, mixed with a saturated aqueous NaHCO$_3$ solution, and extracted with chloroform. The organic layer was dried over anhydrous magnesium sulfate. The resultant was evaporated to remove the solvent under reduced pressure, giving the titled compound (136 mg, 85%).

EI-MS (M$^+$):544

$^1$H-NMR (DMSO-d$_6$-CDCl$_3$): δ 0.18 (6/5H, d, J=6.3 Hz), 0.58 (6/5H, d, J=6.6 Hz), 0.68 (9/5H, d, J=6.6 Hz), 0.85 (9/5H, d, J=6.3 Hz), 1.29 (27/5H, s), 1.37 (18/5H, s), 1.95-2.21 (1H, m), 2.04 (6/5H, s), 2.30-3.00 (2H, m), 2.41 (9/5H, s), 2.81 (9/5H, s), 3.10-3.60 (16/5H, m), 3.55-6.64 (3/5H, m), 4.00-4.10 (2/5H, m), 4.45 (2/5H, d, J=10.2 Hz), 4.70 (2/5H, dd, J=3.9, 11.2 Hz), 4.85 (3/5H, d, J=10.2 Hz), 5.38 (3/5H, dd, J=3.9, 10.2 Hz), 6.51-7.31 (8H, m), 8.98 (1H, d, J=2.6 Hz), 9.50 (1H, brs) Examples 28-64 were conducted according to Scheme 1 and Examples 65-78 were conducted according to Scheme 2. The following Reference Examples show the methods of preparing Intermediates of Schemes 1 and 2. Table C-1 shows structural formulae of Intermediates of Examples 28-64.

TABLE C-1

Intermediates of Examples 28-78

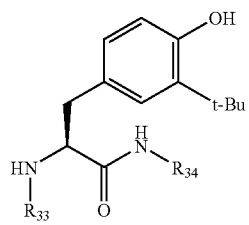 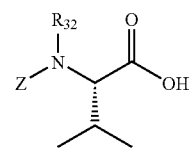 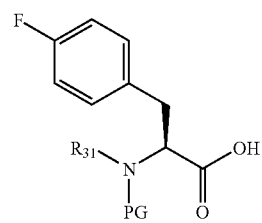

T1: R33 = R34 = H
T2: R33 = H, R = Me
T4: R33 = Me, R34 = H (Example 1 (5))
T5: R33 = R34 = Me
T7: R33 = Et, R34 = H
T8: R33 = Et, R34 = Me
T17: R33 = Me, R34 = CH$_2$SO$_2$CH$_3$
T18: R33 = H, R34 = tBu V1: R32 = Me (Commercial)
V2: R32 = Et P1: PG = Boc, R31 = H (Commercial)
P2: PG = Boc, R31 = Me
P3: PG = Z, R31 = Et
P10: PG = Boc, R31 = Et

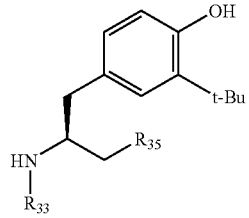 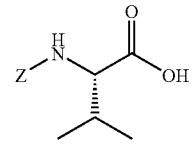

T19: R33 = H, R35 = OH (Example 17)
T20: R33 = Me, R35 = H
T21: R33 = R35 = H
T22: R33 = H, R35 = NHBoc (Example 10)
T23: R33 = Me, R35 = OH V4 (Commercial)

P11

In Table C-1, "(Example 1 (5))", "(Example 17)" and "(Example 10)" mean that the methods of preparing the compounds are described in the corresponding Examples 1 (5), 17 and 10, respectively. "Commercial" means that the compound is commercially available.

REFERENCE EXAMPLE 1

Synthesis of Intermediate T1

A mixture of Tyr(3-tBu)-OMe (12.4 g, 49 mmol) and concentrated aqueous ammonia (240 ml) was stirred at room temperature for 18 hours. The reaction mixture was concentrated under reduced pressure and the thus obtained residue was subjected to silica gel column chromatography ($CHCl_3$: MeOH=10:1), giving Tyr(3-tBu)-$NH_2$ (T1) (10 g, 80%).

$^1$H-NMR ($CDCl_3$): δ 1.40 (9H, s), 2.63 (1H, dd, J=9.6, 13.9 Hz), 3.19 (1H, dd, J=4.0, 13.9 Hz), 3.58 (1H, dd, J=4.0, 9.6 Hz), 5.11 (1H, brs), 5.38 (1H, brs), 6.64 (1H, d, J=7.9 Hz), 6.92 (1H, dd, J=2.0, 7.9 Hz), 7.11 (1H, d, J=2.0 Hz).

REFERENCE EXAMPLE 2

Synthesis of Intermediate T2

A mixture of Tyr(3-tBu)-OMe (12 g, 48 mmol) and a 40% methylamine methanol solution (80 ml) was stirred at room temperature for 14 hours. The reaction mixture was concentrated under reduced pressure, giving Tyr(3-tBu)-NHMe (T2) (12 g) as a crude product.

$^1$H-NMR ($CDCl_3$): δ 1.39 (9H, s), 2.60 (1H, dd, J=9.6, 13.9 Hz), 2.83 (3H, d, J=5.0 Hz), 3.18 (1H, dd, J=4.0, 13.9 Hz), 3.57 (1H, dd, J=4.0, 9.6 Hz), 6.67 (1H, d, J=7.9 Hz), 6.88 (1H, dd, J=1.8, 7.9 Hz), 7.07 (1H, d, J=1.8 Hz).

REFERENCE EXAMPLE 3

Synthesis of Intermediate T5

(1) Synthesis of N-formyl-Tyr(3-tBu)-OMe

To a solution of acetyl chloride (22.6 ml, 299 mmol) in diethyl ether (11), sodium formate (30.6 g, 450 mmol) was added under cooling with ice and stirred at room temperature for 23 hours. The reaction mixture was filtered and evaporated to remove the solvent. The thus obtained residue was added dropwise to a solution of H-Tyr(3-tBu)-OMe (22.2 g, 83.8 mmol) in methylene chloride (500 ml) under cooling with ice, mixed with TEA (46.7 ml, 335 mmol) and stirred at room temperature for 2 hours. The reaction mixture was mixed with saturated aqueous $NaHCO_3$ and extracted with chloroform. The organic layer was washed with saturated brine, dried over anhydrous magnesium sulfate and evaporated to remove the solvent under reduced pressure. The thus obtained residue was subjected to silica gel column chromatography (developing solvent: n-hexane:ethyl acetate=1:1), giving N-formyl-Tyr(3-tBu)-OMe (23.8 g, 100%).

$^1$H-NMR ($CDCl_3$): δ 1.38 (9H, s), 3.09 (2H, d, J=5.3 Hz), 3.76 (3H, s), 4.93 (1H, dd, J=5.3, 13.5 Hz), 5.23 (1H, s), 6.02 (1H, d, J=13.5 Hz), 6.55 (1H, d, J=7.9 Hz), 6.80 (1H, dd, J=2.0, 7.9 Hz), 6.95 (1H, d, J=2.0 Hz), 8.18 (1H, s).

(2) Synthesis of N-Me-Tyr(3-tBu)-OMe

To a solution of N-formyl-Tyr(3-tBu)-OMe (23.8 g, 85.3 mmol) in THF (400 ml), 1.0M borane-THF complex (170 ml) was added dropwise under cooling with ice over 30 min. The mixture was stirred for 20 min., mixed with methanol (50 ml) and further stirred for 30 min. The reaction mixture was mixed with 33% hydrobromic acid/acetic acid (31 ml) and stirred for 2 hours. The mixture was neutralized by saturated aqueous $NaHCO_3$ under cooling with ice and extracted with chloroform. The organic layer was washed with saturated brine, dried over anhydrous magnesium sulfate and evaporated to remove the solvent under reduced pressure. The thus obtained residue was subjected to silica gel column chromatography (developing solvent: chloroform:methanol=20:1), giving N-Me-Tyr(3-tBu)-OMe (20.3 g, 90%).

$^1$H-NMR ($CDCl_3$): δ 1.38 (9H, s), 2.37 (3H, s), 2.89 (2H, d, J=6.6 Hz), 3.42 (1H, t, J=6.6 Hz), 3.68 (3H, s), 6.55 (1H, d, J=7.9 Hz), 6.86 (1H, dd, J=2.0, 7.9 Hz), 7.02 (1H, d, J=2.0 Hz)

(3) Synthesis of N-Me-Tyr(3-tBu)-NHMe

To a solution of N-Me-Tyr(3-tBu)-QMe (8.20 g, 31.1 mmol) in methanol (20 ml), a 30% methylamine methanol solution (200 ml) was added and stirred at room temperature for 16 hours. The reaction mixture was evaporated to remove the solvent under reduced pressure; the thus obtained residue was subjected to silica gel column chromatography (developing solvent: chloroform:methanol=20:1), giving N-Me-Tyr(3-tBu)-NHMe (T5) (6.27 g, 76%).

$^1$H-NMR ($CDCl_3$): δ 1.39 (9H, s), 2.26 (3H, s), 2.58 (1H, dd, J=10.5, 14.8 Hz), 2.84 (2H, d, J=4.9 Hz), 3.06-3.18 (2H, m), 5.00 (1H, brs), 6.62 (1H, d, J=7.9 Hz), 6.89 (1H, dd, J=1.7, 7.9 Hz), 7.08 (1H, d, J=1.7 Hz), 7.15 (1H, brs).

REFERENCE EXAMPLE 4

Synthesis of Intermediate T7

A mixture of Tyr(3-tBu)-$NH_2$ (1.6 g, 6.8 mmol) and acetaldehyde (7.6 ml, 0.14 mol) was stirred under cooling with ice for 10 min. The reaction mixture was concentrated under reduced pressure under cooling with ice; the thus obtained residue was mixed with methanol (34 ml) and then under cooling with ice with sodium borohydride (0.28 g, 7.4 mmol) and stirred at the same temperature for 15 min. The resultant was mixed with water and extracted with ethyl acetate. The organic layer was washed with water, dried and concentrated under reduced pressure; the thus obtained residue was subjected to silica gel column chromatography ($CHCl_3$: MeOH=20:1), giving N-Et-Tyr(3-tBu)-$NH_2$ (T7) (1.3 g, 73%).

$^1$H-NMR ($CDCl_3$): δ 0.96 (3H, t, J=7.3 Hz), 1.40 (9H, s), 2.4-2.7 (3H, m), 3.14 (1H, dd, J=4.0, 13.9 Hz), 3.26 (1H, dd, J=4.0, 9.6 Hz), 5.25 (1H, s), 5.38 (1H, brs), 6.63 (1H, d, J=7.9 Hz), 6.91 (1H, dd, J=2.0, 7.9 Hz), 7.10 (1H, d, J=2.0 Hz), 7.18 (1H, brs).

REFERENCE EXAMPLE 5

Synthesis of Intermediate T8

A mixture of Tyr(3-tBu)-NHMe (1.7 g, 6.8 mmol), acetaldehyde (0.76 ml, 13.6 mmol) and dichloromethane (10 ml) was stirred under cooling with ice for 30 min. The reaction mixture was concentrated under reduced pressure under cooling with ice; the thus obtained residue was mixed with methanol (20 ml) and then under cooling with ice with sodium borohydride (0.28 g, 7.4 mmol) and stirred at the same temperature for 15 min. The resultant was mixed with water and extracted with dichloromethane. The organic layer was washed with water, dried and concentrated under reduced pressure under cooling with ice; the thus obtained residue was subjected to silica gel column chromatography (CHCl₃:MeOH=20:1), giving N-Et-Tyr(3-tBu)-NHMe (T8) (1.7 g, 90%).

¹H-NMR (CDCl₃): δ 0.94 (3H, t, J=7.3 Hz), 1.39 (9H, s), 2.4-2.6 (2H, m), 2.60 (1H, dd, J=9.6, 13.8 Hz), 2.83 (3H, d, J=4.9 Hz), 3.13 (1H, dd, J=4.0, 13.8 Hz), 3.25 (1H, dd, J=4.0, 9.6 Hz), 5.44 (1H, brs),6.64 (1H, d, J=7.9 Hz), 6.88 (1H, dd, J=2.0, 7.9 Hz), 7.07 (1H, d, J=2.0 Hz), 7.27 (1H, brs)

REFERENCE EXAMPLE 6

Synthesis of Intermediate V2

To a solution of Z-Val-OH (50 g) in THF (500 ml), ethyl iodide (127.3 ml, 1592 mmol) was added under cooling with ice and then sodium hydride (60% in oil) (23.88 g, 597 mmol) was added slowly, followed by stirring at 60° C. for 12 hours. The reaction mixture was mixed with water and washed with ether. The thus obtained aqueous layer was rendered acidic by the addition of dilute hydrochloric acid and extracted with ethyl acetate. The resultant was washed with saturated brine, dried over anhydrous magnesium sulfate and evaporated to remove the solvent under reduced pressure. The thus obtained residue was subjected to silica gel column chromatography (H:EA:AcOH=100:50:1), giving Z-N-Et-Val-OH (V2) (29.29 g, 53%).

¹NMR (CDCl₃): δ 0.92 (3H, d, J=6.3 Hz), 1.03 (3H, d, J=6.6 Hz), 1.16 (3H, t., J=6.9 Hz), 2.40-2.60 (1H, m), 3.15-3.58 (2H, m), 3.73 (1H, brd, J=10.9 Hz), 5.20 (2H, brs), 7.36 (5H, brs)

REFERENCE EXAMPLE 7

Synthesis of Intermediate P2

To a solution of Boc-Phe(4-F)-OH (13.4 g, 47.3 mmol) in THF (100 ml), 60% sodium hydride (5.7 g, 142 mmol) and then methyl iodide (23.6 ml, 378 mmol) were added under cooling with ice. The mixture was stirred at room temperature for 38 hours, under cooling with ice, mixed with water and washed with n-hexane. Under cooling with ice, the aqueous layer was rendered acidic by 1N hydrochloric acid and extracted with ethyl acetate. The extract was washed with saturated brine, dried over anhydrous magnesium sulfate and evaporated to remove the solvent under reduced pressure. The thus obtained residue was mixed with ether and n-hexane and the thus formed precipitate was collected by filtration to give Boc-N-Me-Phe(4-F)-OH(P2) (11.4 g, 81%).

¹H-NMR (CDCl₃): δ 1.32 and 1.39 (9H, s), 2.67 and 2.75 (3H, s), 2.94-3.11 (1H, m), 3.20-3.35 (1H, m), 4.53-4.62 (1H, brd), 4.97 (1H, brs), 6.90-7.20 (4H, m)

REFERENCE EXAMPLE 8

Synthesis of Intermediate P3

To a solution of Z-Phe(4-F)-OH (13.9 g, 44.0 mmol) in THF/DMF (73 ml/37 ml), ethyl iodide (28.1 ml, 352 mmol) and 60% sodium hydride (5.28 g, 132 mmol) were added under cooling with ice and stirred at room temperature for 5.5 hours. Water was added slowly to the reaction mixture, followed by washing with ether. The aqueous layer was adjusted to pH 3 by the addition of dilute hydrochloric acid and extracted with ethyl acetate. The extract was washed with saturated brine, dried over anhydrous magnesium sulfate and concentrated under reduced pressure. The thus obtained residue was subjected to silica gel column chromatography (n-hexane:ethyl acetate:acetic acid=100:50:1), giving Z-N-Et-Phe(4-F)-OH(P3) (10.9 g, 72%).

REFERENCE EXAMPLE 9

Synthesis of Intermediate P10

To a solution of Boc-Phe(4-F)-OH (1.0 g, 3.53 mmol) in THF/DMF (6 ml/1.5 ml), ethyl iodide (2.24 ml, 20.8 mmol) and 60% sodium hydride (422 mg, 10.6 mmol) were added under cooling with ice and stirred at room temperature for 19 hours. The reaction mixture was mixed with water slowly and then with a saturated aqueous NH₄Cl solution and extracted with ethyl acetate. The extract was washed with water and saturated brine, dried over anhydrous magnesium sulfate and concentrated under reduced pressure. The thus obtained residue was subjected to silica gel column chromatography (n-hexane:ethyl acetate:methylene chloride=1:1:15), giving Boc-N-Et-Phe(4-F)-OH (P10) (593 mg, 54%).

REFERENCE EXAMPLE 10

Synthesis of Intermediate T17

A suspension of Z-N-Me-Phe(3-tBu-4-benzyloxy)-NH₂ (2.5 g, 5.27 mmol), a 35% aqueous formaldehyde solution (10 ml) and potassium carbonate (2.19 g, 15.8 mmol) in acetonitrile was stirred for 2 hours. The mixture was mixed with water, and extracted with ethyl acetate. The organic layer was washed with a saturated aqueous NH₄Cl solution and then with saturated brine, dried over anhydrous magnesium sulfate and concentrated under reduced pressure; the thus obtained residue was subjected to silica gel column chromatography (n-hexane:ethyl acetate:methylene chloride=1:1:1), giving Z-N-Me-Phe(3-tBu-4-benzyloxy)-NHCH₂OH (2.0 g).

To a solution of the above compound (2.0 g, 3.97 mmol) in 85% formic acid (30 ml), sodium methanesulfinate (1.5 g, 15.3 mmol) was added and then stirred at 50° C. for 1 hour. The reaction mixture was mixed with water and extracted with ethyl acetate. The organic layer was washed with a saturated aqueous NaHCO₃ solution, dried over anhydrous magnesium sulfate and concentrated under reduced pressure; to a solution of the thus obtained residue (1.8 g) in methanol (20 ml), 20% palladium hydroxide/carbon (0.50 g) was added and stirred in a hydrogen atmosphere for 2 days. The reaction mixture was filtered to remove the catalyst and the filtrate was concentrated; the thus obtained residue was subjected to silica gel column chromatography (n-hexane:methanol:methylene chloride=1:1:15), giving N-Me-Phe(3-tBu-4-benzyloxy)-NHCH₂SO₂CH₃ (T17) (890 mg).

REFERENCE EXAMPLE 11

Synthesis of Intermediate T18

To a solution of Z-Tyr(3-tBu)-OMe (1.01 g, 2.62 mmol) in methanol/water (12 ml/3 ml), lithium hydroxide monohydrate (0.17 g, 3.93 mmol) was added and stirred at room temperature for 2 hours. The reaction mixture was washed with ether, rendered acidic by 2N hydrochloric acid and extracted with methylene chloride. The extract was dried over anhydrous magnesium sulfate and evaporated to remove the solvent under reduced pressure, giving crude Z-Tyr(3-tBu)-OH (0.98 g).

To a solution of the above crude compound (0.92 g, 2.48 mmol), WSCI (0.52 g, 2.73 mmol) and HOBT (0.37 g, 2.73 mmol) in DMF (15 ml), tert-butylamine (0.31 ml, 2.48 mmol) and then NMM (0.29 ml, 2.73 mmol) were added under cooling with ice and stirred at room temperature for 2 hours. The reaction mixture was mixed with water, and extracted with ethyl acetate. The organic layer was washed with 2N hydrochloric acid, a saturated aqueous NaHCO$_3$ solution and saturated brine in that order. The extract was dried over anhydrous magnesium sulfate and concentrated under reduced pressure; the thus obtained residue was subjected to silica gel column chromatography (ethyl acetate:n-hexane=1:2), giving Z-Tyr(3-tBu)-NHtBu (1.05 g, 99%).

To a solution of the above compound (1.0 g, 2.34 mmol) in methanol (20 ml), 20% palladium hydroxide/carbon (0.16 g) was added and stirred in a hydrogen atmosphere for 2 hours. The reaction mixture was filtered with Celite and the filtrate was evaporated to remove the solvent under reduced pressure, giving crude Tyr(3-tBu)-NHtBu (T18) (0.60 g, 88%).

REFERENCE EXAMPLE 12

Synthesis of Intermediate T20

(1) Synthesis of 2-(4-benzyloxy-3-tert-butylphenyl)-N-benzyloxycarbonyl-N-methyl-1-methylethylamine To a solution of Z-N-Me-Phe(3-tBu-4-benzyloxy)-OH (27.8 g, 58.5 mmol) in THF (290 ml), ethyl chloroformate (6.2 ml, 64.3 mmol) and N-methyl morpholine 7.7 ml, 70.2 mmol) were added under cooling with ice and stirred. After 2 hours, the reaction mixture was mixed with sodium borohydride (6.7 g, 175 mmol), water (100 ml) and methanol (100 ml) and stirred at room temperature for 6 hours. The reaction mixture was evaporated to remove the solvent under reduced pressure and extracted with ethyl acetate. The organic layer was washed with saturated brine, dried over anhydrous magnesium sulfate and evaporated to remove the solvent under reduced pressure. The thus obtained residue was subjected to silica gel column chromatography (developing solvent: methylene chloride:ethyl acetate:n-hexane=1:1:2), giving 2-(4-benzyloxy-3-tert-butylphenyl)-N-benzyloxycarbonyl-1-hydroxymethyl-N-methylethylamine (12.4 g, 46%).

A solution of the above compound (5.21 g, 11.2 mmol) in methylene chloride (55 ml), TEA (2.34 ml, 16.8 mmol) and methanesulfonyl chloride (0.954 ml, 12.3 mmol) were added under cooling with ice and stirred for 30 min. Under cooling with ice, the reaction mixture was mixed with saturated aqueous NaHCO$_3$ and extracted with methylene chloride. The organic layer was washed with water and saturated brine, dried over anhydrous magnesium sulfate and evaporated to remove the solvent under reduced pressure, giving a mesylate. To a solution of the mesylate in THF (30 ml), a 1M lithium triethyl borohydride/THF solution (22.4 ml, 22.4 mmol) was added. After 1 hour, further lithium triethylborohydride/THF solution (22.4 ml, 22.4 mmol) was added. After 30 min., the mixture was mixed with water under cooling with ice and extracted with chloroform. The organic layer was washed with water and saturated brine, dried over anhydrous magnesium sulfate and evaporated to remove the solvent under reduced pressure; the thus obtained residue was subjected to silica gel column chromatography (developing solvent: ethyl acetate:n-hexane=1:5), giving 2-(4-benzyloxy-3-tert-butylphenyl)-N-benzyloxycarbonyl-N-methyl-1-methylethylamine (3.42 g, 68%).

$^1$H-NMR (CDCl$_3$): δ 1.14 (3H, d, J=6.9 Hz), 1.36 (9H, s), 2.50-2.80 (2H, m), 2.76 and 2.83 (total 3H, s), 4.30-4.58 (1H, m), 4.88-5.10 (4H, m), 6.74-7.14 (3H, m), 7.20-7.50 (10H, m)

(2) Synthesis of 2-(3-tert-butyl-4-hydroxyphenyl)-N-methyl-1-methylethylamine (T20)

A suspension of 2-(4-benzyloxy-3-tert-butylphenyl)-N-benzyloxycarbonyl-N-methyl-1-methylethylamine (3.30 g, 7.35 mmol) and 20% palladium hydroxide/carbon catalyst (350 mg) in methanol (100 ml) was stirred in a hydrogen atmosphere for 1.5 hours. The mixture was filtered to remove the catalyst and the filtrate was evaporated to remove the solvent under reduced pressure, giving 2-(3-tert-butyl-4-hydroxyphenyl)-N-methyl-1-methylethylamine (T20) (1.62 g, 100%).

$^1$H-NMR (CDCl$_3$): δ 1.12 (3H, d, J=6.3 Hz), 1.38 (9H, s), 2.42 (3H, s), 2.64 (2H, d, J=6.6 Hz), 2.75-2.90 (1H, m), 6.55 (1H, d, J=7.9 Hz), 6.84 (1H, dd, J=1.6, 7.9 Hz), 7.04 (1H, d, J=1.6 Hz).

REFERENCE EXAMPLE 13

Synthesis of Intermediate T21

(1) Synthesis of Z-N,O-dibenzyl-Tyr(3-tBu)-OMe

To a solution of Z-Tyr(3-tBu)-OMe (3.0 g, 7.78 mmol) in DMF (20 ml), under cooling with ice, sodium hydride (0.68 g, 17.1 mmol) was added and stirred for 15 min., followed by the addition of benzylbromide (2.3 ml, 19.5 mmol). The reaction mixture was stirred for 3 hours, mixed with a saturated aqueous NaHCO$_3$ solution and extracted with ethyl acetate. The organic layer was washed with water and saturated brine, dried over anhydrous magnesium sulfate and evaporated to remove the solvent under reduced pressure; the thus obtained residue was subjected to silica gel column chromatography (developing solvent: ethyl acetate:n-hexane=1:5), giving the titled compound (4.14 g, 94%).

(2) Synthesis of N-benzyl-2-(4-benzyloxy-3-tert-butylphenyl)-1-methyl-N-(benzyloxycarbonyl)ethylamine To a solution of Z-N,O-dibenzyl-Tyr(3-tBu)-OMe (4.14 g, 7.32 mmol) in ethanol/THF (36 ml/6 ml), a 2M lithium borohydride/THF solution (11.0 ml, 22.0 mmol) was added under cooling with ice and stirred at room temperature overnight. The mixture was mixed with water, and extracted with ethyl acetate. The organic layer was washed with saturated brine, dried over anhydrous magnesium and evaporated to remove the solvent under reduced pressure. The thus obtained residue was dissolved in methylene chloride (50 ml) and under cooling with ice mixed with triethylamine (2.0 ml, 14.4 ml) and then with methanesulfonyl chloride (0.72 ml, 9.36 mmol), followed by stirring for 30 min. The reaction mixture was washed with a saturated aqueous NaHCO$_3$ solution. The organic layer was dried over anhydrous magnesium sulfate and evaporated to remove the solvent under reduced pressure. The thus obtained residue was dissolved in THF (10 ml) and mixed with a 1M lithium triethyl borohydride/THF solution (28.0 ml, 28.0 mmol). The mixture was stirred for 3 hours, mixed with water under cooling with ice and extracted with methylene chloride. The organic layer was dried over anhydrous magnesium sulfate and evaporated to remove the solvent under reduced pressure; the thus obtained residue was subjected to silica gel column chromatography (developing solvent: ethyl acetate:n-hexane=1:5), giving the titled compound (2.35 g, 61%).

(3) Synthesis of 2-(3-tert-butyl-4-hydroxyphenyl)-1-methylethylamine

A suspension of N-benzyl-2-(4-benzyloxy-3-tert-butylphenyl)-1-methyl-N-(benzyloxycarbonyl)-ethylamine (2.35 g, 4.50 mmol) and 20% palladium hydroxide/carbon catalyst (0.50 g) in methanol (30 ml) was stirred in a hydrogen atmosphere overnight. The mixture was filtered to remove the catalyst and the filtrate was evaporated to remove the solvent under reduced pressure, giving 2-(3-tert-butyl-4-hydroxyphenyl)-1-methylethylamine (T21) (0.90 g, 96%).

$^1$H-NMR (CDCl$_3$): δ 1.16 (3H, d, J=6.6 Hz), 1.39 (9H, s), 2.45 (1H, dd, J=4.9, 13.3 Hz), 2.69 (1H, dd, J=4.9, 13.3 Hz), 3.15 (1H, m), 3.52H, brs), 6.58 (1H, d, J=7.9 Hz), 6.83 (1H, dd, J=1.6, 7.9 Hz), 7.03 (1H, d, J=1.6 Hz).

REFERENCE EXAMPLE 14

Synthesis of Intermediate T23

To a solution of Tyr(3-tBu)-OMe (3.0 g, 11.9 mmol) in 1,4-dioxane/water (12 ml/12 ml), sodium carbonate (1.9 g, 17.9 mmol) and then ethyl chlorocarbonate (1.26 ml, 13.1 mmol) were added under cooling with ice and stirred for 2 hours. The reaction mixture was mixed with water, extracted with chloroform, dried over anhydrous magnesium sulfate and evaporated to remove the solvent under reduced pressure. To a solution of the thus obtained residue (3.85 g) in THF (120 ml), lithium aluminum hydride (2.83 g, 59.7 mmol) was added little by little and stirred at 60° C. for 5 hours. The reaction mixture was poured into ice water, stirred and then filtered with Celite for removing insoluble material. The filtrate was extracted with ethyl acetate, dried over anhydrous magnesium sulfate and concentrated under reduced pressure. The thus obtained residue was subjected to silica gel column chromatography (methylene chloride:methanol=3:1), giving 3-(3-tert-butyl-4-hydroxyphenyl)-2-methylaminopropanol (T23) (1.9 g, 67%, in 2 steps).

REFERENCE EXAMPLE 15

Synthesis of Intermediate P11

(1) Synthesis of 2-(4-fluorophenyl)-1-(N-methoxy-N-methylcarbamoyl)ethylcarbamic acid tert-butyl ester To a solution of Boc-Phe(4-F)-OH (5.0 g, 17.7 mmol) in methylene chloride (89 ml), BOP reagent (9.39 g, 21.2 mmol), N,O-dimethylhydroxylamine hydrochloride (2.07 g, 21.2 mmol) and TEA (5.92 ml, 42.5 mmol) were added under cooling with ice and stirred for 30 min. The reaction mixture was mixed with water and extracted with methylene chloride. The organic layer was washed with saturated brine, dried over anhydrous magnesium sulfate and evaporated to remove the solvent under reduced pressure. The thus obtained residue was subjected to silica gel column chromatography (developing solvent: ethyl acetate:n-hexane=1:1), giving the titled compound (5.76 g, 100%).

$^1$H-NMR (CDCl$_3$): δ 1.39 (9H, s), 2.84 (1H, dd, J=6.9, 13.8 Hz), 3.02 (1H, dd, J=5.9, 13.8 Hz), 3.16 (3H, s), 3.68 (3H, s), 4.86-4.96 (1H, m), 5.10-5.24 (1H, m), 6.95 (1H, d, J=8.9 Hz), 6.98 (1H, d, J=8.9 Hz), 7.11 (1H, d, J=8.2 Hz), 7.13 (1H, d, J=8.2 Hz).

(2) Synthesis of 2-(4-fluorophenyl)-1-formylethyl-carbamic acid tert-butyl ester (P11)

To a solution of the above compound (3.30 g, 10.1 mmol) in diethyl ether (150 ml), lithium aluminum hydride (498 mg, 13.1 mmol) was added under cooling with ice and stirred for 30 min. The reaction mixture was mixed with a solution of potassium hydrogen sulfate (2.75 g, 20.2 mmol) in water (20 ml) and stirred for 1 hour. The reaction mixture was filtered and extracted with ethyl acetate. The organic layer was washed with saturated brine, dried over anhydrous magnesium sulfate and evaporated to remove the solvent under reduced pressure. The thus obtained residue was subjected to silica gel column chromatography (developing solvent: ethyl acetate:n-hexane=1:5), giving the titled compound (2.37 g, 88%).

$^1$H-NMR (CDCl$_3$): δ 1.44 (9H, s), 3.00-3.20 (2H, m), 4.34-4.46 (1H, m), 4.9.8-5.06 (1H, m), 6.98 (1H, d, J=8.6 Hz), 7.01 (1H, d, J=8.6 Hz), 7.12 (1H, d, J=8.3 Hz), 7.14 (1H, d, J=8.3 Hz), 9.63 (1H, s).

Scheme 1 shows the synthesis scheme of Examples 28-64.

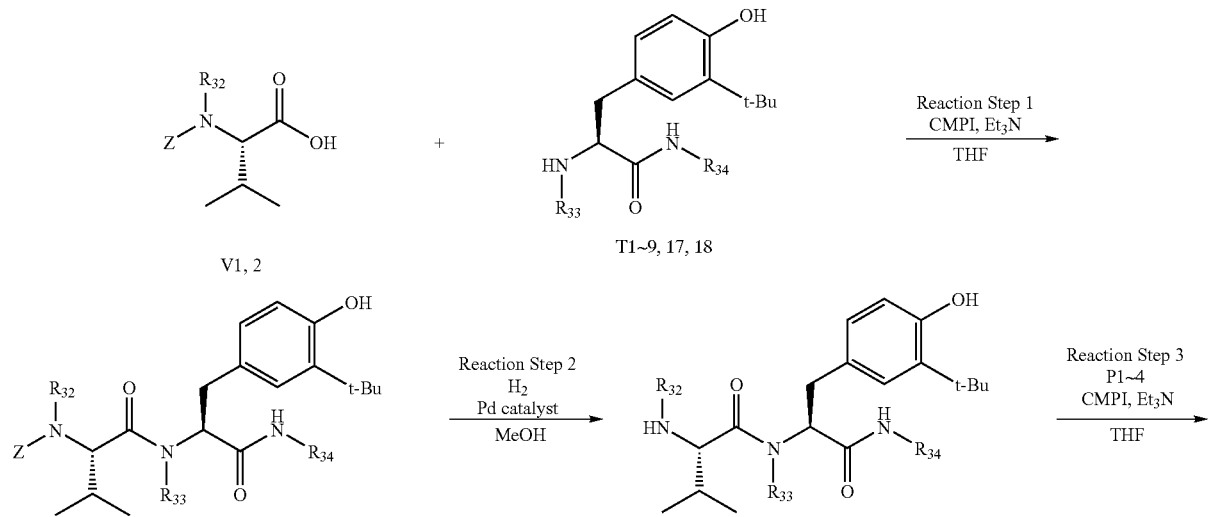

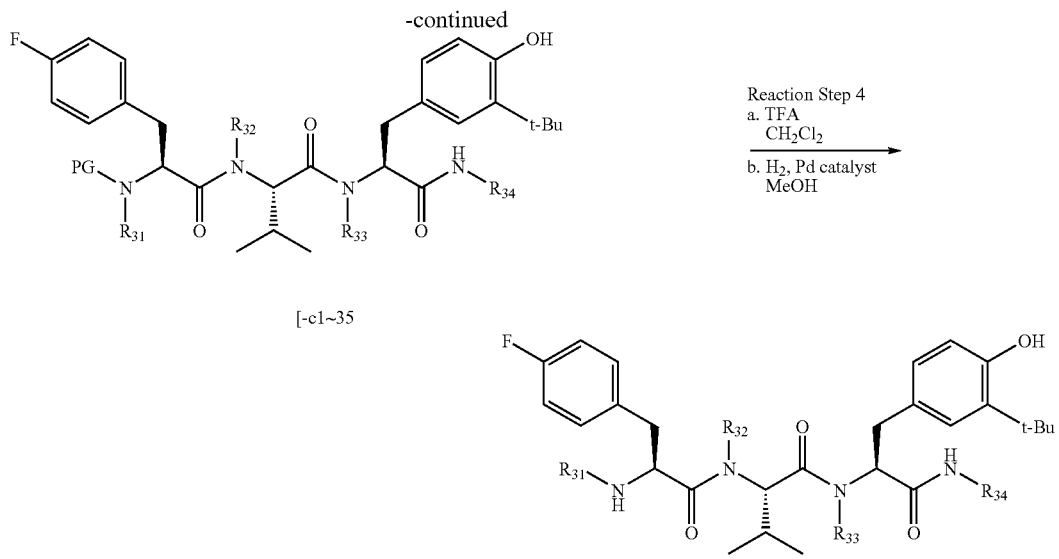

[-c1~35]

Synthesis process shown in scheme 1 is explained below:

Reaction Step 1

To a solution of Compounds T and V and CMPI in THF, TEA was added under cooling with ice and stirred at room temperature. The reaction mixture was mixed with water and extracted with ethyl acetate. The organic layer was washed with saturated brine, dried over anhydrous magnesium sulfate and evaporated to remove the solvent under reduced pressure. The thus obtained residue was subjected to silica gel column chromatography, giving Compound I-a.

Reaction Step 2

To a solution of Compound I-a in methanol, palladium catalyst was added and stirred at room temperature in a hydrogen atmosphere. The mixture was filtered to remove the palladium/carbon and the filtrate was evaporated to remove the solvent under reduced pressure. The thus obtained residue was subjected to silica gel column chromatography, giving Compound I-b.

Reaction Step 3

To a solution of Compounds I-b and P and CMPI in THF, TEA was added under cooling with ice and stirred at room temperature. The reaction mixture was mixed with water and extracted with ethyl acetate. The organic layer was washed with saturated brine, dried over anhydrous magnesium sulfate and evaporated to remove the solvent under reduced pressure. The thus obtained residue was subjected to silica gel column chromatography, giving Compound I-c.

Reaction Step 4a (PG=Boc)

To a solution of Compound I-c in methylene chloride, TFA was added and stirred at room temperature. The reaction mixture was concentrated under reduced pressure, alkalified by adding a saturated aqueous NaHCO$_3$ solution and extracted with methylene chloride. The resultant was dried over anhydrous magnesium sulfate and evaporated to remove the solvent under reduced pressure; the thus obtained residue was subjected to silica gel column chromatography, giving the titled compound.

Reaction Step 4b (PG=Z)

To a solution of Compound I-c in methanol, palladium catalyst was added and stirred at room temperature in a hydrogen atmosphere. The mixture was filtered to remove the palladium/carbon and the filtrate was evaporated to remove the solvent under reduced pressure. The thus obtained residue was subjected to silica gel column chromatography, giving the titled compound.

Scheme 2 shows the synthesis scheme of Examples 65-78.

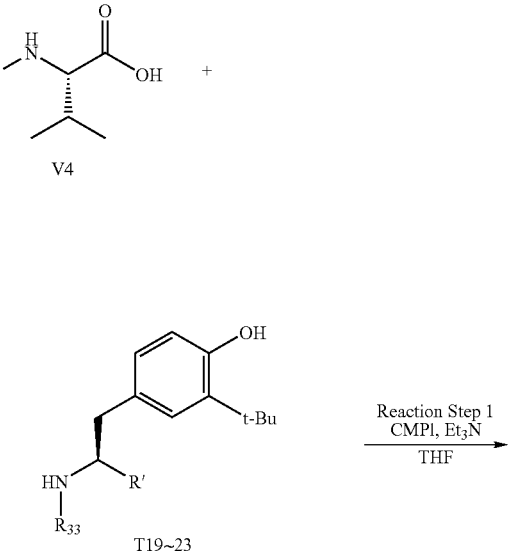

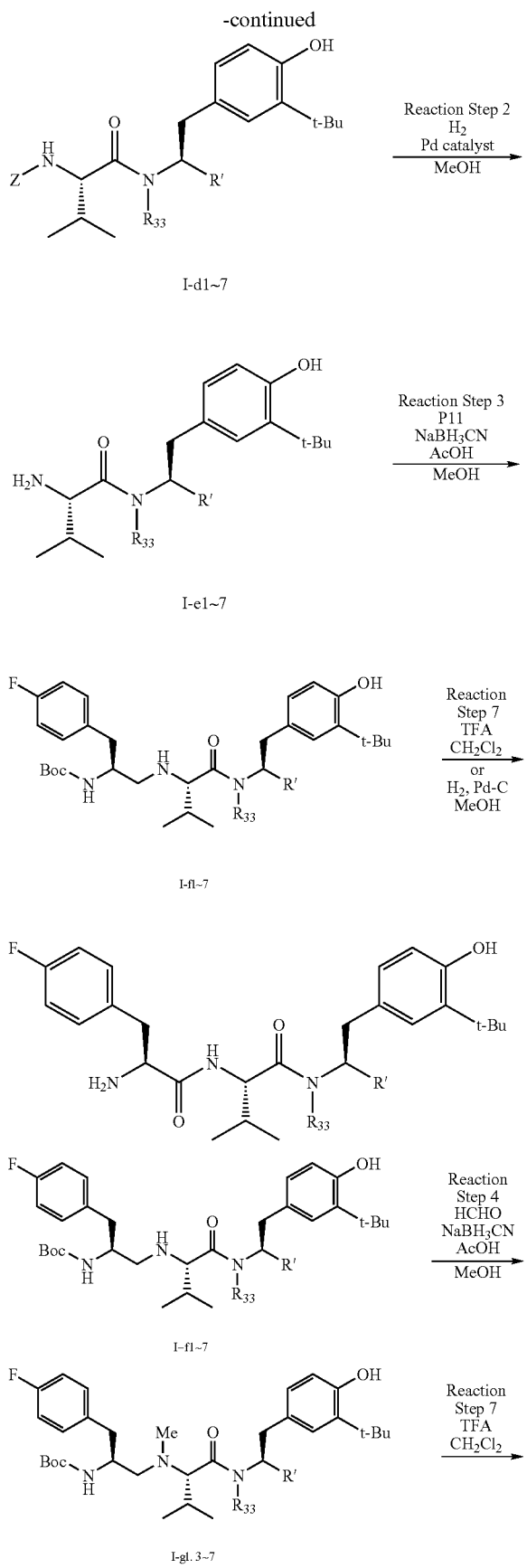

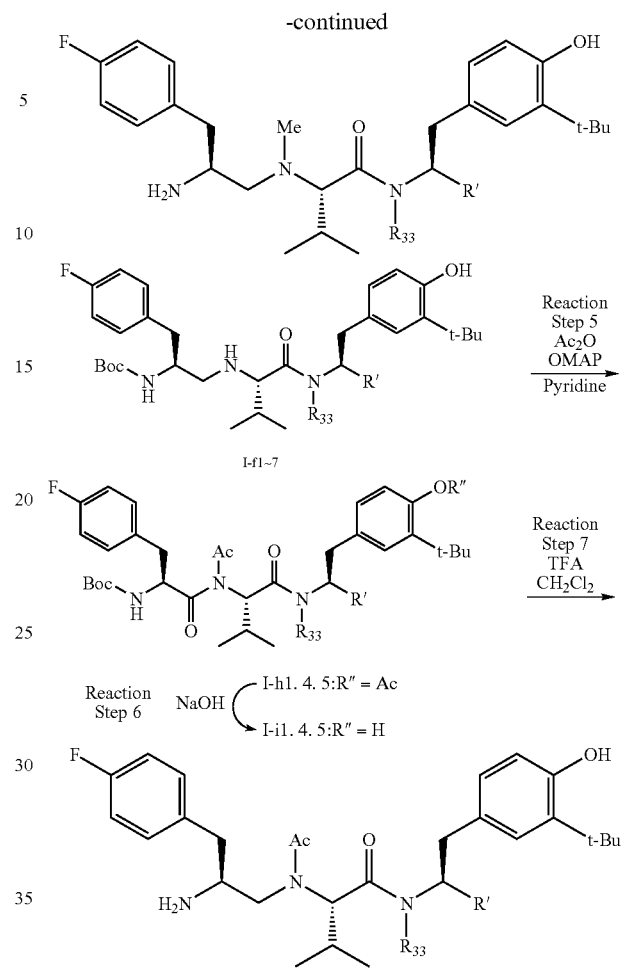

Synthesis process shown in scheme 2 is explained below:

Reaction Step 1

To a solution of Compounds T and V4 and CMPI in THF, TEA was added under cooling with ice and stirred at room temperature. The reaction mixture was mixed with water and extracted with ethyl acetate. The organic layer was washed with saturated brine, dried over anhydrous magnesium sulfate and evaporated to remove the solvent under reduced pressure. The thus obtained residue was subjected to silica gel column chromatography, giving Compound I-d.

Reaction Step 2

To a solution of Compound I-d in methanol, palladium catalyst was added and stirred at room temperature in a hydrogen atmosphere. The mixture was filtered to remove the palladium catalyst and the filtrate was evaporated to remove the solvent under reduced pressure. The thus obtained residue was subjected to silica gel column chromatography, giving Compound I-e.

Reaction Step 3

To a solution of Compounds P11 and I-e in methanol, acetic acid and sodium cyanoborohydride were added under cooling with ice and stirred at room temperature. The reaction mixture was mixed with saturated aqueous $NaHCO_3$ and extracted with chloroform. The organic layer was washed with saturated brine, dried over anhydrous magnesium sulfate and evaporated to remove the solvent under reduced pressure.

The thus obtained residue was subjected to silica gel column chromatography, giving Compound I-f.

Reaction Step 4

To a solution of Compound I-f in methanol, 35% aqueous formaldehyde solution, acetic acid and sodium cyanoborohydride were added under cooling with ice and stirred at room temperature. The reaction mixture was mixed with saturated aqueous $NaHCO_3$ and extracted with chloroform. The organic layer was washed with saturated brine, dried over anhydrous magnesium sulfate and evaporated to remove the solvent under reduced pressure. The thus obtained residue was subjected to silica gel column chromatography, giving Compound I-g.

Reaction Step 5

To a solution of Compound I-f in pyridine, acetic acid anhydride and 4-dimethylaminopyridine were added under cooling with ice and stirred at room temperature. The reaction mixture was mixed with water and extracted with ethyl acetate. The organic layer was washed with a saturated aqueous copper sulfate solution, water and saturated brine, dried over anhydrous magnesium sulfate and evaporated to remove the solvent under reduced pressure. The thus obtained residue was subjected to silica gel column chromatography, giving Compound I-h.

Reaction Step 6

To a solution of Compound I-h in methanol, a 2N aqueous sodium hydroxide solution was added and stirred at room temperature. The reaction mixture was mixed with saturated aqueous $NH_4Cl$ and extracted with chloroform. The organic layer was washed with saturated brine, dried over anhydrous magnesium sulfate and evaporated to remove the solvent under reduced pressure. The thus obtained residue was subjected to silica gel column chromatography, giving Compound I-i.

Reaction Step 7

To a solution of Compound I-f, or I-g, or I-i in methylene chloride, TFA was added and stirred at room temperature. The reaction mixture was concentrated under reduced pressure, alkalified by adding a saturated aqueous $NaHCO_3$ solution and extracted with methylene chloride. The resultant was dried over anhydrous magnesium sulfate and evaporated to remove the solvent under reduced pressure; the thus obtained residue was subjected to silica gel column chromatography, giving the titled compound.

Examples conducted according to Scheme 1 are shown in Tables D-1 to D-43.

TABLE D-1

Structural Formula of Compounds of Example 28-64

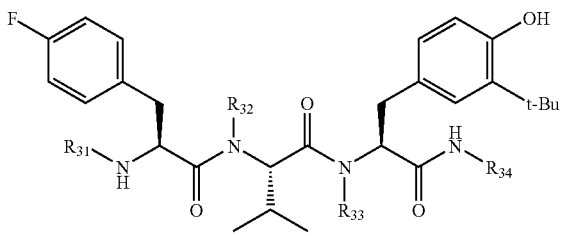

Example 28
Synthesis of Phe(4-F)-N-Me-Val-Tyr(3-tBu)-$NH_2$

| $R_{31}$ | $R_{32}$ | $R_{33}$ | $R_{34}$ |
|---|---|---|---|
| H | Me | H | H |

Reaction 1

| Compound T1:g | Compound V1:g | CMPI g | TEA ml | THF ml | Reaction time hr | Column sol. | Product | Amount g |
|---|---|---|---|---|---|---|---|---|
| 1 | 1.35 | 1.3 | 2.1 | 40 | 19 | EA:H 3:1 | I-a1 | 1.6 |

$^1$H-NMR($CDCl_3$):δ 0.84 and 0.88(6H, d, J=6.6Hz), 1.36(9H, s), 2.15-2.35(1H, m), 2.75(3H, s), 2.8-3.1(2H, m), 4.02(1H, brd, J=11.2Hz), 4.5-4.7(1H, m), 5.13 and 5.15(2H, s), 5.3-5.5, 5.5-5.7, 5.8-6.0, 6.1-6.2, and 6.5-6.8(3H, m), 6.45(1H, d, J=7.9Hz), 6.81(1H, brd, J=7.9Hz), 7.07(1H, brs), 7.37(5H,s)

Reaction 2

| Compound I-a1:g | Pd(OH)$_2$ g | MeOH ml | Reaction time hr | Column sol. | Product | Amount g |
|---|---|---|---|---|---|---|
| 1.5 | 0.3 | 30 | 1 | Not purified | I-b1 | 1.1 |

$^1$H-NMR($CDCl_3$):δ 0.65(3H, d, J=6.9Hz), 0.82(3H, d, J=6.9Hz), 1.37(9H,s), 1.8-2.0(1H,m), 2.30(3H,s), 2.74(1H,d,J=4.3Hz), 2.9-3.2(2H,m), 4.6-4.8(1H,m), 5.3-5.7(1H,m), 6.1-6.3(1H,m), 6.5-6.7(1H,m), 6.93(1H,brd,J=7.9Hz), 7.06(1H,brs), 7.6-7.8(1H,m)

TABLE D-2

Example 28 (Continued from Table D-1)
Synthesis of Phe(4-F)-N-Me-Val-Tyr(3-tBu)-NH$_2$ Reaction 3

| Compound I-b1:g | Compound P1:g | CMPI g | TEA ml | THF ml | Reaction time hr | Column sol. | Product | Amount g |
|---|---|---|---|---|---|---|---|---|
| 0.3 | 0.29 | 0.26 | 0.43 | 5 | 18 | MC:M 20:1 | I-c1 | 0.45 |

$^1$H-NMR (CDCl$_3$): δ 0.77, 0.89, and 1.01(6H, d, J=6.6Hz), 1.33, 1.36, 1.37, and 1.39(18H, s), 2.15-2.4(1H, m), 2.32 and 2.77(3H, s), 2.7-3.0(4H, m), 4.1-4.3, 4.5-4.6, and 4.6-4.8(2H, m), 5.36(1H, brd, J=8.9Hz), 5.44, 5.57, 5.71, 5.75, and 6.18(3H, brs), 6.6-7.2(7H, m), 7.8-7.9(1H, m)

Reaction 4a

| Compound I-c1:g | TFA ml | CH$_2$Cl$_2$ ml | Reaction time hr | Column sol. | Amount g | HPLC min |
|---|---|---|---|---|---|---|
| 0.4 | 2 | 4 | 0.5 | CH:M:N 400:10:1 | 0.32 | 17.8 |

EI-MS(M$^+$): 514
$^1$H-NMR(CDCl$_3$): δ 0.71, 0.79, 0.91, and 0.92(6H, d, J=6.3-6.6Hz), 1.36 and 1.38(9H, s), 2.2-2.4(1H, m), 2.4-3.2(4H, m), 2.70 and 2.83(3H, s), 3.56 and 3.79(1H, dd, J=5.0-5.9, 7.6Hz), 3.94 and 4.44(1H, d, J=10.9-11.2Hz), 4.56 and 4.74(1H, dd, J=6.6-8.9, 14.2-16.2Hz), 5.47(1H, brs), 5.85 and 5.96(1H, brs), 6.4-6.9(3H, m), 6.9-7.2(5H, m), 9.01(1H, d, J=7.9Hz)

TABLE D-3

Example 29
Synthesis of N-Me-Phe(4-F)-N-Me-Val-Tyr(3-tBU)-NH$_2$

| R$_{31}$ | R$_{32}$ | R$_{33}$ | R$_{34}$ |
|---|---|---|---|
| Me | Me | H | H |

Reaction 3

| Compound I-b1:g | Compound P2:g | CMPI g | TEA ml | THF ml | Reaction Time hr | Column sol. | Product | Amount g |
|---|---|---|---|---|---|---|---|---|
| 0.3 | 0.31 | 0.26 | 0.43 | 5 | 20 | MC:M 20:1 | I-C2 | 0.43 |

$^1$H-NMR (CDCl$_3$): δ 0.72, 0.79, and 0.92(6H, d, J=6.6Hz), 1.33, 1.34, 1.37, and 1.40(18H, s), 2.1-2.3(1H, m), 2.24 and 2.67(3H, s), 2.6-3.3(4H, m), 4.40 and 4.50(1H, d, J=10.9-11.6HZ), 4.5-4.8(1H, m), 4.8-4.9 and 5.0-5.2(1H, m), 5.49 and 5.98(2H, brs), 6.16(1H, s), 6.31(1H.brd, J=8.3Hz), 6.5-6.8(2H, m), 6.8-7.3(5H, m)

Reaction 4a

| Compound I-c2:g | TFA ml | CH$_2$Cl$_2$ ml | Reaction Time hr | Column sol. | Amount g | HPLC min |
|---|---|---|---|---|---|---|
| 0.35 | 1.5 | 3 | 0.5 | CH:M:N 400:10:1 | 0.24 | 18.0 |

EI-MS(M$^+$): 528
$^1$H-NMR(CDCl$_3$): δ 0.52. 0.79, and 0.91(6H, d, J=5.0-6.9Hz), 1.33 and 1.39(9H, s), 2.1-2.3(1H, m), 2.24 and 2.36(3H, s), 2.56 and 2.61(3H, s), 2.6-3.2(4H, m), 3.54 and 3.61(1H, dd, J=5.9-6.3, 7.3-7.6Hz), 3.78 and 4.58(1H, d, J=10.9Hz), 4.49 and 4.68(1H, dd, J=7.3, 14.5Hz), 5.38, 5.58, 5.78, and 5.90(2H, brs), 6.6-7.2(7H, m), 9.07(1H, brd, J=7.6Hz)

TABLE D-4

Example 30
Synthesis of N-Et-Phe(4-F)-N-Et-Val-TYr(3-tBu)-NH₂

| $R_{31}$ | $R_{32}$ | $R_{33}$ | $R_{34}$ |
|---|---|---|---|
| Et | Me | H | H |

Reaction 3

| Compound I-b1:g | Compound P3:g | CMPI g | TEA ml | THF ml | Reaction time hr | Column sol. | Product | Amount g |
|---|---|---|---|---|---|---|---|---|
| 0.3 | 0.36 | 0.26 | 0.43 | 5 | 16 | CH:M:N 400:10:1 | I-c3 | 0.42 |

¹H-NMR(CDCl₃): δ 0.41, 0.67, and 0.86(6H, d, J=6.6Hz), 1.0-1.2(3H, m), 1.36(9H, s), 2.1-2.3(1H, m), 2.51 and 2.76(3H, s), 2.6-3.0 and 3.0-3.2(6H, m), 4.1-4.3(1H, m), 4.4-4.6(1H, m), 4.9-5.0 and 5.1-5.3(1H, m), 5.13(2H, s), 5.35(1H, brs), 5.76(2H, brs), 6.1-6.2 and 6.4-7.4(13H, m)

Reaction 4a

| Compound I-c3:g | Pd(OH)₂ g | MeOH ml | Reaction time hr | Column sol. | Amount g | HPLC min |
|---|---|---|---|---|---|---|
| 0.37 | 0.07 | 5 | 1 | CH:M:N 400:10:1 | 0.24 | 18.5 |

EI-MS(M⁺): 542
¹H-NMR(CDCl₃): δ 0.39, 0.77, and 0.90(6H, d, J=6.3-6.9Hz), 1.05 and 1.16(3H, t, J=6.9Hz), 1.32 and 1.39(9H, s), 2.1-2.3(1H, m), 2.3-3.2(6H, m), 2.43 and 2.46(3H, s), 3.5-3.7(1H, m), 3.76 and 4.58(1H, d, J=10.9-11.5Hz), 4.47 and 4.68(1H, dd, J=7.0, 13.9Hz), 5.42, 5.73, and 6.00(2H, brs), 6.6-7.2(7.8H, m), 8.74(0.2H, d, J=7.9Hz)

TABLE D-5

Example 31
Synthesis of Phe(4-F)-N-Me-Val-Tyr(3-tBu)-NHMe

| $R_{31}$ | $R3_2$ | $R_{33}$ | $R_{34}$ |
|---|---|---|---|
| H | Me | H | Me |

Reaction 1

| Compound T2:g | Compound V1:g | CMPI g | TEA ml | THF ml | Reaction time hr | Column sol. | Product | Amount g |
|---|---|---|---|---|---|---|---|---|
| 1.07 | 1.36 | 1.31 | 1.79 | 43 | 2.5 | EA:H 1:1 | I-a2 | 2.11 |

EI-MS(M⁺): 497
¹H-NMR (CDCl₃): δ 0.84 and 0.89(6H, d, J=6.6Hz), 1.36(9H, s), 2.12-2.30(1H, m), 2.71, 2.73, and 2.74(6H, s), 2.70-3.00(2H, m), 4.04(1H, d, J=11.2Hz), 4.40-4.58(1H, m), 4.82-4.86(1H, m), 5.19(2H, s), 5.70-5.80(1H, m), 6.43(1H, d, J=7.9Hz), 6.53(1H, d, J=8.2Hz), 6.80(1H, d, J=8.2Hz), 7.04(1H, s), 7.30-7.42(5H, m)

Reaction 2

| Compound I-a2:g | Pd-C mg | MeOH ml | Reaction time hr | Column sol. | Product | Amount g |
|---|---|---|---|---|---|---|
| 2.01 | 200 | 50 | 2 | C:M 20:1 | I-b2 | 1.43 |

EI-MS(M⁺): 363
¹H-NMR(CDCl₃): δ 0.67 and 0.83(6H, d, J=5.9Hz), 1.37(9H, s), 1.84-2.02(1H, m), 2.31(3H, s), 2.73(1H, d, J=5.9Hz), 2.74(3H, d, J=5.0Hz), 2.90-3.08(2H, m), 4.52(1H, ddd, J=7.2, 7.2, 7.2Hz), 5.51(1H, brs) 5.98(1H, d, J=3.6Hz), 6.61(1H, d, J=7.9Hz), 6.91(1H, dd, J=2.0, 7.9Hz), 7.04(1H, d, J=2.0Hz), 7.68(1H, d, J=7.9Hz)

TABLE D-6

Example 31(Continued from Table D-5)
Synthesis of Phe(4-F)-N-Me-Val-Tyr(3-tBu)-NHMe

Reaction 3

| Compound I-b2:mg | Compound P1:mg | CMPI mg | TEA ml | THF ml | Reaction time hr | Column sol. | Product | Amount mg |
|---|---|---|---|---|---|---|---|---|
| 400 | 387 | 337 | 0.46 | 11 | 13 | EA:H 2:1 | I-c4 | 652 |

EI-MS(M$^+$): 628
$^1$H-NMR(CDCl$_3$): δ 0.75, 0.77, 0.88, and 1.00(total 6H, d, J=5.3-6.3Hz), 1.36, 1.37 and 1.39(total 18H, s), 2.16-2.30(1H, m), 2.72(3H, d, J=4.6Hz), 2.70-3.22(7H, m), 4.38-4.80, and 5.10-5.22(total 3H, m), 5.28 and 5.32(total 1H, brs), 5.54-5.64(1H, m), 6.04-6.12(1H, m), 6.58-7.22(7H, m)

Reaction 4a

| Compound I-c4:mg | TFA ml | CH$_2$Cl$_2$ ml | Reaction time hr | Column sol. | Amount mg | HPLC min |
|---|---|---|---|---|---|---|
| 564 | 2 | 8 | 1.5 | MC:M 20:1 | 367 | 18.9 |

EI-MS(M$^+$): 528
$^1$H-NMR(CDCl$_3$): δ 0.72, 0.81 and 0.92(total 6H, d, J=6.3-6.6Hz), 1.36 and 1.38(total 9H, s), 2.20-2.40(1H, m), 2.50-3.24(10H, m), 3.59(2/3H, dd, J=5.6, 7.6Hz), 3.73(1/5H, d, J=7.0Hz), 3.80(1/3H, dd, J=6.0, 8.3Hz), 3.95(4/5H, d, J=8.9Hz), 4.40-4.54(2/5H, m), 4.63(3/5H, dd, J=6.6, 14.2Hz), 5.65 and 5.78(total 1H, d, J=3.8-4.3Hz), 6.60(1/4H, d, J=8.3Hz), 6.70-7.16(7H, m), 9.07(3/4H, d, J=8.3Hz)

TABLE D-7

Example 32
Synthesis of N-Me-Phe(4-F)-N-Me-Val-Tyr(3-tBu)-NHMe

| R$_{31}$ Me | R$_{32}$ Me | R$_{33}$ H | R$_{34}$ Me |
|---|---|---|---|

Reaction 3

| Compound I-b2:mg | Compound P2:mg | CMPI mg | TEA ml | THF ml | Reaction time hr | Column sol. | Product | Amount mg |
|---|---|---|---|---|---|---|---|---|
| 400 | 392 | 337 | 0.46 | 11 | 15 | EA:H 1:1 | I-c5 | 590 |

EI-MS(M$^+$): 642
$^1$H-NMR(CDCl$_3$): δ 0.72, 0.80, and 0.91(total 6H, d, J=6.2-6.6Hz), 1.23, 1.34, 1.37 and 1.39(total 18H, s), 2.06-2.30(1H, m), 2.25, 2.68, 2.75 and 2.86(total 6H, s), 2.79(3H, d, J= 4.6Hz), 2.50-3.24(4H, m), 4.38-4.92 and 5.08-5.20(total 3H, m), 5.53 and 6.00(total 1H, brs), 5.88 and 6.21(total 1H, d, J=5.0-8.3Hz), 6.52-7.22(7H, m)

Reaction 4a

| Compound I-c5:mg | TFA ml | CH$_2$Cl$_2$ ml | Reaction time hr | Column sol. | Amount mg | HPLC min |
|---|---|---|---|---|---|---|

TABLE D-7-continued

Example 32
Synthesis of N-Me-Phe(4-F)-N-Me-Val-Tyr(3-tBu)-NHMe

| $R_{31}$ | | $R_{32}$ | | $R_{33}$ | | $R_{34}$ | |
|---|---|---|---|---|---|---|---|
| Me | | Me | | H | | Me | |

| 492 | 2 | 8 | 1 | CH:M 20:1 | 305 | 18.9 |

EI-MS(M$^+$): 542
$^1$H-NMR(CDCl$_3$): δ 0.57, 0.79 and 0.91(total 6H, d, J=6.3-6.6Hz), 1.35 and 1.38(total 9H, s), 2.20-2.34(1H, m), 2.25 and 2.40(total 3H, s), 2.63 and 2.64(total 3H, s), 2.71 and 2.73(total 3H, d, J=4.3-4.6Hz), 2.60-3.10(4H, m), 3.55(1/2H, t, J=7.0Hz), 3.67(1/2H, t, J=6.9Hz), 3.81(1/2H, d, J=10.9Hz), 5.30-5.72(2H, m), 6.58-7.20(7H, m), 9.13(1/2H, d, J=8.6Hz)

TABLE D-8

Example 33
Synthesis of N-Et-Phe(4-F)-N-Me-Val-Tyr(3-tBu)-NHMe

| $R_{31}$ | $R_{32}$ | $R_{33}$ | $R_{34}$ |
|---|---|---|---|
| Et | Me | H | Me |

Reaction 3

| Compound I-b2:mg | Compound P3:mg | CMPI mg | TEA ml | THF ml | Reaction time hr | Column sol. | Product | Amount mg |
|---|---|---|---|---|---|---|---|---|
| 490 | 559 | 414 | 0.45 | 8 | 13 | EA:H 1:1 | I-c6 | 747 |

$^1$H-NMR(CDCl$_3$): δ 0.40, 0.47, 0.67 and 0.86(total 6H, d, J=6.3-6.9Hz), 1.06-1.22(3H, m), 1.36 and 1.38(total 9H, s), 2.10-2.26(1H, m), 2.49 and 2.78(total 3H, s), 2.79 and 2.73(total 3H, d, J=4.6-4.9Hz), 2.60-3.40(6H, m), 4.28-4.44(2H, m), 4.90-5.16(3H, m), 5.40-5.68(2H, m), 6.38-7.42(12H, m)

Reaction 4b

| Compound I-c6:mg | Pd-C mg | MeOH ml | Reaction time hr | Column sol. | Amount mg | HPLC min |
|---|---|---|---|---|---|---|
| 660 | 66 | 10 | 12 | CH:M:N 10:1:0.1 | 184 | 19.6 |

EI-MS(M$^+$): 556
$^1$H-NMR(CDCl$_3$): δ 0.40, 0.77 and 0.89(total 6H, d, J=6.6Hz), 1.06 and 1.19(total 3H, t, J=7.0-7.3Hz), 1.34 and 1.38(total 9H, s), 2.10-2.28(1H, m), 2.48(3H, s), 2.30-3.20(6H, m), 2.73 and 2.74(total 3H, d, J=4.6Hz), 3.58-3.70(1H, m), 3.76(3/10H, d, J=11.2Hz), 4.38(7/10H, dt, J=4.9, 7.3Hz), 4.50(7/10H, d, J=11.2Hz), 4.56(3/10H, dt, J=7.3, 7.9Hz), 5.72-5.90(2/3H, m), 6.60-7.18(8H, m), 8.68(1/2H, d, J=7.9Hz)

TABLE D-9

Example 34
Synthesis of N-Me-Phe(4-F)-N-Me-Val-N-Me-Tyr(3-tBu)-NH$_2$

| $R_{31}$ | $R_{32}$ | $R_{33}$ | $R_{34}$ |
|---|---|---|---|
| Me | Me | Me | H |

Reaction 3

| Compound I-b3:g | Compound P2:g | CMPI g | TEA ml | THF ml | Reaction time hr | Column sol. | Product | Amount g |
|---|---|---|---|---|---|---|---|---|
| 0.600 | 0.638 | 0.549 | 0.46 | 16 | 16 | H:EA = 2:1 | I-c7 | 0.729 |

TABLE D-9-continued

Example 34
Synthesis of N-Me-Phe(4-F)-N-Me-Val-N-Me-Tyr(3-tBu)-NH$_2$

| $R_{31}$ | $R_{32}$ | $R_{33}$ | $R_{34}$ |
|---|---|---|---|
| Me | Me | Me | H |

Reaction 4a

| Compound I-c7:g | TFA ml | CH$_2$Cl$_2$ ml | Reaction time hr | Column sol. | Amount g | HPLC min |
|---|---|---|---|---|---|---|
| 0.635 | 3.00 | 15 | 2 | MC:M:H 10:1:1 | 0.413 | 19.6 |

EI-MS(M$^+$): 542

$^1$H-NMR(CDCl$_3$): (two rotamers)δ 0.58, 0.81, 0.82 and 0.93(6H, d, J=6.4-6.9Hz), 1.32 and 1.40 (9H, s), 2.20-2.34(1H, m), 2.22 and 2.24(3H, s), 2.50 and 2.93(3H, s), 2.84 and 3.04(3H, s), 2.52 and 2.74(3H, d, J=6.5-6.9Hz), 3.18-3.41(1H, m), 3.42 and 3.62(1H, t, J=5.0-6.8Hz), 5.03 and 5.13(1H, d, J=10.7-10.9Hz), 5.42-5.49(1H, m), 5.38 and 6.01(1H, brs), 6.38 and 6.62(1H, d, J=8.0Hz), 6.78-6.99(3H, m), 7.04-7.12(3H, m)

TABLE D-10

Example 35
Synthesis of N-Et-Phe(4-F)-N-Me-Val-N-Me-Tyr(3-tBu)-NH$_2$

| $R_{31}$ | $R_{32}$ | $R_{33}$ | $R_{34}$ |
|---|---|---|---|
| Et | Me | Me | H |

Reaction 3

| Compound I-b3:g | Compound P4:g | CMPI g | TEA ml | THF ml | Reaction time hr | Column sol. | Product | Amount g |
|---|---|---|---|---|---|---|---|---|
| 0.460 | 0.520 | 0.420 | 0.53 | 10.0 | 17 | H:EA 2:1 | I-c8 | 0.300 |

Reaction 4a

| Compound I-c8:g | TFA ml | CH$_2$Cl$_2$ ml | Reaction time hr | Column sol. | Amount g | HPLC min |
|---|---|---|---|---|---|---|
| 0.300 | 1.44 | 1.44 | 2 | MC:M:H 10:1:1 | 0.200 | 20.2 |

EI-MS(M$^+$): 556

$^1$H-NMR(CDCl$_3$): (two rotamers)δ 0.54~1.1(6H, m and d, J=6.3Hz), 1.35 and 1.39(9H, s), 2.48 and 2.81(3H, s) 2.97 and 3.07(3H, s), 2.21~3.76(7H, m), 5.55~5.02(3H, m), 6.37 and 6.61(1H, d, J=8.3Hz), 6.78~7.21(6H, m)

TABLE D-11

Example 36
Synthesis of Phe(4-F)-N-Me-Val-N-Me-Tyr(3-tBu)-NH-Me

| $R_{31}$ | $R_{32}$ | $R_{33}$ | $R_{34}$ |
|---|---|---|---|
| H | Me | Me | Me |

Reaction 1

| Compound T5:g | Compound V1:g | CMPI g | TEA ml | THF ml | Reaction time hr | Column sol. | Product | Amount g |
|---|---|---|---|---|---|---|---|---|
| 1.500 | 1.960 | 2.030 | 2.37 | 30.00 | 21 | EA:H:MC 3:2:2 | I-a4 | 2.200 |

Reaction 2

| Compound I-a4:g | Pd(OH)$_2$:g | MeOH ml | Reaction time hr | Column sol. | Product | Amount g |
|---|---|---|---|---|---|---|
| 2.200 | 0.220 | 50.00 | 1 | Not purified | I-b4 | 1.400 |

TABLE D-11-continued

Example 36
Synthesis of Phe(4-F)-N-Me-Val-N-Me-Tyr(3-tBu)-NH-Me

| $R_{31}$ | $R_{32}$ | $R_{33}$ | $R_{34}$ |
|---|---|---|---|
| H | Me | Me | Me |

Reaction 3

| CompoundI I-b4:g | Compound P1:g | CMPI g | TEA ml | THF ml | Reaction time hr | Column sol. | Product | Amount g |
|---|---|---|---|---|---|---|---|---|
| 0.430 | 0.420 | 0.400 | 0.47 | 10.00 | 19 | MC:M:H 10:1:3 | I-c9 | 0.500 |

Reaction 4a

| Compound I-c9:g | TFA ml | $CH_2Cl_2$ ml | Reaction time hr | Column sol. | Amount g | HPLC min |
|---|---|---|---|---|---|---|
| 0.500 | 2.50 | 2.50 | 1 | MC:M:H 15:1:2 | 0.320 | 19.8 |

EI-MS(M$^+$): 542
$^1$H-NMR(CDCl$_3$): (two rotamers)δ 0.51~0.92(6H, d, J=6.6Hz), 1.32 and 1.37(9H, s), 2.24(2H, d, J=8.3Hz) 2.52 and 2.82(3H, s) 2.18~3.89(7H, m), 3.04 and 3.13(3H, s), 5.42~4.82(3H, m), 6.41 and 6.63(1H, d, J=8.2Hz), 6.78~7.19(6H, m)

TABLE D-12

Example 37
Synthesis of N-Me-Phe(4-F)-N-Me-Val-N-Me-Tyr(3-tBu)-NH-Me

| $R_{31}$ | $R_{32}$ | $R_{33}$ | $R_{34}$ |
|---|---|---|---|
| Me | Me | Me | Me |

Reaction 3

| CompoundI I-b4:g | Compound P2:g | CMPI g | TEA ml | THF ml | Reaction time hr | Column sol. | Product | Amount g |
|---|---|---|---|---|---|---|---|---|
| 0.430 | 0.440 | 0.400 | 0.47 | 10.00 | 19 | EA:H:MC 2:1:1 | I-c10 | 0.500 |

Reaction 4a

| Compound I-c10:g | TFA ml | $CH_2Cl_2$ ml | Reaction time hr | Column sol. | Amount g | HPLC min |
|---|---|---|---|---|---|---|
| 0.500 | 2.50 | 2.50 | 1 | MC:M:H 15:1:2 | 0.260 | 20.3 |

EI-MS(M$^+$): 556
$^1$H-NMR(CDCl$_3$): (two rotamers)δ 0.76~0.92(6H, m and d, J=6.3Hz), 1.34 and 1.39(9H, s), 2.25 (3H, d, J=11.6Hz), 2.52 and 2.82(3H, s), 2.95 and 3.07(3H, s), 2.21~3.64(5H, m), 2.71 and 2.76 (3H, d, J=4.3Hz), 5.42~5.01(3H, m), 6.37 and 6.54(1H, d, J=8.2Hz), 6.78~7.11(6H, m)

TABLE D-13

Example 38
Synthesis of N-Et-Phe(4-F)-N-Me-Val-N-Me-Tyr(3-tBu)-NHMe

| $R_{31}$ | $R_{32}$ | $R_{33}$ | $R_{34}$ |
|---|---|---|---|
| Et | Me | Me | Me |

Reaction 3

| CompoundI I-b4:g | Compound P3:g | CMPI g | TEA ml | THF ml | Reaction time hr | Column sol. | Product | Amount g |
|---|---|---|---|---|---|---|---|---|
| 0.450 | 0.560 | 0.460 | 0.50 | 10.00 | 19 | EA:H:MC 2:1:1 | I-c11 | 0.450 |

TABLE D-13-continued

Example 38
Synthesis of N-Et-Phe(4-F)-N-Me-Val-N-Me-Tyr(3-tBu)-NHMe

| $R_{31}$ | $R_{32}$ | $R_{33}$ | $R_{34}$ |
|---|---|---|---|
| Et | Me | Me | Me |

Reaction 4a

| Compound I-c11:g | Pd(OH)$_2$:g | MeOH ml | Reaction time hr | Column sol. | Amount g | HPLC min |
|---|---|---|---|---|---|---|
| 0.450 | 0.050 | 15.00 | 1 | MC:M:H 15:1:2 | 0.220 | 21.4 |

EI-MS(M⁺): 570
$^1$H-NMR(CDCl$_3$): (two rotamers)δ 0.54~1.1(6H, m and d, J=6.3Hz), 1.26 and 1.34(9H, s), 2.77 (3H, s), 2.97(3H, s), 3.07(3H, s), 2.12~3.72(7H, m), 5.38~5.21(3H, m), 6.37 and 6.54(1H, d, J=8.3Hz), 6.78~7.21(6H, m)

TABLE D-14

Example 39
Synthesis of Phe(4-F)-N-Me-Val-N-Et--Tyr(3-tBu)-NH$_2$

| $R_{31}$ | $R_{32}$ | $R_{33}$ | $R_{34}$ |
|---|---|---|---|
| H | Me | Et | H |

Reaction 1

| Compound T7:g | Compound V1:g | CMPI g | TEA ml | THF ml | Reaction time hr | Column sol. | Product | Amount g |
|---|---|---|---|---|---|---|---|---|
| 4.000 | 5.720 | 5.510 | 6.02 | 100 | 24 | EA:H:MC 2:1:1 | I-a5 | 3.310 |

Reaction 2

| Compound I-a5:g | Pd(OH)$_2$:g | MeOH ml | Reaction time hr | Column sol. | Product | Amount g |
|---|---|---|---|---|---|---|
| 3.100 | 0.300 | 70.00 | 1 | MC:M:H 15:1:2 | I-b5 | 1.600 |

Reaction 3

| Compound I-b5:g | Compound P1:g | CMPI g | TEA ml | THF ml | Reaction time hr | Column sol. | Product | Amount g |
|---|---|---|---|---|---|---|---|---|
| 0.400 | 0.430 | 0.370 | 0.46 | 10.00 | 19 | EA:H:MC 2:1:1 | I-c12 | 0.380 |

Reaction 4a

| Compound I-c12:g | TFA ml | CH$_2$Cl$_2$ ml | Reaction time hr | Column sol. | Amount g | HPLC min |
|---|---|---|---|---|---|---|
| 0.380 | 1.50 | 1.50 | 2 | MC:M:H 15:1:2 | 0.150 | 20.5 |

EI-MS(M⁺): 542
$^1$H-NMR(CDCl$_3$): (two rotamers)δ 0.72~1.33(m, 9H), 1.35 and 1.39(9H, s), 2.24(2H, d, J=8.3Hz), 2.70 and 2.90(3H, s), 2.21~3.70(7H, m) 4.92~5.23(3H, m), 6.41 and 6.61(1H, d, J=7.9Hz), 6.80~7.19(6H, m)

TABLE D-15

Example 40
Synthesis of N-Me-Phe(4-F)-N-Me-Val-N-Et-Tyr(3-tBu)-NH$_2$

| R$_{31}$ | R$_{32}$ | R$_{33}$ | R$_{34}$ |
|---|---|---|---|
| Me | Me | Et | H |

Reaction 3

| Compound I-b5:g | Compound P2:g | CMPI g | TEA ml | THF ml | Reaction time hr | Column sol. | Product | Amount g |
|---|---|---|---|---|---|---|---|---|
| 0.440 | 0.450 | 0.380 | 0.48 | 10.00 | 19 | EA:H:MC 2:1:1 | I-c13 | 0.220 |

Reaction 4a

| Compound I-c13:g | TFA ml | CH$_2$Cl$_2$ ml | Reaction time hr | Column sol. | Amount g | HPLC min |
|---|---|---|---|---|---|---|
| 0.220 | 1.50 | 1.50 | 2 | MC:M:H 15:1:2 | 0.130 | 21.0 |

EI-MS(M$^+$): 447
$^1$H-NMR(CDCl$_3$): (two rotamers)δ 0.72~0.95(6H, d, J=6.6Hz), 1.13~1.32(3H, m) 1.35 and 1.39 (9H, s), 2.24(2H, d, J=8.3Hz) 2.21~3.96(7H, m), 2.75 and 3.08(3H, s), 4.92~5.40(3H, m), 6.41 and 6.63(1H, d, J=7.9Hz), 6.78~7.19(6H, m)

TABLE D-16

Example 41
Synthesis of N-Et-Phe(4-F)-N-Me-Val-N-Et-Tyr(3-tBu)-NH$_2$

| R$_{31}$ | R$_{32}$ | R$_{33}$ | R$_{34}$ |
|---|---|---|---|
| Et | Me | Et | H |

Reaction 3

| Compound I-b5:g | Compound P2:g | CMPI g | TEA ml | THF ml | Reaction time hr | Column sol. | Product | Amount g |
|---|---|---|---|---|---|---|---|---|
| 0.490 | 0.480 | 0.420 | 0.52 | 10.00 | 19 | EA:H:MC 2:1:1 | I-c14 | 0.260 |

Reaction 4a

| Compound I-c14:g | Pd(OH)$_2$:g | MeOH ml | Reaction time hr | Column sol. | Amount g | HPLC min |
|---|---|---|---|---|---|---|
| 0.260 | 0.030 | 10.00 | 2 | MC:M:H 15:1:2 | 0.120 | 21.9 |

EI-MS(M$^+$): 570
$^1$H-NMR(CDCl$_3$): (two rotamers)δ 0.74~1.26(12H, m), 1.34 and 1.39(9H, s), 2.84 and 2.67(3H, s), 2.22~3.81(8H, m), 4.7~5.22(3H, m), 6.43 and 6.59(1H, d, J=7.9Hz), 6.81~7.19(6H, m)

TABLE D-17

Example 42
Synthesis of Phe(4-F)-N-Me-Val-N-Et-Tyr(3-tBu)-NHMe

| R$_{31}$ | R$_{32}$ | R$_{33}$ | R$_{34}$ |
|---|---|---|---|
| H | Me | Et | Me |

Reaction 1

| Compound T8:g | Compound V1:g | CMPI g | TEA ml | THF ml | Reaction time hr | Column sol. | Product | Amount g |
|---|---|---|---|---|---|---|---|---|
| 4.20 | 4.80 | 4.62 | 6.31 | 75 | 13 | EA:H 1:1 | I-a6 | 4.33 |

EI-MS(M$^+$): 585
$^1$H-NMR(CDCl$_3$): δ 0.53, 0.80, 0.82 and 0.89(total 6H, d, J=6.3-6.6Hz), 0.96-1.30(3H, m), 1.34, 1.36 and 1.36(total 9H, s), 2.20-2.40(1H, m), 2.46 and 2.75(total 3H, d, J=4.6Hz), 2.57 and 2.95(total 3H, s), 2.66-3.68(4H, m), 4.33, 4.45 and 4.59(total 1H, d, J=10.6Hz), 4.78-4.92 (1H, m), 4.96-5.36(3H, m), 6.30-7.12(4H, m), 7.30-7.44(5H, m)

TABLE D-17-continued

Example 42
Synthesis of Phe(4-F)-N-Me-Val-N-Et-Tyr(3-tBu)-NHMe

| $R_{31}$ | $R_{32}$ | $R_{33}$ | $R_{34}$ |
|---|---|---|---|
| H | Me | Et | Me |

Reaction 2

| Compound I-a6:g | Pd(OH)$_2$ mg | MeOH ml | Reaction time hr | Column sol. | Product | Amount g |
|---|---|---|---|---|---|---|
| 2.81 | 280 | 60 | 1.5 | CH:M 10:1 | I-b6 | 2.10 |

EI-MS(M$^+$): 391
$^1$H-NMR(CDCl$_3$): δ 0.34, 0.73, 0.90 and 0.96(total 6H, d, J=6.3-6.9Hz), 1.13 and 1.18(total 3H, t, J=6.9Hz), 1.36 and 1.37(total 9H, s), 1.60-1.80(1/2H, m), 2.14 and 2.27(total 3H, s), 2.10-2.30(1/2H, m), 2.58(1/2H, d, J=9.6Hz), 2.92-3.64(9/2H, m), 4.50-4.60(1/3H, m), 4.96-5.10(2/3H, m), 5.10-5.30(1H, m), 6.48(2/3H, brs), 6.54(1/3H, d, J=7.9Hz), 6.57(2/3H, d, J=7.9Hz), 6.79(1/3H, dd, J=2.0, 7.9Hz), 6.91(2/3H, dd, J=2.0, 7.9Hz), 7.00(1/3H, d, J=2.0Hz), 7.10(2/3H, d, J=2.0Hz), 8.24-8.34(1/3H, m)

TABLE D-18

Example 42(Continued from Table D-17)
Synthesis of Phe(4-F)-N-Me-Val-N-Et-Tyr(3-tBu)-NHMe

Reaction 3

| Compound I-b6:mg | Compound P1:mg | CMPI mg | TEA ml | THF ml | Reaction time hr | Column sol. | Product | Amount mg |
|---|---|---|---|---|---|---|---|---|
| 457 | 397 | 359 | 0.39 | 6 | 22 | MC:M 20:1 | I-c15 | 724 |

EI-MS(M$^+$): 657
$^1$H-NMR(CDCl$_3$): δ 0.72, 0.78, 0.82 and 0.89(total 6H, d, J=6.3-6.9Hz), 1.08 and 1.16(total 3H, t, J=6.9Hz), 1.33, 1.36, 1.38, and 1.39(total 18H, s), 2.14-2.28(1H, m), 2.54 and 2.98 (total 3H, s), 2.65 and 2.75(total 3H, d, J=4.6-4.9Hz), 2.60-3.64(6H, m), 4.58-5.18(4H, m), 6.32-6.72(2H, m), 6.90-7.18(5H, m)

Reaction 4a

| Compound I-c15:mg | TFA ml | CH$_2$Cl$_2$ ml | Reaction time hr | Column sol. | Amount mg | HPLC min |
|---|---|---|---|---|---|---|
| 651 | 3 | 7 | 1 | MC:M:H 20:1:1 | 354 | 21.5 |

EI-MS(M$^+$): 556
$^1$H-NMR(CDCl$_3$): δ 0.67, 0.82 and 0.92(total 6H, d, J=6.6Hz), 1.10 and 1.15(total 3H, t, J=6.9Hz), 1.34 and 1.39(total 9H, s), 2.24-2.44(1H, m), 2.67 and 2.76(total 3H, d, J=4.3-4.9Hz), 2.73 and 3.05(total 3H, s), 2.50-3.90(7H, m), 4.94-5.08(2H, m), 6.36-7.18(7H, m)

TABLE D-19

Example 43
Synthesis of N-Me-Phe(4-F)-N-Me-Val-N-Et-Tyr(3-tBu)-NHMe

| $R_{31}$ | $R_{32}$ | $R_{33}$ | $R_{34}$ |
|---|---|---|---|
| Me | Me | Et | Me |

Reaction 3

| Compound I-b6:mg | Compound P2:mg | CMPI mg | TEA ml | THF ml | Reaction time hr | Column sol. | Product | Amount mg |
|---|---|---|---|---|---|---|---|---|
| 465 | 424 | 365 | 0.40 | 6 | 21 | EA:H 2:1 | I-c16 | 759 |

$^1$H-NMR(CDCl$_3$): δ 0.45, 0.73, 0.82 and 0.89(total 6H, d, J=6.4-6.9Hz), 1.02(3H, t, J=6.6Hz), 1.29, 1.36, 1.37, 1.39 and 1.42(total 18H, s), 2.20-2.30(1H, m), 2.36, 2.71, 2.93 and 3.67(total 6H, s), 2.77 and 2.90(total 3H, d, J=4.6-4.9Hz), 2.60-3.44(6H, m), 4.80-5.28(total

TABLE D-19-continued

Example 43
Synthesis of N-Me-Phe(4-F)-N-Me-Val-N-Et-Tyr(3-tBu)-NHMe

| $R_{31}$ | $R_{32}$ | $R_{33}$ | $R_{34}$ |
|---|---|---|---|
| Me | Me | Et | Me |

3H, m), 6.09(1H, d, J=4.0Hz), 6.19 and 6.35(total 1H, dd, J=1.3, 7.3Hz), 6.51(1/2H, s), 6.60 and 6.69(total 1H, d, J=7.3Hz), 6.94-7.16(13/2H, m)

Reaction 4a

| Compound I-c16:mg | TFA ml | CH$_2$Cl$_2$ ml | Reaction time hr | Column sol. | Amount mg | HPLC min |
|---|---|---|---|---|---|---|
| 651 | 3 | 7 | 1 | MC:M:H:N 10:1:1:0.1 | 457 | 22.1 |

EI-MS(M$^+$): 570
$^1$H-NMR(CDCl$_3$): δ 0.72, 0.83 and 0.92(total 6H, d, J=6.6Hz), 1.14 and 1.16(total 3H, t, J=6.6-6.9Hz), 1.34 and 1.39(total 9H, s), 2.23 and 2.27(total 3H, s), 2.20-2.40(1H, m), 2.55(1H, d, J=6.3Hz), 2.64-2.88(7H, m), 2.99(1H, dd, J=9.2, 14.9Hz), 3.23(1H, dd, J=6.9, 14.9Hz), 3.40-3.74(3H, m), 5.00-5.12(2H, m), 6.40 and 6.57(total 1H, d, J=7.9-8.2Hz), 6.44(1/2H, brs), 6.80(1/2H, dd, J=1.6, 7.9Hz), 6.90-7.18(11/2H, m)

TABLE D-20

Example 44
Synthesis of N-Et-Phe(4-F)-N-Me-Val-N-Et-Tyr(3-tBu)-NHMe

| $R_{31}$ | $R_{32}$ | $R_{33}$ | $R_{34}$ |
|---|---|---|---|
| Et | Me | Et | Me |

Reaction 3

| Compound I-b6:mg | Compound P3:mg | CMPI g | TEA ml | THF ml | Reaction time hr | Column sol. | Product | Amount g |
|---|---|---|---|---|---|---|---|---|
| 640 | 675 | 501 | 0.55 | 9 | 17 | EA:H 1:1 | I-c17 | 963 |

$^1$H-NMR(CDCl$_3$): δ 0.71, 0.78, 0.88, 1.07 and 1.09(total 6H, d, J=6.3-6.9Hz), 0.98 and 1.18 (total 3H, t, J=6.9Hz), 1.29, 1.35 and 1.39(total 9H, s), 2.14-2.30(1H, m), 2.48-3.56(14H, m), 4.78(1H, d, J=10.6Hz), 4.86-5.24(3H, m), 5.98-6.10(3/2H, m), 6.21(1H, s), 6.59 and 6.64 (total 1H, d, J=7.9Hz), 6.84-7.20(11/2H, m), 7.30-7.44(5H, m)

Reaction 4b

| Compound I-c17:mg | Pd(OH)$_2$ mg | MeOH ml | Reaction time hr | Column sol. | Amount mg | HPLC min |
|---|---|---|---|---|---|---|
| 870 | 87 | 15 | 15 | CH:M 10:1 | 252 | 22.9 |

EI-MS(M$^+$): 584
$^1$H-NMR(CDCl$_3$): δ 0.73, 0.82 and 0.91(total 6H, d, J=6.3-6.6Hz), 1.01, 1.06, 1.13 and 1.16 (total 6H, t, J=6.6-6.9Hz), 1.34 and 1.39(total 9H, s), 2.20-3.04(5H, m), 2.67 and 2.78(total 3H, s), 2.69 and 2.74(total 3H, d, J=4.6-4.9Hz), 3.26(1H, dd, J=7.9, 14.2Hz), 3.45(1H, dd, J=8.9, 13.2Hz), 3.54-3.74(2H, m), 4.94-5.12(5/2H, m), 5.38-5.46(1/2H, m), 6.42 and 6.57 (total 1H, d, J=7.9-8.3Hz), 6.80-7.16(6H, m)

TABLE D-21

Example 45
Synthesis of Phe(4-F)-N-Et-Val-Tyr(3-tBU)-NH$_2$

| $R_{31}$ | $R_{32}$ | $R_{33}$ | $R_{34}$ |
|---|---|---|---|
| H | Et | H | H |

Reaction 1

| Compound T1:g | Compound V2:g | CMPI g | TEA ml | THF ml | Reaction time hr | Column sol. | Product | Amount g |
|---|---|---|---|---|---|---|---|---|
| 3.3 | 4.29 | 4.0 | 4.3 | 80 | 2 | EA:H 3:1 | I-a7 | 6.5 |

$^1$H-NMR(CDCl$_3$): δ 0.7-1.0(9H, m), 1.2-1.4(9H, m), 2.2-2.4(1H, m), 2.8-3.0(1H, m), 3.0-3.15(1H, m), 3.2-3.35(2H, m), 3.6-3.7(1H, brd, J=10.9Hz), 4.45-4.6(1H, m), 5.04(1H, brs), 5.15(1H, s), 5.15-5.25(1H, m), 6.02(1H, brs), 6.47(1H, brd, J=7.3Hz), 6.86(1H, brd, J=7.3Hz), 7.0-7.2(2H, m), 7.3-7.5(5H, m)

Reaction 2

| Compound I-a7:g | Pd(OH)$_2$ g | EtOH ml | Reaction time hr | Column sol. | Product | Amount g |
|---|---|---|---|---|---|---|
| 6.4 | 1.2 | 130 | 1.5 | Not purified | I-b7 | 4.37 |

$^1$H-NMR(CDCl$_3$): δ 0.63(3H, d, J=6.6Hz), 0.83(3H, d, J=6.6Hz), 1.03(3H, t, J=6.9z), 1.37(9H, s), 1.85-2.05(1H, m), 2.4-2.6(2H, m), 2.86(1H, d, J=4.0Hz), 2.9-3.2(2H, m), 4.6-4.8(1H, m), 5.55(1H, brs), 6.22(1H, brs), 6.4-6.6(1H, m), 6.64(1H, d, J=7.3Hz), 6.92(1H, brd, J=7.3Hz), 7.05(1H, brs), 7.90(1H, brd, J=8.3Hz)

TABLE D-22

Example 45(Continued from Table D-21)
Synthesis of Phe(4-F)-N-Et-Val-Tyr(3-tBu)-NH$_2$ Reaction 3

| Compound I-b7:g | Compound P1:g | CMPI g | TEA ml | THF ml | Reaction time hr | Column sol. | Product | Amount g |
|---|---|---|---|---|---|---|---|---|
| 1 | 1.17 | 1.06 | 1.7 | 4 | 13 | EA:H 1:2 | I-c18 | 0.56 |

$^1$H-NMR(CDCl$_3$): δ 0.3-0.9(9H, m), 1.2-1.5(18H, m), 2.2-2.4(1H, m), 2.6-3.4(6H, m), 3.9-4.1, 4.4-4.8, and 4.8-4.9(3H, m), 5.53(1H, brs), 6.25(1H, brs), 6.25-6.45(2H, m), 6.56(1H, brs), 6.6-6.9(1H, m), 6.9-7.1(3H, m), 7.15-7.3(2H, m). 7.6-7.8(1H, m)

Reaction 4a

| Compound I-c18 g | TFA ml | CH$_2$Cl$_2$ ml | Reaction time hr | Column sol. | Amount g | HPLC min |
|---|---|---|---|---|---|---|
| 0.51 | 2 | 4 | 1 | MC:M 20:1 | 0.36 | 19.9 |

EI-MS(M$^+$): 528
$^1$H-NMR(CDCl$_3$): δ 0.60(3H, d, J=6.6Hz). 0.8-0.9(6H, m), 1.38(9H, s), 2.2-2.4(1H, m), 2.68(1H, dd, J=7.3, 13.5Hz), 2.8-3.0(2H, m), 3.0-3.25(3H, m), 3.71(1H, t, J=6.9Hz), 4.21(1H, brd, J=10.9Hz), 4.4-4.6(1H, m), 5.55(1H, brs), 6.23(1H, brs), 6.64(1H, d, J=7.9Hz), 6.86(1H, dd, J=1.7, 7.9Hz), 6.9-7.0(1H, m), 6.97(2H, t, J=8.6Hz), 7.0-7.2(3H, m)

TABLE D-23

Example 46
Synthesis of N-Me-Phe(4-F)-N-Et-Val-Tyr(3-tBu)-NH$_2$

| $R_{31}$ | $R_{32}$ | $R_{33}$ | $R_{34}$ |
|---|---|---|---|
| Me | Et | H | H |

Reaction 3

| Compound I-b7:g | Compound P2:g | CMPI g | TEA ml | THF ml | Reaction time hr | Column sol. | Product | Amount g |
|---|---|---|---|---|---|---|---|---|
| 1.0 | 1.23 | 1.06 | 1.7 | 4 | 14 | MC:M 50:1 | I-c19 | 0.54 |

Reaction 4a

| Compound I-c19:g | TFA ml | CH$_2$Cl$_2$ ml | Reaction time hr | Column sol. | Amount g | HPLC min |
|---|---|---|---|---|---|---|
| 0.48 | 2 | 4 | 0.5 | MC:M 20:1 | 0.26 | 20.4 |

EI-MS(M$^+$): 542
$^1$H-NMR(CDCl$_3$): δ 0.57, 0.68, 0.71, and 0.91(6H, d, J=6.6Hz),
0.99 and 1.05(3H, t, J=6.9Hz), 1.37(9H, s), 2.29 and
2.38(3H, s), 2.3-2.5(1H, m), 2.8-3.4(6H, m), 3.52 and
3.60(1H, t, J=6.6Hz), 3.6-3.9(1H, m), 4.5-4.7(1H, m), 5.66,
5.74, 5.83, and 6.25(2H, brs), 6.66.6-7.2(7H, m),
7.61(1H, brd, J=5.4Hz), 9.16(1H, d, J=7.6Hz)

TABLE D-24

Example 47
Synthesis of N-Et-Phe(4-F)-N-Et-Val-Tyr(3-tBu)-NH$_2$

| $R_{31}$ | $R_{32}$ | $R_{33}$ | $R_{34}$ |
|---|---|---|---|
| Et | Et | H | H |

Reaction 3

| Compound I-b7:g | Compound P3:g | CMPI g | TEA ml | THF ml | Reaction time hr | Column sol. | Product | Amount g |
|---|---|---|---|---|---|---|---|---|
| 1 | 1.42 | 1.06 | 1.7 | 4 | 14 | MC:M 50:1 | I-c20 | 0.86 |

$^1$H-NMR(CDCl$_3$): δ 0.35-1.2(12H, m), 1.36, 1.38, and 1.40(9H, s),
2.2-2.4(1H, m), 2.7-3.0 and 3.2-3.6(8H, m), 3.7-3.9, 4.1-4.3,
4.4-4.6, and 4.9-5.1(3H, m), 5.1-5.5(3H, m), 6.5-6.7, 6.8-7.0,
and 7.0-7.4(12H, m), 7.6-7.8(1H, m).

Reaction 4a

| Compound I-c20 g | Pd(OH)$_2$ g | MeOH ml | Reaction time hr | Column sol. | Amount g | HPLC min |
|---|---|---|---|---|---|---|
| 0.8 | 0.16 | 10 | 1 | MC:M 20:1 | 0.31 | 20.6 |

EI-MS(M$^+$): 556
$^1$H-NMR(CDCl$_3$): δ 0.45, 0.63, 0.67, and 0.73(6H, d, J=6.6Hz), 0.8-
1.2(6H, m), 1.38(9H, s), 2.1-2.7(3H, m), 2.7-3.3(6H, m), 3.5-
3.9(2H, m), 4.4-4.7(1H, m), 5.38(1H, brs), 5.4-5.6(1H, m), 5.9-
6.3(1H, m), 6.62(1H, d, J=7.9Hz), 6.7-7.0(3H, m), 7.0-7.2(3H, m),
7.45-7.65(1H, m)

TABLE D-25

Example 48
Synthesis of Phe(4-F)-N-Et-Val-Tyr(3-tBu)-NHMe

| $R_{31}$ | $R_{32}$ | $R_{33}$ | $R_{34}$ |
|---|---|---|---|
| H | Et | H | Me |

Reaction 1

| Compound T2:g | Compound V2:g | CMPI g | TEA ml | THF ml | Reaction time hr | Column sol. | Product | Amount g |
|---|---|---|---|---|---|---|---|---|
| 4.95 | 6.62 | 6.57 | 8.3 | 120 | 2 | EA:H 3:2 | I-a8 | 9.0 |

Reaction 2

| Compound I-a8:g | Pd(OH)$_2$ g | MeOH ml | Reaction time hr | Column sol. | Product | Amount g |
|---|---|---|---|---|---|---|
| 8.9 | 0.90 | 200 | 1.5 | Not purified | I-b8 | 6.4 |

$^1$H-NMR(CDCl$_3$): δ 0.64(3H, d, J=6.9Hz), 0.84(3H, d, J=6.9Hz), 1.05(3H, t, J=7.1Hz), 1.37(9H, s), 1.90-2.02(1H, m), 2.51(2H, q, J=6.9Hz), 2.73(3H, d, J=4.9Hz), 2.86(1H, d, J=4.3Hz), 2.91-3.07(2H, m), 4.53(1H, dd, J=7.2, 15.2Hz), 6.04(1H, brd, J=4.6Hz), 6.63(1H, d, J=7.9Hz), 6.91(1H, dd, J=2.0, 7.9Hz), 7.03(1H, d, J=2.0Hz), 7.88(1H, d, J=8.3Hz)

TABLE D-26

Example 48(Continued from Table D-25)
Synthesis of Phe(4-F)-N-Et-Val-Tyr(3-tBu)-NHMe

Reaction 3

| Compound I-b:g | Compound P1:g | CMPI g | TEA ml | THF ml | Reaction time hr | Column sol. | Product | Amount g |
|---|---|---|---|---|---|---|---|---|
| 1.70 | 1.91 | 1.72 | 1.9 | 7.5 | 31 | MC:M:N 30:1:0.1 | I-c21 | 0.63 |

Reaction 4a

| Compound I-c21:g | TFA ml | CH$_2$Cl$_2$ ml | Reaction time min | Column sol. | Amount g | HPLC min |
|---|---|---|---|---|---|---|
| 0.54 | 5 | 6 | 15 | MC:M:N 40:1:0.1 | 0.31 | 21.0 |

EI-MS(M$^+$): 542
$^1$H-NMR(CDCl$_3$): δ 0.67(1H, d, J=6.6Hz), 0.72(1H, d, J=6.3Hz), 0.75(2H, d, J=6.6Hz), 0.92(2H, d, J=6.3Hz), 1.02-1.07(3H, m), 1.37(6H, s), 1.39(3H, s), 2.2-2.6(1H, m), 2.65-2.77(3H, m), 2.8-3.2(4H, m), 3.2-3.4(2H, m), 3.5-3.6(1H, m), 3.72(0.3H, m), 3.94(0.7H, d, J=10.9Hz), 4.45-4.63(1H, m), 5.70-5.85(1H, m), 6.04(0.3H, brs), 6.44(0.7H, brs), 6.6-6.8(2H, m), 6.88-7.20(6H, m), 7.45(0.3H, brd), 9.09(0.7H, d, J=7.9Hz)

TABLE D-27

Example 49
Synthesis of N-Me-Phe(4-F)-N-Et-Val-Tyr(3-tBu)-NHMe

| $R_{31}$ | $R_{32}$ | $R_{33}$ | $R_{34}$ |
|---|---|---|---|
| Me | Et | H | Me |

Reaction 3

| Compound I-b8:g | Compound P2:g | CMPI g | TEA ml | THF ml | Reaction time hr | Column sol. | Product | Amount g |
|---|---|---|---|---|---|---|---|---|
| 2.03 | 1.60 | 1.51 | 2.3 | 10 | 24 | MC:M:N 30:1:0.1 | I-c22 | 0.44 |

Reaction 4a

| Compound I-c22:g | TFA ml | CH$_2$Cl$_2$ ml | Reaction time min | Column sol. | Amount g | HPLC min |
|---|---|---|---|---|---|---|
| 0.41 | 3 | 4 | 30 | MC:M:N 30:1:0.1 | 0.23 | 20.8 |

EI-MS(M$^+$): 556
$^1$H-NMR(CDCl$_3$): δ 0.62(5/3H, d, J=6.6Hz), 0.68(4/3H, d, J=6.6Hz), 0.72(4/3H, d, J=6.6Hz), 0.91(5/3H, d, J=6.3Hz), 1.04(5/3H, t, J=7.3Hz), 1.06(4/3H, t, J=6.9Hz), 1.37(5H, s), 1.38(4H, s), 2.2-2.5(1H, m), 2.30(4/3H, s), 2.43(5/3H, s), 2.67(5/3H, d, J=4.6Hz), 2.71(4/3H, d, J=4.9Hz), 2.8-3.8(58/9H, m), 3.83(5/9H, d, J=10.9Hz), 4.48(1H, m), 5.4-6.2(2H, br), 6.62-6.66(1H, m), 6.8-7.2(6H, m), 7.40(4/9H, brd), 9.21(5/9H, d, J=7.9Hz).

TABLE D-28

Example 50
Synthesis of N-Et-Phe(4-F)-N-Et-Val-Tyr(3-tBu)-NHMe

| $R_{31}$ | $R_{32}$ | $R_{33}$ | $R_{34}$ |
|---|---|---|---|
| Et | Et | H | Me |

Reaction 3

| Compound I-b8:g | Compound P3:g | CMPI g | TEA ml | THF ml | Reaction time hr | Column sol. | Product | Amount mg |
|---|---|---|---|---|---|---|---|---|
| 1.52 | 1.53 | 1.13 | 1.23 | 20 | 96 | EA:H 1:1 | I-c23 | 520 |

$^1$H-NMR(CDCl$_3$): δ 0.41, 0.57, 0.62 and 0.72(total 6H, d, J=6.3-6.9Hz), 0.80-1.20(total 6H, m). 1.35, 1.38 and 1.40(total 9H, s), 2.22-2.42(1H, m), 2.66(3H, d, J=4.3Hz), 2.74-3.56(8H, m), 4.37(1H, dd, J=7.3, 7.9Hz), 5.00-5.48(4H, m), 5.78-6.00(1H, m), 6.50-6.66(1H, m), 6.84-7.44(11H, m)

Reaction 4b

| Compound I-c23:mg | Pd(OH)$_2$mg | MeOH ml | Reaction time hr | Column sol. | Amount g | HPLC min |
|---|---|---|---|---|---|---|
| 450 | 45 | 8 | 14 | MC:M:N 20:1:1 | 308 | 21.6 |

EI-MS(M$^+$): 570
$^1$H-NMR(CDCl$_3$): δ 0.47, 0.64, 0.70 and 0.76(total 6H, d, J=6.3-6.6Hz), 0.88-1.24(6H, m), 1.38(9H, s), 2.10-2.64(3H, m), 2.70 and 2.71(total 3H, d, J=4.6Hz), 2.80-3.30(6H, m), 3.58-3.94(2H, m), 4.46(1H, dd, J=7.6-7.9Hz), 5.74-6.08(2H, m), 6.61(1H, d, J=7.9Hz), 6.78-7.20(6H, m), 7.38(1/2H, d, J=6.3Hz), 8.74(1/2H, d, J=7.9Hz)

TABLE D-29

Example 51
Synthesis of Phe(4-F)-N-Et-Val-N-Me-Tyr(3-tBu)-NH₂

| R₃₁ | R₃₂ | R₃₃ | R₃₄ |
|---|---|---|---|
| H | Et | Me | H |

Reaction 1

| Compound T4:g | Compound V2:g | CMPI g | TEA ml | THF ml | Reaction time hr | Column sol. | Product | Amount g |
|---|---|---|---|---|---|---|---|---|
| 3.360 | 4.500 | 4.113 | 3.73 | 110 | 20 | H:ACT 3:2 | I-a9 | 5.970 |

Reaction 2

| Compound I-a9:g | Pd-C g | MeOH ml | Reaction time hr | Column sol. | Product | Amount g |
|---|---|---|---|---|---|---|
| 5.870 | 1.000 | 114 | 1 | Not purified | I-b9 | 3.600 |

Reaction 3

| CompoundI I-b9:g | Compound P1:g | CMPI g | TEA ml | THF ml | Reaction time hr | Column sol. | Product | Amount g |
|---|---|---|---|---|---|---|---|---|
| 1.200 | 1.350 | 1.220 | 1.33 | 6 | 18 | H:EA 2:1 | I-c24 | 1.160 |

Reaction 4a

| Compound Ic24:g | TFA ml | CH₂Cl₂ ml | Reaction time hr | Column sol. | Amount g | HPLC min |
|---|---|---|---|---|---|---|
| 1.06 | 5.00 | 10 | 1.5 | MC:M:H 15:1:2 | 0.251 | 19.3 |

EI-MS(M⁺): 542
¹H-NMR(CDCl₃): (two rotamers)δ 0.30, 0.69, 0.82 and
0.85(6H, d, J=6.4-6.9Hz), 0.92 and 1.12(3H, t, J=3.4-4.1HZ),
1.35 and 1.37(9H, s), 2.25-2.40(1H, m), 2.56-3.37(5H, m), 2.82
and 3.02(3H, s), 3.60-3.77(2H, m), 4.83-5.38(2H, m), 6.02band
6.18(2H, brs), 6.43 and 6.62(1H, d, J=6.8Hz), 6.82-7.15(6H, m)

TABLE D-30

Example 52
Synthesis of N-Me-Phe(4-F)-N-Et-Val-N-Me-Tyr(3-tBu)-NH₂

| R₃₁ | R₃₂ | R₃₃ | R₃₄ |
|---|---|---|---|
| Me | Et | Me | H |

Reaction 3

| CompoundI I-b9:g | Compound P2:g | CMPI g | TEA ml | THF ml | Reaction time hr | Column sol. | Product | Amount g |
|---|---|---|---|---|---|---|---|---|
| 1.200 | 1.420 | 1.220 | 1.33 | 7 | 30 | H:EA 1:2 | I-c25 | 0.740 |

TABLE D-30-continued

Example 52
Synthesis of N-Me-Phe(4-F)-N-Et-Val-N-Me-Tyr(3-tBu)-NH$_2$

| $R_{31}$ | $R_{32}$ | $R_{33}$ | $R_{34}$ |
|---|---|---|---|
| Me | Et | Me | H |

Reaction 4a

| Compound I-c25:g | TFA ml | CH$_2$Cl$_2$ ml | Reaction time hr | Column sol. | Amount g | HPLC min |
|---|---|---|---|---|---|---|
| 0.674 | 3.00 | 10 | 2 | MC:M:H 10:1:2 | 0.278 | 20.0 |

EI-MS(M$^+$): 556
$^1$H-NMR(CDCl$_3$): (two rotamers)δ 0.42, 0.78, 0.84 and 0.91(6H, d, J=6.3-6.9Hz), 0.94 and 1.18(3H. t, J=3.6Hz), 1.35 and 1.37(9H, s), 2.20-2.34(1H, m), 2.29(3H, s), 2.62-3.02(4H, m), 2.93 and 3.04(3H, s), 3.17-3.31(2H, m), 3.45-3.72(1H, m), 5.02 and 5.22(1H, d, J=10.7-10.9 Hz), 5.09 and 5.17(1H, t, J=5.8-6.1Hz), 5.69, 6.07 and 6.57(2H, brs), 6.45 and 6.64(1H, d, J=8.0Hz), 6.78-7.14(6H, m)

TABLE D-31

Example 53
Synthesis of N-Et-Phe(4-F)-N-Et-Val-N-Me-Tyr(3-tBu)-NH$_2$

| $R_{31}$ | $R_{32}$ | $R_{33}$ | $R_{34}$ |
|---|---|---|---|
| Et | Et | Me | H |

Reaction 3

| Compound I I-b9:g | Compound P3:g | CMPI g | TEA ml | THF ml | Reaction time hr | Column sol. | Product | Amount g |
|---|---|---|---|---|---|---|---|---|
| 1.020 | 1.640 | 1.220 | 1.33 | 8 | 12 | MC:M:H 20:1:1 | I-c26 | 1.040 |

Reaction 4b

| Compound I-c26:g | Pd-C g | MeOH ml | Reaction time hr | Column sol. | Amount g | HPLC min |
|---|---|---|---|---|---|---|
| 0.934 | 0.093 | 20 | 3 | MC:M:H = 15:1:2 | 0.201 0.103 | 20.7 22.4 |

Compound of which yielded amount was 0.201 g with HPLC retention time of 20.7 min.
EI-MS(M$^+$): 570
$^1$H-NMR(CDCl$_3$): (two rotamers)δ 0.42, 0.79, 0.84 and 0.91(6H, d and m, J=6.3-6.9Hz), 1.02 and 1.11(6H, t, J=3.6Hz), 1.33 and 1.40(3H, s), 2.20-3.36(9H, m), 2.92 and 3.03(3H, s), 3.51-3.75(1H, m), 5.00-5.38(2H, m), 6.02 and 6.58(2H, brs), 6.42-6.62(1H, d, J=8.0Hz), 6.82-7.20(6H, m)
Compound of which yielded amount was 0.103 g with HPLC retention time of 22.4 min.
EI-MS(M$^+$): 570
$^1$H-NMR(CDCl$_3$): (two rotamers)δ 0.13 and 0.79(4H, t, J=3.4 Hz), 0.62 and 0.89(2H, d, J=6.3-6.9Hz), 0.97 and 1.05(6H, t, J=3.6Hz), 1.34 and 1.41(9H, s), 1.92-2.03(1H, m), 2.21-2.60(2H, m), 3.00 and 3.08(3H, s), 2.74-3.25(4H, m), 3.60-3.72(1H, m), 4.62(1H, d, J=8.0Hz), 4.78-4.82(1H, m), 5.18-5.36(2H, m), 6.02(1H, brs), 6.59 and 6.63(lH, d, J=8.0Hz), 6.81-6.98(3H, m), 7.09-7.20(3H, m)

TABLE D-32

Example 54
Synthesis of Phe(4-F)-N-Et-Val-N-Me-Tyr(3-tBu)-NHMe

| $R_{31}$ | $R_{32}$ | $R_{33}$ | $R_{34}$ |
|---|---|---|---|
| H | Et | Me | Me |

Reaction 1

| Compound T5:g | Compound V2:g | CMPI g | TEA ml | THF ml | Reaction time hr | Column sol. | Product | Amount g |
|---|---|---|---|---|---|---|---|---|
| 3.93 | 5.0 | 4.56 | 5.0 | 150 | 12 | EA:H 2:1 | I-a10 | 5.02 |

EI-MS(M$^+$): 525
$^1$H-NMR(CDCl$_3$): δ 0.23-1.08(9H, m), 1.34. 1.37, 1.39(9H, s), 2.10-3.56(10H, m), 4.25-5.33(5H, m), 6.00-7.48(9H, m)

Reaction 2

| Compound I-a10:g | Pd(OH)$_2$ g | MeOH ml | Reaction time min | Column sol. | Product | Amount g |
|---|---|---|---|---|---|---|
| 4.92 | 0.50 | 94 | 40 | CH:M:N 100:10:1 | I-b10 | 3.42 |

$^1$H-NMR(CDCl$_3$): δ 0.35, 0.69, 0.88, 0.95(6H, d, J=6.6-6.9Hz), 0.82, 1.03(3H, t, J=7.1Hz), 1.37(9H, s), 1.66-1.83(1H, m), 1.92(2H, dd, J=13.9, 6.6Hz), 2.76, 2.79(3H, d, J=4.8Hz), 2.89, 2.99(3H, s), 2.92-3.23(2H, m), 4.55, 5.46(1H, dd, J=10.9, 4.0Hz), 5.71, 5.89(1H, brs), 6.13, 8.19(1H, m), 6.55, 6.60(1H, d, J=7.9Hz), 6.78, 6.91(1H, dd, J=7.9, 1.7Hz), 7.00, 7.07(1H, d, J=1.7Hz)

TABLE D-33

Example 54(Continued from Table D-32)
Synthesis of Phe(4-F)-N-Et-Val-N-Me-Tyr(3-tBu)-NHMe Reaction 3

| Compound I-b10:g | Compound P1:g | CMPI g | TEA ml | THF ml | Reaction time hr | Column sol. | Product | Amount mg |
|---|---|---|---|---|---|---|---|---|
| 1.15 | 1.25 | 1.13 | 1.23 | 20 | 13 | EA:H 2:1 | I-c27 | 434 |

Reaction 4a

| Compound T-c27:mg | TFA ml | CH$_2$Cl$_2$ ml | Reaction time hr | Column sol. | Amount mg | HPLC min |
|---|---|---|---|---|---|---|
| 434 | 2 | 2 | 2.5 | EA:EtOH = 10:1 | 86.0 26.8 | 20.6 22.8 |

Compound of which yielded amount was 86.0 mg with HPLC retention time of 20.6 min.
EI-MS(M$^+$): 556
$^1$H-NMR(CDCl$_3$): δ 0.27-1.18(9H, m), 1.35, 1.39(9H, s), 2.15-3.77(12H, m), 2.84, 3.06(3H, s), 4.87-5.27(2H, m), 5.99-7.20(8H, m)
Compound of which yielded amount was 26.8 mg with HPLC retention time of 22.8 min.
EI-MS(M$^+$): 556
$^1$H-NMR(CDCl$_3$): δ 0.16, 0.40. 0.55, 0.84(6H, d, J=6.3-6.9Hz), 0.83, 1.01(3H, t, J=7.1Hz), 1.36, 1.41(9H, s), 2.00-2.21(1H, m), 2.67, 2.76(3H, d, J=4.8Hz), 3.05, 3.09(3H, s), 2.81-3.30(7H, m), 3.68-3.87(1H, m), 3.72, 3.80(1H, dd, J=7.8, 6.1Hz), 4.61, 5.10(1H, d, J=10.7Hz), 4.66, 5.24(1H, dd, J=9.7, 6.4Hz), 6.05-7.20(8H, m)

TABLE D-34

Example 55
Synthesis of N-Me-Phe(4-F)-N-Et-Val-N-Me-Tyr(3-tBu)-NHMe

| $R_{31}$ | $R_{32}$ | $R_{33}$ | $R_{34}$ |
|---|---|---|---|
| Me | Et | Me | Me |

Reaction 3

| Compound I-b10:g | Compound P2:g | CMPI g | TEA ml | THF ml | Reaction time hr | Column sol. | Product | Amount mg |
|---|---|---|---|---|---|---|---|---|
| 1.0 | 1.14 | 0.98 | 1.07 | 17 | 14 | EA:H 2:1 | I-c28 | 322 |

Reaction 4a

| Compound I-c28:mg | TFA ml | $CH_2Cl_2$ ml | Reaction time hr | Column sol. | Amount mg | HPLC min |
|---|---|---|---|---|---|---|
| 322 | 2 | 2 | 2 | EA:EtOH 10:1 | 101 | 21.1 |
|  |  |  |  |  | 38 | 22.6 |

Compound of which yielded amount was 101 mg with HPLC retention time of 21.1 min.
EI-MS($M^+$): 570
$^1$H-NMR(CDCl$_3$): δ 0.41, 0.79, 0.86, 0.90(6H, d, J=6.3-6.9Hz), 0.94, 1.15(3H, t, J=7.3Hz), 1.34, 1.39(9H, s), 2.27, 2.28(3H, s), 2.71, 2.76(3H, d, J=4.8Hz), 2.15-3.78(9H, m), 2.93, 3.08(3H, s), 4.98-5.32(2H, m), 6.03-7.20(8H, m)
Compound of which yielded amount was 38 mg with HPLC retention time of 22.6 min.
EI-MS($M^+$): 570
$^1$H-NMR(CDCl$_3$): δ 0.10, 0.14, 0.63, 0.85(6H, d, J=6.3-6.9Hz), 0.82, 0.95(3H, t, J=7.1Hz), 1.35, 1.40(9H, s), 2.18, 2.54(3H, s), 2.71, 2.75(3H, d, J=4.8Hz), 2.99, 3.08(3H, s), 1.89-3.27(8H, m). 3.46-3.64(1H, m), 4.54, 5.19(1H, d, J=10.6Hz), 4.66, 5.23(1H, t, J=7.3Hz), 6.51, 6.60(1H, d, J=7.9Hz), 6.07-7.20(7H, m)

TABLE D-35

Example 56
Synthesis of N-Et-Phe(4-F)-N-Et-Val-N-Me-Tyr(3-tBu)-NHMe

| $R_{31}$ | $R_{32}$ | $R_{33}$ | $R_{34}$ |
|---|---|---|---|
| Et | Et | Me | Me |

Reaction 3

| Compound I-b10:g | Compound P3:g | CMPI g | TEA ml | THF ml | Reaction time hr | Column sol. | Product | Amount mg |
|---|---|---|---|---|---|---|---|---|
| 1.0 | 1.32 | 0.98 | 1.07 | 17 | 14 | EA:H 2:1 | I-c29 | 576 |

TABLE D-35-continued

Example 56
Synthesis of N-Et-Phe(4-F)-N-Et-Val-N-Me-Tyr(3-tBu)-NHMe

| $R_{31}$ | $R_{32}$ | $R_{33}$ | $R_{34}$ |
|---|---|---|---|
| Et | Et | Me | Me |

Reaction 4b

| Compound I-c29:mg | Pd-C g | MeOH ml | Reaction time hr | Column sol. | Amount mg | HPLC min |
|---|---|---|---|---|---|---|
| 576 | 0.05 | 5 | 3 | EA:EtOH 15:1 | 192 129 | 22.0 23.6 |

Compound of which yielded amount was 192 mg with HPLC retention time of 22.0 min.
EI-MS(M$^+$): 584
$^1$H-NMR(CDCl$_3$): δ 0.41-1.18(12H, m), 1.35, 1.39(9H, s), 2.12-4.13(14H, m), 2.92, 3.08(3H, s), 4.99-5.27(2H, m), 6.00-7.20(8H, m)
Compound of which yielded amount was 129 mg with HPLC retention time of 23.6 min.
EI-MS(M$^+$): 584
$^1$H-NMR(CDCl$_3$): δ 0.12-1.30(12H, m), 1.36, 1.41(9H, s), 1.93-4.16(14H, m), 2.99, 3.07(3H, s), 4.57-5.23(2H, m), 5.40-7.22(8H, m)

TABLE D-36

Example 57
Synthesis of Phe(4-F)-N-Et-Val-N-Et-Tyr(3-tBu)-NH$_2$

| $R_{31}$ | $R_{32}$ | $R_{33}$ | $R_{34}$ |
|---|---|---|---|
| H | Et | Et | H |

Reaction 1

| Compound T7:g | Compound V2:g | CMPI g | TEA ml | THF ml | Reaction time hr | Column sol. | Product | Amount g |
|---|---|---|---|---|---|---|---|---|
| 16.000 | 24.088 | 23.200 | 25.32 | 400.00 | 60 | EA:H:MC 3:2:2 | I-a11 | 16.000 |

Reaction 2

| Compound I-a11:g | Pd(OH)$_2$:g | MeOH ml | Reaction time hr | Column sol. | Product | Amount g |
|---|---|---|---|---|---|---|
| 9.000 | 0.900 | 200.00 | 2 | MC:M:H 15:1:2 | I-b11 | 4.000 |

Reaction 3

| Compound I-b11:g | Compound P1:g | CMPI g | TEA ml | THF ml | Reaction time hr | Column sol. | Product | Amount g |
|---|---|---|---|---|---|---|---|---|
| 1.100 | 1.150 | 1.040 | 1.13 | 10.00 | 72 | EA:H:MC 3:2:2 | I-c30 | 0.700 |

TABLE D-36-continued

Example 57
Synthesis of Phe(4-F)-N-Et-Val-N-Et-Tyr(3-tBu)-NH$_2$

Reaction 4a

| Compound I-c30:g | TFA ml | CH$_2$CL$_2$ ml | Reaction time hr | Column sol. | Amount g | HPLC min |
|---|---|---|---|---|---|---|
| 0.650 | 2.00 | 2.00 | 2 | MC:M:H 15:1:2 | 0.180 | 20.9 |

EI-MS(M$^+$): 542

$^1$H-NMR (CDCl$_3$): (two rotamers) δ 0.51, 0.82, 0.87 and 0.94(6H, d, J=6.6~6.9Hz), 0.82~1.31(6H, m), 1.35 and 3.81(9H, s), 2.21~3.82(9H, m) 4.83~5.30(3H, m), 6.62 and 6.54(1H, d, J=7.9Hz), 6.80~7.21(6H, m)

TABLE D-37

Example 58
Synthesis of N-Me-Phe(4-F)-N-Et-Val-N-Et-Tyr(3-tBu)-NH$_2$

| R$_{31}$ | R$_{32}$ | R$_{33}$ | R$_{34}$ |
|---|---|---|---|
| Me | Et | Et | H |

Reaction 3

| Compound I-b11:g | Compound P2:g | CMPI g | TEA ml | THF ml | Reaction time hr | Column sol. | Product | Amount g |
|---|---|---|---|---|---|---|---|---|
| 1.240 | 1.360 | 1.170 | 1.28 | 10.00 | 72 | EA:H:MC 3:2:2 | I-c31 | 0.300 |

Reaction 4a

| Compound I-c31:g | TFA ml | CH$_2$Cl$_2$ ml | Reaction time hr | Column sol. | Amount g | HPLC min |
|---|---|---|---|---|---|---|
| 0.280 | 2.00 | 2.00 | 2 | MC:M:H 15:1:2 | 0.170 | 21.2 |

EI-MS(M$^+$): 570

$^1$H-NMR (CDCl$_3$): (two rotamers) δ 0.63~1.30(9H, m and d, J=6.3Hz),), 1.34 and 1.39(9H, s), 2.30 (3H, s), 2.22~3.90(9H, m), 4.97~5.33(3H, m), 6.43 and 6.62(1H, d, J=7.92), 6.81~7.19(6H, m)

TABLE D-38

Example 59
Synthesis of N-Et-Phe(4-F)-N-Et-Val-N-Et-Tyr(3-tBu)-NH$_2$

| R$_{31}$ | R$_{32}$ | R$_{33}$ | R$_{34}$ |
|---|---|---|---|
| Et | Et | Et | H |

Reaction 3

| Compound I-b11:g | Compound P3:g | CMPI g | TEA ml | THF ml | Reaction time hr | Column sol. | Product | Amount g |
|---|---|---|---|---|---|---|---|---|
| 1.500 | 1.980 | 1.470 | 1.60 | 10.00 | 72 | EA:H:MC 3:2:2 | I-c32 | 0.700 |

TABLE D-38-continued

Example 59
Synthesis of N-Et-Phe(4-F)-N-Et-Val-N-Et-Tyr(3-tBu)-NH$_2$

Reaction 4b

| Compound I-c32:g | Pd(OH)$_2$:g | MeOH ml | Reaction time hr | Column sol. | Amount g | HPLC min |
|---|---|---|---|---|---|---|
| 0.650 | 0.065 | 10.00 | 2 | MC:M:H 15:1:2 | 0.240 | 20.0 |

EI-MS(M$^+$): 458

$^1$H-NMR (CDCl$_3$): (two rotamers) δ 0.85~1.27(15H, m), 1.37 and 1.39(9H, s), 2.03~3.63(11H, m), 4.50~4.55(1H, m), 5.02~5.34(2H, m), 6.43 and 6.60(1H, d, J=8.24), 6.81~7.19(6H, m)

TABLE D-39

Example 60
Synthesis of Phe(4-F)-N-Et-Val-N-Et-Tyr(3-tBu)-NHMe

| R$_{31}$ | R$_{32}$ | R$_{33}$ | R$_{34}$ |
|---|---|---|---|
| H | Et | Et | Me |

Reaction 1

| Compound T8:g | Compound V2:g | CMPI g | TEA ml | THF ml | Reaction time hr | Column sol. | Product | Amount g |
|---|---|---|---|---|---|---|---|---|
| 10.000 | 15.000 | 14.000 | 14.96 | 357 | 48 | H:EA 2:1 | I-a12 | 5.610 |

Reaction 2

| Compound I-a12:g | Pd-C g | MeOH ml | Reaction time hr | Column sol. | Product | Amount g |
|---|---|---|---|---|---|---|
| 5.500 | 1.000 | 100 | 2 | H:ACT 1:1 | I-b12 | 2.950 |

Reaction 3

| Compound II-b12:g | Compound P1:g | CMPI g | TEA ml | THF ml | Reaction time hr | Column sol. | Product | Amount g |
|---|---|---|---|---|---|---|---|---|
| 0.900 | 0.943 | 0.850 | 0.93 | 6 | 48 | CH:M:N 300:10:1 | I-c33 | 0.750 |

Reaction 4a

| Compound I-c33:g | TFA ml | CH$_2$Cl$_2$ ml | Reaction time hr | Column sol. | Amount g | HPLC min |
|---|---|---|---|---|---|---|
| 0.742 | 4.00 | 6 | 2 | CH:M:N 300:10:1 | 0.210 | 22.0 |

EI-MS(M$^+$): 570

$^1$H-NMR (CDCl$_3$): (two rotamers) δ 0.64 and 0.78~1.20(12H, d and m, J=7.0~7.9Hz), 1.24 and 1.37(9H, s), 2.20~2.40(1H, m), 2.62~3.08(4H, m), 3.19~3.46(3H, m), 3.57~3.89(2H, m), 4.62~5.11 (2H, m), 6.44~6.62(2H, m), 6.79~7.13(5H, m)

TABLE D-40

Example 61
Synthesis of N-Me-Phe(4-F)-N-Et-Val-N-Et-Tyr(3-tBu)-NHMe

| $R_{31}$ | $R_{32}$ | $R_{33}$ | $R_{34}$ |
|---|---|---|---|
| Me | Et | Et | Me |

Reaction 3

| Compound II-b12:g | Compound P2:g | CMPI g | TEA ml | THF ml | Reaction time hr | Column sol. | Product | Amount g |
|---|---|---|---|---|---|---|---|---|
| 0.979 | 1.077 | 0.925 | 1.00 | 24 | 53 | H:EA 2:1 | I-c34 | 0.410 |

Reaction 4a

| Compound I-c34:g | TFA ml | $CH_2Cl_2$ ml | Reaction time hr | Column sol. | Amount g | HPLC min |
|---|---|---|---|---|---|---|
| 0.400 | 4.00 | 4 | 1 | CH:M:N 200:10:1 | 0.034 | 22.4 |

EI-MS($M^+$): 584

$^1$H-NMR (CDCl$_3$): (two rotamers) δ 0.65 and 0.85-1.20(12H, d and m, J=6.8-7.9Hz), 1.34 and 1.39(9H, s), 2.30 and 2.33(3H, s), 2.30-2.48(1H, m), 2.65-3.89(10H, m), 4.90-5.07(2H, m), 5.10-5.23(2H, m), 6.48-6.58(1H, m), 6.63-7.20(6H, m)

TABLE D-41

Example 62
Synthesis of N-Et-Phe(4-F)-N-Et-Val-N-Et-Tyr(3-tBu)-NHMe

| $R_{31}$ | $R_{32}$ | $R_{33}$ | $R_{34}$ |
|---|---|---|---|
| Et | Et | Et | Me |

Reaction 3

| Compound II-b12:g | Compound P3:g | CMPI g | TEA ml | THF ml | Reaction time hr | Column sol. | Product | Amount g |
|---|---|---|---|---|---|---|---|---|
| 1.000 | 1.277 | 0.945 | 1.10 | 6.00 | 48 | MC:M:H 20:1:1 | I-c35 | 0.540 |

Reaction 4b

| Compound I-c35:g | Pd-C g | MeOH ml | Reaction time hr | Column sol. | Amount g | HPLC min |
|---|---|---|---|---|---|---|
| 0.501 | 0.050 | 67 | 2 | MC:M:H 25:1:3 | 0.240 | 23.2 |

EI-MS($M^+$): 598

$^1$H-NMR (CDCl$_3$): (two rotamers) δ 0.64 and 0.84-0.92(6H, d and m, J=7.9Hz), 1.04. 1.05 and 1.13 (6H, t, J=6.3Hz), 1.33 and 1.39(3H, s), 2.21-2.94(6H, m), 3.12-3.80(6H, m), 4.82-5.08(1H, m), 5.13 and 5.20(1H, d, J=9.7Hz), 6.47 and 6.58(1H, d, J=8.8Hz), 6.79-7.19(6H, m)

TABLE D-42

Example 63
Synthesis of Phe(4-F)-N-Me-Val-Tyr(3-tBu)-NHtBu

| $R_{31}$ | $R_{32}$ | $R_{33}$ | $R_{34}$ |
|---|---|---|---|
| H | Me | H | tBu |

Reaction 1

| Compound T18:g | Compound V2:g | CMPI g | TEA ml | THF ml | Reaction time hr | Column sol. | Product | Amount g |
|---|---|---|---|---|---|---|---|---|
| 0.58 | 0.55 | 0.56 | 0.61 | 10 | 2 | EA:H 1:3 | I-a13 | 1.0 |

Reaction 2

| Compound I-a13:g | Pd(OH)$_2$ g | MeOH ml | Reaction time hr | Column sol. | Product | Amount g |
|---|---|---|---|---|---|---|
| 1.0 | 0.16 | 20 | 5 | Not purified | I-b13 | 0.75 |

Reaction 3

| Compound I-b13:g | Compound P1:g | CMPI g | TEA ml | THF ml | Reaction time hr | Column sol. | Product | Amount g |
|---|---|---|---|---|---|---|---|---|
| 0.37 | 0.34 | 0.33 | 0.38 | 4 | 14 | MC:M:N 50:1:0.1 | I-c36 | 0.58 |

Reaction 4a

| Compound I-c36:g | TFA ml | CH$_2$Cl$_2$ ml | Reaction time min | Column sol. | Amount g | HPLC min |
|---|---|---|---|---|---|---|
| 0.49 | 2 | 4 | 30 | MC:M:N 30:1:0.1 | 0.31 | 23.4 |

EI-MS(M$^+$): 570
$^1$H-NMR(CDCl$_3$):δ 0.72(2H, d, J=6.9Hz), 0.82(1H, d, J=6.6Hz), 0.92-0.96(3H, m), 1.19(3H, s), 1.22(6H, s), 1.37(3H, s), 1.38(6H, s), 2.2-2.4(1H, m), 2.5-3.0(32/5H, m), 3.17(3/5H, dd, J=4.9, 13.9Hz), 3.61(3/5H, br), 3.82(2/5H, br), 3.96(3/5H, d, J=10.9Hz), 4.3-4.6(7/5H, m), 5.25(1/3H, s), 5.41(1/3H, br), 5.48(2/3H, s), 6.03(2/3H, br), 6.6-6.8(2H, m), 6.9-7.2(5H, m), 9.00(1H, d, J=7.9Hz)

TABLE D-43

Example 64
Synthesis of Phe(4-F)-N-Me-Val-N-Me-Tyr(3-tBu)-NHCH$_2$SO$_2$CH$_3$

| $R_{31}$ | $R_{32}$ | $R_{33}$ | $R_{34}$ |
|---|---|---|---|
| H | Me | Me | CH$_2$SO$_2$CH$_3$ |

Reaction 1

| Compound T17:g | Compound V1:g | CMPI g | TEA ml | THF ml | Reaction time hr | Column sol. | Product | Amount g |
|---|---|---|---|---|---|---|---|---|
| 0.840 | 0.782 | 0.753 | 0.82 | 10 | 15 | EA:H:MC 3:2:2 | I-a14 | 1.200 |

Reaction 2

| Compound I-a14:g | Pd(OH)$_2$:g | MeOH ml | Reaction time hr | Column sol. | Product | Amount g |
|---|---|---|---|---|---|---|
| 1.100 | 0.150 | 30.00 | 2 | Not purified | I-b14 | 0.850 |

TABLE D-43-continued

Example 64
Synthesis of Phe(4-F)-N-Me-Val-N-Me-Tyr(3-tBu)-NHCH$_2$SO$_2$CH$_3$

| | | | | Reaction 3 | | | | |
|---|---|---|---|---|---|---|---|---|
| Compound II-b14:g | Compound:g | CMPI g | TEA ml | THF ml | Reaction time hr | Column sol. | Product | Amount g |
| 0.850 | 0.710 | 0.572 | 0.62 | 10.00 | 17 | EA:H:MC 1:1:1 | I-c37 | 1.020 |

| | | Reaction 4a | | | | |
|---|---|---|---|---|---|---|
| Compound I-c37:g | Pd(OH)$_2$:g | MeOH ml | Reaction time hr | Column sol. | Amount g | HPLC min |
| 1.020 | 0.150 | 30.00 | 2 | MC:M:H 15:1:2 | 0.530 | 20.2 |

EI-MS(M$^+$): 620
$^1$H-NMR (CDCl$_3$): (two rotamers) δ 0.78(3H, dd, J=6.6, 12.1Hz), 0.91(3H, dd, J=6.6, 11.2Hz), 1.26 and 1.35(9H, s), 2.00(3H, s), 2.55, 2.63, 2.75, 2.84, 2.99 and 3.16(8H, s), 2.21~5.30(11H, m), 6.43 and 6.55(1H, d, J=7.9Hz), 6.76~7.13(6H, m)

Examples of compounds synthesized according to the scheme 2 are shown in Tables D-44 to D-66.

TABLE D-44

Example 65
Synthesis of 2-(2-amino-3-(4-fluorophenyl)propylamino)-N-(2-(3-tert-butyl-4-hydroxyphenyl)-1-carbamoylethyl)-N-methyl-3-methylbutanamide
Structural Formula of Compounds of Example 65-78

| R$_{32}$ | R$_{33}$ | R' |
|---|---|---|
| H | Me | CONH$_2$ |

| | | | | Reaction 1 | | | | |
|---|---|---|---|---|---|---|---|---|
| Compound T4:g | Compound V4:g | CMPI:g | TEA ml | THF ml | Reaction time hr | Column sol. | Product | Amount g |
| 5.78 | 6.97 | 7.08 | 8.05 | 115 | 19 | EA:H 1:1 | I-d1 | 9.50 |

$^1$H-NMR(CDCl$_3$):δ 0.63, 0.74, 0.89 and 0.94(total 6H, d, J=6.6-6.9Hz),
1.36 and 1.39(total 9H,s), 1.90-2.04(1H,m), 2.80-3.38(2H,m), 2.96 and 3.04(total 3H,s),
4.14-4.22(1/2H,m), 4.40-4.50(1/2H,m), 4.60-4.70(1/2H,m), 4.88-5.40(11/2H,m),
5.88(1/2H,brs), 6.49(1/2H,d,J=7.9Hz), 6.58(1/2H,d,J=7.9Hz), 6.87(1H,d,J=7.9Hz),
7.02-7.14(1H,m), 7.30-7.40(5H,m)

| | | Reaction 2 | | |
|---|---|---|---|---|
| Compound I-dl:g | Pd-C g | MeOH ml | Reaction time hr | Crude Compound I-e1 was used in Reaction 3. |
| 4.23 | 0.50 | 100 | 2 | |

TABLE D-45

Example 65(Continued from Table D-44)
Synthesis of 2-(2-amino-3-(4-fluorophenyl)propylamino)-N-(2-(3-tert-butyl-4-hydroxyphenyl)-1-carbamoylethyl)-N-methyl-3-methylbutanamide

| | | | | | Reaction 3 | | | |
|---|---|---|---|---|---|---|---|---|
| Compound I-e1 | Compound P5:g | NaBH$_3$CN g | AcOH ml | MeOH ml | Reaction time hr | Column sol. | Product | Amount g |
| Crude compound of Reaction 2 | 2.37 | 1.16 | 1.01 | 90 | 1 | EA:H 1:1 | I-f1 | 2.08 |

EI-MS(M$^+$): 600
$^1$H-NMR(CDCl$_3$): δ 0.86 and 1.02(total 6H, d, J=6.6-6.9Hz), 1.31, 1.35, 1.37 and 1.43(total 18H, s), 1.56-1.80(3H, m), 2.58-3.20(7H, m), 3.56-3.66(1H, m), 4.51(1H, d, J=8.6Hz), 5.28(1H, brs), 5.58-5.68(1H, m), 5.93(1H, brs), 6.53(1H, d, J=8.2Hz), 6.82-7.22(7H, m)

| | | | Reaction 7 | | | |
|---|---|---|---|---|---|---|
| Compound I-f1:mg | TFA ml | CH$_2$Cl$_2$ ml | Reaction time hr | Column sol. | Amount mg | HPLC min |
| 360 | 3 | 3 | 0.5 | MC:M:N 10:1:0.1 | 275 | 17.8 |

EI-MS(M$^+$): 500
$^1$H-NMR(CDCl$_3$): δ 0.47, 0.67, 0.92 and 0.95(total 6H, d, J=6.3-6.6Hz), 1.38(9H, s), 1.64-1.80(2H, m), 1.97(1H, dd, J=5.3, 11.6Hz), 2.28(1H, dd, J=9.2, 13.5Hz), 2.72(1H, dd, J=4.0, 13.5Hz), 2.80-3.02(3H, m), 2.94(3H, s), 3.18(1H, dd, J=5.8, 14.5Hz), 5.31(1H, brs), 5.55(1H, dd, J=5.9, 10.9Hz), 6.00(1H, brs), 6.59(1H, d, J=8.2Hz), 6.89(1H, dd, J=1.9, 8.2Hz), 6.97(2H, t, J=8.2Hz), 7.11(2H, t, J=8.2Hz), 7.11(1H, d, J=1.9Hz)

TABLE D-46

Example 66
Synthesis of 2-(2-amino-3-(4-fluorophenyl)-N-methylpropylamino)-N-(2-(3-tert-butyl-4-hydroxyphenyl)-1-carbamoylethyl)-N-methyl-3-methylbutanamide

| R$_{32}$ | R$_{33}$ | R' |
|---|---|---|
| Me | Me | CONH$_2$ |

| | | | | | Reaction 4 | | | |
|---|---|---|---|---|---|---|---|---|
| Compound I-f1:mg | HCHO ml | NaBH$_3$CN mg | AcOH ml | MeOH ml | Reaction time hr | Column sol. | Product | Amount mg |
| 530 | 0.38 | 117 | 0.10 | 8 | 0.5 | H:A 1:1 | I-g1 | 532 |

$^1$H-NMR(CDCl$_3$): δ 0.76, 0.78 and 0.94(total 6H, d, J=5.2-6.6Hz), 1.37 and 1.38(total 18H, s), 1.58-1.76(4H, m), 1.94-2.30(2H, m), 2.49 and 2.89(total 3H, m), 2.60-3.22(4H, m), 3.58-3.76(1H, m), 4.38 and 4.62(total 1H, d, J=8.6Hz), 5.22-5.30(1H, m), 5.64-5.72(1H, m), 6.07(1H, brs), 6.52-6.62(1H, m), 6.94-7.12(6H, m)

TABLE D-46-continued

Example 66
Synthesis of 2-(2-amino-3-(4-fluorophenyl)-N-methylpropylamino)-N-(2-(3-tert-butyl-4-hydroxyphenyl)-1-carbamoylethyl)-N-methyl-3-methylbutanamide

| | | | Reaction 7 | | | |
|---|---|---|---|---|---|---|
| Compound I-g1:mg | TFA ml | $CH_2Cl_2$ ml | Reaction time hr | Column sol. | Amount mg | HPLC min |
| 465 | 4 | 4 | 1 | CH:M:N 10:1:0.1 | 280 | 21.5 |

FAB-MS:515 (M+H$^+$)
$^1$H-NMR(CD$_3$OD): δ 0.14, 0.83, 0.89 and 1.01(total 6H, d, J=6.3-6.6Hz), 1.40 and 1.43(total 9H, s), 1.84-2.18(2H, m), 2.10(3H, s), 2.38-2.50(1H, m), 2.60-3.04(3H, m), 2.91 and 3.06(total 3H, s), 3.18-3.30 and 3.58-3.66(total 3H, m), 4.70 and 5.61(total 1H, dd, J=4.3-5.0, 10.9Hz), 6.66 and 6.69(total 1H, d, J=7.9Hz), 6.92 and 6.96(total 1H, dd, J=1.3, 7.9Hz), 7.04-7.34(5H, m)

TABLE D-47

Example 67
Synthesis of 2-(N-acetyl-2-amino-3-(4-fluorophenyl)propylamino)-N-(2-(3-tert-butyl-4-hydroxyphenyl)-1-carbamoylethyl)-N-methyl-3-methylbutanamide

| $R_{32}$ | $R_{33}$ | R' |
|---|---|---|
| Ac | Me | $CONH_2$ |

| | | | | Reaction 5 | | | |
|---|---|---|---|---|---|---|---|
| Compound I-f1:mg | Ac$_2$O ml | DMAP mg | pyridine ml | Reaction time hr | Column sol. | Product | Amount mg |
| 451 | 3 | 42.9 | 5 | 15 | EA:H 1:1 | I-h1 | 306 |

$^1$H-NMR(CDCl$_3$): δ 0.13, 0.60 and 0.87(total 6H, d, J=6.3-6.6Hz), 1.23, 1.26, 1.32 and 1.36(total 18H, s), 2.06-2.30(3H, m), 2.15, 2.16 and 2.31(total 6H, s), 2.48(1H, dd, J=7.9, 13.2Hz), 2.74-2.94(2H, m), 3.05 and 3.07(total 3H, s), 3.28-3.42(2H, m), 3.88-4.00(1H, m), 4.88(1H, d, J=8.6Hz), 5.08-5.42(3H, m), 6.31(1H, brs), 6.92(2H, d, J=8.2Hz), 6.98(2H, d, J=8.2Hz), 7.08-7.26(3H, m)

| | | | Reaction 6 | | |
|---|---|---|---|---|---|
| Compound I-h1:mg | NaOH ml | MeOH ml | Reaction time hr | Column sol. | Product | Amount mg |
| 412 | 1 | 4 | 1 | EA:H 1:1 | I-i1 | 341 |

$^1$H-NMR(CDCl$_3$): δ 0.05, 0.11, 0.52 and 0.61(total 6H, d, J=6.3-6.9Hz), 1.36, 1.37 and 1.42(total 18H, s), 1.70 and 2.05(total 3H, s), 2.00-2.42(2H, m), 2.80-3.40(5H, m), 3.04 and 3.07(total 3H, s), 3.64-3.88(1H, m), 4.76-5.32(5H, m), 5.92(1H, brs), 6.56(1H, d, J=8.2Hz), 6.88-7.30(6H, m)

TABLE D-48

Example 67(Continued from Table D-47)
Synthesis of 2-(N-acetyl-2-amino-3-(4-fluorophenyl)propylamino)-N-(2-(3-tert-butyl-4-hydroxyphenyl)-1-carbamoylethyl)-N-methyl-3-methylbutanamide Reaction 7

| Compound I-i1 mg | TFA ml | $CH_2Cl_2$ ml | Reaction time hr | Column sol. | Amount mg | HPLC min |
|---|---|---|---|---|---|---|
| 330 | 3 | 2 | 0.5 | CH:M 10:1 | 210 | 23.4 |

$^1$H-NMR(CDCl$_3$): δ 0.69, 0.81 and 0.86(total 6H, d, J=6.3-7.0Hz), 1.38(9H, s), 1.78-1.86(1H, m), 1.85(3H, s), 2.5-2.94(3H, m), 3.05 and 3.07(total 3H, s), 3.04-3.30(1H, m), 3.50-3.84(2H, m), 4.10 and 4.40(total 1H, brs), 4.63 and 4.66(total 1H, brs), 5.06(1H, d, J=10.2Hz), 5.16-5.32(2H, m), 6.54 and 6.65(total 1H, d, J=7.9-8.2Hz), 6.80 and 6.93(total 1H, dd, J=1.5-2.0, 7.9-8.2Hz), 6.98-7.14(5H, m)

TABLE D-49

Example 68
Synthesis of 2-(2-amino-3-(4-fluorophenyl)propylainino)-N-(2-(3-tert-butyl-4-hydroxyphenyl)-1-carbamoylethyl)-N-ethyl-3-methylbutanamide

| $R_{32}$ | $R_{33}$ | R' |
|---|---|---|
| H | Et | $CONH_2$ |

Reaction 1

| Compound T7:g | Compound V4:g | CMPI g | TEA ml | THF ml | Reaction time hr | Column sol. | Product | Amount g |
|---|---|---|---|---|---|---|---|---|
| 1.01 | 1.25 | 1.27 | 1.23 | 10 | 19 | EA:H 1:1 | I-d2 | 0.75 |

$^1$H-NMR(CDCl$_3$): δ 0.72, 0.87, 0.92 and 0.95(total 6H, d, J=6.6-6.9Hz),
1.14-1.30(3H, m), 1.37 and 1.38(total 9H, s),
1.86-1.98(1H, m), 2.76(1/4H, dd, J=6.6, 13.8Hz),
3.12(3/4H, dd, J=7.9, 13.9Hz), 3.24-3.56(3H, m), 4.20 and
4.33(total 1H, dd, J=6.6-8.6, 8.9Hz), 4.60 and 4.71(total
1H, t, J=7.2-7.6Hz), 5.02-5.28(7/2H, m), 5.36(1H, d, J=8.6Hz),
6.26(1/2H, brs), 6.54 and 6.58(total 1H, d, J=7.9-8.2Hz), 6.84-6.92(total
1H, m), 7.08(1H, d, J=1.7Hz), 7.20-7.40(5H, m)

Reaction 2

| Compound I-d2:g | Pd-C g | MeOH ml | Reaction time hr | Crude Compound I-e2 was used in Reaction 3. |
|---|---|---|---|---|
| 0.62 | 0.10 | 12 | 1 | |

TABLE D-50

Example 68(Continued from Table D-49)
Synthesis of 2-(2-amino-3-(4-fluorophenyl)propylamino)-N-(2-(3-tert-butyl-4-hydroxyphenyl)-1-carbamoylethyl)-N-ethyl-3-methylbutanamide

Reaction 3

| Compound I-e2 | Compound P5:mg | NaBH$_3$CN mg | AcOH ml | MeOH ml | Reaction time hr | Column sol. | Product | Amount mg |
|---|---|---|---|---|---|---|---|---|
| Crude compound of Reaction 2 | 400 | 124 | 0.4 | 10 | 1 | EA:H 1:1 | I-f2 | 298 |

$^1$H-NMR(CDCl$_3$): δ 0.65, 0.87, 0.90 and 1.02(total 6H, d, J=6.2-6.9Hz),
1.12 and 1.24(total 3H, t, J=6.9-7.3Hz), 1.35, 1.37,
1.38 and 1.41(total 18H, s), 1.50-1.82(3H, m), 2.58-3.64(7H, m),
4.28-4.54(1H, m), 5.04-5.36(2H, m), 6.20-6.32 and 6.52-6.64(2H, m),
6.80-7.12(6H, m)

Reaction 7

| Compound I-f2 mg | TFA ml | CH$_2$Cl$_2$ ml | Reaction time hr | Column sol. | Amount mg | HPLC min |
|---|---|---|---|---|---|---|
| 331 | 2 | 3 | 0.5 | MC:M 20:1 | 234 | 19.7 |

EI-MS(M$^+$):514
$^1$H-NMR(CDCl$_3$): δ 0.56, 0.75, 0.94 and 0.96(total 6H, d, J=6.6-6.9Hz),
1.17 and 1.26(total 3H, t, J=6.9-7.3Hz), 1.38(9H, s),
1.50-1.80(2H, m), 1.98(1H, dd, J=8.6, 11.2Hz), 2.20-2.50(2H, m),
2.71(1H, dd, J=3.8, 13.2Hz), 2.88-3.50(5H, m), 4.54-4.62 and 4.94-5.02(1H, m),
5.21 and 6.40(total 1H, brs), 6.58(1H, d, J=8.2Hz),
6.82-7.18(6H, m)

TABLE D-51

Example 69
Synthesis of 2-(2-amino-3-(4-fluorophenyl)propylamino)-N-(2-(3-tert-butyl-4-hydroxyphenyl)-1-hydroxymethylethyl)-3-methylbutanamide

| $R_{32}$ | $R_{33}$ | R' |
|---|---|---|
| H | H | $CH_2OH$ |

Reaction 1

| Compound T19:g | Compound V4:g | CMPI g | TEA ml | THF ml | Reaction time hr | Column sol. | Product | Amount g |
|---|---|---|---|---|---|---|---|---|
| 1.2 | 1.62 | 1.65 | 1.8 | 50 | 1.5 | EA:H 1:1 | I-d3 | 2.2 |

$^1$H-NMR(CDCl$_3$): δ 0.81(3H, brd, J=6.3Hz), 0.91(3H, d, J=6.6Hz),
1.38(9H, s), 2.0-2.2(1H, m), 2.49(1H, brs), 2.6-2.9(2H, m), 3.5-3.7(2H, m),
3.92(1H, dd, J=5., 7.9Hz), 5.11(2H, s), 5.1-5.3(2H, m),
6.09(1H, brd, J=7.6Hz), 6.57(1H, d, J=7.9Hz),
6.86(1H, dd, J=1.3, 7.9Hz), 7.04(1H, d, J=1.3Hz), 7.36(5H, s)

Reaction 2

| Compound I-d3 g | Pd-C g | MeOH ml | Reaction time hr | Column sol. | Product | Amount g |
|---|---|---|---|---|---|---|
| 2.2 | 0.2 | 48 | 12 | Not purified | I-e3 | 1.6 |

$^1$H-NMR(CDCl$_3$): δ 0.57(3H, d, J=6.6Hz), 0.89(3H, d, J=6.9Hz),
1.38(9H, s), 2.1-2.3(1H, m), 2.68(1H, dd, J=8.9, 13.9Hz),
2.86(1H, dd, J=6.3, 13.9Hz), 3.23(1H, d, J=3.6Hz),
3.62(1H, dd, J=6.3, 10.9Hz), 3.75(1H, dd, J=3.6, 10.9Hz), 4.0-4.2(1H, m),
5.45(1H, brs), 6.61(1H, d, J=7.9Hz),
6.90(1H, dd, J=2.0, 7.9Hz), 7.05(1H, d, J=2.0Hz),
7.56(1H, brd, J=6.6Hz)

TABLE D-52

Example 69 (Continued from Table D-51)
Synthesis of 2-(2-amino-3-(4-fluorophenyl)propylamino)-N-(2-(3-tert-butyl-4-hydroxyphenyl)-1-hydroxymethylethyl)-3-methylbutanamide

Reaction 3

| Compound I-e3:g | Compound P5:g | NaBH$_3$CN g | AcOH ml | MeOH ml | Reaction time hr | Column sol. | Product | Amount g |
|---|---|---|---|---|---|---|---|---|
| 0.8 | 0.8 | 0.33 | 0.28 | 25 | 1.5 | CH:M:N 300:10:1 | I-f3 | 1.05 |

$^1$H-NMR(CDCl$_3$): δ 0.69(3H, brd, J=5.9Hz), 0.81(3H, d, J=6.9Hz), 1.38(9H, s), 1.42(9H, s),
1.8-2.0(1H, m), 2.35-3.0(6H, m), 3.0-3.2(1H, m), 3.5-3.9(3H, m), 4.1-4.3(1H, m), 4.5-4.7(1H, m),
5.47(1H, brs), 6.62(1H, d, J=7.9Hz), 6.9-7.2(6H, m), 7.36(1H, brd, J=7.6Hz)

Reaction 7

| Compound I-f3:g | TFA ml | CH$_2$Cl$_2$ ml | Reaction time hr | Column sol. | Amount g | HPLC min |
|---|---|---|---|---|---|---|
| 0.3 | 0.5 | 5 | 10 | CH:M:N 200:10:1 | 0.21 | 17.7 |

$^1$H-NMR(CDCl$_3$): 0.72(3H, d, J=6.9Hz), 0.83(3H, d, J=6.9Hz), 1.38(9H, s), 1.8-2.0(1H, m),
2.4-2.9(7H, m), 2.9-3.1(1H, m), 3.50(1H, dd, J=4.6, 11.6Hz), 3.66(1H, dd, J=3.0, 11.6Hz),
4.1-4.3(1H, m), 6.60(1H, d, J=7.9Hz), 6.92(1H, dd, J=1.7, 7.9Hz), 7.0-7.2(6H, m),
7.35(1H, brd, J=8.3Hz)

TABLE D-53

Example 70
Synthesis of 2-(2-amino-3-(4-fluorophenyl)-N-methylpropylamino)-N-(2-(3-tert-butyl-4-hydroxyphenyl)-1-hydroxymethylethyl)-3-methylbutanamide

| $R_{32}$ | $R_{33}$ | R' |
|---|---|---|
| Me | H | $CH_2OH$ |

Reaction 4

| Compound I-f3:g | HCHO ml | NaBH$_3$CN g | AcOH ml | MeOH ml | Reaction time hr | Column sol. | Product | Amount g |
|---|---|---|---|---|---|---|---|---|
| 0.34 | 0.23 | 0.077 | 0.07 | 6 | 1.5 | CH:M:N 300:10:1 | I-g3 | 0.33 |

$^1$H-NMR(CDCl$_3$): δ 0.82(3H, d, J=6.3Hz), 0.94(3H, d, J=6.6Hz), 1.37(9H, s), 1.41(9H, s), 2.06(3H, s), 2.1-2.6(4H, m), 2.70(1H, dd, J=8.9, 14.2Hz), 2.8-3.0(2H, m), 3.5-3.8(3H, m), 4.2-4.5(2H, m), 5.62(1H, brs), 6.4-6.6(1H, m), 6.62(1H, d, J=7.9Hz), 6.9-7.2(6H, m)

Reaction 7

| Compound I-g3:g | TFA ml | CH$_2$Cl$_2$ ml | Reaction time hr | Column sol. | Amount g | HPLC min |
|---|---|---|---|---|---|---|
| 0.3 | 0.5 | 5 | 10 | CH:M:N 200:10:1 | 0.17 | 20.1 |

EI-MS(M$^+$): 487
$^1$H-NMR(CDCl$_3$): 0.79(3H, d, J=6.6Hz), 0.94(3H, d, J=6.6Hz), 1.39(9H, s), 1.9-2.2(1H, m), 2.22(3H, s), 2.2-2.4(3H, m), 2.51(1H, d, J=8.9Hz), 2.6-2.8(2H, m), 2.87(1H, dd, J=6.6, 14.2Hz), 3.0-3.2(1H, m), 3.57(1H, dd, J=5.3, 10.9Hz), 3.72(1H, dd, J=3.6, 10.9Hz), 4.1-4.3(1H, m), 6.19(1H, brd, J=7.3Hz), 6.63(1H, d, J=7.9Hz), 6.89(1H, dd, J=1.7, 7.9Hz), 6.98(2H, t, J=8.6Hz), 7.0-7.2(3H, m)

TABLE D-54

Example 71
Synthesis of 2-(2-amino-3-(4-fluorophenyl)propylamino)-N-(2-(3-tert-butyl-4-hydroxyphenyl)-1-methylethyl)-N-methyl-3-methylbutanamide

| $R_{32}$ | $R_{33}$ | R' |
|---|---|---|
| H | Me | Me |

Reaction 1

| Compound T20:g | Compound V4:g | CMPI g | TEA ml | THF ml | Reaction time hr | Column sol. | Product | Amount g |
|---|---|---|---|---|---|---|---|---|
| 1.62 | 2.22 | 2.25 | 2.46 | 36 | 16 | EA:H 1:1 | I-d4 | 2.74 |

$^1$H-NMR(CDCl$_3$): δ 0.67, 0.72, 0.89 and 0.95(total 6H, d, J=6.6-6.9Hz), 1.08 and 1.20(total 3H, d, J=6.6-6.9Hz), 1.37 and 1.39(total 9H, s), 1.88-2.02(1H, m), 2.60-2.90(2H, m), 2.89(3H, d, J=3.3Hz), 4.30-4.46(1H, m), 4.90-5.00(1H, m), 5.07(2H, s), 6.48 and 6.59(total 1H, d, J=7.9Hz), 6.78-6.88(1H, m), 7.00-7.08(1H, m), 7.30-7.40(5H, m)

Reaction 2

| Compound I-d4:g | Pd—C g | MeOH ml | Reaction time hr | Column sol. | Product | Amount g |
|---|---|---|---|---|---|---|
| 2.68 | 0.25 | 50 | 18 | MC:M 20:1 | I-e4 | 1.35 |

$^1$H-NMR(CDCl$_3$): δ 0.68, 0.85, 0.95 and 0.99(total 6H, d, J=6.6-6.9Hz), 1.11 and 1.24(total 3H, d, J=6.6Hz), 1.88-2.04(1H, m), 2.58-2.70(2H, m), 2.83 and 2.91(total 3H, s), 3.56-3.64(1H, m), 3.95 and 4.99(total 1H, ddd, J=6.6, 6.9, 7.6Hz), 6.62 and 6.67(total 1H, d, J=7.9Hz), 6.77 and 6.88(total 1H, dd, J=1.7, 7.9Hz), 6.98 and 7.02(total 1H, d, J=1.7Hz)

TABLE D-55

Example 71 (Continued from Table D-54)
Synthesis of 2-(2-amino-3-(4-fluorophenyl)propylamino)-N-(2-(3-tert-butyl-4-hydroxyphenyl)-1-methylethyl)-N-methyl-3-methylbutanamide

Reaction 3

| Compound I-e4:g | Compound P5:g | NaBH$_3$CN mg | AcOH ml | MeOH ml | Reaction time hr | Column. sol | Product | Amount g |
|---|---|---|---|---|---|---|---|---|
| 1.26 | 1.58 | 521 | 0.453 | 40 | 1 | EA:H 1:4 | I-f4 | 1.52 |

$^1$H-NMR(CDCl$_3$): δ 0.74, 0.85 and 0.99(total 6H, d, J=6.6-6.9Hz), 1.16(3H, d, J=6.9Hz), 1.30, 1.41 and 1.44(total 18H, s), 1.50-1.70(3H, m), 2.36-2.90(7H, m), 3.52-3.68(1H, m), 4.54-4.64(1H, m), 5.22-5.38(1H, m), 6.51 and 6.60(total 1H, d, J=7.9Hz), 6.80-7.20(6H, m)

Reaction 7

| Compound I-f4:mg | TFA ml | CH$_2$Cl$_2$ ml | Reaction time hr | Column. sol | Amount mg | HPLC min |
|---|---|---|---|---|---|---|
| 330 | 2 | 3 | 0.5 | CH:M:N 10:1:0.1 | 224 | 20.8 |

EI-MS(M$^+$): 471
$^1$H-NMR(CDCl$_3$): δ 0.80, 0.91 and 0.92(total 6H, d, J=6.6Hz), 1.15(3H, d, J=6.9Hz), 1.38 and 1.41(total 9H, s), 1.64-2.04(4H, m), 2.28-3.14(5H, m), 2.79 and 2.92(total 3H, s), 3.90-4.02 and 5.10-5.24(total 1H, m), 6.62 and 6.65(total 1H, d, J=7.4-7.6Hz), 6.74-7.20(6H, m)

TABLE D-56

Example 72
Synthesis of 2-(2-amino-3-(4-fluorophenyl)-N-methylpropylamino)-N-(2-(3-tert-butyl-4-hydroxyphenyl)-1-methylethyl)-N-methyl-3-methylbutanamide

| R$_{32}$ | R$_{33}$ | R' |
|---|---|---|
| Me | Me | Me |

Reaction 4

| Compound I-f4:g | HCHO ml | NaBH$_3$CN mg | AcOH ml | MeOH ml | Reaction time hr | Column sol. | Product | Amount mg |
|---|---|---|---|---|---|---|---|---|
| 520 | 0.39 | 120 | 0.105 | 9 | 0.5 | H:EA 2:1 | I-g4 | 404 |

$^1$H-NMR(CDCl$_3$): δ 0.28, 0.74, 0.81 and 0.91(total 6H, d, J=6.3-6.6Hz), 1.17 and 1.21(total 3H, d, J=6.6-6.9Hz), 1.37 and 1.39(total 18H, s), 1.50-1.60(1H, m), 1.58(3H, s), 1.80-2.52(4H, m), 2.60-3.14(3H, m), 2.71(3H, s), 3.62-3.78(1H, m), 4.42-4.54(1H, m), 5.32-5.44(1H, m), 6.50-7.12(8H, m)

Reaction 7

| Compound I-g4:mg | TFA ml | CH$_2$Cl$_2$ ml | Reaction time hr | Column sol. | Amount mg | HPLC min |
|---|---|---|---|---|---|---|
| 386 | 2 | 4 | 0.5 | CH:M 10:1 | 272 | 24.5 |

FAB-MS: 486(M+H$^+$)
$^1$H-NMR(CDCl$_3$): δ 0.44, 0.79, 0.93 and 0.96(total 6H, d, J=6.6-6.9Hz), 1.13 and 1.20(total 3H, d, J=6.6-6.9Hz), 1.39 and 1.41(total 9H, s), 1.50-1.98(3H, m), 2.04-2.18(1H, m), 2.13 and 2.30(total 3H, s), 2.32-3.10(5H, m), 2.80 and 2.86(total 3H, s), 4.18-4.28 and 5.24-5.36(total 1H, m), 6.57 and 6.61(total 1H, d, J=7.9Hz), 6.72-7.18(6H, m)

TABLE D-57

Example 73
Synthesis of 2-(N-acetyl-2-amino-3-(4-fluorophenyl)propylamino)-N-(2-(3-tert-butyl-4-hydroxyphenyl)-1-methylethyl)-N-methyl-3-methylbutanamide

| $R_{32}$ | $R_{33}$ | R' |
|---|---|---|
| Ac | Me | Me |

Reaction 5

| Compound I-f4:mg | Ac$_2$O ml | DMAP mg | pyridine ml | Reaction time hr | Column sol. | Product | Amount mg |
|---|---|---|---|---|---|---|---|
| 735 | 4 | 158 | 6 | 16.5 | EA:H 1:2 | I-h4 | 489 |

$^1$H-NMR(CDCl$_3$): δ 0.13, 0.54, 0.58 and 0.86(total 6H, d, J=6.3-6.6Hz), 1.13 and 1.15(total 3H, d, J=6.3Hz), 1.30, 1.33, 1.36 and 1.42(total 18H, s), 1.69, 2.08, 2.13 and 2.31(total 6H, s), 2.02-2.84(5H, m), 2.91 and 2.96(total 3H, s), 3.14-3.40(2H, m), 3.82-4.04(1H, m), 4.70-5.28(2H, m), 6.88-7.30(7H, m)

Reaction 6

| Compound I-h4:mg | NaOH ml | MeOH ml | Reaction time hr | Column sol. | Product | Amount mg |
|---|---|---|---|---|---|---|
| 470 | 1 | 6 | 1 | Not purified | I-i4 | 440 |

$^1$H-NMR(CDCl$_3$): δ 0.11, 0.12, 0.51 and 0.64(total 6H, d, J=5.9-6.6Hz), 1.09 and 1.13(total 3H, d, J=6.3-6.6Hz), 1.37, 1.38, 1.40 and 1.43(total 18H, s), 1.66 and 2.03(total 3H, s), 2.00-2.44(3H, m), 2.62-2.72(2H, m), 2.68 and 2.92(total 3H, s), 2.88-3.40(2H, m), 3.72-3.88(1H, m), 4.52-5.32(2H, m), 6.52-7.34(7H, m)

TABLE D-58

Example 73 (Continued from Table D-57)
Synthesis of 2-(N-acetyl-2-amino-3-(4-fluorophenyl)propylamino)-N-(2-(3-tert-butyl-4-hydroxyphenyl)-1-methylethyl)-N-methyl-3-methylbutanamide

Reaction 7

| Compound I-i4 mg | TFA ml | CH$_2$Cl$_2$ ml | Reaction time hr | Column sol. | Amount mg | HPLC min |
|---|---|---|---|---|---|---|
| 351 | 2 | 2 | 0.5 | MC:M:H 20:1:1 | 233 | 27.7 |

$^1$H-NMR(CDCl$_3$): δ 0.27, 0.69, 0.83 and 0.87(total 6H, d, J=6.3-6.9Hz), 1.11(3H, d, J=6.6Hz), 1.39 and 1.40(total 9H, s), 1.78 and 1.83(total 3H, s), 1.80-2.04(1H, m), 2.50-2.74(4H, m), 2.82 and 2.93(total 3H, s), 3.28-3.64(2H, m), 4.00-4.24(1H, m), 4.62 and 4.74(total 1H, s), 4.64-5.10(1H, m), 4.97 and 5.13(total 1H, d, J=10.6-10.9Hz), 6.60-7.18(7H, m)

TABLE D-59

Example 74
Synthesis of 2-(2-amino-3-(4-fluorophenyl)propylamino)-N-(2-(3-tert-butyl-4-hydroxyphenyl)-1-methylethyl)-3-methylbutanamide

| $R_{32}$ | $R_{33}$ | R' |
|---|---|---|
| H | H | Me |

Reaction 1

| Compound T21:g | Compound V4:g | CMPI g | TEA ml | THF ml | Reaction time hr | Column. sol | Product | Amount g |
|---|---|---|---|---|---|---|---|---|
| 3.000 | 4.350 | 4.400 | 6.00 | 80 | 5 | H:EA:MC 5:1:1 | I-d5 | 4.000 |

TABLE D-59-continued

Example 74
Synthesis of 2-(2-amino-3-(4-fluorophenyl)propylamino)-N-(2-(3-tert-butyl-4-hydroxyphenyl)-1-methylethyl)-3-methylbutanamide

Reaction 2

| Compound I-d5:g | Pd(OH)$_2$: g | MeOH ml | Reaction time hr | Column. sol | Product | Amount g |
|---|---|---|---|---|---|---|
| 4.000 | 0.400 | 100 | 1 | MC:Me:H 10:1:1 | I-e5 | 1.200 and 0.500 (diastereomers) |

Reaction 3

| Compound I-e5:g | Compound P5:g | NaBH$_3$CN g | AcOH ml | MeOH ml | Reaction time hr | Column. sol | Product | Amount g |
|---|---|---|---|---|---|---|---|---|
| 1.200 | 1.100 | 0.490 | 0.30 | 30 | 2 | H:EA:MC 3:2:2 | I-f5 | 0.730 |
| 0.480 | 0.628 | 0.207 | 0.3 | 10 | 2 | H:EA 1:1 |  | 0.620 |

TABLE D-60

Example 74 (Continued from Table D-59)
Synthesis of 2-(2-amino-3-(4-fluorophenyl)propylamino)-N-(2-(3-tert-butyl-4-hydroxyphenyl)-1-methylethyl)-3-methylbutanamide

Reaction 7

| Compound I-f5:g | TFA ml | CH$_2$Cl$_2$ ml | Reaction time hr | Column. sol | Amount g | HPLC min |
|---|---|---|---|---|---|---|
| 0.500 | 2.00 | 2 | 1 | MC:M:H 10:1:1 | 0.320 | 20.7 |
| 0.113 | 1.00 | 2 | 1 | CH:M:N 300:10:1 | 0.063 | 20.4 |

Compound of which yielded amount was 0.320 g with HPLC retention time of 20.7 min.
EI-MS(M$^+$): 457

$^1$H-NMR(CDCl$_3$): δ 0.73(3H, d, J=6.9Hz), 0.84(3H, d, J=6.9Hz), 1.08(3H, d, J=6.3Hz), 1.37(9H, s), 1.81~2.00(1H, m), 2.28-2.80(9H, m), 2.90-3.00(1H, m), 4.21~4.38(1H, m), 6.68(1H, d, J=8.2Hz), 6.83~7.18(6H, m)
Compound of which yielded amount was 0.063 g with HPLC retention time of 20.4 min.
EI-MS(M$^+$): 457
$^1$H-NMR(CDCl$_3$): δ 0.88 and 0.92(6H, d, J=6.9Hz), 1.14(3H, d, J=6.6Hz), 1.39(9H, s), 2.00-2.10(1H, m), 2.18-2.44(3H, m), 2.84-2.96(4H, m), 3.63-3.75(1H, m), 4.22-4.31(1H, m), 6.60(1H, d, J=6.8Hz), 6.86-7.26(6H, m)

TABLE D-61

Example 75
Synthesis of 2-((2-amino-3-(4-fluorophenyl)propyl)-N-methylamino)-N-(2-(3-tert-butyl-4-hydroxyphenyl)-1-methylethyl)-3-methylbutanamide

| R$_{32}$ | R$_{33}$ | R' |
|---|---|---|
| Me | H | Me |

Reaction 4

| Compound I-f5:g | HCHO ml | NaBH$_3$CN g | AcOH ml | MeOH ml | Reaction time hr | Column. sol | Product | Amount g |
|---|---|---|---|---|---|---|---|---|
| 0.400 | 0.32 | 0.093 | 0.30 | 10 | 2 | H:EA:MC 3:1:1 | I-g5 | 0.300 |
| 0.500 | 0.380 | 0.118 | 0.10 | 9 | 2 | H:EA:MC 2:1:1 |  | 0.320 |

TABLE D-61-continued

Example 75
Synthesis of 2-((2-amino-3-(4-fluorophenyl)propyl)-
N-methylamino)-N-(2-(3-tert-butyl-4-hydroxyphenyl)-1-methylethyl)-3-methylbutanamide Reaction 7

| Compound I-g5:g | TFA ml | CH$_2$Cl$_2$ ml | Reaction time hr | Column. sol | Amount g | HPLC min |
|---|---|---|---|---|---|---|
| 0.240 | 1.00 | 1 | 1 | MC:M:H 10:1:1 | 0.140 | 23.0 |
| 0.320 | 2:00 | 4 | 1 | CH:M:N 300:10:1 | 0.226 | 22.5 |

Compound of which yielded amount was 0.140 g with HPLC retention time of 23.0 min.
EI-MS(M$^+$+1): 472
$^1$H-NMR(CDCl$_3$): δ 0.82(3H, d, J=6.6Hz), 0.93(3H, d, J=6.6Hz), 1.29(3H, d, J=6.3Hz), 1.38(9H, s), 2.03-2.80(11H, m), 2.20(3H, s), 3.00-3.14(1H, m), 4.33~4.40(1H, m), 5.64(1H, d, J=7.7Hz), 6.68(1H, d, J=7.9Hz), 6.87(1H, d, J=7.9Hz), 6.95~7.18(5H, m)
Compound of which yielded amount was 0.226 g with HPLC retention time of 22.5 min.
EI-MS(M$^+$): 471
$^1$H-NMR(CDCl$_3$): δ 0.68 and 0.95(6H, d, J=6.6Hz), 1.15(3H, d, J=6.6Hz), 1.37(9H, s), 2.01-2.17(1H, m), 2.21(3H, s), 2.32-2.49(4H, m), 2.64-2.72(3H, m), 3.08-3.10(1H, m), 4.22-4.32(1H, q, J=2.5Hz), 5.60(1H, d, J=6.8Hz), 6.65 and 6.84(2H, d, J=7.9Hz), 6.94-7.00(3H, dd, J=6.3, 11.2Hz), 7.13-7.18(2H, m)

TABLE D-62

Example 76
Synthesis of 2-(N-acetyl-2-amino-3-(4-fluorophenyl)propylamino)-N-(2-(3-tert-butyl-4-hydroxyphenyl)-1-methylethyl)-3-methylbutanamide

| R$_{32}$ | R$_{33}$ | R' |
|---|---|---|
| Ac | H | Me |

Reaction 5

| Compound I-f5:g | Ac$_2$O ml | DMAP ml | pyridine ml | Reaction time hr | Column. sol | Product | Amount g |
|---|---|---|---|---|---|---|---|
| 0.630 | 3.00 | 0.21 | 4.50 | 16 | H:EA:MC 3:2:2 | I-h5 | 0.560 |

Reaction 6

| Compound I-h5:g | NaOH ml | MeOH ml | Reaction time hr | Column. sol | Product | Amount g |
|---|---|---|---|---|---|---|
| 0.540 | 2.00 | 4.00 | 1 | Not purified | I-i5 | 0.430 |

Reaction 7

| Compound I-i5:g | TFA ml | CH$_2$Cl$_2$ ml | Reaction time hr | Column. sol | Amount g | HPLC min |
|---|---|---|---|---|---|---|
| 0.430 | 2.00 | 2.00 | 1 | MC:M:H 10:1:1 | 0.185 | 22.5 |

EI-MS(M$^+$+1): 500
$^1$H-NMR(CDCl$_3$): δ 0.70(3H, d, J=5.6Hz), 0.84(3H, d, J=6.6Hz), 1.05(3H, d, J=6.6Hz), 1.37(9H, s), 1.78-1.96(2H, m), 1.90(3H, s), 2.43-2.74(4H, m), 3.07-3.32(2H, m), 3.46-3.56(1H, m), 3.59(1H, d, J=14.5Hz), 4.10-4.72(3H, m), 4.71(2H, s), 6.18-6.22(2H, br), 6.63-6.78(2H, m), 6.95-7.18(5H, m)

TABLE D-63

Example 77
Synthesis of 2-((2-amino-3-(4-fluorophenyl)propyl)-
N-methylamino)-N-(2-(3-tert-butyl-4-hydroxyphenyl)-1-
hydroxymethylethyl)-N,3-dimethylbutanamide

| $R_{32}$ | $R_{33}$ | R' |
|---|---|---|
| Me | Me | $CH_2OH$ |

Reaction 1

| Compound T23:g | Compound V4:g | CMPI g | TEA ml | THF ml | Reaction time hr | Column. sol | Product | Amount g |
|---|---|---|---|---|---|---|---|---|
| 0.928 | 1.470 | 1.497 | 1.64 | 39 | 15 | H:EA:M 2:3:1 | I-d6 | 1.170 |

Reaction 2

| Compound I-d6:g | Pd—C g | MeOH ml | Reaction time hr | Column. sol | Product | Amount g |
|---|---|---|---|---|---|---|
| 1.170 | 0.220 | 25 | 1 | Not purified | I-e6 | 0.836 |

Reaction 3

| Compound I-e6:g | Compound P5:g | NaBH$_3$CN g | AcOH ml | MeOH ml | Reaction time hr | Column. sol | Product | Amount g |
|---|---|---|---|---|---|---|---|---|
| 0.836 | 0.997 | 0.329 | 0.28 | 25 | 1 | MC:M:H 15:1:1 | I-f6 | 1.200 |

Reaction 4

| Compound I-f6:g | HCHO ml | NaBH$_3$CN g | AcOH ml | MeOH ml | Reaction time hr | Column. sol | Product | Amount g |
|---|---|---|---|---|---|---|---|---|
| 0.530 | 0.400 | 0.119 | 0.10 | 9 | 2 | H:ACT 2:1: | I-g6 | 0.341 |

Reaction 7

| Compound I-g6:g | TFA ml | CH$_2$Cl$_2$ ml | Reaction time hr | Column. sol | Amount g | HPLC min |
|---|---|---|---|---|---|---|
| 0.225 | 2.5 | 3 | 1 | CH:M:N 300:10:1 | 0.100 | 24.3 |

EI-MS(M$^+$): 471
$^1$H-NMR(CDCl$_3$): δ 0.12, 0.79, 0.84 and 0.98(6H, d. J=6.6-6.8Hz), 1.20(9H, s),
2.02-3.00(10H, m), 2.18 and 2.58(3H, s), 2.84 and 2.87(3H, s), 3.61-3.82(3H, m), 4.01-4.11 and
4.89-4.97(1H, m), 6.52 and 6.63(2H, d, J=8.1Hz), 6.72 and 6.89(1H, d, J=7.9Hz), 6.93-7.14(4H, m)

TABLE D-64

Example 78
Synthesis of 2-(2-amino-3-(4-fluorophenyl)-N-
methylpropylamino)-N-(1-aminomethyl-2-(3-tert-butyl-4-
hydroxyphenyl)ethyl)-3-methylbutanamide

| $R_{32}$ | $R_{33}$ | R' |
|---|---|---|
| Me | H | $CH_2NH_2$ |

Reaction 1

| Compound T22:g | Compound V4:g | CMPI g | TEA ml | THF ml | Reaction time hr | Column. sol | Product | Amount g |
|---|---|---|---|---|---|---|---|---|
| 0.89 | 0.90 | 0.92 | 0.89 | 13 | 20 | MC:M:N 100:3:0.1 | I-d7 | 1.40 |

TABLE D-64-continued

Example 78
Synthesis of 2-(2-amino-3-(4-fluorophenyl)-N-
methylpropylamino)-N-(1-aminomethyl-2-(3-tert-butyl-4-
hydroxyphenyl)ethyl)-3-methylbutanamide ¹H-NMR(CDCl₃): δ 0.80(3H, d, J=6.6Hz), 0.91(3H, d, J=6.6Hz), 1.37(9H, s),
1.42(9H, s), 2.00-2.15(1H, m), 2.55-2.90(2H, m), 3.10-3.30(2H, m), 3.90-4.20(2H, m),
4.80-4.90(1H, m), 5.11(2H, brs), 5.20-5.40(1H, m), 6.35-6.50(1H, m),
6.57(1H, d, J=7.9Hz), 6.84(1H, dd, J=1.3, 7.9Hz), 7.02(1H, 1.3Hz), 7.36(5H, brs)

Reaction 2

| Compound I-d7:g | Pd—C g | MeOH ml | Reaction time hr | Column. sol | Product | Amount g |
|---|---|---|---|---|---|---|
| 1.40 | 0.40 | 40 | 16 | MC:M:N 100:5:0.1 | I-e7 | 0.89 |

¹H-NMR(CDCl₃): δ 0.56(3H, d, J=6.9Hz), 0.88(3H, d, J=6.9Hz), 1.38(9H, s),
1.43(9H, s), 2.10-2.30(1H, m), 2.65-2.85(2H, m), 3.15-3.35(3H, m), 4.15-4.30(1H, m),
4.95-5.05(1H, m), 6.62(1H, d, J=7.9Hz), 6.88(1H, dd, J=2.0, 7.9Hz), 7.01(1H, d, J=2.0Hz),
7.43(1H, d, J=8.3Hz)

TABLE D-65

Example 78 (Continued from Table D-64)
Synthesis of 2-(2-amino-3-(4-fluorophenyl)-N-
methylpropylamino)-N-(1-aminomethyl-2-(3-tert-butyl-4-hydroxyphenyl)ethyl)-3-methylbutanamide Reaction 3

| Compound I-e7:g | Compound P5:g | NaBH₃CN g | AcOH ml | MeOH ml | Reaction time hr | Column. sol | Product | Amount g |
|---|---|---|---|---|---|---|---|---|
| 1.02 | 1.07 | 0.28 | 0.15 | 26 | 1 | EA:H 1:2 | I-f7 | 1.41 |

¹H-NMR(CDCl₃): δ 0.70(3H, d, J=6.6Hz), 0.82(3H, d, J=6.6Hz), 1.37(9H, s), 1.39(9H, s),
1.44(9H, s), 1.80-2.00(1H, m), 2.20-2.50(1H, m), 2.60-2.90(6H, m), 3.10-3.40(2H, m),
3.70-3.90(1H, m), 4.20-4.30(1H, m), 4.60-4.80(1H, m), 4.95-5.10(1H, m), 6.60(1H, d, J=7.9Hz),
6.85-7.30(6H, m)

Reaction 4

| Compound I-f7:g | HCHO ml | NaBH₃CN g | AcOH ml | MeOH ml | Reaction time hr | Column. sol | Product | Amount g |
|---|---|---|---|---|---|---|---|---|
| 0.75 | 0.48 | 0.14 | 0.13 | 11 | 1 | EA:H 1:2 | I-g7 | 0.76 |

¹H-NMR(CDCl₃): 0.83(3H, d, J=6.6Hz), 0.93(3H, d, J=6.6Hz), 1.36(9H, s),
1.41(18H, s), 1.90-3.10(10H, m), 3.10-3.30(2H, m), 3.60-3.80(1H, m), 4.40-4.60(1H, m),
4.60-4.80(1H, m), 4.90-5.05(1H, m), 6.10-6.20(1H, m), 6.30-6.40(1H, m), 6.63(1H, d, J=7.9Hz),
6.85-7.25(6H, m)

TABLE D-66

Example 78 (Continued from Table D-55)
Synthesis of 2-(2-amino-3-(4-fluorophenyl)-N-
methylpropylamino)-N-(1-aminomethyl-2-(3-tert-butyl-4-
hydroxyphenyl)ethyl)-3-methylbutanamide Reaction 7

| Compound I-g7:g | TFA ml | CH₂Cl₂ ml | Reaction time hr | Column. sol | Amount g | HPLC min |
|---|---|---|---|---|---|---|
| 0.70 | 10 | 0 | 1 | MC:M:N 100:10:1 | 0.46 | 17.7 |

EI-MS(M⁺): 486
¹H-NMR(CDCl₃): δ 0.83(3H, d, J=6.6Hz), 0.95(3H, d, J=6.6Hz),
1.39(9H, s), 2.00-2.90(10H, m), 2.19(3H, s), 2.95-3.10(1H, m),
4.20-4.35(1H, m), 6.06(1H, d, J=8.3Hz), 6.62(1H, d, J=7.9Hz),
6.87(1H, dd, J=1.7, 7.9Hz), 6.94-7.15(5H, m)

Examples 101-121 were carried out according to Scheme 3, Examples 121-131 were carried out according to Scheme 4, Example 132 was carried out according to Scheme 5, Examples 133-135 were carried out according to Scheme 6, Example 136 was carried out according to Scheme 7, Example 137 was carried out according to Scheme 8, Examples 138-165 were carried out according to Scheme 9, Examples 166 and 176 were carried out according to Scheme 10, Examples 167-171 were carried out according to Scheme 11, Examples 172 and 173 were carried out according to Scheme 12, Example 174 was carried out according to Scheme 13, Example 175 was carried out according to the scheme 14, Examples 177-179 were carried out according to Scheme 15, Example 180 was carried out according to Scheme 16, Examples 181 and 182 were carried out according to Scheme 17 and Example 183 was carried out according to Scheme 18.

The processes of synthesizing Intermediates in Schemes 3-8 are shown below as Reference Examples. In addition, structural formulae of Intermediates of Examples 101-137 are shown in Table C-2.

TABLE C-2

Intermediates of Examples 101-137

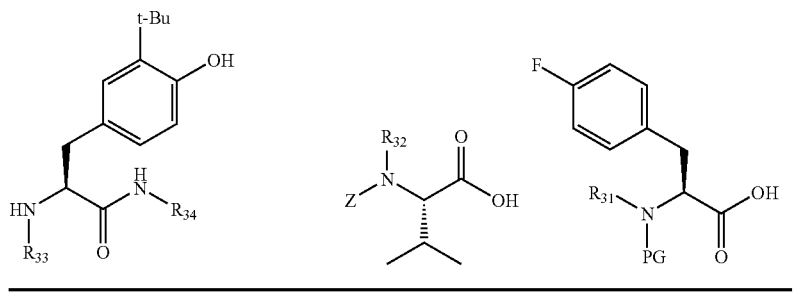

T1: R33 = H, R34 = H
T3: R33 = H, R34 = Et
T6: R33 = Me, R34 = Et
T9: R33 = Et, R34 = Et
T10: R33 = H, R34 = n-Pr
T11: R33 = H, R34 = i-Pr
T12: R33 = Me, R34 = c-Pr
T16: R33 = n-Pr, R34 = H

V1: R32 = Me
V2: R32 = Et

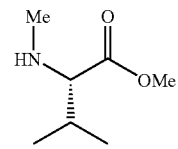

V3

P1: PG = Boc, R31 = H
P2: PG = Boc, R31 = Me
P3: PG = Z, R31 = Et
P4: PG = Z, R31 = H
P5: PG = Z, R31 = Me

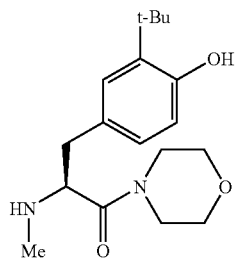

T13

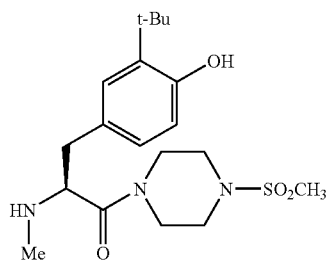

T14

TABLE C-2-continued

Intermediates of Examples 101-137

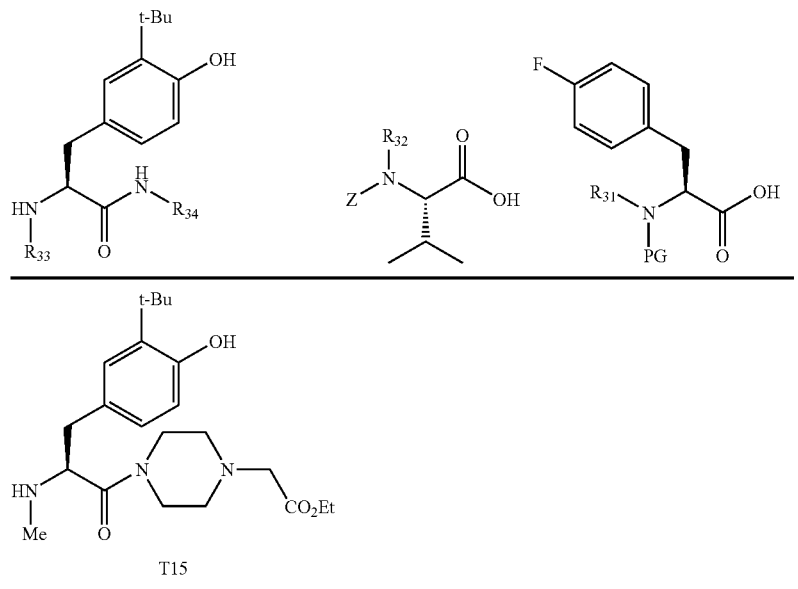

T15

REFERENCE EXAMPLE 16

Synthesis of Intermediates T3 and T9

The synthesis scheme is shown below.

Synthesis scheme of Intermediates T3 and T9

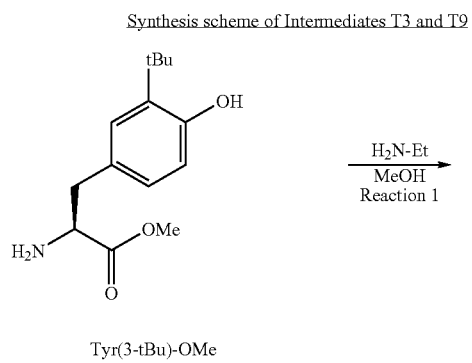

Tyr(3-tBu)-OMe

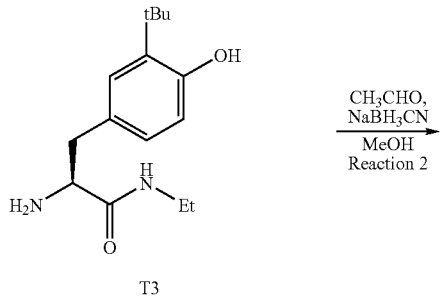

T3

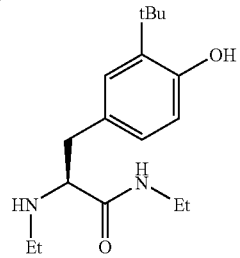

T9

The process of synthesizing Intermediates T3 and T9 is explained below.

Reaction Step 1) Synthesis of Intermediate T3

To a solution of Tyr(3-tBu)-OMe in methanol, a 70% aqueous ethylamine solution was added and stirred at room temperature. The reaction mixture was concentrated under reduced pressure, extracted with dichloromethane, dried over anhydrous magnesium sulfate and filtered. The filtrate was concentrated under reduced pressure and the thus obtained residue was subjected to silica gel column chromatography, giving Compound T3.

Reaction Step 2) Synthesis of T9

To a solution of Compound T3 and acetaldehyde in methanol, $NaBH_3CN$ was slowly added dropwise. The reaction was stopped by the addition of an aqueous $NaHCO_3$ solution and the reaction mixture was concentrated under reduced pressure. The resultant was extracted with dichloromethane, dried over anhydrous magnesium sulfate and filtered. The filtrate was concentrated under reduced pressure and the thus obtained residue was subjected to silica gel column chromatography, giving Compound T9.

The result is shown in Table E-1. In Table E-1, indications "Reaction 1" and "Reaction 2" means Reaction step 1 and Reaction step 2, "Reaction time" means stirring time, "Column sol." means the eluting solvent for silica gel column chromatography, "Product" means the obtained product and "Amount" means the yielded amount of the product. The same manner is applied to the subsequent Tables.

TABLE E-1

Intermediates T3 (Tyr(3-tBu)-NHEt) and T9 (N-Et-Tyr(3-tBu)-NHEt)

Reaction 1

| Tyr(3-tBu)-OMe (g) | Ethyl amine (ml) | MeOH (ml) | Reaction time (hr) | Column sol. | Product | Amount (g) |
|---|---|---|---|---|---|---|
| 14.000 | 168.00 | 56.00 | 18 | nHx:EA = 1:1 | T3 | 12.810 |

Reaction 2

| Compound T3 (g) | CH$_3$CHO (ml) | NaBH$_3$CN (g) | MeOH (ml) | Reaction time (hr) | Column sol. | Amount (g) |
|---|---|---|---|---|---|---|
| 12.810 | 2.98 | 3.350 | 100.00 | 0.5 | MC:MeOH = 20:1 | 8.130 |

REFERENCE EXAMPLE 17

Synthesis of Intermediates T6, T10, T11, T12 and T13

The synthesis scheme is shown below.

Synthesis scheme of Intermediates T6, T10, T11, T12 and T13

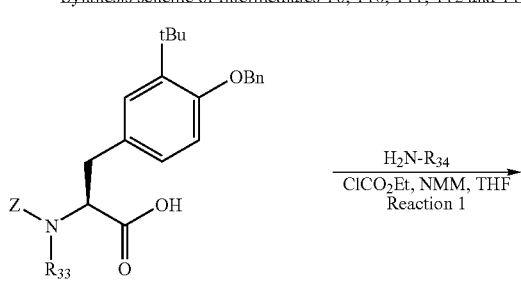

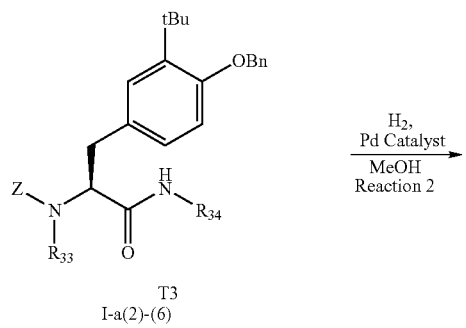

T3
I-a(2)-(6)

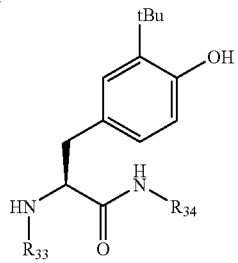

T6, 10, 11, 12, 13

$R_{33}$ and $R_{34}$ in the above reaction scheme indicate substituents shown in Tables E-2 to E-6.

The process of synthesizing Intermediates is explained below.

Reaction Step 1)

To solutions of Z-N-Me-Tyr(O-Bn,3-tBu)-OH and ethyl chloroformate in THF, NMM was added. The mixture was stirred at room temperature and mixed with solutions of alkyl amines in THF. The mixtures were mixed with water, extracted with ethyl acetate, washed with saturated brine, dried over anhydrous magnesium and filtered. The filtrates were concentrated under reduced pressure and the thus obtained residues were subjected to silica gel column chromatography, giving Compounds I-a(2) to I-a(6).

Reaction Step 2)

To solutions of Compounds I-a(2) to I-a(6) in methanol, palladium hydroxide/carbon was added and stirred at room temperature in a hydrogen atmosphere. After filtering reaction mixtures, filtrates were concentrated under reduced pressure and the thus obtained residues were subjected to silica gel column chromatography, giving Compounds T6, T10, T11, T12 and T13. The results are shown in Tables E-2 to E-6.

TABLE E-2

Intermediate T6
N-Me-Tyr(3-tBu)-NHEt

| R33 | R34 |
|---|---|
| Me | Et |

Reaction 1

| Z-N-Me-Tyr(O-Bn,3-tBu)-OH (g) | Ethylamine (ml) | ClCO$_2$Et (ml) | NMM (ml) | THF (ml) | Reaction time (hr) | Column sol. | Product | Amount (g) |
|---|---|---|---|---|---|---|---|---|
| 11.300 | 118.80 | 3.40 | 3.90 | 230.00 | 6 | nHx:EA = 2:1 | I-a(2) | 8.400 |

Reaction 2

| Compound I-a(2) (g) | Pd(OH)$_2$ (g) | MeOH (ml) | Reaction time (hr) | Column sol. | Amount (g) |
|---|---|---|---|---|---|
| 6.200 | 0.600 | 120.00 | 3 | MC:MeOH = 20:1 | 3.600 |

TABLE E-3

Intermediate T10
Tyr(3-tBu)-NH-n-Pr

| R33 | R34 |
|---|---|
| H | n-Pr |

Reaction 1

| Z-N-Me-Tyr(O-Bn,3-tBu)-OH (g) | n-Propylamine (ml) | ClCO$_2$Et (ml) | NMM (ml) | THF (ml) | Reaction time (hr) | Column sol. | Product | Amount (g) |
|---|---|---|---|---|---|---|---|---|
| 1.100 | 1.40 | 0.57 | 0.66 | 30.00 | 2 | nHx:EA:MC = 1:3:1 | I-a(3) | 1.150 |

Reaction 2

| Compound I-a(3) (g) | Pd(OH)$_2$ (g) | MeOH (ml) | Reaction time (hr) | Column sol. | Amount (g) |
|---|---|---|---|---|---|
| 1.150 | 0.200 | 30.00 | 2 | MC:MeOH = 20:1 | 0.580 |

TABLE E-4

Intermediate T11
Tyr(3-tBu)-NH-i-Pr

| R33 | R34 |
|---|---|
| H | i-Pr |

Reaction 1

| Z-N-Me-Tyr(O-Bn,3-tBu)-OH (g) | i-Propyl amine (ml) | ClCO$_2$Et (ml) | NMM (ml) | THF (ml) | Reaction time (hr) | Column sol. | Product | Amount (g) |
|---|---|---|---|---|---|---|---|---|
| 1.300 | 0.72 | 0.54 | 0.46 | 15.00 | 0.6 | nHx:EA = 2:1 | I-a(4) | 1.200 |

Reaction 2

| Compound I-a(4) (g) | Pd(OH)$_2$ (g) | MeOH (ml) | Reaction time (hr) | Column sol. | Amount (g) |
|---|---|---|---|---|---|
| 1.200 | 0.500 | 30.00 | 3.5 | EA:MeOH = 20:1 | 0.660 |

TABLE E-5

Intermediate T12
N-Me-Tyr(3-tBu)-NH-c-Pr

| R33 | R34 |
|---|---|
| Me | c-Pr |

Reaction 1

| Z-N-Me-Tyr(O-Bn,3-tBu)-OH (g) | c-Propyl-amine (ml) | ClCO$_2$Et (ml) | NMM (ml) | THF (ml) | Reaction time (hr) | Column sol. | Product | Amount (g) |
|---|---|---|---|---|---|---|---|---|
| 1.000 | 1.20 | 0.46 | 0.40 | 30.00 | 2 | nHx:EA:MC = 1:3:1 | I-a(5) | 1.050 |

Reaction 2

| Compound I-a(5) (g) | Pd(OH)$_2$ (g) | MeOH (ml) | Reaction time (hr) | Column sol. | Amount (g) |
|---|---|---|---|---|---|
| 1.050 | 0.200 | 30.00 | 2 | MC:MeOH = 20:1 | 0.500 |

Intermediate P5 was synthesized according to a similar method described in Reference Example 7.

TABLE E-6

Intermediate T13
(2S)-3-[3-(tert-butyl)-4-hydroxyphenyl]-2-(methylamino)-1-morpholin-4-ylpropan-1-one

| R33 | R34 |
|---|---|
| Me | morpholine |

Reaction 1

| Z-N-Me-Tyr(O-Bn,3-tBu)-OH (g) | morpholine (g) | ClCO$_2$Et (ml) | NMM (ml) | THF (ml) | Reaction time (hr) | Column sol. | Product | Amount (g) |
|---|---|---|---|---|---|---|---|---|
| 1.200 | 0.660 | 0.27 | 0.42 | 15.00 | 20 | nHx:EA = 1:1 | I-a(6) | 1.200 |

Reaction 2

| Compound I-a(6) (g) | Pd(OH)$_2$ (g) | MeOH (ml) | Reaction time (hr) | Column sol. | Amount (g) |
|---|---|---|---|---|---|
| 1.200 | 0.300 | 20.00 | 20 | MC:MeOH = 20:1 | 0.600 |

REFERENCE EXAMPLE 18

Synthesis of Intermediate T14

The synthesis scheme is shown below.

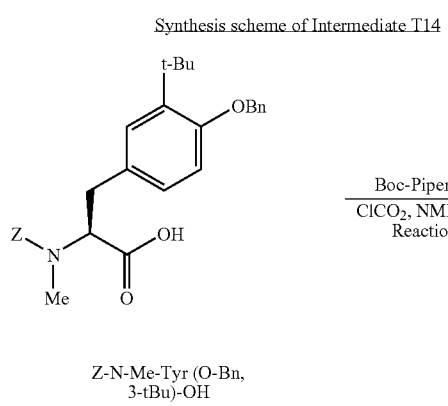

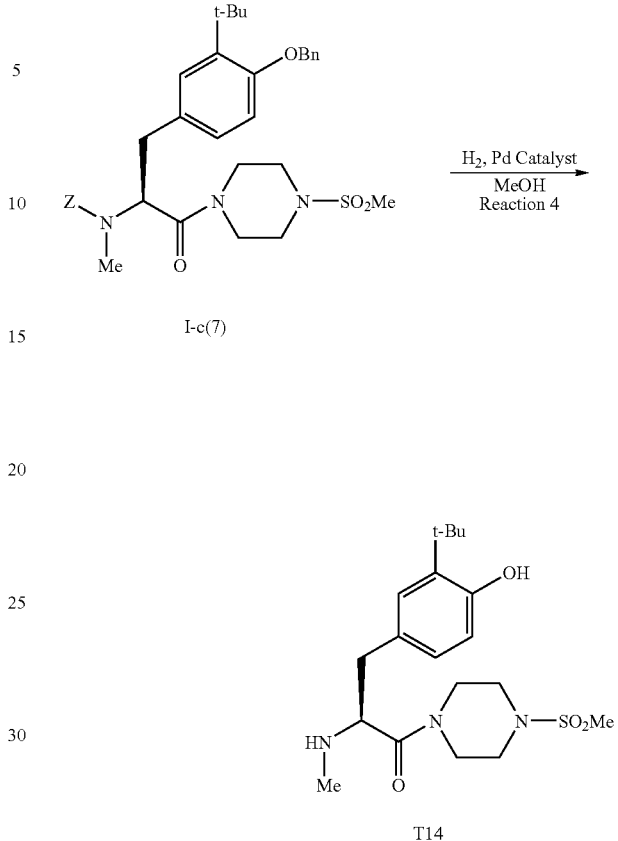

The process of synthesizing Intermediate T14 is explained below.

Reaction Step 1)

Compound I-a(7) was obtained according to the method described in Reaction step 1 of Reference Example 17.

Reaction Step 2)

To a solution of Compound I-a(7) in dichloromethane, TFA was added under cooling and stirred at room temperature.

The reaction mixture was concentrated under reduced pressure, extracted with dichloromethane, washed with saturated brine, dried over anhydrous magnesium sulfate and filtered. The filtrate was concentrated under reduced pressure and the thus obtained residue was subjected to silica gel column chromatography, giving Compound I-b(7).

Reaction Step 3)

To a solution of Compound I-b(7) and ClSO$_2$Me in dichloromethane, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure and the thus obtained residue was subjected to silica gel column chromatography, giving Compound I-c(7).

Reaction Step 4)

Compound T14 was obtained according to the method described in Reaction step 2 of Reference Example 17. Result is shown in Table E-7.

TABLE E-7

Intermediate T14
(2S)-3-[3-(tert-butyl)-4-hydroxyphenyl]-2-(methylamino)-1-[4-(methylsulfonyl)piperazinyl]propane-1-one

Reaction 1

| Z-N—Me-Tyr)O-Bn,3-tBu)-OH (g) | Boc-piperazine (g) | ClCO₂Et (ml) | NMM (ml) | THF (ml) | Reaction time (hr) | Column sol. | Product | Amount (g) |
|---|---|---|---|---|---|---|---|---|
| 1.500 | 0.700 | 0.36 | 0.42 | 15.00 | 20 | nHx:EA = 1:1 | I-a(7) | 1.900 |

Reaction 2

| Compound I-a(7) (g) | TFA (ml) | MC (ml) | Reaction time (hr) | Column sol. | Product | Amount (g) |
|---|---|---|---|---|---|---|
| 1.900 | 5.00 | 20.00 | 4 | MC:MeOH = 20:1 | I-b(7) | 1.400 |

Reaction 3

| Compound I-b(7) (g) | ClSO₂Me (ml) | TEA (ml) | MC (ml) | Reaction time (hr) | Column sol. | Product | Amount (g) |
|---|---|---|---|---|---|---|---|
| 1.400 | 0.46 | 0.82 | 20.00 | 2 | MC:MeOH = 20.1 | I-c(7) | 1.500 |

Reaction 4

| Compound I-c(7) (g) | Pd(OH)₂ (g) | MeOH (ml) | Reaction time (hr) | Column sol. | Amount (g) |
|---|---|---|---|---|---|
| 1.500 | 0.300 | 20.00 | 20 | MC:MeOH = 20:1 | 0.900 |

REFERENCE EXAMPLE 19

Synthesis of Intermediate T15

The synthesis scheme is shown below.

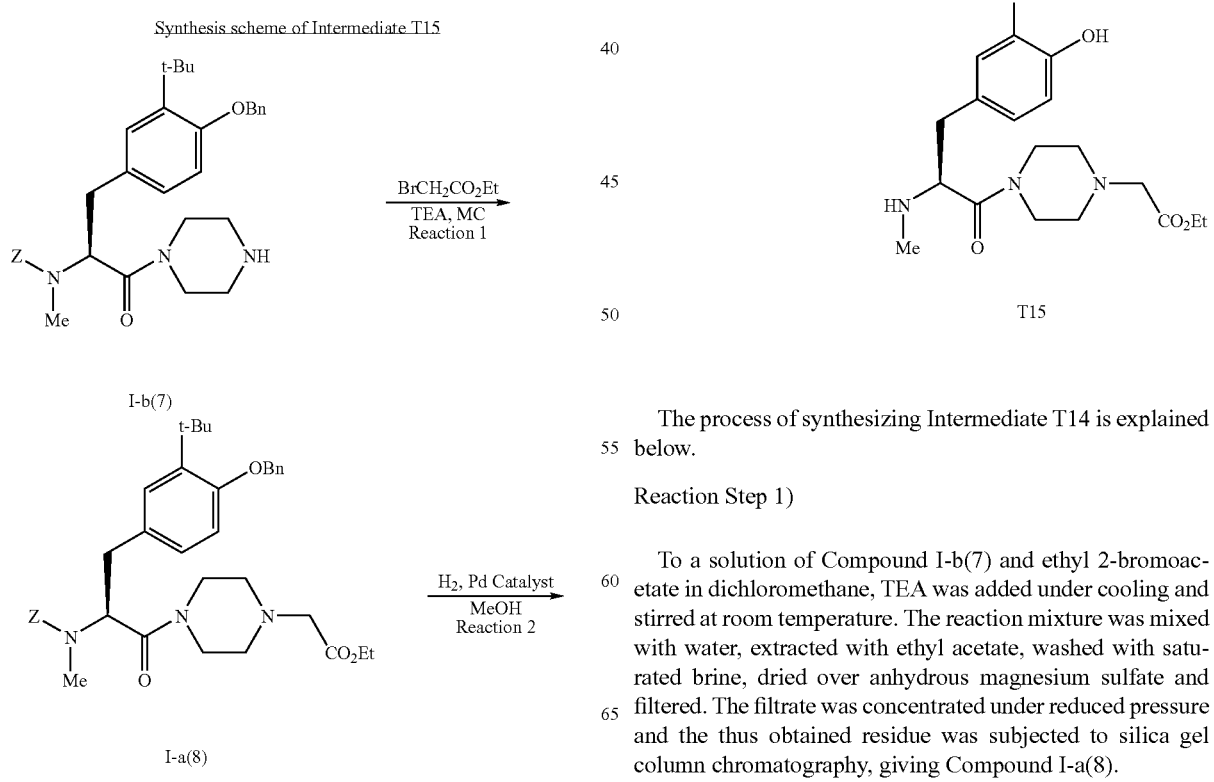

The process of synthesizing Intermediate T14 is explained below.

Reaction Step 1)

To a solution of Compound I-b(7) and ethyl 2-bromoacetate in dichloromethane, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure and the thus obtained residue was subjected to silica gel column chromatography, giving Compound I-a(8).

Reaction Step 2)

Compound T15 was obtained according to the method described in Reaction step 2 of Reference Example 17. Result is shown in Table E-8.

TABLE E-8

Intermediate T15
Ethyl 2-(4-{(2S)-3-[3-(tert-butyl)-4-hydroxyphenyl]-2-(methylamino)propanoyl}piperazinyl)acetate Reaction 1

| Compound I-b(7) (g) | Ethyl bromo acetate (ml) | TEA (ml) | MC (ml) | Reaction time (hr) | Column sol. | Product | Amount (g) |
|---|---|---|---|---|---|---|---|
| 0.970 | 0.30 | 0.40 | 17.00 | 4 | nHx:EA = 3:1 | I-a(8) | 1.000 |

Reaction 2

| Compound I-a(8) (g) | Pd(OH)₂ (g) | MeOH (ml) | Reaction time (hr) | Amount (g) |
|---|---|---|---|---|
| 1.000 | 0.300 | 16.00 | 1 | 0.643 |

REFERENCE EXAMPLE 20

Synthesis of Intermediate T16

The synthesis scheme is shown below.

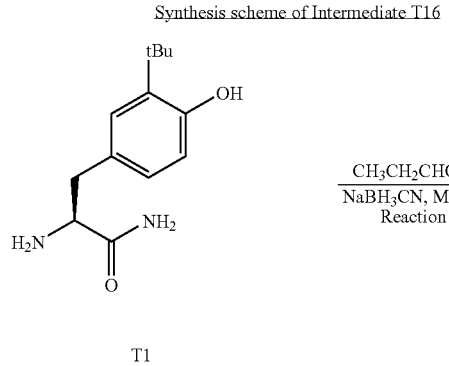

Synthesis scheme of Intermediate T16

T1

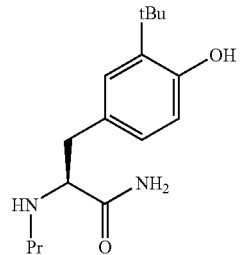

T16

The process of synthesizing Intermediate T16 is explained below.

To a solution of Compound T1 in methanol, propionaldehyde was added, stirred at room temperature for 30 min., mixed with NaBH₃CN and stirred for 2 hours. The reaction mixture was mixed with a saturated aqueous NH₄Cl solution, extracted with ethyl acetate, washed with saturated brine, dried over anhydrous magnesium sulfate and filtered. The filtrate was concentrated under reduced pressure and the thus obtained residue was subjected to silica gel column chromatography, giving Compound T16. Result is shown in Table E-9.

TABLE E-9

Intermediate T16
N-Pr-Tyr(3-tBu)-NH₂
Reaction

| Compound T1 (g) | CH₃CH₂CHO (ml) | NaBH₃CN (g) | MeOH (ml) | Reaction time (hr) | Column sol. | Amount (g) |
|---|---|---|---|---|---|---|
| 4.000 | 1.34 | 1.170 | 70.00 | 2 | nHx:EA = 1:2 | 1.580 |

Scheme 3 shows the synthesis process of Examples 101-121.

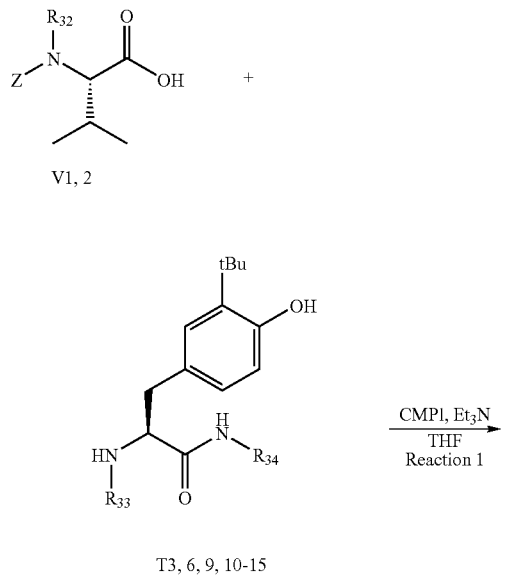

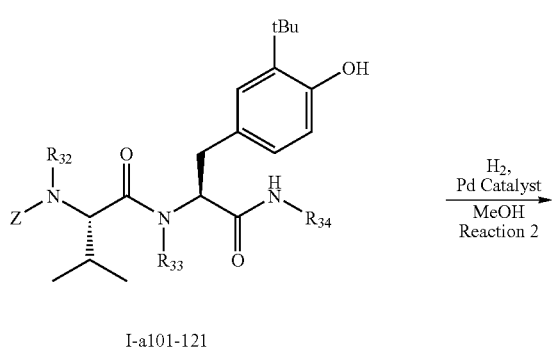

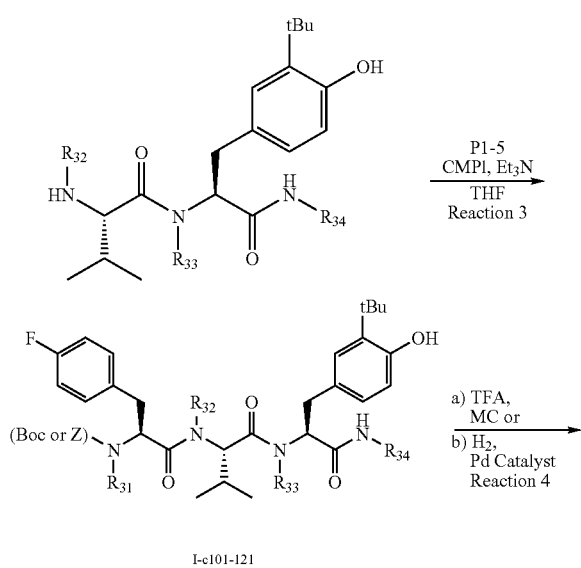

$R_{31}$, $R_{32}$, $R_{33}$ and $R_{34}$ in the above reaction scheme indicate substituents shown in Tables D-101 to D-121.

The synthesis process in scheme 3 is explained below.

Reaction Step 1)

To solutions of Compounds T, Compounds V and CMPI in THF, TEA was added under cooling and stirred at room temperature. The mixtures were mixed with water, extracted with ethyl acetate, washed with a saturated aqueous $NaHCO_3$ solution, dried over anhydrous magnesium sulfate and filtered. The filtrates were concentrated under reduced pressure and the thus obtained residues were subjected to silica gel column chromatography, giving Compounds I-a101 to I-a121.

Reaction Step 2)

To solutions of Compounds I-a101 to I-a121 in methanol, Pd/C was added and stirred at room temperature in a hydrogen atmosphere. After filtering off the Pd/C, the filtrates were concentrated under reduced pressure and the thus obtained residues were subjected to silica gel column chromatography, giving Compounds I-b101 to I-b121.

Reaction Step 3)

To solutions of Compounds I-b101 to I-b121, P1 to P5 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure and the thus obtained residues were subjected to silica gel column chromatography, giving Compounds I-c101 to I-c121.

Reaction Step 4-a)

To solutions of Compounds I-c101 to I-c121 in dichloromethane, TFA was added under cooling and stirred at room temperature. The reaction mixtures were neutralized by the addition of a saturated aqueous $NaHCO_3$ solution, extracted with dichloromethane, washed with saturated brine, dried over anhydrous magnesium sulfate and filtered. The filtrates were concentrated under reduced pressure and the thus obtained residue was subjected to silica gel column chromatography, giving the titled compounds.

Reaction Step 4-b)

To solutions of Compounds I-c101 to I-c121 in methanol, Pd/C or $Pd(OH)_2$ was added and stirred in a hydrogen atmosphere at room temperature. After filtering off the Pd/C or $Pd(OH)_2$, the filtrates were concentrated under reduced pressure and the thus obtained residues were subjected to silica gel column chromatography, giving the titled compounds.

Examples conducted according to Scheme 3 are shown in Tables D-101 to D-121.

TABLE D-101

Example 101
Synthesis of Phe(4-F)-N-Me-Val-Tyr(3-tBu)-NHEt

| R31 | R32 | R33 | R34 |
|---|---|---|---|
| H | Me | H | Et |

Reaction 1

| Compound T3 (g) | Compound V1 (g) | CMPI (g) | TEA (ml) | THF (ml) | Reaction time (hr) | Column sol. | Product | Amount (g) |
|---|---|---|---|---|---|---|---|---|
| 3.000 | 3.000 | 4.350 | 3.30 | 60.00 | 20 | nHx:EA = 1:1 | I-a101 | 5.220 |

Reaction 2

| Compound I-a101 (g) | Pd(OH)$_2$ (g) | MeOH (ml) | Reaction time (hr) | Column sol. | Product | Amount (g) |
|---|---|---|---|---|---|---|
| 4.500 | 0.450 | 45.00 | 20 | MC:MeOH = 20:1 | I-b101 | 2.200 |

Reaction 3

| Compound I-b101 (g) | Compound P4 (g) | CMPI (g) | TEA (ml) | THF (ml) | Reaction time (hr) | Column sol. | Product | Amount (g) |
|---|---|---|---|---|---|---|---|---|
| 0.600 | 0.500 | 0.600 | 0.50 | 15.00 | 20 | nHx:EA = 1:1 | I-c101 | 0.830 |

Reaction 4-b

| Compound I-c101 (g) | Pd(OH)$_2$ (g) | MeOH (ml) | Reaction time (hr) | Column sol. | Amount (g) | HPLC min |
|---|---|---|---|---|---|---|
| 0.830 | 0.100 | 10.00 | 20 | MC:MeOH = 10:1 | 0.170 | 18.42 |

ESI-MS(M$^+$+1): 557
1H-NMR(CDCl$_3$): δ 0.59-1.05(9H, m), 1.37(9H, s), 2.25-2.39(1H, m), 2.58-3.24(9H, m), 3.58-3.97(2H, m), 4.44-4.62(1H, m), 5.59-5.77(1H, m), 6.60-7.72(8H, m), 9.03 and 9.06(1H, d, J=7.9Hz)

TABLE D-102

Example 102
N-Me-Phe(4-F)-N-Me-Val-Tyr(3-tBu)-NHEt

| R31 | R32 | R33 | R34 |
|---|---|---|---|
| Me | Me | H | Et |

Reaction 1

| Compound T3 (g) | Compound V1 (g) | CMPI (g) | TEA (ml) | THF (ml) | Reaction time (hr) | Column sol. | Product | Amount (g) |
|---|---|---|---|---|---|---|---|---|
| 3.000 | 3.000 | 4.350 | 3.30 | 60.00 | 20 | nHx:EA = 1:1 | I-a102 | 5.220 |

Reaction 2

| Compound I-a102 (g) | Pd(OH)$_2$ (g) | MeOH (ml) | Reaction time (hr) | Column sol. | Product | Amount (g) |
|---|---|---|---|---|---|---|
| 4.500 | 0.450 | 45.00 | 20 | MC:MeOH = 20:1 | I-b102 | 2.200 |

Reaction 3

| Compound I-b102 (g) | Compound P2 (g) | CMPI (g) | TEA (ml) | THF (ml) | Reaction time (hr) | Column sol. | Product | Amount (g) |
|---|---|---|---|---|---|---|---|---|
| 1.000 | 1.000 | 1.310 | 0.72 | 20.00 | 20 | nHx:EA = 1:1 | I-c102 | 1.560 |

TABLE D-102-continued

Example 102
N-Me-Phe(4-F)-N-Me-Val-Tyr(3-tBu)-NHEt

| R31 | R32 | R33 | R34 |
|-----|-----|-----|-----|
| Me  | Me  | H   | Et  |

Reaction 4-a

| Compound I-c102 (g) | TFA (ml) | MC (ml) | Reaction time (hr) | Column sol. | Amount (g) | HPLC min |
|---|---|---|---|---|---|---|
| 1.500 | 1.70 | 10.00 | 4 | MC:MeOH = 10:1 | 0.28 | 18.73 |

ESI-MS(M$^+$+1): 557
1H-NMR(CDCl$_3$): (two rotamers)δ 0.57, 0.79, 0.92 and 1.00(9H, d and m, J=6.3-6.8Hz), 1.34 and 1.38(9H, s), 2.25, 2.40 and 2.58, 2.65(6H, s), 2.05-2.40(1H, m), 2.67-3.25(6H, m), 3.55 and 3.68(1H, m), 3.84, 4.40 and 4.55(2H, d and m, J=10.9Hz), 5.56 and 5.72(1H, m), 6.65-7.17(8H, m), 9.15 and 9.18(1H, d, J=8.2Hz)

TABLE D-103

Example 103
N-Et-Phe(4-F)-N-Me-Val-Tyr(3-tBu)-NHEt

| R31 | R32 | R33 | R34 |
|-----|-----|-----|-----|
| Et  | Me  | H   | Et  |

Reaction 1

| Compound T3 (g) | Compound V1 (g) | CMPI (g) | TEA (ml) | THF (ml) | Reaction time (hr) | Column sol. | Product | Amount (g) |
|---|---|---|---|---|---|---|---|---|
| 3.000 | 3.000 | 4.350 | 3.30 | 60.00 | 20 | nHx:EA = 1:1 | I-a103 | 5.220 |

Reaction 2

| Compound I-a103 (g) | Pd(OH)$_2$ (g) | MeOH (ml) | Reaction time (hr) | Column sol. | Product | Amount (g) |
|---|---|---|---|---|---|---|
| 4.500 | 0.450 | 45.00 | 20 | MC:MeOH = 20:1 | I-b103 | 2.200 |

Reaction 3

| Compound I-b103 (g) | Compound P3 (g) | CMPI (g) | TEA (ml) | THF (ml) | Reaction time (hr) | Column sol. | Product | Amount (g) |
|---|---|---|---|---|---|---|---|---|
| 0.800 | 0.670 | 1.050 | 0.57 | 20.00 | 20 | nHx:EA = 1:1 | I-c103 | 0.800 |

Reaction 4-b

| Compound I-c103 (g) | Pd(OH)$_2$ (g) | MeOH (ml) | Reaction time (hr) | Column sol. | Amount (g) | HPLC min |
|---|---|---|---|---|---|---|
| 0.800 | 0.100 | 10.00 | 20 | MC:MeOH = 10:1 | 0.220 | 19.27 |

ESI-MS(M$^+$+1): 571
1H-NMR(CDCl$_3$): (two rotamers)δ 0.42-1.20(12H, m), 1.35 and 1.39(9H, s), 2.05-2.26(1H, m), 2.31-2.54(1H, m), 2.40 and 2.50 (3H, s), 2.62-3.26(6H, m), 3.62-3.80(1H, m), 4.34-4.58(1H, m), 5.79-5.87(1H, m), 6.60-7.04(7H, m)

TABLE D-104

Example 104
Phe(4-F)-N-Me-Val-N-Me-Tyr(3-tBu)-NHEt

| R31 | R32 | R33 | R34 |
|-----|-----|-----|-----|
| H   | Me  | Me  | Et  |

Reaction 1

| Compound T6 (g) | Compound V1 (g) | CMPI (g) | TEA (ml) | THF (ml) | Reaction time (hr) | Column sol. | Product | Amount (g) |
|---|---|---|---|---|---|---|---|---|
| 2.500 | 3.570 | 3.440 | 2.50 | 90.00 | 8 | nHx:EA = 1:2 | I-a104 | 4.200 |

TABLE D-104-continued

Example 104
Phe(4-F)-N-Me-Val-N-Me-Tyr(3-tBu)-NHEt

| R31 | R32 | R33 | R34 |
|---|---|---|---|
| H | Me | Me | Et |

Reaction 2

| Compound I-a104 (g) | Pd/C (g) | MeOH (ml) | Reaction time (hr) | Column sol. | Product | Amount (g) |
|---|---|---|---|---|---|---|
| 4.200 | 0.400 | 75.00 | 5 | MC:MeOH = 20:1 | I-b104 | 3.900 |

Reaction 3

| Compound I-b104 (g) | Compound P4 (g) | CMPI (g) | TEA (ml) | THF (ml) | Reaction time (hr) | Column sol. | Product | Amount (g) |
|---|---|---|---|---|---|---|---|---|
| 1.300 | 1.600 | 1.300 | 0.90 | 30.00 | 18 | nHx:EA = 1:2 | I-c104 | 0.920 |

Reaction 4-b

| Compound I-c104 (g) | Pd/C (g) | MeOH (ml) | Reaction time (hr) | Column sol. | Amount (g) | HPLC min |
|---|---|---|---|---|---|---|
| 0.920 | 0.100 | 10.00 | 3 | MC:MeOH = 20:1 | 0.210 | 19.57 |

ESI-MS(M$^+$+1): 557
1H-NMR(CDCl$_3$): (two rotamers)δ 0.56, 0.77, 0.79 and 0.92(6H, d, J=6.4-6.7Hz), 1.01-1.12(3H, m), 1.38 and 1.33(9H, s), 2.19-2.68(2H, m), 2.52 and 2.83(3H, s), 2.68-3.42(4H, m), 3.00 and 3.02(3H, s), 3.65-3.87(1H, m), 4.90-5.11 and 5.35-5.47(2H, m), 5.95-6.08(1H, m), 6.36 and 6.62(1H, d, J=7.8-7.9Hz), 6.68-7.16(6H, m)

TABLE D-105

Example 105
N-Me-Phe(4-F)-N-Me-Val-N-Me-Tyr(3-tBu)-NHEt

| R31 | R32 | R33 | R34 |
|---|---|---|---|
| Me | Me | Me | Et |

Reaction 1

| Compound T6 (g) | Compound V1 (g) | CMPI (g) | TEA (ml) | THF (ml) | Reaction time (hr) | Column sol. | Product | Amount (g) |
|---|---|---|---|---|---|---|---|---|
| 2.500 | 3.570 | 3.440 | 2.50 | 90.00 | 8 | nHx:EA = 1:2 | I-a105 | 4.200 |

Reaction 2

| Compound I-a105 (g) | Pd/C (g) | MeOH (ml) | Reaction time (hr) | Column sol. | Product | Amount (g) |
|---|---|---|---|---|---|---|
| 4.200 | 0.400 | 75.00 | 5 | MC:MeOH = 20:1 | I-b105 | 3.900 |

Reaction 3

| Compound I-b105 (g) | Compound P2 (g) | CMPI (g) | TEA (ml) | THF (ml) | Reaction time (hr) | Column sol. | Product | Amount (g) |
|---|---|---|---|---|---|---|---|---|
| 1.300 | 1.480 | 1.300 | 0.90 | 30.00 | 18 | nHx:EA = 1:2 | I-c105 | 1.020 |

Reaction 4-a

| Compound I-c105 (g) | TFA (ml) | MC (ml) | Reaction time (hr) | Column sol. | Amount (g) | HPLC min |
|---|---|---|---|---|---|---|
| 1.020 | 2.30 | 23.00 | 6 | MC:MeOH = 20:1 | 0.200 | 20.213 |

ESI-MS(M$^+$+1): 571
1H-NMR(CDCl$_3$): (two rotamers)δ 0.63, 0.80, 0.81 and 0.92(6H, d, J=6.4-6.9Hz), 1.06(3H, t, J=7.3Hz), 1.34 and 1.39 (9H, s), 2.13-2.33(1H, m), 2.22 and 2.25(3H, s), 2.53 and 2.82(3H s), 2.54(1H, s), 2.60-2.70(2H, m), 2.74-2.90(1H, m), 2.95 and 3.06(3H, s), 3.45 and 3.59(1H, t, J=5-6.8Hz), 5.07 and 5.15(1H, d, J=10.6-10.9Hz), 5.05 and 5.38(1H, dd, J=8.1-9.3, 6.1-6.8Hz), 6.0(1H, t, J=5.0Hz), 6.40 and 6.61(1H, d, J=8.0Hz), 6.75(3H, m), 7.02-7.18(3H, m)

TABLE D-106

Example 106
N-Et-Phe(4-F)-N-Me-Val-N-Me-Tyr(3-tBu)-NHEt

| R31 | R32 | R33 | R34 |
|---|---|---|---|
| Et | Me | Me | Et |

Reaction 1

| Compound T6 (g) | Compound V1 (g) | CMPI (g) | TEA (ml) | THF (ml) | Reaction time (hr) | Column sol. | Product | Amount (g) |
|---|---|---|---|---|---|---|---|---|
| 2.500 | 3.570 | 3.440 | 2.50 | 90.00 | 8 | nHx:EA = 1:2 | I-a106 | 4.200 |

Reaction 2

| Compound I-a106 (g) | Pd/C (g) | MeOH (ml) | Reaction time (hr) | Column sol. | Product | Amount (g) |
|---|---|---|---|---|---|---|
| 4.200 | 0.400 | 75.00 | 5 | MC:MeOH = 20:1 | I-b106 | 3.900 |

Reaction 3

| Compound I-b106 (g) | Compound P3 (g) | CMPI (g) | TEA (ml) | THF (ml) | Reaction time (hr) | Column sol. | Product | Amount (g) |
|---|---|---|---|---|---|---|---|---|
| 1.300 | 1.740 | 1.300 | 0.90 | 30.00 | 15 | nHx:EA = 1:2 | I-c106 | 1.050 |

Reaction 4-b

| Compound I-c106 (g) | Pd/C (g) | MeOH (ml) | Reaction time (hr) | Column sol. | Amount (g) | HPLC min |
|---|---|---|---|---|---|---|
| 1.050 | 0.100 | 14.00 | 3 | MC:MeOH = 20:1 | 0.200 | 20.950 |

ESI-MS(M$^+$+1): 585
1H-NMR(CDCl$_3$): (two rotamers)δ 0.65, 0.79, 0.8 and 0.91(6H, d, J=6.0Hz), 0.97-1.08(6H, m), 1.34 and 1.39(9H, s), 2.21-2.38(2H, m), 2.46-2.59(2H, m), 2.61-2.9(2H, m), 2.5 and 2.75(3H, s), 2.96 and 3.06(3H, s), 3.17-3.46(2H, m), 3.55 and 3.68(1H, t, J=7.0Hz), 5.01-5.36(2H, m), 5.97-6.0(1H, m), 6.41 and 6.59(1H, d, J=8.0Hz), 6.79-6.98(3H, m), 7.04-7.17(3H, m)

TABLE D-107

Example 107
Phe(4-F)-N-Me-Val-N-Et-Tyr(3-tBu)-NHEt

| R31 | R32 | R33 | R34 |
|---|---|---|---|
| H | Me | Et | Et |

Reaction 1

| Compound T9 (g) | Compound V1 (g) | CMPI (g) | TEA (ml) | THF (ml) | Reaction time (hr) | Column sol. | Product | Amount (g) |
|---|---|---|---|---|---|---|---|---|
| 6.000 | 16.300 | 26.200 | 14.30 | 30.00 | 15 | nHx:EA = 2:1 | I-a107 | 3.030 |

Reaction 2

| Compound I-a107 (g) | Pd(OH)$_2$ (g) | MeOH (ml) | Reaction time (hr) | Column sol. | Product | Amount (g) |
|---|---|---|---|---|---|---|
| 8.000 | 1.200 | 50.00 | 15 | MC:MeOH = 10:1 | I-b107 | 5.000 |

Reaction 3

| Compound I-b107 (g) | Compound P4 (g) | CMPI (g) | TEA (ml) | THF (ml) | Reaction time (hr) | Column sol. | Product | Amount (g) |
|---|---|---|---|---|---|---|---|---|
| 0.800 | 0.815 | 0.606 | 0.40 | 30.00 | 18 | nHx:EA = 1:2 | I-c107 | 1.040 |

TABLE D-107-continued

Example 107
Phe(4-F)-N-Me-Val-N-Et-Tyr(3-tBu)-NHEt

| R31 | R32 | R33 | R34 |
|---|---|---|---|
| H | Me | Et | Et |

Reaction 4-b

| Compound I-c107 (g) | Pd/C (g) | MeOH (ml) | Reaction time (hr) | Column sol. | Amount (g) | HPLC min |
|---|---|---|---|---|---|---|
| 1.047 | 0.156 | 20.00 | 3.5 | MC:MeOH = 20:1 | 0.252 | 21.09 |

ESI-MS(M$^+$+1): 571
1H-NMR(CDCl$_3$): (two rotamers)δ 0.74, 0.80 and 0.92(6H, d, J=7.0-7.9Hz), 0.97-1.20(6H, m), 1.32 and 1.36(9H, s), 2.20-3.13(5H, m), 2.74 and 3.05(3H, s), 3.15-3.35(3H, m), 3.35-3.95(3H, m), 4.92-5.10(2H, m), 6.44 and 6.73(1H, d, J=8.8Hz), 6.50(3/5H, m), 6.75(3/5H, dd, J=7.9, 1.7Hz), 6.90-7.29(29/5H, m)

TABLE D-108

Example 108
N-Me-Phe(4-F)-N-Me-Val-N-Et-Tyr(3-tBu)-NHEt

| R31 | R32 | R33 | R34 |
|---|---|---|---|
| Me | Me | Et | Et |

Reaction 1

| Compound T9 (g) | Compound V1 (g) | CMPI (g) | TEA (ml) | THF (ml) | Reaction time (hr) | Column sol. | Product | Amount (g) |
|---|---|---|---|---|---|---|---|---|
| 6.000 | 16.300 | 26.200 | 14.30 | 30.00 | 15 | nHx:EA = 2:1 | I-a108 | 3.030 |

Reaction 2

| Compound I-a108 (g) | Pd(OH)$_2$ (g) | MeOH (ml) | Reaction time (hr) | Column sol. | Product | Amount (g) |
|---|---|---|---|---|---|---|
| 8.000 | 1.200 | 50.00 | 15.00 | MC:MeOH = 10:1 | I-b108 | 5.000 |

Reaction 3

| Compound I-b108 (g) | Compound P2 (g) | CMPI (g) | TEA (ml) | THF (ml) | Reaction time (hr) | Column sol. | Product | Amount (g) |
|---|---|---|---|---|---|---|---|---|
| 1.022 | 1.130 | 0.966 | 0.70 | 20.00 | 19 | nHx:EA = 1:2 | I-c108 | 1.590 |

Reaction 4-a

| Compound I-c108 (g) | TFA (ml) | MC (ml) | Reaction time (hr) | Column sol. | Amount (g) | HPLC min |
|---|---|---|---|---|---|---|
| 1.590 | 1.80 | 10.00 | 3 | MC:MeOH = 20:1 | 0.251 | 21.54 |

ESI-MS(M$^+$+1): 585
1H-NMR(CDCl$_3$): (two rotamers)δ 0.78-0.90 and 0.95(6H, m and d, J=7.9Hz), 0.97-1.10(3H, m), 1.10 and 1.22 (3H, m), 1.31 and 1.39(9H, s), 2.21-2.25(3H, s), 2.19-2.40(1H, m), 2.55-3.35(7H, m), 2.69 and 2.72(3H, s), 3.42-3.75(3H, m), 4.95-5.10(1H, m), 5.12(1H, d, J=10.6Hz), 6.44 and 6.58(1H, d, J=8.8Hz), 6.50(3/5H, m), 6.79(3/5H, dd, J=8.1, 2.5Hz), 6.88-7.00(12/5H, m), 7.05-7.20(12/5H, m) 7.27(1H, brs)

TABLE D-109

Example 109
N-Et-Phe(4-F)-N-Me-Val-N-Et-Tyr(3-tBu)-NHEt

| R31 | R32 | R33 | R34 |
|---|---|---|---|
| Et | Me | Et | Et |

Reaction 1

| Compound T9 (g) | Compound V1 (g) | CMPI (g) | TEA (ml) | THF (ml) | Reaction time (hr) | Column sol. | Product | Amount (g) |
|---|---|---|---|---|---|---|---|---|
| 6.000 | 16.300 | 26.200 | 14.30 | 30.00 | 15 | nHx:EA = 2:1 | I-a109 | 3.030 |

TABLE D-109-continued

Example 109
N-Et-Phe(4-F)-N-Me-Val-N-Et-Tyr(3-tBu)-NHEt

| R31 | R32 | R33 | R34 |
|---|---|---|---|
| Et | Me | Et | Et |

Reaction 2

| Compound I-a109 (g) | Pd(OH)$_2$ (g) | MeOH (ml) | Reaction time (hr) | Column sol. | Product | Amount (g) |
|---|---|---|---|---|---|---|
| 8.000 | 1.200 | 50.00 | 15 | MC:MeOH = 10:1 | I-b109 | 5.000 |

Reaction 3

| Compound I-b109 (g) | Compound P3 (g) | CMPI (g) | TEA (ml) | THF (ml) | Reaction time (hr) | Column sol. | Product | Amount (g) |
|---|---|---|---|---|---|---|---|---|
| 0.800 | 0.819 | 0.606 | 0.40 | 16.00 | 18 | nHx:EA = 1:2 | I-c109 | 1.000 |

Reaction 4-b

| Compound I-c109 (g) | Pd/C (g) | MeOH (ml) | Reaction time (hr) | Column sol. | Amount (g) | HPLC min |
|---|---|---|---|---|---|---|
| 1.000 | 0.150 | 20.00 | 15 | MC:MeOH = 20:1 | 0.127 | 21.920 |

ESI-MS(M$^+$+1): 599
1H-NMR(CDCl$_3$): (two rotamers)δ 0.78-0.88 and 0.92(6H, m and d, J=7.4Hz), 0.98-1.18(6H, m), 1.20(3H, q, J=6.4Hz), 1.34 and 1.38(9H, s), 2.20-2.43(2H, m), 2.43-3.35(8H, m), 2.68 and 2.80(3H, s), 3.42-3.78(3H, m), 4.90-5.12(1H, m), 5.12(1H, d, J=10.6Hz), 6.42 and 6.58(1H, d, J=15.3Hz), 6.50(1/3H, m), 6.80(2/3H, dd, J=8.8, 2.1Hz), 6.85-7.00(3H, m), 7.05-7.17(10/3H, m), 7.30(2/3H, brs).

TABLE D-110

Example 110
Phe(4-F)-N-Et-Val-Tyr(3-tBu)-NHEt

| R31 | R32 | R33 | R34 |
|---|---|---|---|
| H | Et | H | Et |

Reaction 1

| Compound T3 (g) | Compound V2 (g) | CMPI (g) | TEA (ml) | THF (ml) | Reaction time (hr) | Column sol. | Product | Amount (g) |
|---|---|---|---|---|---|---|---|---|
| 6.000 | 6.240 | 8.700 | 6.60 | 120.00 | 20 | nHx:EA = 1:1 | I-a110 | 9.540 |

Reaction 2

| Compound I-a110 (g) | Pd(OH)$_2$ (g) | MeOH (ml) | Reaction time (hr) | Column sol. | Product | Amount (g) |
|---|---|---|---|---|---|---|
| 6.000 | 0.600 | 60.00 | 20 | MC:MeOH = 20:1 | I-b110 | 3.570 |

Reaction 3

| Compound I-b110 (g) | Compound P1 (g) | CMPI (g) | TEA (ml) | THF (ml) | Reaction time (hr) | Column sol. | Product | Amount (g) |
|---|---|---|---|---|---|---|---|---|
| 1.200 | 1.500 | 2.000 | 1.00 | 20.00 | 20 | nHx:EA = 1:1 | I-c110 | 0.400 |

Reaction 4-a

| Compound I-c110 (g) | TFA (ml) | MC (ml) | Reaction time (hr) | Column sol. | Amount (g) | HPLC min |
|---|---|---|---|---|---|---|
| 0.400 | 0.60 | 3.00 | 4 | MC:MeOH = 20:1 | 0.200 | 20.25 |

ESI-MS(M$^+$+1): 557
1H-NMR(CDCl$_3$): δ 0.62-1.16(12H, m), 1.38(9H, s), 2.25-2.45(1H, m), 2.62-3.86(9H, m), 3.92 and 3.95(1H, d, J=10.0Hz), 4.44-5.56(1H, m), 5.67-5.90(1H, m), 6.60-7.20(7H, m), 9.05 and 9.08(1H, d, J=7.8Hz)

TABLE D-111

Example 111
N-Me-Phe(4-F)-N-Et-Val-Tyr(3-tBu)-NHEt

| R31 | R32 | R33 | R34 |
|---|---|---|---|
| Me | Et | H | Et |

Reaction 1

| Compound T3 (g) | Compound V2 (g) | CMPI (g) | TEA (ml) | THF (ml) | Reaction time (hr) | Column sol. | Product | Amount (g) |
|---|---|---|---|---|---|---|---|---|
| 6.000 | 6.240 | 8.700 | 6.60 | 120.00 | 20 | nHx:EA = 1:1 | I-a111 | 9.540 |

Reaction 2

| Compound I-a111 (g) | Pd(OH)₂ (g) | MeOH (ml) | Reaction time (hr) | Column sol. | Product | Amount (g) |
|---|---|---|---|---|---|---|
| 6.000 | 0.600 | 60.00 | 20 | MC:MeOH = 20:1 | I-b111 | 3.570 |

Reaction 3

| Compound I-b111 (g) | Compound P2 (g) | CMPI (g) | TEA (ml) | THF (ml) | Reaction time (hr) | Column sol. | Product | Amount (g) |
|---|---|---|---|---|---|---|---|---|
| 1.000 | 1.600 | 2.000 | 1.00 | 20.00 | 20 | nHx:EA = 1:1 | I-c111 | 0.400 |

Reaction 4-a

| Compound I-c111 (g) | TFA (ml) | MC (ml) | Reaction time (hr) | Column sol. | Amount (g) | HPLC min |
|---|---|---|---|---|---|---|
| 0.400 | 0.60 | 3.00 | 4 | MC:MeOH = 20:1 | 0.300 | 20.77 |

ESI-MS(M$^+$+1): 571
1H-NMR(CDCl$_3$): (two rotamers)δ 0.67 and 0.80-1.16(12H, d and m, J=6.8Hz), 1.37(9H, s), 2.30(3H, s), 2.35-2.39(1H, m), 2.79-3.22(8H, m), 3.53-3.59(1H, m), 4.04-4.15(1H, m), 4.39-4.46(1H, m), 5.73-5.77(1H, m), 6.61 and 6.64(1H, d, J=8.2Hz), 6.84-7.19(6H, m)

TABLE D-112

Example 112
N-Et-Phe(4-F)-N-Et-Val-Tyr(3-tBu)-NHEt

| R31 | R32 | R33 | R34 |
|---|---|---|---|
| Et | Et | H | Et |

Reaction 1

| Compound T3 (g) | Compound V2 (g) | CMPI (g) | TEA (ml) | THF (ml) | Reaction time (hr) | Column sol. | Product | Amount (g) |
|---|---|---|---|---|---|---|---|---|
| 6.000 | 6.240 | 8.700 | 6.60 | 120.00 | 20 | nHx:EA = 1:1 | I-a112 | 9.540 |

Reaction 2

| Compound I-a112 (g) | Pd(OH)₂ (g) | MeOH (ml) | Reaction time (hr) | Column sol. | Product | Amount (g) |
|---|---|---|---|---|---|---|
| 6.200 | 0.600 | 60.00 | 20 | MC:MeOH = 20:1 | I-b112 | 3.570 |

Reaction 3

| Compound I-b112 (g) | Compound P3 (g) | CMPI (g) | TEA (ml) | THF (ml) | Reaction time (hr) | Column sol. | Product | Amount (g) |
|---|---|---|---|---|---|---|---|---|
| 1.000 | 1.585 | 2.000 | 1.00 | 20.00 | 20 | nHx:EA = 1:1 | I-c112 | 0.550 |

TABLE D-112-continued

Example 112
N-Et-Phe(4-F)-N-Et-Val-Tyr(3-tBu)-NHEt

| R31 | R32 | R33 | R34 |
|---|---|---|---|
| Et | Et | H | Et |

Reaction 4-b

| Compound I-c112 (g) | Pd(OH)$_2$ (g) | MeOH (ml) | Reaction time (hr) | Column sol. | Amount (g) | HPLC min |
|---|---|---|---|---|---|---|
| 0.400 | 0.050 | 4.00 | 20 | MC:MeOH = 30:1 | 0.098 | 21.090 |

ESI-MS(M$^+$+1): 585
1H-NMR(CDCl$_3$): (two rotamers)δ 0.48 and 0.71-1.31(15H, d and m, J=7.4Hz), 1.37(9H, s), 2.20-2.61(2H, m), 2.71-3.34(10H, m), 3.60-3.82(2H, m), 4.40-4.56(1H, m), 5.80-5.98(1H, m), 6.67-7.01(3H, m), 7.02-7.16(3H, m), 7.48 and 7.50(1H, d, J=6.8Hz), 8.73 and 8.76(1H, d, J=7.9Hz)

TABLE D-113

Example 113
Phe(4-F)-N-Et-Val-N-Me-Tyr(3-tBu)-NHEt

| R31 | R32 | R33 | R34 |
|---|---|---|---|
| H | Et | Me | Et |

Reaction 1

| Compound T6 (g) | Compound V2 (g) | CMPI (g) | TEA (ml) | THF (ml) | Reaction time (hr) | Column sol. | Product | Amount (g) |
|---|---|---|---|---|---|---|---|---|
| 4.170 | 8.720 | 5.880 | 4.20 | 150.00 | 20 | nHx:EA = 1:2 | I-a113 | 5.500 |

Reaction 2

| Compound I-a113 (g) | Pd/C (g) | MeOH (ml) | Reaction time (hr) | Column sol. | Product | Amount (g) |
|---|---|---|---|---|---|---|
| 5.500 | 0.500 | 100.00 | 2 | MC:MeOH = 20:1 | I-b113 | 3.200 |

Reaction 3

| Compound I-b113 (g) | Compound P1 (g) | CMPI (g) | TEA (ml) | THF (ml) | Reaction time (hr) | Column sol. | Product | Amount (g) |
|---|---|---|---|---|---|---|---|---|
| 1.000 | 0.850 | 0.760 | 0.60 | 20.00 | 18 | nHx:EA = 1:2 | I-c113 | 0.320 |

Reaction 4-a

| Compound I-c113 (g) | TFA (ml) | MC (ml) | Reaction time (hr) | Column sol. | Amount (g) | HPLC min |
|---|---|---|---|---|---|---|
| 0.320 | 0.70 | 7.40 | 6 | MC:MeOH = 20:1 | 0.020 | 20.260 |

ESI-MS(M$^+$+1): 571
1H-NMR(CDCl$_3$): (two rotamers)δ 0.36-0.96(8H, m), 0.98-1.10(4H, m), 1.35 and 1.39(9H, s), 2.28-2.41(1H, m), 2.84 and 3.04(3H, s), 2.55-3.39(8H, m), 3.68-3.78(1H, m), 4.90-5.32(2H, m)6.45 and 6.65(1H, d, J=6.0Hz), 6.77-7.23(6H, m)

TABLE D-114

Example 114
N-Me-Phe(4-F)-N-Et-Val-N-Me-Tyr(3-tBu)-NHEt

| R31 | R32 | R33 | R34 |
|---|---|---|---|
| Me | Et | Me | Et |

Reaction 1

| Compound T6 (g) | Compound V2 (g) | CMPI (g) | TEA (ml) | THF (ml) | Reaction time (hr) | Column sol. | Product | Amount (g) |
|---|---|---|---|---|---|---|---|---|
| 4.170 | 8.720 | 5.880 | 4.20 | 150.00 | 20 | nHx:EA = 1:2 | I-a114 | 5.500 |

TABLE D-114-continued

Example 114
N-Me-Phe(4-F)-N-Et-Val-N-Me-Tyr(3-tBu)-NHEt

| R31 | R32 | R33 | R34 |
|---|---|---|---|
| Me | Et | Me | Et |

Reaction 2

| Compound I-a114 (g) | Pd/C (g) | MeOH (ml) | Reaction time (hr) | Column sol. | Product | Amount (g) |
|---|---|---|---|---|---|---|
| 5.500 | 0.500 | 100.00 | 2 | MC:MeOH = 20:1 | I-b114 | 3.200 |

Reaction 3

| Compound I-b114 (g) | Compound P2 (g) | CMPI (g) | TEA (ml) | THF (ml) | Reaction time (hr) | Column sol. | Product | Amount (g) |
|---|---|---|---|---|---|---|---|---|
| 1.000 | 0.850 | 0.760 | 0.60 | 20.00 | 20 | nHx:EA = 1:2 | I-c114 | 0.300 |

Reaction 4-a

| Compound I-c114 (g) | TFA (ml) | MC (ml) | Reaction time (hr) | Column sol. | Amount (g) | HPLC min |
|---|---|---|---|---|---|---|
| 0.300 | 0.70 | 6.80 | 6 | MC:MeOH = 20:1 | 0.030 | 20.880 |

ESI-MS(M$^+$+1): 585
1H-NMR(CDCl$_3$): (two rotamers)δ 0.51, 0.81, 0.87 and 0.91(6H, d, J=6.3-6.9Hz), 0.94, 1.04 and 1.17(6H, t, J=3.6Hz), 1.34 and 1.39(9H, s), 2.18-2.62(1H, m), 2.38(3H, s), 2.57-2.88(3H, m), 2.91-3.38(5H, m), 2.94 and 3.06(3H, s), 3.49 and 3.57(1H, t, J=6.4-7.2Hz), 5.49-5.32(2H, m), 6.02-6.1 and 6.53-6.59(1H, m), 6.45 and 6.64 (1H, d, J=8.0Hz), 6.76-7.03(3H, m), 7.08-7.19(3H, m)

TABLE D-115

Example 115
N-Et-Phe(4-F)-N-Et-Val-Me-Tyr(3-tBu)-NHEt

| R31 | R32 | R33 | R34 |
|---|---|---|---|
| Et | Et | Me | Et |

Reaction 1

| Compound T6 (g) | Compound V2 (g) | CMPI (g) | TEA (ml) | THF (ml) | Reaction time (hr) | Column sol. | Product | Amount (g) |
|---|---|---|---|---|---|---|---|---|
| 4.170 | 8.720 | 5.880 | 4.20 | 150.00 | 20 | nHx:EA = 1:2 | I-a115 | 5.500 |

Reaction 2

| Compound I-a115 (g) | Pd/C (g) | MeOH (ml) | Reaction time (hr) | Column sol. | Product | Amount (g) |
|---|---|---|---|---|---|---|
| 5.500 | 0.500 | 100.00 | 2 | MC:MeOH = 20:1 | I-b115 | 3.200 |

Reaction 3

| Compound I-b115 (g) | Compound P3 (g) | CMPI (g) | TEA (ml) | THF (ml) | Reaction time (hr) | Column sol. | Product | Amount (g) |
|---|---|---|---|---|---|---|---|---|
| 1.000 | 0.850 | 0.760 | 0.60 | 20.00 | 18 | nHx:EA = 1:2 | I-c115 | 0.300 |

Reaction 4-b

| Compound (g) | Pd/C (ml) | MeOH (ml) | Reaction time (hr) | Column sol. | Amount (g) | HPLC min |
|---|---|---|---|---|---|---|
| 0.300 | 0.030 | 4.00 | 3 | MC:MeOH = 20:1 | 0.040 | 21.59 |

ESI-MS(M$^+$+1): 599
1H-NMR(CDCl$_3$): (two rotamers)δ 0.38-1.17(15H, m), 1.34, 1.36 and 1.38(9H, s), 3.38-2.12(1H, m), 3.55(1H, t, J=6.3Hz), 3.47-3.72(1H, m), 4.88-5.37(2H, m), 5.79-6.09 and 6.63-6.7(1H, m), 6.42 and 6.62(1H, dd, J=8.3, 7.4Hz), 7.05-7.22(6H, m)

TABLE D-116

Example 116
Phe(4-F)-N-Et-Val-N-Et-Tyr(3-tBu)-NHEt

| R31 | R32 | R33 | R34 |
|---|---|---|---|
| H | Et | Et | Et |

Reaction 1

| Compound T9 (g) | Compound V2 (g) | CMPI (g) | TEA (ml) | THF (ml) | Reaction time (hr) | Column sol. | Product | Amount (g) |
|---|---|---|---|---|---|---|---|---|
| 5.020 | 9.110 | 17.550 | 9.50 | 100.00 | 16 | nHx:EA = 3:1 | I-a116 | 3.030 |

Reaction 2

| Compound I-a116 (g) | Pd(OH)$_2$ (g) | MeOH (ml) | Reaction time (hr) | Column sol. | Product | Amount (g) |
|---|---|---|---|---|---|---|
| 3.030 | 0.454 | 60.00 | 14 | MC:MeOH = 10:1 | I-b116 | 2.24 |

Reaction 3

| Compound I-b116 (g) | Compound P4 (g) | CMPI (g) | TEA (ml) | THF (ml) | Reaction time (hr) | Column sol. | Product | Amount (g) |
|---|---|---|---|---|---|---|---|---|
| 0.600 | 0.680 | 0.549 | 0.40 | 12.00 | 18 | nHx:EA = 1:1 | I-c116 | 0.200 |

Reaction 4-b

| Compound I-c116 (g) | Pd/C (g) | MeOH (ml) | Reaction time (hr) | Column sol. | Amount (g) | HPLC min |
|---|---|---|---|---|---|---|
| 0.200 | 0.030 | 4.00 | 3 | MC:MeOH = 20:1 | 0.053 | 21.59 |

ESI-MS(M$^+$+1): 585
1H-NMR(CDCl$_3$): (two rotamers)δ 0.60 and 0.78-1.30(15H, d and m, J=7.9Hz), 1.34 and 1.38(9H, s), 2.22-2.50 (1H, m), 2.52-3.00(3H, m), 3.00-3.54(6H, m), 3.54-3.94(2H, m), 4.82-5.05(1H, m), 5.10(1H, m), 6.45-6.70(2H, m), 6.80(3/4H, m), 6.91-7.25(21/4H, m)

TABLE D-117

Example 117
N-Me-Phe(4-F)-N-Et-Val-N-Et-Tyr(3-tBu)-NHEt

| R1 | R2 | R3 | R4 |
|---|---|---|---|
| Me | Et | Et | Et |

Reaction 1

| Compound T9 (g) | Compound V2 (g) | CMPI (g) | TEA (ml) | THF (ml) | Reaction time (hr) | Column sol. | Product | Amount (g) |
|---|---|---|---|---|---|---|---|---|
| 5.020 | 9.110 | 17.550 | 9.50 | 100.00 | 16 | nHx:EA = 3:1 | I-a117 | 3.030 |

Reaction 2

| Compound I-a117 (g) | Pd(OH)$_2$ (g) | MeOH (ml) | Reaction time (hr) | Column sol. | Product | Amount (g) |
|---|---|---|---|---|---|---|
| 3.030 | 0.454 | 60.00 | 14 | MC:MeOH = 10:1 | I-b117 | 2.240 |

Reaction 3

| Compound I-b117 (g) | Compound P2 (g) | CMPI (g) | TEA (ml) | THF (ml) | Reaction time (hr) | Column sol. | Product | Amount (g) |
|---|---|---|---|---|---|---|---|---|
| 0.845 | 0.681 | 0.585 | 0.40 | 16.00 | 48 | nHx:EA = 1:1 | I-c117 | 0.378 |

TABLE D-117-continued

Example 117
N-Me-Phe(4-F)-N-Et-Val-N-Et-Tyr(3-tBu)-NHEt

| R1 | R2 | R3 | R4 |
|----|----|----|----|
| Me | Et | Et | Et |

Reaction 4-a

| Compound I-c117 (g) | TFA (ml) | MC (ml) | Reaction time (hr) | Column sol. | Amount (g) | HPLC min |
|---|---|---|---|---|---|---|
| 0.378 | 0.80 | 4.00 | 3 | MC:MeOH = 20:1 | 0.056 | 22.20 |

ESI-MS(M⁺+1): 599
1H-NMR(CDCl$_3$): (two rotamers)δ 0.75 and 0.83-1.10(10H, d and m, J=7.9Hz), 1.10-1.30(5H, m), 1.35 and 1.39(9H, s), 2.30 and 2.33(3H, s), 2.30-2.48(1H, m), 2.65-3.89(12H, m), 4.90 and 5.07(1H, m), 5.18 and 5.23 (1H, d, J=9.7Hz), 6.48 and 6.58(1H, d, J=8.8Hz), 6.63(1/2H, m), 6.80(1H, dd, J=8.1, 1.8Hz), 6.90-7.0(7/2H, m), 7.05(1/2H, d, J=1.7Hz), 7.06-7.20(5/2H, m)

TABLE D-118

Example 118
N-Et-Phe(4-F)-N-Et-Val-N-Et-Tyr(3-tBu)-NHEt

| R31 | R32 | R33 | R34 |
|-----|-----|-----|-----|
| Et  | Et  | Et  | Et  |

Reaction 1

| Compound T9 (g) | Compound V2 (g) | CMPI (g) | TEA (ml) | THF (ml) | Reaction time (hr) | Column sol. | Product | Amount (g) |
|---|---|---|---|---|---|---|---|---|
| 5.020 | 9.110 | 17.550 | 9.50 | 100.0 | 16 | nHx:EA = 3:1 | I-a118 | 3.030 |

Reaction 2

| Compound I-a118 (g) | Pd(OH)$_2$ (g) | MeOH (ml) | Reaction time (hr) | Column sol. | Product | Amount (g) |
|---|---|---|---|---|---|---|
| 3.030 | 0.454 | 60.00 | 14 | MC:MeOH = 10:1 | I-b118 | 2.240 |

Reaction 3

| Compound I-b118 (g) | Compound P3 (g) | CMPI (g) | TEA (ml) | THF (ml) | Reaction time (hr) | Column sol. | Product | Amount (g) |
|---|---|---|---|---|---|---|---|---|
| 0.520 | 0.642 | 0.475 | 0.30 | 10.00 | 48 | nHx:EA = 1:1 | I-c118 | 0.174 |

Reaction 4-b

| Compound I-c118 (g) | Pd/C (g) | MeOH (ml) | Reaction time (hr) | Column sol. | Amount (g) | HPLC min |
|---|---|---|---|---|---|---|
| 0.174 | 0.026 | 4.00 | 3 | MC:MeOH = 20:1 | 0.141 | 22.84 |

ESI-MS(M⁺+1): 613
1H-NMR(CDCl$_3$): (two rotamers)δ 0.75 and 0.80-0.98(8H, d and m, J=7.9Hz), 0.98-1.08(6H, m), 1.08-1.23 (4H, m), 1.34 and 1.38(9H, s), 2.23-2.88(6H, m), 2.93-3.88(9H, m), 4.92 and 5.08(1H, m), 5.15 and 5.22(1H, d, J=9.7Hz), 6.49 and 6.57(1H, d, J=8.8Hz), 6.63(1/2H, m), 6.80(1/2H, dd, J=8.1, 1.7Hz), 6.85-7.00(3H, m), 7.05 (1/2H, d, J=1.7Hz), 7.08-7.20(5/2H, m)

TABLE D-119

Example 119
Phe(4-F)-N-Me-Val-Tyr(3-tBu)-NH-n-Pr

| R31 | R32 | R33 | R34 |
|-----|-----|-----|-----|
| H   | Me  | H   | n-Pr |

Reaction 1

| Compound T10 (g) | Compound V1 (g) | CMPI (g) | TEA (ml) | THF (ml) | Reaction time (hr) | Column sol. | Product | Amount (g) |
|---|---|---|---|---|---|---|---|---|
| 0.580 | 0.640 | 0.670 | 0.92 | 10.00 | 18 | nHx:EA = 1:1 | I-a119 | 1.030 |

TABLE D-119-continued

Example 119
Phe(4-F)-N-Me-Val-Tyr(3-tBu)-NH-n-Pr

| R31 | R32 | R33 | R34 |
|---|---|---|---|
| H | Me | H | n-Pr |

Reaction 2

| Compound I-a119 (g) | Pd(OH)$_2$ (g) | MeOH (ml) | Reaction time (hr) | Column sol. | Product | Amount (g) |
|---|---|---|---|---|---|---|
| 1.030 | 0.200 | 10.00 | 2 | MC:MeOH = 15:1 | I-b119 | 0.76 |

Reaction 3

| Compound I-b119 (g) | Compound P1 (g) | CMPI (g) | TEA (ml) | THF (ml) | Reaction time (hr) | Column sol. | Product | Amount (g) |
|---|---|---|---|---|---|---|---|---|
| 0.760 | 0.660 | 0.650 | 1.07 | 10.00 | 19 | nHx:EA = 1:2 | I-c119 | 1.100 |

Reaction 4-a

| Compound I-c119 (g) | TFA (ml) | MC (ml) | Reaction time (hr) | Column sol. | Amount (g) | HPLC min |
|---|---|---|---|---|---|---|
| 1.100 | 6.66 | 13.30 | 2 | MC:MeOH = 15:1 | 0.210 | 20.10 |

ESI-MS(M$^+$+1): 557
1H-NMR(CDCl$_3$): (two rotamers)δ 0.68-0.92(9H, m), 1.38 and 1.39(9H, s), 2.69 and 2.85(3H, s), 1.37-3.20(7H, m), 3.62-3.90(1H, m), 3.93(1H, d, J=10.9Hz), 4.42-4.57(1H, m), 6.62-7.17(7H, m)

TABLE D-120

Example 120
Phe(4-F)-N-Me-Val-Tyr(3-tBu)-NH-i-Pr

| R31 | R32 | R33 | R34 |
|---|---|---|---|
| H | Me | H | i-Pr |

Reaction 1

| Compound T11 (g) | Compound V1 (g) | CMPI (g) | TEA (ml) | THF (ml) | Reaction time (hr) | Column sol. | Product | Amount (g) |
|---|---|---|---|---|---|---|---|---|
| 0.660 | 0.630 | 0.910 | 0.66 | 10.00 | 3 | nHx:EA = 1:1 | I-a120 | 1.210 |

Reaction 2

| Compound I-a120 (g) | Pd/C (g) | MeOH (ml) | Reaction time (hr) | Column sol. | Product | Amount (g) |
|---|---|---|---|---|---|---|
| 1.210 | 0.500 | 20.00 | 2 | MC:MeOH = 20:1 | I-b120 | 0.900 |

Reaction 3

| Compound I-b120 (g) | Compound P1 (g) | CMPI (g) | TEA (ml) | THF (ml) | Reaction time (hr) | Column sol. | Product | Amount (g) |
|---|---|---|---|---|---|---|---|---|
| 0.900 | 0.650 | 0.880 | 0.64 | 15.00 | 3 | nHx:EA = 2:1 | I-c120 | 1.300 |

Reaction 4-a

| Compound I-c120 (g) | TFA (ml) | MC (ml) | Reaction time (hr) | Column sol. | Amount (g) | HPLC min |
|---|---|---|---|---|---|---|
| 1.300 | 5.00 | 20.00 | 2 | MC:MeOH = 25:1 | 0.960 | 19.99 |

ESI-MS(M$^+$+1): 557
1H-NMR(CDCl$_3$): (two rotamers)δ 0.70-1.07(12H, m), 1.35 and 1.38(9H, s), 1.72(2H, brs), 2.29-2.37(1H, m), 2.72 and 2.83(3H, s), 2.52-2.74(4H, m), 3.60 and 3.81(1H, dd, J=8.2, 3.0Hz), 3.85-3.98(2H, m), 4.42-4.60(1H, m), 5.48 and 5.69(1H, d, J=7.8Hz), 6.62-6.80(2H, m), 6.90-6.98(3H, m), 7.06-7.11(2H, m), 9.07(1H, d, J=8.2Hz)

TABLE D-121

Example 121
Phe(4-F)-N-Me-Val-N-Me-Tyr(3-tBu)-NH-c-Pr

| R31 | R32 | R33 | R34 |
|---|---|---|---|
| H | Me | Me | c-Pr |

Reaction 1

| Compound T12 (g) | Compound V1 (g) | CMPI (g) | TEA (ml) | THF (ml) | Reaction time (hr) | Column sol. | Product | Amount (g) |
|---|---|---|---|---|---|---|---|---|
| 0.500 | 0.520 | 0.600 | 0.70 | 10.00 | 18 | nHx:EA:MC = 1:1:1 | I-a121 | 0.850 |

Reaction 2

| Compound I-a121 (g) | Pd(OH)$_2$ (g) | MeOH (ml) | Reaction time (hr) | Column sol. | Product | Amount (g) |
|---|---|---|---|---|---|---|
| 0.850 | 0.200 | 10.00 | 2 | MC:MeOH = 15:1 | I-b121 | 0.400 |

Reaction 3

| Compound I-b121 (g) | Compound P1 (g) | CMPI (g) | TEA (ml) | THF (ml) | Reaction time (hr) | Column sol. | Product | Amount (g) |
|---|---|---|---|---|---|---|---|---|
| 0.400 | 0.540 | 0.550 | 0.57 | 10.00 | 19 | nHx:EA:MC = 1:3:1 | I-c121 | 0.720 |

Reaction 4-a

| Compound I-c121 (g) | TFA (ml) | MC (ml) | Reaction time (hr) | Column sol. | Amount (g) | HPLC min |
|---|---|---|---|---|---|---|
| 0.700 | 3.30 | 6.60 | 2 | MC:MeOH = 15:1 | 0.210 | 18.12 |

ESI-MS(M$^+$+1): 569
1H-NMR(CDCl$_3$): (two rotamers)δ 0.17-0.88(11H, m), 1.31 and 1.34(9H, s), 2.28, 2.63, 2.90 and 3.93(6H, s), 2.11-3.08(6H, m), 4.43-5.26(3H, m), 6.48 and 6.61(1H, d, J=7.9Hz), 6.62-7.16(6H, m)

Scheme 4 shows the synthesis process of Examples 122-131

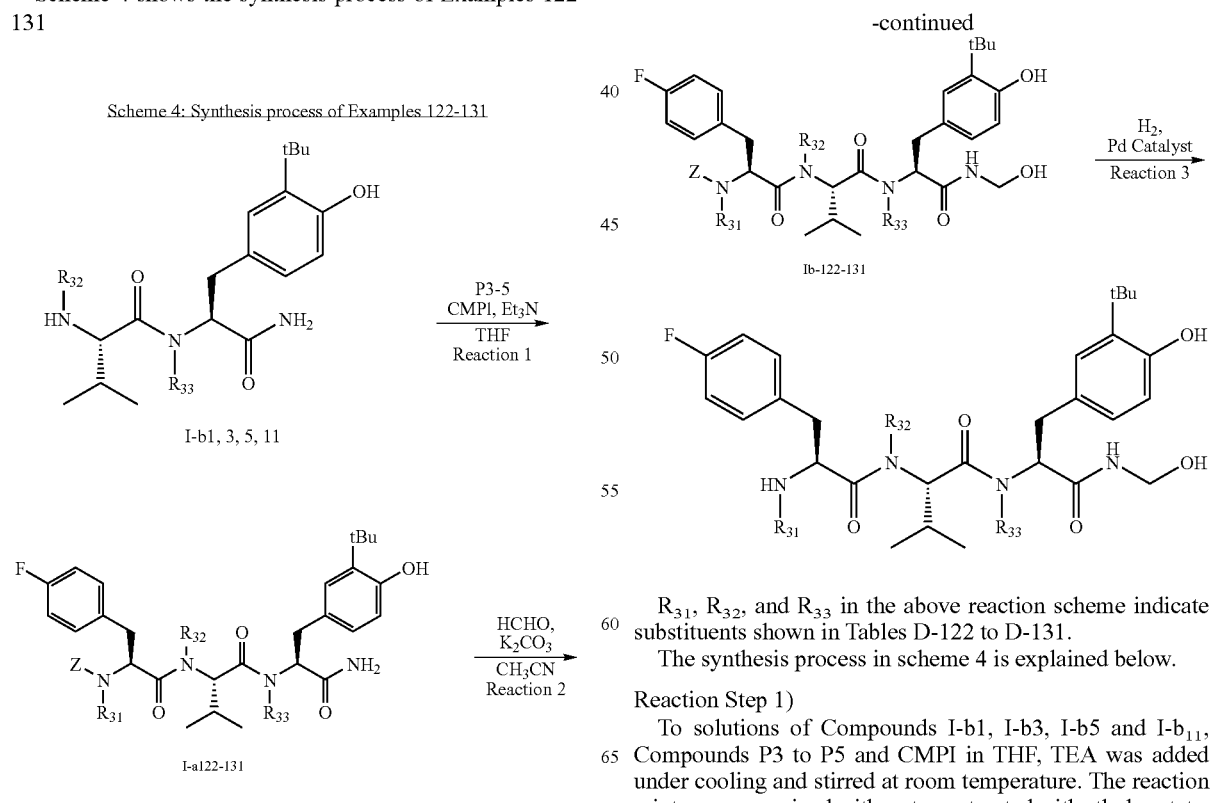

$R_{31}$, $R_{32}$, and $R_{33}$ in the above reaction scheme indicate substituents shown in Tables D-122 to D-131.

The synthesis process in scheme 4 is explained below.

Reaction Step 1)

To solutions of Compounds I-b1, I-b3, I-b5 and I-b$_{11}$, Compounds P3 to P5 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure and the thus obtained residues were subjected to silica gel column chromatography, giving Compounds I-a122 to I-a131.

Reaction Step 2)

To solutions of Compounds I-a122 to I-a131 in $CH_3CN$, 38% HCHO and an aqueous $K_2CO_3$ solution were added and stirred at room temperature. The reaction mixtures were mixed with a saturated aqueous $NH_4Cl$ solution, extracted with ethyl acetate, washed with saturated brine, dried over anhydrous magnesium sulfate and filtered. The filtrates were concentrated under reduced pressure and the thus obtained residue was subjected to silica gel column chromatography, giving Compounds I-b122 to I-b131.

Reaction Step 3)

To solutions of Compounds I-b122 to I-b131 in methanol, Pd/C was added and stirred in a hydrogen atmosphere at room temperature. After filtering off the Pd/C, the filtrates were concentrated under reduced pressure and the thus obtained residues were subjected to silica gel column chromatography, giving the titled compounds.

Examples conducted according to Scheme 4 are shown in Tables D-122 to D-131.

TABLE D-122

Example 122
Phe(4-F)-N-Me-Val-Tyr(3-tBu)-NHCH$_2$OH

| R31 | R32 | R33 |
|---|---|---|
| H | Me | H |

Reaction 1

| Compound I-b1 (g) | Compound P4 (g) | CMPI (g) | TEA (ml) | THF (ml) | Reaction time (hr) | Column sol. | Product | Amount (g) |
|---|---|---|---|---|---|---|---|---|
| 0.700 | 0.760 | 0.610 | 0.56 | 40.00 | 4 | nHx:EA = 2:1 | I-a122 | 1.000 |

Reaction 2

| Compound I-a122 (g) | HCHO (ml) | K$_2$CO$_3$ (g) | CH$_3$CN (ml) | Reaction time (hr) | Column sol. | Product | Amount (g) |
|---|---|---|---|---|---|---|---|
| 1.000 | 1.15 | 0.430 | 30.00 | 2 | nHx:EA:MC = 1:3:1 | I-b122 | 0.900 |

Reaction 3

| Compound I-b122 (g) | Pd/C (g) | MeOH (ml) | Reaction time (hr) | Column sol. | Amount (g) | HPLC min |
|---|---|---|---|---|---|---|
| 0.900 | 0.140 | 13.00 | 2 | EA:MeOH = 15:1 | 0.560 | 15.91 |

ESI-MS(M$^+$+1): 545
1H-NMR(CDCl$_3$): (two rotamers)δ 0.69, 0.75, 0.83 and 0.90(6H, d, J=6.4-6.7Hz), 1.34 and 1.35(9H, s), 2.22-3.17 (5H, m)2.68 and 2.88(3H, s), 3.57 and 3.82(1H, dd, J=8.0-8.5, 5.5-6.0Hz), 4.51-4.74(3H, m), 6.61-9.02(8H, m)

TABLE D-123

Example 123
N-Me-Phe(4-F)-N-Me-Val-Tyr(3-tBu)-NHCH$_2$OH

| R31 | R32 | R33 |
|---|---|---|
| Me | Me | H |

Reaction 1

| Compound I-b1 (g) | Compound P5 (g) | CMPI (g) | TEA (ml) | THF (ml) | Reaction time (hr) | Column sol. | Product | Amount (g) |
|---|---|---|---|---|---|---|---|---|
| 0.500 | 0.569 | 0.439 | 0.60 | 20.00 | 16 | nHx:EA = 1:1 | I-a123 | 0.920 |

Reaction 2

| Compound I-a123 (g) | HCHO (ml) | K$_2$CO$_3$ (g) | CH$_3$CN (ml) | Reaction time (hr) | Column sol. | Product | Amount (g) |
|---|---|---|---|---|---|---|---|
| 0.910 | 1.00 | 0.380 | 25.00 | 2 | nHx:EA = 1:1 | I-b123 | 0.927 |

TABLE D-123-continued

Example 123
N-Me-Phe(4-F)-N-Me-Val-Tyr(3-tBu)-NHCH$_2$OH

| R31 | R32 | R33 |
|---|---|---|
| Me | Me | H |

Reaction 3

| Compound I-b123 (g) | Pd/C (g) | MeOH (ml) | Reaction time (hr) | Column sol. | Amount (g) | HPLC min |
|---|---|---|---|---|---|---|
| 0.270 | 0.100 | 10.00 | 1.5 | EA:MeOH = 30:1 | 0.228 | 16.04 |

ESI-MS(M$^+$ +1):559
1H-NMR(CDCl$_3$): (two rotamers) δ 0.52, 0.77 and 0.89(6H, d, J=6.5-6.8Hz), 1.31 and 1.37(9H, s), 2.08-2.17(1H, m), 2.24 and 2.28(3H, s), 2.46 and 2.56(3H, s), 258-3.06(4H, m), 3.54-4.35(2H, m), 6.62-7.34(7H, m)

TABLE D-124

Example 124
N-Et-Phe(4-F)-N-Me-Val-Tyr(3-tBu)-NHCH$_2$OH

| R31 | R32 | R33 |
|---|---|---|
| Et | Me | H |

Reaction 1

| Compound I-b1 (g) | Compound P3 (g) | CMPI (g) | TEA (ml) | THF (ml) | Reaction time (hr) | Column sol. | Product | Amount (g) |
|---|---|---|---|---|---|---|---|---|
| 0.630 | 0.750 | 0.555 | 0.75 | 20.00 | 26 | nHx:EA = 1:1 | I-a124 | 0.987 |

Reaction 2

| Compound I-a124 (g) | HCHO (ml) | K$_2$CO$_3$ (g) | CH$_3$CN (ml) | Reaction time (hr) | Column sol. | Product | Amount (g) |
|---|---|---|---|---|---|---|---|
| 0.980 | 1.10 | 0.400 | 25.00 | 2 | nHx:EA = 1:1 | I-b124 | 0.911 |

Reaction 3

| Compound I-b124 (g) | Pd/C (g) | MeOH (ml) | Reaction time (hr) | Column sol. | Amount (g) | HPLC min |
|---|---|---|---|---|---|---|
| 0.910 | 0.200 | 15.00 | 3 | MC:MeOH = 15:1 | 0.250 | 16.36 |

ESI-MS(M$^+$ +1):573
1H-NMR(CDCl$_3$): (two rotamers) δ 0.50, 0.75, 0.82 and 0.85(6H, d, J=6.3-7.0Hz), 0.98 and 1.12(3H, t, J=6.7Hz), 1.40 and 1.45 (9H, s), 2.15(1H, m), 2.42 and 2.46(3H, s), 2.40(2H, m), 2.60-3.10(5H, m), 3.63(1H, dd, J=10.6, 6.0Hz), 4.50(1H, m), 4.70(2H, m), 6.70(4H, m), 6.90(1H, m), 7.00(1H, s), 7.12(1H s), 7.20 and 7.40(1H, m), 8.75(1H, d, J=6.6Hz)

TABLE D-125

Example 125
N-Me-Phe(4-F)-N-Me-Val-N-Me-Tyr(3-tBu)-NHCH$_2$OH

| R31 | R32 | R33 |
|---|---|---|
| Me | Me | Me |

Reaction 1

| Compound I-b3 (g) | Compound P5 (g) | CMPI (g) | TEA (ml) | THF (ml) | Reaction time (hr) | Column sol. | Product | Amount (g) |
|---|---|---|---|---|---|---|---|---|
| 1.200 | 1.420 | 1.100 | 0.92 | 30.00 | 14 | nHx:EA:MC = 1:2:1 | I-a125 | 1.800 |

Reaction 2

| Compound I-a125 (g) | HCHO (ml) | K$_2$CO$_3$ (g) | CH$_3$CN (ml) | Reaction time (hr) | Column sol. | Product | Amount (g) |
|---|---|---|---|---|---|---|---|
| 1.790 | 1.970 | 0.730 | 52.00 | 2 | nHx:EA:MC = 1:3:1 | I-b125 | 1.500 |

TABLE D-125-continued

Example 125
N-Me-Phe(4-F)-N-Me-Val-N-Me-Tyr(3-tBu)-NHCH$_2$OH

| R31 | R32 | R33 |
|---|---|---|
| Me | Me | Me |

Reaction 3

| Compound I-b125 (g) | Pd/C (g) | MeOH (ml) | Reaction time (hr) | Column sol. | Amount (g) | HPLC min |
|---|---|---|---|---|---|---|
| 1.500 | 0.230 | 20.00 | 2 | EA:MeOH = 10:1 | 0.970 | 17.27 |

ESI-MS(M$^+$ +1):573
1H-NMR(CDCl$_3$): (two rotamers) d 0.57, 0.79 and 0.92(6H, d, J=6.3-6.8Hz), 1.34 ad 1.38(9H, s), 2.22 and 2.25(3H, s) 2.29(1H, m), 2.52 and 2.82(3H, s), 2.55-2.89(3H, m), 2.92 and 3.04(3H, s), 3.20 and 3.39(1H, dd, J=11.1-14.1,6.3-7.3Hz), 3.46 and 3.61 (1H, t, J=6.8-6.9Hz), 4.59-4.76(2H, m), 5.03 and 5.14(1H, d, J=10.5Hz), 5.11 and 5.37(1H, dd, J=6.3, 9.73Hz), 6.39 and 6.61(1H, d, J=7.9-8.2 Hz), 6.77-7.12(6H, m)

TABLE D-126

Example 126
N-Et-Phe(4-F)-N-Me-Val-N-Me-Tyr(3-tBu)-NHCH$_2$OH

| R31 | R32 | R33 |
|---|---|---|
| Et | Me | Me |

Reaction 1

| Compound I-b3 (g) | Compound P3 (g) | CMPI (g) | TEA (ml) | THF (ml) | Reaction time (hr) | Column sol. | Product | Amount (g) |
|---|---|---|---|---|---|---|---|---|
| 1.400 | 1.720 | 1.270 | 1.07 | 38.00 | 14 | nHx:EA: = 2:1 | I-a126 | 2.110 |

Reaction 2

| Compound I-a126 (g) | HCHO (ml) | K$_2$CO$_3$ (g) | CH$_3$CN (ml) | Reaction time (hr) | Column sol. | Product | Amount (g) |
|---|---|---|---|---|---|---|---|
| 2.050 | 2.20 | 0.820 | 59.00 | 2 | nHx:EA:MC = 1:3:1 | I-b126 | 2.000 |

Reaction 3

| Compound I-b126 (g) | Pd/C (g) | MeOH (ml) | Reaction time (hr) | Column sol. | Amount (g) | HPLC min |
|---|---|---|---|---|---|---|
| 1.950 | 0.290 | 27.00 | 2 | EA:MeOH = 10:1 | 1.350 | 18.09 |

ESI-MS(M$^+$ +1):587
1H-NMR(CDCl$_3$): (two rotamers) δ 0.60, 0.79 and 0.91(6H, d, J=6.4-6.5Hz), 1.00 and 1.04(t, 3H, J=6.7-7.2Hz), 1.34 and 1.39 (9H, s), 218-2.89(7H, m) 2.52 and 2.77(3H, s), 2.95 and 3.04(3H, s), 3.22 and 3.39(1H, dd, J=14.0-15.0, 7.9-7.6Hz), 3.57 and 3.70(t, 1H, J=6.8, 6.9Hz), 4.59-4.73(2H, m), 5.05 and 5.13(1H, d, J=10.6-10.7Hz), 5.13 and 5.31(1H, dd, J=9.0, 7.3Hz), 6.45 and 6.62(1H, d, J=7.9 and 8.04Hz), 6.78-7.12(6H, m)

TABLE D-127

Example 127
Phe(4-F)-N-Me-Val-N-Et-Tyr(3-tBu)-NHCH$_2$OH

| R31 | R32 | R33 |
|---|---|---|
| H | Me | Et |

Reaction 1

| Compound I-b5 (g) | Compound P4 (g) | CMPI (g) | TEA (ml) | THF (ml) | Reaction time (hr) | Column sol. | Product | Amount (g) |
|---|---|---|---|---|---|---|---|---|
| 0.760 | 1.240 | 0.990 | 0.91 | 20.00 | 12 | nHx:EA = 1:1 | I-a127 | 0.440 |

TABLE D-127-continued

Example 127
Phe(4-F)-N-Me-Val-N-Et-Tyr(3-tBu)-NHCH$_2$OH

| R31 | | | | R32 | | | R33 | |
|---|---|---|---|---|---|---|---|---|
| H | | | | Me | | | Et | |

| | | | | Reaction 2 | | | | |
|---|---|---|---|---|---|---|---|---|
| Compound I-a127 (g) | HCHO (ml) | K$_2$CO$_3$ (g) | CH$_3$CN (ml) | Reaction time (hr) | Column sol. | Product | Amount (g) | |
| 0.420 | 0.76 | 0.035 | 5.00 | 12 | nHx:EA = 1:1 | I-b127 | 0.370 | |

| | | | | Reaction 3 | | | |
|---|---|---|---|---|---|---|---|
| Compound I-b127 (g) | Pd/C (g) | MeOH (ml) | Reaction time (hr) | Column sol. | Amount (g) | HPLC min | |
| 0.350 | 0.050 | 15.00 | 3 | MC:MeOH = 20:1 | 0.100 | 18.26 | |

ESI-MS(M$^+$ +1):573
1H-NMR(CDCl$_3$): (two rotamers) δ 0.67, 0.81 and 0.91(6H, d, J=5.9-6.9Hz), 1.07 and 1.16(3H, t, J=6.8 and 6.1Hz), 1.33 and 1.38(9H, s), 2.24-2.49(2H, m), 2.58-2.75(1H, m), 2.78 and 3.05(3H, s), 2.83-3.03(1H, m), 3.15-3.30(1H, m), 3.37-3.44(1H, m), 3.55-3.65(1H, m), 3.75-3.90(1H, m), 4.55-4.76(2H, m), 4.85-5.06(2H, m), 6.43 and 6.61(1H, d, J=8.1-8.4Hz), 6.75-7.1(6H, m), 7.36 and 8.03(1H, brs)

TABLE D-128

Example 128
N-Me-Phe(4-F)-N-Me-Val-N-Et-Tyr(3-tBu)-NHCH$_2$OH

| R31 | | | | R32 | | | R33 | |
|---|---|---|---|---|---|---|---|---|
| Me | | | | Me | | | Et | |

| | | | | Reaction 1 | | | | |
|---|---|---|---|---|---|---|---|---|
| Compound I-b5 (g) | Compound P5 (g) | CMPI (g) | TEA (ml) | THF (ml) | Reaction time (hr) | Column sol. | Product | Amount (g) |
| 0.700 | 1.230 | 0.950 | 0.91 | 20.00 | 12 | nHx:EA = 1:1 | I-a128 | 0.640 |

| | | | | Reaction 2 | | | | |
|---|---|---|---|---|---|---|---|---|
| Compound I-a128 (g) | HCHO (ml) | K$_2$CO$_3$ (g) | CH$_3$CN (ml) | Reaction time (hr) | Column sol. | Product | Amount (g) | |
| 0.610 | 1.10 | 0.051 | 3.00 | 12 | nHx:EA = 1:1 | I-b128 | 0.560 | |

| | | | | Reaction 3 | | | |
|---|---|---|---|---|---|---|---|
| Compound I-b128 (g) | Pd/C (g) | MeOH (ml) | Reaction time (hr) | Column sol. | Amount (g) | HPLC min | |
| 0.540 | 0.080 | 23.00 | 1 | MC:MeOH = 20:1 | 0.200 | 18.85 | |

ESI-MS(M$^+$ +1):587
1H-NMR(CDCl$_3$): (two rotamers) δ 0.77, 0.83, 0.84 and 0.93(6H, d, J=6.4-6.8Hz),1.12 and 1.18(3H, t, J=7.0-7.1Hz), 1.34 and 1.38(9H, s), 2.25(3H, s), 2.29-2.39(1H, m), 2.64-3.01(3H, m), 2.75 and 2.85(3H, s), 3.21-3.33(1H, m), 3.42-3.69(3H, m), 4.58-4.76(2H, m), 4.88-4.94 and 5.10-5.19(1H, m), 5.12(1H, dd, J=10.5, 2.6Hz), 6.50 and 6.61(1H, d, J=8.0Hz), 6.80-6.98(3H, m), 7.07-7.15(3H, m), 7.42 and 8.29(1H, t, J=6.0-6.4Hz)

TABLE D-129

Example 129
N-Et-Phe(4-F)-N-Me-Val-N-Et-Tyr(3-tBu)-NHCH$_2$OH

| R31 | | | | R32 | | | R33 | |
|---|---|---|---|---|---|---|---|---|
| Et | | | | Me | | | Et | |

| | | | | Reaction 1 | | | | |
|---|---|---|---|---|---|---|---|---|
| Compound I-b5 (g) | Compound P3 (g) | CMPI (g) | TEA (ml) | THF (ml) | Reaction time (hr) | Column sol. | Product | Amount (g) |
| 1.000 | 1.370 | 1.010 | 0.92 | 25.00 | 12 | nHx:EA = 1:1 | I-a129 | 0.970 |

TABLE D-129-continued

Example 129
N-Et-Phe(4-F)-N-Me-Val-N-Et-Tyr(3-tBu)-NHCH$_2$OH

| R31 | R32 | R33 |
|---|---|---|
| Et | Me | Et |

Reaction 2

| Compound I-a129 (g) | HCHO (ml) | K$_2$CO$_3$ (g) | CH$_3$CN (ml) | Reaction time (hr) | Column sol. | Product | Amount (g) |
|---|---|---|---|---|---|---|---|
| 0.950 | 1.70 | 0.079 | 6.00 | 12 | nHx:EA = 1:1 | I-b129 | 0.790 |

Reaction 3

| Compound I-b129 (g) | Pd/C (g) | MeOH (ml) | Reaction time (hr) | Column sol. | Amount (g) | HPLC min |
|---|---|---|---|---|---|---|
| 0.780 | 0.120 | 30.00 | 2 | MC:MeOH = 20:1 | 0.300 | 19.68 |

ESI-MS(M$^+$ +1):601
1H-NMR(CDCl$_3$): (two rotamers) δ 0.76, 0.82, 0.83 and 0.92(6H, d, J=6.4-6.9Hz), 1.00-1.28(6H, m), 1.34 and 1.38(9H, s), 2.25-2.43(2H, m), 2.49-2.59(1H, m), 2.65-2.97(3H, m), 2.72 and 2.79(3H, s), 3.17-3.33(1H, m), 3.41-3.76(3H, m), 4.52-4.74(2H, m), 4.85-4.90 and 5.12-5.16(1H, m), 5.09(1H, dd J=10.7, 3.5Hz), 6.48 and 6.59(1H, d, J=8.0-8.4Hz), 6.80-6.98(3H, m), 7.08-7.17 (3H, m), 7.38 and 8.32(1H, t, J=5.7Hz)

TABLE D-130

Example 130
Phe(4-F)-N-Et-Val-N-Et-Tyr(3-tBu)-NHCH$_2$OH

| R31 | R32 | R33 |
|---|---|---|
| H | Et | Et |

Reaction 1

| Compound I-b11 (g) | Compound P4 (g) | CMPI (g) | TEA (ml) | THF (ml) | Reaction time (hr) | Column sol. | Product | Amount (g) |
|---|---|---|---|---|---|---|---|---|
| 0.770 | 1.250 | 1.000 | 0.68 | 25.00 | 30 | nHx:EA = 1:1 | I-a130 | 0.200 |

Reaction 2

| Compound I-a130 (g) | HCHO (ml) | K$_2$CO$_3$ (g) | CH$_3$CN (ml) | Reaction time (hr) | Column sol. | Product | Amount (g) |
|---|---|---|---|---|---|---|---|
| 0.200 | 0.36 | 0.400 | 4.00 | 12 | nHx:EA = 1:1 | I-b130 | 0.100 |

Reaction 3

| Compound I-b130 (g) | Pd/C (g) | MeOH (ml) | Reaction time (hr) | Column sol. | Amount (g) | HPLC min |
|---|---|---|---|---|---|---|
| 0.100 | 0.015 | 5.00 | 1 | MC:MeOH = 25:1 | 0.016 | 18.41 |

ESI-MS(M$^+$ +1):587
1H-NMR(CDCl$_3$): (two rotamers) d 0.54, 0.81, 0.87 and 0.93(6H, d, J=6.0-6.8Hz), 1.12 and 1.19(6H, t, J=6.8-7.2Hz), 1.36 and 1.39(9H, s), 2.25-2.43(1H, m), 2.60-2.74(1H, m), 2.78-2.99(2H, m), 3.16-3.50(4H, m), 3.56-3.80(2H, m), 4.53-4.74(2H, m), 4.83-4.88 and 4.99-5.11(2H, m), 6.48 and 6.63(1H, d, J=7.9Hz), 6.80-6.85 and 6.96-7.18(6H, m), 7.46-7.49 and 7.58-

TABLE D-131

Example 131
N-Me-Phe(4-F)-N-Et-Val-N-Et-Tyr(3-tBu)-NHCH$_2$OH

| R31 | R32 | R33 |
|---|---|---|
| Me | Et | Et |

Reaction 1

| Compound I-b11 (g) | Compound P5 (g) | CMPI (g) | TEA (ml) | THF (ml) | Reaction time (hr) | Column sol. | Product | Amount (g) |
|---|---|---|---|---|---|---|---|---|
| 0.770 | 1.340 | 1.000 | 0.68 | 25.00 | 30 | nHx:EA = 1:1 | I-a131 | 0.170 |

TABLE D-131-continued

Example 131
N-Me-Phe(4-F)-N-Et-Val-N-Et-Tyr(3-tBu)-NHCH₂OH

| | R31<br>Me | | | R32<br>Et | | | R33<br>Et | |
|---|---|---|---|---|---|---|---|---|
| | | | | Reaction 2 | | | | |
| Compound<br>I-a131 (g) | HCHO<br>(ml) | K₂CO₃<br>(g) | CH₃CN<br>(ml) | Reaction time<br>(hr) | Column sol. | Product | Amount (g) | |
| 0.170 | 0.31 | 0.014 | 4.00 | 12 | nHx:EA = 1:1 | I-b131 | 0.080 | |
| | | | | Reaction 3 | | | | |
| Compound<br>I-b131 (g) | Pd/C<br>(g) | MeOH<br>(ml) | Reaction time<br>(hr) | | Column sol. | | Amount<br>(g) | HPLC min |
| 0.080 | 0.012 | 4.00 | 1 | | MC:MeOH = 25:1 | | 0.040 | 18.97 |

ESI-MS(M⁺ +1):601
1H-NMR(CDCl₃): (two rotamers) δ 0.64(1H, d, J=6.4Hz), 0.85-0.97(7H, m), 1.10-1.19(4H, m), 1.33 and 1.37(9H, s), 2.25-2.43 (1H, m), 2.29 and 2.31(3H, s), 2.67-2.86(3H, m), 3.12-3.65 and 3.74-3.81(6H, m), 4.52-4.72(2H, m), 4.87-4.92 and 5.09-5.19 (2H, m), 6.45 and 6.59(1H, d, J=8.0 and 8.4Hz), 6.78(2/3H, dd, J=7.9, 1.5Hz), 6.90-6.98(7/3H, m), 7.04(2/3H, d, J=1.5Hz), 7.10-7.16(7/3H, m), 7.50 and 7.90(1H, t, J=6.3 and 6.0Hz)

Scheme 5 shows the synthesis process of Example 132.

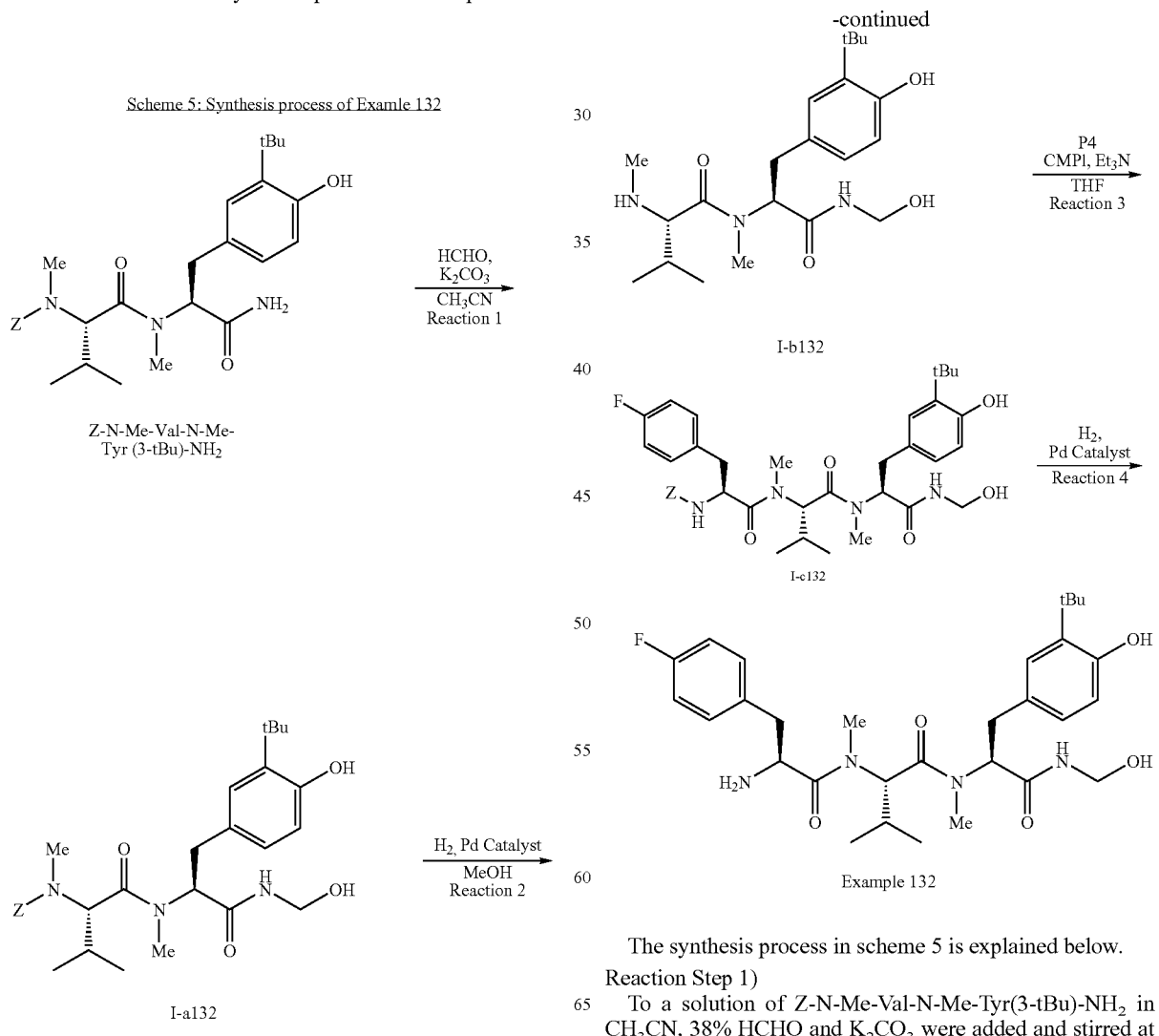

The synthesis process in scheme 5 is explained below.

Reaction Step 1)

To a solution of Z-N-Me-Val-N-Me-Tyr(3-tBu)-NH₂ in CH₃CN, 38% HCHO and K₂CO₃ were added and stirred at room temperature. The reaction mixture was mixed with a saturated aqueous NH₄Cl solution, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-a132.

Reaction Step 2)

To a solution of Compound I-a132 in methanol, Pd/C was added and stirred in a hydrogen atmosphere at room temperature. After filtering off the Pd/C, the filtrate was concentrated under reduced pressure; the thus obtained residue was purified by column chromatography (silica gel) to give Compound I-b132.

Reaction Step 3)

To a solution of Compound I-b132, Compound P4 and CMPI in THF, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure; the a thus obtained residue was purified by column chromatography (silica gel) to give Compound I-c132.

Reaction Step 4)

To a solution of Compound I-c132 in methanol, Pd/C was added and stirred in a hydrogen atmosphere at room temperature. After filtering off the Pd/C, the filtrate was concentrated under reduced pressure; the thus obtained residue was purified by column chromatography (silica gel) to give the titled compound.

Table D-132 shows Example conducted according to Scheme 5.

TABLE D-132

Example 132
Phe(4-F)-N-Me-Val-N-Me-Tyr(3-tBu)-NHCH₂OH

| R31 | R32 | R33 |
|---|---|---|
| H | Me | Me |

Reaction 1

| Z-N-Me-Val-N-Me-Tyr(3-tBu)-NH₂ (g) | HCHO (ml) | K₂CO₃ (g) | CH₃CN (ml) | Reaction time (hr) | Column sol. | Product | Amount (g) |
|---|---|---|---|---|---|---|---|
| 2.000 | 3.00 | 1.100 | 71.00 | 2 | nHx:EA:MC = 1:3:1 | I-a132 | 2.000 |

Reaction 2

| Compound I-a132 (g) | Pd/C (g) | MeOH (ml) | Reaction time (hr) | Column sol. | Product | Amount (g) |
|---|---|---|---|---|---|---|
| 1.950 | 0.290 | 50.00 | 1 | EA:MeOH = 7:1 | I-b132 | 0.730 |

Reaction 3

| Compound I-b132 (g) | Compound P4 (g) | CMPI (g) | TEA (ml) | THF (ml) | Reaction time (hr) | Column sol. | Product | Amount (g) |
|---|---|---|---|---|---|---|---|---|
| 0.730 | 0.880 | 0.700 | 0.50 | 35.00 | 4 | nHx:EA = 1:4 | I-c132 | 0.700 |

Reaction 4

| Compound I-c132 (g) | Pd/C (g) | MeOH (ml) | Reaction time (hr) | Column sol. | Amount (g) | HPLC min |
|---|---|---|---|---|---|---|
| 0.700 | 0.110 | 10.00 | 4 | MC:MeOH = 20:1 | 0.410 | 16.64 |

ESI-MS(M⁺ +1):559

1H-NMR(CDCl₃): (two rotamers) δ 0.49, 0.74, 0.78 and 0.91(6H, d, J=5.9-6.6Hz), 1.33 and 1.37(9H, s), 2.20-2.97(4H, m), 2.54, 2.81 and 3.00(6H, s), 3.16 and 3.35(1H, dd, J=13.7-15.1, 6.2-6.5Hz), 3.71 and 3.85(1H, dd, J=8.1-9.4, 4.5-5.0Hz), 4.64 and 4.69 (2H, d, J=6.0-6.4Hz), 4.79 and 5.06(1H, d, J=10.2-10.6Hz), 5.00 and 5.36(1H, dd, J=9.2, 5.5Hz), 6.43 and 6.64(1H, d, J=7.8Hz), 6.71-7.12(6H, m)

Scheme 6 shows the synthesis process of Examples 133-135.

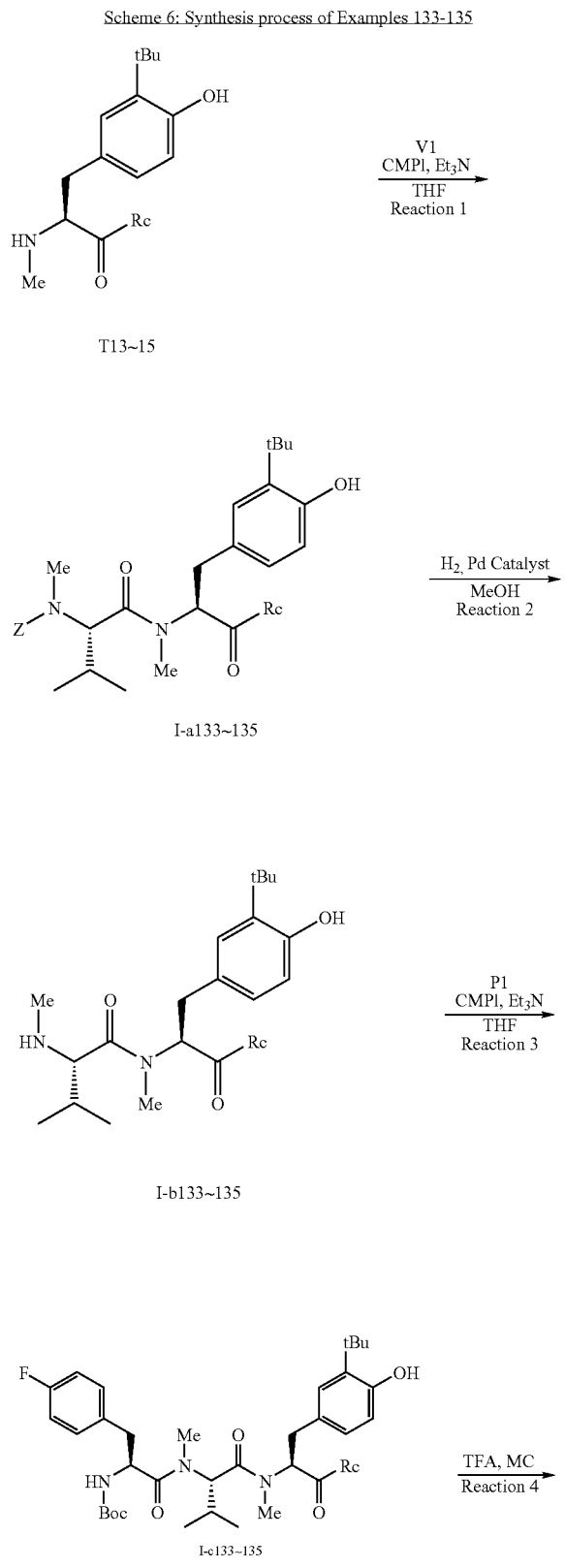

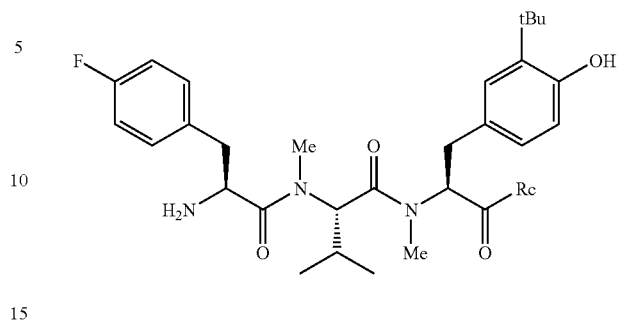

Rc in the above Scheme indicates the substituent shown in Tables D-133 to D-135.

The synthesis process in scheme 6 is explained below.

Reaction Step 1)

To solutions of Compounds T13 to T15, Compound VI and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-a133 to I-a135.

Reaction Step 2)

To solutions of Compound I-a133 to I-a135 in methanol, palladium hydroxide/carbon was added and stirred in a hydrogen atmosphere at room temperature. The reaction mixtures were filtered and the filtrates were concentrated under reduced pressure; the thus obtained residues were purified by column chromatography (silica gel) to give Compounds I-b133 to I-b135.

Reaction Step 3)

To solutions of Compounds I-b133 to I-b135, Compound P1 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-c133 to I-c135.

Reaction Step 4)

To solutions of Compounds I-c133 to I-c135 in dichloromethane, TFA was added under cooling and stirred at room temperature. The reaction mixtures were neutralized by the addition of a saturated aqueous NaHCO3 solution, extracted with dichloromethane, washed with saturated brine, dried over anhydrous magnesium sulfate and filtered. The filtrates were concentrated under reduced pressure; the thus obtained residues were purified by column chromatography (silica gel) to give the titled compounds.

Tables D-133 to D-135 show Examples conducted according to Scheme 6.

TABLE D-133

Example 133
(2S)-2-[(2S)-2-amino-3-(4-fluorophenyl)-N-methylpropanoylamino]-N-
((1S)-1-{[3-(tert-butyl)-4-hydroxyphenyl]methyl}-2-morpholin-
4-yl-2-oxoethyl)-3-methyl-N-methylbutanamide
R
4-morpholine Reaction 1

| Compound T13 (g) | Compound V1 (g) | CMPI (g) | TEA (ml) | THF (ml) | Reaction time (hr) | Column sol. | Product | Amount (g) |
|---|---|---|---|---|---|---|---|---|
| 0.600 | 0.490 | 0.720 | 0.50 | 20.00 | 20 | nHx:EA = 1:1 | I-a133 | 0.900 |

Reaction 2

| Compound I-a133 (g) | Pd(OH)$_2$ (g) | MeOH (ml) | Reaction time (hr) | Column sol. | Product | Amount (g) |
|---|---|---|---|---|---|---|
| 0.900 | 0.100 | 20.00 | 20 | MC:MeOH = 20:1 | I-b133 | 0.600 |

Reaction 3

| Compound I-b33 (g) | Compound P1 (g) | CMPI (g) | TEA (ml) | THF (ml) | Reaction time (hr) | Column sol. | Product | Amount (g) |
|---|---|---|---|---|---|---|---|---|
| 0.600 | 0.450 | 0.530 | 0.40 | 20.00 | 20 | nHx:EA = 1:1 | I-c133 | 0.850 |

Reaction 4

| Compound I-c133 (g) | TFA (ml) | MC (ml) | Reaction time (hr) | Column sol. | Amount (g) | HPLC min |
|---|---|---|---|---|---|---|
| 0.850 | 3.00 | 10.00 | 4 | MC:MeOH = 20:1 | 0.600 | 19.77 |

ESI-MS(M$^+$ +1):599
1H-NMR(CDCl$_3$): (two rotamers) δ 0.78 and 0.85(6H, d, J=6.2-6.7Hz), 1.37(9H, s), 2.23-2.28(1H, m), 2.24(3H, s), 2.48-2.56 (1H, m), 2.79-2.87(5H, m), 3.02-3.09(1H, m), 3.40-3.74(10H, m), 5.01-5.05(1H, J=10.0Hz), 5.79-5.84(1H, m), 6.39 and 6.41(1H, d, J=7.9Hz), 6.74-6.77(1H, m), 6.99-7.18(6H, m)

TABLE D-134

Example 134
(2S)-2-[(2S)-2-amino-3-(4-fluorophenyl)-N-methylpropanoylamino]-N-
((1S)-1-{[3-(tert-butyl)-4-hydroxyphenyl]methyl}-2-[4-
(methylsulfonyl)piperazinyl]-2-oxoethyl)-3-methyl-N-methylbutanamide
R
4-(methylsulfonyl) piperazine Reaction 1

| Compound T14 (g) | Compound V1 (g) | CMPI (g) | TEA (ml) | THF (ml) | Reaction time (hr) | Column sol. | Product | Amount (g) |
|---|---|---|---|---|---|---|---|---|
| 1.200 | 0.790 | 1.100 | 0.84 | 20.00 | 20 | nHx:EA = 1:1 | I-a134 | 1.500 |

Reaction 2

| Compound I-a134 (g) | Pd(OH)$_2$ (g) | MeOH (ml) | Reaction time (hr) | Column sol. | Product | Amount (g) |
|---|---|---|---|---|---|---|
| 1.500 | 0.300 | 20.00 | 20 | MC:MeOH = 20:1 | I-b134 | 0.900 |

Reaction 3

| Compound I-b134 (g) | Compound P1 (g) | CMPI (g) | TEA (ml) | THF (ml) | Reaction time (hr) | Column sol. | Product | Amount (g) |
|---|---|---|---|---|---|---|---|---|
| 0.700 | 0.520 | 0.430 | 0.38 | 15 | 2 | nHx:EA = 1:1 | I-c134 | 0.700 |

TABLE D-134-continued

Example 134
(2S)-2-[(2S)-2-amino-3-(4-fluorophenyl)-N-methylpropanoylamino]-N-((1S)-1-{[3-(tert-butyl)-4-hydroxyphenyl]methyl}-2-[4-(methylsulfonyl)piperazinyl]-2-oxoethyl)-3-methyl-N-methylbutanamide

R 4-(methylsulfonyl) piperazine

Reaction 4

| Compound I-c134 (g) | TFA (ml) | MC (ml) | Reaction time (hr) | Column sol. | Amount (g) | HPLC min |
|---|---|---|---|---|---|---|
| 0.700 | 3.00 | 10.00 | 4 | MC:MeOH = 20:1 | 0.350 | 19.94 |

ESI-MS(M$^+$ +1):677

1H-NMR(CDCl$_3$): (two rotamers) δ 0.79 and 0.85(6H, d, J=6.2-6.7Hz), 1.37(9H, s), 2.23-2.28(1H, m), 2.52-2.69(4H, m), 2.73 (3H, s), 2.75-2.89(7H, m), 3.01-3.16(4H, m), 3.58-3.78(1H, m), 5.03 and 5.07(1H, d, J=10.6Hz), 5.75-5.81(1H, m), 6.42 and 6.45 (1H, d, J=7.9Hz), 6.76-6.80(1H, m), 6.99-7.18(6H, m)

TABLE D-135

Example 135
Ethyl 2-[4-((2S)-2-{(2S)-2-[(2S)-2-amino-3-(4-fluorophenyl)-N-methylpropanoylamino]-3,N-dimethylbutanoylamino}-3-[3-(tert-butyl)-4-hydroxyphenyl]propanoyl)piperazinyl]acetate

R ethyl-2-piperazinylacetate

Reaction 1

| Compound T15 (g) | Compound V1 (g) | CMPI (g) | TEA (ml) | THF (ml) | Reaction time (hr) | Column sol. | Product | Amount (g) |
|---|---|---|---|---|---|---|---|---|
| 0.643 | 0.547 | 0.527 | 0.50 | 16.00 | 16 | nHx:EA = 2:3 | I-a135 | 0.827 |

Reaction 2

| Compound I-a135 (g) | Pd(OH)$_2$ (g) | MeOH (ml) | Reaction time (hr) | Column sol. | Product | Amount (g) |
|---|---|---|---|---|---|---|
| 0.827 | 0.250 | 13.00 | 1 | MC:MeOH = 20:1 | I-b135 | 0.645 |

Reaction 3

| Compound I-b135 (g) | Compound P1 (g) | CMPI (g) | TEA (ml) | THF (ml) | Reaction time (hr) | Column sol. | Product | Amount (g) |
|---|---|---|---|---|---|---|---|---|
| 0.645 | 0.458 | 0.413 | 0.40 | 12 | 16 | nHx:EA = 2:3 | I-c135 | 0.796 |

Reaction 4

| Compound I-c135 (g) | TFA (ml) | MC (ml) | Reaction time (hr) | Column sol. | Amount (g) | HPLC min |
|---|---|---|---|---|---|---|
| 0.796 | 2.00 | 5.00 | 1 | MC:MeOH = 30:1 | 0.430 | 17.1 |

ESI-MS(M$^+$ +1):684

1H-NMR(CDCl$_3$): (two rotamers) δ 0.77 and 0.84(6H, d, J=6.4-6.8Hz), 1.26(3H, t, J=7.1Hz), 1.26(9H, s), 2.22-2.30(1H, m), 2.47-2.54(1H, m), 3.00-3.07(1H, m) 2.40, 2.81 and 3.18(6H, s), 3.54-3.73(5H, m), 4.18(2H, q, J=7.1Hz), 5.03(2H, d, J=10.4Hz), 5.85(1H, t, J=2.3Hz), 6.40(1H, d, J=7.9Hz), 6.72-6.75(1H, dd, J=9.7, 1.9Hz), 7.00-7.26(5H, m)

Scheme 7 shows the synthesis process of Example 136.

Scheme 8 shows the synthesis process of Example 137.

Scheme 7: Synthesis process of Example 136

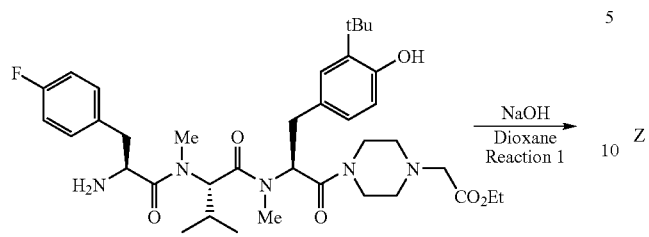

Example 135

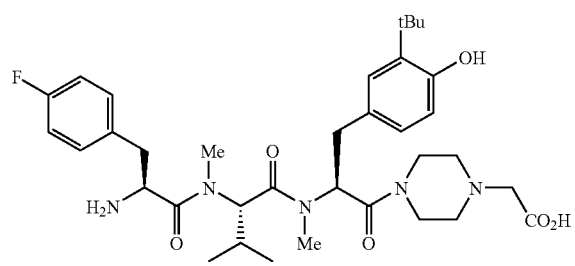

Example 136

Scheme 8: Synthesis process of Example 137

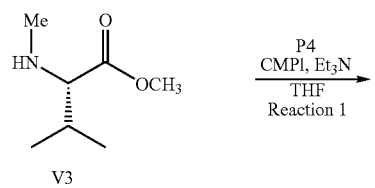

V3

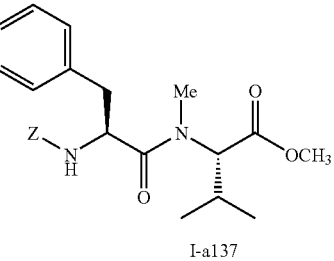

I-a137

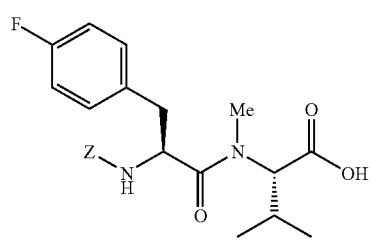

I-b137

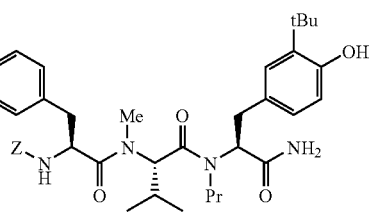

I-c137

Reaction Step 1)

The compound obtained in Example 135 was added to a dioxane solution, mixed with a 2N-NaOH solution and stirred at room temperature. The reaction mixture was mixed with water, extracted with ethyl acetate, washed with saturated brine, dried over anhydrous magnesium sulfate and filtered. The filtrate was concentrated under reduced pressure; the thus obtained residue was purified by column chromatography (silica gel) to give the titled compound.

Table D-136 shows Example conducted according to Scheme 7.

TABLE D-136

Example 136
2-[4-((2S)-2-{(2S)-2-[(2S)-2-amino-3-(4-fluorophenyl)-N-methylpropanoylamino]-3,N-dimethylbutanoylamino}-3-[3-(tert-butyl)-4-hydroxyphenyl]propanoyl)piperazinyl]acetic acid
Reaction

| Compound of Example 135 (g) | NaOH (g) | $H_2O$ (ml) | Dioxane (ml) | Reaction time (hr) | Column sol. | Amount (g) | HPLC min |
|---|---|---|---|---|---|---|---|
| 0.375 | 0.400 | 5.00 | 5.00 | 16 | MC:MeOH = 20:1 | 0.200 | 14.97 |

ESI-MS(M$^+$ +1):656

1H-NMR(CD3OD): (two rotamers) δ 0.78 and 0.82(6H, d, J=6.1Hz), 1.27(9H, s), 2.12-2.29(1H, m), 2.74-3.12(8H, m), 3.61-3.82(4H, m), 2.48, 2.94, 3.25 and 3.55(6H, s), 4.50-456(1H, q, J=10.5Hz), 5.02(1H, d, J=10.5Hz), 5.73(1H, t, J=7.9Hz), 6.74-6.78(1H, dd, J=9.4, 2.2Hz), 7.00-7.27(6H, m)

-continued

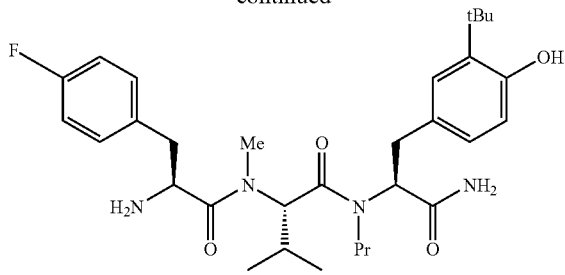

Example 137

The synthesis process in scheme 8 is explained below.

Reaction Step 1)

To a solution of Compound V3, Compound P4 and CMPI in THF, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-a137.

Reaction Step 2)

To a solution of Compound I-a137 in methanol, NaOH and water were added and stirred at room temperature. The reaction mixture was mixed with a saturated aqueous $NH_4Cl$ solution, concentrated under reduced pressure, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-b137.

Reaction Step 3)

To a solution of Compound I-b137, Compound T16 and CMPI in THF, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-c137.

Reaction Step 4)

To a solution of Compound I-c137 in methanol, Pd/C was added and stirred in a hydrogen atmosphere at room temperature. After filtering off the Pd/C, the filtrate was concentrated under reduced pressure; the thus obtained residue was purified by column chromatography (silica gel) to give the titled compound.

Table D-137 shows Example conducted according to Scheme 8.

TABLE D-137

Example 137
Phe(4-F)-N-Me-Val-N-Pr-Tyr(3-tBu)-$NH_2$

| Reaction 1 | | | | | | | | |
|---|---|---|---|---|---|---|---|---|
| Compound V3 (g) | Compound P4 (g) | CMPI (g) | TEA (ml) | THF (ml) | Reaction time (hr) | Column sol. | Product | Amount (g) |
| 1.146 | 3.000 | 2.410 | 2.20 | 28.00 | 12 | nHx:EA = 5:1 | I-a137 | 1.877 |

| Reaction 2 | | | | | | |
|---|---|---|---|---|---|---|
| Compound I-a137 (g) | NaOH (g) | $H_2O$ (ml) | MeOH (ml) | Reaction time (hr) | Product | Amount (g) |
| 1.870 | 0.646 | 8.00 | 40.00 | 8 | I-b137 | 1.710 |

| Reaction 3 | | | | | | | | |
|---|---|---|---|---|---|---|---|---|
| Compound I-b137 (g) | Compound T10 (g) | CMPI (g) | TEA (ml) | THF (ml) | Reaction time (hr) | Column sol. | Product | Amount (g) |
| 1.710 | 0.709 | 0.976 | 0.88 | 14.00 | 12 | nHx:EA = 3:2 | I-c137 | 0.610 |

| Reaction 4 | | | | | | |
|---|---|---|---|---|---|---|
| Compound I-c137 (g) | Pd/C (g) | MeOH (ml) | Reaction time (hr) | Column sol. | Amount (g) | HPLC min |
| 0.400 | 0.080 | 16.00 | 1 | MC:MeOH = 25:1 | 0.128 | 22.7 |

ESI-MS($M^+$ +1):557
1H-NMR($CDCl_3$): δ 0.66(3H, d, J=6.6Hz), 0.80(3H, d, J=6.5Hz), 0.84(3H, t, J=7.4Hz), 1.33(9H, s), 1.43-1.59(2H, m), 2.20-2.28 (1H, m), 2.53(1H, dd, J=13.5, 9.1Hz), 2.60-2.75(2H, m), 2.95(1H, dd, J=13.8, 4.8Hz), 3.01(3H, s), 3.20(1H, dd, J=14.1, 6.2Hz), 3.32(1H, dd, J=13.6, 10.9Hz), 3.52-3.63(1H, m), 3.89-3.93(1H, m), 4.21-4.28(1H, m), 4.89(1H, d, J=10.6Hz), 5.48(1H, brs), 6.51 (1H, d, J=7.9Hz), 6.73(1H, dd, J=7.9, 1.9Hz), 6.82(1H, brs), 6.99-7.10(3H, m), 7.11-7.16 (2H,m)

The processes of synthesizing Intermediates of Schemes 9-14 are shown below as Reference Examples. In addition, structural formulae of Intermediates of Examples 138-176 are shown in Tables C-3 and C-4.

TABLE C-3

Intermediates of Examples 138-176

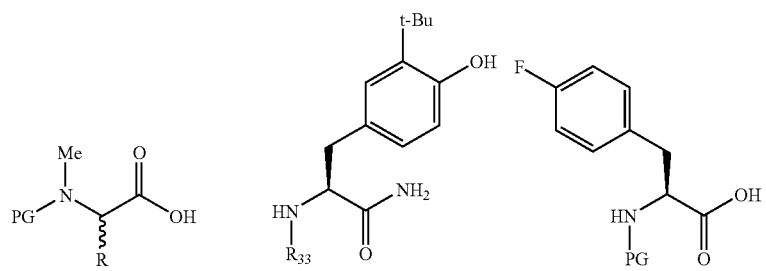

I1: R = Et,
I2: R = Et(D)
I3: R = n-Pr,
I4: R = n-Pr(D)
I5: R = s-Bu (commercial),
I6: R = s-Bu(D)
I7: R = i-Bu (commercial),
I8: R = i-Bu(D)
I9: R = Allyl,
I10: R = Allyl(L,D-mixture)
I11: R = neo-Pentyl,
I12: R = neo-Pentyl(D)
I13: R = CH$_2$CF$_3$(L,D-mixture)
I14: R = c-Hex,
I15: R = c-Hex(D)
I16: R = CH$_2$c-Hex,
I17: R = CH$_2$ c-Hex(D)
I18: R = CH$_2$Ph,
I19: R = CH$_2$Ph(D)
I20: R = CH$_2$Ph(4-F),
I21: R = CH$_2$Ph(4-F)(D)
I22: R = CH$_2$Ph(4-Cl),
I23: R = CH$_2$Ph(4-Cl)(D)
I24: R = CH$_2$Ph(4-OBn),
I25: R = CH$_2$Ph(4-OBn)(D)
I26: R = CH$_2$(2-thienyl),
I27: R = CH$_2$(2-thienly)(D)
I28: R = CH$_2$c-Pr
I38: R = tBu
I29: N-Me-Phg-OMe,
I30: N-Me-D-Phg-OMe T1: R33 = H
T4: R33 = Me P1: PG = Z or Boc
P4: PG = Z or Boc

TABLE C-4

Intermediates of Examples 138-176 (continued)

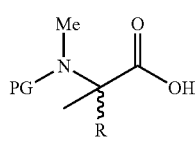

I31: R = CH$_2$Ph, I32: R = CH$_2$Ph(D)

I33: R = i-Bu

I34: R = Et(D)

I35: R = i-Pr(D)

TABLE C-4-continued

Intermediates of Examples 138-176 (continued)

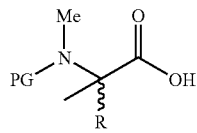

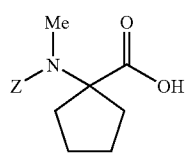

I36

TABLE C-4-continued

Intermediates of Examples 138-176 (continued)

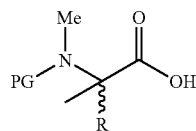

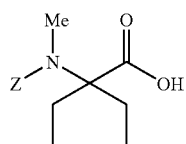

I37

In Tables C-3 and C-4, "commercial" means that the compound is commercially available, "(D)" means a D-amino acid in stereochemistry and those which are not indicated as (D) are L-amino acids. PG in the Intermediate (I) means Z or Boc.

REFERENCE EXAMPLE 21

Synthesis of Intermediates I1 to I28

The synthesis scheme is shown below.

Synthesis scheme of Intermediates I1 to I28

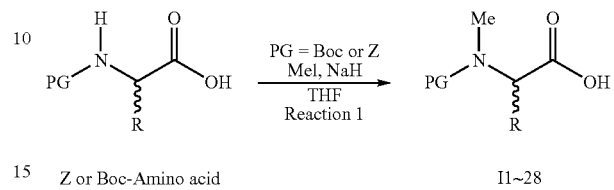

Z or Boc-Amino acid      I1~28

The synthesis process of Intermediates I1 to I28 is explained below.

Reaction Step 1)

To solutions of Z- and Boc-protected amino acids in THF, NaH and MeI were added under cooling and stirred at room temperature. The reaction mixtures were mixed with water, adjusted to pH 3-4 by the addition of 1N HCl, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I1 to I28.

Results are shown in Tables E-10 to E-35.

TABLE E-10

Intermediates I1: Z-N-Me-Abu-OH
R
Et
Reaction

| Z-Abu-OH (g) | Methyl iodide (ml) | NaH (g) | THF (ml) | Reaction time (hr) | Column sol. | Amount (g) |
|---|---|---|---|---|---|---|
| 2.000 | 4.20 | 1.340 | 40.00 | 15 | MC:MeOH = 10:1 | 1.400 |

TABLE E-11

Intermediate I2: Boc-N-Me-D-Abu-OH
R
Et:D
Reaction

| Boc-(D)-Abu-OH (g) | Methyl iodide (ml) | NaH (g) | THF (ml) | Reaction time (hr) | Column sol. | Amount (g) |
|---|---|---|---|---|---|---|
| 0.750 | 1.83 | 0.738 | 18.00 | 48 | MC:MeOH = 8:1 | 0.810 |

TABLE E-12

Intermediate I3: Z-N-Me-Nva-OH
R
n-Pr
Reaction

| Z-Nva-OH (g) | Methyl iodide (ml) | NaH (g) | THF (ml) | Reaction time (hr) | Column sol. | Amount (g) |
|---|---|---|---|---|---|---|
| 2.000 | 5.00 | 0.960 | 30.00 | 24 | MC:MeOH = 10:1 | 2.090 |

TABLE E-13

Intermediate I4: Boc-N-Me-D-Nva-OH
R
n-Pr:D
Reaction

| Boc-(D)-Nva-OH (g) | Methyl iodide (ml) | NaH (g) | THF (ml) | Reaction time (hr) | Column sol. | Amount (g) |
|---|---|---|---|---|---|---|
| 1.000 | 2.87 | 0.552 | 25.00 | 40 | MC:MeOH = 10:1 | 1.000 |

TABLE E-14

Intermediate I6: Boc-N-Me-D-Ile-OH
R
s-Bu:D
Reaction

| Boc-(D)-Ile-OH (g) | Methyl iodide (ml) | NaH (g) | THF (ml) | Reaction time (hr) | Column sol. | Amount (g) |
|---|---|---|---|---|---|---|
| 0.500 | 1.35 | 0.866 | 17.00 | 12 | MC:MeOH = 10:1 | 0.490 |

TABLE E-15

Intermediate I8: Boc-N-Me-D-Leu-OH
R
i-Bu:D
Reaction

| Boc-(D)-Leu-OH (g) | Methyl iodide (ml) | NaH (g) | THF (ml) | Reaction time (hr) | Column sol. | Amount (g) |
|---|---|---|---|---|---|---|
| 1.000 | 2.49 | 1.600 | 17.00 | 12 | MC:MeOH = 15:1 | 0.960 |

TABLE E-16

Intermediate I9:
(2S)-2-[N-(tert-butoxycarbonyl)-methylamino]pent-4-enoic acid
R
Allyl
Reaction

| (2S)-2-[(tert-butoxy)carbonylamino]pent-4-enoic acid (g) | Methyl iodide (ml) | NaH (g) | THF (ml) | Reaction time (hr) | Column sol. | Amount (g) |
|---|---|---|---|---|---|---|
| 0.660 | 1.79 | 1.150 | 12.00 | 12 | MC:MeOH = 10:1 | 0.570 |

TABLE E-17

Intermediate I10:
2-[N-(tert-butoxycarbonyl)-methylamino]pent-4-enoic acid
R
Allyl: D,L-mixture
Reaction

| 2-[(tert-butoxy)carbonyl-amino]pent-4-enoic acid (g) | Methyl iodide (ml) | NaH (g) | THF (ml) | Reaction time (hr) | Column sol. | Amount (g) |
|---|---|---|---|---|---|---|
| 2.656 | 7.67 | 4.924 | 51.00 | 12 | MC:MeOH = 15:1 | 2.360 |

TABLE E-18

Intermediate I11: BOC-N-Me-Leu(γ-Me)-OH
R
neo-Pent
Reaction

| BOC-Leu(gamma-Me)-OH (g) | Methyl iodide (ml) | NaH (g) | THF (ml) | Reaction time (hr) | Column sol. | Amount (g) |
|---|---|---|---|---|---|---|
| 1.930 | 4.86 | 3.120 | 40.00 | 48 | MC:MeOH = 10:1 | 1.500 |

TABLE E-19

Intermediate I12: BOC-N-Me-D-Leu(γ-Me)-OH
R
neo-Pent:D
Reaction

| BOC-(D)-Leu(gamma-Me)-OH (g) | Methyl iodide (ml) | NaH (g) | THF (ml) | Reaction time (hr) | Column sol. | Amount (g) |
|---|---|---|---|---|---|---|
| 1.000 | 2.50 | 1.630 | 20.00 | 24 | MC:MeOH = 10:1 | 1.110 |

TABLE E-20

Intermediate I13: 2-[N-(phenylmethoxy)carbonyl-methylamino]-4,4,4-trifluorobutanoic acid
R
$CH_2CF_3$:L,D-mixture
Reaction

| Z-2-amino-4,4,4-trifluorobutanoic acid (g) | Methyl iodide (ml) | NaH (g) | THF (ml) | Reaction time (hr) | Column sol. | Amount (g) |
|---|---|---|---|---|---|---|
| 0.75 | 1.61 | 1.03 | 20.00 | 12 | MC:MeOH = 10:1 | 0.567 |

TABLE E-21

Intermediate I14: Boc-N-Me-Chg-OH
R
c-Hex
Reaction

| Boc-Chg-OH (g) | Methyl iodide (ml) | NaH (g) | THF (ml) | Reaction time (hr) | Column sol. | Amount (g) |
|---|---|---|---|---|---|---|
| 2.000 | 3.60 | 2.300 | 40.00 | 20 | MC:MeOH = 30:1 | 1.500 |

TABLE E-22

Intermediate I15: Boc-N-Me-D-Chg-OH
R
c-Hex:D
Reaction

| Boc-(D)-Chg-OH (g) | Methyl iodide (ml) | NaH (g) | THF (ml) | Reaction time (hr) | Column sol. | Amount (g) |
|---|---|---|---|---|---|---|
| 1.500 | 2.70 | 1.740 | 30.00 | 20 | MC:MeOH = 30:1 | 1.150 |

TABLE E-23

Intermediate I16: Boc-N-Me-Cha-OH
R
$CH_2$c-Hex
Reaction

| Boc-Cha-OH (g) | Methyl iodide (ml) | NaH (g) | THF (ml) | Reaction time (hr) | Column sol. | Amount (g) |
|---|---|---|---|---|---|---|
| 2.000 | 3.40 | 1.100 | 23.00 | 18 | MC:MeOH = 10:1 | 1.300 |

TABLE E-24

Intermediate I17: Boc-N-Me-D-Cha-OH
R
$CH_2$c-Hex:D
Reaction

| Boc-(D)-Cha-OH (g) | Methyl iodide (ml) | NaH (g) | THF (ml) | Reaction time (hr) | Column sol. | Amount (g) |
|---|---|---|---|---|---|---|
| 1.000 | 1.72 | 0.552 | 11.50 | 18 | MC:MeOH = 10:1 | 1.000 |

TABLE E-25

Intermediate I18: Boc-N-Me-Phe-OH
R
$CH_2$Ph
Reaction

| Boc-Phe-OH (g) | Methyl iodide (ml) | NaH (g) | THF (ml) | Reaction time (hr) | Column sol. | Amount (g) |
|---|---|---|---|---|---|---|
| 1.000 | 1.66 | 0.400 | 20.00 | 20 | MC:MeOH = 20:1 | 0.800 |

TABLE E-26

Intermediate I19: Boc-N-Me-D-Phe-OH
R
$CH_2$Ph:D
Reaction

| Boc-(D)-Phe-OH (g) | Methyl iodide (ml) | NaH (g) | THF (ml) | Reaction time (hr) | Column sol. | Amount (g) |
|---|---|---|---|---|---|---|
| 0.890 | 1.66 | 0.400 | 20.00 | 20 | MC:MeOH = 20:1 | 0.800 |

TABLE E-27

Intermediate I20: Boc-N-Me-Phe(4-F)-OH
R
$CH_2$Phe(4-F)
Reaction

| Boc-Phe-(4-F)-OH (g) | Methyl iodide (ml) | NaH (g) | THF (ml) | Reaction time (hr) | Column sol. | Amount (g) |
|---|---|---|---|---|---|---|
| 15.000 | 27.00 | 6.360 | 180.00 | 24 | MC:MeOH = 10:1 | 15.000 |

TABLE E-28

Intermediate I21: Boc-N-Me-D-Phe(4-F)-OH
R
$CH_2Phe(4-F):D$
Reaction

| Boc-(D)-Phe(4-F)-OH (g) | Methyl iodide (ml) | NaH (g) | THF (ml) | Reaction time (hr) | Column sol. | Amount (g) |
|---|---|---|---|---|---|---|
| 1.000 | 1.76 | 0.424 | 12.00 | 18 | MC:MeOH = 10:1 | 1.000 |

TABLE E-29

Intermediate I22: Boc-N-Me-Phe(4-Cl)-OH
R
$CH_2Ph(4-Cl)$
Reaction

| Boc-Phe(4-Cl)-OH (g) | Methyl iodide (ml) | NaH (g) | THF (ml) | Reaction time (hr) | Column sol. | Amount (g) |
|---|---|---|---|---|---|---|
| 2.000 | 3.32 | 0.800 | 40.00 | 18 | MC:MeOH = 20:1 | 1.630 |

TABLE E-30

Intermediate I23: Boc-N-Me-D-Phe(4-Cl)-OH
R
$CH_2Ph(4-Cl):D$
Reaction

| Boc-(D)-Phe(4-Cl)-OH (g) | Methyl iodide (ml) | NaH (g) | THF (ml) | Reaction time (hr) | Column sol. | Amount (g) |
|---|---|---|---|---|---|---|
| 1.000 | 1.66 | 0.401 | 20.00 | 18 | MC:MeOH = 20:1 | 0.781 |

TABLE E-31

Intermediate I24: Boc-N-Me-Phe(4-OBn)-OH
R
$CH_2Ph(4-OBn)$
Reaction

| Boc-Phe(4-OBn)-OH (g) | Methyl iodide (ml) | NaH (g) | THF (ml) | Reaction time (hr) | Column sol. | Amount (g) |
|---|---|---|---|---|---|---|
| 2.500 | 3.35 | 0.808 | 50.00 | 36 | MC:MeOH = 20:1 | 2.590 |

TABLE E-32

Intermediate I25: Z-N-Me-D-Phe(4-OBn)-OH
R
$CH_2Ph(4-OBn):D$
Reaction

| Z-(D)-Phe(4-OBn)-OH (g) | Methyl iodide (ml) | NaH (g) | THF (ml) | Reaction time (hr) | Column sol. | Amount (g) |
|---|---|---|---|---|---|---|
| 2.000 | 2.51 | 0.592 | 40.00 | 36 | MC:MeOH = 20:1 | 2.060 |

TABLE E-33

Intermediate I26: Boc-N-Me-Ala(β-2-thienyl)-OH
R
CH$_2$(2-Thienyl)
Reaction

| Boc-Ala(beta-2-thienyl)-OH (g) | Methyl iodide (ml) | NaH (g) | THF (ml) | Reaction time (hr) | Column sol. | Amount (g) |
|---|---|---|---|---|---|---|
| 1.000 | 1.84 | 0.443 | 20.00 | 18 | MC:MeOH = 20;1 | 0.916 |

TABLE E-34

Intermediate I27: Boc-N-Me-D-Ala(β-2-thienyl)-OH
R
CH$_2$(2-Thienyl):D
Reaction

| Boc-(D)-Ala(beta-2-thienyl)-OH (g) | Methyl iodide (ml) | NaH (g) | THF (ml) | Reaction time (hr) | Column sol. | Amount (g) |
|---|---|---|---|---|---|---|
| 1.000 | 1.84 | 0.443 | 20.00 | 18 | MC:MeOH = 20:1 | 1.040 |

TABLE E-35

Intermediate I28: Z-N-Me-Ala(β-c-Pr)-OH
R
CH$_2$c-Propyl
Reaction

| Z-N-Ala(beta-c-Pr)-OH (g) | Methyl iodide (ml) | NaH (g) | THF (ml) | Reaction time (hr) | Column sol. | Amount (g) |
|---|---|---|---|---|---|---|
| 1.500 | 2.84 | 0.680 | 15.00 | 15 | MC:MeOH = 10:1 | 1.160 |

REFERENCE EXAMPLE 22

Synthesis of Intermediate I29

The synthesis scheme is shown below.

Synthesis scheme of Intermediate I29

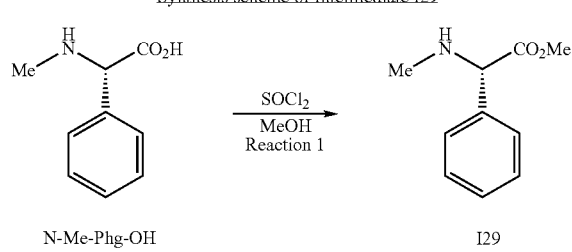

N-Me-Phg-OH        I29

The synthesis process of Intermediate I29 is explained below.

Reaction Step 1)

To a solution of N-Me-Phg-OH in methanol, SOCl$_2$ was slowly added dropwise under cooling and then stirred under reflux. The reaction mixture was concentrated under reduced pressure to give crude Compound 129.

Result is shown in Table E-36.

TABLE E-36

Intermediate I29: N-Me-Phg-OMe
Reaction

| N-Me-Phg-OH (g) | SOCl$_2$ (ml) | MeOH (ml) | Reaction time (hr) | Amount (g) |
|---|---|---|---|---|
| 2.000 | 1.32 | 20.00 | 3.00 | 2.000 |

REFERENCE EXAMPLE 23

Synthesis of Intermediate I30

The synthesis scheme is shown below.

Synthesis scheme of Intermediate I30

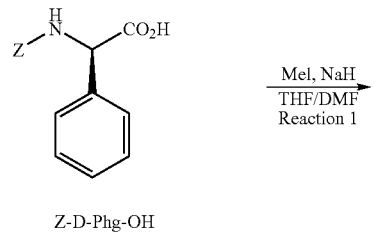

Z-D-Phg-OH

269

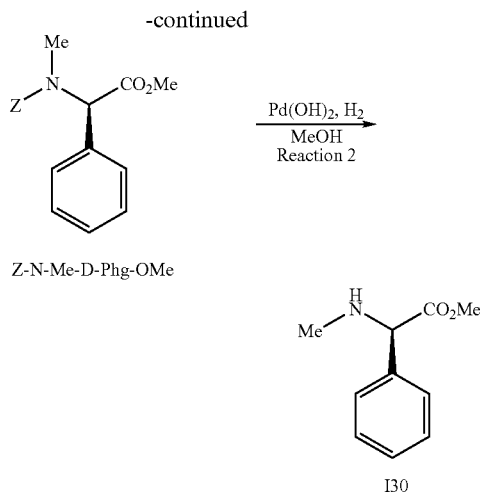

Z-N-Me-D-Phg-OMe

270

The synthesis process of Intermediate I30 is explained below.

Reaction Step 1)

To a solution of Z-D-Phg-OH and $CH_3$ I in THF and DMF, NaH was slowly added dropwise and then stirred at room temperature. The reaction mixture was mixed with water, extracted with ethyl acetate, washed with saturated brine, dried over anhydrous magnesium sulfate and filtered. The filtrate was concentrated under reduced pressure; the thus obtained residue was purified by column chromatography (silica gel) to give Z-N-Me-D-Phg-OMe.

Reaction Step 2)

To a solution of Z-N-Me-D-Phg-OMe in methanol, palladium hydroxide/carbon was added and stirred in a hydrogen atmosphere at room temperature. The reaction mixture was filtered and the filtrate was concentrated under reduced pressure; the thus obtained residue was purified by column chromatography (silica gel), giving Compound I30.

Result is shown in Table E-37.

TABLE E-37

Intermediate I30: N-Me-D-Phg-OMe

R
Ph:D

| | | | Reaction1 | | | | |
|---|---|---|---|---|---|---|---|
| Z-N-Me-(D)-Phg-OH (g) | Methyl iodide (ml) | NaH (g) | THF/DMF (ml) | Reaction time (hr) | Column sol. | Product | Amount (g) |
| 2.000 | 3.49 | 0.842 | 20.00 (10.00/10.00) | 16 | nHx:EA = 5:1 | Z-N-Me-(D)-Phg-OMe | 2.200 |

| | | | Reaction2 | | |
|---|---|---|---|---|---|
| Z-N-Me-(D)-Phg-OMe (g) | Pd(OH)$_2$ (g) | MeOH (ml) | Reaction time (hr) | Column sol. | Amount (g) |
| 2.200 | 0.330 | 40.00 | 12 | nHx:EA = 5:1 | 1.240 |

REFERENCE EXAMPLE 24

Synthesis of Intermediates 131-135

The synthesis scheme is shown below.

Synthesis scheme of Intermediates I31-I35

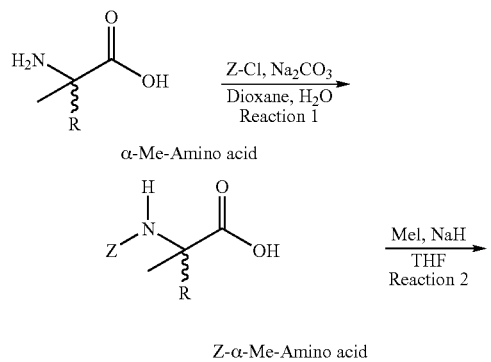

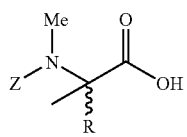

I31~I35

The synthesis process of Intermediates I31 to I35 is explained below.

Reaction Step 1)

To solutions of α-Me-amino acids and $Na_2CO_3$ in dioxane and water, Z—Cl was slowly added dropwise under cooling while stirring. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel), giving Z-α-Me-amino acids.

Reaction Step 2)

T solutions of the Z-a-Me-Amino acid and CH₃I in THF, NaH was slowly added dropwise under cooling. The reaction mixtures were adjusted to pH 3-4 by the addition of 1N HCl, extracted with ethyl acetate, washed with saturated brine, dried over anhydrous magnesium sulfate and filtered. The filtrates were concentrated under reduced pressure; the thus obtained residues were purified by column chromatography (silica gel) to giving Compounds I31 to I35.

Results are shown in Tables E-38 to E-42.

TABLE E-38

Intermediate I31: Z-N-Me-α-Me-Phe-OH

R
CH₂Ph

Reaction1

| alpha-Me-Phe-OH (g) | Z-Cl (ml) | Na₂CO₃ (g) | Dioxane (ml) | H₂O (ml) | Reaction time (hr) | Column sol. | Product | Amount (g) |
|---|---|---|---|---|---|---|---|---|
| 1.000 | 0.90 | 0.900 | 25.00 | 25.00 | 5 | MC:MeOH = 10:1 | Z-alpha-Me-Phe-OH | 0.890 |

Reaction2

| Z-alpha-Me-Phe-OH (g) | Methyl iodide (ml) | NaH (g) | THF (ml) | Reaction time (hr) | Column sol. | Amount (g) |
|---|---|---|---|---|---|---|
| 0.890 | 1.40 | 0.340 | 28.00 | 15 | MC:MeOH = 10:1 | 1.180 |

TABLE E-39

Intermediate I32: Z-N-Me-α-Me-D-Phe-OH

R
CH₂Ph:D

Reaction1

| alpha-Me-(D)-Phe-OH (g) | Z-Cl (ml) | Na₂CO₃ (g) | Dioxane (ml) | H₂O (ml) | Reaction time (hr) | Column sol. | Product | Amount (g) |
|---|---|---|---|---|---|---|---|---|
| 1.000 | 0.90 | 0.900 | 25.00 | 25.00 | 5 | MC:MeOH = 10:1 | Z-alpha-Me-(D)-Phe-OH | 0.810 |

Reaction2

| Z-alpha-Me-(D)-Phe-OH (g) | Methyl iodide (ml) | NaH (g) | THF (ml) | Reaction time (hr) | Column sol. | Amount (g) |
|---|---|---|---|---|---|---|
| 0.810 | 1.40 | 0.340 | 28.00 | 15 | MC:MeOH = 10:1 | 1.050 |

TABLE E-40

Intermediate I33: Z-N-Me-α-Me-Leu-OH

R
i-Bu

Reaction1

| alpha-Me-Leu-OH (g) | Z-Cl (ml) | Na₂CO₃ (g) | Dioxane (ml) | H₂O (ml) | Reaction time (hr) | Column sol. | Product | Amount (g) |
|---|---|---|---|---|---|---|---|---|
| 1.970 | 2.10 | 2140 | 30.00 | 20.00 | 24 | MC:MeOH = 10:1 | Z-alpha-Me-Leu-OH | 2.000 |

Reaction2

| Z-alpha-Me-Leu-OH (g) | Methyl iodide (ml) | NaH (g) | THF (ml) | Reaction time (hr) | Column sol. | Amount (g) |
|---|---|---|---|---|---|---|
| 2.000 | 4.40 | 2.000 | 35.00 | 12 | MC:MeOH = 10:1 | 1.780 |

TABLE E-41

Intermediate I34: Z-N-Me-α-Me-D-Abu-OH
R
CH₂CH₃:D

Reaction 1

| alpha-Me-(D)-Abu-OH (g) | Z-Cl (ml) | Na₂CO₃ (g) | THF (ml) | H₂O (ml) | Reaction time (hr) | Column sol. | Product | Amount (g) |
|---|---|---|---|---|---|---|---|---|
| 0.250 | 0.36 | 0.450 | 10.00 | 2.00 | 3 | MC:MeOH = 10:1 | Z-alpha-Me-(D)-Et-OH | 0.177 |

Reaction 2

| Z-alpha-Me-(D)-Abu-OH (g) | Methyl iodide (ml) | NaH (g) | THF (ml) | Reaction time (hr) | Column sol. | Amount (g) |
|---|---|---|---|---|---|---|
| 0.750 | 0.42 | 0.190 | 10.00 | 12 | MC:MeOH = 10:1 | 0.152 |

TABLE E-42

Intermediate I35: Z-N-Me-α-Me-D-Val-OH
R
i-Pr:D

Reaction 1

| alpha-Me-(D)-Val-OH (g) | Z-Cl (ml) | Na₂CO₃ (g) | Dioxane (ml) | H₂O (ml) | Reaction time (hr) | Column sol. | Product | Amount (g) |
|---|---|---|---|---|---|---|---|---|
| 1.000 | 1.31 | 1.454 | 4.00 | 4.00 | 12 | MC:MeOH = 15:1 | Z-alpha-Me-(D)-Val-OH | 0.170 |

Reaction 2

| Z-alpha-Me-(D)-Val-OH (g) | Methyl iodide (ml) | NaH (g) | THF (ml) | Reaction time (hr) | Column sol. | Amount (g) |
|---|---|---|---|---|---|---|
| 0.170 | 0.40 | 0.128 | 3.00 | 12 | MC:MeOH = 10:1 | 0.170 |

REFERENCE EXAMPLE 25

Synthesis of Intermediate I36, I37

The synthesis scheme is shown below.

Synthesis scheme of Intermediates I36 and I37

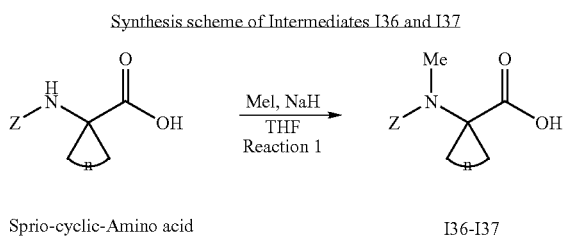

Sprio-cyclic-Amino acid        I36-I37

The synthesis process of Intermediates I36 and I37 is explained below.

Reaction Step 1)

To solutions of a spiro-cyclic-amino acids and CH₃I in THF, NaH was slowly added dropwise under cooling. The reaction mixtures were adjusted to pH 3-4 by the addition of 1N HCl, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I36 and I37.

Results are shown in Tables E-43 and E-44.

TABLE E-43

Intermediate I36:
1-[N-methyl(phenylmethoxy)carbonylamino]cyclopentanecarboxylic acid Reaction

| Z-1-amino-1-cyclo pentanecarboxylic acid (g) | Methyl iodide (ml) | NaH (g) | THF (ml) | Reaction time (hr) | Column sol. | Amount (g) |
|---|---|---|---|---|---|---|
| 2.000 | 3.79 | 0.912 | 26.00 | 18 | MC:MeOH = 20:1 | 1.730 |

TABLE E-44

Intermediate I37:
1-[N-methyl(phenylmethoxy)carbonylamino]cyclohexanecarboxylic acid Reaction

| Z-1-amino-1-cyclo hexanecarboxylic acid (g) | Methyl iodide (ml) | NaH (g) | THF (ml) | Reaction time (hr) | Column sol. | Amount (g) |
|---|---|---|---|---|---|---|
| 4.000 | 7.19 | 1.730 | 80.00 | 18 | MC:MeOH = 20:1 | 4.190 |

REFERENCE EXAMPLE 26

Synthesis of Intermediate I38

The synthesis scheme is shown below.

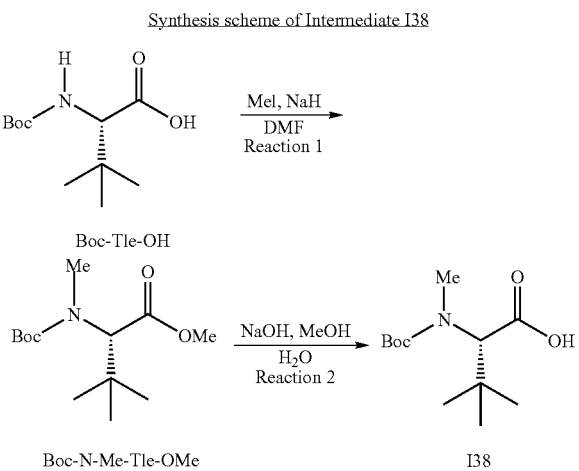

The synthesis process of Intermediate I38 is explained below.

Reaction Step 1)

To a solution of Boc-Tle-OH in DMF, NaH and MeI were added under cooling and stirred at room temperature. The reaction mixture was mixed with 1N HCl, extracted with ethyl acetate, dried over anhydrous magnesium sulfate and filtered. The filtrate was concentrated under reduced pressure to give Boc-N-Me-Tle-OMe.

Reaction Step 2)

To a solution of Boc-N-Me-Tle-OMe in methanol and water, NaOH was added and stirred at room temperature. The reaction mixture was adjusted to pH 3-4 by the addition of 1N HCl, extracted with ethyl acetate, washed with saturated brine, dried over anhydrous magnesium sulfate and filtered. The filtrate was concentrated under reduced pressure; the thus obtained residue was purified by column chromatography (silica gel), giving Intermediate I38.

Result is shown in Table E-45.

TABLE E-45

Intermediate I38: Boc-N-Me-Tle-OH

| | | Reaction 1 | | | | |
|---|---|---|---|---|---|---|
| Boc-Tle-OH (g) | Methyl iodide (ml) | NaH (g) | DMF (ml) | Reaction time (hr) | Product | Amount (g) |
| 1.000 | 2.70 | 0.865 | 18.00 | 16 | Boc-N-Me-Tle-OMe | 1.180 |

TABLE E-45-continued

Intermediate I38: Boc-N-Me-Tle-OH

Reaction 2

| Boc-N-Me-Tle-OMe (g) | NaOH (g) | MeOH (ml) | H$_2$O (ml) | Reaction time (hr) | Column sol. | Amount (g) |
|---|---|---|---|---|---|---|
| 1.180 | 0.550 | 10.00 | 2.00 | 22 | MC:MeOH = 10:1 | 0.900 |

Scheme 9 shows the synthesis process of Examples 138-165.

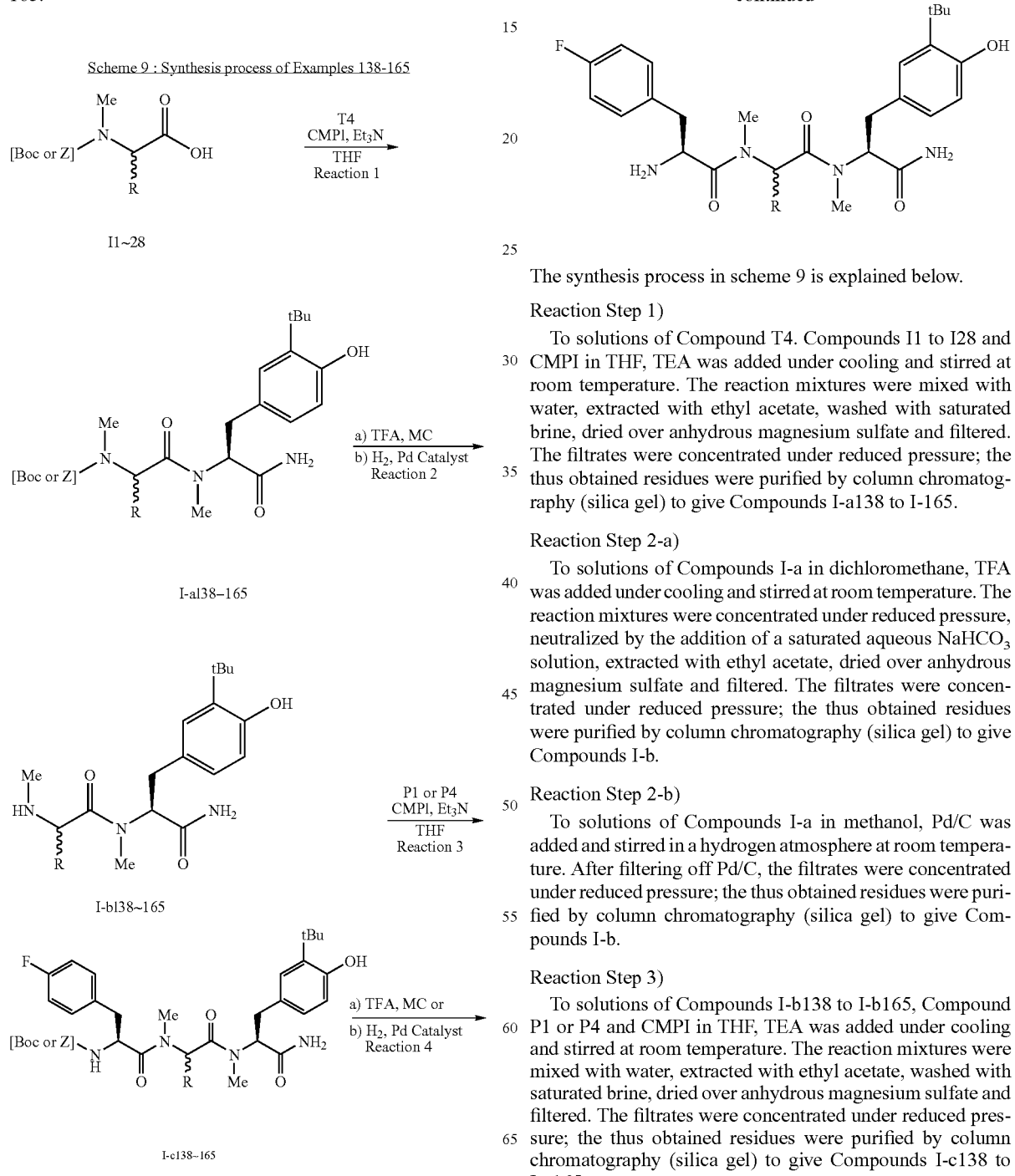

The synthesis process in scheme 9 is explained below.

Reaction Step 1)

To solutions of Compound T4. Compounds I1 to I28 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-a138 to I-165.

Reaction Step 2-a)

To solutions of Compounds I-a in dichloromethane, TFA was added under cooling and stirred at room temperature. The reaction mixtures were concentrated under reduced pressure, neutralized by the addition of a saturated aqueous NaHCO$_3$ solution, extracted with ethyl acetate, dried over anhydrous magnesium sulfate and filtered. The filtrates were concentrated under reduced pressure; the thus obtained residues were purified by column chromatography (silica gel) to give Compounds I-b.

Reaction Step 2-b)

To solutions of Compounds I-a in methanol, Pd/C was added and stirred in a hydrogen atmosphere at room temperature. After filtering off Pd/C, the filtrates were concentrated under reduced pressure; the thus obtained residues were purified by column chromatography (silica gel) to give Compounds I-b.

Reaction Step 3)

To solutions of Compounds I-b138 to I-b165, Compound P1 or P4 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-c138 to I-c165.

Reaction Step 4-a)

To solutions of Compounds I-c in dichloromethane, TFA was added under cooling and stirred at room temperature. The reaction mixtures were concentrated under reduced pressure, neutralized by the addition of a saturated aqueous $NaHCO_3$ solution, extracted with ethyl acetate, dried over anhydrous magnesium sulfate and filtered. The filtrates were concentrated under reduced pressure; the thus obtained residues were purified by column chromatography (silica gel) to give the titled compounds.

Reaction Step 4-b)

To solutions of Compounds I-c in methanol, Pd/C was added and stirred in a hydrogen atmosphere at room temperature. After filtering off Pd/C, the filtrates were concentrated under reduced pressure; the thus obtained residues were purified by column chromatography (silica gel) to give the titled compounds.

Compounds which were synthesized in Examples according to Scheme 9 are shown in Tables D-138 to D-165. In the tables "A" indicated after the Example number means "less polar isomer" and "B" means "more polar isomer". For example, Compound of Example 150A is "less polar isomer" of Phe(4-F)-N-Me-Ala($\beta$-$CF_3$)—N-Me-Tyr(3-tBu)-$NH_2$ and Compound of Example 150B is "more polar isomer" of Phe(4-F)-N-Me-Ala($\beta$-$CF_3$)—N-Me-Tyr(3-tBu)-$NH_2$.

TABLE D-138

Example 138
Phe(4-F)-N-Me-Abu-N-Me-Tyr(3-tBu)-$NH_2$
R
Et

Reaction 1

| Compound T4 (g) | Compound I1 (g) | CMPI (g) | TEA (ml) | THF (ml) | Reaction time (hr) | Column sol. | Product | Amount (g) |
|---|---|---|---|---|---|---|---|---|
| 0.800 | 0.960 | 0.980 | 0.90 | 30.00 | 12 | nHx:EA = 1:2 | I-a138 | 1.420 |

Reaction 2-b

| Compound I-a138 (g) | Pd/C (g) | MeOH (ml) | Reaction time (hr) | Column sol. | Product | Amount (g) |
|---|---|---|---|---|---|---|
| 1.400 | 0.430 | 28.00 | 2 | MC:MeOH = 15:1 | I-b138 | 0.950 |

Reaction 3

| Compound I-b138 (g) | Compound P1 (g) | CMPI (g) | TEA (ml) | THF (ml) | Reaction time (hr) | Column sol. | Product | Amount (g) |
|---|---|---|---|---|---|---|---|---|
| 0.890 | 0.860 | 0.780 | 0.70 | 5.00 | 72 | nHx:EA = 1:1 | I-c128 | 0.720 |

Reaction 4-a

| Compound I-c138 (g) | TFA (ml) | MC (ml) | Reaction time (hr) | Column sol. | Amount (g) | HPLC min |
|---|---|---|---|---|---|---|
| 0.720 | 1.80 | 9.00 | 3 | MC:MeOH = 15:1 | 0.420 | 17.07 |

ESI-MS($M^+$+1): 515
1H-NMR($CD_3OD$): (two rotamers)$\delta$ 0.55 and 0.88(3H, t, J=7.2-7.6Hz), 1.39 and 1.44(9H, s), 1.56-1.85(2H, m), 2.23, 2.62, 2.91 and 2.98(6H, s), 2.56-3.01(4H, m), 3.26(1H, dt, J=3.0-4.7, 13.9-15.4Hz), 3.78 and 3.97 (1H, dd, J=8.4, 5.1Hz), 5.28 and 5.55(1H, dd, J=7.8-11.6, 4.8-6.0Hz), 6.59 and 6.74(1H, d, J=8.0Hz), 6.69-7.30(6H, m)

TABLE D-139

Example 139
Phe(4-F)-N-Me-D-Abu-N-Me-Tyr(3-tBu)-$NH_2$
R
Et:D

Reaction 1

| Compound T4 (g) | Compound I2 (g) | CMPI (g) | TEA (ml) | THF (ml) | Reaction time (hr) | Column sol. | Product | Amount (g) |
|---|---|---|---|---|---|---|---|---|
| 0.770 | 0.800 | 0.950 | 0.85 | 60.00 | 12 | nHx:EA = 1:2 | I-a139 | 1.100 |

TABLE D-139-continued

Example 139
Phe(4-F)-N-Me-D-Abu-N-Me-Tyr(3-tBu)-NH$_2$
R
Et:D

Reaction 2-a

| Compound I-a139 (g) | TFA (ml) | MC (ml) | Reaction time (hr) | Column sol. | Product | Amount (g) |
|---|---|---|---|---|---|---|
| 1.100 | 4.90 | 26.00 | 1 | MC:MeOH = 8:1 | I-b139 | 0.770 |

Reaction 3

| Compound I-b139 (g) | Compound P1 (g) | CMPI (g) | TEA (ml) | THF (ml) | Reaction time (hr) | Column sol. | Product | Amount (g) |
|---|---|---|---|---|---|---|---|---|
| 0.770 | 0.750 | 0.670 | 0.60 | 44.00 | 72 | nHx:EA = 1:2 | I-c139 | 1.310 |

Reaction 4-a

| Compound I-c139 (g) | TFA (ml) | MC (ml) | Reaction time (hr) | Column sol. | Amount (g) | HPLC min |
|---|---|---|---|---|---|---|
| 1.300 | 4.20 | 21.00 | 2 | MC:MeOH = 15:1 | 0.620 | 19.96 |

ESI-MS(M$^+$+1): 515
1H-NMR(CD$_3$OD): δ 0.48(3H, t, J=7.5Hz), 1.36(9H, s), 1.38-1.43(2H, m), 2.59 and 2.87(3H, s), 2.73 (1H, dd, J=13.2, 7.5Hz), 2.81-2.92(2H, m), 3.02 and 3.14(3H, s), 3.37(1H, dd, J=15.0, 6.1Hz), 3.93(1H, t, J=6.8-7.1Hz), 4.82(1H, t, J=7.7Hz), 5.34(1H, brs), 5.50(1H, dd, J=11.3, 5.9Hz), 6.42(1H, brs), 6.57 (1H, d, J=7.8Hz), 6.88(1H, dd, J=7.7, 2.0Hz), 6.96(2H, t, J=8.6Hz), 7.08(1H, d, J=2.3Hz), 7.13(2H, m)

TABLE D-140

Example 140
Phe(4-F)-N-Me-Nva-N-Me-Tyr(3-tBu)-NH$_2$
R
n-Pr

Reaction 1

| Compound T4 (g) | Compound I3 (g) | CMPI (g) | TEA (ml) | THF (ml) | Reaction time (hr) | Column sol. | Product | Amount (g) |
|---|---|---|---|---|---|---|---|---|
| 0.830 | 0.800 | 0.847 | 0.84 | 30.00 | 24 | nHx:EA = 1:2 | I-a140 | 1.372 |

Reaction 2-b

| Compound I-a140 (g) | Pd/C (g) | MeOH (ml) | Reaction time (hr) | Column sol. | Product | Amount (g) |
|---|---|---|---|---|---|---|
| 1.372 | 0.200 | 80.00 | 2 | MC:MeOH = 10:1 | I-b140 | 0.895 |

Reaction 3

| Compound I-b140 (g) | Compound P4 (g) | CMPI (g) | TEA (ml) | THF (ml) | Reaction time (hr) | Column sol. | Product | Amount (g) |
|---|---|---|---|---|---|---|---|---|
| 0.500 | 0.480 | 0.387 | 0.40 | 20.00 | 16 | nHx:EA = 1:2 | I-c140 | 0.744 |

Reaction 4-b

| Compound I-c140 (g) | Pd/C (g) | MeOH (ml) | Reaction time (hr) | Column sol. | Amount (g) | HPLC min |
|---|---|---|---|---|---|---|
| 0.727 | 0.200 | 50.00 | 2 | MC:MeOH = 10:1 | 0.450 | 19.05 |

ESI-MS(M$^+$+1): 529
1H-NMR(CDCl$_3$+CD$_3$OD): (two rotamers)δ 0.20 and 0.70-1.20(3H, m), 0.65 and 0.75(3H, t, J=6.9Hz), 1.50-1.70(1H, m), 1.33 and 1.38(9H, s), 2.30 and 2.69(3H, s), 2.47 and 2.70(2H, m), 2.72(3H, s), 2.80 and 2.92 (2H, m), 3.65 and 3.85(1H, m), 4.83(1H, m), 5.84(1H, m), 6.48(1H, d, J=9.69Hz), 6.70-6.82(1H, m), 6.90-7.20(5H, m)

TABLE D-141

Example 141
Phe(4-F)-N-Me-D-Nva-N-Me-Tyr(3-tBu)-NH$_2$
R
n-Pr:D

Reaction 1

| Compound T4 (g) | Compound I4 (g) | CMPI (g) | TEA (ml) | THF (ml) | Reaction time (hr) | Column sol. | Product | Amount (g) |
|---|---|---|---|---|---|---|---|---|
| 0.650 | 0.547 | 0.665 | 0.70 | 20.00 | 16 | nHx:EA = 1:2 | I-a141 | 0.670 |

Reaction 2-a

| Compound I-a141 (g) | TFA (ml) | MC (ml) | Reaction time (hr) | Column sol. | Product | Amount (g) |
|---|---|---|---|---|---|---|
| 0.670 | 1.50 | 10.00 | 2 | MC:MeOH = 10:1 | I-b141 | 0.500 |

Reaction 3

| Compound I-b141 (g) | Compound P4 (g) | CMPI (g) | TEA (ml) | THF (ml) | Reaction time (hr) | Column sol. | Product | Amount (g) |
|---|---|---|---|---|---|---|---|---|
| 0.490 | 0.480 | 0.387 | 0.40 | 20.00 | 16 | nHx:EA = 1:2 | I-c141 | 0.680 |

Reaction 4-b

| Compound I-c141 (g) | Pd/C (g) | MeOH (ml) | Reaction time (hr) | Column sol. | Amount (g) | HPLC min |
|---|---|---|---|---|---|---|
| 0.680 | 0.100 | 20.00 | 2 | MC:MeOH = 10:1 | 0.358 | 22.27 |

ESI-MS(M$^+$+1): 529
1H-NMR(CDCl$_3$+CD$_3$OD): (two rotamers)δ 0.65-0.90(2H, m), 0.75(3H, t, J=6.9Hz), 1.20-1.50(2H, m), 1.37 and 1.39(9H, s), 2.75(2H, brs), 2.85 and 2.87(3H, s), 2.80(1H, m), 3.00 and 3.02(3H, s), 3.45(1H, m), 3.95 (1H, t, J=7.2Hz), 4.91(1H, t, J=7.5Hz), 5.40(2H, m, brs), 6.40(1H, brs), 6.60(1H, d, J=9.3Hz), 6.37(1H, d, 9.3Hz), 6.90-7.18(5H, m)

TABLE D-142

Example 142
Phe(4-F)-N-Me-Ile-N-Me-Tyr(3-tBu)-NH$_2$
R
s-Bu

Reaction 1

| Compound T4 (g) | Compound I5 (g) | CMPI (g) | TEA (ml) | THF (ml) | Reaction time (hr) | Column sol. | Product | Amount (g) |
|---|---|---|---|---|---|---|---|---|
| 0.750 | 1.000 | 0.910 | 0.83 | 19.00 | 12 | nHx:EA = 2:3 | I-a142 | 1.350 |

Reaction 2-b

| Compound I-a142 (g) | Pd/C (g) | MeOH (ml) | Reaction time (hr) | Column sol. | Product | Amount (g) |
|---|---|---|---|---|---|---|
| 1.300 | 0.190 | 50.00 | 2 | MC:MeOH = 20:1 | I-b142 | 0.920 |

Reaction 3

| Compound I-b142 (g) | Compound P1 (g) | CMPI (g) | TEA (ml) | THF (ml) | Reaction time (hr) | Column sol. | Product | Amount (g) |
|---|---|---|---|---|---|---|---|---|
| 0.920 | 0.830 | 0.750 | 0.67 | 25.00 | 12 | nHx:EA = 2:3 | I-c142 | 1.170 |

TABLE D-142-continued

Example 142
Phe(4-F)-N-Me-Ile-N-Me-Tyr(3-tBu)-NH$_2$
R
s-Bu

Reaction 4-a

| Compound I-c142 (g) | TFA (ml) | MC (ml) | Reaction time (hr) | Column sol. | Amount (g) | HPLC min |
|---|---|---|---|---|---|---|
| 1.150 | 2.75 | 13.00 | 3 | MC:MeOH = 20:1 | 0.710 | 19.710 |

ESI-MS(M$^+$+1): 543
1H-NMR(CDCl$_3$+CD$_3$OD): (two rotamers)δ 0.38, 0.81, 0.85 and 0.88(6H, d, J=6.0-6.5Hz), 0.93-1.02(1H, m), 1.18-1.29(1H, m), 1.34 and 1.39(9H, s), 1.97-2.11(1H, m), 2.38-2.93(3H, m), 2.50, 2.86, 2.95 and 3.00 (6H, s), 3.11-3.18(1H, m), 3.69 and 3.84(1H, dd, J=8.0-8.9, 4.0-5.5Hz), 4.91-4.96 and 5.02-5.14(4/3H, m), 5.45(2/3H, dd, J=10.2, 5.7Hz), 6.48(2/3H, d, J=7.9Hz), 6.65-6.71(1H, m), 6.91-7.12(16/3H, m)

TABLE D-143

Example 143
Phe(4-F)-N-Me-D-Ile-N-Me-Tyr(3-tBu)-NH$_2$
R
s-Bu:D

Reaction 1

| Compound T4 (g) | Compound I6 (g) | CMPI (g) | TEA (ml) | THF (ml) | Reaction time (hr) | Column sol. | Product | Amount (g) |
|---|---|---|---|---|---|---|---|---|
| 0.420 | 0.490 | 0.510 | 0.46 | 10.00 | 12 | nHx:EA = 2:3 | I-a143 | 0.330 |

Reaction 2-a

| Compound I-a143 (g) | TFA (ml) | MC (ml) | Reaction time (hr) | Column sol. | Product | Amount (g) |
|---|---|---|---|---|---|---|
| 0.310 | 0.94 | 4.70 | 3 | MC:MeOH = 10:1 | I-b143 | 0.240 |

Reaction 3

| Compound I-b143 (g) | Compound P1 (g) | CMPI (g) | TEA (ml) | THF (ml) | Reaction time (hr) | Column sol. | Product | Amount (g) |
|---|---|---|---|---|---|---|---|---|
| 0.240 | 0.220 | 0.200 | 0.18 | 6.00 | 12 | nHx:EA = 2:3 | I-c143 | 0.34 |

Reaction 4-a

| Compound I-c143 (g) | TFA (ml) | MC (ml) | Reaction time (hr) | Column sol. | Amount (g) | HPLC min |
|---|---|---|---|---|---|---|
| 0.330 | 1.20 | 6.00 | 4 | MC:MeOH = 10:1 | 0.140 | 23.200 |

ESI-MS(M$^+$+1): 543
1H-NMR(CDCl$_3$): δ 0.27(3H, d, J=6.8Hz), 0.67-0.80(4H, m), 0.88-0.97(1H, m), 1.36(9H, s), 1.74-1.85(1H, m), 2.71(1H, dd, J=13.9, 7.2Hz), 2.84-3.00(2H, m), 2.96(3H, s), 3.12(3H, s), 3.35(1H, dd, J=14.6, 5.2Hz), 3.96(1H, t, J=7.0Hz), 4.79(1H, d, J=11.0Hz), 5.46(1H, dd, J=11.5, 5.4Hz), 5.50(1H, brs), 6.35(1H, brs), 6.58 (1H, d, J=8.0Hz), 6.90-7.05(4H, m), 7.12-7.16(2H, m)

TABLE D-144

Example 144
Phe(4-F)-N-Me-Leu-N-Me-Tyr(3-tBu)-NH$_2$
R
i-Bu

Reaction 1

| Compound T4 (g) | Compound I7 (g) | CMPI (g) | TEA (ml) | THF (ml) | Reaction time (hr) | Column sol. | Product | Amount (g) |
|---|---|---|---|---|---|---|---|---|
| 0.747 | 1.000 | 0.910 | 0.83 | 19.00 | 12 | nHx:EA = 2:3 | I-a144 | 1.320 |

TABLE D-144-continued

Example 144
Phe(4-F)-N-Me-Leu-N-Me-Tyr(3-tBu)-NH$_2$
R
i-Bu

Reaction 2-b

| Compound I-a144 (g) | Pd/C (g) | MeOH (ml) | Reaction time (hr) | Column sol. | Product | Amount (g) |
|---|---|---|---|---|---|---|
| 1.300 | 0.190 | 50.00 | 2 | MC:MeOH = 20:1 | I-b144 | 0.940 |

Reaction 3

| Compound I-b143 (g) | Compound P1 (g) | CMPI (g) | TEA (ml) | THF (ml) | Reaction time (hr) | Column sol. | Product | Amount (g) |
|---|---|---|---|---|---|---|---|---|
| 0.940 | 0.850 | 0.760 | 0.69 | 25.00 | 12 | nHx:EA = 2:3 | I-c144 | 1.230 |

Reaction 4-a

| Compound I-c144 (g) | TFA (ml) | MC (ml) | Reaction time (hr) | Column sol. | Amount (g) | HPLC min |
|---|---|---|---|---|---|---|
| 1.210 | 2.90 | 14.50 | 3 | MC:MeOH = 20:1 | 0.750 | 19.380 |

ESI-MS(M$^+$+1): 543
1H-NMR(CD$_3$OD): (two rotamers)δ 0.66, 0.73, 0.94 and 0.96(6H, d, J=6.0-6.6Hz), 1.37 and 1.40(9H, s), 1.40-1.52(2H, m), 1.55-1.68(1H, m), 2.26 and 2.65(3H, s), 2.53-2.69(1H, m), 2.69-3.00(1H, m), 2.86 and 3.00(3H, s), 3.09-3.29(1H, m), 3.72-3.78 and 3.90-3.94(1H, m), 4.56-4.64(1H, m), 4.94-5.06(1H, m), 5.39-5.52(1H, m), 6.55-6.78(2H, m), 6.94-7.30(5H, m)

TABLE D-145

Example 145
Phe(4-F)-N-Me-D-Leu-N-Me-Tyr(3-tBu)-NH$_2$
R
i-Bu:D

Reaction 1

| Compound T4 (g) | Compound I8 (g) | CMPI (g) | TEA (ml) | THF (ml) | Reaction time (hr) | Column sol. | Product | Amount (g) |
|---|---|---|---|---|---|---|---|---|
| 0.810 | 0.960 | 1.000 | 0.91 | 25.00 | 12 | nHx:EA = 2:3 | I-a145 | 1.450 |

Reaction 2-a

| Compound I-a145 (g) | TFA (ml) | MC (ml) | Reaction time (hr) | Column sol. | Product | Amount (g) |
|---|---|---|---|---|---|---|
| 1.430 | 4.60 | 23.00 | 3 | MC:MeOH = 5:1 | I-b145 | 1.140 |

Reaction 3

| Compound I-b145 (g) | Compound P1 (g) | CMPI (g) | TEA (ml) | THF (ml) | Reaction time (hr) | Column sol. | Product | Amount (g) |
|---|---|---|---|---|---|---|---|---|
| 1.140 | 1.010 | 0.910 | 0.83 | 25.00 | 12 | nHx:EA = 2:3 | I-c145 | 0.940 |

Reaction 4-a

| Compound I-c145 (g) | TFA (ml) | MC (ml) | Reaction time (hr) | Column sol. | Amount (g) | HPLC min |
|---|---|---|---|---|---|---|
| 0.920 | 2.20 | 11.00 | 3 | MC:MeOH = 5:1 | 0.60 | 21.40 |

ESI-MS(M$^+$+1): 543
1H-NMR(CDCl$_3$): δ 0.72(3H, d, J=4.3Hz), 0.73(3H, d, J=4.1Hz), 0.81-0.92(2H, m), 1.24-1.30(1H, m), 1.36 (9H, s), 2.73-2.90(3H, m), 2.84(3H, s), 2.99(3H, s), 3.30(1H, dd, J=14.6, 5.6Hz), 3.96(1H, t, J=7.2Hz), 5.02 (1H, dd, J=9.9, 4.9Hz), 5.44(1H, dd, J=10.9, 5.6Hz), 5.63(1H, brs), 6.38(1H, brs), 6.57(1H, d, J=8.4Hz), 6.85 (1H, dd, J=7.8, 1.9Hz), 6.91-7.01(3H, m), 7.09-7.13(2H, m)

TABLE D-146

Example 146
(2S)-2-[(2S)-2-amino-3-(4-fluorophenyl)-N-methylpropanoylamino]-N-{(1S)-2-[3-(tert-butyl)-4-hydroxyphenyl]-1-carbamoylethyl}-N-methylpent-4-enamide
R
Allyl

Reaction 1

| Compound T4 (g) | Compound I9 (g) | CMPI (g) | TEA (ml) | THF (ml) | Reaction time (hr) | Column sol. | Product | Amount (g) |
|---|---|---|---|---|---|---|---|---|
| 0.573 | 0.630 | 0.700 | 0.64 | 14.00 | 12 | nHx:EA = 2:3 | I-a146 | 0.900 |

Reaction 2-a

| Compound I-a146 (g) | TFA (ml) | MC (ml) | Reaction time (hr) | Column sol. | Product | Amount (g) |
|---|---|---|---|---|---|---|
| 0.870 | 2.90 | 14.0 | 3 | MC:MeOH = 10:1 | I-b146 | 0.660 |

Reaction 3

| Compound I-b146 (g) | Compound P1 (g) | CMPI (g) | TEA (ml) | THF (ml) | Reaction time (hr) | Column sol. | Product | Amount (g) |
|---|---|---|---|---|---|---|---|---|
| 0.660 | 0.620 | 0.560 | 0.51 | 17.00 | 12 | nHx:EA = 2:3 | I-c146 | 0.570 |

Reaction 4-a

| Compound I-c146 (g) | TFA (ml) | MC (ml) | Reaction time (hr) | Column sol. | Amount (g) | HPLC min |
|---|---|---|---|---|---|---|
| 0.550 | 1.35 | 5.40 | 3 | MC:MeOH = 10:1 | 0.36 | 17.750 |

ESI-MS(M$^+$+1): 527
1H-NMR(CDCl$_3$): (two rotamers)δ 0.97-1.04(1/2H, m), 1.34 and 1.36(9H, s), 2.12-2.24(1/2H, m), 2.32-2.75 (2H, m), 2.34 and 2.66(3H, s), 2.84-2.99(2H, m), 2.97(3H, s), 3.07-3.18(1H, m), 3.62-3.66 and 3.83-3.87(1H, m), 4.80-5.09(3H, m), 5.25-5.33 and 5.63-5.76(1H, m), 5.35-5.46(1H, m), 5.39(1H, brs), 6.06(0.5H, brs), 6.41 and 6.58(1H, d, J=8.2 and 8.0Hz), 6.74 and 6.83(1H, dd, J=7.9, 1.9Hz), 6.92-7.00(2H, m), 7.03-7.14(3H, m), 7.36(1/2H, brs)

TABLE D-147

Example 147
(2R)-2-[(2S)-2-amino-3-(4-fluorophenyl)-N-methylpropanoylamino]-N-{(1S)-2-[3-(tert-butyl)-4-hydroxyphenyl]-1-carbamoylethyl}-N-methylpent-4-enamide
R
Allyl:D

Reaction 1

| Compound T4 (g) | Compound I10 (g) | CMPI (g) | TEA (ml) | THF (ml) | Reaction time (hr) | Column sol. | Product | Amount (g) |
|---|---|---|---|---|---|---|---|---|
| 1.180 | 1.300 | 1.440 | 1.30 | 30.00 | 12 | nHx:EA = 1:1 | I-a147 | 0.340 |

Reaction 2-a

| Compound I-a147 (g) | TFA (ml) | MC (ml) | Reaction time (hr) | Column sol. | Product | Amount (g) |
|---|---|---|---|---|---|---|
| 0.330 | 1.10 | 5.00 | 3 | MC:MeOH = 7:1 | I-b147 | 0.270 |

Reaction 3

| Compound I-b147 (g) | Compound P1 (g) | CMPI (g) | TEA (ml) | THF (ml) | Reaction time (hr) | Column sol. | Product | Amount (g) |
|---|---|---|---|---|---|---|---|---|
| 0.270 | 0.240 | 0.220 | 0.30 | 6.00 | 12 | nHx:EA = 2:3 | I-c147 | 0.370 |

TABLE D-147-continued

Example 147
(2R)-2-[(2S)-2-amino-3-(4-fluorophenyl)-N-methylpropanoylamino]-N-{(1S)-2-[3-(tert-butyl)-4-hydroxyphenyl]-1-carbamoylethyl}-N-methylpent-4-enamide
R
Allyl:D

Reaction 4-a

| Compound I-c147 (g) | TFA (ml) | MC (ml) | Reaction time (hr) | Column sol. | Amount (g) | HPLC min |
|---|---|---|---|---|---|---|
| 0.350 | 1.30 | 5.00 | 3 | MC:MeOH = 7:1 | 0.24 | 20.320 |

ESI:MS(M$^+$+1): 527
1H-NMR(CDCl$_3$): δ 1.35(9H, s), 1.99-2.16(2H, m), 2.64-2.72(1H, m), 2.79-2.89(2H, m), 2.87(3H, s), 2.97 (3H, s), 3.31(1H, d, J=15.3, 5.9Hz), 3.90(1H, t, J=7.0Hz), 4.87-4.93(2H, m), 5.01(1H, dd, J=9.0, 6.7Hz), 5.16-5.29(1H, m), 5.44(1H, dd, J=10.5, 6.0Hz), 5.50(1H, brs), 6.37(1H, brs), 6.57(1H, d, J=7.8Hz), 6.85(1H, dd, J=7.9, 1.9Hz), 6.92-6.98(2H, m), 7.02(1H, d, J=2.2Hz), 7.09-7.13(2H, m)

TABLE D-148

Example 148
Phe(4-F)-N-Me-Leu(γ-Me)-N-Me-Tyr(3-tBu)-NH$_2$
R
neo-Pent

Reaction 1

| Compound T4 (g) | Compound I11 (g) | CMPI (g) | TEA (ml) | THF (ml) | Reaction time (hr) | Column sol. | Product | Amount (g) |
|---|---|---|---|---|---|---|---|---|
| 0.630 | 0.780 | 0.770 | 0.35 | 25.00 | 48 | nHx:EA = 1:2 | I-a148 | 0.850 |

Reaction 2-a

| Compound I-a148 (g) | TFA (ml) | MC (ml) | Reaction time (hr) | Column sol. | Product | Amount (g) |
|---|---|---|---|---|---|---|
| 0.800 | 2.50 | 12.50 | 4 | MC:MeOH = 9:1 | I-b148 | 0.600 |

Reaction 3

| Compound I-b148 (g) | Compound P4 (g) | CMPI (g) | TEA (ml) | THF (ml) | Reaction time (hr) | Column sol. | Product | Amount (g) |
|---|---|---|---|---|---|---|---|---|
| 0.600 | 0.580 | 0.470 | 0.42 | 30.00 | 12 | nHx:EA:MC = 1:2:1 | I-c148 | 0.950 |

Reaction 4-b

| Compound I-c148 (g) | Pd/C (g) | MeOH (ml) | Reaction time (hr) | Column sol. | Amount (g) | HPLC min |
|---|---|---|---|---|---|---|
| 0.950 | 0.140 | 13.00 | 3 | MC:MeOH = 20:1 | 0.58 | 20.96 |

ESI-MS(M$^+$+1): 557
1H-NMR(CD$_3$OD): (two rotamers) δ 0.71 and 0.99(9H, s), 1.43 and 1.46(9H, s), 1.28-1.40(2H, m), 2.43, 2.81, 2.97 and 3.07(6H, s), 2.23-3.04(4H, m), 3.25-3.28(1H, m), 3.79(2/3H, m), 3.92(1/3H, dd, J=9.8, 4.6Hz), 5.58 and 5.53 (1H, dd, J=6.9-8.2, 4.8-6.9Hz), 6.61 and 6.80(1H, d, J=8.2Hz), 6.74-7.37(6H, m)

TABLE D-149

Example 149
Phe(4-F)-N-Me-D-Leu(γ-Me)-N-Me-Tyr(3-tBu)-NH$_2$
R
neoPent:D

Reaction 1

| Compound T4 (g) | Compound I12 (g) | CMPI (g) | TEA (ml) | THF (ml) | Reaction time (hr) | Column sol. | Product | Amount (g) |
|---|---|---|---|---|---|---|---|---|
| 0.800 | 0.990 | 0.980 | 0.90 | 30.00 | 12 | nHx:EA = 1:2 | I-a149 | 1.250 |

TABLE D-149-continued

Example 149
Phe(4-F)-N-Me-D-Leu(γ-Me)-N-Me-Tyr(3-tBu)-NH$_2$
R
neoPent:D

Reaction 2-a

| Compound I-a149 (g) | TFA (ml) | MC (ml) | Reaction time (hr) | Column sol. | Product | Amount (g) |
|---|---|---|---|---|---|---|
| 1.250 | 3.90 | 19.50 | 3 | MC:MeOH = 20:1 | I-b149 | 0.99 |

Reaction 3

| Compound I-b149 (g) | Compound P4 (g) | CMPI (g) | TEA (ml) | THF (ml) | Reaction time (hr) | Column sol. | Product | Amount (g) |
|---|---|---|---|---|---|---|---|---|
| 1.000 | 0.970 | 0.780 | 0.71 | 50.00 | 5 | nHx:EA = 1:2 | I-c149 | 1.500 |

Reaction 4-b

| Compound I-c149 (g) | Pd/C (g) | MeOH (ml) | Reaction time (hr) | Column sol. | Amount (g) | HPLC min |
|---|---|---|---|---|---|---|
| 1.500 | 0.230 | 20.00 | 2 | MC:MeOH = 20:1 | 0.83 | 22.63 |

ESI-MS(M$^+$+1): 557
1H-NMR(CD$_3$OD): (two rotamer) δ 0.62 and 0.84(9H, s), 0.88 and 1.35(2H, s), 1.40(9H, s), 2.45 and 2.82(3H, s), 2.84-2.95(3H, m), 3.04 and 3.10(3H, s), 3.23(1H, dd, J=14.7, 4.9Hz), 4.65(1H, dd, J=8.0, 2.3Hz), 5.28(1H, m), 5.45 (1H, dd, J=11.8, 5.1Hz), 6.63(1H, d, J=7.9Hz), 6.88(1H, dd, J=8.0, 2.3Hz), 7.01(2H, m), 7.10(1H, d, J=2.3Hz), 7.25 (2H, dd, J=8.5, 5.4Hz)

TABLE D-150A

Example 150A(less polar)
Phe(4-F)-N-Me-Ala(β-CF$_3$)-N-Me-Tyr(3-tBu)-NH$_2$
R
CH$_2$CF$_3$:L, D-mixture

Reaction 1

| Compound T4 (g) | Compound I13 (g) | CMPI (g) | TEA (ml) | THF (ml) | Reaction time (hr) | Column sol. | Product | Amount (g) |
|---|---|---|---|---|---|---|---|---|
| 0.500 | 0.560 | 0.560 | 0.51 | 20.00 | 5.000 | nHx:EA = 1:1 | I-a150 | 0.980 |

Reaction 2-b

| Compound I-a150 (g) | Pd/C (g) | MeOH (ml) | Reaction time (hr) | Column sol. | Product | Amount (g) |
|---|---|---|---|---|---|---|
| 0.980 | 0.500 | 20.00 | 2 | MC:MeOH = 15:1 | I-b150A | 0.360 (less polar) |
|  |  |  |  |  | I-b150B | 0.280 (more polar) |

Reaction 3

| Compound I-b150A (g) | Compound P4 (g) | CMPI (g) | TEA (ml) | THF (ml) | Reaction time (hr) | Column sol. | Product | Amount (g) |
|---|---|---|---|---|---|---|---|---|
| 0.360 | 0.310 | 0.270 | 0.27 | 15.00 | 12 | nHx:EA = 1:1 | I-c150A | 0.32 |

Reaction 4-b

| Compound I-c150A (g) | Pd/C (g) | MeOH (ml) | Reaction time (hr) | Column sol. | Amount (g) | HPLC min |
|---|---|---|---|---|---|---|
| 0.310 | 0.150 | 10.00 | 2 | EA:MeOH = 15:1 | 0.200 | 18.66 |

ESI-MS(M$^+$+1): 569
1H-NMR(CD3OD): (two rotamers) δ 1.38 and 1.41(9H, s), 2.20, 2.56, 2.91, and 2.99(6H, s), 2.38-3.03(4H, m), 3.25 and 3.31(1H, d, J=4.8Hz), 3.72(1H, t, J=7.2Hz), 4.73(1H, brs), 5.53 and 5.57(1H d, J=4.6Hz), 5.80(1H, q, J=4.4Hz), 6.55-6.79(2H, m), 7.00-7.15(3H, m), 7.25-7.30(2H, m)

TABLE D-150B

Example 150B(more polar)
Phe(4-F)-N-Me-Ala(β-CF$_3$)-N-Me-Tyr(3-tBu)-NH$_2$
R
CH$_2$CF$_3$:L, D-mixture

Reaction 3

| Compound I-b150B (g) | Compound P4 (g) | CMPI (g) | TEA (ml) | THF (ml) | Reaction time (hr) | Column sol. | Product | Amount (g) |
|---|---|---|---|---|---|---|---|---|
| 0.270 | 0.240 | 0.200 | 0.20 | 15.00 | 12.00 | nHx:EA = 1:1 | I-c150B | 0.300 |

Reaction 4-b

| Compound I-c150B (g) | Pd/C (g) | MeOH (ml) | Reaction time (hr) | Column sol. | Amount (g) | HPLC min |
|---|---|---|---|---|---|---|
| 0.300 | 0.150 | 10.00 | 2 | EA:MeOH = 20:1 | 0.170 | 21.51 |

ESI-MS(M$^+$+1): 569
1H-NMR(CD$_3$OD): (two rotamers) δ 1.40(9H, s), 2.19-2.40(2H, m), 2.73 and 2.76(1H, d, J=7.0Hz), 2.89(3H, s), 292-296(1H, m), 2.98(3H, s), 3.21 and 3.24(1H, d, J=6.1Hz), 4.03(1H, t, J=7.2Hz), 4.52-4.61(1H, m), 5.36 (1H, q, J=5.5Hz), 5.61(1H, t, J=7.0Hz), 6.67(1H, d, J=8.0Hz), 6.89(1H, dd, J=7.9, 2.4Hz), 7.01-7.10(3H, m), 7.24-7.29(2H, m)

TABLE D-151

Example 151
Phe(4-F)-N-Me-Chg-N-Me-Tyr(3-tBu)-NH$_2$
R
c-Hex

Reaction 1

| Compound T4 (g) | Compound I14 (g) | CMPI (g) | TEA (ml) | THF (ml) | Reaction time (hr) | Column sol. | Product | Amount (g) |
|---|---|---|---|---|---|---|---|---|
| 1.290 | 1.500 | 2.650 | 1.45 | 30.00 | 20 | nHx:EA = 1:1 | I-a151 | 0.700 |

Reaction 2-a

| Compound I-a151 (g) | TFA (ml) | MC (ml) | Reaction time (hr) | Column sol. | Product | Amount (g) |
|---|---|---|---|---|---|---|
| 0.700 | 4.00 | 20.00 | 4 | MC:MeOH = 20:1 | I-b151 | 0.400 |

Reaction 3

| Compound I-b151 (g) | Compound P1 (g) | CMPI (g) | TEA (ml) | THF (ml) | Reaction time (hr) | Column sol. | Product | Amount (g) |
|---|---|---|---|---|---|---|---|---|
| 0.400 | 0.380 | 0.760 | 0.41 | 20.00 | 20 | nHx:EA = 1:1 | I-c151 | 0.500 |

Reaction 4-a

| Compound I-c151 (g) | TFA (ml) | MC (ml) | Reaction time (hr) | Column sol. | Amount (g) | HPLC min |
|---|---|---|---|---|---|---|
| 0.500 | 4.00 | 20.00 | 4 | MC:MeOH = 20:1 | 0.400 | 20.140 |

ESI-MS(M$^+$+1): 569
1H-NMR(CDCl$_3$): (two rotamers) δ 0.72-1.68(10H, m), 1.35 and 1.40(9H, s), 1.82-2.10(1H, m), 2.30-2.65(1H, m), 2.52(3H, s), 2.70-2.90(1H, m), 2.75(3H, s), 2.75-2.90(1H, m), 3.05-3.40(3H, m), 3.60-3.85(1H, m), 5.05-5.20(2H, m), 6.35-6.75(2H, m), 6.75-7.20(5H, m)

TABLE D-152

Example 152
Phe(4-F)-N-Me-D-Chg-N-Me-Tyr(3-tBu)-NH$_2$
R
c-Hex:D

Reaction 1

| Compound T4 (g) | Compound I15 (g) | CMPI (g) | TEA (ml) | THF (ml) | Reaction time (hr) | Column sol. | Product | Amount (g) |
|---|---|---|---|---|---|---|---|---|
| 0.600 | 0.620 | 1.520 | 0.69 | 20.00 | 20 | nHx:EA = 1:1 | I-a152 | 0.540 |

Reaction 2-a

| Compound I-a152 (g) | TFA (ml) | MC (ml) | Reaction time (hr) | Column sol. | Product | Amount (g) |
|---|---|---|---|---|---|---|
| 0.540 | 3.00 | 15.00 | 4 | MC:MeOH = 20:1 | I-b152 | 0.250 |

Reaction 3

| Compound I-b152 (g) | Compound P1 (g) | CMPI (g) | TEA (ml) | THF (ml) | Reaction time (hr) | Column sol. | Product | Amount (g) |
|---|---|---|---|---|---|---|---|---|
| 0.250 | 0.240 | 0.470 | 0.26 | 15.00 | 20 | nHx:EA = 1:1 | I-c152 | 0.350 |

Reaction 4-a

| Compound I-c152 (g) | TFA (ml) | MC (ml) | Reaction time (hr) | Column sol. | Amount (g) | HPLC min |
|---|---|---|---|---|---|---|
| 0.350 | 3.00 | 10.00 | 4 | MC:MeOH = 20:1 | 0.27 | 22.040 |

ESI-MS(M$^+$+1): 569
1H-NMR(CDCl3): (two rotamers) δ 0.65-1.70(11H, m), 1.38(9H, s), 2.15-2.35(1H, m), 2.25(3H, s), 2.75-3.05 (1H, m), 2.95(3H, s), 3.10-3.25(3H, m), 5.20-5.27(2H, m), 5.55-5.65(1H, m), 6.15-6.25(2H, m), 6.54 and 6.57 (2H, d, J=8.4 Hz), 6.75-6.95(1H, m), 7.05-7.15(2H, m)

TABLE D-153

Example 153
Phe(4-F)-N-Me-Cha-N-Me-Tyr(3-tBu)-NH$_2$
R
CH$_2$c-Hex

Reaction 1

| Compound T4 (g) | Compound I16 (g) | CMPI (g) | TEA (ml) | THF (ml) | Reaction time (hr) | Column sol. | Product | Amount (g) |
|---|---|---|---|---|---|---|---|---|
| 0.950 | 1.300 | 1.150 | 1.10 | 38.00 | 15 | nHx:EA = 1:1 | I-a153 | 1.600 |

Reaction 2-a

| Compound I-a153 (g) | TFA (ml) | MC (ml) | Reaction time (hr) | Column sol. | Product | Amount (g) |
|---|---|---|---|---|---|---|
| 1.600 | 4.80 | 24.00 | 3 | MC:MeOH = 20:1 | I-b153 | 0.840 |

Reaction 3

| Compound I-b153 (g) | Compound P1 (g) | CMPI (g) | TEA (ml) | THF (ml) | Reaction time (hr) | Column sol. | Product | Amount (g) |
|---|---|---|---|---|---|---|---|---|
| 0.840 | 0.680 | 0.620 | 0.60 | 20.00 | 15 | nHx:EA = 1:1 | I-c153 | 1.100 |

Reaction 4-a

| Compound I-c153 (g) | TFA (ml) | MC (ml) | Reaction time (hr) | Column sol. | Amount (g) | HPLC min |
|---|---|---|---|---|---|---|
| 1.100 | 2.40 | 12.00 | 3 | MC:MeOH = 30:1 | 0.50 | 21.154 |

ESI-MS(M$^+$+1): 583
1H-NMR(CDCl$_3$): (two rotamers) δ 0.09-1.88(13H, m), 1.35 and 1.26(9H, s), 2.32-2.80(2H, m), 2.46 and 2.74 (3H, s), 2.83-3.27(3H, m), 2.99 and 3.03(3H, s), 3.59-3.73 and 3.81-3.95(1H, m), 4.62-4.74 and 5.11-5.25(1H, m), 5.27-5.59(2H, m), 6.08(1/2H, brs), 6.44 and 6.63(1H, d, J=7.9-8.3Hz), 6.77 and 6.87(1H, dd, J=7.2-7.5 1.8-1.9Hz), 6.92-7.20(5H, m), 7.59(1/2H, brs)

TABLE D-154

Example 154
Phe(4-F)-N-Me-D-Cha-N-Me-Tyr(3-tBu)-NH$_2$
R
CH$_2$c-Hex:D

Reaction 1

| Compound T4 (g) | Compound I17 (g) | CMPI (g) | TEA (ml) | THF (ml) | Reaction time (hr) | Column sol. | Product | Amount (g) |
|---|---|---|---|---|---|---|---|---|
| 0.730 | 1.000 | 0.900 | 0.80 | 29.00 | 15 | nHx:EA = 1:1 | I-a154 | 1.200 |

Reaction 2-a

| Compound I-a154 (g) | TFA (ml) | MC (ml) | Reaction time (hr) | Column sol. | Product | Amount (g) |
|---|---|---|---|---|---|---|
| 1.200 | 3.60 | 18.00 | 3 | MC:MeOH = 20:1 | I-b154 | 0.740 |

Reaction 3

| Compound I-b154 (g) | Compound P1 (g) | CMPI (g) | TEA (ml) | THF (ml) | Reaction time (hr) | Column sol. | Product | Amount (g) |
|---|---|---|---|---|---|---|---|---|
| 0.740 | 0.600 | 0.540 | 0.50 | 17.00 | 15 | nHx:EA = 1:1 | I-c154 | 0.900 |

Reaction 4-a

| Compound I-c154 (g) | TFA (ml) | MC (ml) | Reaction time (hr) | Column sol. | Amount (g) | HPLC min |
|---|---|---|---|---|---|---|
| 0.900 | 2.00 | 10.00 | 3 | MC:MeOH = 30:1 | 0.24 | 25.144 |

ESI-MS(M$^+$+1): 583
1H-NMR(CDCl$_3$): δ 0.62-1.37(13H, m), 1.37(9H, m), 2.67-3.10(7H, m), 2.88(3H, s), 2.97(3H, s), 3.30 and 3.35 (1H, d, J=3.3-3.4Hz), 3.95(1H, t, J=6.9Hz), 5.04 and 5.08(1H, d, J=4.2-4.5Hz), 5.43 and 5.47(1H, d, J=5.4-5.8Hz), 5.52(1H, brs), 6.37(1H, brs), 6.58(1H, d, J=7.9Hz), 6.79-7.09(4H, m), 7.11(1H, d, J=5.2Hz), 7.14(1H, d, J=5.4Hz)

TABLE D-155

Example 155
Phe(4-F)-N-Me-Phe-N-Me-Tyr(3-tBu)-NH$_2$
R
CH$_2$Ph

Reaction 1

| Compound T4 (g) | Compound I18 (g) | CMPI (g) | TEA (ml) | THF (ml) | Reaction time (hr) | Column sol. | Product | Amount (g) |
|---|---|---|---|---|---|---|---|---|
| 0.800 | 1.000 | 1.230 | 0.89 | 20.00 | 20 | nHx:EA = 1:1 | I-a155 | 1.390 |

Reaction 2-b

| Compound I-a155 (g) | Pd/C (g) | MeOH (ml) | Reaction time (hr) | Column sol. | Product | Amount (g) |
|---|---|---|---|---|---|---|
| 1.390 | 0.300 | 20.00 | 20 | MC:MeOH = 20:1 | I-b155 | 0.840 |

Reaction 3

| Compound I-b155 (g) | Compound P1 (g) | CMPI (g) | TEA (ml) | THF (ml) | Reaction time (hr) | Column sol. | Product | Amount (g) |
|---|---|---|---|---|---|---|---|---|
| 0.770 | 0.710 | 0.720 | 0.52 | 15.00 | 20 | nHx:EA = 1:1 | I-c155 | 0.997 |

Reaction 4-a

| Compound I-c155 (g) | TFA (ml) | MC (ml) | Reaction time (hr) | Column sol. | Amount (g) | HPLC min |
|---|---|---|---|---|---|---|
| 0.997 | 3.00 | 10.00 | 4 | MC:MeOH = 20:1 | 0.68 | 19.710 |

ESI-MS(M$^+$+1): 577
1H-NMR(CDCl$_3$): (two rotamers) δ 1.40 and 1.42(9H, s), 2.54(3H, s), 2.61-3.04(5H, m), 3.15-3.39(4H, m), 3.67-3.85(1H, m), 5.32-5.72(2H, m), 6.57-6.72(1H, m), 6.98-7.29(10H, m)

TABLE D-156

Example 156
Phe(4-F)-N-Me-D-Phe-N-Me-Tyr(3-tBu)-NH$_2$
R
CH$_2$Ph:D

Reaction 1

| Compound T4 (g) | Compound I19 (g) | CMPI (g) | TEA (ml) | THF (ml) | Reaction time (hr) | Column sol. | Product | Amount (g) |
|---|---|---|---|---|---|---|---|---|
| 0.800 | 0.800 | 1.230 | 0.89 | 20.00 | 20 | nHx:EA = 1:1 | I-a156 | 1.140 |

Reaction 2-a

| Compound I-a156 (g) | TFA (ml) | MC (ml) | Reaction time (hr) | Column sol. | Product | Amount (g) |
|---|---|---|---|---|---|---|
| 1.140 | 3.00 | 10.00 | 4 | MC:MeOH = 20:1 | I-b156 | 0.990 |

Reaction 3

| Compound I-b156 (g) | Compound P1 (g) | CMPI (g) | TEA (ml) | THF (ml) | Reaction time (hr) | Column sol. | Product | Amount (g) |
|---|---|---|---|---|---|---|---|---|
| 0.770 | 0.710 | 0.720 | 0.52 | 20.00 | 20 | nHx:EA = 1:1 | I-c156 | 0.960 |

Reaction 4-a

| Compound I-c156 (g) | TFA (ml) | MC (ml) | Reaction time (hr) | Column sol. | Amount (g) | HPLC min |
|---|---|---|---|---|---|---|
| 0.960 | 3.00 | 10.00 | 4 | MC:MeOH = 20:1 | 0.73 | 21.960 |

ESI-MS(M$^+$+1): 577
1H-NMR(CDCl$_3$): δ 1.42(9H, s), 2.47-2.65(4H, m), 2.97-3.25(2H, m), 3.04(3H, s), 3.15(3H, s), 3.32-3.51(3H, m), 4.01-4.15(1H, m), 6.75-6.80(1H, m), 6.82-7.45(1H, m)

TABLE D-157

Example 157
Phe(4-F)-N-Me-Phe(4-F)-N-Me-Tyr(3-tBU)-NH$_2$
R
CH$_2$Phe(4-F)

Reaction 1

| Compound T4 (g) | Compound I20 (g) | CMPI (g) | TEA (ml) | THF (ml) | Reaction time (hr) | Column sol. | Product | Amount (g) |
|---|---|---|---|---|---|---|---|---|
| 0.960 | 1.370 | 1.180 | 1.10 | 38.00 | 15 | nHx:EA = 1:2 | I-a157 | 1.880 |

Reaction 2-a

| Compound I-a157 (g) | TFA (ml) | MC (ml) | Reaction time (hr) | Column sol. | Product | Amount (g) |
|---|---|---|---|---|---|---|
| 1.880 | 5.40 | 27.00 | 3 | MC:MeOH = 20:1 | I-b157 | 1.220 |

Reaction 3

| Compound I-b157 (g) | Compound P1 (g) | CMPI (g) | TEA (ml) | THF (ml) | Reaction time (hr) | Column sol. | Product | Amount (g) |
|---|---|---|---|---|---|---|---|---|
| 1.220 | 0.780 | 0.710 | 0.60 | 23.00 | 18 | nHx:EA = 1:2 | I-c157 | 1.550 |

Reaction 4-a

| Compound I-c157 (g) | TFA (ml) | MC (ml) | Reaction time (hr) | Column sol. | Amount (g) | HPLC min |
|---|---|---|---|---|---|---|
| 1.550 | 3.30 | 16.00 | 3 | MC:MeOH = 20:1 | 0.73 | 21.035 |

ESI-MS(M$^+$+1): 595
1H-NMR(CDCl$_3$): (two rotamers) δ 1.28 and 1.35(9H, s), 2.30-3.25(12H, m), 2.38 and 2.56(3H, s), 2.86 and 2.99(3H, s), 3.49-3.72(1H, m), 4.84-5.17(1H, m), 5.18-5.41(2H, m), 5.51-5.78(1H, m), 6.38 and 6.43(1H, d, J=8.3Hz), 6.60-7.23(10H, m)

TABLE D-158

Example 158
Phe(4-F)-N-Me-D-Phe(4-F)-N-Me-Tyr(3-tBu)-NH₂
R
CH₂Phe(4-F):D

Reaction 1

| Compound T4 (g) | Compound I21 (g) | CMPI (g) | TEA (ml) | THF (ml) | Reaction time (hr) | Column sol. | Product | Amount (g) |
|---|---|---|---|---|---|---|---|---|
| 0.700 | 1.000 | 0.850 | 0.80 | 27.00 | 18 | nHx:EA = 1:2 | I-a158 | 1.120 |

Reaction 2-a

| Compound I-a158 (g) | TFA (ml) | MC (ml) | Reaction time (hr) | Column sol. | Product | Amount (g) |
|---|---|---|---|---|---|---|
| 1.120 | 3.30 | 16.50 | 3 | MC:MeOH = 20:1 | I-b158 | 0.880 |

Reaction 3

| Compound I-b158 (g) | Compound P1 (g) | CMPI (g) | TEA (ml) | THF (ml) | Reaction time (hr) | Column sol. | Product | Amount (g) |
|---|---|---|---|---|---|---|---|---|
| 0.880 | 0.560 | 0.500 | 0.50 | 16.00 | 15 | nHx:EA = 1:2 | I-c158 | 0.900 |

Reaction 4-a

| Compound I-c158 (g) | TFA (ml) | MC (ml) | Reaction time (hr) | Column sol. | Amount (g) | HPLC min |
|---|---|---|---|---|---|---|
| 0.900 | 2.00 | 10.00 | 3 | MC:MeOH = 20:1 | 0.30 | 23.049 |

ESI-MS(M⁺+1): 595
1H-NMR(CDCl₃): (two rotamers) d 1.34 and 1.37(9H, s), 2.38-2.51(1H, m), 2.53-2.82(5H, m), 2.86(3H, s), 2.88(3H, s), 3.04-3.15(1H, m), 3.21 and 3.26(1H, d, J=6.4-6.3), 3.78-3.95(1H, m), 5.26-5.38(1H, m), 5.38-5.52 (1H, m), 5.62(1H, brs), 6.27(1H, brs), 6.79(1H, d, J=8.1Hz), 6.78(1H, d, J=8.7Hz), 6.83-7.22(9H, m)

TABLE D-159

Example 159
Phe(4-F)-N-Me-Phe(4-Cl)-N-Me-Tyr(3-tBu)-NH₂
R
CH₂Ph(4-Cl)

Reaction 1

| Compound T4 (g) | Compound I22 (g) | CMPI (g) | TEA (ml) | THF (ml) | Reaction time (hr) | Column sol. | Product | Amount (g) |
|---|---|---|---|---|---|---|---|---|
| 1.080 | 1.630 | 1.330 | 0.91 | 20.00 | 16 | nHx:EA = 1:1 | I-a159 | 2.000 |

Reaction 2-a

| Compound I-a159 (g) | TFA (ml) | MC (ml) | Reaction time (hr) | Column sol. | Product | Amount (g) |
|---|---|---|---|---|---|---|
| 2.000 | 5.60 | 25.00 | 1 | MC:MeOH = 20:1 | I-b159 | 1.13 |

Reaction 3

| Compound I-b159 (g) | Compound P1 (g) | CMPI (g) | TEA (ml) | THF (ml) | Reaction time (hr) | Column sol. | Product | Amount (g) |
|---|---|---|---|---|---|---|---|---|
| 1.130 | 0.861 | 0.777 | 0.53 | 20.00 | 3 | nHx:EA = 1:1 | I-c159 | 0.908 |

Reaction 4-a

| Compound I-c159 (g) | TFA (ml) | MC (ml) | Reaction time (hr) | Column sol. | Amount (g) | HPLC min |
|---|---|---|---|---|---|---|
| 0.908 | 1.96 | 10.00 | 3 | MC:MeOH = 20:1 | 0.625 | 21.59 |

ESI-MS(M⁺+1): 612
1H-NMR(CDCl₃): (two rotamers) d 1.28 and 1.35(9H, s), 2.38 and 2.55(3H, s), 2.40-3.32(6H, m), 2.85 and 3.0(3H, s), 3.56 and 3.72(1H, t, J=8.8Hz), 4.92(2/5H, m), 5.20-5.50(5/2H, m), 5.60 and 5.78(3/5H, brs), 6.35-7.40(25/2H, m)

TABLE D-160

Example 160
Phe(4-F)-N-Me-D-Phe(4-Cl)-N-Me-Tyr(3-tBu)-NH$_2$
R
CH$_2$Ph(4-Cl):D

Reaction 1

| Compound T4 (g) | Compound I22 (g) | CMPI (g) | TEA (ml) | THF (ml) | Reaction time (hr) | Column sol. | Product | Amount (g) |
|---|---|---|---|---|---|---|---|---|
| 0.519 | 0.781 | 0.639 | 0.44 | 10.00 | 16 | nHx:EA = 1:1 | I-a160 | 0.947 |

Reaction 2-a

| Compound I-a160 (g) | TFA (ml) | MC (ml) | Reaction time (hr) | Column sol. | Product | Amount (g) |
|---|---|---|---|---|---|---|
| 0.947 | 5.60 | 15.00 | 1 | MC:MeOH = 20:1 | I-b160 | 0.624 |

Reaction 3

| Compound I-b160 (g) | Compound P1 (g) | CMPI (g) | TEA (ml) | THF (ml) | Reaction time (hr) | Column sol. | Product | Amount (g) |
|---|---|---|---|---|---|---|---|---|
| 1.130 | 0.476 | 0.430 | 0.30 | 15.00 | 3 | nHx:EA = 1:1 | I-c160 | 0.46 |

Reaction 4-a

| Compound I-c160 (g) | TFA (ml) | MC (ml) | Reaction time (hr) | Column sol. | Amount (g) | HPLC min |
|---|---|---|---|---|---|---|
| 0.460 | 1.00 | 5.00 | 3 | MC:MeOH = 20:1 | 0.300 | 19.53 |

ESI-MS(M$^+$+1): 612
1H-NMR(CDCl$_3$): d 1.35(9H, s), 1.30-2.96(5H, m), 2.88(3H, s), 2.89(3H, s), 3.03-3.35(1H, m), 3.83(3/4H, m), 5.29(2H, s), 5.43(6/4H, m), 6.20(3/4H, brs), 6.52(1H, d, J=8.8Hz), 6.78(1H, d, J=8.8Hz), 6.90-7.32(10H, m)

TABLE D-161

Example 161
Phe(4-F)-N-Me-Tyr-N-Me-Tyr(3-tBU)-NH$_2$
R
CH$_2$Ph(4-OH)

Reaction 1

| Compound T4 (g) | Compound I24 (g) | CMPI (g) | TEA (ml) | THF (ml) | Reaction time (hr) | Column sol. | Product | Amount (g) |
|---|---|---|---|---|---|---|---|---|
| 1.300 | 2.600 | 1.730 | 1.09 | 30.00 | 3 | nHx:EA = 1:1 | I-a161 | 2.610 |

Reaction 2-a

| Compound I-a161 (g) | TFA (ml) | MC (ml) | Reaction time (hr) | Column sol. | Product | Amount (g) |
|---|---|---|---|---|---|---|
| 2.610 | 6.47 | 33.00 | 3 | MC:MeOH = 20:1 | I-b161 | 1.300 |

Reaction 3

| Compound I-b161 (g) | Compound P4 (g) | CMPI (g) | TEA (ml) | THF (ml) | Reaction time (hr) | Column sol. | Product | Amount (g) |
|---|---|---|---|---|---|---|---|---|
| 1.300 | 1.200 | 0.964 | 0.70 | 30.00 | 3 | nHx:EA = 1:1 | I-c161 | 1.880 |

Reaction 4-b

| Compound I-c161 (g) | Pd/C (g) | MeOH (ml) | Reaction time (hr) | Column sol. | Amount (g) | HPLC min |
|---|---|---|---|---|---|---|
| 1.880 | 0.282 | 40.00 | 3 | MC:MeOH = 20:1 | 0.500 | 17.94 |

ESI-MS(M$^+$+1): 593
1H-NMR(CD$_3$OD): (two rotamers) d 1.41 and 1.42(9H, s), 2.32 and 2.39(3H, s), 2.90 and 3.07(3H, s), 2.59-3.50(7H, m), 3.72 and 3.85(1/2H, m), 5.05 and 5.30(1/2H, m), 5.60(1H, m), 6.50-7.43(11H, m)

TABLE D-162

Example 162
Phe(4-F)-N-Me-D-Tyr-N-Me-Tyr(3-tBu)-NH$_2$
R
CH$_2$Ph(4-OH):D

Reaction 1

| Compound T4 (g) | Compound I25 (g) | CMPI (g) | TEA (ml) | THF (ml) | Reaction time (hr) | Column sol. | Product | Amount (g) |
|---|---|---|---|---|---|---|---|---|
| 0.920 | 2.000 | 1.220 | 0.77 | 30.00 | 3 | nHx:EA = 1:1 | I-a162 | 1.550 |

Reaction 2-b

| Compound I-a162 (g) | Pd/C (g) | MeOH (ml) | Reaction time (hr) | Column sol. | Product | Amount (g) |
|---|---|---|---|---|---|---|
| 1.550 | 0.233 | 20.00 | 12 | MC:MeOH = 20:1 | I-b162 | 0.977 |

Reaction 3

| Compound I-b162 (g) | Compound P4 (g) | CMPI (g) | TEA (ml) | THF (ml) | Reaction time (hr) | Column sol. | Product | Amount (g) |
|---|---|---|---|---|---|---|---|---|
| 0.977 | 1.080 | 0.871 | 0.64 | 20.00 | 3 | nHx:EA = 1:1 | I-c162 | 1.330 |

Reaction 4-b

| Compound I-c162 (g) | Pd/C (g) | MeOH (ml) | Reaction time (hr) | Column sol. | Amount (g) | HPLC min |
|---|---|---|---|---|---|---|
| 1.330 | 0.200 | 30.00 | 3 | MC:MeOH = 20:1 | 0.500 | 18.54 |

ESI-MS(M$^+$+1): 593
1H-NMR(CD$_3$OD): δ 1.45(9H, s), 2.42-2.75(4H, m), 3.02(3H, s), 2.34-3.15(2H, m), 3.32(1/5H, dd, J=7.6, 8.8Hz), 4.03(4/5H, t, J=8.8Hz), 5.42-5.65(2H, m), 6.65-7.25(12H, m)

TABLE D-163

Example 163
Phe(4-F)-N-Me-Ala(β-2-thienyl)-N-Me-Tyr(3-tBu)-NH$_2$
R
CH$_2$(2-Thienyl)

Reaction 1

| Compound T4 (g) | Compound I26 (g) | CMPI (g) | TEA (ml) | THF (ml) | Reaction time (hr) | Column sol. | Product | Amount (g) |
|---|---|---|---|---|---|---|---|---|
| 0.670 | 0.916 | 0.820 | 0.56 | 20.00 | 16 | nHx:EA = 1:1 | I-a163 | 1.280 |

Reaction 2-a

| Compound I-a163 (g) | TFA (ml) | MC (ml) | Reaction time (hr) | Column sol. | Product | Amount (g) |
|---|---|---|---|---|---|---|
| 1.280 | 3.80 | 19.00 | 3 | MC:MeOH = 20:1 | I-b163 | 0.513 |

Reaction 3

| Compound I-b163 (g) | Compound P1 (g) | CMPI (g) | TEA (ml) | THF (ml) | Reaction time (hr) | Column sol. | Product | Amount (g) |
|---|---|---|---|---|---|---|---|---|
| 0.513 | 0.418 | 0.379 | 0.30 | 20.00 | 3 | nHx:EA = 1:1 | I-c163 | 0.587 |

Reaction 4-a

| Compound I-c163 (g) | TFA (ml) | MC (ml) | Reaction time (hr) | Column sol. | Amount (g) | HPLC min |
|---|---|---|---|---|---|---|
| 0.587 | 1.32 | 10.00 | 3 | MC:MeOH = 20:1 | 0.35 | 23.7 |

ESI-MS(M$^+$+1): 583
1H-NMR(CDCl$_3$+ CD$_3$OD): (two rotamers) δ 1.30 and 1.35(9H, s), 1.80(1/3H, m), 2.25, 2.58 and 2.88, 3.0(6H, s), 2.0-3.25(5H, m), 3.35(2/3H, m), 3.60(1H, m), 4.90(1/3H, m), 5.27(2/3H, m), 5.37-5.64(1H, m), 6.40-6.72(2H, m), 6.72-7.20(8H, m)

TABLE D-164

Example 164
Phe(4-F)-N-Me-D-Ala(β-2-thienyl)-N-Me-Tyr(3-tBu)-NH$_2$
R
CH$_2$(2-Thienyl):D

Reaction 1

| Compound T4 (g) | Compound I26 (g) | CMPI (g) | TEA (ml) | THF (ml) | Reaction time (hr) | Column sol. | Product | Amount (g) |
|---|---|---|---|---|---|---|---|---|
| 0.760 | 1.040 | 0.930 | 0.64 | 20.00 | 16 | nHx:EA = 1:1 | I-a164 | 1.430 |

Reaction 2-a

| Compound I-a164 (g) | TFA (ml) | MC (ml) | Reaction time (hr) | Column sol. | Product | Amount (g) |
|---|---|---|---|---|---|---|
| 1.430 | 4.43 | 25.00 | 3 | MC:MeOH = 20:1 | I-b164 | 0.500 |

Reaction 3

| Compound I-b164 (g) | Compound P1 (g) | CMPI (g) | TEA (ml) | THF (ml) | Reaction time (hr) | Column sol. | Product | Amount (g) |
|---|---|---|---|---|---|---|---|---|
| 0.500 | 0.400 | 0.360 | 0.28 | 20.00 | 3 | nHx:EA = 1:1 | I-c164 | 0.857 |

Reaction 4-a

| Compound I-c164 (g) | TFA (ml) | MC (ml) | Reaction time (hr) | Column sol. | Amount (g) | HPLC min |
|---|---|---|---|---|---|---|
| 0.857 | 1.92 | 15.00 | 3 | MC:MeOH = 20:1 | 0.33 | 21.7 |

ESI-MS(M$^+$+1): 583
1H-NMR(CDCl$_3$): δ 1.35(9H, s), 2.17-3.20(7H, m), 2.91(3H, s), 2.95(3H, s), 3.28(1/2H, dd, J=15.8, 7.9Hz), 3.85(1/2H, t, J=7.9Hz), 5.35 and 5.45(2H, m), 5.65(1H, brs), 6.28(2/3H, brs), 6.48-7.30(28/3H, m)

TABLE D-165

Example 165
Phe(4-F)-N-Me-Ala(β-c-Pr)-N-Me-Tyr(3-tBu)-NH$_2$
R
CH$_2$c-Pr

Reaction 1

| Compound T4 (g) | Compound I28 (g) | CMPI (g) | TEA (ml) | THF (ml) | Reaction time (hr) | Column sol. | Product | Amount (g) |
|---|---|---|---|---|---|---|---|---|
| 0.820 | 1.100 | 1.000 | 0.90 | 33.00 | 17 | nHx:EA = 1:1 | I-a165 | 1.260 |

Reaction 2-b

| Compound I-a165 (g) | Pd/C (ml) | MeOH (ml) | Reaction time (hr) | Column sol. | Product | Amount (g) |
|---|---|---|---|---|---|---|
| 1.260 | 0.120 | 24.00 | 3 | MC:MeOH = 30:1 | I-b165 | 0.600 |

Reaction 3

| Compound I-b165 (g) | Compound P1 (g) | CMPI (g) | TEA (ml) | THF (ml) | Reaction time (hr) | Column sol. | Product | Amount (g) |
|---|---|---|---|---|---|---|---|---|
| 0.600 | 0.540 | 0.490 | 0.50 | 16.00 | 18 | nHx:EA = 1:1 | I-c165 | 0.590 |

Reaction 4-a

| Compound I-c165 (g) | TFA (ml) | MC (ml) | Reaction time (hr) | Column sol. | Amount (g) | HPLC min |
|---|---|---|---|---|---|---|
| 0.590 | 1.40 | 7.00 | 3 | MC:MeOH = 30:1 | 0.300 | 18.61 |

ESI-MS(M$^+$ +1): 541
1H-NMR(CD$_3$OD): (two rotamers) δ 0.85-0.78(5H, m), 1.39-1.91(2H, m), 1.47 and 1.49(9H, s), 2.34 and 2.69 (3H, s), 2.49-3.38(4H, m), 2.98 and 3.03(3H, s), 3.75-3.48(1H, m), 5.06-5.15 and 5.49-5.67(2H, m), 6.65-6.88 (2H, m), 7.04-7.43(5H, m)

Scheme 10 shows the synthesis process of Examples 166 and 176.

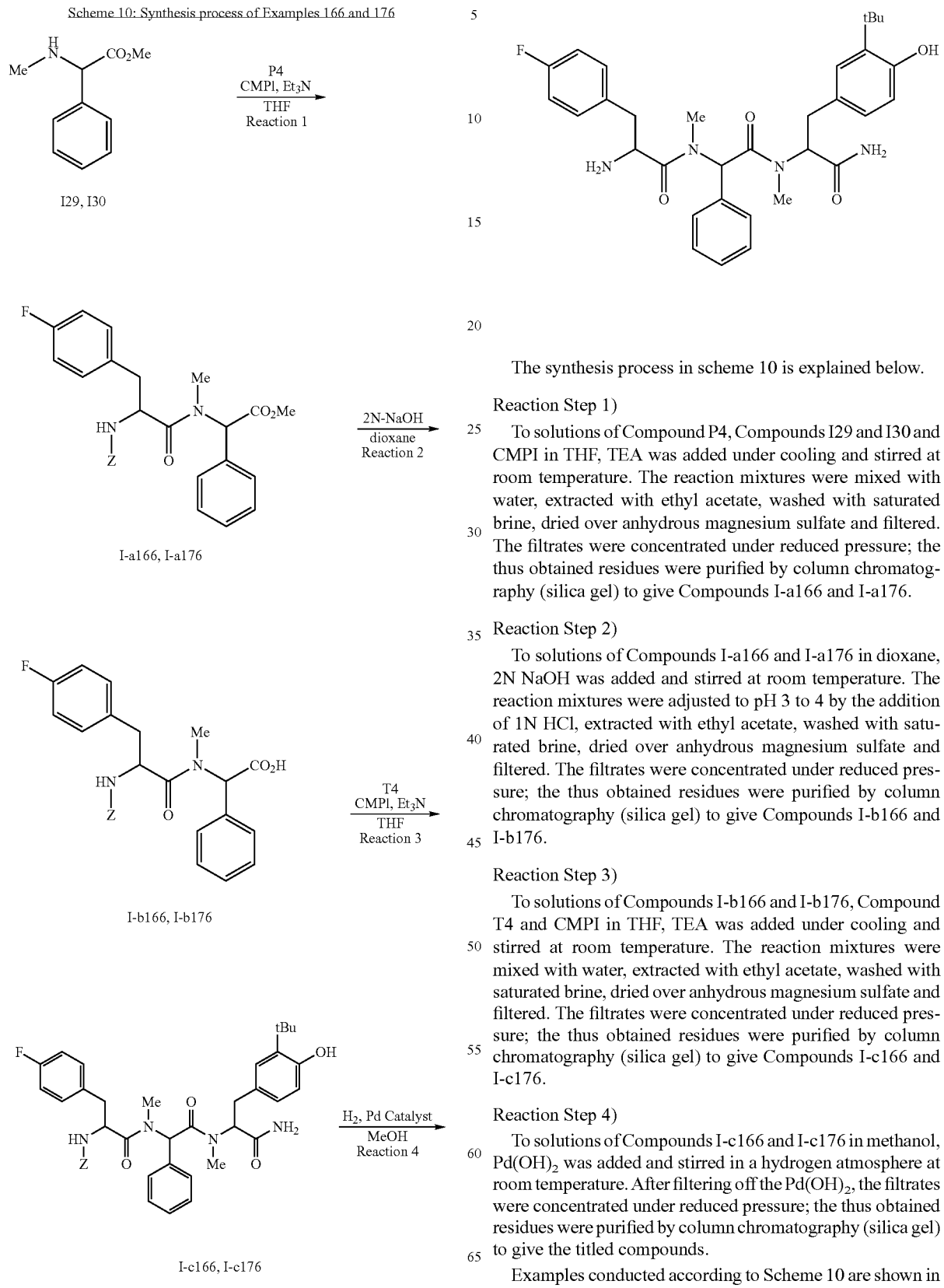

The synthesis process in scheme 10 is explained below.

Reaction Step 1)

To solutions of Compound P4, Compounds I29 and I30 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-a166 and I-a176.

Reaction Step 2)

To solutions of Compounds I-a166 and I-a176 in dioxane, 2N NaOH was added and stirred at room temperature. The reaction mixtures were adjusted to pH 3 to 4 by the addition of 1N HCl, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-b166 and I-b176.

Reaction Step 3)

To solutions of Compounds I-b166 and I-b176, Compound T4 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-c166 and I-c176.

Reaction Step 4)

To solutions of Compounds I-c166 and I-c176 in methanol, Pd(OH)$_2$ was added and stirred in a hydrogen atmosphere at room temperature. After filtering off the Pd(OH)$_2$, the filtrates were concentrated under reduced pressure; the thus obtained residues were purified by column chromatography (silica gel) to give the titled compounds.

Examples conducted according to Scheme 10 are shown in Tables D-166 and D-176.

TABLE D-166

Example 166
Phe(4-F)-N-Me-Phg-N-Me-Tyr(3-tBu)-NH$_2$

Reaction 1

| Compound I29 (g) | Compound P4 (g) | CMPI (g) | TEA (ml) | THF (ml) | Reaction time (hr) | Column sol. | Product | Amount (g) |
|---|---|---|---|---|---|---|---|---|
| 0.630 | 1.000 | 1.170 | 1.22 | 30.00 | 3 | nHx:EA = 1:1 | I-a166 | 1.070 |

Reaction 2

| Compound I-a166 (g) | 2N NaOH (ml) | dioxane (ml) | Reaction time (hr) | Column sol. | Product | Amount (g) |
|---|---|---|---|---|---|---|
| 1.070 | 2.50 | 20.00 | 3 | MC:MeOH = 20:1 | I-b166 | 1.030 |

Reaction 3

| Compound I-b166 (g) | Compound T4 (g) | CMPI (g) | TEA (ml) | THF (ml) | Reaction time (hr) | Column sol. | Product | Amount (g) |
|---|---|---|---|---|---|---|---|---|
| 1.030 | 0.504 | 0.668 | 0.42 | 20.00 | 3 | nHx:EA = 1:1 | I-c166 | 0.595 |

Reaction 4

| Compound I-c166 (g) | Pd(OH)$_2$ (g) | MeOH (ml) | Reaction time (hr) | Column sol. | Amount (g) | HPLC min |
|---|---|---|---|---|---|---|
| 0.595 | 0.100 | 10.00 | 3 | MC:MeOH = 20:1 | 0.480 | 20.00 |

ESI-MS(M$^+$+1): 563
1H-NMR(CD$_3$OD): (two rotamers) δ 1.40 and 1.49(9H, s), 2.75 and 2.90(3H, s), 2.95 and 3.15(3H, s), 2.53-3.50(5H, m) 4.12(1H, m), 4.74 and 5.32(1H, m), 6.40-7.58(15H, m)

TABLE D-176

Example 176
Phe(4-F)-N-Me-D-Phg-N-Me-Tyr(3-tBu)-NH$_2$

Reaction 1

| Compound I30 (g) | Compound P4 (g) | CMPI (g) | TEA (ml) | THF (ml) | Reaction time (hr) | Column sol. | Product | Amount (g) |
|---|---|---|---|---|---|---|---|---|
| 0.646 | 2.160 | 2.300 | 1.45 | 20.00 | 3 | nHx:EA = 1:1 | I-a176 | 1.030 |

Reaction 2

| Compound I-a176 (g) | 2N NaOH (ml) | dioxane (ml) | Reaction time (hr) | Column sol. | Product | Amount (g) |
|---|---|---|---|---|---|---|
| 1.030 | 2.40 | 20.00 | 3 | MC:MeOH = 20:1 | I-b176 | 0.540 |

Reaction 3

| Compound I-b176 (g) | Compound T4 (g) | CMPI (g) | TEA (ml) | THF (ml) | Reaction time (hr) | Column sol. | Product | Amount (g) |
|---|---|---|---|---|---|---|---|---|
| 0.540 | 0.268 | 0.355 | 0.22 | 10.00 | 3 | nHx:EA = 1:1 | I-c176 | 0.450 |

Reaction 4

| Compound I-c176 (g) | Pd(OH)$_2$ (g) | MeOH (ml) | Reaction time (hr) | Column sol. | Amount (g) | HPLC min |
|---|---|---|---|---|---|---|
| 0.450 | 0.070 | 10.00 | 3 | MC:MeOH = 20:1 | 0.270 | 20.98 |

ESI-MS(M$^+$+1): 563
1H-NMR(CD$_3$OD): δ 1.46(9H, s), 2.50(3H, s), 2.82(3H, s), 2.72-3.13(3H, m), 3.402H, m), 4.20(1H, m), 5.48(1H, dd, J=13.2, 6.2Hz), 6.25(1H, brs), 6.35(2H, d, J=8.8Hz), 6.75(1H, d, J=8.8Hz), 6.90(1H, dd, J=8.8, 1.7Hz), 7.05-7.45(8H, m)

Scheme 11 shows the synthesis process of Examples 167-171.

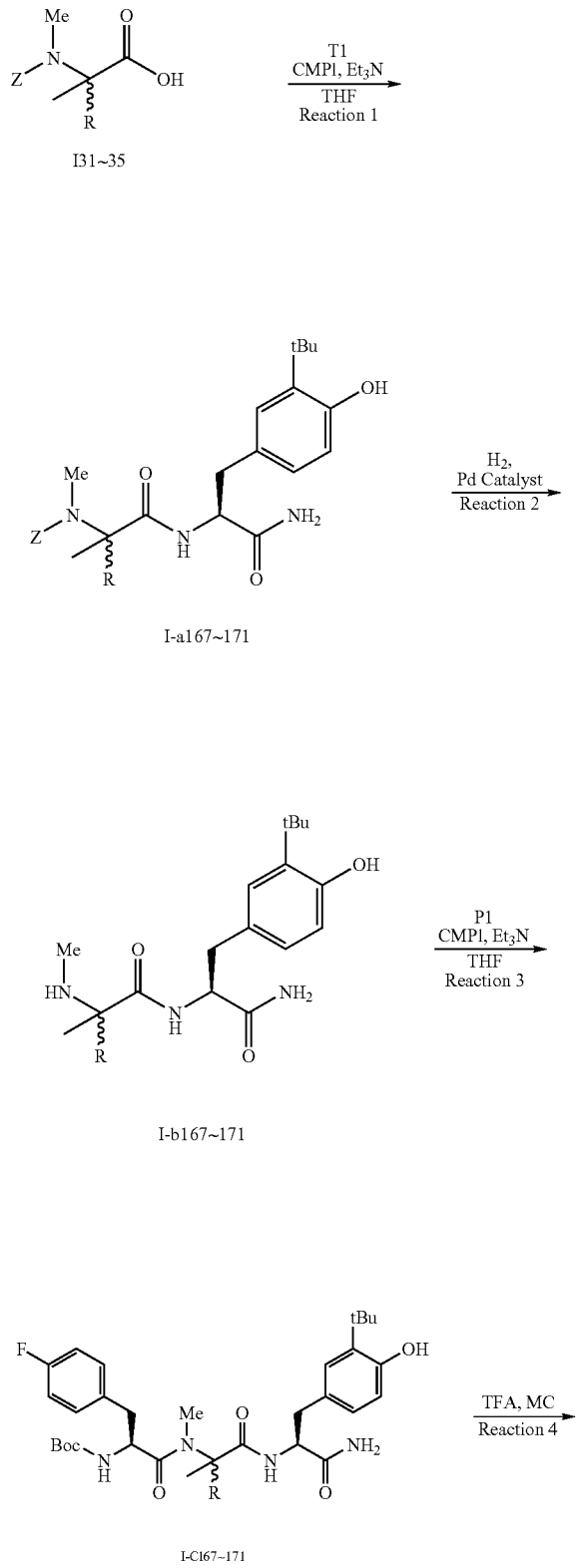

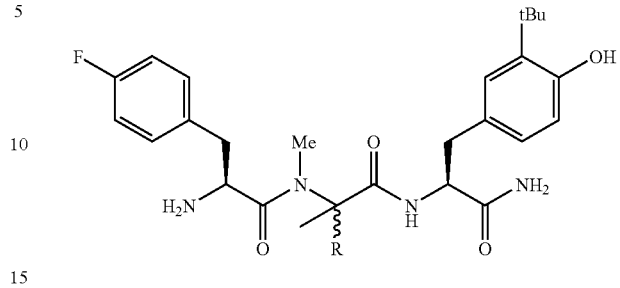

The synthesis process in scheme 11 is explained below.

Reaction Step 1)

To solutions of Compound T1, Compounds I131 to I35 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-a167 to I-a171.

Reaction Step 2)

To solutions of Compounds I-a167 to I-a171 in methanol, Pd/C was added and stirred in a hydrogen atmosphere at room temperature. After filtering off the Pd/C, the filtrates were concentrated under reduced pressure; the thus obtained residues were purified by column chromatography (silica gel) to give Compounds I-b167 to I-b171.

Reaction Step 3)

To solutions of Compounds I-b167 to I-b171, Compound P1 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-c167 to I-c171.

Reaction Step 4)

To solutions of Compounds I-c167 to I-c171 in dichloromethane, TFA was added under cooling and stirred at room temperature. The reaction mixtures were concentrated under reduced pressure, neutralized by the addition of a saturated NaHCO$_3$ aqueous solution, extracted with ethyl acetate, dried over anhydrous magnesium sulfate and filtered. The filtrates were concentrated under reduced pressure; the thus obtained residues were purified by column chromatography (silica gel) to give the titled compounds.

Examples conducted according to Scheme 11 are shown in Tables D-167 to D-171.

TABLE D-167

Example 167
Phe(4-F)-N-Me-α-Me-Phe-Tyr(3-tBu)-NH₂
R
CH₂Phe

Reaction 1

| Compound T1 (g) | Compound I31 (g) | CMPI (g) | TEA (ml) | THF (ml) | Reaction time (hr) | Column sol. | Product | Amount (g) |
|---|---|---|---|---|---|---|---|---|
| 0.570 | 1.180 | 0.900 | 0.80 | 24.00 | 5 | nHx:EA = 1:2 | I-a167 | 0.360 |

Reaction 2

| Compound I-a167 (g) | Pd/C (g) | MeOH (ml) | Reaction time (hr) | Product | Amount (g) |
|---|---|---|---|---|---|
| 0.360 | 0.040 | 6.00 | 3 | I-b167 | 0.260 |

Reaction 3

| Compound I-b167 (g) | Compound P1 (g) | CMPI (g) | TEA (ml) | THF (ml) | Reaction time (hr) | Column sol. | Product | Amount (g) |
|---|---|---|---|---|---|---|---|---|
| 0.260 | 0.420 | 0.780 | 0.40 | 6.30 | 120 | nHx:EA = 1:2 | I-c167 | 0.060 |

Reaction 4

| Compound I-c167 (g) | TFA (ml) | MC (ml) | Reaction time (hr) | Column sol. | Amount (g) | HPLC min |
|---|---|---|---|---|---|---|
| 0.060 | 0.20 | 0.70 | 3 | MC:MeOH = 20:1 | 0.01 | 21.813 |

ESI-MS(M⁺+1): 577
1H-NMR(CDCl₃): δ 1.30(3H, s), 1.34(9H, s), 2.37-2.62(3H, m), 2.51(3H, s), 3.07(1H, d, J=14.5Hz), 3.24-3.41 (2H, m), 3.73(1H, t, J=8.3Hz), 4.48-4.57(1H, m), 5.37-5.58(2H, m), 6.50(1H, d, J=9.0Hz), 6.75(1H, d, J=9.3Hz), 6.77(1H, s), 6.97-7.37(9H, m)

TABLE D-168

Example 168
Phe(4-F)-N-Me-α-Me-Phe-Tyr(3-tBu)-NH₂:Diastereomeric mixture
R
CH₂Phe:D

Reaction 1

| Compound T1 (g) | Compound I32 (g) | CMPI (g) | TEA (ml) | THF (ml) | Reaction time (hr) | Column sol. | Product | Amount (g) |
|---|---|---|---|---|---|---|---|---|
| 0.390 | 0.820 | 0.640 | 0.60 | 16.00 | 5 | nHx:EA = 1:2 | I-a168 | 0.670 |

Reaction 2

| Compound I-a168 (g) | Pd/C (g) | MeOH (ml) | Reaction time (hr) | Product | Amount (g) |
|---|---|---|---|---|---|
| 0.670 | 0.060 | 12.00 | 3 | I-b168 | 0.500 |

Reaction 3

| Compound I-b168 (g) | Compound P1 (g) | CMPI (g) | TEA (ml) | THF (ml) | Reaction time (hr) | Column sol. | Product | Amount (g) |
|---|---|---|---|---|---|---|---|---|
| 0.500 | 0.810 | 1.400 | 1.20 | 12.00 | 120 | nHx:EA = 2:1 | I-c168 | 0.210 |

Reaction 4

| Compound I-c168 (g) | TFA (ml) | MC (ml) | Reaction time (hr) | Column sol. | Amount (g) | HPLC min |
|---|---|---|---|---|---|---|
| 0.210 | 0.53 | 2.60 | 3 | MC:MeOH = 20:1 | 0.070 | 20.15/20.93 |

ESI-MS(M⁺+1): 577
1H-NMR(CDCl₃): (two rotamers) δ 1.12-1.41(3H, m), 1.35(9H, s), 1.98 and 2.40(3H, s), 2.36(1H, s), 2.46-2.78 (2H, m), 2.82-3.28(4H, m), 3.42-3.83(2H, m), 4.52-4.72(1H, m), 5.38-5.56(1H, m), 5.98-6.22(1H, m), 6.61-6.28 (2H, m), 6.35-7.38(10H, m)

TABLE D-169

Example 169
Phe(4-F)-N-Me-α-Me-Leu-Tyr(3-tBu)-NH$_2$
R
i-Bu

Reaction 1

| Compound T1 (g) | Compound I33 (g) | CMPI (g) | TEA (ml) | THF (ml) | Reaction time (hr) | Column sol. | Product | Amount (g) |
|---|---|---|---|---|---|---|---|---|
| 1.560 | 1.770 | 2.310 | 1.68 | 60.00 | 12 | nHx:EA = 1:1.5:1 | I-a169 | 2.390 |

Reaction 2

| Compound I-a169 (g) | Pd/C (g) | MeOH (ml) | Reaction time (hr) | Product | Amount (g) |
|---|---|---|---|---|---|
| 2.390 | 0.360 | 80.00 | 12 | I-b169 | 1.490 |

Reaction 3

| Compound I-b169 (g) | Compound P1 (g) | CMPI (g) | TEA (ml) | THF (ml) | Reaction time (hr) | Column sol. | Product | Amount (g) |
|---|---|---|---|---|---|---|---|---|
| 1.490 | 1.230 | 1.510 | 1.10 | 78.00 | 12 | nHx:EA = 1:2 | I-c169 | 0.910 |

Reaction 4-a

| Compound I-c169 (g) | TFA (ml) | MC (ml) | Reaction time (hr) | Column sol. | Amount (g) | HPLC min |
|---|---|---|---|---|---|---|
| 0.850 | 1.30 | 1.30 | 4 | MC:MeOH = 25:1 | 0.130 | 21.50 |

ESI-MS(M$^+$+1): 543
1H-NMR(CD$_3$OD): δ 0.79(6H, t, J=7.0Hz), 1.27(3H, s), 1.46(9H, s), 1.51-1.79(3H, m), 2.54-2.67(2H, m), 2.76(3H, s), 3.04(1H, dd, J=14.3, 5.6Hz), 3.21(1H, dd, J=14.0, 6.8Hz), 3.81(1H, t, J=6.5-7.1Hz), 4.56(1H, dd, J=14.1, 6.4Hz), 5.39(1H, brs), 5.78(1H, brs), 6.61(1H, d, J=7.8Hz), 6.93-7.14(6H, m), 7.45(1H, brs)

TABLE D-170

Example 170
Phe(4-F)-N-Me-α-Me-D-Abu-Tyr(3-tBu)-NH$_2$
R
Et:D

Reaction 1

| Compound T1 (g) | Compound I34 (g) | CMPI (g) | TEA (ml) | THF (ml) | Reaction time (hr) | Column sol. | Product | Amount (g) |
|---|---|---|---|---|---|---|---|---|
| 0.147 | 0.150 | 0.220 | 0.16 | 3.00 | 12 | nHx:EA = 1:1 | I-a170 | 0.251 |

Reaction 2

| Compound I-a170 (g) | Pd/C (g) | MeOH (ml) | Reaction time (hr) | Product | Amount (g) |
|---|---|---|---|---|---|
| 0.250 | 0.150 | 5.00 | 3 | I-b170 | 0.151 |

Reaction 3

| Compound I-b170 (g) | Compound P1 (g) | CMPI (g) | TEA (ml) | THF (ml) | Reaction time (hr) | Column sol. | Product | Amount (g) |
|---|---|---|---|---|---|---|---|---|
| 0.150 | 0.18 | 0.160 | 0.12 | 3.00 | 16 | nHx:EA = 1:1 | I-c170 | 0.145 |

Reaction 4

| Compound I-c170 (g) | TFA (ml) | MC (ml) | Reaction time (hr) | Column sol. | Amount (g) | HPLC min |
|---|---|---|---|---|---|---|
| 0.140 | 0.60 | 3.00 | 2.5 | EA:MeOH = 20:1 | 0.075 | 19.5 |

ESI-MS(M$^+$+1): 515
1H-NMR(CDCl$_3$): δ 0.57(3H, t, J=7.6Hz), 1.21(3H, s), 1.37(9H, s), 1.63-1.82(2H, m), 1.70-1.92(2H, m), 2.59-2.71(2H, m), 2.72(3H, s), 3.03-3.21(2H, m), 3.84(1H, t, J=7.0Hz), 4.60(1H, q, J=6.0Hz), 5.51(1H, brs), 5.84(1H, d, J=7.3Hz), 6.62(1H, d, J=8.0Hz), 6.91-7.03(5H, m), 7.09-7.14(2H, m), 7.54(1H, s)

TABLE D-171

Example 171
Phe(4-F)-N-Me-α-Me-D-Val-Tyr(3-tBu)-NH$_2$
R
i-Pr:D

Reaction 1

| Compound T1 (g) | Compound I35 (g) | CMPI (g) | TEA (ml) | THF (ml) | Reaction time (hr) | Column sol. | Product | Amount (g) |
|---|---|---|---|---|---|---|---|---|
| 0.144 | 0.170 | 0.150 | 0.17 | 3.6 | 12 | nHx:EA = 3:2 | I-a171 | 0.120 |

Reaction 2

| Compound I-a171 (g) | Pd/C (g) | MeOH (ml) | Reaction time (hr) | Product | Amount (g) |
|---|---|---|---|---|---|
| 0.120 | 0.020 | 5.00 | 1.5 | I-b171 | 0.080 |

Reaction 3

| Compound I-b171 (g) | Compound P1 (g) | CMPI (g) | TEA (ml) | THF (ml) | Reaction time (hr) | Column sol. | Product | Amount (g) |
|---|---|---|---|---|---|---|---|---|
| 0.080 | 0.190 | 0.170 | 0.12 | 2.00 | 30 | nHx:EA = 2:3 | I-c171 | 0.050 |

Reaction 4

| Compound I-c171 (g) | TFA (ml) | MC (ml) | Reaction time (hr) | Column sol. | Amount (g) | HPLC min |
|---|---|---|---|---|---|---|
| 0.050 | 0.36 | 1.00 | 3 | MC:MeOH = 7:1 | 0.02 | 20.40 |

ESI-MS(M$^+$+1): 529
1H-NMR(CDCl$_3$): δ 0.69(3H, d, J=6.7Hz), 0.85(3H, d, J=6.7Hz), 1.16(3H, s), 1.36(9H, s), 1.76-1.92(1H, m), 2.27-2.44(1H, m), 2.52-2.70(2H, m), 2.82(3H, s), 3.03-3.24(2H, m), 4.54-4.62(1H, m), 5.47(1H, brs), 5.76(1H, d, J=7.5Hz), 6.60(1H, d, J=8.1Hz), 6.87-7.06(4H, m), 7.09-7.16(2H, m), 7.37(1H, brs)

Scheme 12 shows the synthesis process of Examples 172 and 173.

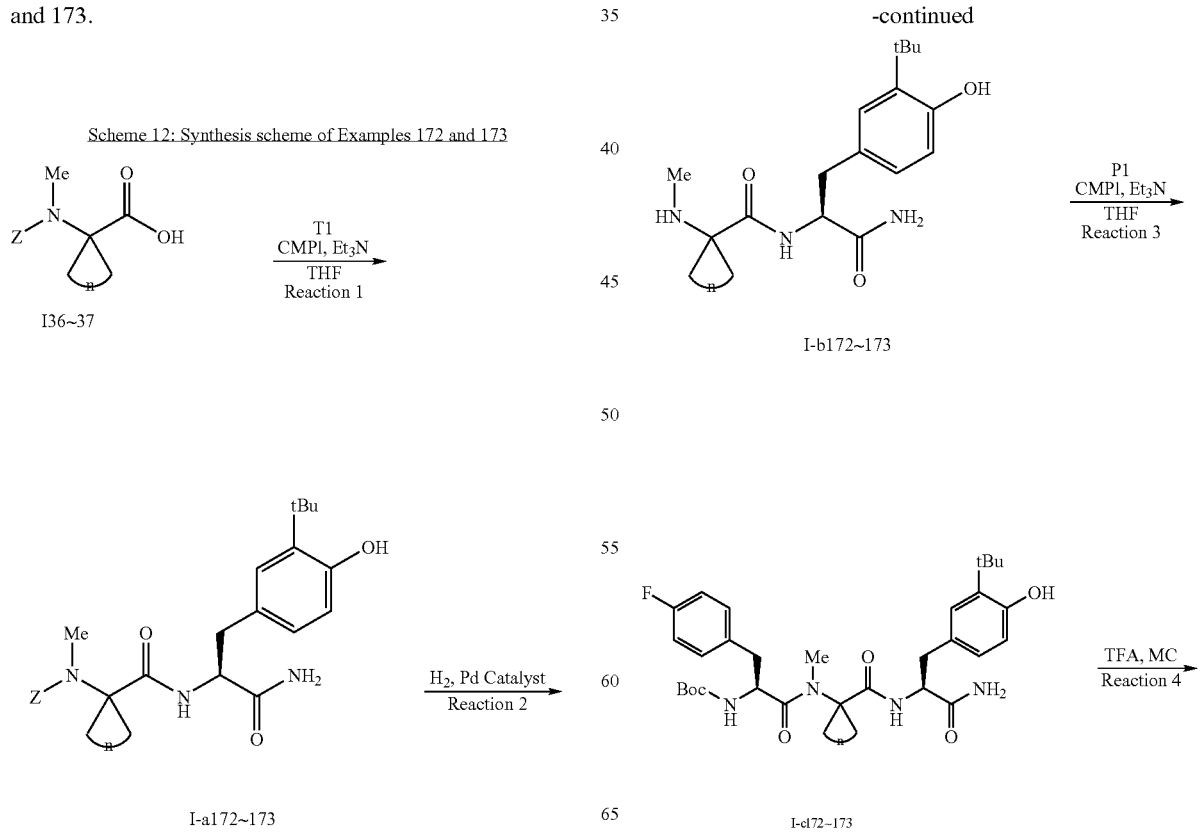

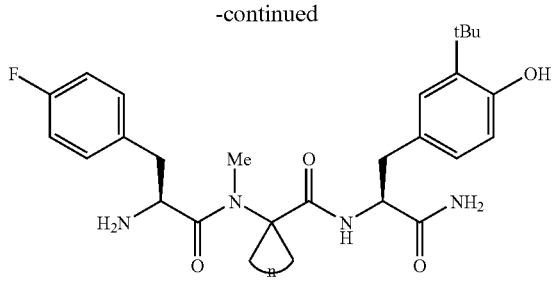

The synthesis process in scheme 12 is explained below.

Reaction Step 1)

To solutions of Compound T1, Compounds I36 and I37 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-a172 and I-173.

Reaction Step 2)

To solutions of Compounds I-a172 and I-a173 in methanol, Pd(OH)$_2$ was added and stirred in a hydrogen atmosphere at room temperature. After filtering off the Pd(OH)$_2$, the filtrates were concentrated under reduced pressure; the thus obtained residues were purified by column chromatography (silica gel) to give Compounds I-b172 and I-b173.

Reaction Step 3)

To solutions of Compounds I-b172 and I-b173, Compound P1 and CMPI in THF, TEA was added under cooling and stirred at room temperature. The reaction mixtures were mixed with water, extracted with ethyl acetate, washed with saturated brine, dried over anhydrous magnesium sulfate and filtered. The filtrates were concentrated under reduced pressure; the thus obtained residues were purified by column chromatography (silica gel) to give Compounds I-c172 and I-c173.

(Reaction Step 4)

To solutions of Compounds I-c172 and I-c173 in dichloromethane, TFA was added under cooling and stirred at room temperature. The reaction mixtures were concentrated under reduced pressure, neutralized by the addition of a saturated aqueous NaHCO$_3$ solution, extracted with ethyl acetate, dried over anhydrous magnesium sulfate and filtered. The filtrates were concentrated under reduced pressure; the thus obtained residues were purified by column chromatography (silica gel) to give the titled compounds.

Examples conducted according to Scheme 12 are shown in Tables D-172 and D-173.

TABLE D-172

Example 172
(2S)-N-[(N-{(1S)-2-[3-(tert-butyl)-4-hydroxyphenyl]-1-carbamoylethyl}carbamoyl)cyclopentyl]-2-amino-3-(4-fluorophenyl)-N-methylpropanamide

| | | | Reaction 1 | | | | | |
|---|---|---|---|---|---|---|---|---|
| Compound T1 (g) | Compound I36 (g) | CMPI (g) | TEA (ml) | THF (ml) | Reaction time (hr) | Column sol. | Product | Amount (g) |
| 0.600 | 1.050 | 0.973 | 0.70 | 20.00 | 3 | nHx:EA = 1:1 | I-a172 | 1.210 |

| | | Reaction 2 | | | |
|---|---|---|---|---|---|
| Compound I-a172 (g) | Pd(OH)$_2$ (g) | MeOH (ml) | Reaction time (hr) | Product | Column sol. |
| 1.210 | 0.182 | 30.00 | 3 | I-b172 | MC:MeOH = 20:1 |

| | | | Reaction 3 | | | | | |
|---|---|---|---|---|---|---|---|---|
| Compound I-b172 (g) | Compound P1 (g) | CMPI (g) | TEA (ml) | THF (ml) | Reaction time (hr) | Column sol. | Product | Amount (g) |
| 0.744 | 1.170 | 1.050 | 0.72 | 20.00 | 52 | nHx:EA = 1:1 | I-c172 | 0.518 |

| | | Reaction 4 | | | | |
|---|---|---|---|---|---|---|
| Compound I-c172 (g) | TFA (ml) | MC (ml) | Reaction time (hr) | Column sol. | Amount (g) | HPLC min |
| 0.518 | 1.330 | 10.00 | 3 | MC:MeOH = 20:1 | 0.130 | 19.59 |

ESI-MS(M$^+$+1): 527

1H-NMR(CDCl$_3$): (two rotamers) δ 1.30 and 1.40(9H, s), 1.15-2.42(8H, m), 2.52-2.80(2H, m), 2.86 and 2.92(3H, s), 3.02-3.35(2H, m), 3.58 and 3.85(1H, m), 4.30 and 4.61(1H, m). 5.68(1H, brs), 6.08-6.42(1H, m), 6.51-7.39(7H, m)

TABLE D-173

Example 173
(2S)-N-[(N-{(1S)-2-[3-(tert-butyl)-4-hydroxyphenyl]-1-
carbamoylethyl}carbamoyl)cyclopentyl]-2-amino-3-(4-fluorophenyl)-
N-methylpropanamide

Reaction 1

| Compound T1 (g) | Compound I37 (g) | CMPI (g) | TEA (ml) | THF (ml) | Reaction time (hr) | Column sol. | Product | Amount (g) |
|---|---|---|---|---|---|---|---|---|
| 0.708 | 1.310 | 0.766 | 0.84 | 20.00 | 3 | nHx:EA = 1:1 | I-a173 | 1.400 |

Reaction 2

| Compound I-a173 (g) | Pd(OH)$_2$ (g) | MeOH (ml) | Reaction time (hr) | Product | Amount (g) |
|---|---|---|---|---|---|
| 1.400 | 0.210 | 30.00 | 3 | I-b173 | 0.934 |

Reaction 3

| Compound I-b173 (g) | Compound P1 (g) | CMPI (g) | TEA (ml) | THF (ml) | Reaction time (hr) | Column sol. | Product | Amount (g) |
|---|---|---|---|---|---|---|---|---|
| 0.930 | 1.410 | 1.270 | 0.87 | 30.00 | 120 | nHx:EA = 1:1 | I-c173 | 0.271 |

Reaction 4

| Compound I-c173 (g) | TFA (ml) | MC (ml) | Reaction time (hr) | Column sol. | Amount (g) | HPLC min |
|---|---|---|---|---|---|---|
| 0.271 | 0.700 | 5.00 | 3 | MC:MeOH = 20:1 | 0.030 | 24.76 |

ESI-MS(M$^+$+1): 541
1H-NMR(CDCl$_3$): (two rotamers) δ 1.30 and 1.40(9H, s), 1.15-2.50(10H, m), 2.52-2.80(2H, m), 2.86 and 2.92 (3H, s), 3.02-3.35(2H, m), 3.58 and 3.85(1H, m), 4.30 and 4.61(1H, m), 5.68(1H, brs), 6.08-6.42(1H, m), 6.51-7.39(7H, m)

Scheme 13 shows the synthesis process of Example 174.

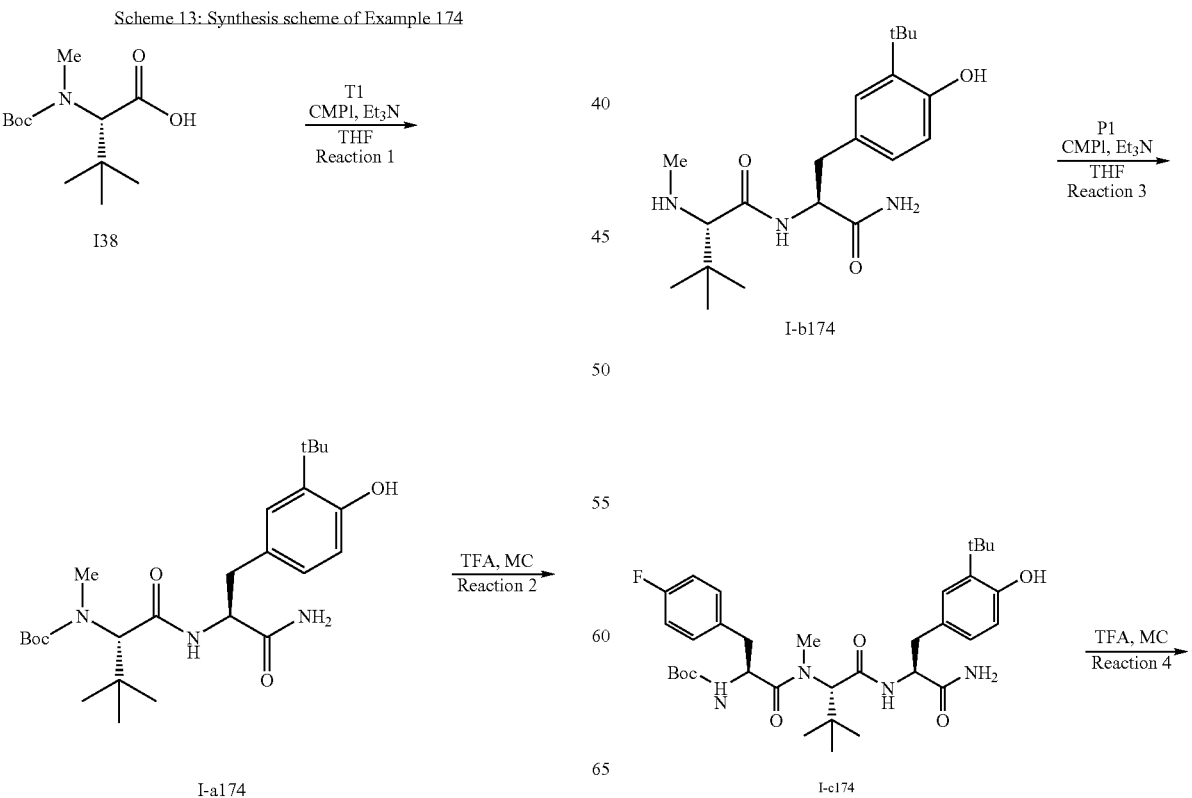

-continued

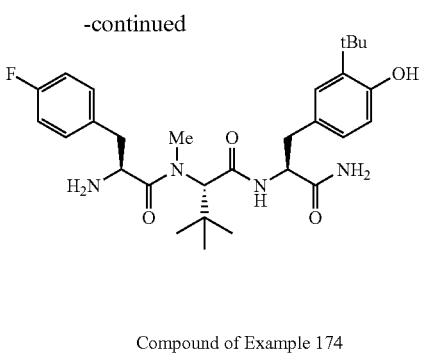

Compound of Example 174

The synthesis process in scheme 13 is explained below.

Reaction Step 1)

To a solution of Compound T1, Compound I38 and CMPI in THF, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-a174.

Reaction Step 2)

To a solution of Compound I-a174 in dichloromethane, TFA was added under cooling and stirred at room temperature. The reaction mixture was concentrated under reduced pressure, neutralized by adding a saturated aqueous NaHCO₃ solution, extracted with ethyl acetate, dried over anhydrous magnesium sulfate and filtered. The filtrate was concentrated under reduced pressure; the thus obtained residue was purified by column chromatography (silica gel) to give Compound I-b174.

(Reaction Step 3)

To a solution of Compound I-b174, Compound P1 and CMPI in THF, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-c174.

(Reaction Step 4)

To a solution of Compound I-c174 in dichloromethane, TFA was added under cooling and stirred at room temperature. The reaction mixture was concentrated under reduced pressure, neutralized by adding a saturated aqueous NaHCO₃ solution, extracted with ethyl acetate, dried over anhydrous magnesium sulfate and filtered. The filtrate was concentrated under reduced pressure; the thus obtained residue was purified by column chromatography (silica gel) to give the titled compound.

Example conducted according to Scheme 13 is shown in Table D-174.

TABLE D-174

Example 174
Phe(4-F)-N-Me-Tle-Tyr(3-tBu)-NH$_2$

| Reaction 1 | | | | | | | | |
|---|---|---|---|---|---|---|---|---|
| Compound T1 (g) | Compound I38 (g) | CMPI (g) | TEA (ml) | THF (ml) | Reaction time (hr) | Column sol. | Product | Amount (g) |
| 0.633 | 0.660 | 0.756 | 0.37 | 15.00 | 24 | nHx:EA = 1:2 | I-a174 | 0.670 |

| Reaction 2 | | | | | | |
|---|---|---|---|---|---|---|
| Compound I-a174 (g) | TFA (ml) | MC (ml) | Reaction time (hr) | Column sol. | Product | Amount (g) |
| 0.670 | 2.00 | 10.00 | 1 | MC:MeOH = 10:1 | I-b174 | 0.518 |

| Reaction 3 | | | | | | | | |
|---|---|---|---|---|---|---|---|---|
| Compound I-b174 (g) | Compound P1 (g) | CMPI (g) | TEA (ml) | THF (ml) | Reaction time (hr) | Column sol. | Product | Amount (g) |
| 0.518 | 0.809 | 0.730 | 0.40 | 10.00 | 36 | nHx:EA = 1:2 | I-c174 | 0.393 |

| Reaction 4 | | | | | | |
|---|---|---|---|---|---|---|
| Compound I-c174 (g) | TFA (ml) | MC (ml) | Reaction time (hr) | Column sol. | Amount (g) | HPLC min |
| 0.393 | 1.00 | 5.00 | 1 | MC:MeOH = 15:1 | 0.162 | 17.54 |

ESI-MS(M⁺+1): 529
1H-NMR(CDCl$_3$): (two rotamers) δ 1.02 and 1.03 (9H, s), 1.35 and 1.36(9H, s), 2.75(3H, s), 2.70 and 3.00(4H, m), 3.12(1H, dd, J=10.3, 6.3Hz), 3.60 and 3.82(1H, m), 4.64(1H, m), 5.50(1H, brs), 5.80 and 6.00(1H, brs), 6.70(1H, s), 6.80-7.15(6H, m)

Scheme 14 shows the synthesis process of Example 175.

Scheme 14: Synthesis scheme of Example 175

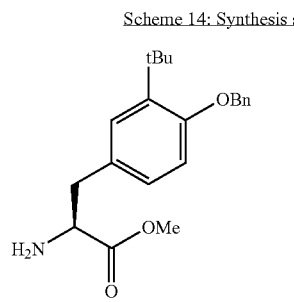

Tyr(O-Bn, 3-tBu)-OMe

Boc-Tle-OH
CMPI, Et₃N
———————→
THF
Reaction 1

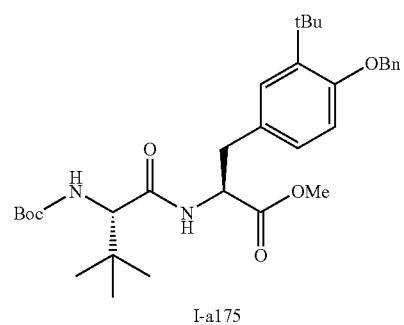

I-a175

NaH, MeI
————→
DMF
Reaction 2

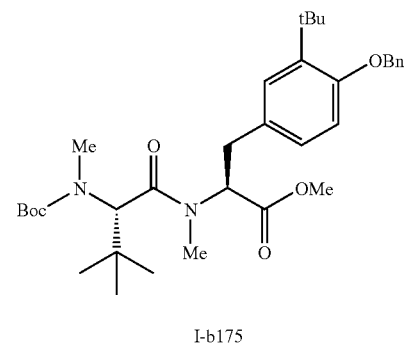

I-b175

NH₄OH
————→
MeOH
Reaction 3

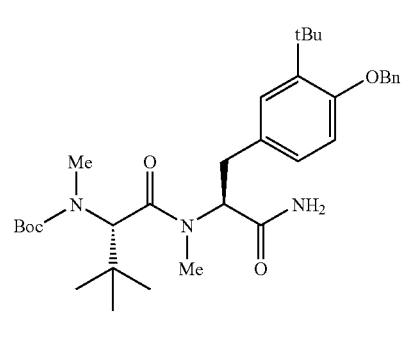

I-c175

TFA
——→
MC
Reaction 4

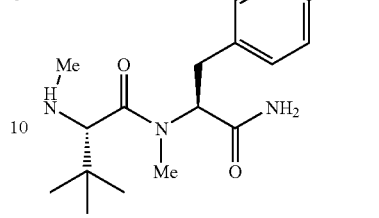

P4
CMPI, Et₃N
————————→
THF
Reaction 5

I-d175

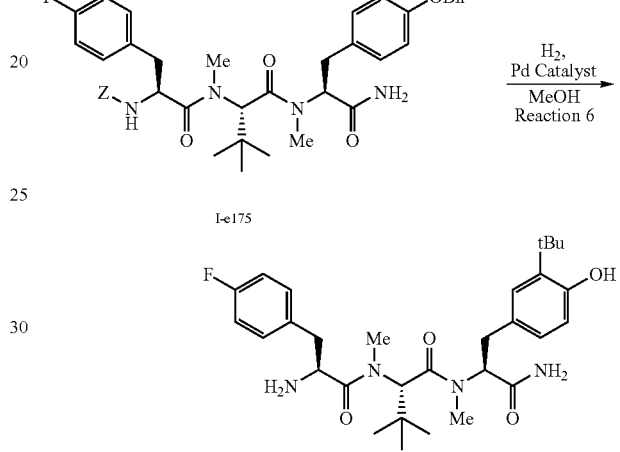

I-e175

H₂,
Pd Catalyst
——————→
MeOH
Reaction 6

Example 175

The synthesis process in scheme 14 is explained below.

Reaction Step 1)

To a solution of Tyr(O-Bn,3-tBu)-OMe, Compound Boc-Tle-OH and CMPI in THF, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-a175.

Reaction Step 2)

To a solution of Compound I-a175 in DMF, NaH and MeI were added under cooling and stirred at room temperature. The reaction mixture was mixed with water under cooling, neutralized by the addition of 1N HCl and extracted with EA/nHx (½). The organic layer was washed three times with saturated brine, dried over anhydrous magnesium sulfate and filtered. The filtrate was concentrated under reduced pressure; the thus obtained residue was purified by column chromatography (silica gel) to give Compound I-b175.

Reaction Step 3)

To a solution of Compound I-b175 in methanol, 28% aqueous ammonia was added and stirred at room temperature. The reaction mixture was concentrated under reduced pressure, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-c175.

Reaction Step 4)

To a solution of Compound I-c175 in dichloromethane, TFA was added under cooling and stirred at room temperature. The reaction mixture was concentrated under reduced pressure, neutralized by the addition of a saturated aqueous NaHCO$_3$ solution, extracted with ethyl acetate, dried over anhydrous magnesium sulfate and filtered. The filtrate was concentrated under reduced pressure; the thus obtained residue was purified by column chromatography (silica gel) to give Compound I-d175.

Reaction Step 5)

To a solution of Compound I-d175, Compound P4 and CMPI in THF, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-e175.

Reaction Step 6)

To a solution of Compound I-e175 in methanol, Pd(OH)$_2$ was added and stirred in a hydrogen atmosphere at room temperature. After filtering off the Pd(OH)$_2$, the filtrate was concentrated under reduced pressure; the thus obtained residue was purified by column chromatography (silica gel) to give the titled compound.

Example conducted according to Scheme 14 is shown in Table D-175.

TABLE D-175

Example 175
Phe(4-F)-N-Me-Tle-N-Me-Tyr(3-tBu)-NH$_2$

Reaction 1

| Tyr(O-Bn,3-tBu)-OMe (g) | Boc-Tle-OH (g) | CMPI (g) | TEA (ml) | THF (ml) | Reaction time (hr) | Column sol. | Product | Amount (g) |
|---|---|---|---|---|---|---|---|---|
| 1.720 | 1.280 | 1.410 | 1.40 | 34.00 | 12 | nHxEA = 5:1 | I-a175 | 2.200 |

Reaction 2

| Compound I-a175 (g) | NaH (g) | Methyl Iodide (ml) | DMF (ml) | Reaction time (hr) | Column sol. | Product | Amount (g) |
|---|---|---|---|---|---|---|---|
| 2.200 | 0.480 | 2.22 | 22.00 | 1 | nHx:EA = 5:1 | I-b175 | 1.930 |

Reaction 3

| Compound I-b175 (g) | NH$_4$OH (ml) | MeOH (ml) | Reaction time (hr) | Column sol. | Product | Amount (g) |
|---|---|---|---|---|---|---|
| 1.930 | 130.00 | 230.00 | 20 | nHx:EA = 2:1 | I-c175 | 0.564 |

Reaction 4

| Compound I-c175 (g) | TFA (ml) | MC (ml) | Reaction time (hr) | Column sol. | Product | Amount (g) |
|---|---|---|---|---|---|---|
| 0.680 | 2.78 | 8.00 | 1.5 | MC:MeOH = 20:1 | I-d175 | 0.500 |

Reaction 5

| Compound I-d175 (g) | Compound P1 (g) | CMPI (g) | TEA (ml) | THF (ml) | Reaction time (hr) | Column sol. | Product | Amount (g) |
|---|---|---|---|---|---|---|---|---|
| 0.500 | 0.951 | 0.546 | 0.50 | 12.50 | 12 | nHxEA = 2:1 | I-d175 | 0.254 |

Reaction 6

| Compound I-d175 (g) | Pd(OH)$_2$ (g) | MeOH (ml) | Reaction time (hr) | Column sol. | Amount (g) | HPLC min |
|---|---|---|---|---|---|---|
| 0.250 | 0.050 | 10.00 | 3 | MC:MeOH = 15:1 | 0.098 | 19.280 |

ESI-MS(M$^+$+1): 543

1H-NMR(CDCl$_3$): δ 0.80(9H, s), 1.37(9H, s), 2.68(1H, dd, J=13.6, 7.3Hz), 285-3.01(2H, m), 2.92(3H, s), 2.98(3H, s), 3.11-3.22(1H, m), 3.94(1H, t, J=7.0Hz), 5.19(1H, s), 5.22(1H, brs), 5.37(1H, dd, J=10.5, 5.6Hz), 5.98(1H, brs), 6.55(1H, d, J=7.9Hz), 6.88(1H, dd, J=8.0, 2.2Hz), 6.94-7.00(2H, m),7.07-7.14(3H, m)

Methods of producing Intermediates in the scheme 15 are shown as Reference Examples in the following. The structural formulae of Intermediates of Examples 177-180 are shown in Table C-5.

TABLE C-5

Intermediates of Examples 177-180

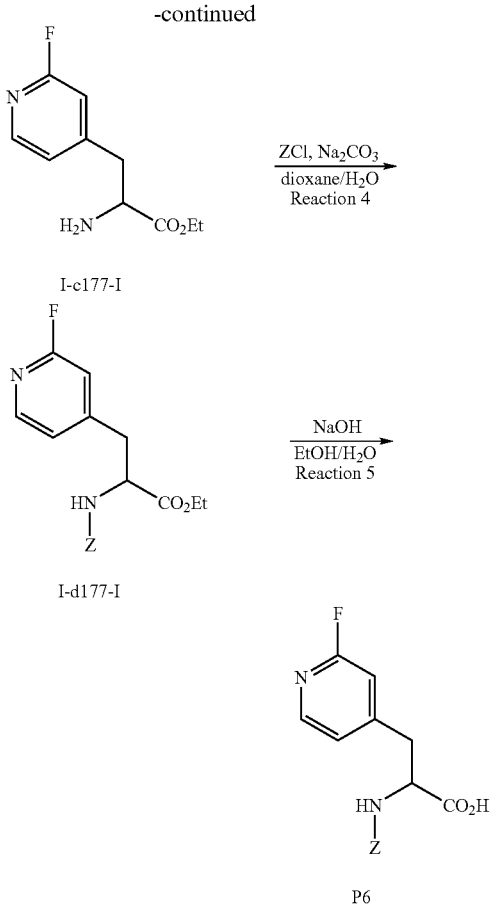

REFERENCE EXAMPLE 27

Synthesis of Intermediates P6-P8

The synthesis scheme is shown below.

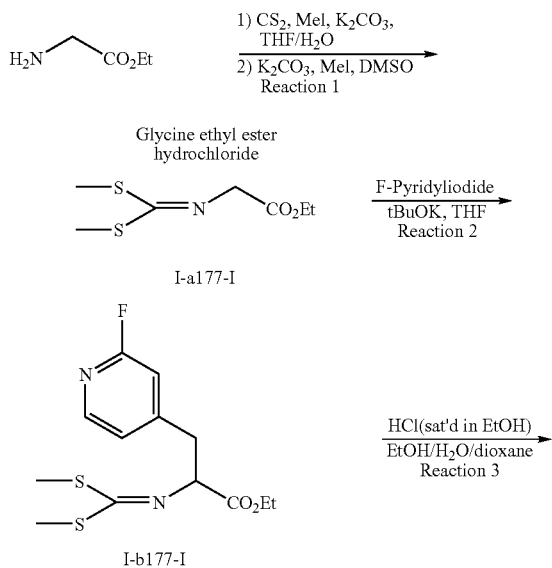

The synthesis methods of Intermediates P6-P8 are explained below.

F-Pyridyl iodide [2-fluoro-4-(iodomethyl)pyridine and 2-fluoro-5-(iodomethyl)pyridine] were synthesized referring to J. Med. Chem., 1998, 41(23), 4615. P7 and P8 were synthesized according to a similar method of synthesizing P6 using the above 2-fluoro-5-(iodomethyl)pyridine and 4-(iodomethyl)-1-(trifluoromethyl)benzene.

Reaction Step 1)

To a solution of glycine ethyl ester hydrochloride, $CS_2$ and water in THF, $K_2CO_3$ and $CH_3I$ were added dropwise and then stirred at room temperature. After the completion of the reaction, the reaction mixture was mixed with water, extracted with ethyl acetate, washed with saturated brine, dried over anhydrous magnesium sulfate and filtered. The filtrate was concentrated under reduced pressure; to a solution of the thus obtained residue in a mixture of DMSO and water, $K_2CO_3$ was added dropwise gradually and then under cooling with ice, $CH_3I$ was added dropwise gradually, followed by stirring at room temperature. The reaction mixture was mixed with water, extracted with $Et_2O$, washed with saturated brine, dried over anhydrous magnesium sulfate and filtered. The filtrate was concentrated under reduced pressure; the thus obtained residue was purified by column chromatography (silica gel) to give Compound I-a177-I.

Reaction Step 2)

To a solution of Compound I-a177-I and t-BuOK in THF, F-pyridyl iodide was added dropwise gradually at −78° C. while stirring. The reaction mixture was mixed with water, extracted with Et$_2$O, washed with saturated brine, dried over anhydrous magnesium sulfate and filtered. The filtrate was concentrated under reduced pressure; the thus obtained residue was purified by column chromatography (silica gel) to give Compound I-b177-I.

Reaction Step 3)

To a solution of Compound I-b177-I in a mixture of ethanol, water and dioxane, a saturated HCl/ethanol solution was added and stirred at room temperature. The reaction mixture was concentrated under reduced pressure, extracted with dichloromethane, washed with saturated brine, dried over anhydrous magnesium sulfate and filtered. The filtrate was concentrated under reduced pressure; the thus obtained residue was purified by column chromatography (silica gel) to give Compound I-c177-I.

Reaction Step 4)

To a solution of Compound I-c177-I and Na$_2$CO$_3$ in a mixture of dioxane and water, Z—Cl was added dropwise gradually under cooling and stirred at room temperature. The reaction mixture was mixed with water, extracted with Et$_2$O, washed with saturated brine, dried over anhydrous magnesium sulfate and filtered. The filtrate was concentrated under reduced pressure; the thus obtained residue was purified by column chromatography (silica gel) to give Compound I-d177-I.

Reaction Step 5)

To a solution of Compound I-d177-I in dioxane, 2N NaOH was added and stirred at room temperature. The reaction mixture was adjusted to pH 3-4 by the addition of 1N HCl, extracted with ethyl acetate, washed with saturated brine, dried over anhydrous magnesium sulfate and filtered. The filtrate was concentrated under reduced pressure; the thus obtained residue was purified by column chromatography (silica gel) to give Intermediate P6.

The results are shown in Tables E-46 to E-48.

TABLE E-46

Intermediate P6
3-(2-fluoro-4-pyridyl)-2-[(phenylmethoxy)carbonylamino]propanoic acid

| Reaction 1-a | | | | | | | |
|---|---|---|---|---|---|---|---|
| Gly-OEt HCl (g) | K$_2$CO$_3$ (g) | Methyl iodide (ml) | CS$_2$ (ml) | THF/H$_2$O (ml) | Reaction time (hr) | Product | Amount (g) |
| 20.000 | 19.890 | 8.96 | 8.66 | 60.00/14.00 | 1 | Crude intermediate | 27.061 |

| Reaction 1-b | | | | | | | |
|---|---|---|---|---|---|---|---|
| Crude intermediate (g) | K$_2$CO$_3$ (g) | Methyl iodide (ml) | DMSO/H$_2$O (ml) | Reaction time (hr) | Column sol. | Product | Amount (g) |
| 12.000 | 8.590 | 3.90 | 60.00/14.00 | 0.5 | nHx:EA = 5:1 | I-a177-1 | 11.7000 |

| Reaction 2 | | | | | | | |
|---|---|---|---|---|---|---|---|
| I-a177-1 (g) | 2-fluoro-4-(iodomethyl)pyridine (ml) | tBuOK (g) | THF (ml) | Reaction time (hr) | Column sol. | Product | Amount (g) |
| 2.000 | 2.520 | 1.190 | 32.00 | 2.50 | nHx:EA = 7:1 | I-b177-1 | 2.480 |

| Reaction 3 | | | | | | |
|---|---|---|---|---|---|---|
| I-b177-1 (g) | HCl (sat'd in EtOH) (ml) | EtOH/H$_2$O (ml) | Dioxane (ml) | Reaction time (hr) | Product | Amount (g) |
| 2.480 | 11.50 | 11.50/11.50 | 6 | 16 | I-c177-1 | 1.33 |

| Reaction 4 | | | | | | |
|---|---|---|---|---|---|---|
| I-c177-1 (g) | ZCl (ml) | Na$_2$CO$_3$ (g) | Dioxane/H$_2$O (ml) | Reaction time (hr) | Product | Amount (g) |
| 1.330 | 0.99 | 1.000 | 18.00/18.00 | 2 | I-d177-1 | 1.36 |

| Reaction 5 | | | | |
|---|---|---|---|---|
| I-d177-1 (g) | NaOH (g) | EtOH/H$_2$O (ml) | Reaction time (hr) | Amount (g) |
| 1.330 | 0.314 | 30.00/10.00 | 1.500 | 1.200 |

TABLE E-47

Intermediate P7
3-(2-fluoro-5-pyridyl)-2-[(phenylmethoxy)carbonylamino]propanoic acid

Reaction 1-a

| Gly-OEt HCl (g) | $K_2CO_3$ (g) | Methyl iodide (ml) | $CS_2$ (ml) | $THF/H_2O$ (ml) | Reaction time (hr) | Product | Amount (g) |
|---|---|---|---|---|---|---|---|
| 20.000 | 19.890 | 8.96 | 8.66 | 60.00/14.00 | 1 | Crude intermediate | 27.061 |

Reaction 1-b

| Crude intermediate (g) | $K_2CO_3$ (g) | Methyl iodide (ml) | $DMSO/H_2O$ (ml) | Reaction time (hr) | Column sol. | Product | Amount (g) |
|---|---|---|---|---|---|---|---|
| 12.000 | 8.590 | 3.90 | 60.00/14.00 | 0.5 | nHx:EA = 5:1 | I-a178-1 | 11.7000 |

Reaction 2

| I-a178-1 (g) | 2-fluoro-5-(iodomethyl)pyridine (ml) | tBuOK (g) | THF (ml) | Reaction time (hr) | Column sol. | Product | Amount (g) |
|---|---|---|---|---|---|---|---|
| 3.990 | 8.37 | 2.380 | 60.00 | 3.00 | nHx:EA | I-b178-1 | 4.300 |

Reaction 3

| 1-b178-1 (g) | HCl (sat'd in EtOH) (ml) | $EtOH/H_2O$ (ml) | Dioxane (ml) | Reaction time (hr) | Product | Amount (g) |
|---|---|---|---|---|---|---|
| 4.300 | 20.00 | 12.00/12.00 | 10.00 | 16 | I-c178-1 | 1.880 |

Reaction 4

| I-c178-1 (g) | ZCl (ml) | $Na_2CO_3$ (g) | Dioxane/H2O (ml) | Reaction time (hr) | Product | Amount (g) |
|---|---|---|---|---|---|---|
| 1.880 | 1.40 | 1.410 | 25.00/25.00 | 2 | I-d178-1 | 2.940 |

Reaction 5

| I-d178-1 (g) | NaOH (g) | $EtOH/H_2O$ (ml) | Reaction time (hr) | Amount (g) |
|---|---|---|---|---|
| 2.620 | 0.606 | 40.00/10.00 | 1.500 | 2.400 |

TABLE E-48

Intermediate P8
2-[(Phenylmethoxy)carbonylamino]-3-[4-(trifluoromethyl)phenyl]propanoic acid

Reaction 1-a

| Gly-OEt—HCl (g) | $K_2CO_3$ (g) | Methyl iodide (ml) | $CS_2$ (ml) | $THF/H_2O$ (ml) | Reaction time (hr) | Product | Amount (g) |
|---|---|---|---|---|---|---|---|
| 20.000 | 19.890 | 8.96 | 8.66 | 60.00/14.00 | 1 | Crude intermediate | 27.061 |

Reaction 1-b

| Crude intermediate (g) | $K_2CO_3$ (g) | Methyl iodide (ml) | $DMSO/H_2O$ (ml) | Reaction time (hr) | Column sol. | Product | Amount (g) |
|---|---|---|---|---|---|---|---|
| 12.000 | 8.590 | 3.90 | 60.00/14.00 | 0.5 | nHx:EA = 5:1 | I-a179-1 | 11.700 |

Reaction 2

| I-a179-1 (g) | 4-(iodomethyl)-1-(trifluoromethyl)benzene (ml) | tBuOK (g) | THF (ml) | Reaction time (hr) | Column sol. | Product | Amount (g) |
|---|---|---|---|---|---|---|---|
| 2.120 | 3.220 | 1.270 | 40.00 | 2 | nHx:EA = 7:1 | I-b179-1 | 3.730 |

TABLE E-48-continued

Intermediate P8
2-[(Phenylmethoxy)carbonylamino]-3-[4-(trifluoromethyl)phenyl]propanoic acid

| | | Reaction 3 | | | | |
|---|---|---|---|---|---|---|
| I-b179-1 (g) | HCl (sat'd in EtOH)(ml) | EtOH/H$_2$O (ml) | Dioxane (ml) | Reaction time (hr) | Product | Amount (g) |
| 1.620 | 6.50 | 6.50/6.50 | 3.00 | 16 | I-c179-1 | 0.737 |

| | | | Reaction 4 | | | |
|---|---|---|---|---|---|---|
| I-c179-1 (g) | ZCl (ml) | Na$_2$CO$_3$ (g) | Dioxane/ H$_2$O (ml) | Reaction time (hr) | Product | Amount (g) |
| 0.737 | 0.45 | 0.450 | 9.00/9.00 | 1 | I-d179-1 | 1.090 |

| | | Reaction 5 | | |
|---|---|---|---|---|
| I-d177-1 (g) | NaOH (g) | EtOH/H$_2$O (ml) | Reaction time (hr) | Amount (g) |
| 1.090 | 0.186 | 9.00/9.00 | 1.5 | 1.010 |

REFERENCE EXAMPLE 28

Synthesis of Intermediate P9

The synthesis scheme is shown below.

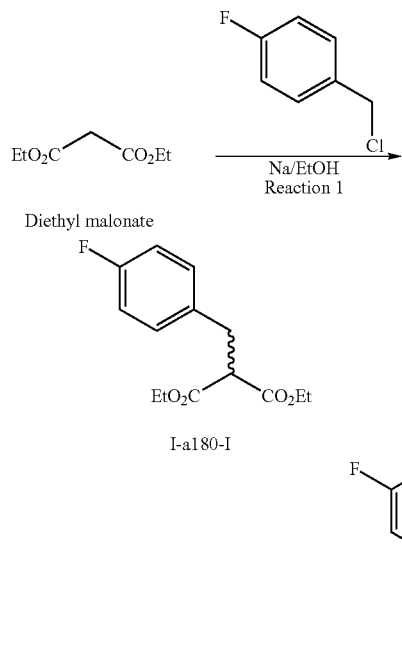

The synthesis method of Intermediates P9 is explained below.

Reaction Step 1)

To a solution of Na-metal in ethanol, diethyl malonate and 4-(chloromethyl)-1-fluorobenzene were added dropwise and then stirred at room temperature. The reaction mixture was concentrated under reduced pressure, mixed with water, extracted with Et$_2$O, washed with saturated brine, dried over anhydrous magnesium sulfate and filtered. The filtrate was concentrated under reduced pressure to give Compound I-a180-I in a crude form.

Reaction Step 2)

To a solution of Compound I-a180-I in ethanol, KOH was added and stirred at room temperature. The reaction mixture was concentrated under reduced pressure, mixed with water and washed with Et$_2$O. The aqueous layer was adjusted to a pH of 3-4 by the addition of 1N HCl, extracted with ethyl acetate, washed with saturated brine, dried over anhydrous magnesium sulfate and filtered. The filtrate was concentrated under reduced pressure; the thus obtained residue was purified by column chromatography (silica gel) to give Intermediate P9.

Result is shown in Table E-49.

TABLE E-49

Intermediate P9
2-(Ethoxycarbonyl)-3-(4-fluorophenyl)propanoic acid

| | | Reaction 1 | | | |
|---|---|---|---|---|---|
| Diethyl malonate (g) | 4-(chloromethyl)-1-fluorobenzene (ml) | Na-metal (g) | EtOH (ml) | Product | Amount (g) |
| 15.000 | 10.90 | 2.180 | 120.00 | I-a180-I | 25.000 |

| | Reaction 2 | | |
|---|---|---|---|
| I-a180-I (g) | KOH (g) | EtOH (ml) | Amount (g) |
| 2.160 | 5.170 | 160.00 | 1.400 |

The synthesis scheme of Examples 177A to 179B is shown in Scheme 15.

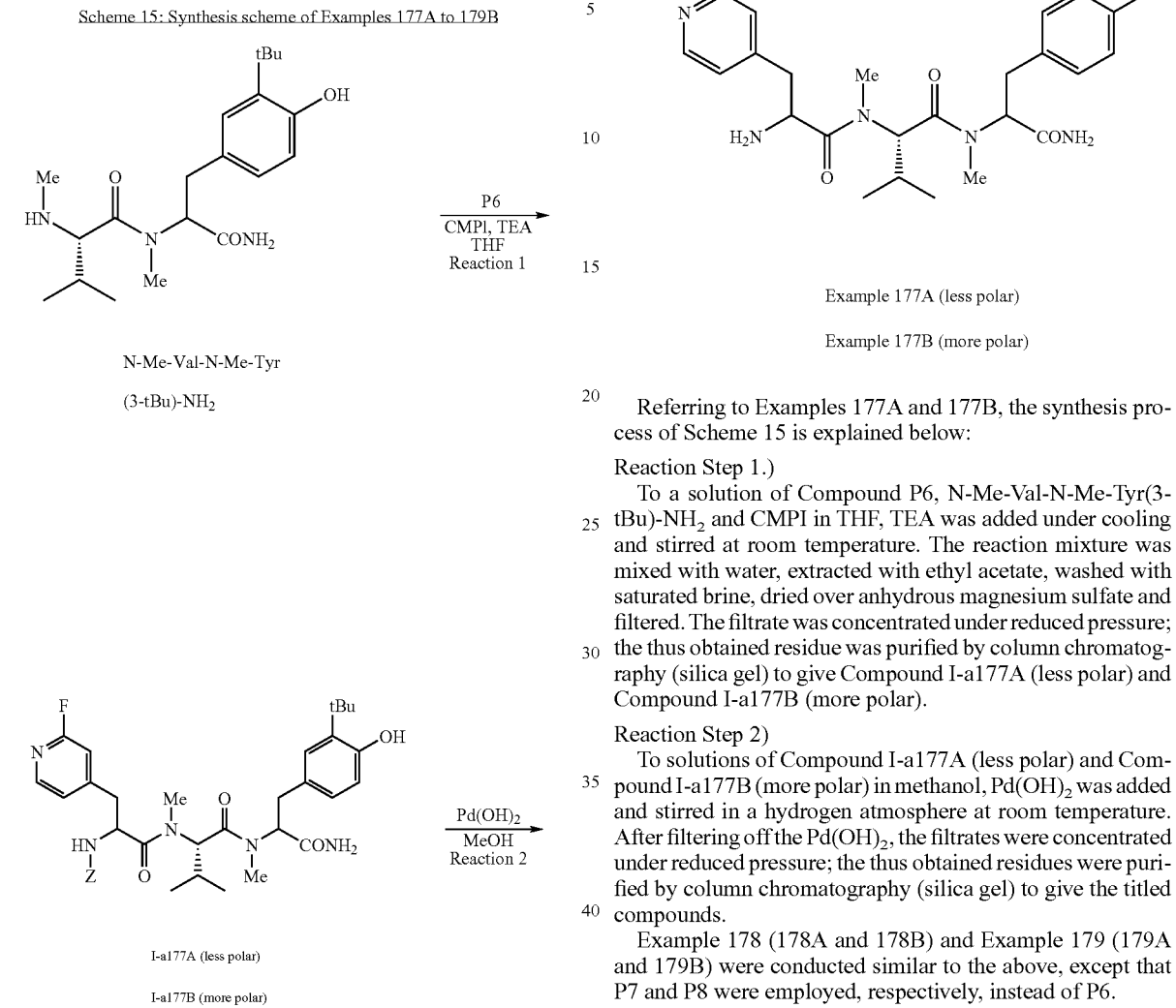

N-Me-Val-N-Me-Tyr(3-tBu)-NH₂

I-a177A (less polar)
I-a177B (more polar)

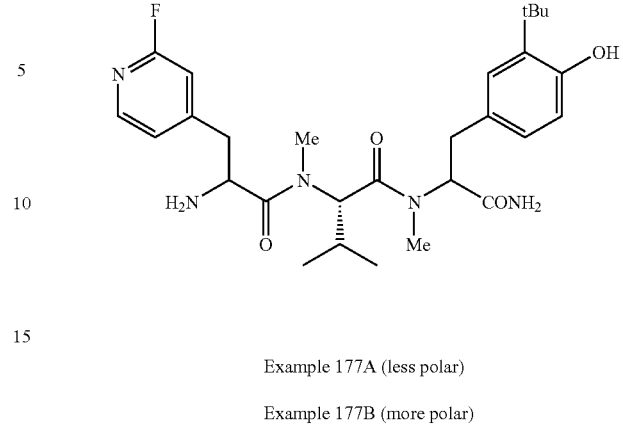

Example 177A (less polar)
Example 177B (more polar)

Referring to Examples 177A and 177B, the synthesis process of Scheme 15 is explained below:

Reaction Step 1.)
To a solution of Compound P6, N-Me-Val-N-Me-Tyr(3-tBu)-NH₂ and CMPI in THF, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-a177A (less polar) and Compound I-a177B (more polar).

Reaction Step 2)
To solutions of Compound I-a177A (less polar) and Compound I-a177B (more polar) in methanol, Pd(OH)₂ was added and stirred in a hydrogen atmosphere at room temperature. After filtering off the Pd(OH)₂, the filtrates were concentrated under reduced pressure; the thus obtained residues were purified by column chromatography (silica gel) to give the titled compounds.

Example 178 (178A and 178B) and Example 179 (179A and 179B) were conducted similar to the above, except that P7 and P8 were employed, respectively, instead of P6.

Examples conducted according to Scheme 15 are shown in Tables D-177A to D-179B.

TABLE D-177A

Example 177A: Less polar
(2S)—N—{(1S)-2-[3-(tert-butyl)-4-hydroxyphenyl]-1-carbamoyl ethyl}-2-[2-amino-3-(2-fluoro-4-pyridyl)-N-methylpropanoylamino]-3-methyl-N-methylbutanamide

| | | | Reaction 1 | | | | | |
|---|---|---|---|---|---|---|---|---|
| N—Me-Val-N—Me-Tyr(3-tBu)-NH₂ (g) | Compound P6 (g) | CMPI (g) | TEA (ml) | THF (ml) | Reaction time (hr) | Column sol. | Product | Amount (g) |
| 0.776 | 0.886 | 0.711 | 0.45 | 30.00 | 16 | nHx:EA = 1:1 | I-a177A | 0.275 |
| | | | | | | | I-a177B | 0.288 |

TABLE D-177A-continued

Example 177A: Less polar
(2S)—N—{(1S)-2-[3-(tert-butyl)-4-hydroxyphenyl]-1-carbamoyl
ethyl}-2-[2-amino-3-(2-fluoro-4-pyridyl)-N-methylpropanoylamino]-3-methyl-N-methylbutanamide

| | | | Reaction 2 | | | |
|---|---|---|---|---|---|---|
| Compound I-a177A (g) | Pd(OH)$_2$ (g) | MeOH (ml) | Reaction time (hr) | Column sol. | Amount (g) | HPLC min |
| 0.275 | 0.042 | 20.00 | 3 | MC:MeOH = 20:1 | 0.160 | 17.50 |

ESI-MS(M$^+$ + 1):530

1H-NMR(CDCl$_3$): (two rotamers) δ 0.32, 0.42 and 0.60, 0.88(6H, d, J=7.1-7.9 Hz), 1.37 and 1.42(9H, s), 2.00-2.20(1H, m), 2.52 and 2.91, 2.95(6H, s), 2.60-3.28(4H, m), 2.95(3H, s), 3.75(1/2H, dd, J=8.8, 6.1 Hz), 3.95(1/2H, t, J=8.8 Hz), 4.65 and 5.00(1H, d, J=8.8 Hz), 4.96 and 5.47(1H, dd, J=8.8, 7.0 Hz), 5.60 and 6.05(1H, brs), 6.60 and 6.15(1H, d, J=8.8 Hz), 6.70 and 7.04(2H, m), 6.92 and 7.12(2H, m), 8.12(1H, m)

TABLE D-177B

Example 177B: more polar
(2S)—N—{(1S)-2-[3-(tert-butyl)-4-hydroxyphenyl]-1-carbamoyl-
ethyl}-2-[2-amino-3-(2-fluoro-4-pyridyl)-N-methylpropanoyl
amino]-3-methyl-N-methylbutanamide

| | | | Reaction 2 | | | |
|---|---|---|---|---|---|---|
| Compound I-a177B (g) | Pd(OH)$_2$ (g) | MeOH (ml) | Reaction time (hr) | Column sol. | Amount (g) | HPLC min |
| 0.288 | 0.043 | 20.00 | 3 | MC:MeOH = 20:1 | 0.160 | 15.48 |

ESI-MS(M$^+$ + 1):530

1H-NMR(CDCl$_3$): (two rotamers) δ 0.46, 0.72 and 0.78, 0.91(6H, d, J=7.1-7.9 Hz), 1.32 and 1.38(9H, s), 2.15-2.40(1H, m), 2.50, 2.83, and 3.0, 3.08(6H, s), 2.40-3.40(5H, m), 3.70 and 3.90 (1H, dd, J=8.8, 3.5-4.4 Hz), 4.81 and 5.05(1H, d, J=9.7 Hz), 4.99 and 5.52(2H, m), 6.05 and 6.49 (1H, brs), 6.48 and 6.64(1H, d, J=7.9 Hz), 6.74 and 6.76, 6.82(2H, brs), 6.90-7.18(2H, m), 8.12 (1H, d, J=6.2 Hz)

TABLE D-178A

Example 178A: less polar
(2S)—N—{(1S)-2-[3-(tert-butyl)-4-hydroxyphenyl]-1-carbamoyl-
ethyl}-2-[2-amino-3-(2-fluoro-5-pyridyl)-N-methylpropanoyl
amino]-3-methyl-N-methylbutanamide

| | | | | Reaction 1 | | | | |
|---|---|---|---|---|---|---|---|---|
| N—Me-Val-N—Me-Tyr(3-tBu)-NH$_2$ (g) | Compound P7 (g) | CMPI (g) | TEA (ml) | THF (ml) | Reaction time (hr) | Column sol. | Product | Amount (g) |
| 1.000 | 1.140 | 0.917 | 0.58 | 20.00 | 3 | nHx:EA = 1:1 | I-a178A | 0.380 |
| | | | | | | | I-a178B | 0.100 |

TABLE D-178A-continued

Example 178A: less polar
(2S)—N—{(1S)-2-[3-(tert-butyl)-4-hydroxyphenyl]-1-carbamoyl-
ethyl}-2-[2-amino-3-(2-fluoro-5-pyridyl)-N-methylpropanoyl
amino]-3-methyl-N-methylbutanamide

| | | | | Reaction 2 | | | |
|---|---|---|---|---|---|---|---|
| Compound I-a178A (g) | Pd(OH)$_2$ (g) | MeOH (ml) | Reaction time (hr) | Column sol. | | Amount (g) | HPLC min |
| 0.380 | 0.057 | 10.00 | 3 | MC:MeOH = 20:1 | | 0.210 | 17.76 |

ESI-MS(M$^+$ + 1):530

1H-NMR(CDCl$_3$): (two rotamers) δ 0.32, 0.42 and 0.60, 0.89(6H, d, J=7.1-7.9 Hz), 1.37 and 1.42(9H, s), 2.00-2.30(1H, m), 2.50, 2.90 and 2.94, 2.95(6H, s), 2.58-3.29(4H, m), 3.70(1/2H, dd, J=8.8, 6.1 Hz), 3.90(1/2H, t, J=8.8 Hz), 4.67 and 5.04(1H, d, J=8.8 Hz), 4.95 and 5.47 (1H, dd, J=8.8, 7.0 Hz), 5.70(1H, brs), 6.05 and 6.55(1H, brs), 6.58 and 6.65(1H, d, J=8.8 Hz), 6.75-6.99(2H, m), 7.10 and 7.18(1H, brs), 7.58-7.75(1H, m), 8.12(1H, m)

TABLE D-178B

Example 178B: more polar
(2S)—N—{(1S)-2-[3-(tert-butyl)-4-hydroxyphenyl]-1-carbamoyl-
ethyl}-2-[2-amino-3-(2-fluoro-5-pyridyl)-N-methylpropanoyl
amino]-3-methyl-N-methylbutanamide

| | | | | Reaction 2 | | |
|---|---|---|---|---|---|---|
| Compound I-a178B (g) | Pd(OH)$_2$ (g) | MeOH (ml) | Reaction time (hr) | Column sol. | Amount (g) | HPLC min |
| 0.100 | 0.015 | 5.00 | 3 | MC:MeOH = 20:1 | 0.040 | 15.65 |

ESI-MS(M$^+$ + 1):530

1H-NMR(CDCl$_3$): (two rotamers) δ 0.50, 0.75 and 0.77, 0.95(6H, d, J=7.1-7.9 Hz), 1.32 and 1.39(9H, s), 2.00-2.30(1H, m), 2.47, 2.83 and 3.0, 3.05(6H, s), 2.18-3.42(4H, m), 3.61 and 3.82 (1H, dd, J=8.8, 3.5-4.0 Hz), 4.85 and 5.07(1H, d, J=9.7 Hz), 5.57 and 5.70, 5.79, 6.11(2H, m and brs), 6.55 and 6.65(1H, d, J=7.9-8.8 Hz), 6.73, 6.88 and 6.97(2H, m), 7.13(1H, brs), 7.60-7.75 (1H, m), 7.97 and 8.05(1H, brs)

TABLE D-179A

Example 179A: less polar
(2S)—N—{(1S)-2-[3-(tert-butyl)-4-hydroxyphenyl]-1-carbamoyl-
ethyl}-2-{2-amino-N-methyl-3-[4-(trifluoromethyl)phenyl]propanoylamino}-3-methyl-N-methylbutanamide

| | | | | | Reaction 1 | | | |
|---|---|---|---|---|---|---|---|---|
| N—Me-Val-N—Me-Tyr(3-tBu)-NH$_2$ (g) | Compound P8 (g) | CMPI (g) | TEA (ml) | THF (ml) | Reaction time (hr) | Column sol. | Product | Amount (g) |
| 0.513 | 0.626 | 0.435 | 0.3 | 30.00 | 3 | nHx:EA = 1:1 | I-a179A | 0.330 |
| | | | | | | | I-a179B | 0.332 |

TABLE D-179A-continued

Example 179A: less polar
(2S)—N—{(1S)-2-[3-(tert-butyl)-4-hydroxyphenyl]-1-carbamoyl-
ethyl}-2-{2-amino-N-methyl-3-[4-(trifluoromethyl)phenyl]propanoylamino}-3-methyl-N-methylbutanamide Reaction 2

| Compound I-a179A (g) | Pd(OH)₂ (g) | MeOH (ml) | Reaction time time (hr) | Column sol. | Amount (g) | HPLC min |
|---|---|---|---|---|---|---|
| 0.330 | 0.049 | 10.00 | 3 | MC:MeOH = 20:1 | 0.136 | 19.89 |

ESI-MS(M⁺ + 1):579
1H-NMR(CDCl₃): (two rotamers) δ 0.49, 0.74 and 0.79, 0.93(6H, d, J=6.3-6.8 Hz), 1.34 and 1.39(9H, s), 2.25-2.48(1H, m), 2.53, 2.79 and 3.01, 3.05(6H, s), 2.58-3.40(4H, m), 3.74 and 3.90(1H, m), 4.87 and 5.07(1H, d, J=10.5-10.9 Hz), 5.38-5.10(2H, m), 6.20(2/3H, brs), 6.40 and 6.65(1H, d, J=7.9 Hz), 6.58(1/3H, brs), 6.73 and 6.97(1H, d, J=7.9-8.4 Hz), 7.12(1H, m), 7.27-7.30(2H, m), 7.55-7.60(2H, m)

TABLE D-179B

Example 179B: more polar
(2S)—N—{(1S)-2-[3-(tert-butyl)-4-hydroxyphenyl]-1-carbamoyl-
ethyl}-2-{2-amino-N-methyl-3-[4-(trifluoromethyl)phenyl]propanoyl-
amino}-3-methyl-N-methylbutanamide
Reaction 2

| Compound I-a179B (g) | Pd(OH)₂ (g) | MeOH (ml) | Reaction time (hr) | Column sol. | Amount (g) | HPLC min |
|---|---|---|---|---|---|---|
| 0.332 | 0.049 | 10.00 | 3 | MC:MeOH = 20:1 | 0.123 | 22.09 |

ESI-MS(M⁺ + 1):579
1H-NMR(CDCl₃): (two rotamers) δ 0.33, 0.36 and 0.55, 0.87(6H, d, J=6.4-6.9 Hz), 1.37 and 1.41(9H, s), 2.00-2.20(1H, m), 2.56, 2.92 and 2.98(6H, s), 2.60-3.21(4H, m), 3.77 and 3.96(1H, m), 4.67 and 5.02(1H, d, J=10.6-10.9 Hz), 4.96 and 5.45(1H, dd, J=9.0-11.3, 3.4-6.0 Hz), 5.67 and 6.04(1H, brs), 6.57 and 6.63(1H, d, J=7.9 Hz), 6.74 and 6.94(1H, dd, J=8.0-9.8, 1.8-2.1 Hz), 7.08 and 7.16(1H, d, J=1.9 Hz), 7.27-7.37(2H, m), 7.52-7.60(2H, m)

Scheme 16 shows synthesis process of Examples 180A and B.

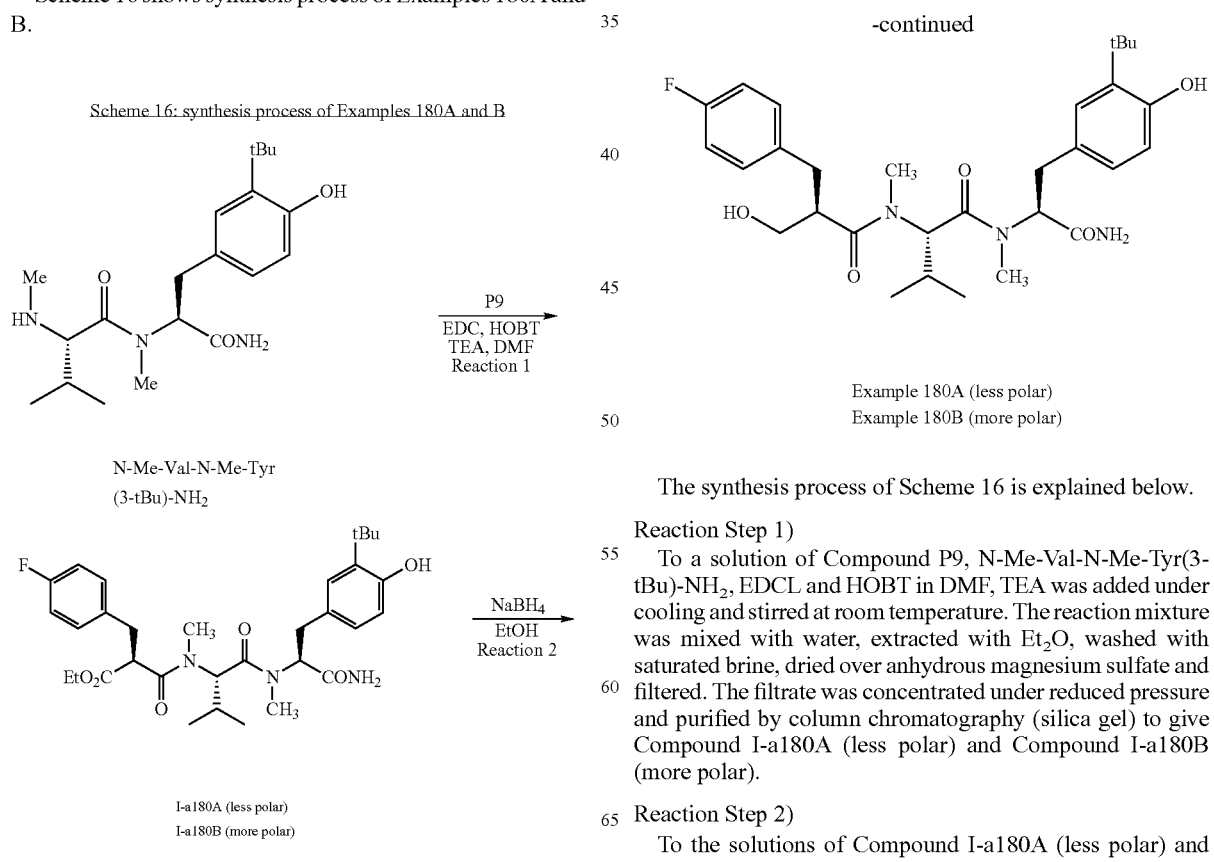

Example 180A (less polar)
Example 180B (more polar)

The synthesis process of Scheme 16 is explained below.

Reaction Step 1)

To a solution of Compound P9, N-Me-Val-N-Me-Tyr(3-tBu)-NH₂, EDCL and HOBT in DMF, TEA was added under cooling and stirred at room temperature. The reaction mixture was mixed with water, extracted with Et₂O, washed with saturated brine, dried over anhydrous magnesium sulfate and filtered. The filtrate was concentrated under reduced pressure and purified by column chromatography (silica gel) to give Compound I-a180A (less polar) and Compound I-a180B (more polar).

Reaction Step 2)

To the solutions of Compound I-a180A (less polar) and Compound I-a180B (more polar) in ethanol, NaBH₄ was added under cooling and stirred at room temperature. The reaction mixtures were mixed with a 1N HCl solution, extracted with Et$_2$O, washed with saturated brine, dried over anhydrous magnesium sulfate and filtered. The filtrates were concentrated under reduced pressure; the thus obtained residues were purified by column chromatography (silica gel) to give the titled compounds (less polar compound and more polar compound). Tables D-180A and B show Examples conducted according to Scheme 16.

TABLE D-180A

Example 180A: Less polar
(2S)—N—{(1S)-2-[3-(tert-butyl)-4-hydroxyphenyl]-1-carbamoyl-ethyl}-2-{2-[(4-fluorophenyl)methyl]-3-hydroxy-N-methylpropanoylamino}-3-methyl-N-methylbutanamide Reaction 1

| N—Me-Val-N—Me-Tyr(3-tBu)-NH$_2$ (g) | Compound P9 (g) | EDCI (g) | HOBT (g) | TEA (ml) | THF (ml) | Reaction time (hr) | Column sol. | Product | Amount (g) |
|---|---|---|---|---|---|---|---|---|---|
| 1.500 | 1.29 | 1.030 | 0.824 | 1.08 | 30.00 | 2.5 | nHx:EA = 1:1 | I-a180A | 0.700 |
|  |  |  |  |  |  |  |  | I-a180B | 0.820 |

Reaction 2

| Compound I-a180A (g) | NaBH$_4$ (g) | EtOH (ml) | Reaction time (hr) | Column sol. | Amount (g) | HPLC min |
|---|---|---|---|---|---|---|
| 0.700 | 0.490 | 30.00 | 3 | MC:MeOH = 20:1 | 0.17 | 21.83 |

ESI-MS(M$^+$ + 1):544

1H-NMR(CDCl$_3$): (two rotamers) δ 0.48, 0.74 and 0.76, 0.92(6H, d, J=6.0-7.2 Hz), 1.35 and 1.39(9H, s), 2.05-2.50(1H, m), 2.50, 2.80 and 2.98, 3.01(6H, s), 2.40-3.36(5H, m), 3.50-3.70(2H, m), 3.50-3.70(2H, m), 4.90 and 5.08(1H, d, J=10.6 Hz), 5.45(1H, m), 5.50 and 6.05(1H, brs), 5.70 and 6.20(1H, brs), 6.44 and 6.64(1H, d, J=8.8-8.3 Hz), 6.73-7.15(7H, m)

TABLE D-180B

Example 180B: more polar
(2S)—N—{(1S)-2-[3-(tert-butyl)-4-hydroxyphenyl]-1-carbamoyl-ethyl}-2-{2-[(4-fluorophenyl)methyl]-3-hydroxy-N-methylpropanoylamino}-3-methyl-N-methylbutanamide Reaction 2

| Compound I-a180B (g) | NaBH$_4$ (g) | EtOH (ml) | Reaction time (hr) | Column sol. | Amount (g) | HPLC min |
|---|---|---|---|---|---|---|
| 0.820 | 0.492 | 30.00 | 3 | MC:MeOH = 20:1 | 0.060 | 23.95 |

ESI-MS(M$^+$ + 1):544

1H-NMR(CDCl$_3$): (two rotamers) δ 0.17-0.20 and 0.44, 0.84(6H, m and d, J=6.5-6.7 Hz), 1.36 and 1.40(9H, s), 2.00-2.20(1H, m), 2.41 and 2.90, 2.92(6H, s), 2.67-4.00(13H, m),4.73 and 5.00(1H, d, J=10.5 Hz), 5.20 and 5.35(1H, m), 5.83 and 6.18(1H, brs), 6.38 and 6.51 (1H, brs), 6.62 and 6.65(1H, d, J=7.9 Hz), 6.75-7.20(8H, m)

The synthesis scheme of Examples 181 and 182 is shown in Scheme 17.

Scheme 17: Synthesis scheme of Examples 181 and 182

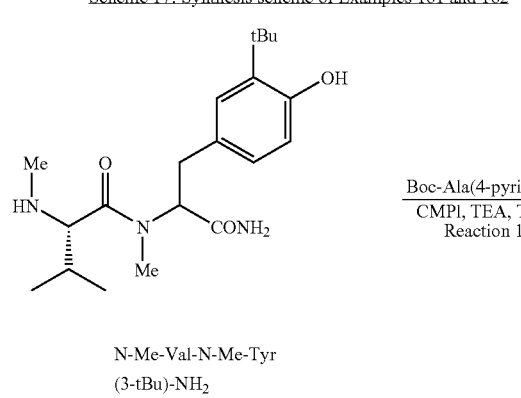

N-Me-Val-N-Me-Tyr
(3-tBu)-NH$_2$

Boc-Ala(4-pyri)-OH
―――――――――――→
CMPI, TEA, THF
Reaction 1

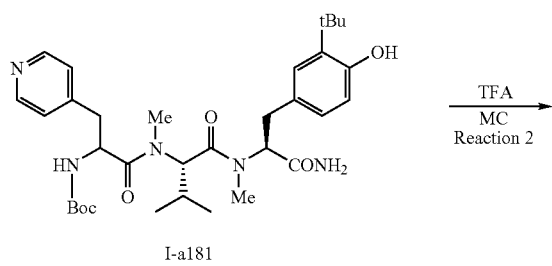

I-a181

TFA
――→
MC
Reaction 2

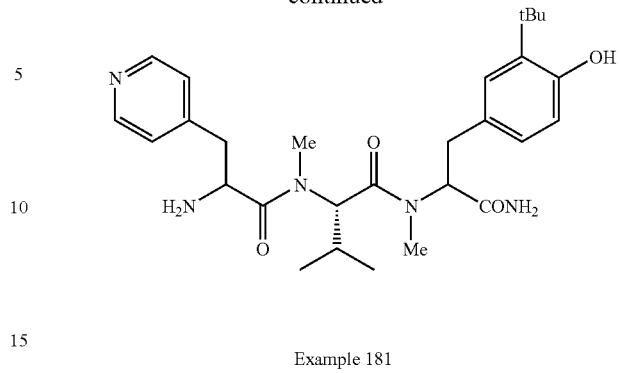

Example 181

Referring to Example 181, the synthesis process of Scheme 17 is explained below:

Reaction Step 1)

To a solution of Compound Boc-Ala(β-4-pyridyl)-OH, N-Me-Val-N-Me-Tyr(3-tBu)-NH$_2$ and CMPI in THF, TEA was added under cooling and stirred at room temperature. The reaction mixture was mixed with water, extracted with ethyl acetate washed with saturated brine, dried over anhydrous magnesium sulfate and filtered. The filtrate was concentrated under reduced pressure; the thus obtained residue was purified by column chromatography (silica gel) to give Compound I-a181.

Reaction Step 2)

To a solution of Compound I-a181 in dichloromethane, TEA was added under cooling and stirred at room temperature. The reaction mixture was concentrated under reduced pressure, extracted with dichloromethane, washed with saturated brine, dried over anhydrous magnesium sulfate and filtered. The filtrate was concentrated under reduced pressure; the thus obtained residue was purified by column chromatography (silica gel) to give the titled compound.

Compound of Example 182 was obtained according to a similar process to Example 181 using Boc-Ala(β-4-pyridyl)-OH.

Examples conducted according to Scheme 17 are shown in Tables D-181 and D-182.

TABLE D-181

| Example 181 Ala(β-4-pyridyl)-N—Me-Val-N—Me-Tyr(3-tBu)-NH$_2$ | | | | | | | | |
|---|---|---|---|---|---|---|---|---|
| Reaction 1 | | | | | | | | |
| N—Me-Val-N—Me-Tyr(3-tBu)-NH$_2$ (g) | Boc-Ala(beta-4-pyridyl)-OH (g) | CMPI (g) | TEA (ml) | THF (ml) | Reaction time (hr) | Column sol. | Product | Amount (g) |
| 0.680 | 0.500 | 0.960 | 0.52 | 15.00 | 24 | MC:MeOH = 30:1 | I-a181 | 0.800 |
| Reaction 2 | | | | | | | | |
| Compound I-a181 (g) | TFA | MC (ml) | Reaction time (hr) | Column sol. | | Amount (g) | HPLC min | |
| 0.800 | 4.00 | 20.00 | 3 | MC:MeOH = 20:1 | | 0.450 | 13.30 | |

ESI-MS(M$^+$ + 1):512
1H-NMR(CDCl$_3$): (two rotamers) δ 0.40, 0.72 and 0.82, 0.96(6H, d, J=6.3-6.7 Hz), 1.37 and 1.42(9H, s), 2.05-2.30(1H, m), 2.51, 2.89 and 2.94, 2.96(6H, s), 2.59-3.30(4H, m), 4.65-5.05(1H, m), 5.30(1H, s), 5.45-5.05(1H, m), 6.30-6.45(1H, m), 6.60-7.05(2H, m), 7.10-7.20(2H, m), 8.20-8.25(2H, m)

TABLE D-182

Example 182
Phe(4-CN)-N—Me-Val-N—Me-Tyr(3-tBu)-NH$_2$

| | | | Reaction 1 | | | | | |
|---|---|---|---|---|---|---|---|---|
| N—Me-Val-N—Me-Tyr(3-tBu)-NH$_2$ (g) | Boc-Phe(4-CN)-OH (g) | CMPI (g) | TEA (ml) | THF (ml) | Reaction time (hr) | Column sol. | Product | Amount (g) |
| 0.620 | 0.500 | 0.660 | 0.48 | 15.00 | 24 | MC:MeOH = 30:1 | I-a182 | 0.900 |

| | | Reaction 2 | | | | |
|---|---|---|---|---|---|---|
| Compound I-a182 (g) | TFA | MC (ml) | Reaction time (hr) | Column sol. | Amount (g) | HPLC min |
| 0.900 | 4.00 | 20.00 | 4 | MC:MeOH = 20:1 | 0.520 | 16.82 |

ESI-MS(M$^+$ + 1):536

1H-NMR(CDCl$_3$): (two rotamers) δ 0.48, 0.76 and 0.85, 0.94(6H, d, J=6.3-6.8 Hz), 1.37 and 1.43(9H, s), 2.20-2.70(1H, m), 2.55, 2.85 and 2.95, 3.05(6H, s), 3.15-3.40(2H, m), 3.65-3.85(2H, m), 4.75-5.20(2H, m), 5.40-5.50(1H, m), 6.40-6.65(1H, m), 6.75-6.85(1H, m), 6.95-7.15(1H, m), 7.25-7.35(2H, m), 7.58-7.63(2H, m)

The synthesis scheme of Example 183 is shown in Scheme 18.

Scheme 18: Synthesis scheme of Example 183

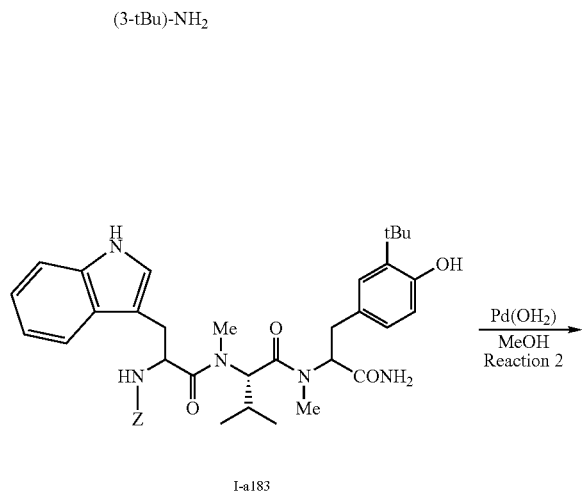

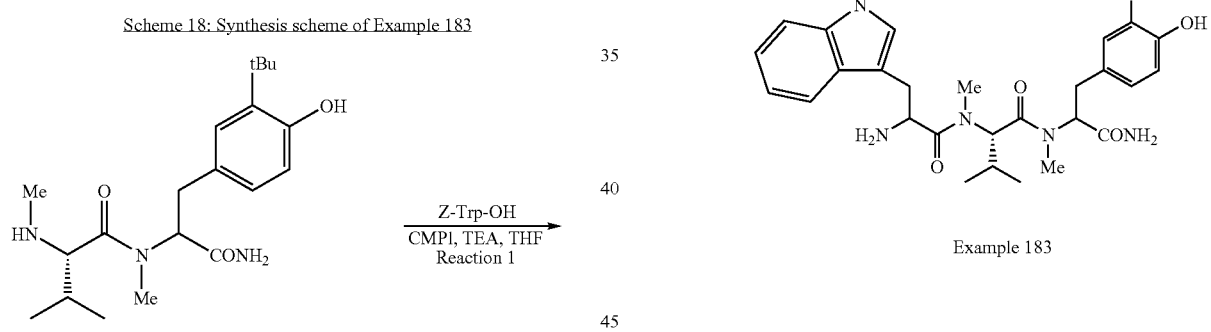

Example 183

The synthesis process of Scheme 18 is explained below:

Reaction Step 1)

To a solution of Z-Trp-OH,N-Me-Val-N-Me-Tyr(3-tBu)-NH$_2$ and CMPI in THF, TEA was added under cooling and stirred at room temperature. The reaction mixture was mixed with water, extracted with ethyl acetate, washed with saturated brine, dried over anhydrous magnesium sulfate and filtered. The filtrate was concentrated under reduced pressure; the thus obtained residue was purified by column chromatography (silica gel) to give Compound I-a183.

Reaction Step 2)

To a solution of Compound I-a183 in methanol, Pd(OH)$_2$ was added and stirred in a hydrogen atmosphere at room temperature. After filtering off the Pd(OH)$_2$, the filtrate was concentrated under reduced pressure; the thus obtained residue was purified by column chromatography (silica gel) to give the titled compound.

Example conducted according to Scheme 18 is shown in Table D-183.

TABLE D-183

Example 183
Trp-N—Me-Val-N—Me-Tyr(3-tBu)-NH$_2$

Reaction 1

| N—Me-Val-N—Me-Tyr(3-tBu)-NH$_2$ (g) | Z-Trp-OH (g) | CMPI (g) | TEA (ml) | THF (ml) | Reation time (hr) | Column sol. | Product | Amount (g) |
|---|---|---|---|---|---|---|---|---|
| 0.620 | 0.700 | 0.660 | 0.48 | 15.00 | 24 | MC:MeOH = 30:1 | I-a183 | 0.700 |

Reaction 2

| Compound I-a183 (g) | Pd(OH)$_2$ | MeOH (ml) | Reaction time (hr) | Column sol. | Amount (g) | HPLC min |
|---|---|---|---|---|---|---|
| 0.700 | 0.100 | 20.00 | 24 | MC:MeOH = 20.1 | 0.380 | 18.14 |

ESI-MS(M$^+$ + 1):550
1H-NMR(CDCl$_3$): (two rotamers) δ 0.39, 0.73 and 0.79, 0.93(6H, d, J=6.3-6.7 Hz), 1.33 and 1.39(9H, s), 2.15-2.35(2H, m), 2.37, 2.75 and 2.95, 3.05(6H, s), 2.60-3.15(2H, m), 3.25-3.40(2H, m), 3.80-4.05(1H, m), 4.70-5.10(1H, m), 6.30-6.55(1H, m), 6.65-7.20(5H, m), 7.40-7.60 (2H, m)

TEST EXAMPLE 1

Motilin receptor binding test

A motilin receptor binding test was conducted in the following manner [Vantrappen et al., Regul. Peptides, 15, 143 (1986)]. The duodenum was extracted from a slaughtered rabbit, had the mucous membrane separated and homogenized in 50 mM Tris buffer to prepare a protein sample. The protein sample was incubated together with $^{125}$I motilin 25 pM and thereafter the radioactivity bound to the protein was measured. Specific binding was defined as the difference between the radioactivity in the case of adding a great excess amount of motilin ($10^{-7}$ M) and that in the case of no adding. The activity of the compound was expressed by IC$_{50}$ (in nM), as the concentration sufficient to reduce the specific binding by 50%. Result is shown in Tables F-1 to F-3.

TEST EXAMPLE 2

Action on the Contraction of a Specimen of Longitudinal Muscle in the Duodenum Extracted from a Rabbit The action on the motilin-induced contraction of a specimen of longitudinal muscle in the duodenum extracted from a rabbit was investigated by the following method. A duodenum specimen (5×15 mm) extracted from a slaughtered rabbit was suspended in an organ bath (10 ml) such that the longitudinal muscle would run vertically; the bath was filled with a Krebs solution kept at 28° C. A mixed gas (95% O$_2$ and 5% CO$_2$) was continuously bubbled into the Krebs solution and the contraction of the duodenum specimen was recorded isotonically (with a 1-g load) via an isotonic transducer (ME-3407, ME Commercial, Tokyo, Japan). The degree of contraction was expressed in relative values, with the contraction by acetylcholine at a dose of $10^{-4}$ M being taken as 100%. The activity of the compound was calculated as pA$_2$ value indicating its effect on the dose-dependent muscle contraction by the motilin put into the organ bath. The result is shown in Tables F-1 to F-3.

TABLE F-1

| Example No. | Motilin receptor binding test, IC$_{50}$ (nM) | Contraction suppressing test, pA$_2$ |
|---|---|---|
| 1 | 0.89 | 8.8 |
| 2 | 0.71 | 8.7 |
| 3 | 1.5 | 8.7 |
| 4 | 1.6 | 8.3 |
| 8 | 0.35 | 9.5 |
| 9 | 1.0 | 9.0 |
| 12 | 0.52 | 9.3 |
| 14 | 0.70 | 9.3 |
| 15 | 0.82 | 8.5 |
| 16 | 0.41 | 9.4 |
| 17 | 0.70 | 9.1 |
| 19 | 2.2 | 8.7 |
| 21 | 0.27 | 9.8 |
| 22 | 0.52 | 8.3 |
| 23 | 0.67 | 9.3 |
| 24 | 0.94 | 9.1 |

TABLE F-2

| Example No. | Motilin receptor binding test, IC$_{50}$ (nM) | Contraction suppressing test, pA$_2$ |
|---|---|---|
| 26 | 7.3 | 8.0 |
| 27 | 1.2 | 8.6 |
| 28 | 0.52 | 9.0 |
| 29 | 0.45 | 8.7 |
| 30 | 0.81 | 9.1 |
| 31 | 0.79 | 9.5 |
| 32 | 0.76 | 9.1 |
| 33 | 1.7 | 8.4 |
| 34 | 1.5 | 9.4 |
| 35 | 1.7 | 8.8 |
| 36 | 2.3 | 8.8 |
| 37 | 0.60 | 8.8 |
| 38 | 3.0 | 8.2 |
| 39 | 2.0 | 8.7 |
| 40 | 1.6 | 8.6 |
| 41 | 3.1 | 8.4 |
| 42 | 1.2 | 8.3 |
| 43 | 1.9 | 8.5 |
| 44 | 3.6 | 8.5 |
| 63 | 0.62 | 8.4 |
| 64 | 1.0 | 9.0 |
| 101 | 0.24 | 8.9 |

TABLE F-2-continued

| Example No. | Motilin receptor binding test, IC$_{50}$ (nM) | Contraction suppressing test, pA$_2$ |
|---|---|---|
| 102 | 0.31 | 9.0 |
| 103 | 0.86 | 8.9 |

TABLE F-3

| Example No. | Motilin receptor binding test, IC$_{50}$ (nM) | Contraction suppressing test, pA$_2$ |
|---|---|---|
| 104 | 0.32 | 9.1 |
| 105 | 0.31 | 9.8 |
| 106 | 0.62 | 9.8 |
| 107 | 0.39 | 8.7 |
| 108 | 0.43 | 9.0 |
| 109 | 0.17 | 8.7 |
| 119 | 0.40 | 9.4 |
| 120 | 0.27 | 9.0 |
| 121 | 0.41 | 8.9 |
| 122 | 0.47 | 9.0 |
| 123 | 0.70 | 9.1 |
| 124 | 0.98 | 9.1 |
| 125 | 1.0 | 9.0 |
| 126 | 1.9 | 9.2 |
| 127 | 1.7 | 8.7 |
| 128 | 1.5 | 8.7 |
| 129 | 4.0 | 8.5 |
| 132 | 0.86 | 8.9 |

TABLE F-4

| Example No. | Motilin receptor binding test, IC$_{50}$ (nM) | Contraction suppressing test, pA$_2$ |
|---|---|---|
| 133 | 1.1 | 8.2 |
| 134 | 1.5 | 8.3 |
| 135 | 0.70 | 8.5 |
| 136 | 6.8 | 7.6 |
| 140 | 4.0 | 8.2 |
| 142 | 0.62 | 8.6 |
| 144 | 2.0 | 8.5 |
| 148 | 4.1 | 8.4 |
| 151 | 0.36 | 8.2 |
| 155 | 2.5 | 8.1 |
| 157 | 6.1 | 8.1 |
| 163 | 2.4 | 7.8 |
| 165 | 2.8 | 8.2 |
| 166 | 1.8 | 9.8 |
| 182 | 2.3 | 8.5 |
| 183 | 0.57 | 9.5 |

INDUSTRIAL APPLICABILITY

The compounds of the present invention function as a motilin receptor antagonist and are useful as medicines including therapeutics of irritable bowel syndrome.

The invention claimed is:

1. A compound of Formula (1):

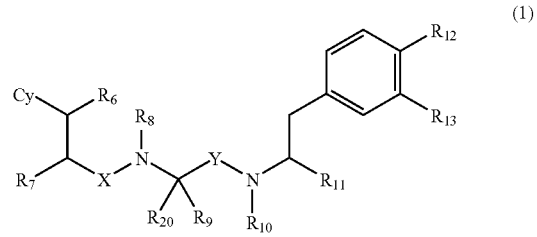

wherein:

Cy is a group of Formula (2):

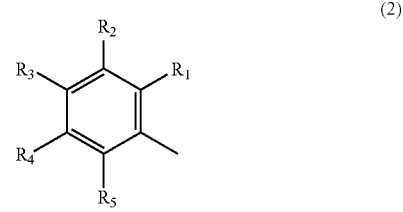

$R_1$, $R_2$, $R_3$, $R_4$ and $R_5$ are hydrogen, halogen, or hydroxy and at least one of $R_1$, $R_2$, $R_3$, $R_4$ and $R_5$ is halogen;

$R_6$ is hydrogen;

$R_7$ is straight-chained or branched $C_{1-3}$alkyl, substituted with one or more hydroxyl groups, or amino optionally substituted with one or more straight-chained or branched $C_{1-3}$ alkyl groups which many be the same or different;

$R_8$ is hydrogen, methyl or ethyl;

$R_9$ is straight-chained or branched $C_{1-6}$ alkyl optionally substituted with one or more groups which may be the same or different and are selected from the group consisting of phenyl, para-hydroxyphenyl, para-fluorophenyl, para-chlorophenyl, $C_{3-7}$ cycloalkyl, halogen and thienyl, $C_{3-7}$cycloalkyl; or phenyl;

$R_{20}$ is hydrogen;

$R_{10}$ is hydrogen or methyl or ethyl;

$R_{11}$ is straight-chained or branched $C_{1-3}$ alkyl optionally substituted with one or more groups which may be the same or different and are selected from the group consisting of amino; hydroxyl, carbamoyl, methanesulfonyl, ureide, guanidyl, N'-cyano-N''-methylguanidyl, sulfamoylamino, carbamoylmethylamino and methanesulfonylamino, and —CO—N($R_{14}$)$R_{15}$;

$R_{12}$ is hydroxy;

$R_{13}$ straight-chained or branched $C_{1-6}$ alkyl;

$R_{14}$ and $R_{15}$, which may be the same or different, are each hydrogen, straight-chained or branched $C_{1-4}$ alkyl optionally substituted with hydroxyl or methanesulfonyl; $C_{3-7}$cycloalkyl, straight-chained or branched $C_{1-4}$ alkoxy, straight-chained or branched $C_{1-4}$ alkylsulfonyl, or pyridyl;

X is carbonyl or methylene;

Y is carbonyl;

or a pharmaceutically acceptable salt thereof.

2. The compound according to claim 1, wherein Cy in Formula (1) is a group of Formula (2); or a pharmaceutically acceptable salt thereof.

3. The compound according to claim 1,
wherein Cy in Formula (1) is a group of Formula (2) in which at least one of $R_1, R_2, R_3, R_4$ and $R_5$ is halogen and the others are hydrogen or hydroxy;
or a pharmaceutically acceptable salt thereof.

4. The compound according to claim 1,
wherein Cy in Formula (1) is a group of Formula (2) in which $R_3$ is halogen or $R_2$ and $R_3$ are the same kind of halogen;
or a pharmaceutically acceptable salt thereof.

5. The compound according to claim 1,
wherein Cy in Formula (1) is a group of Formula (2) in which $R_3$ is halogen and $R_1, R_2, R_4$ and $R_5$ are hydrogen, or $R_2$ and $R_3$ are the same kind of halogen and $R_1, R_4$ and $R_5$ are hydrogen;
or a pharmaceutically acceptable salt thereof.

6. The compound according to claim 1, wherein $R_7$ in Formula (1) is hydrogen or amino optionally substituted with one or more of the same of different kinds of straight-chained or branched $C_{1-3}$ alkyl; or
a pharmaceutically acceptable salt thereof.

7. The compound according to claim 1, wherein $R_8$ in Formula (1) is hydrogen or methyl;
or a pharmaceutically acceptable salt thereof.

8. The compound according to claim 1, wherein $R_9$ in Formula (1) is methyl, isopropyl, isobutyl, sec-butyl, tert-butyl, 3-pentyl, neopentyl, cyclohexyl, phenyl, benzyl, para-hydroxybenzyl, cyclohexylmethyl or para-fluorobenzyl;
or a pharmaceutically acceptable salt thereof.

9. The compound according to claim 1, wherein $R_{11}$ in Formula (1) is methyl, hydroxymethyl, carbamoylmethyl, methanesulfonylmethyl, ureidemethyl, sulfamoylaminomethyl, methanesulfonylaminomethyl, ethylcarbamoyl, n-propylcarbamoyl, isopropylcarbamoyl, tertbutylcarbamoyl, methoxycarbamoyl, methylcarbamoyl, methanesulfonylmethylcarbamoyl, methoxymethylcarbamoyl;
or a pharmaceutically acceptable salt thereof.

10. The compound according to claim 1, wherein $R_{13}$ in Formula (1) is isopropyl, tert-butyl (tBu), or 1,1-dimethylpropyl;
or a pharmaceutically acceptable salt thereof.

11. The compound according to claim 1, wherein in Formula (1) Cy is a group of Formula (2) in which at least one of $R_1, R_2, R_3, R_4$ and $R_5$ is halogen and the others are hydrogen or hydroxy;
$R_8$ is hydrogen or methyl;
$R_9$ is methyl, isopropyl, isobutyl, sec-butyl, tert-butyl, 3-pentyl, neopentyl, cyclohexyl phenyl;
$R_{11}$ is methyl, hydroxymethyl, carbamoylmethyl, methanesulfonylmethyl, ureidemethyl, sulfamoylaminomethyl, methanesulfonylaminomethyl, methylcarbamoyl, ethylcarbamoyl, n-propylcarbamoyl, isopropylcarbamoyl, methanesulfonylmethylcarbamoyl, methoxymethylcarbamoyl, or methoxycarbamoyl;
$R_{13}$ is isopropyl, tert-butyl (tBu), 1,1-dimethylpropyl- or 1,1-dimethyl-2-propenyl;
or a pharmaceutically acceptable salt thereof.

12. The compound according to claim 1 which is selected from the group of compounds consisting of Phe(4-F)-N-Me-Val-N-Me-Tyr(3-tBu)-NH$_2$, Phe(4-Cl)-N-Me-Val-N-Me-Tyr(3-tBu)-NH$_2$, Phe(3,4-F$_2$)-N-Me-Val-N-Me-Tyr(3-tBu)-NH$_2$, Phe(3-F)-N-Me-Val-N-Me-Tyr(3-tBu)-NH$_2$, Phe(4-F)-N-Me-Val-N-Me-Tyr(3-tBu)-NHOMe, 2-((2-amino-3-(4-fluorophenyl)propionyl)-N-methylamino)-3-methylbutyric acid 2-(3-tertbutyl-4-hydroxyphenyl)-1-(2-pyridylcarbamoyl)ethylamide, N-(2-(2-((2-amino-3-(4-fluorophenyl)propionyl)-N-methylamino)-3-methyl-butyrylamino)-3-(3-tBu-4-hydroxyphenyl)propyl)urea, N-(2-(2-(2-amino-3-(4-fluorophenylpropanoyl-N-methylamino)-3-methyl)butyrylamino)-3-(3-tertbutyl-4-hydroxyphenyl)propyl) sulfamide, N-[2-(3-tertbutyl-4-hydroxyphenyl)-1-(methanesulfonylaminomethyl)ethyl]-2-[N-(4-fluorophenylalanyloyl)methylamino]-3-methylbutanamide, 2-((2-amino-3-(4-fluorophenyl)propionyl)-N-methylamino)-3-methylbutyric acid 2-(3-t-butyl-4-hydroxyphenyl)-1-carbamidemethylethylamide, 2-((2-amino-3-(4-fluorophenyl)propionyl)-N-methylamino)-3-methylbutyric acid 2-(3-t-butyl-4-hydroxyphenyl)-1-methanesulfonylmethylethylamide, 2-(2-((2-amino-3-(4-fluorophenyl)propionyl)-N-methylamino)-3-methyl-butyrylamino)-3-(3-tBu-4-hydroxyphenyl)propanol, 2-(1-(2-((2-amino-3-(4-fluorophenyl)propionyl)-N-methylamino)-3-methyl-butyrylamino)-2-(3-tertbutyl-4-hydroxyphenyl)ethyl)-6-methyl-4-pyrimidinone, 2-((2-amino-3-(4-fluorophenyl)propionyl)-N-methylamino)-3-methylbutyric acid 2-(3-t-butyl-4-hydroxyphenyl)-1-(1,3,4-oxadiazol-2-yl)ethylamide, 2-((2-amino-3-(4-fluorophenyl)propionyl)-N-methylamino)-3-methylbutyric acid 2-(3-t-butyl-4-hydroxyphenyl)-1-(1,2,4-oxadiazol-5-yl)ethylamide, 2-((2-amino-3-(4-fluorophenyl)propionyl)-N-methylamino)-3-methylbutyric acid 2-(3-tertbutyl-4-hydroxyphenyl)-1-(thiazol-2-yl)ethylamide, 2-((2-amino-3-(4-fluorophenyl)propionyl)-N-methylamino)-3-methylbutyric acid 2-(3-t-butyl-4-hydroxyphenyl)-1-(1,3,4-triazol-2-yl)ethylamide, Tyr(2-F)-N-Me-Val-N-Me-Tyr(3-tBu)-NH$_2$, Tyr(3-F)-N-Me-Val-N-Me-Tyr(3-tBu)-NH$_2$, Phe(4-F)-N-Me-Val-Tyr(3-tBu)-NH$_2$, N-Me-Phe(4-F)-N-Me-Val-Tyr(3-tBu)-NH$_2$, N-Et-Phe(4-F)-N-Me-Val-Tyr(3-tBu)-NH$_2$, Phe(4-F)-N-Me-Val-Tyr(3-tBu)-NHMe, N-Me-Phe(4-F)-N-Me-Val-Tyr(3-tBu)-NHMe, N-Et-Phe(4-F)-N-Me-Val-Tyr(3-tBu)-NHMe, N-Me-Phe(4-F)-N-Me-Val-N-Me-Tyr(3-tBu)-NH$_2$, N-Et-Phe(4-F)-N-Me-Val-N-Me-Tyr(3-tBu)-NH$_2$, Phe(4-F)-N-Me-Val-N-Me-Tyr(3-tBu)-NHMe, N-Me-Phe(4-F)-N-Me-Val-N-Me-Tyr(3-tBu)-NHMe, N-Et-Phe(4-F)-N-Me-Val-N-Me-Tyr(3-tBu)-NHMe, Phe(4-F)-N-Me-Val-N-Et-Tyr(3-tBu)-NH$_2$, N-Me-Phe(4-F)-N-Me-Val-N-Et-Tyr(3-tBu)-NH$_2$, N-Et-Phe(4-F)-N-Me-Val-N-Et-Tyr(3-tBu)-NH$_2$, Phe(4-F)-N-Me-Val-N-Et-Tyr(3-tBu)-NHMe, N-Me-Phe(4-F)-N-Me-Val-N-Et-Tyr(3-tBu)-NHMe, N-Et-Phe(4-F)-N-Me-Val-N-Et-Tyr(3-tBu)-NHMe, Phe(4-F)-N-Me-Val-Tyr(3-tBu)-NHtBu, Phe(4-F)-N-Me-Val-N-Me-Tyr(3-tBu)-NHCH$_2$SO$_2$CH$_3$, Phe(4-F)-N-Me-Val-Tyr(3-tBu)-NHEt, N-Me-Phe(4-F)-N-Me-Val-Tyr(3-tBu)-NHEt, N-Et-Phe(4-F)-N-Me-Val-Tyr(3-tBu)-NHEt, Phe(4-F)-N-Me-Val-Tyr(3-tBu)-NHCH$_2$OH, N-Me-Phe(4-F)-N-Me-Val-Tyr(3-tBu)-NHCH$_2$OH, N-Et-Phe(4-F)-N-Me-Val-Tyr(3-tBu)-NHCH$_2$OH, Phe(4-F)-N-Me-Val-N-Me-Tyr(3-tBu)-NHEt, N-Me-Phe(4-F)-N-Me-Val-N-Me-Tyr(3-tBu)-NHEt, N-Et-Phe(4-F)-N-Me-Val-N-Me-Tyr(3-tBu)-NHEt, Phe(4-F)-N-Me-Val-N-Me-Tyr(3-tBu)-NHCH$_2$OH, N-Me-Phe(4-F)-N-Me-Val-N-Me-Tyr(3-tBu)-NHCH$_2$OH, N-Et-Phe(4-F)-N-Me-Val-N-Me-Tyr(3-tBu)-NHCH$_2$OH, Phe(4-F)-N-Me-Val-N-Et-Tyr(3-tBu)-NHEt, N-Me-Phe(4-F)-N-Me-Val-N-Et-Tyr(3-tBu)-NHEt, N-Et-Phe(4-F)-N-Me-Val-N-Et-Tyr(3-tBu)-NHEt, Phe(4-F)-N-Me-Val-N-Et-Tyr(3-tBu)-NHCH$_2$OH, N-Me-Phe(4-F)-N-Me-Val-N-Et-Tyr(3-tBu)-NHCH$_2$OH, N-Et-Phe(4-F)-N-Me-Val-N-Et-Tyr(3-tBu)-NHCH$_2$OH, Phe(4-F)-N-Me-Val-N-Me-Tyr(3-tBu)-NHcPr, and Phe(4-F)-N-Me-Val-Tyr(3-tBu)-NHnPr Phe(4-F)-N-Me-Val-Tyr(3-tBu)-NHiPr;
or a pharmaceutically acceptable salt thereof.

13. A pharmaceutical composition containing the compound according to claim 1 as an active ingredient and an inert pharmaceutically acceptable carrier.

14. A motilin receptor antagonist composition containing an effective amount of the compound according to claim 1 and an inert pharmaceutically acceptable carrier.

15. A compound of Formula (4):

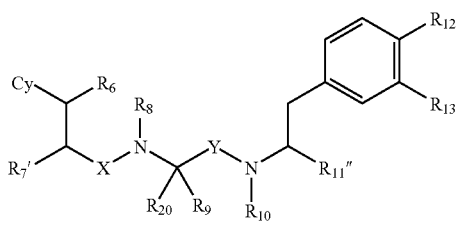

(4)

wherein
Cy, $R_6$, $R_8$, $R_9$, $R_{20}$, $R_{10}$, $R_{12}$, $R_{13}$, X and Y are as defined in claim 1;
$R_7'$ is straight-chained or branched $C_{1-3}$alkyl substituted with one or more protected hydroxyl groups, or protected amino optionally substituted with one or more straight-chained or branched $C_{1-3}$ alkyl groups which may be the same or different; and
$R_{11}''$ is straight-chained or branched $C_{1-3}$ alkyl optionally substituted with one or more groups which may be the same or different and are selected from the group consisting of amino, hydroxyl, carbamoyl, methanesulfonyl, ureide, guanidyl, N'-cyano-N''-methylguanidyl, sulfamoylamino, carbamoylmethylamino, and methanesulfonylamino, and —CO—N($R_{14}$)$R_{15}$, wherein $R_{14}$ and $R_{15}$ are as defined in claim 1,
or a pharmaceutically acceptable salt thereof.

16. A compound of Formula (5):

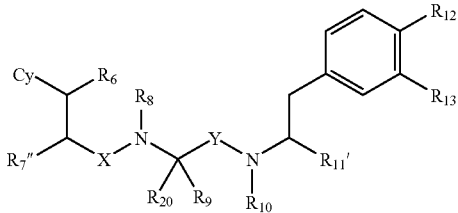

(5)

wherein:
Cy, $R_6$, $R_8$, $R_9$, $R_{20}$, $R_{10}$, $R_{12}$, $R_{13}$, X and Y are as defined in claim 1;
$R_7''$ is straight-chained or branched $C_{1-3}$alkyl substituted with one or more optionally protected hydroxyl groups or amino optionally substituted with one or more different straight-chained or branched $C_{1-3}$ alkyl groups which may be the same or different; and
$R_{11}'$ is straight-chained or branched $C_{1-3}$alkyl optionally substituted with one or more groups which may be the same or different and are selected from the group consisting of protected amino; protected hydroxyl, protected carbamoyl, protected ureide, protected guanidyl, protected N'-cyano-N''-methylguanidyl, protected sulfamoylamino, protected carbamoylmethylamino and protected methanesulfonylamino; —CO—N($R_{14}$)$R_{15}$ wherein $R_{14}$ and $R_{15}$ are those defined in claim 1 which are appropriately protected
or a pharmaceutically acceptable salt thereof.

17. A compound of Formula (6):

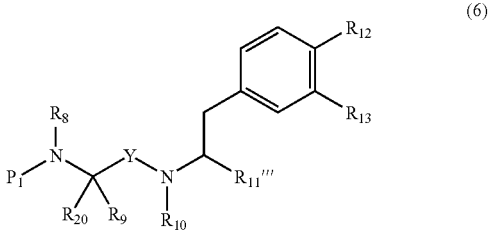

(6)

wherein:
$R_8$ is hydrogen, methyl or ethyl;
$R_9$, is straight-chained or branched $C_{1-6}$ alkyl optionally substituted with one or more groups which may be the same or different ant are selected from the group consisting of phenyl, para-hydroxyphenyl, para-fluorophenyl, para-chlorophenyl, $C_{3-7}$ cycloalkyl, halogen and thienyl;
$R_{20}$ is hydrogen or methyl or;
$R_{10}$ is hydrogen or methyl or ethyl;
$R_{12}$ is hydroxy;
$R_{13}$ is straight-chained or branched $C_{1-6}$ alkyl; and
Y is carbonyl;
$P_1$ is hydrogen or a protecting group of amine; and
$R_{11}'''$ is straight-chained or branched $C_{1-3}$alkyl, carboxyl, straight-chained or branched $C_{1-3}$alkyl optionally substituted with one or more groups which may be the same or different and are selected from the group consisting of amino hydroxyl, carbamoyl, methanesulfonyl, ureide, guanidyl, N'-cyano-N''-methylguanidyl, sulfamoylamino, carbamoylmethylamino and methanesulfonylamino; straight-chained or branched $C_{1-3}$ alkyl having protected amino or and —CO—N($R_{14}$)$R_{15}$ wherein $R_{14}$ and $R_{15}$, which may be the same or different, are hydrogen, straight-chained or branched $C_{1-4}$ alkyl optionally substituted with hydroxy, $C_{3-7}$ cycloalkyl, straight-chained or branched $C_{1-4}$ alkoxy, straight-chained or branched $C_{1-4}$alkylsulfonyl, or pyridyl; or
a pharmaceutically acceptable salt thereof.

18. The compound according to claim 1, wherein the substitution of the optionally substituted straight-chained or branched $C_{1-3}$ alkyl as $R_7$ in formula (1) is halogen, hydroxyl or amino.

* * * * *